United States Patent
Holladay et al.

(10) Patent No.: US 9,725,465 B2
(45) Date of Patent: Aug. 8, 2017

(54) BIARYL ACETAMIDE COMPOUNDS AND METHODS OF USE THEREOF

(71) Applicant: Ambit Biosciences Corporation, San Diego, CA (US)

(72) Inventors: Mark W. Holladay, San Diego, CA (US); Gang Liu, San Diego, CA (US); Martin W. Rowbottom, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

(21) Appl. No.: 14/473,597

(22) Filed: Aug. 29, 2014

(65) Prior Publication Data

US 2015/0065468 A1    Mar. 5, 2015

Related U.S. Application Data

(60) Provisional application No. 61/872,400, filed on Aug. 30, 2013.

(51) Int. Cl.

| | | |
|---|---|---|
| *C07D 498/08* | (2006.01) | |
| *A61K 31/4365* | (2006.01) | |
| *A61K 31/437* | (2006.01) | |
| *A61K 31/4375* | (2006.01) | |
| *A61K 31/47* | (2006.01) | |
| *A61K 31/498* | (2006.01) | |
| *A61K 31/4985* | (2006.01) | |
| *A61K 31/5377* | (2006.01) | |
| *A61K 31/5386* | (2006.01) | |
| *A61K 31/655* | (2006.01) | |
| *A61K 45/06* | (2006.01) | |
| *C07D 413/12* | (2006.01) | |
| *C07D 471/04* | (2006.01) | |
| *C07D 487/04* | (2006.01) | |
| *C07D 495/04* | (2006.01) | |
| *C07D 403/12* | (2006.01) | |
| *C07D 413/14* | (2006.01) | |
| *C07D 498/14* | (2006.01) | |

(52) U.S. Cl.
CPC .......... *C07D 498/08* (2013.01); *A61K 31/437* (2013.01); *A61K 31/4365* (2013.01); *A61K 31/4375* (2013.01); *A61K 31/47* (2013.01); *A61K 31/498* (2013.01); *A61K 31/4985* (2013.01); *A61K 31/5377* (2013.01); *A61K 31/5386* (2013.01); *A61K 31/655* (2013.01); *A61K 45/06* (2013.01); *C07D 403/12* (2013.01); *C07D 413/12* (2013.01); *C07D 413/14* (2013.01); *C07D 471/04* (2013.01); *C07D 487/04* (2013.01); *C07D 495/04* (2013.01); *C07D 498/14* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |

(Continued)

FOREIGN PATENT DOCUMENTS

| | | |
|---|---|---|
| WO | 01/12189 A1 | 2/2001 |
| WO | 03/007959 A1 | 1/2003 |

(Continued)

OTHER PUBLICATIONS

Blume-Jensen and Hunter, "Oncogenic kinase signaling," Nature 411(6835): 355-365 (2001).

Fabian et al., "A small molecule-kinase interaction map for clinical kinase inhibitors," Nat. Biotechnol. 23(3):329-336 (2005) (Epub Feb. 13, 2005).

Frotscher et al., "Design, synthesis, and biological evaluation of (hydroxyphenyl)naphthalene and -quinoline derivatives: potent and selective nonsteroidal inhibitors of 17beta-hydroxysteroid dehydrogenase type 1 (17beta-HSD1) for the treatment of estrogen-dependent diseases," J. Med. Chem. 51(7):2158-2169 (2008) (Epub Mar. 7, 2008).

Heinrich, "Targeting FLT3 kinase in acute myelogenous leukemia: progress, perils, and prospects," Mini Rev. Med. Chem. 4(3):255-271 (2004).

(Continued)

*Primary Examiner* — David K O'Dell
(74) *Attorney, Agent, or Firm* — Jones Day

(57) ABSTRACT

Biaryl acetamide compounds and compositions and their methods of use are provided for modulating the activity of class III receptor tyrosine kinases and for the treatment, prevention or amelioration of one or more symptoms of disease of disorder mediated by class III receptor tyrosine kinases.

4 Claims, No Drawings

(56) References Cited

U.S. PATENT DOCUMENTS

| | | | |
|---|---|---|---|
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,218,418 | B1 | 4/2001 | Pevarello et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 7,034,049 | B1 | 4/2006 | Pevarello et al. |
| 7,452,993 | B2 | 11/2008 | Arnold et al. |
| 7,626,021 | B2 | 12/2009 | Arnold et al. |
| 2009/0143352 | A1 | 6/2009 | Arnold et al. |
| 2012/0322795 | A1* | 12/2012 | Berry et al. ............... 514/227.8 |

FOREIGN PATENT DOCUMENTS

| | | |
|---|---|---|
| WO | 2004/014899 A1 | 2/2004 |
| WO | 2006/131552 A1 | 12/2006 |
| WO | 2008/071456 A2 | 6/2008 |
| WO | 2009/111279 A1 | 9/2009 |
| WO | 2010/054058 A1 | 5/2010 |
| WO | 2010/101849 A1 | 9/2010 |
| WO | 2011/022473 A1 | 2/2011 |
| WO | 2011/037780 A1 | 3/2011 |
| WO | 2011/84486 A1 | 7/2011 |
| WO | 2012/082817 A1 | 6/2012 |
| WO | 2014/004863 A2 | 1/2014 |

OTHER PUBLICATIONS

Kiyoi et al., "Clinical significance of FLT3 in leukemia," Int. J. Hematol. 82(2):85-92 (2005).

Krause and Van Etten, "Tyrosine kinases as targets for cancer therapy," N. Engl. J. Med. (2005) 353(2):172-187 (2005).

Rowbottom et al., "Identification of 1-(3-(6,7-dimethoxyquinazolin-4-yloxy)phenyl)-3-(5-(1,1,1-trifluoro-2-methylpropan-2-yl)isoxazol-3-yl)urea hydrochloride (CEP-32496), a highly potent and orally efficacious inhibitor of V-RAF murine sarcoma viral oncogene homologue B1 (BRAF) V600E," J. Med. Chem. 55(3):1082-1105 (2012) (Epub Jan. 23, 2012).

Smith et al., "Validation of ITD mutations in FLT3 as a therapeutic target in human acute myeloid leukaemia," Nature 485(7397):260-263 (2012).

Still et al., "Rapid Chromatographic Technique for Preparative Separations with Moderate Resolution," J. Org. Chem. 43(14):2923-2925 (1978).

Von Bubnoff et al., "FMS-like tyrosine kinase 3-internal tandem duplication tyrosine kinase inhibitors display a nonoverlapping profile of resistance mutations in vitro," Cancer Res. 69(7):3032-3041 (2009).

* cited by examiner

BIARYL ACETAMIDE COMPOUNDS AND METHODS OF USE THEREOF

RELATED APPLICATION

This application claims priority to U.S. Provisional Application No. 61/872,400, filed Aug. 30, 2013, the disclosure of which is incorporated by reference herein in its entirety.

FIELD OF THE INVENTION

Provided herein are biaryl acetamide compounds. In certain embodiments, the compounds are modulators of one or more members of the class III receptor tyrosine kinase family, including one or more of FLT3 wildtype, FLT3-ITD and the tyrosine kinase domain mutants of FLT3. Also provided are compositions comprising the compounds and methods of use thereof. The compounds provided are useful in the treatment, prevention or amelioration of a disease or disorder related to the kinase activity of one or more of the class III receptor tyrosine kinases, including one or more of FLT3 wildtype, FLT3-ITD and the tyrosine kinase domain mutants of FLT3, or otherwise useful in the treatment, prevention, or amelioration of one or more symptoms associated with such diseases or disorders.

BACKGROUND OF THE INVENTION

Hematological cancers are cancers originating in blood-forming tissue, such as bone marrow, or in the cells of the immune system. Hematological cancers include leukemia, lymphoma, and multiple myeloma and they account for nearly 10% of newly diagnosed cancer in the United States.

One type of hematological cancer, acute myeloid leukemia (AML), is a hematological cancer characterized by abnormal proliferation of myeloid progenitor cells having lost the ability to differentiate. According to statistics collected by the American Cancer Society, the estimated incidence of AML in the United States is nearly 15,000 new cases in 2013 with an estimated mortality of at least 10,000 for that same year. The standard of care for AML has changed little over the decades, comprising the administration of various combinations of cytotoxic chemotherapy drugs (commonly the two-drug regimen of cytarabine and daunorubicin), with the goal of eliminating leukemic blasts while restoring normal blood counts. According to the National Cancer Institute, standard chemotherapy results in about 65% complete response rate, with more than 25% of adults expected to survive three of more years. However, given the high rate of relapse and low tolerance to chemotherapy in older patients, researchers have been investigating targeted therapies that specifically inhibit protein targets that have been identified as mediators of leukemic blast cell survival.

One such identified protein target is the FMS-like tyrosine kinase III, or FLT3, which is a kinase protein belonging to the class III receptor tyrosine kinase family, which also includes the receptors, PDGFRα, PDGFRβ, KIT, RET, and CSF1R. FLT3 is a receptor tyrosine kinase that plays a role in the regulation of normal hematopoiesis and which is overexpressed in leukemic blast cells (See Heinrich *Mini Reviews in Medicinal Chemistry* 2004 4(3):255-271, Kiyoi et al. *Int J Hematol* 2005 82:85-92). About 30% of all AML patients are also found to have an activating mutation in the FLT3 gene in the form of internal tandem duplications called FLT3-ITD which is associated with poor prognosis and higher rate of relapse. FLT3 inhibitors that have been studied or are currently being studied in the clinic include PKC412 (midostaurin), CEP701 (lestarutinib), SU-5416 (semaxinib) and AC220 (quizartinib). More recently, acquired drug resistance mutations conferring resistance against FLT3 inhibitors have been identified in patients who received FLT3-targeted therapy (See Smith et al. *Nature* 2012 485(7397): 260-263 and von Bubnoff et al. *Cancer Res.* 2009 69(7): 3032-3041).

There remains a need to provide novel classes of compounds that are useful in the treatment of FLT3-mediated diseases or disorders, including those that have acquired resistance to FLT3-targeted therapy. Such classes of compounds would also be useful in the treatment of inflammatory and autoimmune disorders as FLT3 is expressed in a large portion of dendritic cell progenitors and plays a role in the proliferation and differentiation of these progenitors into dendritic cells which are the main initiators of T-cell mediated immune response.

SUMMARY OF THE INVENTION

Provided herein are compounds of Formula I or pharmaceutically acceptable salts, solvates, hydrates, clathrates, single stereoisomers, mixture of stereoisomers or racemic mixture of stereoisomers thereof. In certain embodiments, the compounds are modulators of class III receptor tyrosine kinase family. In certain embodiments, the compounds have activity as modulators of one or more of FLT3 wild type, FLT3-ITD and tyrosine kinase domain mutants of FLT3. The compounds are useful as medical treatments, pharmaceutical compositions and methods of modulating the activity of one or more of FLT3, CSF1R, KIT, RET, PDGFRα and PDGFRβ kinases, including wildtype and/or mutated forms of CSF1R, FLT3, KIT, RET, PDGFRα and PDGFRβ kinases. In certain embodiments, the compounds are useful as medical treatments, pharmaceutical compositions and methods of modulating the activity of one or more of wildtype FLT3, FLT3-ITD and tyrosine kinase domain mutants of FLT3.

In one embodiment, the compound provided herein is a compound of Formula I. In one embodiment, the compound provided herein is a pharmaceutically acceptable salt of the compound of Formula I. In one embodiment, the compound provided herein is a solvate of the compound of Formula I. In one embodiment, the compound provided herein is a hydrate of compound of Formula I. In one embodiment, the compound provided herein is a prodrug of the compound of Formula I. In one embodiment, the compound provided herein is a clathrate of the compound of Formula I.

In certain embodiments, provided herein are compounds having the Formula I:

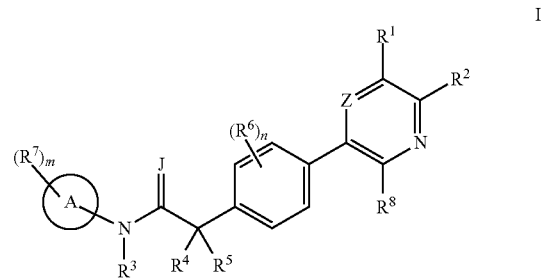

or a pharmaceutically acceptable salt, solvate, clathrate, hydrate, a single stereoisomer, a mixture of stereoisomers or a racemic mixture of stereoisomers thereof, wherein:

Ring A is azolyl;

J is O or S;

Z is N or $CR^9$;

$R^1$ and $R^2$, together with the carbon atoms to which they are attached, form a 6-membered aryl or a 5- or 6-membered heteroaryl, where the substituents, when present, are one, two, three or four Q groups, selected from (i) and (ii):

(i) each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, $-R''OR^{x'}$, $-R''OR'OR^{x'}$, $-R''OR'OC(O)R^{x'}$, $-R''OR'OC(O)N(R^y)(R^z)$, $-R''OR'N(R^y)(R^z)$, $-R''OR'N=N^+=N$, $-R''OR'N(R^y)C(O)R^{x+}$, $-R''OR'N(R^y)C(O)N(R^y)(R^z)$, $-R''OR'N(R^y)C(O)OR^{x''}$, $-R''OR'N(R^y)S(O)_tR^{x''}$, $-R''OR'S(O)_tR^{x''}$, $-R''OR'S(O)_tN(R^y)(R^z)$, $-R''OR'C(O)R^{x'}$, $-R''OR'C(=NOR'')R^{x'}$, $-R''C(O)N(R^y)(R^z)$, $-R''N(R^y)(R^z)$, $-R''N(R^y)R'OR^{x'}$, $-R''N(R^y)R'OC(O)R^{x'}$, $-R''N(R^y)R'OC(O)N(R^y)(R^z)$, $-R''N(R^y)R'N(R^y)(R^z)$, $-R''N(R^y)R'N(R^y)C(O)R^{x'}$, $-R''N(R^y)R'N(R^y)C(O)N(R^y)(R^z)$, $-R''N(R^y)R'N(R^y)C(O)OR^{x''}$, $-R''N(R^y)R'N(R^y)S(O)_tR^{x''}$, $-R''N(R^y)R'S(O)_tR^{x''}$, $-R''N(R^y)R'S(O)_tN(R^y)(R^z)$, $-R''N(R^y)R'C(O)R^{x'}$, $-R''N(R^y)R'C(O)N(R^y)(R^z)$, $-R''N(R^y)S(O)_tR^{x''}$, $-R''N(R^y)S(O)_tR'OR^{x'}$, $-R''N(R^y)C(O)R^{x'}$, $-R''N(R^y)C(O)R'OR^{x'}$, $-R''C(O)N(R^y)(R^z)$, $-R''C(O)N(R^y)N(R^y)(R^z)$, $-R''C(O)N(R^y)R'OR^{x'}$, $-R''C(O)N(R^y)R'OC(O)R^{x'}$, $-R''C(O)N(R^y)R'OC(O)N(R^y)(R^z)$, $-R''C(O)N(R^y)R'N(R^y)(R^z)$, $-R''C(O)N(R^y)R'N(R^y)C(O)R^{x'}$, $-R''C(O)N(R^y)R'N(R^y)C(O)N(R^y)(R^z)$, $-R''C(O)N(R^y)R'N(R^y)C(O)OR^{x'}$, $-R''C(O)N(R^y)R'N(R^y)S(O)_tR^{x''}$, $-R''C(O)N(R^y)R'S(O)_tR^{x''}$, $-R''C(O)N(R^y)R'S(O)_tN(R^y)(R^z)$, $-R''C(O)N(R^y)R'C(O)R^{x'}$, $-R''C(O)N(R^y)R'C(O)N(R^y)(R^z)$, $-R''C(O)OR^{x'}$, $-R''C(O)OR'OR^{x'}$, $-R''C(O)R^{x'}$, $-R''C(O)R'OR^{x'}$, $-R''S(O)_tR^{x''}$, $-R''S(O)_tR'OR^{x'}$, $-R''OP(O)(OH)_2$, and $-R''OS(O)_2(OH)$ where the alkyl, alkenyl, alkynyl, cycloalkyl, cycloalkylalkyl, aryl, aralkyl, heterocyclyl, heterocyclylalkyl, heteroaryl or heteroaralkyl is each independently optionally substituted with 1 to 5 groups each independently selected from halo, alkyl, haloalkyl and $-R''OR^{x'}$; and (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl is each independently optionally substituted with one or more deuterium atoms or 1 to 4 groups each independently selected from halo, alkyl, haloalkyl, cyano, $-C(O)N(R^y)(R^z)$, $-R''OR^{x'}$, $-R''OR'OR^{x'}$, $-R''N(R^y)(R^z)$, $-R''S(O)_tR^{x''}$, heteroaryl and heterocyclyl;

each t is independently 0, 1 or 2;

$R^3$ is hydrogen, alkyl or haloalkyl;

$R^4$ and $R^5$ are selected from (i) and (ii):

(i) $R^4$ and $R^5$ are each independently hydrogen, deuterium, halo, alkyl, alkenyl, alkynyl, haloalkyl, hydroxy, alkoxy or amino; and (ii) $R^4$ and $R^5$, together with the carbon atom to which they are attached, form cycloalkly or heterocylyl;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, $-R''OR^{x'}$, $-R''N(R^y)(R^z)$, $-R''C(O)N(R^y)(R^z)$ and $-R''S(O)_tR^{x''}$;

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, $-R''OR^{x'}$, $-R''OR'OR^{x'}$ and $-R''OR'N(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl; or two $R^7$s, together with the atoms to which they are attached, form a heterocyclyl optionally substituted with one or more deuterium atoms or 1 to 4 groups each independently selected from deuterium, halo, alkyl and haloalkyl;

$R^8$ and $R^9$ are each independently hydrogen, deuterium, halo, alkyl, haloalkyl, cyano, $-C(O)N(R^y)(R^z)$, $-R''OR^{x'}$, $-R''OR'OR^{x'}$, $-R''N(R^y)(R^z)$, $-R''S(O)_tR^{x''}$, $-N=N^+=N$, cycloalkyl, cycloalkylalkyl, aryl, aralkyl, heterocyclyl, heterocyclylalkyl, heteroaryl or heteroaralkyl;

each $R''$ is independently alkylene, alkenylene, alkynylene or a direct bond wherein the alkylene, alkenylene or alkynylene is optionally substituted with one or more deuterium atoms;

each $R^v$ is independently alkylene, alkenylene or alkynylene wherein the alkylene, alkenylene or alkynylene is optionally substituted with one or more deuterium atoms;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, $-R''OP(O)(OH)_2$, and $-R''OS(O)_2(OH)$;

each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, $-R''OP(O)(OH)_2$, and $-R''OS(O)_2(OH)$;

each $R^y$ and $R^z$ is independently selected from (i), (ii) and (iii) as follows:

(i) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(ii) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (iii) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino;

m is an integer from 0 to 4, and n is an integer from 0 to 4;

wherein the compound is selected such that when ring A is pyrazolyl, m is 1 and Z is CH, $R^7$ is not cyclopropyl.

Also provided are pharmaceutical compositions formulated for administration by an appropriate route and means containing effective concentrations of one or more of the compounds provided herein, or pharmaceutically acceptable salts, solvates, hydrates and prodrugs thereof, and optionally comprising at least one pharmaceutical carrier.

In one embodiment, the pharmaceutical compositions deliver amounts effective for the treatment, prevention, or amelioration of diseases or disorders that are modulated or otherwise affected by one or more of FLT3, CSF1R, KIT, RET, PDGFRα and PDGFRβ kinases, or one or more symptoms or causes thereof. Such diseases or disorders include without limitation, cancers, nonmalignant proliferation diseases, atherosclerosis, restenosis following vascular angioplasty, fibroproliferative disorders, inflammatory diseases or disorders related to immune dysfunction, infectious diseases, and/or diseases or disorders that can be treated, prevented or managed by modulating the various activities of kinases including dimerization, ligand binding and phosphotransferase activities or by modulating the expression of kinases, wherein such methods comprise administering to a subject, e.g., a human, in need of such treatment, prevention or management a therapeutically and prophylactically effective amount of a compound provided herein. Such diseases or disorders are further described herein.

In another embodiment, the pharmaceutical compositions deliver amounts effective for the treatment, prevention, or amelioration of diseases or disorders that are modulated or otherwise affected by one or more of FLT3 wild type, FLT3-ITD and tyrosine kinase domain mutants of FLT3, or otherwise effective for the treatment, prevention or amelioration of one or more symptoms or causes thereof. Such diseases or disorders include without limitation, hematological cancers including acute myeloid leukemia (AML), acute lymphoblastic leukemia (ALL) and myelodysplastic syndromes (MDS), that can be treated, prevented or managed by modulating the various activities of kinases including dimerization, ligand binding and phosphotransferase activities or by modulating the expression of kinases, wherein such methods comprise administering to a subject, e.g., a human, in need of such treatment, prevention or management a therapeutically and prophylactically effective amount of a compound provided herein. Such diseases or disorders are further described herein.

Also provided herein are combination therapies using one or more compounds or compositions provided herein, or pharmaceutically acceptable derivatives thereof, in combination with other pharmaceutically active agents for the treatment of the diseases and disorders described herein.

In one embodiment, such additional pharmaceutical agents include one or more chemotherapeutic agents, antiproliferative agents, anti-inflammatory agents, immunomodulatory agents or immunosuppressive agents.

The compounds or compositions provided herein, or pharmaceutically acceptable derivatives thereof, may be administered simultaneously with, prior to, or after administration of one or more of the above agents. Pharmaceutical compositions containing a compound provided herein and one or more of the above agents are also provided.

In certain embodiments, provided herein are methods of treating, preventing or ameliorating a disease or disorder that is modulated or otherwise affected by one or more of CSF1R, FLT3, KIT, RET, PDGFRα and PDGFRβ kinases including one or more of wild type and/or mutant CSF1R, FLT3, KIT, RET, PDGFRα and PDGFRβ kinases, or one or more symptoms or causes thereof. In certain embodiments, provided herein are methods of treating, preventing or ameliorating a disease or disorder that is modulated or otherwise affected by one or more of FLT3 wild type, FLT3-ITD and tyrosine kinase domain mutants of FLT3.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

DETAILED DESCRIPTION OF THE INVENTION

Provided herein are compounds of Formula I that have activity as modulators of one or more members of the class III receptor tyrosine kinase family. Provided herein also are compounds of Formula I that have activity as modulators of one or more of FLT3 wild type, FLT3-ITD and tyrosine kinase domain mutants of FLT3. Also provided are methods of treating, preventing or ameliorating diseases or disorders that are modulated by one or more members of the class III receptor tyrosine kinase family, or by one or more of FLT3 wild type, FLT3-ITD and tyrosine kinase domain mutants of FLT3, as well as pharmaceutical compositions and dosage forms useful for such methods. The methods and compositions are described in detail in the sections below.

A. Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

"Alkyl" as used herein and unless otherwise indicated, refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, examples of which include methyl, ethyl, n-propyl, 1-methylethyl (iso-propyl), n-butyl, n-pentyl, 1,1-dimethylethyl (t-butyl), and the like.

"Alkenyl" as used herein and unless otherwise indicated, refers to a straight or branched hydrocarbon chain group consisting solely of carbon and hydrogen atoms, containing at least one double bond, having from two to ten, two to eight or two to six carbon atoms, and which is attached to the rest of the molecule by a single bond or a double bond, examples of which include ethenyl, prop-1-enyl, but-1-enyl, pent-1-enyl, penta-1,4-dienyl, and the like.

"Alkynyl" as used herein and unless otherwise indicated, refers to a straight or branched hydrocarbon chain group consisting solely of carbon and hydrogen atoms, containing at least one triple bond, having from two to ten two to eight or two to six carbon atoms, and which is attached to the rest of the molecule by a single bond or a triple bond, examples of which include ethynyl, prop-1-ynyl, but-1-ynyl, pent-1-ynyl, pent-3-ynyl and the like.

"Alkylene" and "alkylene chain" as used herein and unless otherwise indicated, refer to a straight or branched divalent hydrocarbon chain consisting solely of carbon and hydrogen, containing no unsaturation and having from one to eight or one to six carbon atoms, examples of which include methylene, ethylene, propylene, s-butylene and the like. The alkylene chain may be attached to the rest of the molecule through the replacement of any two hydrogen atoms within the chain.

"Alkenylene" or "alkenylene chain" as used herein and unless otherwise indicated, refers to a straight or branched chain unsaturated divalent group consisting solely of carbon and hydrogen atoms, having from two to eight carbon atoms, wherein the unsaturation is present only as double bonds and wherein the double bond can exist between any two carbon atoms in the chain, examples of which include ethenylene, prop-1-enylene, but-2-enylene and the like. The alkenylene chain may be attached to the rest of the molecule through replacement of any two hydrogen atoms within the chain.

"Alkoxy" as used herein and unless otherwise indicated, refers to a monovalent group having the formula —OR''' wherein R''' is alkyl optionally substituted with one or more halogen atoms.

"Alkynylene" or "alkynylene chain" as used herein and unless otherwise indicated, refers to a straight or branched chain unsaturated divalent group consisting solely of carbon and hydrogen atoms, having from two to eight carbon atoms, wherein the unsaturation is present only as triple bonds and wherein the triple bond can exist between any two carbon atoms in the chain, examples of which include ethynylene, prop-1-ynylene, but-2-ynylene, pent-1-ynylene, pent-3-ynylene and the like. The alkynylene chain may be attached to the rest of the molecule through replacement of any two hydrogen atoms within the chain.

"Amino" as used herein and unless otherwise indicated, refers to a monovalent group having the formula —NR'R'' wherein R' and R'' are each independently hydrogen, alkyl or haloalkyl where the alkyl is optionally substituted with one or more halogen atoms.

"Aminoalkyl" as used herein and unless otherwise indicated, refers to a monovalent alkyl group substituted with an amino group.

"Aralkyl" as used herein and unless otherwise indicated, refers to a monovalent alkyl group substituted with aryl. In certain embodiments, both alkyl and aryl may be optionally substituted with one or more substituents.

"Aryl" as used herein and unless otherwise indicated, refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphthene, indene, indane, and fluorene.

"Azolyl" as used herein and unless otherwise indicated, refers to a 5-membered heteroaryl ring system containing at least one nitrogen atom. Exemplary azolyl rings include pyrrole, imidazole, pyrazole, thiazole, isothiazole, oxazole, isoxazole, thiadiazole, triazole and oxadiazole.

"Deuterium" as used herein and unless otherwise indicated, refers to the heavy isotope of hydrogen represented by the symbol D or $^2H$. As used herein, when a particular position in a compound is designated as having deuterium, it is understood that the compound is an isotopically enriched compound and the abundance of deuterium at that position in the compound is substantially greater than its natural abundance of 0.0156%.

"Cycloalkenyl" as used herein and unless otherwise indicated, refers to a stable monovalent monocyclic or bicyclic hydrocarbon group consisting solely of carbon and hydrogen atoms, having from three to ten carbon atoms, which is partially unsaturated. Examples of cycloalkenyl include cyclopropene, cyclobutylene, cyclopentene and cyclohexene.

"Cycloalkyl" as used herein and unless otherwise indicated, refers to refers to a stable monovalent monocyclic or bicyclic hydrocarbon group consisting solely of carbon and hydrogen atoms, having from three to ten carbon atoms which is saturated examples of which include cyclopropyl, cyclobutyl, cyclopentyl, cyclohexyl, decalinyl, norbornanyl, adamantyl, bicyclo[2.2.2]octane.

"Cycloalkylalkyl" as used herein and unless otherwise indicated, refers to a monovalent alkyl group substituted with cycloalkyl. In certain embodiments, both alkyl and cycloalkyl may be optionally substituted with one or more substituents.

"Enantiomerically pure" or "pure enantiomer" as used herein denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight more than 98.5% by weight, more than 99% by weight, more than 99.2% by weight, more than 99.5% by weight, more than 99.6% by weight, more than 99.7% by weight, more than 99.8% by weight or more than 99.9% by weight, of a single enantiomer to the exclusion of its corresponding non-superimposable mirror image.

"FLT3" (also known as CD135, stem cell tyrosine kinase (STK1) or fetal liver kinase 2 (FLK2)), refers to the kinase protein belonging to the class III receptor tyrosine kinase family and that plays a role in regulating hematopoiesis. The term "FLT3", "FLT3 kinase" or "FLT3 receptor" as used herein and unless otherwise indicated, encompasses polymorphic variants, alleles, mutants and fragments thereof. An illustrative polypeptide sequence for human FLT3 is available as UniProtKB accession no. P36888 for isoform 1 of human FLT3. Another representative human FLT3 polypeptide sequence is available as reference sequence NP_004110.2 in the NCBI polypeptide sequence database.

"FLT3 inhibitors" as used herein and unless otherwise indicated, are small molecules, peptides or antibodies that have inhibitory activity against FLT3 or that are used in FLT3-targeted therapy. FLT3 inhibitors include but are not limited to AC220 (quizartinib), CEP-701 (lestaurtinib), PKC-412 (midostaurin), MLN518, sorafenib (Nexavar®), sunitinib (Sutent®), SU-5416 (semaxinib), KW-2449, ponatinib (AP-24534), crenolanib (CP-868-596), ASP2215, IMC-EB10, CHIR-258, ABT-869, CHIR-258, LS104, AG1296, D-65476, GTP-14564, Ki23819, KRN383, FI-700, Ki11502, NVP-AST487 and VX-322.

"FLT3-ITD" or "FLT3-ITD mutation" refers to one or more insertion mutations of variable length and sequence in the juxtamembrane domain of FLT3 wherein the insertion is an internal tandem duplication (ITD), or alternatively, refers to the FLT3 comprising one or more of said mutations. When a FLT3-ITD mutation comprises more than one insertion mutation, the additional mutation or mutations may occur on the same FLT3 receptor, or the additional mutation or mutations may occur on a separate allele or occur in a different leukemic clone in the case where the mutation is polyclonal.

"Halo, "halogen" or "halide" as used herein and unless otherwise indicated, means F, Cl, Br or I.

"Haloalkyl" as used herein and unless otherwise indicated, refers to an alkyl group, in certain embodiments, $C_{1-6}$ alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl) cyclopropyl, 4,4-difluorocyclohexyl and 2,2,2-trifluoro-1,1-dimethyl-ethyl.

"Heteroaralkyl" as used herein and unless otherwise indicated, refers to a monovalent alkyl group substituted with heteroaryl. In certain embodiments, both alkyl and heteroaryl may be optionally substituted with one or more substituents.

"Heteroaryl" as used herein and unless otherwise indicated refers to a 5- to 15-membered monocyclic aromatic ring or a multicyclic aromatic ring system wherein the monocyclic ring or at least one ring of the multicyclic ring system contains one to five heteroatoms each independently selected from O, S, or N, with the remaining ring atoms being carbon atoms. Each ring of a heteroaryl group can contain up to two O atoms, up to two S atoms, and/or up to four N atoms, provided that the total number of heteroatoms in each ring is four or less and each ring contains at least one carbon atom. Examples of such heteroaryl groups include, but are not limited to, furanyl, pyrrolyl, thienyl, imidazolyl, pyrazolyl, oxazolyl, isoxazolyl, thiazolyl, isothiazolyl, triazolyl, oxadiazolyl, thiadiazolyl, tetrazolyl, pyrimidinyl, pyridinyl, pyridazinyl, pyrazinyl, benzimidazolyl, benzoisoxazolyl, benzopyranyl, benzothiadiazolyl, benzothiazolyl, pyridopyridyl, pyrrolopyridyl, quinolinyl, quinoxalinyl, quinazolinyl, naphthridinyl, 1,5-naphthyridinyl, 1,6-naphthridinyl, thieno[3,2-b]pyridinyl, thieno[2,3-b]pyridinyl, 1H-pyrazolo[4,3-b]pyridinyl, 1H-pyrrolo[2,3-b]pyridinyl, 5H-pyrrolo[2,3-b]pyrazinyl, 1H-imidazo[4,5-b]pyrazinyl, 1H-pyrazolo[3,4-b]pyridinyl, thiadiazolopyrimidyl, and thienopyridyl.

"Heterocyclyl", as used herein and unless otherwise indicated, refers to a 3- to 15-membered monocyclic non-aromatic ring or a multicyclic ring system that contains at least one non-aromatic ring, wherein the ring or at least one ring contains one to five heteroatoms each independently selected from O, S(O)$_t$ (where t is 0, 1 or 2), or N; and the remaining ring atoms being carbon atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Exemplary heterocylic radicals include but are not limited to, homopiperazinyl, morpholinyl, piperidinyl, piperazinyl, pyranyl, pyrrolidinyl, tetrahydrofuranyl, tetrahydropyranyl, ethylene oxide, oxetanyl, azetidinyl, quinuclidinyl, octahydroquinolizinyl, decahydroquinolizinyl, azabicyclo[3.2.1]octanyl, azabicyclo[2.2.2]octanyl, 6,7,8,9-tetrahydro-5H-pyrazino[2,3-b]indolyl, azabicyclo[3.1.1] heptanyl, azabicyclo[2.1.1]heptanyl, and azabicyclo[3.3.1] nonanyl.

"Heterocyclylalkyl" as used herein and unless otherwise indicated, refers to a monovalent alkyl group substituted with heterocyclyl. In certain embodiments, both alkyl and heterocyclyl may be optionally substituted with one or more substituents.

"Hydrate" as used herein and unless otherwise indicated, refers to a compound provided herein or a salt thereof, that further includes a stoichiometric or non-stoichiometeric amount of water bound by non-covalent intermolecular forces.

"$IC_{50}$" refers to an amount, concentration or dosage of a particular test compound that achieves a 50% inhibition of a maximal response, such as cell growth or proliferation measured via any of the in vitro or cell based assays described herein.

The term "isotopically enriched" refers to the percentage of incorporation of a less prevalent isotope (e.g., D for hydrogen) of an element at a given position in a molecule in the place of a more prevalent isotope (e.g., $^1H$ for hydrogen) of the element. As used herein, when an atom at a particular position in a molecule is designated as a particular less prevalent isotope, it is understood that the abundance of that isotope at that position is substantially greater than its natural abundance.

"Oxo" refers to the group =O attached to a carbon atom.

"Pharmaceutically acceptable salts" include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

"Solvate" as used herein and unless otherwise indicated, refers to a solvate formed from the association of one or more solvent molecules to a compound provided herein. The term "solvate" includes hydrates (e.g., mono-hydrate, dihydrate, trihydrate, tetrahydrate and the like).

"Substantially pure" as used herein means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

"Targeted therapy" as used herein and unless otherwise indicated, refers to a small molecule, peptide or antibody therapeutic, or the use thereof, that targets a specific biological molecule that plays a role in carcinogenesis or the growth or survival of cancer cells. In one embodiment, targeted therapy refers to tyrosine kinase inhibitors (TKI) which include but are not limited to imatinib (Gleevec®), sorafenib (Nexavar®), gefitinib (Iressa®), sunitinib (Sutent®) and quizartinib (AC220), or the use of thereof in cancer therapy. In certain embodiments, targeted therapy refers to receptor tyrosine kinase inhibitors (RTK). In certain embodiments, targeted therapy refers to class III receptor tyrosine kinase inhibitors. In certain embodiments, FLT3-targeted therapy refers to FLT3 inhibitors, or the use of FLT3 inhibitors in cancer therapy.

"Tyrosine kinase domain of FLT3" or "FLT3 tyrosine kinase domain" refers to the region of FLT3 possessing tyrosine kinase catalytic activity. In certain embodiments, the tyrosine kinase domain of FLT3 encompasses approximately amino acid position 604 to 958 of human FLT3 (sequence available as UniProtKB accession no. P36888 for isoform 1 of human FLT3 or NCBI reference sequence NP_004110.2). In yet another embodiment, the FLT3 tyrosine kinase domain comprises a first tyrosine kinase domain (TK1) encompassing approximately amino acid positions 604-710 and a second tyrosine kinase domain (TK2) encompassing approximately amino acid positions 781-958, of human FLT3 (UniProtKB accession no. P36888 for isoform 1 of human FLT3 or NCBI reference sequence NP_004110.2). In yet another embodiment, the FLT3 tyrosine kinase domain encompasses approximately amino acid position 610 to 943 of human FLT3 (UniProtKB accession no. P36888 for isoform 1 of human FLT3 or NCBI reference sequence NP_004110.2).

"Tyrosine kinase domain mutation of FLT3" or "FLT3 tyrosine kinase domain mutation" as used herein and unless otherwise indicated, refers to one or more mutations in the FLT3 tyrosine kinase domain, or alternatively, refers to FLT3 comprising one or more of said mutations (the protein itself referred to as "FLT3 tyrosine kinase domain mutant"). The mutation in the FLT3 tyrosine kinase domain may be an insertion, deletion or point mutation. In certain embodiments, the mutation in the FLT3 tyrosine kinase domain comprises at least one point mutation in the tyrosine kinase domain. In yet another embodiment, the point mutation in the FLT3 tyrosine kinase domain is at positions E608, N676, F691, C828, D835, D839, N841, Y842 or M855. In yet another embodiment, the point mutation in the FLT3 tyrosine kinase domain is selected from E608K, N676D, N676I, N676S, F691I, F691L, C828S, D835Y, D835V, D835H, D835F, D835E, D839G, D839H, N841C, Y842C, Y842D, Y842H, Y842N, Y842S and M855T. In yet another embodiment, "tyrosine kinase domain mutation of FLT3" refers to a point mutation at position F691, D835 or Y842 or refers to FLT3 comprising at least one point mutation at those positions. In yet another embodiment, "tyrosine kinase domain mutation of FLT3" refers to one or more point mutations selected from F691L, D835Y, D835V, D835H, D835F, D835E and Y842 or refers to FLT3 comprising at least one of said point mutations. In yet another embodiment, the tyrosine kinase domain mutation of FLT3 further comprises one or more additional mutations in the FLT3 juxtamembrane domain. In yet another embodiment, the tyrosine kinase domain mutation of FLT3 further comprises one or more additional FLT3-ITD mutations. In yet another embodiment, the tyrosine kinase domain mutation of FLT3 comprises one or more point mutations at position N676, F691, C828, D835, D839, N841, Y842 or M855 and which further comprises one or more additional FLT3-ITD mutations. In yet another embodiment, the tyrosine kinase domain mutation of FLT3 comprises one or more point mutations selected from N676D, N676I, N676S, F691I, F691L, C828S, D835Y, D835V, D835H, D835F, D835E, D839G, D839H, N841C, Y842C, Y842D, Y842H, Y842N, Y842S and M855T and which further comprises one or more additional FLT3-ITD mutations. When a FLT3 tyrosine kinase domain mutation comprises more than one point mutation, the additional point mutation or mutations may occur on the same FLT3 receptor, or the additional point mutation or mutations may occur on a separate allele or occur in a different leukemic clone in the case where the mutation is polyclonal.

The term "juxtamembrane region" or "juxtamembrane domain" of FLT3 refers to the region of FLT3 that connects the transmembrane helix to the tyrosine kinase domain. The juxtamembrane region or juxtamembrane domain of human FLT3 encompasses approximately amino acid residues 572-603 of human FLT3 (sequence available as UniProtKB accession no. P36888 for isoform 1 of human FLT3 or NCBI reference sequence NP_004110.2).

The term "wildtype" refers to the most prevalent gene or allele found in an organism. In certain embodiments, "wildtype" refers to the gene or allele that is free of mutations. In yet another embodiment, "wildtype FLT3" refers to the FLT3 gene or allele, inclusive of allelic variations and mutations except for the FLT3 tyrosine kinase domain mutation and the FLT3-ITD mutation.

Unless stated otherwise specifically described in the specification, it is understood that the substitution can occur on any atom of the alkyl, alkenyl, alkynyl, cycloalkyl, heterocyclyl, aryl or heteroaryl group.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure controls.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors (such as inhibitors of PI3K, JAK, BRAF, Akt, MEK, MAPK, Pim-1 and other FLT3 inhibitors), inhibitors of STAT activation and radiation treatment.

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

As used herein, the abbreviations for any protective groups, amino acids and other compounds are, unless indicated otherwise, in accord with their common usage, recognized abbreviations, or the IUPAC-IUB Commission on Biochemical Nomenclature (see, *Biochem.* 1972, 11:942-944).

B. Compounds

In certain embodiments, provided herein are compounds having the Formula I:

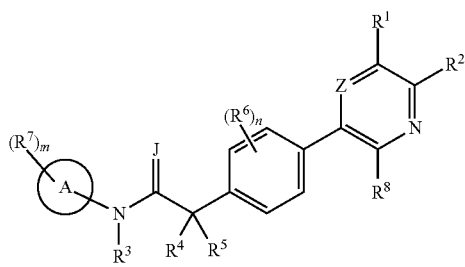

I or a pharmaceutically acceptable salt, solvate, clathrate, hydrate, a single stereoisomer, a mixture of stereoisomers or a racemic mixture of stereoisomers thereof, wherein:

Ring A is azolyl;
J is O or S;
Z is N or $CR^9$;
$R^1$ and $R^2$, together with the carbon atoms to which they are attached, form a 6-membered aryl or a 5- or 6-membered heteroaryl, where the substituents, when present, are one, two, three or four Q groups, selected from (i) and (ii):

(i) each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R″OR$^{x'}$, —R″OR′OR$^{x'}$, —R″OR′OC(O)R$^{x'}$, —R″OR′OC(O)N(R$^{y'}$)(R$^z$), —R″OR′N(R$^{y'}$)(R$^z$), —R″OR′N=N$^+$=N, —R″OR′N(R$^{y'}$)C(O)R$^{x+}$, —R″OR′N(R$^{y'}$)C(O)N(R$^{y'}$)(R$^z$), —R″OR′N(R$^{y'}$)C(O)OR$^{x'}$, —R″OR′N(R$^{y'}$)S(O)$_t$R$^{x''}$, —R″OR′S(O)$_t$R$^{x''}$, —R″OR′S(O)$_t$N(R$^{y'}$)(R$^z$), —R″OR′C(O)R$^{x'}$, —R″OR′C(O)N(R$^{y'}$)(R$^z$), —R″N(R$^{y'}$)(R$^z$), —R″N(R$^{y'}$)R′OR$^{x'}$, —R″N(R$^{y'}$)R′OC(O)R$^{x'}$, —R″N(R$^{y'}$)R′OC(O)N(R$^{y'}$)(R$^z$), —R″N(R$^{y'}$)R′N(R$^{y'}$)(R$^z$), —R″N(R$^{y'}$)R′N(R$^{y'}$)C(O)R$^{x'}$, —R″N(R$^{y'}$)R′N(R$^{y'}$)C(O)N(R$^{y'}$)(R$^z$), —R″N(R$^{y'}$)R′N(R$^{y'}$)C(O)OR$^{x'}$, —R″N(R$^{y'}$)R′N(R$^{y'}$)S(O)$_t$R$^{x'}$, —R″N(R$^{y'}$)R′S(O)$_t$R$^{x'}$, —R″N(R$^{y'}$)S(O)$_t$N(R$^{y'}$)(R$^z$), —R″N(R$^{y'}$)R′C(O)R$^{x'}$, —R″N(R$^{y'}$)R′C(O)N(R$^{y'}$)(R$^z$), —R″N(R$^{y'}$)S(O)$_t$R$^{x''}$, —R″N(R$^{y'}$)S(O)$_t$R′OR$^{x'}$, —R″N(R$^{y'}$)C(O)R$^{x'}$, —R″N(R$^{y'}$)C(O)R′OR$^{x'}$, —R″C(O)N(R$^{y'}$)(R$^z$), —R″C(O)N(R$^{y'}$)N(R$^{y'}$)(R$^z$), —R″C(O)N(R$^{y'}$)R′OR$^{x'}$, —R″C(O)N(R$^{y'}$)R′OC(O)R$^{x'}$, —R″C(O)N(R$^{y'}$)R′OC(O)N(R$^{y'}$)(R$^z$), —R″C(O)N(R$^{y'}$)R′N(R$^{y'}$)(R$^z$), —R″C(O)N(R$^{y'}$)R′N(R$^{y'}$)C(O)R$^{x'}$, —R″C(O)N(R$^{y'}$)R′N(R$^{y'}$)C(O)N(R$^{y'}$)(R$^z$), —R″C(O)N(R$^{y'}$)R′N(R$^{y'}$)C(O)OR$^{x''}$, —R″C(O)N(R$^{y'}$)R′N(R$^{y'}$)S(O)$_t$R$^{x''}$, —R″C(O)N(R$^{y'}$)R′S(O)$_t$R$^{x''}$, —R″C(O)N(R$^{y'}$)R′S(O)$_t$N(R$^{y'}$)(R$^z$), —R″C(O)N(R$^{y'}$)R′C(O)R$^{x'}$, —R″C(O)N(R$^{y'}$)R′C(O)N(R$^{y'}$)(R$^z$), —R″C(O)OR$^{x'}$, —R″C(O)OR′OR$^{x'}$, —R″C(O)R$^{x'}$, —R″C(O)R′OR$^{x'}$, —R″S(O)$_t$R$^{x'}$, —R″S(O)$_t$R′OR$^{x'}$, —R″OP(O)(OH)$_2$, and —R″OS(O)$_2$(OH), where the alkyl, alkenyl, alkynyl, cycloalkyl, cycloalkylalkyl, aryl, aralkyl, heterocyclyl, heterocyclylalkyl, heteroaryl or heteroaralkyl is each independently optionally substituted with 1 to 5 groups each independently selected from halo, alkyl, haloalkyl and —R″OR$^{x'}$; and (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl is each independently optionally substituted with one or more deuterium atoms or 1 to 4 groups each independently selected from halo, alkyl, haloalkyl, cyano, —C(O)N(R$^{y'}$)(R$^z$), —R″OR$^{x'}$, —R″OR′OR$^{x'}$, —R″N(R$^{y'}$)(R$^z$), —R″S(O)$_t$R$^{x''}$, heteroaryl and heterocyclyl;

each t is independently 0, 1 or 2;
$R^3$ is hydrogen, alkyl or haloalkyl;
$R^4$ and $R^5$ are each independently hydrogen, deuterium, halo, alkyl, alkenyl, alkynyl, haloalkyl, hydroxy, alkoxy or amino;
each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —R″OR$^{x'}$, —R″N(R$^{y'}$)(R$^z$) and —R″S(O)$_t$R$^{x''}$;
each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R″OR$^{x'}$, —R″OR′OR$^{x'}$ and —R″OR′N(R$^{y'}$)(R$^z$) where the alkyl, alkenyl, alkynyl, cycloalkyl, cycloalkylalkyl, aryl, aralkyl, heterocyclyl, heterocyclylalkyl, heteroaryl, heteroaralkyl;

$R^8$ and $R^9$ are each independently hydrogen, deuterium, halo, alkyl, haloalkyl, cyano, —C(O)N($R^y$)($R^z$), —$R^uOR^{x'}$, —$R^uOR'OR^{x'}$, —$R^uN(R^y)(R^z)$, —$R^uS(O)_tR^{x''}$, —N=N$^+$=N, cycloalkyl, cycloalkylalkyl, aryl, aralkyl, heterocyclyl, heterocyclylalkyl, heteroaryl or heteroaralkyl;

each $R^u$ is independently alkylene, alkenylene, alkynylene or a direct bond wherein the alkylene, alkenylene or alkynylene is optionally substituted with one or more deuterium atoms;

each $R^v$ is independently alkylene, alkenylene or alkynylene wherein the alkylene, alkenylene or alkynylene is optionally substituted with one or more deuterium atoms;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —$R^uOP(O)(OH)_2$, and —$R^uOS(O)_2(OH)$;

each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, —$R^uOP(O)(OH)_2$, and —$R^uOS(O)_2(OH)$;

each $R^y$ and $R^z$ is independently selected from (i), (ii) and (iii) as follows:
 (i) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;
 (ii) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and
 (iii) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino;

m is an integer from 0 to 4, and
n is an integer from 0 to 4;

wherein the compound is selected such that when ring A is pyrazolyl, m is 1 and Z is CH, $R^7$ is not cyclopropyl.

In certain embodiments, provided herein are compounds having the Formula I:

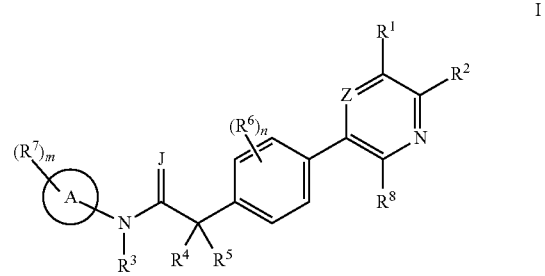

or a pharmaceutically acceptable salt, solvate, clathrate, hydrate, a single stereoisomer, a mixture of stereoisomers or a racemic mixture of stereoisomers thereof, wherein:
 Ring A is azolyl;
 J is O or S;
 Z is N or $CR^9$;
 $R^1$ and $R^2$, together with the carbon atoms to which they are attached, form an aryl or heteroaryl, where the substituents, when present, are one, two, three or four Q groups, selected from (i) and (ii):
 (i) each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^x$, —$R^uOR'OR^x$, —$R^uOR'N(R^y)(R^z)$, —$R^uN(R^y)(R^z)$, —N($R^y$)$R^uOR$, —N($R^y$)$R^vS(O)_tR^x$, —N($R^y$)$S(O)_tR^x$, —N($R^y$)$R^vN(R^y)(R^z)$, —C(O)N($R^y$)($R^z$), —C(O)O$R^x$, —C(O)N($R^y$)$R^vOR^x$, —C(O)N($R^y$)$R^vN(R^y)(R^z)$, —C(O)N($R^y$)$R^vS(O)_tR^x$, —C(O)N($R^y$)$R^vN(R^y)S(O)_tR^x$, —C(O)$R^x$ and —$R^uS(O)_tR^x$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —$R^uOR^x$; and
 (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl are optionally substituted with 1 to 4 groups each independently selected from deuterium, halo, alkyl, haloalkyl, cyano, —C(O)N($R^y$)($R^z$), —$R^uOR^x$, —$R^uOR'OR^x$, —$R^uN(R^y)(R^z)$, —$R^uS(O)_tR^x$, heteroaryl and heterocyclyl;
 each t is independently 0, 1 or 2;
 $R^3$ is hydrogen, alkyl or haloalkyl;
 $R^4$ and $R^5$ are each independently hydrogen, deuterium, halo, alkyl, alkenyl, alkynyl, haloalkyl, hydroxy, alkoxy or amino;
 each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R^uOR^x$ and —$R^uN(R^y)(R^z)$;
 each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^x$, —$R^uOR'OR^x$ and —$R^uOR'N(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^x$ of —$R''OR^x$ and —$R''OR^vOR^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —$R''N(R^y)(R^z)$;

$R^8$ is hydrogen, deuterium, halo, alkyl, haloalkyl, cyano, —C(O)N($R^y$)($R^z$), —$R''OR^x$, —$R''OR^vOR^x$, —$R''N(R^y)(R^z)$, —$R''S(O)_rR^x$, heteroaryl and heterocyclyl;

$R^9$ is hydrogen, deuterium, halo, alkyl, haloalkyl, cyano, —C(O)N($R^y$)($R^z$), —$R''OR^x$, —$R''OR^vOR^x$, —$R''N(R^y)(R^z)$, —$R''S(O)_rR^x$, heteroaryl and heterocyclyl;

each $R^u$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl;

each $R^y$ and $R^z$ is independently selected from (i) and (ii) as follows:
(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and
(ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups;

m is an integer from 0 to 4, and
n is an integer from 0 to 4;
wherein the compound is selected such that when ring A is pyrazolyl, m is 1 and Z is CH, $R^7$ is not cyclopropyl.

In certain embodiments, provided herein are compounds of Formula I or a pharmaceutically acceptable salt, solvate, clathrate, hydrate, a single stereoisomer, a mixture of stereoisomers or a racemic mixture of stereoisomers thereof, wherein Ring A is optionally substituted isoxazolyl.

In certain embodiments, provided herein are compounds of Formula I or a pharmaceutically acceptable salt, solvate, clathrate, hydrate, a single stereoisomer, a mixture of stereoisomers or a racemic mixture of stereoisomers thereof, wherein: substituted Ring A is

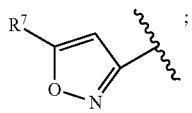

$R^7$ is selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R''OR^x$, —$R''OR^vOR^x$ and —$R''OR^vN(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^x$ of —$R''OR^x$ and —$R''OR^vOR^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —$R''N(R^y)(R^z)$;

each $R^u$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl; and each $R^y$ and $R^z$ is independently selected from (i) and (ii) as follows:
(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and
(ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups.

In certain embodiments, provided herein are compounds of Formula I wherein substituted Ring A is:

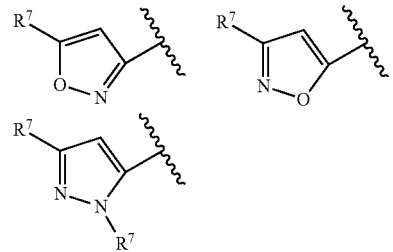

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R''OR^x$, —$R''OR^vOR^x$ and —$R''OR^vN(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^x$ of —$R''OR^x$ and —$R''OR^vOR^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —$R''N(R^y)(R^z)$;
each $R^u$ is independently alkylene, alkenylene, alkynylene or a direct bond; each $R^v$ is independently alkylene, alkenylene or alkynylene; each $R^x$ is independently hydrogen, alkyl, haloalkyl, alkenyl, alkynyl or heterocyclyl; and each $R^y$ and $R^z$ is independently selected from (i) and (ii) as follows:

$R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and $R^y$ and $R^z$, together with the nitrogen atom to which they are attached, form a heterocyclyl optionally substituted with one, two, three, four or five halo, haloalkyl, alkyl, alkenyl, alkynyl or oxo groups.

In certain embodiments, provided herein are compounds of Formula I wherein $R^7$ is selected from —CH(CH$_3$)$_2$, —C(CH$_3$)$_2$CH$_2$OH, —CF$_3$, —C(CH$_3$)$_3$, —CF$_2$(CH$_3$), —C(CH$_3$)(CH$_2$F)$_2$, —C(CH$_3$)$_2$CF$_3$, —C(CH$_3$)$_2$CH$_2$F, —CF(CH$_3$)$_2$, cyclopropyl, cyclobutyl, cyclopentyl, cyclohexyl,

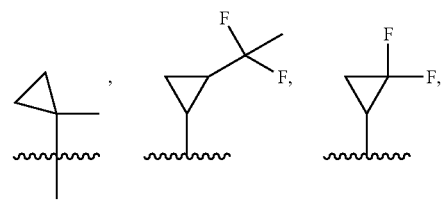

-continued

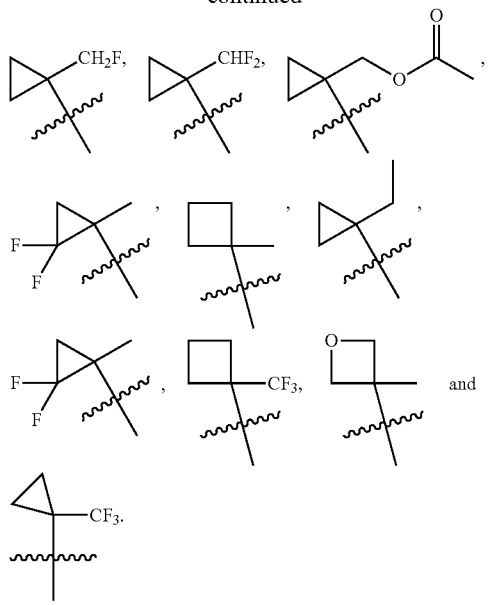

In certain embodiments, provided herein are compounds of Formula I wherein wherein $R^4$ and $R^5$ are both hydrogen or halo. In yet another embodiment, provided herein are compounds of Formula I wherein $R^4$ and $R^5$ are both hydrogen.

In certain embodiments, provided herein are compounds of Formula I wherein $R^1$ and $R^2$, together with the carbon atoms to which they are attached, form an aryl or heteroaryl, where the substituents, when present, are one, two, three or four Q groups, each independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R''OR^x$, —$R''OR'OR^x$, —$R''OR'N(R^y)(R^z)$, —$R''N(R^y)(R^z)$, —$N(R^y)R'OR$, —$N(R^y)R'S(O)_tR^x$, —$N(R^y)S(O)_tR^x$, —$N(R^y)R'N(R^y)(R^z)$, —$C(O)N(R^y)(R^z)$, —$C(O)OR^x$, —$C(O)N(R^y)R'OR^x$, —$C(O)N(R^y)R'N(R^y)(R^z)$, —$C(O)N(R^y)R'S(O)_tR^x$, —$C(O)N(R^y)R'N(R^y)S(O)_tR^x$, —$C(O)R^x$ and —$R''S(O)_tR^x$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —$R''OR^x$; and the other variables are as described elsewhere herein.

In certain embodiments, provided herein are compounds having the Formula I:

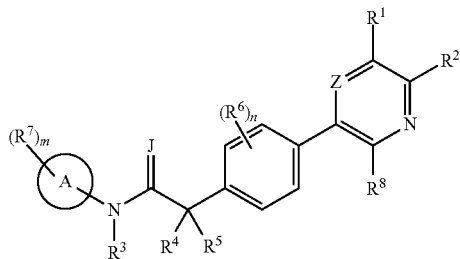

I or a pharmaceutically acceptable salt, solvate, clathrate, hydrate, a single stereoisomer, a mixture of stereoisomers or a racemic mixture of stereoisomers thereof, wherein:

J is O or S;
Z is N or $CR^9$;
$R^1$ and $R^2$, together with the carbon atoms to which they are attached, form a 6-membered aryl or a 5- or 6-membered heteroaryl, where the substituents, when present, are one, two, three or four Q groups, selected from (i) and (ii):

(i) each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R''OR^{x'}$, —$R''OR'OR^{x'}$, —$R''OR'OC(O)R^{x'}$, —$R''OR'OC(O)N(R^y)(R^z)$, —$R''OR'N(R^y)(R^z)$, —$R''OR'N=N^+=N$, —$R''OR'N(R^y)C(O)R^{x+}$, —$R''OR'N(R^y)C(O)N(R^y)(R^z)$, —$R''OR'S(O)_tR^{x''}$, —$R''OR'S(O)_tN(R^y)(R^z)$, —$R''OR'C(O)R^{x'}$, —$R''OR'C(O)N(R^y)(R^z)$, —$R''N(R^y)(R^z)$, —$R''N(R^y)R'OR^{x'}$, —$R''N(R^y)R'OC(O)R^{x'}$, —$R''N(R^y)R'OC(O)N(R^y)(R^z)$, —$R''N(R^y)R'N(R^y)(R^z)$, —$R''N(R^y)R'N(R^y)C(O)R^{x'}$, —$R''N(R^y)R'N(R^y)C(O)N(R^y)(R^z)$, —$R''N(R^y)R'S(O)_tR^{x''}$, —$R''N(R^y)S(O)_tR^{x''}$, —$R''N(R^y)S(O)_tR'OR^{x'}$, —$R''N(R^y)C(O)R^{x'}$, —$R''N(R^y)C(O)R'OR^{x'}$, —$R''C(O)N(R^y)(R^z)$, —$R''C(O)N(R^y)R'OR^{x'}$, —$R''C(O)N(R^y)R'N(R^y)(R^z)$, —$R''C(O)N(R^y)R'N(R^y)S(O)_tR^{x''}$, —$R''C(O)N(R^y)R'S(O)_tR^{x'}$, —$R''C(O)N(R^y)R'S(O)_tN(R^y)(R^z)$, —$R''C(O)OR^{x'}$, and —$R''S(O)_tR^{x''}$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —$R''OR^{x'}$; and (ii) two adjacent Q groups, together with the atoms to which they are attached may form cycloalkyl, cycloalkenyl or heterocyclyl, where the cycloalkyl, cycloalkenyl or heterocycyl are optionally substituted with one or more deuterium atoms or 1 to 4 groups each independently selected from deuterium, halo, alkyl, haloalkyl, cyano, —$C(O)N(R^y)(R^z)$, —$R''OR^{x'}$, —$R''OR'OR^{x'}$, —$R''N(R^y)(R^z)$, —$R''S(O)_tR^{x'}$, heteroaryl and heterocyclyl;

each t is independently 0, 1 or 2;
$R^3$ is hydrogen, alkyl or haloalkyl;
$R^4$ and $R^5$ are each independently hydrogen, deuterium, halo, alkyl, or haloalkyl; each $R^6$ is independently selected from deuterium, halo, cyano, alkyl or haloalkyl;

each $R^7$ is independently selected from deuterium, halo, alkyl, alkenyl, alkynyl, haloalkyl, cycloalkyl, aryl, heterocyclyl, heteroaryl, —$R''OR^{x'}$ or —$R''OR'OR^{x'}$; where the alkyl, alkenyl, alkynyl, cycloalkyl, aryl, heterocyclyl, heteroaryl and the $R^{x'}$ of —$R''OR^{x'}$ and —$R''OR'OR^{x'}$ are optionally substituted with 1 to 9 groups each independently selected from deuterium, halo, cyano, alkyl, alkenyl, alkynyl, haloalkyl, cyanoalkyl, hydroxyalkyl, cycloalkyl, heterocyclyl, aryl, heteroaryl, hydroxy, alkoxy, and —$R''N(R^y)(R^z)$; or two $R^7$s, together with the atoms to which they are attached, form a heterocyclyl optionally substituted with 1 to 4 groups each independently selected from deuterium, halo, alkyl and haloalkyl;

$R^8$ and $R^9$ are each independently hydrogen, deuterium, halo, alkyl, haloalkyl, cyano, —$C(O)N(R^y)(R^z)$, —$R''OR^{x'}$, —$R''OR'OR^{x'}$, —$R''N(R^y)(R^z)$, —$R''S(O)_tR^{x''}$, —$N=N^+=N$, cycloalkyl, cycloalkylalkyl, aryl, aralkyl, heterocyclyl, heterocyclylalkyl, heteroaryl or heteroaralkyl;

each $R''$ is independently alkylene, alkenylene, alkynylene or a direct bond;

each $R^v$ is independently alkylene, alkenylene or alkynylene;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where each alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, is independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —$R^u$OP(O)(OH)$_2$, and —$R^u$OS(O)$_2$(OH);

each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where each alkyl, haloalkyl, cyanoalkyl, alkenyl, alkynyl cycloalkyl, cycloalkylalkyl, heterocyclyl, heterocyclylalkyl, aryl, aralkyl, heteroaryl, or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, —$R^u$OP(O)(OH)$_2$, and —$R^u$OS(O)$_2$(OH);

each $R^y$ and $R^z$ is independently selected from (i), (ii) and (iii) as follows:
(i) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is optionally substituted with one or more deuterium atoms and where the cycloalkyl, cycloalkylalkyl, heterocyclyl, heterocyclylalkyl, aryl, aralkyl, heteroaryl or heteroaralkyl are optionally substituted with one or more deuterium atoms or 1 to 5 groups each independently selected from halo, cyano, alkyl, haloalkyl, hydroxy, alkoxy, haloalkoxy and amino;
(ii) $R^y$ and $R^z$, together with the nitrogen atom to which they are attached, form a heterocyclyl optionally substituted with one or more deuterium atoms or 1-5 groups each independently selected from halo, cyano, haloalkyl, alkyl, alkenyl, alkynyl, hydroxy, alkoxy, haloalkoxy, amino, and oxo; and
(iii) $R^y$ and $R^z$, together with the nitrogen atom to which they are attached, form a heteroaryl optionally substituted with one or more deuterium atoms or 1-5 groups each independently selected from halo, cyano, haloalkyl, alkyl, alkenyl, alkynyl, hydroxy, alkoxy, haloalkoxy and amino;

m is an integer from 0 to 4, and n is an integer from 0 to 4;

wherein the compound is selected such that when ring A is pyrazolyl, m is 1 and Z is CH, $R^7$ is not cyclopropyl.

In certain embodiments, provided herein are compounds having the Formula I:

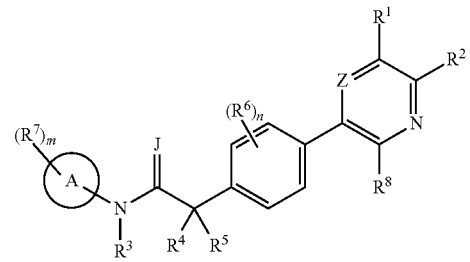

or a pharmaceutically acceptable salt, solvate, clathrate, hydrate, a single stereoisomer, a mixture of stereoisomers or a racemic mixture of stereoisomers thereof, wherein Ring A is azolyl;

J is O or S;

Z is N or $CR^9$;

$R^1$ and $R^2$, together with the carbon atoms to which they are attached, form an aryl or heteroaryl, where the substituents, when present, are one, two, three or four Q groups, selected from (i) and (ii):
(i) each Q is each independently selected from deuterium, halo, cyano, alkyl, alkenyl, alkynyl, haloalkyl, —$R^u$OR$^x$, —$R^u$OR'OR$^x$, —$R^u$OR'N(R$^y$)(R$^z$), —$R^u$N(R$^y$)(R$^z$), —N(R$^y$)R'OR, —N(R$^y$)R'S(O)$_t$R$^x$, —N(R$^y$)S(O)$_t$R$^x$, —N(R$^y$)R'N(R$^y$)(R$^z$), —C(O)N(R$^y$)(R$^z$), —C(O)OR$^x$, —C(O)N(R$^y$)R'OR$^x$, —C(O)N(R$^y$)R'N(R$^y$)(R$^z$), —C(O)N(R$^y$)R'S(O)$_t$R$^x$ and —C(O)R$^x$; and
(ii) two adjacent Q groups, together with the atoms to which they are attached may form cycloalkenyl or heterocyclyl where the cycloalkenyl or heterocyclyl is optionally substituted with one, two or three groups selected from —$R^u$OR$^x$ and —$R^u$N(R$^y$)(R$^z$);

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R^u$OR$^x$ and —$R^u$N(R$^y$)(R$^z$);

each $R^7$ is independently selected from deuterium, halo, alkyl, alkenyl, alkynyl, haloalkyl, cycloalkyl, cycloalkylalkyl, —$R^u$OR$^x$, where the alkyl, alkenyl, alkynyl, cycloalkyl and cycloalkylalkyl are optionally substituted with 1 to 9 groups each independently selected from deuterium, halo, alkyl, hydroxy, and alkoxy;

$R^8$ is hydrogen, deuterium, halo, alkyl, haloalkyl, or —$R^u$N(R$^y$)(R$^z$);

$R^9$ is hydrogen, deuterium, halo, alkyl, haloalkyl, or —$R^u$N(R$^y$)(R$^z$);

each $R^u$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl;

each $R^y$ and $R^z$ is independently selected from (i) and (ii) as follows:
(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups;

m is an integer from 0 to 4, and n is an integer from 0 to 4;

wherein the compound is selected such that when ring A is pyrazolyl, m is 1 and Z is CH, $R^7$ is not cyclopropyl.

In one embodiment, provided herein are compounds of Formula I wherein $R^1$ and $R^2$, together with the carbon atoms to which they are attached, form an aryl or heteroaryl, where the substituents, when present, are one, two, three or four Q groups, each independently selected from halo, cyano, alkyl, —$R^uOR^x$, —$R^uOR^vOR^x$, —$R^uN(R^y)(R^z)$, —C(O)N($R^y$)($R^z$), —C(O)O$R^x$, —C(O)N($R^y$)$R^vOR^x$, —C(O)N($R^y$)$R^vN(R^y)(R^z)$, —C(O)N($R^y$)$R^vS(O)_tR^x$ and —C(O)$R^x$;

each $R^u$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl; and each $R^y$ and $R^z$ is independently selected from (i) and (ii) as follows:

(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups.

In certain embodiments, provided herein are compounds of Formula I, wherein $R^1$ and $R^2$, together with the carbon atoms to which they are attached, form an optionally substituted 5- or 6-membered nitrogen-containing heteroaryl.

In certain embodiments, provided herein are compounds of Formula I, or a pharmaceutically acceptable salt, solvate, clathrate, hydrate, a single stereoisomer, a mixture of stereoisomers or a racemic mixture of stereoisomers thereof, wherein:

Ring A is azolyl;

J is O or S;

Z is N or $CR^9$;

$R^1$ and $R^2$, together with the carbon atoms to which they are attached, form a 5-membered nitrogen-containing heteroaryl, where the substituents, when present, are one, two, three or four Q groups, selected from (i) and (ii):

(i) each Q is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^x$, —$R^uOR^vOR^x$, —$R^uOR^vN(R^y)(R^z)$, —$R^uN(R^y)(R^z)$, —N($R^y$)$R^vOR$, —N($R^y$)$R^vS(O)_tR^x$, —N($R^y$)S(O)$_tR^x$, —N($R^y$)$R^vN(R^y)(R^z)$, —C(O)N($R^y$)($R^z$), —C(O)O$R^x$, —C(O)N($R^y$)$R^vOR^x$, —C(O)N($R^y$)$R^vN(R^y)(R^z)$, —C(O)N($R^y$)$R^vS(O)_tR^x$, —C(O)N($R^y$)$R^vN(R^y)S(O)_tR^x$, —C(O)$R^x$ and —$R^uS(O)_tR^x$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —$R^uOR^x$; and (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl are optionally substituted with 1 to 4 groups each independently selected from deuterium, halo, alkyl, haloalkyl, cyano, —C(O)N($R^y$)($R^z$), —$R^uOR^x$, —$R^uOR^vOR^x$, —$R^uN(R^y)(R^z)$, —$R^uS(O)_tR^x$, heteroaryl and heterocyclyl;

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R^uOR^x$ and —$R^uN(R^y)(R^z)$;

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^x$, —$R^uOR^vOR^x$ and —$R^uOR^vN(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^x$ of —$R^uOR^x$ and —$R^uOR^vOR^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —$R^uN(R^y)(R^z)$;

$R^8$ is hydrogen, deuterium, halo, alkyl, haloalkyl, cyano, —C(O)N($R^y$)($R^z$), —$R^uOR^x$, —$R^uOR^vOR^x$, —$R^uN(R^y)(R^z)$, —$R^uS(O)_tR^x$, heteroaryl or heterocyclyl;

$R^9$ is hydrogen, deuterium, halo, alkyl, haloalkyl, cyano, —C(O)N($R^y$)($R^z$), —$R^uOR^x$, —$R^uOR^vOR^x$, —$R^uN(R^y)(R^z)$, —$R^uS(O)_tR^x$, heteroaryl or heterocyclyl;

each $R^u$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl;

each $R^y$ and $R^z$ is independently selected from (i) and (ii) as follows:

(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups;

m is an integer from 0 to 4, and n is an integer from 0 to 4.

In certain embodiments, provided herein are compounds having the Formula I wherein substituted Ring A is:

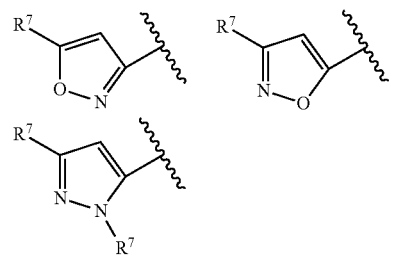

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R"OR$^{x'}$, —R"OR$^v$OR$^{x'}$ and —R"OR$^v$N(R$^y$)(R$^z$) where the alkyl, alkenyl, alkynyl, cycloalkyl, cycloalkylalkyl, aryl, aralkyl, heterocyclyl, heterocyclylalkyl, heteroaryl, heteroaralkyl and the R$^{x'}$ of —R"OR$^{x'}$ and —R"OR$^v$OR$^{x'}$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —R"N(R$^y$)(R$^z$);

each R$^u$ is independently alkylene, alkenylene, alkynylene or a direct bond wherein the alkylene, alkenylene or alkynylene is optionally substituted with one or more deuterium atoms;

each R$^v$ is independently alkylene, alkenylene or alkynylene wherein the alkylene, alkenylene or alkynylene is optionally substituted with one or more deuterium atoms;

each R$^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —R"OP(O)(OH)$_2$, and —R"OS(O)$_2$(OH);

each R$^y$ and R$^z$ is independently selected from (i), (ii) and (iii) as follows:

(i) each R$^y$ and R$^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(ii) R$^y$ and R$^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (iii) R$^y$ and R$^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino.

In certain embodiments, provided herein are compounds having the Formula I wherein ring A is isoxazolyl substituted with 0 to 2 R$^7$ groups; Z is N and the other variables are as stated for Formula I. In certain embodiments, provided herein are compounds having the Formula I wherein ring A is

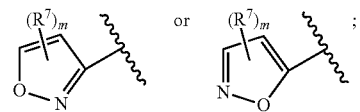

m is an integer from 0 to 2; Z is N and the other variables are as stated for Formula I.

In certain embodiments, provided herein are compounds having the Formula I wherein A is

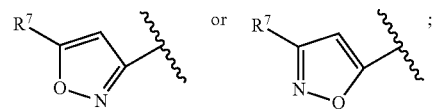

Z is N and the other variables are as stated for Formula I.

In certain embodiments, provided herein are compounds having the Formula I wherein Z is N.

In certain embodiments, provided herein are compounds having the Formula I wherein one, two, three or four Q groups, selected from (i) and (ii):

(i) each one, two, three or four Q groups is each independently selected from deuterium, halo, cyano, alkyl, alkenyl, alkynyl, haloalkyl, —R"OR$^x$, —R"OR$^v$OR$^x$, —R"OR$^v$N(R$^y$)(R$^z$), —R"N(R$^y$)(R$^z$), —N(R$^y$)R$^v$OR, —N(R$^y$)R$^v$S(O)$_t$R$^x$, —N(R$^y$)S(O)$_t$R$^x$, —N(R$^y$)R$^v$N(R$^y$)(R$^z$), —C(O)N(R$^y$)(R$^z$), —C(O)OR$^x$, —C(O)N(R$^y$)R$^v$OR$^x$, —C(O)N(R$^y$)R$^v$N(R$^y$)(R$^z$), —C(O)N(R$^y$)R$^v$S(O)$_t$R$^x$ and —C(O)R$^x$ (ii) two adjacent Q groups, together with the atoms to which they are attached may form cycloalkenyl or heterocyclyl where the cycloalkenyl or heterocyclyl is optionally substituted with one, two or three groups selected from —R"OR$^x$ and —R"N(R$^y$)(R$^z$);

each t is independently 0, 1 or 2;

each R$^u$ is independently alkylene, alkenylene, alkynylene or a direct bond;

each R$^v$ is independently alkylene, alkenylene or alkynylene;

each R$^x$ is independently hydrogen, alkyl, haloalkyl, alkenyl, alkynyl or heterocyclyl; and each R$^y$ and R$^z$ is independently selected from (i) and (ii) as follows:

(i) R$^y$ and R$^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) R$^y$ and R$^z$, together with the nitrogen atom to which they are attached, form a heterocyclyl optionally substituted with one, two, three, four or five halo, haloalkyl, alkyl, alkenyl, alkynyl or oxo groups.

In certain embodiments, provided herein are compounds of Formula I wherein R$^8$ is hydrogen. In certain embodiments, provided herein are compounds of Formula I wherein R$^8$ and R$^9$ are both hydrogen.

In certain embodiments, provided herein are compounds having the Formula II:

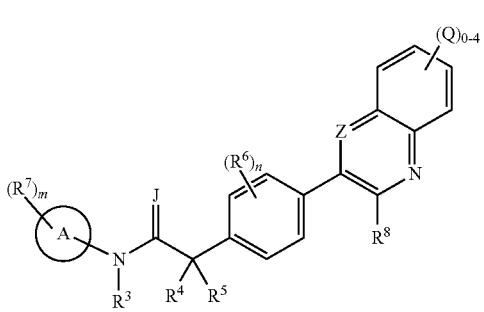

or a pharmaceutically acceptable salt, solvate, clathrate, hydrate, a single stereoisomer, a mixture of stereoisomers or a racemic mixture of stereoisomers thereof, wherein:

Ring A is azolyl;
J is O or S;
Z is N or $CR^9$;
each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^{x'}$, —$R^uOR'OR^{x'}$, —$R^uOR'OC(O)R^{x'}$, —$R^uOR'OC(O)N(R^y)(R^z)$, —$R^uOR'N(R^y)(R^z)$, —$R^uOR'N=N^+=N$, —$R^uOR'N(R^y)C(O)R^{x'}$, —$R^uOR'N(R^y)C(O)N(R^y)(R^z)$, —$R^uOR'N(R^y)C(O)OR^{x''}$, —$R^uOR'N(R^y)S(O)_tR^{x''}$, —$R^uOR'S(O)_tR^{x''}$, —$R^uOR'S(O)_tN(R^y)(R^z)$, —$R^uOR'C(O)R^{x'}$, —$R^uOR'C(=NOR^x)R^{x'}$, —$R^uOR'C(O)N(R^y)(R^z)$, —$R^uN(R^y)(R^z)$, —$R^uN(R^y)R'OR^{x'}$, —$R^uN(R^y)R'OC(O)R^{x'}$, —$R^uN(R^y)R'OC(O)N(R^y)(R^z)$, —$R^uN(R^y)R'N(R^y)(R^z)$, —$R^uN(R^y)R'N(R^y)C(O)R^{x'}$, —$R^uN(R^y)R'N(R^y)C(O)N(R^y)(R^z)$, —$R^uN(R^y)R'N(R^y)C(O)R^{x'}$, —$R^uN(R^y)R'N(R^y)S(O)_tR^{x'}$, —$R^uN(R^y)R'S(O)_tR^{x''}$, —$R^uN(R^y)R'S(O)_tN(R^y)(R^z)$, —$R^uN(R^y)R'C(O)R^{x'}$, —$R^uN(R^y)R'C(O)N(R^y)(R^z)$—$R^uN(R^y)S(O)_tR^{x''}$, —$R^uN(R^y)S(O)_tR'OR^{x'}$, —$R^uN(R^y)C(O)R^{x'}$, —$R^uN(R^y)C(O)R'OR^{x''}$, —$R^uC(O)N(R^y)(R^z)$, —$R^uC(O)N(R^y)N(R^y)(R^z)$, —$R^uC(O)N(R^y)R'OR^{x'}$, —$R^uC(O)N(R^y)R'OC(O)R^{x'}$, —$R^uC(O)N(R^y)R'OC(O)N(R^y)(R^z)$, —$R^uC(O)N(R^y)R'N(R^y)(R^z)$, —$R^uC(O)N(R^y)R'N(R^y)C(O)R^{x'}$, —$R^uC(O)N(R^y)R'N(R^y)C(O)N(R^y)(R^z)$, —$R^uC(O)N(R^y)R'N(R^y)C(O)OR^{x''}$, —$R^uC(O)N(R^y)R'N(R^y)S(O)_tR^{x''}$, —$R^uC(O)N(R^y)R'S(O)_tR^{x''}$, —$R^uC(O)N(R^y)R'S(O)_tN(R^y)(R^z)$, —$R^uC(O)N(R^y)R'C(O)R^{x'}$, —$R^uC(O)N(R^y)R'C(O)N(R^y)(R^z)$, —$R^uC(O)OR^{x'}$, —$R^uC(O)OR'OR^{x'}$, —$R^uC(O)R^{x'}$, —$R^uC(O)R'OR^{x'}$, —$R^uS(O)_tR^{x''}$, —$R^uS(O)_tR'OR^{x'}$, —$R^uOP(O)(OH)_2$, and —$R^uOS(O)_2(OH)$ where the alkyl, alkenyl, alkynyl, cycloalkyl, cycloalkylalkyl, aryl, aralkyl, heterocyclyl, heterocyclylalkyl, heteroaryl or heteroaralkyl is each independently optionally substituted with 1 to 5 groups each independently selected from halo, alkyl, haloalkyl and —$R^uOR^{x'}$;
each t is independently 0, 1 or 2;
$R^3$ is hydrogen, alkyl or haloalkyl;
$R^4$ and $R^5$ are each independently hydrogen, deuterium, halo, alkyl, alkenyl, alkynyl, haloalkyl, hydroxy, alkoxy or amino;
each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R^uOR^{x'}$, —$R^uN(R^y)(R^z)$, —$R^uC(O)N(R^y)(R^z)$ and —$R^uS(O)_tR^{x''}$;
each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^{x'}$, —$R^uOR'OR^{x'}$ and —$R^uOR'N(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^{x'}$ of —$R^uOR^{x'}$ and —$R^uOR'OR^{x'}$ is each independently optionally substituted with 1 to 9 groups each independently selected from deuterium, halo, cyano, alkyl, alkenyl, alkynyl, haloalkyl, cyanoalkyl, hydroxyalkyl, cycloalkyl, heterocyclyl, aryl, heteroaryl, hydroxy, alkoxy, and —$R^uN(R^y)(R^z)$; or
two $R^7$s, together with the atoms to which they are attached, form a heterocyclyl optionally substituted with one or more deuterium atoms or 1 to 4 groups each independently selected from deuterium, halo, alkyl and haloalkyl;
$R^8$ and $R^9$ are each independently hydrogen, deuterium, halo, alkyl, haloalkyl, cyano, —$C(O)N(R^y)(R^z)$, —$R^uOR^{x'}$, —$R^uOR'OR^{x'}$, —$R^uN(R^y)(R^z)$, —$R^uS(O)_tR^{x''}$, —$N=N^+=N$, cycloalkyl, cycloalkylalkyl, aryl, aralkyl, heterocyclyl, heterocyclylalkyl, heteroaryl or heteroaralkyl;
each $R^u$ is independently alkylene, alkenylene, alkynylene or a direct bond wherein the alkylene, alkenylene or alkynylene is optionally substituted with one or more deuterium atoms;
each $R^v$ is independently alkylene, alkenylene or alkynylene wherein the alkylene, alkenylene or alkynylene is optionally substituted with one or more deuterium atoms;
each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —$R^uOP(O)(OH)_2$, and —$R^uOS(O)_2(OH)$;
each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, —$R^uOP(O)(OH)_2$, and —$R^uOS(O)_2(OH)$;
each $R^y$ and $R^z$ is independently selected from (i), (ii) and (iii) as follows:
  (i) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;
  (ii) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (iii) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino;

m is an integer from 0 to 4, and n is an integer from 0 to 4;

wherein the compound is selected such that when ring A is pyrazolyl, m is 1 and Z is CH, $R^7$ is not cyclopropyl.

In certain embodiments, provided herein are compounds having the Formula II:

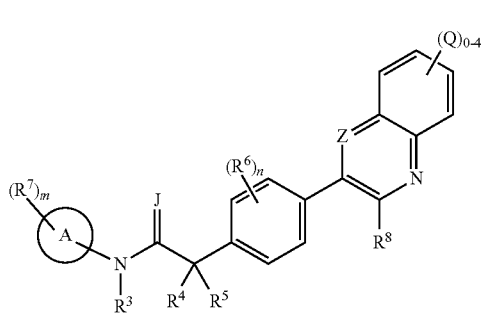

or a pharmaceutically acceptable salt, solvate, clathrate, hydrate, a single stereoisomer, a mixture of stereoisomers or a racemic mixture of stereoisomers thereof, wherein:

Ring A is azolyl;

J is O or S;

Z is N or $CR^9$;

one, two, three or four Q groups are selected from (i) and (ii):

(i) each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^x$, —$R^uOR^vOR^x$, —$R^uOR^vN(R^y)$ $(R^z)$, —$R^uN(R^y)(R^z)$, —$N(R^y)R^vOR$, —$N(R^y)R^vS(O)_tR^x$, —$N(R^y)S(O)_tR^x$, —$N(R^y)R^vN(R^y)(R^z)$, —$C(O)N(R^y)(R^z)$, —$C(O)OR^x$, —$C(O)N(R^y)R^vOR^x$, —$C(O)N(R^y)R^vN(R^y)$ $(R^z)$, —$C(O)N(R^y)R^vS(O)_tR^x$, —$C(O)N(R^y)R^vN(R^y)S(O)_t$ $R^x$, —$C(O)R^x$ and —$R^uS(O)_tR^x$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —$R^uOR^x$; and (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl are optionally substituted with 1 to 4 groups each independently selected from deuterium, halo, alkyl, haloalkyl, cyano, —$C(O)N(R^y)$ $(R^z)$, —$R^uOR^x$, —$R^uOR^vOR^x$, —$R^uN(R^y)(R^z)$, —$R^uS(O)_t$ $R^x$, heteroaryl and heterocyclyl;

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R^uOR^x$ and —$R^uN(R^y)(R^z)$;

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^x$, —$R^uOR^vOR^x$ and —$R^uOR^vN(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^x$ of —$R^uOR^x$ and —$R^uOR^vOR^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —$R^uN(R^y)(R^z)$;

$R^8$ is hydrogen, deuterium, halo, alkyl, haloalkyl, cyano, —$C(O)N(R^y)(R^z)$, —$R^uOR^x$, —$R^uOR^vOR^x$, —$R^uN(R^y)$ $(R^z)$, —$R^uS(O)_tR^x$, heteroaryl or heterocyclyl;

$R^9$ is hydrogen, deuterium, halo, alkyl, haloalkyl, cyano, —$C(O)N(R^y)(R^z)$, —$R^uOR^x$, —$R^uOR^vOR^x$, —$R^uN(R^y)$ $(R^z)$, —$R^uS(O)_tR^x$, heteroaryl or heterocyclyl;

each $R^u$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl;

each $R^y$ and $R^z$ is independently selected from (i) and (ii) as follows:

(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups;

m is an integer from 0 to 4, and n is an integer from 0 to 4;

wherein the compound is selected such that when ring A is pyrazolyl, m is 1 and

Z is CH, $R^7$ is not cyclopropyl.

In certain embodiments, provided herein are compounds having the Formula II wherein Z is N. In certain embodiments, provided herein are compounds having the Formula II wherein ring A is isoxazolyl substituted with 0-2 $R^7$ groups wherein the variables are as stated for Formula II.

In certain embodiments, provided herein are compounds having the Formula II wherein one, two, three or four Q groups, selected from (i) and (ii):

(i) each one, two, three or four Q groups is each independently selected from deuterium, halo, cyano, alkyl, alkenyl, alkynyl, haloalkyl, —$R^uOR^x$, —$R^uOR^vOR^x$, —$R^uOR^vN(R^y)(R^z)$, —$R^uN(R^y)(R^z)$, —$N(R^y)R^vOR$, —$N(R^y)R^vS(O)_tR^x$, —$N(R^y)S(O)_tR^x$, —$N(R^y)R^vN(R^y)(R^z)$, —$C(O)N(R^y)(R^z)$, —$C(O)OR^x$, —$C(O)N(R^y)R^vOR^x$, —$C(O)N(R^y)R^vN(R^y)(R^z)$, —$C(O)N(R^y)R^vS(O)_tR^x$ and —$C(O)R^x$; and (ii) two adjacent Q groups, together with the atoms to which they are attached may form cycloalkenyl or heterocyclyl where the cycloalkenyl or heterocyclyl is optionally substituted with one, two or three groups selected from —$R^uOR^x$ and —$R^uN(R^y)(R^z)$.

In certain embodiments, provided herein are compounds having the Formula II wherein Q is one, two or three groups each independently selected from —$R^uOR^x$ and —$R^uOR^vOR^x$; each $R^u$ is independently alkylene, alkenylene, alkynylene or a direct bond; each R$^v$ is independently alkylene, alkenylene or alkynylene; and each R$^x$ is independently hydrogen, alkyl, haloalkyl, alkenyl, alkynyl or heterocyclyl; and the other variables are as described elsewhere herein.

In certain embodiments, provided herein are compounds having the Formula IIa:

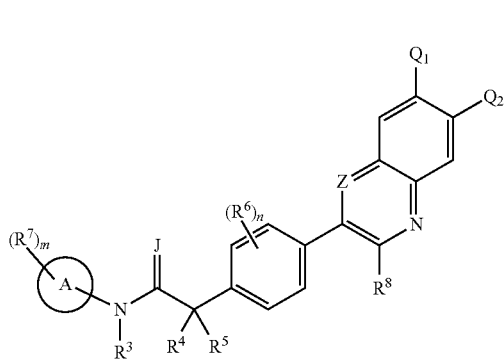

IIa or a pharmaceutically acceptable salt, solvate, clathrate, hydrate, a single stereoisomer, a mixture of stereoisomers or a racemic mixture of stereoisomers thereof, wherein:

Ring A is azolyl;

J is O or S;

Z is N or CR$^9$;

Q$^1$ and Q$^2$ are each independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R$^u$OR$^{x'}$, —R$^u$OR$^v$OR$^{x'}$, —R$^u$OR$^v$OC(O)R$^{x'}$, —R$^u$OR$^v$OC(O)N(R$^y$)(R$^z$), —R$^u$OR$^v$N(R$^y$)(R$^z$), —R$^u$OR$^v$N=N$^+$=N, —R$^u$OR$^v$N(R$^y$)C(O)R$^{x'}$, —R$^u$OR$^v$N(R$^y$)C(O)N(R$^y$)(R$^z$), —R$^u$OR$^v$N(R$^y$)C(O)OR$^{x''}$—R$^u$OR$^v$N(R$^y$)S(O)$_t$R$^{x''}$—R$^u$OR$^v$S(O)$_t$R$^{x''}$, —R$^u$OR$^v$S(O)$_t$N(R$^y$)(R$^z$), —R$^u$OR$^v$C(O)R$^{x'}$, —R$^u$OR$^v$C(O)N(R$^y$)(R$^z$), —R$^u$N(R$^y$)(R$^z$), —R$^u$N(R$^y$)R$^v$OR$^{x'}$, —R$^u$N(R$^y$)R$^v$OC(O)R$^{x'}$, —R$^u$N(R$^y$)R$^v$OC(O)N(R$^y$)(R$^z$), —R$^u$N(R$^y$)R$^v$N(R$^y$)(R$^z$), —R$^u$N(R$^y$)R$^v$N(R$^y$)C(O)R$^{x'}$, —R$^u$N(R$^y$)R$^v$N(R$^y$)C(O)N(R$^y$)(R$^z$), —R$^u$N(R$^y$)R$^v$N(R$^y$)C(O)OR$^{x''}$, —R$^u$N(R$^y$)R$^v$N(R$^y$)S(O)$_t$R$^{x''}$, —R$^u$N(R$^y$)R$^v$S(O)$_t$R$^{x''}$—R$^u$N(R$^y$)R$^v$S(O)$_t$N(R$^y$)(R$^z$), —R$^u$N(R$^y$)R$^v$C(O)R$^{x'}$, —R$^u$N(R$^y$)R$^v$C(O)N(R$^y$)(R$^z$), —R$^u$N(R$^y$)S(O)$_t$R$^{x''}$—R$^u$N(R$^y$)S(O)$_t$R$^v$OR$^{x'}$, —R$^u$N(R$^y$)C(O)R$^{x'}$, —R$^u$N(R$^y$)C(O)R$^v$OR$^{x'}$, —R$^u$C(O)N(R$^y$)(R$^z$), —R$^u$C(O)N(R$^y$)N(R$^y$)(R$^z$), —R$^u$C(O)N(R$^y$)R$^v$OR$^{x'}$, —R$^u$C(O)N(R$^y$)R$^v$OC(O)R$^{x'}$, —R$^u$C(O)N(R$^y$)R$^v$OC(O)N(R$^y$)(R$^z$), —R$^u$C(O)N(R$^y$)R$^v$N(R$^y$)(R$^z$), —R$^u$C(O)N(R$^y$)R$^v$N(R$^y$)C(O)R$^{x'}$, —R$^u$C(O)N(R$^y$)R$^v$N(R$^y$)C(O)N(R$^y$)(R$^z$), —R$^u$C(O)N(R$^y$)R$^v$N(R$^y$)C(O)OR$^{x''}$, —R$^u$C(O)N(R$^y$)R$^v$N(R$^y$)S(O)$_t$R$^{x''}$, —R$^u$C(O)N(R$^y$)R$^v$S(O)$_t$R$^{x''}$—R$^u$C(O)N(R$^y$)R$^v$S(O)$_t$N(R$^y$)(R$^z$), —R$^u$C(O)N(R$^y$)R$^v$C(O)R$^{x'}$, —R$^u$C(O)N(R$^y$)R$^v$C(O)N(R$^y$)(R$^z$), —R$^u$C(O)OR$^{x'}$, —R$^u$C(O)OR$^v$OR$^{x'}$, —R$^u$C(O)R$^{x'}$, —R$^u$C(O)R$^v$OR$^{x'}$, —R$^u$S(O)$_t$R$^{x''}$, —R$^u$S(O)$_t$R$^v$OR$^{x'}$, —R$^u$OP(O)(OH)$_2$, and —R$^u$OS(O)$_2$(OH), where the alkyl, alkenyl, alkynyl, cycloalkyl, cycloalkylalkyl, aryl, aralkyl, heterocyclyl, heterocyclylalkyl, heteroaryl or heteroaralkyl is each independently optionally substituted with 1 to 5 groups each independently selected from halo, alkyl, haloalkyl and —R$^u$OR$^{x'}$;

each t is independently 0, 1 or 2;

R$^3$ is hydrogen, alkyl or haloalkyl;

R$^4$ and R$^5$ are each independently hydrogen, deuterium, halo, alkyl, alkenyl, alkynyl, haloalkyl, hydroxy, alkoxy or amino;

each R$^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —R$^u$OR$^{x'}$, —R$^u$N(R$^y$)(R$^z$), —R$^u$C(O)N(R$^y$)(R$^z$) and —R$^u$S(O)$_t$R$^{x''}$;

each R$^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R$^u$OR$^{x'}$, —R$^u$OR$^v$OR$^{x'}$ and —R$^u$OR$^v$N(R$^y$)(R$^z$) where the alkyl, alkenyl, alkynyl, cycloalkyl, cycloalkylalkyl, aryl, aralkyl, heterocyclyl, heterocyclylalkyl, heteroaryl, heteroaralkyl and the R$^{x'}$ of —R$^u$OR$^{x'}$ and —R$^u$OR$^v$OR$^{x'}$ is each independently optionally substituted with 1 to 9 groups each independently selected from deuterium, halo, cyano, alkyl, alkenyl, alkynyl, haloalkyl, cyanoalkyl, hydroxyalkyl, cycloalkyl, heterocyclyl, aryl, heteroaryl, hydroxy, alkoxy, and —R$^u$N(R$^y$)(R$^z$); or two R$^7$s, together with the atoms to which they are attached, form a heterocyclyl optionally substituted with one or more deuterium atoms or 1 to 4 groups each independently selected from deuterium, halo, alkyl and haloalkyl;

each R$^u$ is independently alkylene, alkenylene, alkynylene or a direct bond wherein the alkylene, alkenylene or alkynylene is optionally substituted with one or more deuterium atoms;

each R$^v$ is independently alkylene, alkenylene or alkynylene wherein the alkylene, alkenylene or alkynylene is optionally substituted with one or more deuterium atoms;

each R$^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —R$^u$OP(O)(OH)$_2$, and —R$^u$OS(O)$_2$(OH);

each R$^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, —R$^u$OP(O)(OH)$_2$, and —R$^u$OS(O)$_2$(OH);

each R$^y$ and R$^z$ is independently selected from (i), (ii) and (iii) as follows:
 (i) each R$^y$ and R$^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(ii) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (iii) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino;

and the other variables are as stated for Formula II.

In certain embodiments, provided herein are compounds having the Formula IIa:

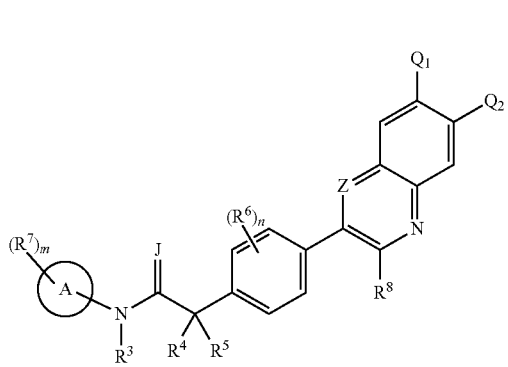

IIa or a pharmaceutically acceptable salt, solvate, clathrate, hydrate, a single stereoisomer, a mixture of stereoisomers or a racemic mixture of stereoisomers thereof, wherein:

Ring A is azolyl;

J is O or S;

Z is N or $CR^9$;

$Q^1$ and $Q^2$ are each independently selected from hydrogen, deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^{x'}$, —$R^uOR'OR^{x'}$, —$R^uOR'OC(O)R^{x'}$, —$R^uOR'OC(O)N(R^y)(R^z)$, —$R^uOR'N(R^y)(R^z)$, —$R^uOR'N=N^+=N$, —$R^uOR'N(R^y)C(O)R^{x'}$, —$R^uOR'N(R^y)C(O)N(R^y)(R^z)$, —$R^uOR'N(R^y)C(O)OR^{x''}$—$R^uOR'N(R^y)S(O)_tR^{x''}$—$R^uOR'S(O)_tR^{x''}$, —$R^uOR'S(O)_tN(R^y)(R^z)$, —$R^uOR'C(O)R^{x'}$, —$R^uOR'C(O)N(R^y)(R^z)$, —$R^uN(R^y)(R^z)$, —$R^uN(R^y)R'OR^{x'}$, —$R^uN(R^y)R'OC(O)R^{x'}$, —$R^uN(R^y)R'OC(O)N(R^y)(R^z)$, —$R^uN(R^y)R'N(R^y)(R^z)$, —$R^uN(R^y)R'N(R^y)C(O)R^{x'}$, —$R^uN(R^y)R'N(R^y)C(O)N(R^y)(R^z)$, —$R^uN(R^y)R'N(R^y)C(O)OR^{x''}$, —$R^uN(R^y)R'N(R^y)S(O)_tR^{x''}$, —$R^uN(R^y)R'S(O)_tR^{x''}$—$R^uN(R^y)R'S(O)_tN(R^y)(R^z)$, —$R^uN(R^y)R'C(O)R^{x'}$, —$R^uN(R^y)R'C(O)N(R^y)(R^z)$, —$R^uN(R^y)S(O)_tR^{x''}$—$R^uN(R^y)S(O)_tR'OR^{x'}$, —$R^uN(R^y)C(O)R^{x'}$, —$R^uN(R^y)C(O)R'OR^{x'}$, —$R^uC(O)N(R^y)(R^z)$, —$R^uC(O)N(R^y)N(R^y)(R^z)$, —$R^uC(O)N(R^y)R'OR^{x'}$, —$R^uC(O)N(R^y)R'OC(O)R^{x'}$, —$R^uC(O)N(R^y)R'OC(O)N(R^y)(R^z)$, —$R^uC(O)N(R^y)R'N(R^y)(R^z)$, —$R^uC(O)N(R^y)R'N(R^y)C(O)R^{x'}$, —$R^uC(O)N(R^y)R'N(R^y)C(O)N(R^y)(R^z)$, —$R^uC(O)N(R^y)R'N(R^y)C(O)OR^{x''}$, —$R^uC(O)N(R^y)R'N(R^y)S(O)_tR^{x''}$, —$R^uC(O)N(R^y)R'S(O)_tR^{x''}$—$R^uC(O)N(R^y)R'S(O)_tN(R^y)(R^z)$, —$R^uC(O)N(R^y)R'C(O)R^{x'}$, —$R^uC(O)N(R^y)R'C(O)N(R^y)(R^z)$, —$R^uC(O)OR^{x'}$, —$R^uC(O)OR'OR^{x'}$, —$R^uC(O)R^{x'}$, —$R^uC(O)R'OR^{x'}$, —$R^uS(O)_tR^{x''}$, —$R^uS(O)_tR'OR^{x'}$, —$R^uOP(O)(OH)_2$, and —$R^uOS(O)_2(OH)$, where the alkyl, alkenyl, alkynyl, cycloalkyl, cycloalkylalkyl, aryl, aralkyl, heterocyclyl, heterocyclylalkyl, heteroaryl or heteroaralkyl is each independently optionally substituted with 1 to 5 groups each independently selected from halo, alkyl, haloalkyl and —$R^uOR^{x'}$; where both $Q^1$ and $Q^2$ are not hydrogen at the same time;

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R^uOR^{x'}$, —$R^uN(R^y)(R^z)$, —$R^uC(O)N(R^y)(R^z)$ and —$R^uS(O)_tR^{x''}$;

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^{x'}$, —$R^uOR'OR^{x'}$ and —$R^uOR'N(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^{x'}$ of —$R^uOR^{x'}$ and —$R^uOR'OR^{x'}$ is each independently optionally substituted with 1 to 9 groups each independently selected from deuterium, halo, cyano, alkyl, alkenyl, alkynyl, haloalkyl, cyanoalkyl, hydroxyalkyl, cycloalkyl, heterocyclyl, aryl, heteroaryl, hydroxy, alkoxy, and —$R^uN(R^y)(R^z)$; or two $R^7$s, together with the atoms to which they are attached, form a heterocyclyl optionally substituted with one or more deuterium atoms or 1 to 4 groups each independently selected from deuterium, halo, alkyl and haloalkyl;

each $R^u$ is independently alkylene, alkenylene, alkynylene or a direct bond wherein the alkylene, alkenylene or alkynylene is optionally substituted with one or more deuterium atoms;

each $R^v$ is independently alkylene, alkenylene or alkynylene wherein the alkylene, alkenylene or alkynylene is optionally substituted with one or more deuterium atoms;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —$R^uOP(O)(OH)_2$, and —$R^uOS(O)_2(OH)$;

each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, —$R^uOP(O)(OH)_2$, and —$R^uOS(O)_2(OH)$;

each $R^y$ and $R^z$ is independently selected from (i), (ii) and (iii) as follows:

(iv) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(v) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (vi) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino; and the other variables are as stated for Formula II.

In certain embodiments, provided herein are compounds having the Formula IIa wherein ring A is isoxazolyl substituted with 0-2 $R^7$ groups, wherein the variables are as stated for Formula IIa.

In certain embodiments, provided herein are compounds having the Formula II or IIa wherein substituted Ring A is:

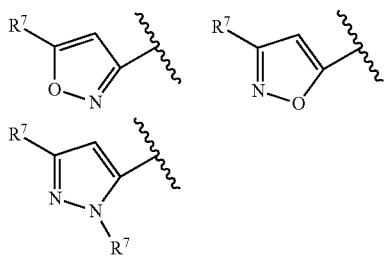

each $R^7$ is independently selected from halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R″OR$^{x'}$, —R″OR$^y$OR$^{x'}$ and —R″OR$^y$N(R$^y$)(R$^z$) where the alkyl, alkenyl, alkynyl, cycloalkyl, cycloalkylalkyl, aryl, aralkyl, heterocyclyl, heterocyclylalkyl, heteroaryl, heteroaralkyl and the R$^{x'}$ of —R″OR$^{x'}$ and —R″OR$^y$OR$^{x'}$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —R″N(R$^y$)(R$^z$);

each R″ is independently alkylene, alkenylene, alkynylene or a direct bond wherein the alkylene, alkenylene or alkynylene is optionally substituted with one or more deuterium atoms;

each R$^v$ is independently alkylene, alkenylene or alkynylene wherein the alkylene, alkenylene or alkynylene is optionally substituted with one or more deuterium atoms;

each R$^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —R″OP(O)(OH)$_2$, and —R″OS(O)$_2$(OH);

each R$^y$ and R$^z$ is independently selected from (i), (ii) and (iii) as follows:

(i) each R$^y$ and R$^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(ii) R$^y$ and R$^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (iii) R$^y$ and R$^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino.

In certain embodiments, provided herein are compounds having the Formula II or IIa wherein substituted Ring A is:

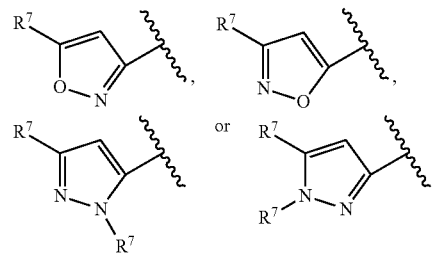

each $R^7$ is selected as follows:

(i) each $R^7$ is independently selected from halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R″OR$^{x'}$, —R″OR$^y$OR$^{x'}$ and —R″OR$^y$N(R$^y$)(R$^z$) where the alkyl, alkenyl, alkynyl, cycloalkyl, cycloalkylalkyl, aryl, aralkyl, heterocyclyl, heterocyclylalkyl, heteroaryl, heteroaralkyl and the R$^{x'}$ of —R″OR$^{x'}$ and —R″OR$^y$OR$^{x'}$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —R″N(R$^y$)(R$^z$); or (ii) two R$^7$ groups, together with the atoms to which they are attached, form a heterocyclyl, optionally substituted with one or more deuterium atoms or 1 to 4 groups each independently selected from halo, alkyl and haloalkyl;

each R″ is independently alkylene, alkenylene, alkynylene or a direct bond wherein the alkylene, alkenylene or alkynylene is optionally substituted with one or more deuterium atoms;

each $R^v$ is independently alkylene, alkenylene or alkynylene wherein the alkylene, alkenylene or alkynylene is optionally substituted with one or more deuterium atoms;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —$R^uOP(O)(OH)_2$, and —$R^uOS(O)_2(OH)$;

each $R^y$ and $R^z$ is independently selected from (i), (ii) and (iii) as follows:

(iv) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(v) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (vi) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino.

In certain embodiments, provided herein are compounds having the Formula IIa wherein ring A: is

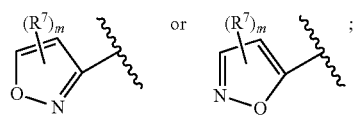

m is an integer from 0 to 2 and the other variables are as stated for Formula IIa. In certain embodiments, provided herein are compounds having the Formula IIa wherein ring A is

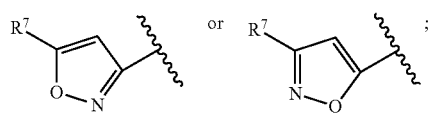

and the other variables are as stated for Formula IIa.

In certain embodiments, provided herein are compounds having the Formula IIa, wherein Z is N.

In certain embodiments, provided herein are compounds having the Formula IIa, wherein A is isoxazolyl substituted with 0 to 2 $R^7$ groups, Z is N; each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R^uOR^{x'}$, —$R^uOR^vOR^{x'}$ and —$R^uOR^vN(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^{x'}$ of —$R^uOR^{x'}$ and —$R^uOR^vOR^{x'}$ is each independently optionally substituted with 1 to 9 groups each independently selected from deuterium, halo, cyano, alkyl, alkenyl, alkynyl, haloalkyl, cyanoalkyl, hydroxyalkyl, cycloalkyl, heterocyclyl, aryl, heteroaryl, hydroxy, alkoxy, and —$R^uN(R^y)(R^z)$;

each $R^u$ is independently alkylene, alkenylene, alkynylene or a direct bond wherein the alkylene, alkenylene or alkynylene is optionally substituted with one or more deuterium atoms;

each $R^v$ is independently alkylene, alkenylene or alkynylene wherein the alkylene, alkenylene or alkynylene is optionally substituted with one or more deuterium atoms;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl, cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, —$R^uOP(O)(OH)_2$, and —$R^uOS(O)_2(OH)$;

each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where the alkyl, haloalkyl, cyanoalkyl, alkenyl, alkynyl cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, —$R^uOP(O)(OH)_2$, and —$R^uOS(O)_2(OH)$;

each $R^y$ and $R^z$ is independently selected from (i), (ii) and (iii) as follows:

(i) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is each independently optionally substituted with one or more deuterium atoms and where the cycloalkyl, cycloalkylalkyl, heterocyclyl, heterocyclylalkyl, aryl, aralkyl, heteroaryl or heteroaralkyl is each independently optionally substituted with one or more deuterium atoms or 1 to 5 groups each independently selected from halo, cyano, alkyl, haloalkyl, hydroxy, alkoxy, haloalkoxy and amino;

(ii) $R^y$ and $R^z$, together with the nitrogen atom to which they are attached, form a heterocyclyl optionally substituted with one or more deuterium atoms or 1 to 5 groups each independently selected from halo, cyano, haloalkyl, alkyl, alkenyl, alkynyl, hydroxy, alkoxy, haloalkoxy, amino, and oxo; and (iii) $R^y$ and $R^z$, together with the nitrogen atom to which they are attached, form a heteroaryl optionally substituted with one or more deuterium atoms or 1 to 5 groups each independently selected from halo, cyano, haloalkyl, alkyl, alkenyl, alkynyl, hydroxy, alkoxy, haloalkoxy and amino;

and the other variables are as stated for Formula IIa. In certain embodiments, provided herein are compounds of Formula II or IIa wherein $R^8$ is hydrogen. In certain embodiments, provided herein are compounds of Formula II or IIa wherein $R^8$ and $R^9$ are both hydrogen.

In certain embodiments, provided herein are compounds having the Formula III:

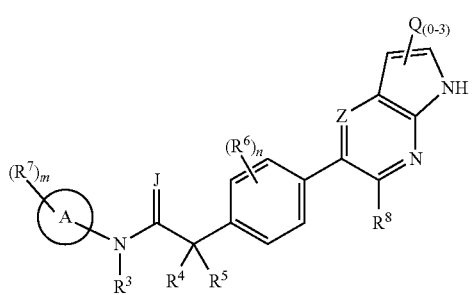

III or a pharmaceutically acceptable salt, solvate, clathrate, hydrate, a single stereoisomer, a mixture of stereoisomers or a racemic mixture of stereoisomers thereof, wherein:

Ring A is azolyl;

J is O or S;

Z is N or $CR^9$;

one, two or three Q groups are selected from (i) and (ii):

(i) each of the one, two or three Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R"OR$^x$, —R"OR'OR$^x$, —R"OR'N(R$^y$)(R$^z$), —R"N(R$^y$)(R$^z$), —N(R$^y$)R'OR, —N(R$^y$)R'S(O)$_t$R$^x$, —N(R$^y$)S(O)$_t$R$^x$, —N(R$^y$)R'N(R$^y$)(R$^z$), —C(O)N(R$^y$)(R$^z$), —C(O)OR$^x$, —C(O)N(R$^y$)R'OR$^x$, —C(O)N(R$^y$)R'N(R$^y$)(R$^z$), —C(O)N(R$^y$)R'S(O)$_t$R$^x$, —C(O)N(R$^y$)R'N(R$^y$)S(O)$_t$R$^x$, —C(O)R$^x$ and —R"S(O)$_t$R$^x$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —R"OR$^x$; and (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl are optionally substituted with 1 to 4 groups each independently selected from deuterium, halo, alkyl, haloalkyl, cyano, —C(O)N(R$^y$)(R$^z$), —R"OR$^x$, —R"OR'OR$^x$, —R"N(R$^y$)(R$^z$), —R"S(O)$_t$R$^x$, heteroaryl and heterocyclyl;

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —R"OR$^x$ and —R"N(R$^y$)(R$^z$);

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —R"OR$^x$, —R"OR'OR$^x$ and —R"OR'N(R$^y$)(R$^z$) where the alkyl, alkenyl, alkynyl, cycloalkyl, cycloalkylalkyl, aryl, aralkyl, heterocyclyl, heterocyclylalkyl, heteroaryl, heteroaralkyl and the R$^x$ of —R"OR$^x$ and —R"OR'OR$^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —R"N(R$^y$)(R$^z$);

$R^8$ is hydrogen, deuterium, halo, alkyl, haloalkyl, cyano, —C(O)N(R$^y$)(R$^z$), —R"OR$^x$, —R"OR'OR$^x$, —R"N(R$^y$)(R$^z$), —R"S(O)$_t$R$^x$, heteroaryl or heterocyclyl;

$R^9$ is hydrogen, deuterium, halo, alkyl, haloalkyl, cyano, —C(O)N(R$^y$)(R$^z$), —R"OR$^x$, —R"OR'OR$^x$, —R"N(R$^y$)(R$^z$), —R"S(O)$_t$R$^x$, heteroaryl or heterocyclyl;

each R" is independently alkylene, alkenylene, alkynylene or a direct bond;

each R' is independently alkylene, alkenylene or alkynylene;

each R$^x$ is independently hydrogen, alkyl, haloalkyl, alkenyl, alkynyl or heterocyclyl;

each R$^y$ and R$^z$ is independently selected from (i) and (ii) as follows:

(i) R$^y$ and R$^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) R$^y$ and R$^z$, together with the nitrogen atom to which they are attached, form a heterocyclyl optionally substituted with one, two, three, four or five halo, haloalkyl, alkyl, alkenyl, alkynyl or oxo groups;

m is an integer from 0 to 4, and n is an integer from 0 to 4.

In certain embodiments, provided herein are compounds having the Formula III wherein Z is N. In certain embodiments, provided herein are compounds having the Formula III wherein one, two, three or four Q groups, selected from (i) and (ii):

(i) each one, two, three or four Q groups is each independently selected from deuterium, halo, cyano, alkyl, alkenyl, alkynyl, haloalkyl, —R"OR$^x$, —R"OR'OR$^x$, —R"OR'N(R$^y$)(R$^z$), —R"N(R$^y$)(R$^z$), —N(R$^y$)R'OR, —N(R$^y$)R'S(O)$_t$R$^x$, —N(R$^y$)S(O)$_t$R$^x$, —N(R$^y$)R'N(R$^y$)(R$^z$), —C(O)N(R$^y$)(R$^z$), —C(O)OR$^x$, —C(O)N(R$^y$)R'OR$^x$, —C(O)N(R$^y$)R'N(R$^y$)(R$^z$), —C(O)N(R$^y$)R'S(O)$_t$R$^x$ and —C(O)R$^x$; and (ii) two adjacent Q groups, together with the atoms to which they are attached may form cycloalkenyl or heterocyclyl where the cycloalkenyl or heterocyclyl is optionally substituted with one, two or three groups selected from —R"OR$^x$ and —R"N(R$^y$)(R$^z$);

In certain embodiments, provided herein are compounds having the Formula II wherein Q is one, two or three groups each independently selected from —R"OR$^x$ and —R"OR'OR$^x$; each R" is independently alkylene, alkenylene, alkynylene or a direct bond; each R' is independently alkylene, alkenylene or alkynylene; and each R$^x$ is independently hydrogen, alkyl, haloalkyl, alkenyl, alkynyl or heterocyclyl; and the other variables are as described elsewhere herein.

In certain embodiments, provided herein are compounds having the Formula IV:

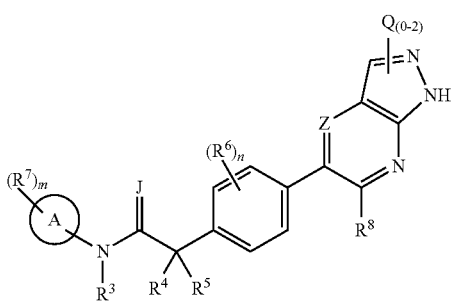

IV or a pharmaceutically acceptable salt, solvate, clathrate, hydrate, a single stereoisomer, a mixture of stereoisomers or a racemic mixture of stereoisomers thereof, wherein:

Ring A is optionally substituted azolyl;

J is O or S;

Z is N or $CR^9$;

one or two Q groups are selected from (i) and (ii):

(i) each of the one or two Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R''OR^x$, —$R''OR^yOR^x$, —$R''OR^yN(R^y)(R^z)$, —$R''N(R^y)(R^z)$, —$N(R^y)R^yOR$, —$N(R^y)R^yS(O)_tR^x$, —$N(R^y)S(O)_tR^x$, —$N(R^y)R^yN(R^y)(R^z)$, —$C(O)N(R^y)(R^z)$, —$C(O)OR^x$, —$C(O)N(R^y)R^yOR^x$, —$C(O)N(R^y)R^yN(R^y)(R^z)$, —$C(O)N(R^y)R^yS(O)_tR^x$, —$C(O)N(R^y)R^yN(R^y)S(O)_tR^x$, —$C(O)R^x$ and —$R''S(O)_tR^x$ where the alkyl, alkenyl, alkynyl, cycloalkyl, cycloalkylalkyl, aryl, aralkyl, heterocyclyl, heterocyclylalkyl, heteroaryl and heteroaralkyl are optionally substituted with 1 to 5 groups each independently selected from halo, alkyl, haloalkyl and —$R''OR^x$;

(ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl are optionally substituted with 1 to 4 groups each independently selected from deuterium, halo, alkyl, haloalkyl, cyano, —$C(O)N(R^y)(R^z)$, —$R''OR^x$, —$R''OR^yOR^x$, —$R''N(R^y)(R^z)$, —$R''S(O)_tR^x$, heteroaryl and heterocyclyl;

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino;

each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, —$R''OR^x$ and —$R''N(R^y)(R^z)$;

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, —$R''OR^x$, —$R''OR^yOR^x$ and —$R''OR^yN(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^x$ of —$R''OR^x$ and —$R''OR^yOR^x$ are optionally substituted with 1 to 9 groups each independently selected from deuterium, halo, cyano, alkyl, alkenyl, alkynyl, cycloalkyl, heterocyclyl, aryl, heteroaryl, hydroxy, alkoxy, and —$R''N(R^y)(R^z)$;

$R^8$ is hydrogen, deuterium, halo, alkyl, haloalkyl, cyano, —$C(O)N(R^y)(R^z)$, —$R''OR^x$, —$R''OR^yOR^x$, —$R''N(R^y)(R^z)$, —$R''S(O)_tR^x$, heteroaryl or heterocyclyl;

$R^9$ is hydrogen, deuterium, halo, alkyl, haloalkyl, cyano, —$C(O)N(R^y)(R^z)$, —$R''OR^x$, —$R''OR^yOR^x$, —$R''N(R^y)(R^z)$, —$R''S(O)_tR^x$, heteroaryl or heterocyclyl;

each $R''$ is independently alkylene, alkenylene, alkynylene or a direct bond;

each $R^v$ is independently alkylene, alkenylene or alkynylene;

each $R^x$ is independently hydrogen, alkyl, haloalkyl, alkenyl, alkynyl or heterocyclyl;

each $R^y$ and $R^z$ is independently selected from (i) and (ii) as follows:

(i) $R^y$ and $R^z$ are each independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl; and (ii) $R^y$ and $R^z$, together with the nitrogen atom to which they are attached, form a heterocyclyl optionally substituted with one, two, three, four or five halo, haloalkyl, alkyl, alkenyl, alkynyl or oxo groups;

m is an integer from 0 to 4, and n is an integer from 0 to 4.

In certain embodiments, provided herein are compounds having the Formula IV wherein Z is N. In certain embodiments, provided herein are compounds having the Formula IV wherein one, two, three or four Q groups, selected from (i) and (ii):

(i) each one, two, three or four Q groups is each independently selected from deuterium, halo, cyano, alkyl, alkenyl, alkynyl, haloalkyl, —$R''OR^x$, —$R''OR^yOR^x$, —$R''OR^yN(R^y)(R^z)$, —$R''N(R^y)(R^z)$, —$N(R^y)R^yOR$, —$N(R^y)R^yS(O)_tR^x$, —$N(R^y)S(O)_tR^x$, —$N(R^y)R^yN(R^y)(R^z)$, —$C(O)N(R^y)(R^z)$, —$C(O)OR^x$, —$C(O)N(R^y)R^yOR^x$, —$C(O)N(R^y)R^yN(R^y)(R^z)$, —$C(O)N(R^y)R^yS(O)_tR^x$ and —$C(O)R^x$; and (ii) two adjacent Q groups, together with the atoms to which they are attached may form cycloalkenyl or heterocyclyl where the cycloalkenyl or heterocyclyl is optionally substituted with one, two or three groups selected from —$R''OR^x$ and —$R''N(R^y)(R^z)$; In certain embodiments, provided herein are compounds having the Formula II wherein Q is one, two or three groups each independently selected from —$R''OR^x$ and —$R''OR^yOR^x$; each $R''$ is independently alkylene, alkenylene, alkynylene or a direct bond; each $R^v$ is independently alkylene, alkenylene or alkynylene; and each $R^x$ is independently hydrogen, alkyl, haloalkyl, alkenyl, alkynyl or heterocyclyl; and the other variables are as described elsewhere herein.

In certain embodiments, provided herein are compounds having the Formula V:

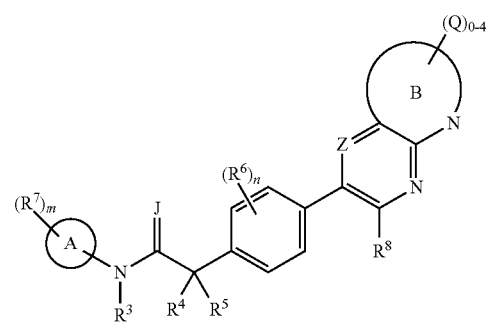

or a pharmaceutically acceptable salt, solvate, clathrate, hydrate, a single stereoisomer, a mixture of stereoisomers or a racemic mixture of stereoisomers thereof, wherein:

Ring A is optionally substituted azolyl;

J is O or S;

Z is N or $CR^9$;

Ring B is a 5- or 6-membered heteroaryl, where the substituents, when present, are one, two, three or four Q groups, selected from (i) and (ii):

(i) each of the one, two, three or four Q groups is independently selected from deuterium, halo, cyano, alkyl, alkenyl, alkynyl, haloalkyl, cycloalkyl, cycloalkylalkyl, aryl, aralkyl, heterocyclyl, heterocyclylalkyl, heteroaryl, heteroaralkyl, $-R^uOR^{x'}$, $-R^uOR'OR^{x'}$, $-R^uOR'OC(O)R^{x'}$, $-R^uOR'OC(O)N(R^y)(R^z)$, $-R^uOR'N(R^y)(R^z)$, $-R^uOR'N=N^+=N$, $-R^uOR'N(R^y)C(O)R^{x+}$, $-R^uOR'N(R^y)C(O)N(R^y)(R^z)$, $-R^uOR'N(R^y)C(O)OR^{x''}$, $-R^uOR'N(R^y)S(O)_tR^{x''}$—$R^uOR'S(O)_tR^{x''}$, $-R^uOR'S(O)_tN(R^y)(R^z)$, $-R^uOR'C(O)R^{x'}$, $-R^uOR'C(O)N(R^y)(R^z)$, $-R^uN(R^y)(R^z)$, $-R^uN(R^y)R'OR^{x'}$, $-R^uN(R^y)R'OC(O)R^{x'}$, $-R^uN(R^y)R'OC(O)N(R^y)(R^z)$, $-R^uN(R^y)R'N(R^y)(R^z)$, $-R^uN(R^y)R'N(R^y)C(O)R^{x'}$, $-R^uN(R^y)R'N(R^y)C(O)N(R^y)(R^z)$, $-R^uN(R^y)R'N(R^y)C(O)OR^{x''}$, $-R^uN(R^y)R'N(R^y)S(O)_tR^{x''}$, $-R^uN(R^y)R'S(O)_tR^{x''}$, $-R^uN(R^y)R'S(O)_tN(R^y)(R^z)$, $-R^uN(R^y)R'C(O)R^{x'}$, $-R^uN(R^y)R'C(O)N(R^y)(R^z)$, $-R^uN(R^y)S(O)_tR^{x''}$, $-R^uN(R^y)S(O)_tR'OR^{x'}$, $-R^uN(R^y)C(O)R^{x'}$, $-R^uN(R^y)C(O)R'OR^{x'}$, $-R^uC(O)N(R^y)(R^z)$, $-R^uC(O)N(R^y)N(R^y)(R^z)$, $-R^uC(O)N(R^y)R'OR^{x'}$, $-R^uC(O)N(R^y)R'OC(O)R^{x'}$, $-R^uC(O)N(R^y)R'OC(O)N(R^y)(R^z)$, $-R^uC(O)N(R^y)R'N(R^y)(R^z)$, $-R^uC(O)N(R^y)R'N(R^y)C(O)R^{x'}$, $-R^uC(O)N(R^y)R'N(R^y)C(O)N(R^y)(R^z)$, $-R^uC(O)N(R^y)R'N(R^y)C(O)OR^{x''}$, $-R^uC(O)N(R^y)R'N(R^y)S(O)_tR^{x''}$, $-R^uC(O)N(R^y)R'S(O)_tR^{x''}$, $-R^uC(O)N(R^y)R'S(O)_tN(R^y)(R^z)$, $-R^uC(O)N(R^y)R'C(O)R^{x'}$, $-R^uC(O)N(R^y)R'C(O)N(R^y)(R^z)$, $-R^uC(O)OR^{x'}$, $-R^uC(O)OR'OR^{x'}$, $-R^uC(O)R^{x'}$, $-R^uC(O)R'OR^{x'}$, $-R^uS(O)_tR^{x''}$, $-R^uS(O)_tR'OR^{x'}$, $-R^uOP(O)(OH)_2$ and $-R^uOS(O)_2(OH)$ where the alkyl, alkenyl, alkynyl, cycloalkyl, cycloalkylalkyl, aryl, aralkyl, heterocyclyl, heterocyclylalkyl, heteroaryl or heteroaralkyl is each optionally substituted with one or more deuterium atoms or 1 to 5 groups each independently selected from halo, alkyl, haloalkyl and $-R^uOR^{x'}$; and (ii) two adjacent Q groups, together with the atoms to which they are attached may form cycloalkyl, cycloalkenyl, heterocyclyl, aryl or heteroaryl where the cycloalkyl, cycloalkenyl, heterocyclyl, aryl or heteroaryl is optionally substituted with one or more deuterium atoms or 1 to 4 groups each independently selected from halo, alkyl, haloalkyl, cyano, $-C(O)N(R^y)(R^z)$, $-R^uOR^{x'}$, $-R^uOR'OR^{x'}$, $-R^uN(R^y)(R^z)$, $-R^uS(O)_tR^{x''}$, heteroaryl and heterocyclyl;

each t is independently 0, 1 or 2;

$R^3$ is hydrogen, alkyl or haloalkyl;

$R^4$ and $R^5$ are each independently hydrogen, deuterium, halo, alkyl, alkenyl, alkynyl, haloalkyl, hydroxy, alkoxy or amino; and each $R^6$ is independently selected from deuterium, halo, cyano, alkyl, alkenyl, alkynyl, haloalkyl, hydroxyalkyl, cycloalkyl, cycloalkylalkyl, aryl, heterocyclyl, heteroaryl, $-R^uOR^{x'}$, $-R^uN(R^y)(R^z)$ and $-R^uS(O)_tR^{x''}$;

each $R^7$ is independently selected from deuterium, halo, alkyl, alkenyl, alkynyl, haloalkyl, cycloalkyl, cycloalkylalkyl, aryl, aralkyl, heterocyclyl, heterocyclylalkyl, heteroaryl, heteroaralkyl, $-R^uOR^{x'}$, $-R^uOR'OR^{x'}$ and $-R^uOR'N(R^y)(R^z)$ where the alkyl, alkenyl, alkynyl, cycloalkyl, cycloalkylalkyl, aryl, aralkyl, heterocyclyl, heterocyclylalkyl, heteroaryl, heteroaralkyl and the $R^{x'}$ of $-R^uOR^{x'}$ and $-R^uOR'OR^{x'}$ are optionally substituted with 1 to 9 groups each independently selected from deuterium, halo, cyano, alkyl, alkenyl, alkynyl, haloalkyl, cyanoalkyl, hydroxyalkyl, cycloalkyl, heterocyclyl, aryl, heteroaryl, hydroxy, alkoxy, and $-R^uN(R^y)(R^z)$;

$R^8$ and $R^9$ are each independently hydrogen, deuterium, halo, alkyl, haloalkyl, cyano, $-C(O)N(R^y)(R^z)$, $-R^uOR^{x'}$, $-R^uOR'OR^{x'}$, $-R^uN(R^y)(R^z)$, $-R^uS(O)_tR^{x''}$, $-N=N^+=N$, cycloalkyl, cycloalkylalkyl, aryl, aralkyl, heterocyclyl, heterocyclylalkyl, heteroaryl or heteroaralkyl;

each $R^u$ is independently alkylene, alkenylene, alkynylene or a direct bond wherein the alkylene, alkenylene or alkynylene is optionally substituted with one or more deuterium atoms;

each $R^v$ is independently alkylene, alkenylene or alkynylene wherein the alkylene, alkenylene or alkynylene is optionally substituted with one or more deuterium atoms;

each $R^{x'}$ is independently hydrogen, alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where each alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, is independently optionally substituted with one or more deuterium atoms or 1 to 5 groups each independently selected from halo, cyano, alkyl, alkenyl, alkynyl, haloalkyl, aminoalkyl, cyanoalkyl, hydroxyalkyl, cycloalkyl, heterocyclyl, aryl, heteroaryl, hydroxy, alkoxy, haloalkoxy, amino, aminoalkyl, $-R^uOP(O)(OH)_2$, and $-R^uOS(O)_2(OH)$;

each $R^{x''}$ is independently alkyl, haloalkyl, cyanoalkyl, alkenyl, alkynyl, cycloalkyl, cycloalkylalkyl, heterocyclyl, heterocyclylalkyl, aryl, aralkyl, heteroaryl, or heteroaralkyl, where each alkyl, haloalkyl, cyanoalkyl, alkenyl, alkynyl cycloalkyl, cycloalkylalkyl, heterocyclyl, heterocyclylalkyl, aryl, aralkyl, heteroaryl, or heteroaralkyl is each independently optionally substituted with one or more deuterium atoms or 1 to 5 groups each independently selected from halo, cyano, alkyl, haloalkyl, aminoalkyl, hydroxy, alkoxy, haloalkoxy, amino, aminoalkyl, $-R^uOP(O)(OH)_2$, and $-R^uOS(O)_2(OH)$;

each $R^y$ and $R^z$ is independently selected from (i), (ii) and (iii) as follows:

(i) each $R^y$ and $R^z$ is independently hydrogen, alkyl, alkenyl, alkynyl, haloalkyl, alkoxyalkyl, haloalkoxyalkyl, hydroxyalkyl, cycloalkyl, cycloalkylalkyl, heterocyclyl, heterocyclylalkyl, aryl, aralkyl, heteroaryl or heteroaralkyl where the alkyl, alkenyl, alkynyl, alkoxyalkyl or hydroxyalkyl is optionally substituted with one or more deuterium atoms and where the cycloalkyl, cycloalkylalkyl, heterocyclyl, heterocyclylalkyl, aryl, aralkyl, heteroaryl or heteroaralkyl are optionally substituted with one or more deuterium atoms or 1 to 5 groups each independently selected from halo, cyano, alkyl, haloalkyl, hydroxy, alkoxy, haloalkoxy and amino;

(ii) $R^y$ and $R^z$, together with the nitrogen atom to which they are attached, form a heterocyclyl optionally substituted with one or more deuterium atoms or 1-5 groups each independently selected from halo, cyano, haloalkyl, alkyl, alkenyl, alkynyl, hydroxy, alkoxy, haloalkoxy, amino, and oxo; and (iii) $R^y$ and $R^z$, together with the nitrogen atom to which they are attached, form a heteroaryl optionally substituted with one or more deuterium atoms or 1-5 groups each independently selected from halo, cyano, haloalkyl, alkyl, alkenyl, alkynyl, hydroxy, alkoxy, haloalkoxy and amino;

m is an integer from 0 to 4, and n is an integer from 0 to 4.

In certain embodiments, n is 0 or 1. In certain embodiments, n is 0. In certain embodiments, n is 1. In certain embodiments, n is 1 and $R^6$ is halo. In certain embodiments, n is 1 and $R^6$ is fluoro.

In certain embodiments, provided herein is a compound of Formula V, wherein ring A is optionally substituted isoxazolyl.

In certain embodiments, provided herein is a compound of Formula I wherein the compound is selected from:

2-(4-(6,7-dimethoxyquinoxalin-2-yl)phenyl)-N-(5-(1-(trifluoromethyl)cyclopropyl)isoxazol-3-yl)acetamide;

2-(4-(7-methoxyquinolin-3-yl)phenyl)-N-(5-(1-(trifluoromethyl)cyclopropyl)isoxazol-3-yl)acetamide;

2-(4-(5H-pyrrolo[2,3-b]pyrazin-2-yl)phenyl)-N-(5-(1-(trifluoromethyl)cyclopropyl)isoxazol-3-yl)acetamide;

2-(4-(6,7-dimethoxyquinoxalin-2-O-2-fluorophenyl)-N-(5-(1-(trifluoromethyl)cyclopropyl)isoxazol-3-yl)acetamide;

2-(4-(6,7-dimethoxyquinolin-3-yl)phenyl)-N-(5-(1-(trifluoromethyl)cyclopropyl)isoxazol-3-yl)acetamide;

N-(5-(tert-butyl)isoxazol-3-yl)-2-(4-(6,7-dimethoxyquinoxalin-2-yl)phenyl)acetamide;

2-(4-(3-aminoquinoxalin-2-yl)phenyl)-N-(5-(1-(trifluoromethyl)cyclopropyl)isoxazol-3-yl)acetamide;

2-(4-(6,7-dimethoxyquinoxalin-2-yl)phenyl)-N-(5-(1,1,1-trifluoro-2-methylpropan-2-yl)isoxazol-3-yl)acetamide;

2-(4-(5-methyl-5H-pyrrolo[2,3-b]pyrazin-3-yl)phenyl)-N-(5-(1-(trifluoromethyl)cyclopropyl)isoxazol-3-yl)acetamide;

2-(4-(thieno[3,2-b]pyridin-6-yl)phenyl)-N-(5-(1-(trifluoromethyl)cyclopropyl)isoxazol-3-yl)acetamide;

2-(4-(1,5-naphthyridin-3-yl)phenyl)-N-(5-(1-(trifluoromethyl)cyclopropyl)isoxazol-3-yl)acetamide;

2-(4-(1,6-naphthyridin-3-yl)phenyl)-N-(5-(1-(trifluoromethyl)cyclopropyl)isoxazol-3-yl)acetamide;

2-(4-(5,7-dimethoxyquinolin-3-yl)phenyl)-N-(5-(1-(trifluoromethyl)cyclopropyl)isoxazol-3-yl)acetamide;

2-(4-(1H-imidazo[4,5-b]pyrazin-5-yl)phenyl)-N-(5-(1-(trifluoromethyl)cyclopropyl)isoxazol-3-yl)acetamide;

2-(4-(1H-pyrazolo[3,4-b]pyridin-5-yl)phenyl)-N-(5-(1-(trifluoromethyl)cyclopropyl)isoxazol-3-yl)acetamide;

2-(4-(6,7-dimethoxyquinoxalin-2-yl)phenyl)-N-(5-(1-hydroxy-2-methylpropan-2-yl)isoxazol-3-yl)acetamide;

2-(4-(6,7,8,9-tetrahydro-5H-pyrazino[2,3-b]indol-2-yl)phenyl)-N-(5-(1-(trifluoromethyl)cyclopropyl)isoxazol-3-yl)acetamide;

2-(4-(1H-pyrrolo[2,3-b]pyridin-5-yl)phenyl)-N-(5-(1-(trifluoromethyl)cyclopropyl)isoxazol-3-yl)acetamide;

2-(4-(thieno[2,3-b]pyridin-5-yl)phenyl)-N-(5-(1-(trifluoromethyl)cyclopropyl)isoxazol-3-yl)acetamide;

2-(4-(2-methyl-3H-imidazo[4,5-b]pyridin-6-yl)phenyl)-N-(5-(1-(trifluoromethyl)cyclopropyl)isoxazol-3-yl)acetamide;

2-(4-(1-methyl-1H-pyrazolo[4,3-b]pyridin-6-yl)phenyl)-N-(5-(1-(trifluoromethyl)cyclopropyl)isoxazol-3-yl)acetamide;

2-(4-(6-methoxyquinoxalin-2-yl)phenyl)-N-(5-(1-(trifluoromethyl)cyclopropyl)isoxazol-3-yl)acetamide;

2-(4-(7-methoxyquinoxalin-2-yl)phenyl)-N-(5-(1-(trifluoromethyl)cyclopropyl)isoxazol-3-yl)acetamide;

2-(4-(6-(2-methoxyethoxy)quinoxalin-2-yl)phenyl)-N-(5-(1-(trifluoromethyl)cyclopropyl)isoxazol-3-yl)acetamide;

2-(4-(1H-pyrrolo[2,3-b]pyridin-5-yl)phenyl)-N-(5-(tert-butyl)isoxazol-3-yl)acetamide;

2-(4-(1H-pyrrolo[2,3-b]pyridin-5-yl)phenyl)-N-(5-(1,1,1-trifluoro-2-methylpropan-2-yl)isoxazol-3-yl)acetamide;

N-(5-(tert-butyl)isoxazol-3-yl)-2-(2-fluoro-4-(1H-pyrrolo[2,3-b]pyridin-5-yl)phenyl)acetamide;

2-(2-fluoro-4-(1H-pyrrolo[2,3-b]pyridin-5-yl)phenyl)-N-(5-(1-(trifluoromethyl)cyclopropyl)isoxazol-3-yl)acetamide;

2-(2-fluoro-4-(1H-pyrrolo[2,3-b]pyridin-5-yl)phenyl)-N-(5-(1,1,1-trifluoro-2-methylpropan-2-yl)isoxazol-3-yl)acetamide;

2-(2-fluoro-4-(5H-pyrrolo[2,3-b]pyrazin-2-yl)phenyl)-N-(5-(1-(trifluoromethyl)cyclopropyl)isoxazol-3-yl)acetamide;

2-(4-(1H-pyrazolo[3,4-b]pyridin-5-yl)phenyl)-N-(5-(tert-butyl)isoxazol-3-yl)acetamide;

N-(5-(tert-butyl)isoxazol-3-yl)-2-(2-fluoro-4-(1H-pyrazolo[3,4-b]pyridin-5-yl)phenyl)acetamide;

2-(2-fluoro-4-(1H-pyrazolo[3,4-b]pyridin-5-yl)phenyl)-N-(5-(1-(trifluoromethyl)cyclopropyl)isoxazol-3-yl)acetamide;

2-(2-fluoro-4-(1H-pyrazolo[3,4-b]pyridin-5-yl)phenyl)-N-(5-(1,1,1-trifluoro-2-methylpropan-2-yl)isoxazol-3-yl)acetamide;

2-(4-(3-methoxy-1H-pyrazolo[3,4-b]pyridin-5-yl)phenyl)-N-(5-(1,1,1-trifluoro-2-methylpropan-2-yl)isoxazol-3-yl)acetamide;

2-(4-(5,7-dimethoxyquinolin-3-yl)-2-fluorophenyl)-N-(5-(1-(trifluoromethyl)cyclopropyl)isoxazol-3-yl)acetamide;

N-(5-(tert-butyl)isoxazol-3-yl)-2-(4-(3-cyano-1H-pyrazolo[3,4-b]pyridin-5-yl)phenyl)acetamide;

N-(5-(tert-butyl)isoxazol-3-yl)-2-(4-(3-chloro-1H-pyrazolo[3,4-b]pyridin-5-yl)phenyl)acetamide;

2-(4-(3-ethoxy-1H-pyrazolo[3,4-b]pyridin-5-yl)phenyl)-N-(5-(1,1,1-trifluoro-2-methylpropan-2-yl)isoxazol-3-yl)acetamide;

N-(5-(tert-butyl)isoxazol-3-yl)-2-(4-(3-methyl-1H-pyrazolo[3,4-b]pyridin-5-yl)phenyl)acetamide;

2-(4-(3H-[1,2,3]triazolo[4,5-b]pyridin-6-yl)phenyl)-N-(5-(1,1,1-trifluoro-2-methylpropan-2-yl)isoxazol-3-yl)acetamide;

2-(4-(6,7-dimethoxyquinoxalin-2-yl)-3-fluorophenyl)-N-(5-(1-(trifluoromethyl)cyclopropyl)isoxazol-3-yl)acetamide;

N-(5-(tert-butyl)isoxazol-3-yl)-2-(4-(6,7-dimethoxyquinoxalin-2-yl)-2-fluorophenyl)acetamide;

2-(4-(1H-pyrazolo[3,4-b]pyridin-5-yl)phenyl)-N-(5-(1,1,1-trifluoro-2-methylpropan-2-yl)isoxazol-3-yl)acetamide;

5-(4-(2-((5-(tert-butyl)isoxazol-3-yl)amino)-2-oxoethyl)phenyl)-N,N-dimethyl-1H-pyrazolo[3,4-b]pyridine-3-carboxamide;

2-(4-(6,7-dimethoxyquinoxalin-2-yl)-2-fluorophenyl)-N-(5-(1,1,1-trifluoro-2-methylpropan-2-yl)isoxazol-3-yl)acetamide;

2-(4-(3-(2-methoxyethoxy)-1H-pyrazolo[3,4-b]pyridin-5-yl)phenyl)-N-(5-(1,1,1-trifluoro-2-methylpropan-2-yl)isoxazol-3-yl)acetamide;

2-(4-(3-(piperidin-4-yloxy)-1H-pyrazolo[3,4-b]pyridin-5-yl)phenyl)-N-(5-(1,1,1-trifluoro-2-methylpropan-2-yl)isoxazol-3-yl)acetamide formate salt;

2-(4-(3-(piperidin-4-yloxy)-1H-pyrazolo[3,4-b]pyridin-5-yl)phenyl)-N-(5-(1,1,1-trifluoro-2-methylpropan-2-yl)isoxazol-3-yl)acetamide;

5-(4-(2-((5-(tert-butyl)isoxazol-3-yl)amino)-2-oxoethyl)phenyl)-N,N-dimethyl-1H-pyrrolo[2,3-b]pyridine-2-carboxamide;

N-(5-(tert-butyl)isoxazol-3-yl)-2-(4-(2-(hydroxymethyl)-1H-pyrrolo[2,3-b]pyridin-5-yl)phenyl)acetamide;

N-(5-(tert-butyl)isoxazol-3-yl)-2-(2-fluoro-4-(3-methyl-1H-pyrazolo[3,4-b]pyridin-5-yl)phenyl)acetamide;
N-(5-(tert-butyl)isoxazol-3-yl)-2-(4-(2-((dimethylamino)methyl)-1H-pyrrolo[2,3-b]pyridin-5-yl)phenyl)acetamide;
2-(2-fluoro-4-(3-methoxy-1H-pyrazolo[3,4-b]pyridin-5-yl)phenyl)-N-(5-(1-(trifluoromethyl)cyclopropyl)isoxazol-3-yl)acetamide;
N-(5-(tert-butyl)isoxazol-3-yl)-2-(4-(3-((methylamino)methyl)-1H-pyrrolo[2,3-b]pyridin-5-yl)phenyl)acetamide;
N-(5-(tert-butyl)isoxazol-3-yl)-2-(2-fluoro-4-(3-(hydroxymethyl)-1H-pyrazolo[3,4-b]pyridin-5-yl)phenyl)acetamide;
2-(2-fluoro-4-(1H-pyrazolo[3,4-b]pyridin-5-yl)phenyl)-N-(5-(1-(trifluoromethyl)cyclobutyl)isoxazol-3-yl)acetamide;
N-(5-(tert-butyl)isoxazol-3-yl)-2-(2-fluoro-4-(3-((methylamino)methyl)-1H-pyrazolo[3,4-b]pyridin-5-yl)phenyl)acetamide;
N-(5-(tert-butyl)isoxazol-3-yl)-2-(4-(3-((dimethylamino)methyl)-1H-pyrazolo[3,4-b]pyridin-5-yl)-2-fluorophenyl)acetamide;
N-(5-(tert-butyl)isoxazol-3-yl)-2-(4-(3-((dimethylamino)methyl)-1H-pyrrolo[2,3-b]pyridin-5-yl)phenyl)acetamide formate salt;
N-(5-(tert-butyl)isoxazol-3-yl)-2-(4-(3-((dimethylamino)methyl)-1H-pyrrolo[2,3-b]pyridin-5-yl)phenyl)acetamide;
N-(5-(tert-butyl)isoxazol-3-yl)-2-(4-(3-(hydroxymethyl)-1H-pyrrolo[2,3-b]pyridin-5-yl)phenyl)acetamide;
2-(4-(3-(dimethylamino)-1H-pyrazolo[3,4-b]pyridin-5-yl)-2-fluorophenyl)-N-(5-(1-(trifluoromethyl)cyclopropyl)isoxazol-3-yl)acetamide;
N-(5-(tert-butyl)isoxazol-3-yl)-2-(2-fluoro-4-(3-(1-hydroxyethyl)-1H-pyrazolo[3,4-b]pyridin-5-yl)phenyl)acetamide;
2-(2-fluoro-4-(3-methoxy-1H-pyrazolo[3,4-b]pyridin-5-yl)phenyl)-N-(5-(1,1,1-trifluoro-2-methylpropan-2-yl)isoxazol-3-yl)acetamide;
5-(4-(2-((5-(tert-butyl)isoxazol-3-yl)amino)-2-oxoethyl)phenyl)-N-(2-hydroxyethyl)-1H-pyrrolo[2,3-b]pyridine-2-carboxamide;
5-(4-(2-((5-(tert-butyl)isoxazol-3-yl)amino)-2-oxoethyl)phenyl)-N-methyl-1H-pyrrolo[2,3-b]pyridine-2-carboxamide;
5-(4-(2-((5-(tert-butyl)isoxazol-3-yl)amino)-2-oxoethyl)phenyl)-N-(2-(dimethylamino)ethyl)-1H-pyrrolo[2,3-b]pyridine-2-carboxamide;
5-(4-(2-((5-(tert-butyl)isoxazol-3-yl)amino)-2-oxoethyl)phenyl)-N-(3-(dimethylamino)propyl)-N-methyl-1H-pyrrolo[2,3-b]pyridine-2-carboxamide;
5-(4-(2-((5-(tert-butyl)isoxazol-3-yl)amino)-2-oxoethyl)phenyl)-N-(2-(methylsulfonyl)ethyl)-1H-pyrrolo[2,3-b]pyridine-2-carboxamide;
5-(4-(2-((5-(tert-butyl)isoxazol-3-yl)amino)-2-oxo ethyl)phenyl)-N-(1-methylpiperidin-4-yl)-1H-pyrrolo[2,3-b]pyridine-2-carboxamide;
2-(2-fluoro-4-(2-(hydroxymethyl)-1H-pyrrolo[2,3-b]pyridin-5-yl)phenyl)-N-(5-(1-(trifluoromethyl)cyclopropyl)isoxazol-3-yl)acetamide;
2-(4-(1H-pyrrolo[2,3-b]pyridin-5-yl)phenyl)-N-(3-(tert-butyl)isoxazol-5-yl)acetamide;
2-(4-(6,7-dimethoxyquinoxalin-2-yl)phenyl)-N-(3-(1-(trifluoromethyl)cyclopropyl)isoxazol-5-yl)acetamide;
N-(3-(tert-butyl)isoxazol-5-yl)-2-(4-(6,7-dimethoxyquinoxalin-2-yl)phenyl)acetamide;
((2-(3-fluoro-4-(2-oxo-2-((5-(1-(trifluoromethyl)cyclopropyl)isoxazol-3-yl)amino)ethyl)phenyl)quinoxaline-6,7-diyl)bis(oxy))bis(ethane-2,1-diyl) diacetate;
2-(4-(6,7-bis(2-hydroxyethoxy)quinoxalin-2-yl)-2-fluorophenyl)-N-(5-(1-(trifluoromethyl)cyclopropyl)isoxazol-3-yl)acetamide;
2-(4-(2,3-dihydro-[1,4]dioxino[2,3-g]quinoxalin-7-yl)-2-fluorophenyl)-N-(5-(1-(trifluoromethyl)cyclopropyl)isoxazol-3-yl)acetamide;
2-(2-fluoro-4-(6-methoxy-7-(2-methoxyethoxy)quinoxalin-2-yl)phenyl)-N-(5-(1-(trifluoromethyl)cyclopropyl)isoxazol-3-yl)acetamide;
2-(2-fluoro-4-(7-methoxy-6-(2-methoxyethoxy)quinoxalin-2-yl)phenyl)-N-(5-(1-(trifluoromethyl)cyclopropyl)isoxazol-3-yl)acetamide;
2-(2-fluoro-4-(6-hydroxy-7-methoxyquinoxalin-2-yl)phenyl)-N-(5-(1-(trifluoromethyl)cyclopropyl)isoxazol-3-yl)acetamide;
2-(2-fluoro-4-(7-methoxy-6-(2-morpholinoethoxy)quinoxalin-2-yl)phenyl)-N-(5-(1-(trifluoromethyl)cyclopropyl)isoxazol-3-yl)acetamide;
2-(2-fluoro-4-(7-(2-hydroxyethoxy)-6-methoxyquinoxalin-2-yl)phenyl)-N-(5-(1-(trifluoromethyl)cyclopropyl)isoxazol-3-yl)acetamide;
2-(2-fluoro-4-(7-methoxy-6-(2-(4-methylpiperazin-1-yl)ethoxy)quinoxalin-2-yl)phenyl)-N-(5-(1-(trifluoromethyl)cyclopropyl)isoxazol-3-yl)acetamide;
2-(4-(6-(2-(3,3-difluoropyrrolidin-1-yl)ethoxy)-7-methoxyquinoxalin-2-yl)-2-fluorophenyl)-N-(5-(1-(trifluoromethyl)cyclopropyl)isoxazol-3-yl)acetamide;
2-(4-(6-bromo-7-methoxyquinoxalin-2-yl)-2-fluorophenyl)-N-(5-(1-(trifluoromethyl)cyclopropyl)isoxazol-3-yl)acetamide;
2-(4-(6-(2,3-dihydroxypropyl)-7-methoxyquinoxalin-2-yl)-2-fluorophenyl)-N-(5-(1-(trifluoromethyl)cyclopropyl)isoxazol-3-yl)acetamide;
2-(2-fluoro-4-(7-methoxy-6-((2-morpholinoethyl)amino)quinoxalin-2-yl)phenyl)-N-(5-(1-(trifluoromethyl)cyclopropyl)isoxazol-3-yl)acetamide;
2-(4-(7-ethoxy-6-methoxyquinolin-3-yl)-2-fluorophenyl)-N-(5-(1-(trifluoromethyl)cyclopropyl)isoxazol-3-yl)acetamide;
2-(2-Fluoro-4-{6-[2-(3-fluoro-4-hydroxy-piperidin-1-yl)-ethoxy]-7-methoxy-quinolin-3-yl}-phenyl)-N-[5-(2,2,2-trifluoro-1,1-dimethyl-ethyl)-isoxazol-3-yl]-acetamide;
2-(2-fluoro-4-(7-(2-hydroxyethoxy)-6-methoxyquinolin-3-yl)phenyl)-N-(5-(1-(trifluoromethyl)cyclopropyl)isoxazol-3-yl)acetamide;
2-(4-(6-(azetidin-3-yloxy)-7-methoxyquinoxalin-2-O-2-fluorophenyl)-N-(5-(1-(trifluoromethyl)cyclopropyl)isoxazol-3-yl)acetamide;
2-(2-fluoro-4-(7-methoxy-6-((1-methylazetidin-3-yl)oxy)quinoxalin-2-yl)phenyl)-N-(5-(1-(trifluoromethyl)cyclopropyl)isoxazol-3-yl)acetamide;
2-(2-fluoro-4-(7-(2-hydroxyethoxy)-6-methoxyquinolin-3-yl)phenyl)-N-(5-(1,1,1-trifluoro-2-methylpropan-2-yl)isoxazol-3-yl)acetamide;
N-(5-(tert-butyl)isoxazol-3-yl)-2-(2-fluoro-4-(7-methoxy-6-(2-morpholinoethoxy)quinoxalin-2-yl)phenyl)acetamide;
2-(4-(7-methoxy-6-(2-morpholinoethoxy)quinoxalin-2-yl)phenyl)-N-(5-(1,1,1-trifluoro-2-methylpropan-2-yl)isoxazol-3-yl)acetamide;
2-(2-fluoro-4-(7-methoxy-6-(2-morpholinoethoxy)quinoxalin-2-yl)phenyl)-N-(1-methyl-3-(1,1,1-trifluoro-2-methylpropan-2-yl)-1H-pyrazol-5-yl)acetamide;

2-(2-fluoro-4-(7-methoxy-6-(2-morpholinoethoxy)quinoxalin-2-yl)phenyl)-N-(3-(1-methylcyclopropyl)isoxazol-5-yl)acetamide;

2-(4-(6-(2-(3,3-dimethylmorpholino)ethoxy)-7-methoxy-quinoxalin-2-yl)-2-fluorophenyl)-N-(5-(1-(trifluoromethyl)cyclopropyl)isoxazol-3-yl)acetamide;

N-(5-tert-butylisoxazol-3-yl)-2-[4-[3-(3-hydroxyoxetan-3-yl)-1H-pyrrolo[2,3-b]pyridin-5-yl]phenyl]acetamide;

2-[2-fluoro-4-[2-(hydroxymethyl)-2,3-dihydrooxazolo[3,4]pyrazolo[1,3-b]pyridin-8-yl]phenyl]-N-[5-[1-(trifluoromethyl)cyclopropyl]isoxazol-3-yl]acetamide;

N-(5-tert-butylisoxazol-3-yl)-2-[4-[2-(4-methylpiperazine-1-carbonyl)-1H-pyrrolo[2,3-b]pyridin-5-yl]phenyl]acetamide;

5-[4-[2-[(5-tert-butylisoxazol-3-yl)amino]-2-oxo-ethyl]phenyl]-N-[2-(dimethylamino)ethyl]-1H-pyrazolo[3,4-b]pyridine-3-carboxamide;

N-(5-tert-butylisoxazol-3-yl)-2-[4-[3-(triazol-2-yl)-1H-pyrazolo[3,4-b]pyridin-5-yl]phenyl]acetamide;

2-[4-[3-(2,2-difluoroethoxy)-1H-pyrazolo[3,4-b]pyridin-5-yl]-2-fluoro-phenyl]-N-[5-[1-(trifluoromethyl)cyclopropyl]isoxazol-3-yl]acetamide;

N-(5-tert-butylisoxazol-3-yl)-2-[4-[3-(triazol-1-yl)-1H-pyrazolo[3,4-b]pyridin-5-yl]phenyl]acetamide;

2-[2-fluoro-4-[3-(2-fluoroethoxy)-1H-pyrazolo[3,4-b]pyridin-5-yl]phenyl]-N-[5-[1-(trifluoromethyl)cyclopropyl]isoxazol-3-yl]acetamide;

2-[4-[6-[2-(4-ethylpiperazin-1-yl)ethoxy]-7-methoxy-quinoxalin-2-yl]-2-fluoro-phenyl]-N-[5-[1-(trifluoromethyl)cyclopropyl]isoxazol-3-yl]acetamide;

5-[3-fluoro-4-[2-oxo-2-[[5-[1-(trifluoromethyl)cyclopropyl]isoxazol-3-yl]amino]ethyl]phenyl]-1H-pyrrolo[2,3-b]pyridine-2-carboxylic acid;

5-[3-fluoro-4-[2-oxo-2-[[5-[1-(trifluoromethyl)cyclopropyl]isoxazol-3-yl]amino]ethyl]phenyl]-N-(2-methylsulfonylethyl)-1H-pyrrolo[2,3-b]pyridine-2-carboxamide;

N-[2-(dimethylamino)ethyl]-5-[3-fluoro-4-[2-oxo-2-[[5-[1-(trifluoromethyl)cyclopropyl]isoxazol-3-yl]amino]ethyl]phenyl]-1H-pyrrolo[2,3-b]pyridine-2-carboxamide;

N-(5-tert-butylisoxazol-3-yl)-2-[4-[3-(1-methylpyrazol-4-yl)-1H-pyrazolo[3,4-b]pyridin-5-yl]phenyl]acetamide;

2-[4-[2-[3-(dimethylamino)pyrrolidine-1-carbonyl]-1H-pyrrolo[2,3-b]pyridin-5-yl]-2-fluoro-phenyl]-N-[5-[1-(trifluoromethyl)cyclopropyl]isoxazol-3-yl]acetamide;

2-[2-fluoro-4-[2-(3-hydroxyazetidine-1-carbonyl)-1H-pyrrolo[2,3-b]pyridin-5-yl]phenyl]-N-[5-[1-(trifluoromethyl)cyclopropyl]isoxazol-3-yl]acetamide;

N-(azetidin-3-yl)-5-[3-fluoro-4-[2-oxo-2-[[5-[1-(trifluoromethyl)cyclopropyl]isoxazol-3-yl]amino]ethyl]phenyl]-1H-pyrrolo[2,3-b]pyridine-2-carboxamide;

5-[3-fluoro-4-[2-oxo-2-[[5-[1-(trifluoromethyl)cyclopropyl]isoxazol-3-yl]amino]ethyl]phenyl]-N-(1-methylazetidin-3-yl)-1H-pyrrolo[2,3-b]pyridine-2-carboxamide;

2-[2-fluoro-4-[3-[2-(trifluoromethoxy)ethoxy]-1H-pyrazolo[3,4-b]pyridin-5-yl]phenyl]-N-[5-(2,2,2-trifluoro-1,1-dimethyl-ethyl)isoxazol-3-yl]acetamide;

2-[2-fluoro-4-(5,6,7-trimethoxy-3-quinolyl)phenyl]-N-[5-(2,2,2-trifluoro-1,1-dimethyl-ethyl)isoxazol-3-yl]acetamide;

N-(5-tert-butylisoxazol-3-yl)-2-[4-(5,6,7-trimethoxy-3-quinolyl)phenyl]acetamide;

2-[4-[2-(dimethylaminocarbamoyl)-1H-pyrrolo[2,3-b]pyridin-5-yl]-2-fluoro-phenyl]-N-[5-[1-(trifluoromethyl)cyclopropyl]isoxazol-3-yl]acetamide;

2-[4-(6,7-diethoxyquinoxalin-2-yl)-2-fluoro-phenyl]-N-[5-[1-(trifluoromethyl)cyclopropyl]isoxazol-3-yl]acetamide;

2-[4-([1,3]dioxolo[4,5-g]quinoxalin-6-yl)-2-fluoro-phenyl]-N-[5-[1-(trifluoromethyl)cyclopropyl]isoxazol-3-yl]acetamide;

2-[4-[6,7-bis(2-methoxyethoxy)quinoxalin-2-yl]phenyl]-N-(5-tert-butylisoxazol-3-yl)acetamide;

2-[2-fluoro-4-[(2R)-2-(hydroxymethyl)-2,3-dihydro-[1,4]dioxino[2,3-g]quinoxalin-7-yl]phenyl]-N-[5-[1-(trifluoromethyl)cyclopropyl]isoxazol-3-yl]acetamide;

2-[2-fluoro-4-[(3R)-3-(hydroxymethyl)-2,3-dihydro-[1,4]dioxino[2,3-g]quinoxalin-7-yl]phenyl]-N-[5-[1-(trifluoromethyl)cyclopropyl]isoxazol-3-yl]acetamide;

2-[4-(3-amino-6,7-dimethoxy-quinoxalin-2-yl)-2-fluoro-phenyl]-N-[5-[1-(trifluoromethyl)cyclopropyl]isoxazol-3-yl]acetamide;

2-[2-fluoro-4-(3,6,7-trimethoxyquinoxalin-2-yl)phenyl]-N-[5-[1-(trifluoromethyl)cyclopropyl]isoxazol-3-yl]acetamide;

2-[4-[6,7-bis(2-methoxyethoxy)quinoxalin-2-yl]-2-fluoro-phenyl]-N-[5-[1-(trifluoromethyl)cyclopropyl]isoxazol-3-yl]acetamide;

2-[2-fluoro-4-[6-methoxy-7-(2-methoxyethoxy)-3-quinolyl]phenyl]-N-[5-[1-(trifluoromethyl)cyclopropyl]isoxazol-3-yl]acetamide;

2-[[3-[3-fluoro-4-[2-oxo-2-[[5-[1-(trifluoromethyl)cyclopropyl]isoxazol-3-yl]amino]ethyl]phenyl]-6-methoxy-7-quinolyl]oxy]ethyl acetate;

2-[4-(6,7-dimethoxy-3-quinolyl)-2-fluoro-phenyl]-N-[5-[1-(trifluoromethyl)cyclopropyl]isoxazol-3-yl]acetamide;

2-[4-(6,7-dimethoxy-3-quinolyl)-2-fluoro-phenyl]-N-[5-(2,2,2-trifluoro-1,1-dimethyl-ethyl)isoxazol-3-yl]acetamide;

2-[2-[3-fluoro-4-[2-oxo-2-[[5-[1-(trifluoromethyl)cyclopropyl]isoxazol-3-yl]amino]ethyl]phenyl]-7-methoxy-quinoxalin-6-yl]oxyethyl acetate;

2-[2-fluoro-4-[6-(2-hydroxyethoxy)-7-methoxy-quinoxalin-2-yl]phenyl]-N-[5-[1-(trifluoromethyl)cyclopropyl]isoxazol-3-yl]acetamide;

ethyl 3-[3-fluoro-4-[2-oxo-2-[[5-[1-(trifluoromethyl)cyclopropyl]isoxazol-3-yl]amino]ethyl]phenyl]-6,7-dimethoxy-quinoxaline-2-carboxylate;

3-[3-fluoro-4-[2-oxo-2-[[5-[1-(trifluoromethyl)cyclopropyl]isoxazol-3-yl]amino]ethyl]phenyl]-6,7-dimethoxy-quinoxaline-2-carboxylic acid;

2-[2-fluoro-4-[7-methoxy-6-(2-pyrrolidin-1-ylethoxy)quinoxalin-2-yl]phenyl]-N-[5-[1-(trifluoromethyl)cyclopropyl]isoxazol-3-yl]acetamide;

3-[3-fluoro-4-[2-oxo-2-[[5-[1-(trifluoromethyl)cyclopropyl]isoxazol-3-yl]amino]ethyl]phenyl]-6,7-dimethoxy-quinoxaline-2-carboxamide;

2-[2-[3-fluoro-4-[2-oxo-2-[[5-[1-(trifluoromethyl)cyclopropyl]isoxazol-3-yl]amino]ethyl]phenyl]-7-methoxy-quinoxalin-6-yl]oxyethyl N,N-dimethylcarbamate;

2-[2-fluoro-4-[3-(hydroxymethyl)-6,7-dimethoxy-quinoxalin-2-yl]phenyl]-N-[5-[1-(trifluoromethyl)cyclopropyl]isoxazol-3-yl]acetamide;

2-[4-(4-chloro-6,7-dimethoxy-3-quinolyl)-2-fluoro-phenyl]-N-[5-(2,2,2-trifluoro-1,1-dimethyl-ethyl)isoxazol-3-yl]acetamide;

N-(5-tert-butyl-2-methyl-pyrazol-3-yl)-2-[4-(6,7-dimethoxyquinoxalin-2-yl)-2-fluoro-phenyl]acetamide;

N-(5-tert-butyl-2-phenyl-pyrazol-3-yl)-2-[4-(6,7-dimethoxyquinoxalin-2-yl)-2-fluoro-phenyl]acetamide;

2-[4-(4-azido-6,7-dimethoxy-3-quinolyl)-2-fluoro-phenyl]-N-[5-(2,2,2-trifluoro-1,1-dimethyl-ethyl)isoxazol-3-yl]acetamide;

2-[4-[6-(1-ethylazetidin-3-yl)oxy-7-methoxy-quinoxalin-2-yl]-2-fluoro-phenyl]-N-[5-[1-(trifluoromethyl)cyclopropyl]isoxazol-3-yl]acetamide;

2-[4-(4-amino-6,7-dimethoxy-3-quinolyl)-2-fluoro-phenyl]-N-[5-(2,2,2-trifluoro-1,1-dimethyl-ethyl)isoxazol-3-yl]acetamide;

2-[2-fluoro-4-[7-methoxy-6-(oxetan-3-yloxy)quinoxalin-2-yl]phenyl]-N-[5-[1-(trifluoromethyl)cyclopropyl]isoxazol-3-yl]acetamide;

2-[2-fluoro-4-(4,6,7-trimethoxy-3-quinolyl)phenyl]-N-[5-(2,2,2-trifluoro-1,1-dimethyl-ethyl)isoxazol-3-yl]acetamide;

2-[4-(3-chloro-6,7-dimethoxy-quinoxalin-2-yl)-2-fluoro-phenyl]-N-[5-[1-(trifluoromethyl)cyclopropyl]isoxazol-3-yl]acetamide;

2-[2-fluoro-4-[7-methoxy-6-(oxetan-3-yloxy)quinoxalin-2-yl]phenyl]-N-[5-(2,2,2-trifluoro-1,1-dimethyl-ethyl)isoxazol-3-yl]acetamide;

2-[4-[6-(azetidin-3-yloxy)-7-methoxy-quinoxalin-2-yl]-2-fluoro-phenyl]-N-[5-(2,2,2-trifluoro-1,1-dimethyl-ethyl)isoxazol-3-yl]acetamide;

2-[4-[6-(1-ethylazetidin-3-yl)oxy-7-methoxy-quinoxalin-2-yl]-2-fluoro-phenyl]-N-[5-(2,2,2-trifluoro-1,1-dimethyl-ethyl)isoxazol-3-yl]acetamide;

2-[2-fluoro-4-[7-methoxy-6-(1-methylazetidin-3-yl)oxy-quinoxalin-2-yl]phenyl]-N-[5-(2,2,2-trifluoro-1,1-dimethyl-ethyl)isoxazol-3-yl]acetamide;

2-[4-(8-amino-3-quinolyl)-2-fluoro-phenyl]-N-[5-(2,2,2-trifluoro-1,1-dimethyl-ethyl)isoxazol-3-yl]acetamide;

2-[4-(6,7-dimethoxy-3-hydroxy-quinoxalin-2-yl)-2-fluoro-phenyl]-N-[5-[1-(trifluoromethyl)cyclopropyl]isoxazol-3-yl]acetamide;

N-(3-tert-butyl-1H-pyrazol-5-yl)-2-[4-(6,7-dimethoxyquinoxalin-2-yl)-2-fluoro-phenyl]acetamide;

2-[4-[6,7-bis[2-(dimethylamino)-2-oxo-ethoxy]quinoxalin-2-yl]-2-fluoro-phenyl]-N-[5-[1-(trifluoromethyl)cyclopropyl]isoxazol-3-yl]acetamide;

2-[2-fluoro-4-(6-methoxypyrido[2,3-b]pyrazin-3-yl)phenyl]-N-[5-[1-(trifluoromethyl)cyclopropyl]isoxazol-3-yl]acetamide;

2-[2-fluoro-4-(6-methoxypyrido[2,3-b]pyrazin-2-yl)phenyl]-N-[5-[1-(trifluoromethyl)cyclopropyl]isoxazol-3-yl]acetamide;

2-[4-(7-benzyloxy-6-methoxy-quinoxalin-2-yl)-2-fluoro-phenyl]-N-[5-[1-(trifluoromethyl)cyclopropyl]isoxazol-3-yl]acetamide;

2-[2-fluoro-4-(7-hydroxy-6-methoxy-quinoxalin-2-yl)phenyl]-N-[5-[1-(trifluoromethyl)cyclopropyl]isoxazol-3-yl]acetamide;

2-[4-[7-[2-(dimethylamino)ethoxy]-6-methoxy-quinoxalin-2-yl]-2-fluoro-phenyl]-N-[5-[1-(trifluoromethyl)cyclopropyl]isoxazol-3-yl]acetamide;

2-[2-fluoro-4-[7-methoxy-6-(2-methoxyethoxy)quinoxalin-2-yl]phenyl]-N-[5-(2,2,2-trifluoro-1,1-dimethyl-ethyl)isoxazol-3-yl]acetamide;

2-[2-fluoro-4-[6-methoxy-7-(2-methoxyethoxy)quinoxalin-2-yl]phenyl]-N-[5-(2,2,2-trifluoro-1,1-dimethyl-ethyl)isoxazol-3-yl]acetamide;

N-(5-tert-butyl-2-methyl-pyrazol-3-yl)-2-[2-fluoro-4-[6-methoxy-7-(2-methoxyethoxy)quinoxalin-2-yl]phenyl]acetamide;

N-(5-tert-butyl-2-methyl-pyrazol-3-yl)-2-[2-fluoro-4-[7-methoxy-6-(2-methoxyethoxy)quinoxalin-2-yl]phenyl]acetamide;

2-[4-(6-benzyloxy-7-methoxy-quinoxalin-2-yl)-2-fluoro-phenyl]-N-[5-[1-(trifluoromethyl)cyclopropyl]isoxazol-3-yl]acetamide;

2-[2-fluoro-4-(6-hydroxy-7-methoxy-quinoxalin-2-yl)phenyl]-N-[5-(2,2,2-trifluoro-1,1-dimethyl-ethyl)isoxazol-3-yl]acetamide;

2-[2-fluoro-4-[6-(2-hydroxyethoxy)-7-methoxy-quinoxalin-2-yl]phenyl]-N-[5-(2,2,2-trifluoro-1,1-dimethyl-ethyl)isoxazol-3-yl]acetamide;

2-[4-[6-(2-azidoethoxy)-7-methoxy-quinoxalin-2-yl]-2-fluoro-phenyl]-N-[5-[1-(trifluoromethyl)cyclopropyl]isoxazol-3-yl]acetamide;

2-[4-[6-(2-aminoethoxy)-7-methoxy-quinoxalin-2-yl]-2-fluoro-phenyl]-N-[5-[1-(trifluoromethyl)cyclopropyl]isoxazol-3-yl]acetamide;

2-[4-[6-(2-acetamidoethoxy)-7-methoxy-quinoxalin-2-yl]-2-fluoro-phenyl]-N-[5-[1-(trifluoromethyl)cyclopropyl]isoxazol-3-yl]acetamide;

2-[4-(6,7-dimethoxy-3-methyl-quinoxalin-2-yl)-2-fluoro-phenyl]-N-[5-[1-(trifluoromethyl)cyclopropyl]isoxazol-3-yl]acetamide;

2-[2-fluoro-4-[7-(2-hydroxyethoxy)-6-methoxy-quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(2-morpholinoethoxy)quinoxalin-2-yl]phenyl]-N-[5-(2,2,2-trifluoro-1,1-dimethyl-ethyl)isoxazol-3-yl]acetamide;

2-[4-(6,7-dimethoxyquinoxalin-2-yl)-2-fluoro-phenyl]-N-[2-methyl-5-[1-(trifluoromethyl)cyclopropyl]pyrazol-3-yl]acetamide;

N-[2-tert-butyl-5-[1-(trifluoromethyl)cyclopropyl]pyrazol-3-yl]-2-[4-(6,7-dimethoxyquinoxalin-2-yl)-2-fluoro-phenyl]acetamide;

2-[4-[6-[2-(2,6-dimethylmorpholin-4-yl)ethoxy]-7-methoxy-quinoxalin-2-yl]-2-fluoro-phenyl]-N-[5-[1-(trifluoromethyl)cyclopropyl]isoxazol-3-yl]acetamide;

2-[2-fluoro-4-[7-methoxy-6-[2-(methylamino)ethoxy]quinoxalin-2-yl]phenyl]-N-[5-[1-(trifluoromethyl)cyclopropyl]isoxazol-3-yl]acetamide;

2-[4-[6-[2-[acetylmethyl)amino]ethoxy]-7-methoxy-quinoxalin-2-yl]-2-fluoro-phenyl]-N-[5-[1-(trifluoromethyl)cyclopropyl]isoxazol-3-yl]acetamide;

2-[2-fluoro-4-[7-methoxy-6-(2-methoxyethoxy)-3-quinolyl]phenyl]-N-[5-(2,2,2-trifluoro-1,1-dimethyl-ethyl)isoxazol-3-yl]acetamide;

2-[2-fluoro-4-[6-(2-hydroxyethoxy)-7-methoxy-3-quinolyl]phenyl]-N-[5-(2,2,2-trifluoro-1,1-dimethyl-ethyl)isoxazol-3-yl]acetamide;

2-[2-fluoro-4-[6-(2-hydroxyethoxy)-7-methoxy-3-quinolyl]phenyl]-N-[5-[1-(trifluoromethyl)cyclopropyl]isoxazol-3-yl]acetamide;

2-[4-(6,7-dimethoxyquinoxalin-2-yl)-2-fluoro-phenyl]-N-[3-[1-(trifluoromethyl)cyclopropyl]-1H-pyrazol-5-yl]acetamide;

2-[4-(6,7-dimethoxyquinoxalin-2-yl)-2-fluoro-phenyl]-N-[2-methyl-5-(2,2,2-trifluoro-1,1-dimethyl-ethyl)pyrazol-3-yl]acetamide;

2-[4-(6,7-dimethoxyquinoxalin-2-yl)-2-fluoro-phenyl]-N-[3-(2,2,2-trifluoro-1,1-dimethyl-ethyl)-1H-pyrazol-5-yl]acetamide;

2-[4-[6-(cyanomethoxy)-7-methoxy-quinoxalin-2-yl]-2-fluoro-phenyl]-N-[5-[1-(trifluoromethyl)cyclopropyl]isoxazol-3-yl]acetamide 2-[2-fluoro-4-(7-hydroxy-6-methoxy-quinoxalin-2-yl)phenyl]-N-[5-(2,2,2-trifluoro-1,1-dimethyl-ethyl)isoxazol-3-yl]acetamide;

2-[2-fluoro-4-[7-methoxy-6-[2-(1,2,4-triazol-1-yl)ethoxy]quinoxalin-2-yl]phenyl]-N-[5-[1-(trifluoromethyl)cyclopropyl]isoxazol-3-yl]acetamide;

2-[4-[6-[2-(dimethylamino)-2-oxo-ethoxy]-7-methoxy-quinoxalin-2-yl]-2-fluoro-phenyl]-N-[5-[1-(trifluoromethyl)cyclopropyl]isoxazol-3-yl]acetamide;

2-[2-fluoro-4-[6-methoxy-7-(2-morpholinoethoxy)quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(2-methoxyethoxy)-3-quinolyl]phenyl]-N-[5-[1-(trifluoromethyl)cyclopropyl]isoxazol-3-yl]acetamide;

2-[2-fluoro-4-[7-methoxy-6-(2-morpholinoethoxy)-3-quinolyl]phenyl]-N-[5-(2,2,2-trifluoro-1,1-dimethyl-ethyl)isoxazol-3-yl]acetamide;

2-[2-fluoro-4-[7-methoxy-6-(2-morpholinoethoxy)-3-quinolyl]phenyl]-N-[5-[1-(trifluoromethyl)cyclopropyl]isoxazol-3-yl]acetamide;

2-[2-fluoro-4-[7-[2-[(3S)-3-hydroxypyrrolidin-1-yl]ethoxy]-6-methoxy-quinoxalin-2-yl]phenyl]-N-[5-(2,2,2-trifluoro-1,1-dimethyl-ethyl)isoxazol-3-yl]acetamide;

2-[4-[6-(2-aminoethoxy)-7-methoxy-3-quinolyl]-2-fluoro-phenyl]-N-[5-[1-(trifluoromethyl)cyclopropyl]isoxazol-3-yl]acetamide;

2-[4-[6-(2-acetamidoethoxy)-7-methoxy-3-quinolyl]-2-fluoro-phenyl]-N-[5-[1-(trifluoromethyl)cyclopropyl]isoxazol-3-yl]acetamide;

2-[4-(6,7-dimethoxyquinoxalin-2-yl)-2-fluoro-phenyl]-N-(4,4-dimethyl-5,6-dihydropyrrolo[1,2-b]pyrazol-2-yl)acetamide;

2-[2-fluoro-4-[6-(3-hydroxypropoxy)-7-methoxy-quinoxalin-2-yl]phenyl]-N-[5-[1-(trifluoromethyl)cyclopropyl]isoxazol-3-yl]acetamide;

2-[2-fluoro-4-[6-methoxy-7-[2-(methylamino)ethoxy]quinoxalin-2-yl]phenyl]-N-[5-(2,2,2-trifluoro-1,1-dimethyl-ethyl)isoxazol-3-yl]acetamide;

2-[2-fluoro-4-[6-methoxy-7-(2-morpholinoethoxy)-3-quinolyl]phenyl]-N-[5-(2,2,2-trifluoro-1,1-dimethyl-ethyl)isoxazol-3-yl]acetamide;

2-[4-[7-[2-[acetylmethyl]amino]ethoxy]-6-methoxy-quinoxalin-2-yl]-2-fluoro-phenyl]-N-[5-(2,2,2-trifluoro-1,1-dimethyl-ethyl)isoxazol-3-yl]acetamide;

2-[2-fluoro-4-[7-[2-[(3R)-3-hydroxypyrrolidin-1-yl]ethoxy]-6-methoxy-3-quinolyl]phenyl]-N-[5-(2,2,2-trifluoro-1,1-dimethyl-ethyl)isoxazol-3-yl]acetamide;

2-[2-fluoro-4-[7-[2-[2-hydroxyethyl(methyl)amino]ethoxy]-6-methoxy-3-quinolyl]phenyl]-N-[5-(2,2,2-trifluoro-1,1-dimethyl-ethyl)isoxazol-3-yl]acetamide;

2-[2-fluoro-4-[7-[2-(2-hydroxyethylamino)ethoxy]-6-methoxy-3-quinolyl]phenyl]-N-[5-(2,2,2-trifluoro-1,1-dimethyl-ethyl)isoxazol-3-yl]acetamide;

2-[2-fluoro-4-[7-[(2R)-2-hydroxypropoxy]-6-methoxy-quinoxalin-2-yl]phenyl]-N-[5-[1-(trifluoromethyl)cyclopropyl]isoxazol-3-yl]acetamide;

2-[2-fluoro-4-[6-methoxy-7-(3-morpholinopropoxy)quinoxalin-2-yl]phenyl]-N-[5-(2,2,2-trifluoro-1,1-dimethyl-ethyl)isoxazol-3-yl]acetamide;

2-[4-[6-(2-aminoethoxy)-7-methoxy-3-quinolyl]-2-fluoro-phenyl]-N-[5-(2,2,2-trifluoro-1,1-dimethyl-ethyl)isoxazol-3-yl]acetamide;

2-[4-[6-(2-acetamidoethoxy)-7-methoxy-3-quinolyl]-2-fluoro-phenyl]-N-[5-(2,2,2-trifluoro-1,1-dimethyl-ethyl)isoxazol-3-yl]acetamide;

2-[2-fluoro-4-[6-[2-(4-hydroxy-1-piperidyl)ethoxy]-7-methoxy-3-quinolyl]phenyl]-N-[5-(2,2,2-trifluoro-1,1-dimethyl-ethyl)isoxazol-3-yl]acetamide;

2-[4-[6-[2-(4,4-difluoro-1-piperidyl)ethoxy]-7-methoxy-3-quinolyl]-2-fluoro-phenyl]-N-[5-(2,2,2-trifluoro-1,1-dimethyl-ethyl)isoxazol-3-yl]acetamide;

2-[2-fluoro-4-[6-[(2R)-2-hydroxypropoxy]-7-methoxy-quinoxalin-2-yl]phenyl]-N-[5-[1-(trifluoromethyl)cyclopropyl]isoxazol-3-yl]acetamide;

2-[2-fluoro-4-[7-methoxy-6-(3-morpholinopropoxy)quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-[2-(1,2,4-triazol-1-yl)ethoxy]quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-[2-(1,2,4-triazol-4-yl)ethoxy]quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(3-morpholinopropoxy)quinoxalin-2-yl]phenyl]-N-[5-[1-(trifluoromethyl)cyclopropyl]isoxazol-3-yl]acetamide;

2-[2-fluoro-4-[6-methoxy-7-(3-morpholinopropoxy)quinoxalin-2-yl]phenyl]-N-[5-[1-(trifluoromethyl)cyclopropyl]isoxazol-3-yl]acetamide;

2-[4-[7-(3-acetamidopropoxy)-6-methoxy-quinoxalin-2-yl]-2-fluoro-phenyl]-N-[5-[1-(trifluoromethyl)cyclopropyl]isoxazol-3-yl]acetamide;

N-(5-tert-butylisoxazol-3-yl)-2-[4-[7-methoxy-6-(2-morpholinoethoxy)quinoxalin-2-yl]phenyl]acetamide;

2-[4-[6-[2-(1,1-dioxo-1,4-thiazinan-4-yl)ethoxy]-7-methoxy-quinoxalin-2-yl]-2-fluoro-phenyl]-N-[5-[1-(trifluoromethyl)cyclopropyl]isoxazol-3-yl]acetamide;

2-[4-(6,7-dimethoxyquinoxalin-2-yl)-3-fluoro-phenyl]-N-[5-(2,2,2-trifluoro-1,1-dimethyl-ethyl)isoxazol-3-yl]acetamide;

2-[4-(6,7-dimethoxyquinoxalin-2-yl)-2,5-difluoro-phenyl]-N-[5-[1-(trifluoromethyl)cyclopropyl]isoxazol-3-yl]acetamide;

2-[4-(6,7-dimethoxyquinoxalin-2-yl)-2,5-difluoro-phenyl]-N-[5-(2,2,2-trifluoro-1,1-dimethyl-ethyl)isoxazol-3-yl]acetamide;

2-[4-[6,7-bis(2-acetamidoethoxy)quinoxalin-2-yl]-2-fluoro-phenyl]-N-[5-(2,2,2-trifluoro-1,1-dimethyl-ethyl)isoxazol-3-yl]acetamide;

2-[4-[6,7-bis[2-[acetyl(methyl)amino]ethoxy]quinoxalin-2-yl]-2-fluoro-phenyl]-N-[5-(2,2,2-trifluoro-1,1-dimethyl-ethyl)isoxazol-3-yl]acetamide;

2-[2-fluoro-4-[7-methoxy-6-(3-methylsulfonylpropoxy)quinoxalin-2-yl]phenyl]-N-[5-[1-(trifluoromethyl)cyclopropyl]isoxazol-3-yl]acetamide;

2-[2-fluoro-4-[7-methoxy-6-[2-(6-oxa-3-azabicyclo[3.1.1]heptan-3-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-(2-oxa-5-azabicyclo[2.2.1]heptan-5-yl)ethoxy]quinoxalin-2-yl]phenyl]-N-[5-[1-(trifluoromethyl)cyclopropyl]isoxazol-3-yl]acetamide;

2-[4-(6,7-dimethoxyquinoxalin-2-yl)-2,6-difluoro-phenyl]-N-[5-(2,2,2-trifluoro-1,1-dimethyl-ethyl)isoxazol-3-yl]acetamide;

2-[4-(6,7-dimethoxyquinoxalin-2-yl)-2,6-difluoro-phenyl]-N-[5-[1-(trifluoromethyl)cyclopropyl]isoxazol-3-yl]acetamide;

2-[4-[7-(3-aminopropoxy)-6-methoxy-quinoxalin-2-yl]-2-fluoro-phenyl]-N-[5-[1-(trifluoromethyl)cyclopropyl]isoxazol-3-yl]acetamide;

2-[2-fluoro-4-[7-methoxy-6-(2-morpholinoethoxy)quinoxalin-2-yl]phenyl]-N-[2-methyl-5-[1-(trifluoromethyl)cyclopropyl]pyrazol-3-yl]acetamide;

2-[5-(6,7-dimethoxyquinoxalin-2-yl)-3-fluoro-2-pyridyl]-N-[5-(2,2,2-trifluoro-1,1-dimethyl-ethyl)isoxazol-3-yl]acetamide;

2-[2-fluoro-4-[7-methoxy-6-(2-morpholinoethoxy)quinoxalin-2-yl]phenyl]-N-[3-[1-(trifluoromethyl)cyclopropyl]-1H-pyrazol-5-yl]acetamide;

2-[4-[7-methoxy-6-(2-morpholinoethoxy)quinoxalin-2-yl]phenyl]-N-[5-[1-(trifluoromethyl)cyclopropyl]isoxazol-3-yl]acetamide;

2-[2-fluoro-4-[6-methoxy-7-(2-morpholinoethoxy)-3-quinolyl]phenyl]-N-[5-[1-(trifluoromethyl)cyclopropyl]isoxazol-3-yl]acetamide;

2-[4-[6-(1,2-dihydroxy-1-methyl-ethyl)-7-methoxy-quinoxalin-2-yl]-2-fluoro-phenyl]-N-[5-[1-(trifluoromethyl)cyclopropyl]isoxazol-3-yl]acetamide;

2-[2-fluoro-4-[6-methoxy-7-(2-morpholinoethoxy)quinoxalin-2-yl]phenyl]-N-[5-[1-(trifluoromethyl)cyclopropyl]isoxazol-3-yl]acetamide;

2-[2-fluoro-4-[7-methoxy-6-(2-morpholinoethoxy)quinoxalin-2-yl]phenyl]-N-[3-(2,2,2-trifluoro-1,1-dimethyl-ethyl)-1H-pyrazol-5-yl]acetamide;

2-[4-[7-(2,3-dihydroxypropoxy)-6-methoxy-quinoxalin-2-yl]-2-fluoro-phenyl]-N-[5-[1-(trifluoromethyl)cyclopropyl]isoxazol-3-yl]acetamide;

2-[4-[6-(3-acetamidopropoxy)-7-methoxy-quinoxalin-2-yl]-2-fluoro-phenyl]-N-[5-[1-(trifluoromethyl)cyclopropyl]isoxazol-3-yl]acetamide;

2-[4-[6-(2,3-dihydroxypropoxy)-7-methoxy-quinoxalin-2-yl]-2-fluoro-phenyl]-N-[5-[1-(trifluoromethyl)cyclopropyl]isoxazol-3-yl]acetamide;

2-[2-fluoro-4-[7-(2-hydroxy-2-methyl-propoxy)-6-methoxy-quinoxalin-2-yl]phenyl]-N-[5-[1-(trifluoromethyl)cyclopropyl]isoxazol-3-yl]acetamide;

2-[2-fluoro-4-[7-methoxy-6-[2-(1,4-oxazepan-4-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-(2-piperazin-1-ylethoxy)quinoxalin-2-yl]phenyl]-N-[5-[1-(trifluoromethyl)cyclopropyl]isoxazol-3-yl]acetamide;

2-[2-fluoro-4-[7-methoxy-6-[2-[(2R)-2-methylmorpholin-4-yl]ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-[(3S)-3-methylmorpholin-4-yl]ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-(9-oxa-3-azabicyclo[3.3.1]nonan-3-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-(3-oxa-8-azabicyclo[3.2.1]octan-8-yl)ethoxy]quinoxalin-2-yl]phenyl]-N-[5-[1-(trifluoromethyl)cyclopropyl]isoxazol-3-yl]acetamide;

2-[2-fluoro-4-[6-(2-hydroxy-2-methyl-propoxy)-7-methoxy-quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-[2-[(3R)-3-methylmorpholin-4-yl]ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-[(2S)-2-methylmorpholin-4-yl]ethoxy]quinoxalin-2-yl]phenyl]-N-[5-[1-(trifluoromethyl)cyclopropyl]isoxazol-3-yl]acetamide; and 2-[2-fluoro-4-[6-(2-hydroxy-2-methyl-propoxy)-7-methoxy-quinoxalin-2-yl]phenyl]-N-[5-[1-(trifluoromethyl)cyclopropyl]isoxazol-3-yl]acetamide.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a CH bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

In another embodiment, provided herein are methods of using the disclosed compounds and compositions, or pharmaceutically acceptable salts, solvates, or hydrates thereof, for the local or systemic treatment or prophylaxis of human and veterinary diseases, disorders and conditions modulated or otherwise affected mediated via one or more of the receptor kinases selected from FLT3, CSF1R, KIT, RET, PDGFRα and PDGFRβ.

Formulation of Pharmaceutical Compositions

The pharmaceutical compositions provided herein contain therapeutically effective amounts of one or more of compounds provided herein that are useful in the prevention, treatment, or amelioration of CSF1R, FLT3, KIT, and/or PDGFRβ kinase mediated diseases or one or more of the symptoms thereof.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art.

In the compositions, effective concentrations of one or more compounds or pharmaceutically acceptable salts, solvates, hydrates, clathrates, single stereoisomers, mixture of stereoisomers or racemic mixture of stereoisomers or prodrug is (are) mixed with a suitable pharmaceutical carrier or vehicle. The concentrations of the compounds in the compositions are effective for delivery of an amount, upon administration, that treats, prevents, or ameliorates one or more of the symptoms of CSF1R, FLT3, KIT, and/or PDGFRβ kinase mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of CSF1R, FLT3, KIT, and/or PDGFRβ kinase mediated diseases.

Typically a therapeutically effective dosage should produce a serum concentration of active ingredient of from about 1 ng/ml to about 50-100 μg/ml. The pharmaceutical compositions typically should provide a dosage of from about 10 mg to about 4000 mg of compound per kilogram of body weight per day. Pharmaceutical dosage unit forms are prepared to provide from about 10 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing CSF1R, FLT3, KIT, and/or PDGFRβ kinase mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as CSF1R, FLT3, KIT, and/or PDGFRβ kinase mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In one embodiment, the composition is administered as an aqueous solution with hydroxypropyl-beta-cyclodextrin (HPBCD) as an excipient. In one embodiment, the aqueous solution contains about 1% to about 50% HPBCD. In one embodiment, the aqueous solution contains about 1%, 3%, 5%, 10% or about 20% HPBCD.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, hydroxypropyl-beta-cyclodextrin (HPBCD) or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, 100-500 mg, 10-500 mg, 50-250 mg or 25-100 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity of the therapeutic target, i.e., thus requiring only a fraction of the systemic dose. In some embodiments, a controlled release device is introduced into a subject in proximity of the site of inappropriate immune activation or a tumor. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Evaluation of the Activity of the Compounds

Standard physiological, pharmacological and biochemical procedures are available for testing the compounds to identify those that possess biological activities that modulate the activity of FLT3, CSF1R, KIT, RET, PDGFRα and/or PDGFRβ kinase.

Such assays include, for example, biochemical assays such as binding assays, radioactivity incorporation assays, as well as a variety of cell based assays.

In certain embodiments, the compounds disclosed herein are tested in a Ba/F3 cell viabilityassay to determine their cellular potency against one or both of FLT3-ITD and FLT3 tyrosine kinase domain mutants. Ba/F3 is an IL-3-dependent, murine macrophage cell line and in this particular embodiment, the assay depends on the overexpression of the FLT3 mutant constructs and the constitutive activation of the exogenous FLT3 for IL-3 independence and viability. In certain embodiments, this assay assesses the potency of compounds as FLT3 inhibitors by measuring the reduction of Cell Titer Blue Reagent® by viable cells remaining after 72 hours of compound treatment. In certain other embodiments, the compounds disclosed herein are tested in a FLT3 phosphorylation assay to determine their cellular potency against one or both of FLT3-ITD and FLT3 tyrosine kinase domain mutants. In certain embodiments, the FLT3 phosphorylation assay assesses the potency of compounds as FLT3 inhibitors by measuring the reduction in formation of phosphorylated FLT3 in the cells. Exemplary assays are described in the Example section.

In certain embodiments, competition binding assays were performed as described in Fabian et al., *Nature Biotechnology* 2005, 23, 329-336.

In one embodiment, the compounds provided herein were found to have Kds of about or less than about 50 or 100 nM against FLT3 kinase. In one embodiment, the compounds provided herein have Kds of about 1 nM or less, 3 nM or less, 5 nM or less, 0.1-2 nM, 2-5 nM, 5-10 nM, 10-25 nM, 25-50 nM, or 50-100 nM, against FLT3 kinase. In one embodiment, the compounds provided herein have Kds of less than about 50, 20, 10, 5, 4, 3, 2, or 1 nM against FLT3 kinase. In another embodiment, the compounds provided herein have Kds of about or less than about 5 nM, 3 nM or 1 nM against FLT3 kinase.

In one embodiment, the compounds provided herein were found to have Kds of about or less than about 50 nM or 100 nM against KIT kinase. In one embodiment, the compounds provided herein have Kds of about 1 nM or less, 3 nM or less, 0.1-2 nM, 2-5 nM, 5-10 nM, 10-25 M or 25-50 nM, against KIT kinase. In one embodiment, the compounds provided herein have Kds of less than about 50, 20, 10, 5 or 1 nM against KIT kinase. In another embodiment, the compounds provided herein have Kds of about or less than about 5 nM, 3 nM or 1 nM against KIT kinase.

In one embodiment, the compounds provided herein were found to have Kds of about or less than about 100 nM or 50 nM against PDGFRβ kinase. In one embodiment, the compounds provided herein have Kds of about 1 nM or less, 3 nM or less, 0.1-2 nM, 2-5 nM, 5-10 nM, or 10-25 M, against PDGFRβ kinase. In one embodiment, the compounds provided herein have Kds of less than about 50, 20, 10, 5 or 1 nM against PDGFRβ kinase. In another embodiment, the compounds provided herein have Kds of about or less than about 5 nM, 3 nM or 1 nM against PDGFRβ kinase.

In one embodiment, the compounds provided herein were found to have Kds of about or less than about 50 nM or 100 nM against CSF1R kinase. In one embodiment, the compounds provided herein were found to have Kds of less than about 50, 20, 10, 5 or 1 nM against CSF1R kinase. In one embodiment, the compounds provided herein were found to have Kds of less than about 100, 50, 20, 10, 5, 4, 3, 2, or 1 nM against CSF1R kinase. In another embodiment, the compounds provided herein were found to have Kds of about or less than about 5 nM, 3 nM or 1 nM against CSF1R kinase.

Methods of Use of the Compounds and Compositions

Also provided herein are methods of using the disclosed compounds and compositions, or pharmaceutically acceptable salts, solvates, hydrates, clathrates, single stereoisomers, mixture of stereoisomers, racemic mixture of stereoisomers or prodrugs thereof, for the treatment, prevention, or amelioration of a disease or disorder that is mediated or otherwise affected via protein kinase activity or one or more symptoms of diseases or disorders that are mediated or otherwise affected via protein kinase activity (see, Krause and Van Etten, *N Engl J Med* (2005) 353(2):172-187, Blume-Jensen and Hunter, *Nature* (2001) 411(17): 355-365 and Plowman et al., DN&P, 7: 334-339 (1994)).

In certain embodiments, provided herein are methods of treating the following diseases or disorders:

1) carcinomas include Kit-mediated and/or CSF1R-mediated carcinomas, adenocarcinoma, squamous cell carcinoma, adenosquamous carcinoma, teratocarcinoma, head and neck cancer, brain cancer, intracranial carcinoma, glioblastoma including PDGFR-mediated glioblastoma, glioblastoma multiforme including PDGFR-mediated glioblastoma multiforme, neuroblastoma, cancer of the larynx, multiple endocrine neoplasias 2A and 2B (MENS 2A and MENS 2B) including RET-mediated MENS, thyroid cancer, including sporadic and familial medullary thyroid carcinoma, papillary thyroid carcinoma, parathyroid carcinoma including any RET-mediated thyroid carcinoma, follicular thyroid cancer, anaplastic thyroid cancer, bronchial carcinoid, oat cell carcinoma, lung cancer, small-cell lung cancer including FLT3 and/or Kit-mediated small cell lung cancer, stomach/gastric cancer, gastrointestinal cancer, gastrointestinal stromal tumors (GIST) including Kit-mediated GIST and PDGFRα mediated GIST, colon cancer, colorectal cancer, pancreatic cancer, islet cell carcinoma, hepatic/liver cancer, metastases to the liver, bladder cancer, renal cell cancer including PDGFR-mediated renal cell cancer, cancers of the genitourinary tract, ovarian cancer including Kit-mediated and/or PDGFR-mediated and/or CSF1R-mediated ovarian cancer, endometrial cancer including CSF1R-mediated endometrial cancer, cervical cancer, breast cancer including FLT3-mediated and/or PDGFR-mediated and/or CSF1R-mediated breast cancer, prostate cancer including Kit-mediated prostate cancer, germ cell tumors including Kit-mediated germ cell tumors, seminomas including Kit-mediated seminomas, dysgerminomas, including Kit-mediated dysgerminomas, melanoma including PDGFR-mediated melanoma, metastases to the bone including CSF1R-mediated bone metastases, metastatic tumors including CSF1R-mediated metastatic tumors, stromal tumors, neuroendocrine tumors, tumor angiogenesis including CSF1R-mediated tumor angiogenesis, mixed mesodermal tumors and cancers promoted by tumor-associated macrophages;

2) sarcomas including PDGFR-mediated sarcomas, osteosarcoma, osteogenic sarcoma, bone cancer, glioma including PDGFR-mediated and/or CSF1R-mediated glioma, astrocytoma, vascular tumors, Kaposi's sarcoma, carcinosarcoma, hemangiosarcomas, lymphangiosarcoma;

3) hematological cancers including: i) leukemia which includes, acute myeloid leukemia (AML) including FLT3-mediated and/or KIT-mediated and/or CSF1R-mediated acute myeloid leukemia, acute promyelocytic leukemia (APL), chronic myeloid leukemias (CML) including FLT3-mediated and/or PDGFR-mediated chronic myeloid leukemia, myelodysplastic leukemias including FLT3-mediated myelodysplastic leukemia, acute megakaryoblastic leukemia including CSF1R-mediated acute megakaryoblastic leukemia, acute lymphoblastic leukemia (ALL), B-cell acute lymphoblastic leukemias, T-cell acute lymphoblastic leukemias, natural killer (NK) cell leukemia including FLT3-mediated and/or KIT-mediated ALL, FLT3-mediated and/or KIT-mediated B-cell acute lymphoblastic leukemias, FLT3 and/or KIT-mediated T-cell acute lymphoblastic leukemias or FLT3 and/or KIT-mediated NK cell leukemia, chronic eosinophilic leukemia (CEL) including PDGFR-mediated CEL, chronic myelomonocytic leukemia (CMML), mast cell leukemia including Kit-mediated mast cell leukemia, or systemic mastocytosis including KIT-mediated systemic mastocytosis, mast cell tumors, hairy cell leukemia and chronic lymphocytic leukemia;

ii) lymphoma which includes Hodgkin's lymphoma, lymphoproliferative diseases, B-cell lymphoma, T-cell lymphoma, and natural killer (NK) cell lymphoma, any of which may be FLT3 mediated and/or PDGFR-mediated and iii) multiple myeloma, myeloproliferative diseases (MPD), myelodysplastic syndrome, including FLT3 mediated and/or KIT-mediated myelodysplastic syndrome (MDS) and Langerhans cell histiocytosis including CSF1R-mediated and FLT3-mediated Langerhans cell histiocytosis and idiopathic hypereosinophilic syndrome (HES) including PDGFR-mediated HES;

4) Nonmalignant proliferation diseases; atherosclerosis including CSF1R mediated atherosclerosis or PDGFR-mediated atherosclerosis, restenosis following vascular angioplasty including PDGFR-mediated restenosis, and fibroproliferative disorders such as obliterative bronchiolitis and idiopathic myelofibrosis, both of which may be PDGFR-mediated, pulmonary fibrosis and obesity;

5) Inflammatory diseases or immune disorders including autoimmune diseases, which include, but is not limited to, tissue transplant rejection, graft-versus-host disease, wound healing, kidney disease, multiple sclerosis, thyroiditis, type 1 diabetes, sarcoidosis, allergic rhinitis, nephritis, Alzheimer's disease, inflammatory bowel disease including Crohn's disease and ulcerative colitis (UC), systemic lupus erythematosis (SLE), arthritis, osteoarthritis, rheumatoid arthritis, psoriatic arthritis, inflammatory arthritis, osteoporosis, asthma and chronic obstructive pulmonary disease (COPD), including any of the aforementioned diseases which are FLT3-mediated and/or CSF1R-mediated and/or KIT-mediated;

6) Bone diseases including disorders relating to the mineralization, formation and resorption of the bone, including but not limited to osteoporosis, glucocorticoid-induced osteoporosis, periodontitis, bone loss due to cancer therapy, periprosthetic osteolysis, Paget's disease, hypercalcemia, osteomyelitis, and bone pain; and 7) Infectious diseases mediated either via viral or bacterial pathogens and sepsis, including KIT-mediated and/or CSF1R-mediated sepsis.

Also provided are methods of modulating the various activities of kinases including dimerization, ligand binding and phosphotransferase activities or methods of modulating the expression of kinases, in a cell, tissue or whole organism, using the compounds and compositions provided herein, or pharmaceutically acceptable derivatives thereof. In one embodiment, provided herein are methods of modulating the activity of FLT3 activity in a cell, tissue or whole organism using the compounds and compositions provided herein, or pharmaceutically acceptable derivatives thereof. In one embodiment, provided herein are methods of modulating the activity of CSF1R activity in a cell, tissue or whole organism using the compounds and compositions provided herein, or pharmaceutically acceptable derivatives thereof. In one embodiment, provided herein are methods of modulating the activity of KIT activity in a cell, tissue or whole organism using the compounds and compositions provided herein, or pharmaceutically acceptable derivatives thereof In one embodiment, the methods provided herein are for treating tumor-associated osteolysis, osteoporosis including ovariectomy-induced bone loss, orthopedic implant failure, renal inflammation and glomerulonephritis, transplant rejection including renal and bone marrow allografts and skin xenograft, obesity, Alzheimer's Disease and Langerhans cell histiocytosis. In one embodiment, the methods provided herein are for treating chronic skin disorders including psoriasis.

In another embodiment, a method for treating periodontitis, Langerhans cell histiocytosis, osteoporosis, Paget's disease of bone (PDB), bone loss due to cancer therapy, periprosthetic osteolysis, glucocorticoid-induced osteoporosis, rheumatoid arthritis, psoriatic arthritis, osteoarthritis, and/or inflammatory arthritis is provided herein.

In one embodiment, the methods provided herein are for treating bone diseases including disorders relating to the mineralization, formation and resorption of the bone, including but not limited to osteoporosis, Paget's disease, hypercalcemia, osteolysis, osteomyelitis, and bone pain.

In one embodiment, the methods provided herein are for treating cancers, including, but not limited to head and neck cancer, (originating in lip, oral cavity, oropharynx, hypopharynx, larynx, nasopharynx, nasal cavity and paranasal sinuses or salivary glands); lung cancer, including small cell lung cancer, non-small cell lung cancer; gastrointestinal tract cancers, including esophageal cancer, gastric cancer, colorectal cancer, anal cancer, pancreatic cancer, liver cancer, gallbladder cancer, extrahepatic bile duct cancer, cancer of the ampulla of vater; breast cancer; gynecologic cancers, including, cancer of uterine cervix, cancer of the uterine body, vaginal cancer, vulvar cancer, ovarian cancer, gestational trophoblastic cancer neoplasia; testicular cancer; urinary tract cancers, including, renal cancer, urinary bladder cancer, penile cancer, urethral cancer; neurologic tumors; endocrine neoplasms, including carcinoid and islet cell tumors, pheochromocytoma, adrenal cortical carcinoma, parathyroid carcinoma and metastases to endocrine glands. In another embodiment, the methods provided herein are for treating carcinoma, breast cancer, ovarian cancer, bone metastases, osteoporosis, Paget's disease, hypercalcemia, osteolysis, osteomyelitis, bone pain, inflammatory bowel disease (IBD), Crohn's disease, ulcerative colitis (UC), systemic lupus erythematosis (SLE), arthritis, osteoarthritis, rheumatoid arthritis, osteoporosis, asthma, chronic obstructive pulmonary disease (COPD), psoriasis and multiple sclerosis. In another embodiment, provided herein are methods for treating inflammatory diseases of the eye including conjunctivitis, uveitis, iritis, scleritis, blepheritis, meibomitis and optical neuritis. In yet another embodiment, provided herein are methods for treating glaucoma, diabetic retinopathy and macular degeneration.

Further examples of cancers are basal cell carcinoma; squamous cell carcinoma; chondrosarcoma (a cancer arising in cartilage cells); mesenchymal-chondrosarcoma; soft tissue sarcomas, including, malignant tumours that may arise in any of the mesodermal tissues (muscles, tendons, vessels that carry blood or lymph, joints and fat); soft tissue sarcomas include; alveolar soft-part sarcoma, angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma; gestational trophoblastic tumour (malignancy in which the tissues formed in the uterus following conception become cancerous); Hodgkin's lymphoma and laryngeal cancer.

In one embodiment, the cancer is a leukemia. In one embodiment, the leukemia is chronic lymphocytic leukemia, chronic myelocytic leukemia, acute lymphoblastic leukemia, acute myeloid leukemia, and acute myeloblastic leukemia.

In another embodiment, the leukemia is acute leukemia. In one embodiment, the acute leukemia is acute myeloid leukemia (AML). In one embodiment, acute myeloid leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the acute myeloid leukemia is undifferentiated AML (M0). In yet another embodiment, the acute myeloid leukemia is myeloblastic leukemia (M1). In yet another embodiment, the acute myeloid leukemia is myeloblastic leukemia (M2). In yet another embodiment, the acute myeloid leukemia is promyelocytic leukemia (M3 or M3 variant [M3V]). In yet another embodiment, the acute myeloid leukemia is myelomonocytic leukemia (M4 or M4 variant with eosinophilia [M4E]). In yet another embodiment, the acute myeloid leukemia is monocytic leukemia (M5). In yet another embodiment, the acute myeloid leukemia is erythroleukemia (M6). In yet another embodiment, the acute myeloid leukemia is megakaryoblastic leukemia (M7). In yet another embodiment, the acute myeloid leukemia is promyelocytic leukemia In another embodiment, the acute leukemia is acute lymphoblastic leukemia (also known as acute lymphocytic leukemia or ALL). In one embodiment, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1-Mature-appearing lymphoblasts (T-cells or pre-B-cells), L2-Immature and pleomorphic (variously shaped) lymphoblasts (T-cells or pre-B-cells), and L3-Lymphoblasts (B-cells; Burkitt's cells). In another embodiment, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In certain embodiments, provided herein are methods of using the compounds and compositions disclosed herein, or pharmaceutically acceptable salts, solvates, hydrates, clathrates, single stereoisomers, mixture of stereoisomers, racemic mixture of stereoisomers or prodrugs thereof, for the treatment, prevention, or amelioration of a disease selected from an inflammatory disease, an autoimmune disease and cancer that is associated with or is mediated by overexpression of FLT3 or the FLT3 ligand. In certain embodiments, the disease is mediated by overexpression of wildtype FLT3. In certain embodiments, provided herein are methods of using the compounds and compositions disclosed herein, or pharmaceutically acceptable salts, solvates, hydrates, clathrates, single stereoisomers, mixture of stereoisomers, racemic mixture of stereoisomers or prodrugs thereof, for the treatment, prevention, or amelioration of a hematological cancer associated with or is mediated by one or more FLT3 tyrosine kinase domain mutation. In certain embodiments, the hematological cancer is associated with or is mediated by one or more FLT3 mutations selected from FLT3-ITD mutations and FLT3 tyrosine kinase domain mutations. In certain embodiments, the hematological cancer is associated with or is mediated by one or more FLT3-ITD mutations and one or more FLT3 tyrosine kinase domain mutations. In certain embodiments, the hematological cancer is leukemia or myelodysplastic syndromes (MDS). In yet another embodiment, the hematological cancer is acute myeloid leukemia (AML), acute lymphoblastic leukemia (ALL) or myelodysplastic syndromes. In yet another embodiment, the FLT3 tyrosine kinase domain mutation confers drug resistance to FLT3-targeted therapy. In yet another embodiment, the FLT3 tyrosine kinase domain mutation comprises one or more point mutations at any one of positions E608, N676, F691, C828, D835, D839, N841, Y842 and M855. In yet another embodiment, the FLT3 tyrosine kinase domain mutation comprises one or more point mutations selected from E608K, N676D, N676I, N676S, F691I, F691L, C828S, D835Y, D835V, D835H, D835F, D835E, D839, N841, Y842C, Y842D, Y842H, Y842N, Y842S and M855T. In certain embodiments, the FLT3 tyrosine kinase domain mutation comprises one or more FLT3-ITD mutations and one or more point mutations at positions selected from E608, F691, D835 and Y842. In yet another embodiment, the tyrosine kinase domain mutation of FLT3 comprises one or more FLT3-ITD mutations and one or more point mutations selected from E608K, F691L, D835Y, D835V, D835F, Y842C and Y842H. In certain embodiments, the tyrosine kinase domain mutation of FLT3 comprises one or more FLT3-ITD mutations and a point mutation at one or both of F691 and D835. In yet another embodiment, the tyrosine kinase domain mutation of FLT3 comprises the FLT3-ITD mutation and one or more point mutation selected from F691L, D835Y, D835V and D835F. In yet another embodiment, the acquired mutation confers drug resistance to one or more of sorafenib, midostaurin (PKC-412), SU5614 and quizartinib (AC220).

In one embodiment, the resistance to quizartinib (AC220) is associated with, attributable to or mediated by a mutation in FLT3 comprising at least one point mutation at positions E608, F691, D835 and Y842. In another embodiment, the resistance to quizartinib (AC220) associated with, attributable to or mediated by polyclonal mutations in FLT3 comprising at least two point mutations selected from positions E608, F691, D835 and Y842. In one embodiment, the resistance to quizartinib (AC220) is associated with, attributable to or mediated by a mutation in FLT3 comprising at least one point mutation at positions F691, D835 and Y842. In one embodiment, the resistance to quizartinib (AC220) is associated with, attributable to or mediated by a mutation in FLT3 comprising at least one point mutation at positions F691 and D835. In yet another embodiment, the resistance to quizartinib (AC220) is associated with, attributable to or mediated by a mutation in FLT3 comprising at least one point mutation selected from E608K, F691L, D835F, D835Y, D835V, Y842C and Y842H. In yet another embodiment, the mutation in FLT3 further comprises a FLT3-ITD mutation.

In one embodiment, the resistance to sorafenib is associated with, attributable to or mediated by a mutation in FLT3 comprising at least one point mutation selected from F691L, Y842H, Y842N and Y842S. In one embodiment, the resistance to PKC-412 is associated with, attributable to or mediated by a mutation in FLT3 comprising at least one point mutation selected from N676D, N676I, N676S and F691L. In one embodiment, the resistance to SU5614 is associated with, attributable to or mediated by a mutation in FLT3 comprising at least one point mutation selected from C828S, D835Y, D835V, D835H, D835F, D835E, D839G, D839H, N841C, Y842C, Y842D, and M855T.

In certain embodiments, provided herein are methods comprising the steps of detecting a FLT3 tyrosine kinase domain mutation in a patient with a hematological cancer and administering to the patient found to have the FLT3 tyrosine kinase domain mutation the compounds and compositions disclosed herein, or pharmaceutically acceptable salts, solvates, hydrates, clathrates, single stereoisomers, mixture of stereoisomers, racemic mixture of stereoisomers or prodrugs thereof. In certain embodiments, the FLT3 tyrosine kinase domain mutation is detected using a PCR-based genetic test using blood, marrow or saliva from the patient. In certain embodiments, the patient with the hematological cancer is known to have the FLT3-ITD mutation. In certain embodiments, the patient with the hematological cancer received FLT3-targeted therapy.

In certain embodiments, the FLT3 tyrosine kinase domain mutation is a point mutation of the "gatekeeper" residue F691. In certain embodiments, the FLT3 tyrosine kinase domain mutation is in the TK2 domain. In certain embodiments, the FLT3 tyrosine kinase domain mutation is a mutation of the activation loop residue D835 or Y842. In certain embodiments, the FLT3 tyrosine kinase domain mutation is in the TK1 domain.

In certain embodiment, provided herein is a method of modulating FLT3, CSF1R, KIT, RET, PDGFRα and/or PDGFRβ comprising administering a compound of Formula I. In certain embodiments, provided herein is a method of modulating FLT3 wildtype, FLT3-ITD or a FLT3 tyrosine kinase domain mutant, comprising administering a compound of Formula I.

The active ingredient(s) in one embodiment are administered in an amount sufficient to deliver to a patient a therapeutically effective amount of the active compound in order to treat, prevent or ameliorate the diseases or disorders described herein, or the symptoms thereof, without causing serious toxic effects in a treated subject.

A typical dose of the compound may be in the range of from about 0.01 to about 200 mg per kg body weight of the recipient per day, or from about 0.5 to about 100 mg per kg body weight per day or from about 0.5 to about 50 mg per kg of body weight per day. The effective dosage range of the pharmaceutically acceptable derivatives is calculated based on the weight of the parent compound to be delivered. If the derivative compound itself exhibits activity, then the effective dosage can be estimated as above using the weight of the derivative, or by other means known to those of ordinary skill in the art. Alternatively, a typical dose of the compound may be in the range of from about 1 mg to about 2000 mg per day.

The compounds are conveniently administered in units of any suitable dosage form, including but not limited to one containing from about 1 to 2000 mg, from about 10 to 1000 mg, or from about 25 to 700 mg of active ingredient per unit dosage form. In one embodiment, the unit dose is selected from 10, 25, 50, 100, 200 and 250 mgs. For example, an oral dosage of from about 25 to 1000 mg is usually convenient, for example, in one or multiple dosage forms of 10, 25, 50, 100, 200 and 250 mgs. Also contemplated are doses of 0.1-50 mg, 0.1-20 mg, or 0.1-10 mg. Furthermore, lower doses may be utilized in the case of administration by a non-oral route, as for example, by injection or inhalation.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose (QD) or as divided doses throughout a day. In particular embodiments, the compound or composition is administered four times per day (QID). In particular embodiments, the compound or composition is administered three times per day (TID). In particular embodiments, the compound or composition is administered two times per day (BID). In particular embodiments, the compound or composition is administered once per day (QD).

The administration can also be continuous (i.e., daily for consecutive days or every day) or intermittent. The term "intermittent" or "intermittently" as used herein is intended to mean stopping and starting at either regular or irregular intervals. For example, intermittent administration of the compound of Formula I may be administration for one to six days per week or administration on alternate days.

In one embodiment, the compound or composition provided herein is administered intermittently. In yet another embodiment, the compound or composition provided herein is administered intermittently once weekly, twice weekly or three times weekly. In yet another embodiment, the compound or composition provided herein is administered once weekly. In yet another embodiment, the compound or composition provided herein is administered twice weekly. In yet another embodiment, the compound or composition provided herein is administered three times weekly. In one embodiment, the compound or composition provided herein is administered QD intermittently once weekly, twice weekly or three times weekly. In yet another embodiment, the compound or composition provided herein is administered QD once weekly. In another embodiment, the compound or composition provided herein is administered QD twice weekly. In another embodiment, the compound or composition provided herein is administered QD three times weekly.

It is to be understood that for any particular subject, specific dosage regimens should be adjusted over time to meet individual needs, and will vary depending upon absorption, inactivation and excretion rates of the drug. The concentrations set forth here are exemplary only and are not intended to limit the scope or practice of the claimed composition. The active ingredient may be administered all at once, or may be divided into a number of smaller doses to be administered at varying intervals of time.

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the examples may be substituted with other suitable reagents. See, e.g., Smith & March, *Advanced Organic Chemistry*, $5^{th}$ ed. (2001).

Combination Therapy

It is to be understood by those skilled in the art that the compounds of Formula I provided herein, and pharmaceutically acceptable salts, solvates, hydrates, single stereoisomers, mixture of stereoisomers or racemic mixture of stereoisomers thereof, and including pharmaceutical compositions and formulations containing the compounds, can be used in a wide variety of combination therapies to treat the conditions and diseases described above. Thus, also contemplated herein is the use of the compound of Formula I and pharmaceutically acceptable salts, solvates, hydrates, single stereoisomers, mixture of stereoisomers or racemic mixture of stereoisomers thereof, in combination with other active pharmaceutical agents for the treatment of the diseases and disorders described herein.

In one embodiment, such additional pharmaceutical agents include without limitation anti-cancer agents (including chemotherapeutic agents and anti-proliferative agents), anti-inflammatory agents, immunomodulatory agents or immunosuppressive agents.

In certain embodiments, the anti-cancer agents include anti-metabolites (e.g., 5-fluoro-uracil, cytarabine, clofarabine, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (e.g. estramustine phosphate, prednimustine), hormones or hormone agonists, antagonists, partial agonists or partial antagonists, kinase inhibitors including inhibitors of PI3K, Akt, BRAF (e.g. dabrafenib, trametinib, vemurafenib, ipilimumab), JAK (e.g. rutxolitinib, tofacitinib), MEK, MAPK, Pim-1 and other FLT3 inhibitors (e.g. PKC-412, ASP2215)), inhibitors of STAT activation, and radiation treatment.

In certain embodiments, the additional pharmaceutical agent is a FLT3 inhibitor. In yet another embodiment, the additional pharmaceutical agent is quizartinib (AC220).

In certain embodiments, the anti-inflammatory agents include matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, glucocorticoid receptor agonists (e.g., corticosteroids, methylprednisone, prednisone, and cortisone) or antifolates such as methotrexate.

The compound or composition provided herein, or pharmaceutically acceptable salt of the compound, may be administered simultaneously with, prior to, or after administration of one or more of the above agents.

Pharmaceutical compositions containing a compound provided herein or pharmaceutically acceptable salt thereof, and one or more of the above agents are also provided.

Also provided, in one embodiment, is a combination therapy that treats or prevents the onset of the symptoms, or associated complications of cancer and related diseases and disorders, said therapy comprising the administration to a subject in need thereof, one of the compounds or compositions disclosed herein, or pharmaceutically acceptable salts thereof, with one or more anti-cancer agents. Also provided, in another embodiment, is a combination therapy that treats or prevents the onset of the symptom of osteoporosis and related diseases and disorders, said therapy comprising the administration to a subject in need thereof, one of the compounds or compositions disclosed herein, or pharmaceutically acceptable salts thereof, with one or more anti-inflammatory or immunomodulatory agents. Also provided, in yet another embodiment, is a combination therapy that treats or prevents the onset of the symptom of rheumatoid arthritis and related diseases and disorders, said therapy comprising the administration to a subject in need thereof, one of the compounds or compositions disclosed herein, or pharmaceutically acceptable salts thereof, with one or more anti-inflammatory or immunomodulatory agents.

Preparation of Compounds

Starting materials in the synthesis examples provided herein are either available from commercial sources or via literature procedures (e.g., March *Advanced Organic Chemistry: Reactions, Mechanisms, and Structure*, (1992) 4th Ed.; Wiley Interscience, New York). All commercially available compounds were used without further purification unless otherwise indicated. NMR spectra are reported according to the significant peaks observed, and typically include multiplicity (s, singlet; d, double; t, triplet; q, quartet; m, multiplet; br s, broad singlet) and number of protons and may also include coupling constants for certain multiplets. Chemical shifts are reported as parts per million (δ) relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% $HCO_2H$ or 0.05% AcOH). Preparative reverse phase HPLC was typically performed using a Varian HPLC system equipped with a Phenomenex phenylhexyl, a Phenomenex Luna C18, or a Varian Pursuit diphenyl reverse phase column. Typical elution conditions utilized a gradient containing an increasing composition of organic cosolvent (0.05% AcOH/$CH_3CN$, 0.05% AcOH/MeOH, 0.05% $HCO_2H$/$CH_3CN$, or 0.05% $HCO_2H$/MeOH) to aqueous cosolvent (0.05% aq AcOH or (0.05% aq $HCO_2H$). Silica gel chromatography was either performed manually using methodology analogous to the published procedure for flash chromatography (Still et al. (1978) *J. Org. Chem.* 43:2923), or on an automated system (for example, Biotage SP instrument) using pre-packed silica gel columns. It is understood that in the following description, combinations of substituents and/or variables of the depicted formulae are permissible only if such contributions result in stable compounds under standard conditions.

It will also be appreciated by those skilled in the art that in the process described below, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, Protective Groups in Organic Synthesis (1991), 2nd Ed., Wiley-Interscience.

One of ordinary skill in the art could readily ascertain which choices of protecting group are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is, E/Z isomers, enantiomers and/or diastereomers.

Compounds of formula (I) may be generally prepared as depicted in the following schemes, and unless otherwise noted, the various substituents are as defined elsewhere herein.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| t-BuOK | potassium tert-butoxide |
| DCM | dichloromethane |
| DIAD | diisopropyl azodicarboxylate |
| DIEA | diisopropylethylamine |
| dba | dibenzylideneacetone |
| dppf | (diphenylphosphino)ferrocene |
| EDCI | N-(3-dimethylaminopropyl)-N'-ethylcarbodiimide hydrochloride |
| EtOAc | ethyl acetate |
| EtOH | ethanol |
| HATU | O-(7-azabenzotriazol-lyl)-N,N,N',N'-tetramethyluronium hexafluorophosphate |
| HOBt | 1-hydroxybenzotriazole |
| LC-MS | (tandem) liquid chromatography-mass spectrometry |
| MeOH | methanol |
| PG | protecting group |
| Psi | pounds per square inch |
| PyBOP | benzotriazol-1-yl-oxytripyrrolidino phosphonium hexafluorophosphate |
| TEA | triethylamine |
| $Tf_2O$ | trifluoromethanesulfonic anhydride |

In an illustrative method, the biaryl acetamide compounds of formula (I) may be routinely prepared according to the synthetic route outlined in Scheme 1. The halogen/sulfonate groups X of compounds I can participate in Suzuki couplings with 4,4,4',4',5,5,5',5'-octamethyl-2,2'-bi(1,3,2-dioxaborolane) in a reaction promoted by a catalyst such as, but not limited to, tetrakis(triphenylphosphine)palladium or [1,1'-bis(diphenylphosphino)ferrocene]dichloropalladium (II), and promoted by a base such as, but not limited to, KOAc or NaOAc, in a solvent such as, but not limited to, DMF or 1,4-dioxane to give the aryl acetic acid boronic ester derivatives 2. The optionally substituted azolyl amines 3 can be condensed with the dioxaborolane-substituted phenylacetic acids 2 using a coupling reagent such as, but not limited to, EDCI or HATU, to give the phenylacetamide derivatives 4. The condensation can be conducted in a solvent such as, but not limited to, THF or DMF, and is promoted with a base such as, but not limited to, DIEA or DMAP, and by heating as necessary at an elevated temperature. The resulting boronic esters 4 can then be coupled with halogen/sulfonate-substituted azines 5 using a Pd-catalyzed Suzuki coupling protocol to give the biaryl acetamide derivatives 6. The coupling reaction can be promoted with a catalyst such as, but not limited to, Pd(PPh$_3$)$_4$ or Pd(dppf)Cl$_2$, can be conducted in a solvent such as, but not limited to, CH$_3$CN or 1,4-dioxane, and can be promoted with a base, such as, but not limited to, aq Na$_2$CO$_3$ or CsF, and by heating as necessary at an elevated temperature either with an oil bath or in a microwave reactor.

Scheme 1: General synthesis of biaryl acetamides.

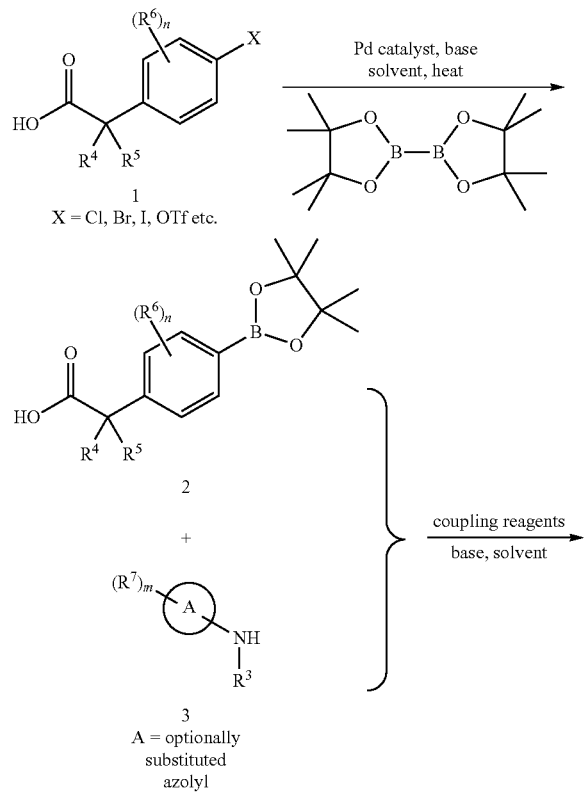

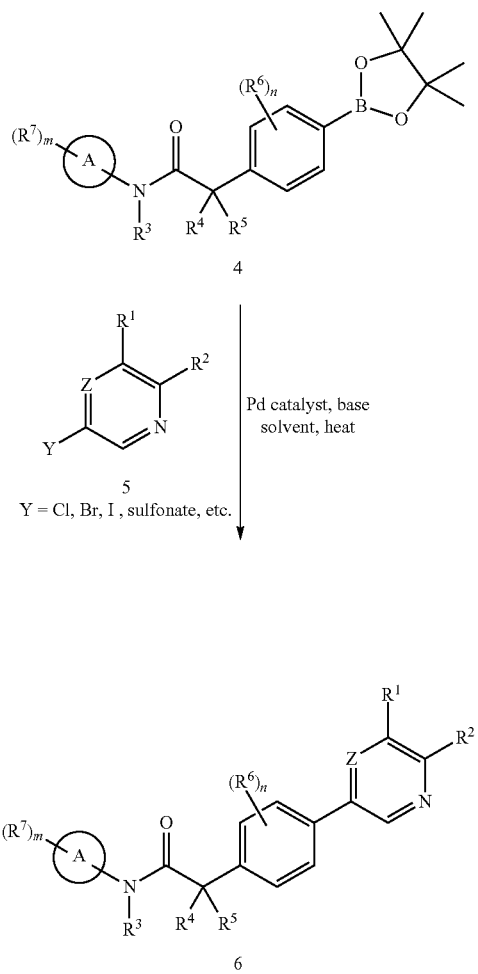

In an illustrative method, the biaryl acetamide compounds of formula (I) may be routinely prepared according to the synthetic route outlined in Scheme 2. Phenylacetic acids 1 can be converted to the corresponding acid chlorides 7 using a reagent such as, but not limited to, SOCl$_2$ or (COCl)$_2$. The reaction can be conducted in a solvent such as, but not limited to, DCM or benzene, and promoted with a catalyst such as, but not limited to, DMF or DMA, and by heating as necessary at an elevated temperature. The optionally substituted azolyl amines 3 can be condensed with phenylacetyl chlorides 7 to afford phenyl acetamides 8 promoted by a base, such as, but not limited to, pyridine, lutidine, or DIEA. The reaction can be conducted in a solvent such as, but not limited to, DCM, THF, or DMF and promoted with a catalyst such as, but not limited to, DMAP, and by heating as necessary at elevated temperatures. Meanwhile, halogen/sulfonate-substituted azines 5 can be converted to boronic ester derivatives 9 using a Pd-catalyzed Suzuki coupling protocol as described in Scheme 1. Subsequent coupling between acetamides 8 and boronic esters 9 using a Pd-catalyzed Suzuki coupling protocol as described in Scheme 1 affords biaryl acetamides 6.

Scheme 2: General synthesis of biaryl acetamides.

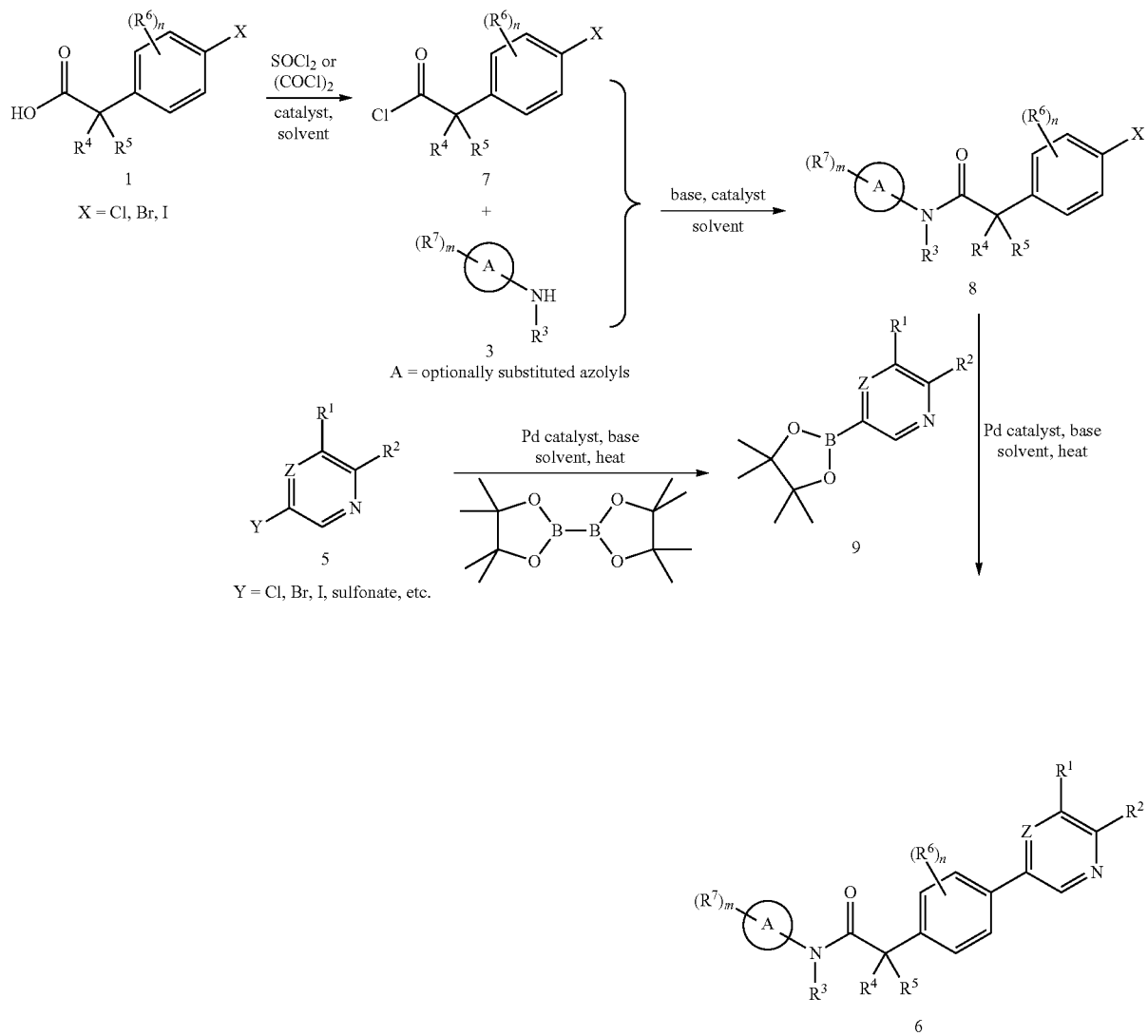

In an illustrative method, halogen-substituted azine derivatives 5 may be routinely prepared according to the synthetic routes outlined in Scheme 3. The readily available aryl/heteroaryl amines 10 can be condensed with bromomalonaldehyde in a solvent such as, but not limited to, MeOH or EtOH and promoted by an acid such as, but not limited to, HBr or HCl, at elevated temperatures to give bicyclic bromides 11a and 11b. Aryl/heteroaryl diamines 12 can be condensed with a glycoxylic ester in a solvent such as, but not limited to, EtOH or MeOH, and at elevated temperature to generate fused hydroxypyrazines 13a and 13b. Then 13a and 13b can be converted to the corresponding halides 14a and 14b using a reagent such as, but not limited to, POCl$_3$, POBr$_3$, PBr$_3$, or PCl$_5$ with heating as required required, whereby 14b is an example of structure 5 that is used in Schemes 1 and 2. Unsubstituted-azine derivatives 15 can be converted to halogen substituted-azines 5 using appropriate halogenation reagents such as, but not limited to, N-chlorosuccinimide, N-bromosuccinimide, or N-iodosuccinimide. The reaction can be conducted in a solvent such as, but not limited to, CH$_3$CN or DCM with heating as necessary.

Scheme 3: General synthesis of halogen-substituted azines.

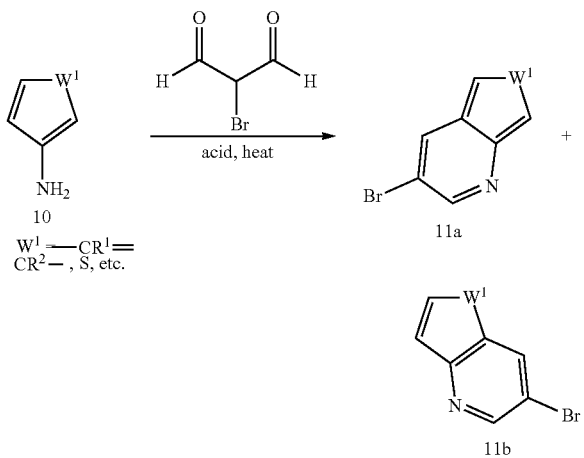

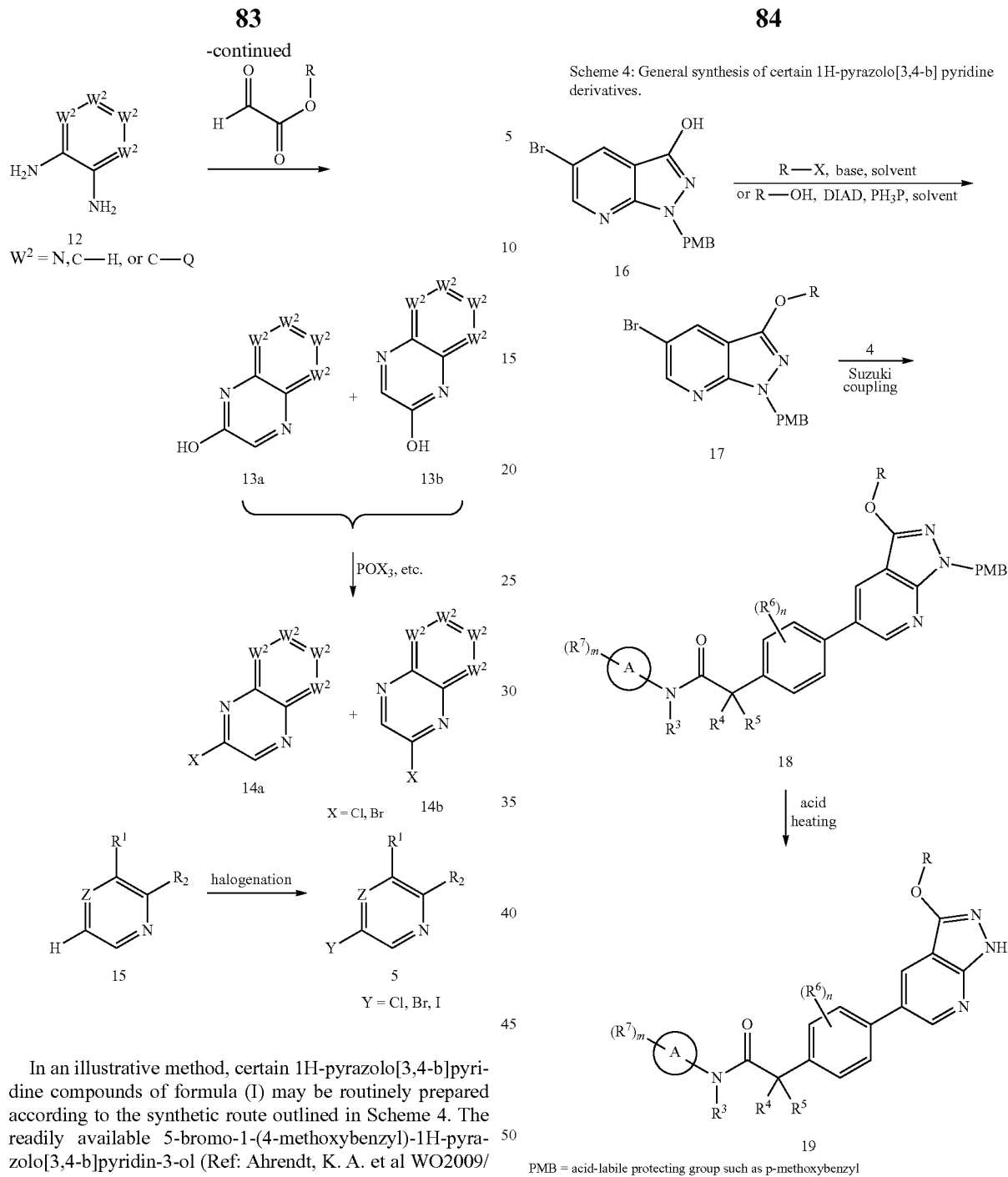

Scheme 4: General synthesis of certain 1H-pyrazolo[3,4-b] pyridine derivatives.

PMB = acid-labile protecting group such as p-methoxybenzyl

In an illustrative method, certain 1H-pyrazolo[3,4-b]pyridine compounds of formula (I) may be routinely prepared according to the synthetic route outlined in Scheme 4. The readily available 5-bromo-1-(4-methoxybenzyl)-1H-pyrazolo[3,4-b]pyridin-3-ol (Ref: Ahrendt, K. A. et al WO2009/111279 A1, 2009) can be alkylated with alkyl halides using a base such as, but not limited to, NaH or t-BuOK, in a solvent such as, but not limited to, DMF or DMSO, to generate compounds 17. Alternatively, compounds 17 can also be prepared from 16 using a Mitsunobu protocol with various alcohols. The reaction can be effected with a combination of reagents such as, but not limited to, DIAD/Ph$_3$P or DEAD/Ph$_3$P, in solvents such as, but not limited to, THF or DCM. Subsequently, compounds 17 can be coupled with a boronic ester 4 from Scheme 1 using a Pd-catalyzed Suzuki coupling protocol as described in Scheme 1 to yield biaryl acetamides 18. The protecting group can be removed by treatment with an acids such as, but not limited to, TFA or HCl, to afford 1H-pyrazolo[3,4-b]pyridine-based biaryl acetamides 19.

In an illustrative method, certain 1H-pyrazolo[3,4-b]pyridine compounds of formula (I) may also be routinely prepared according to the synthetic route outlined in Scheme 5. The readily available 5-bromo-1-(tetrahydro-2H-pyran-2-yl)-1H-pyrazolo[3,4-b]pyridine-3-carbaldehyde 20 (Ref: Hood, J. et al. WO2011/84486 A1, 2011) can be coupled with a boronic ester 4 from Scheme 1 using a Pd-catalyzed Suzuki coupling protocol as described in Scheme 1 to yield biaryl acetamides 21. The aldehydes 21 can be reduced to the corresponding alcohols with a reducing agent such as, but not limited to, NaBH$_4$ or LiBH$_4$, in a solvent such as, but not limited to, MeOH or THF. The THP group of the resulting alcohols can be removed to yield 1H-pyrazolo[3, 4-b]pyridine compounds 22 by treatment with an acid such as, but not limited to, TFA or HCl. The aldehydes 21 can also undergo reductive amination with various amines using a reducing agents such as, but not limited to, NaCNBH$_3$ or Na(OAc)$_3$BH in a solvent system such as, but not limited to, pH~4 buffer in MeOH or dichloroethane in the presence of AcOH. THP protecting group cleavage with an acid such as, but not limited to, TFA or HCl affords 1H-pyrazolo[3,4-b]pyridine compounds 23. The aldehydes 21 can also react with Grignard reagents, optionally at low temperature, in a solvent such as, but not limited to, THF or DME, followed by THP deprotection with an acid, as above, to provide 1H-pyrazolo[3,4-b]pyridine compounds 24 containing a secondary alcohol.

dine-2-carboxylic acid 25 can be coupled with the boronate esters 4 from Scheme 1 using a Pd-catalyzed Suzuki coupling protocol as described in Scheme 1 to yield biaryl acetamides 26, which can be converted to the carboxamides 27 through condensation with various amines using a coupling reagent such as, but not limited to, EDCI or HATU and promoted with a base such as, but not limited to, DIEA or TEA in a solvent such as, but not limited to, DCM, THF, or DMF. Alternatively, the acid 25 can be coupled with an amine first, followed by Suzuki coupling with a boronate ester 4 to generate biaryl acetamides 27. Alternatively, acid 25 can be reduced to alcohol 28 with a reducing agent such as, but not limited to, borane-tetrahydrofuran or borane-dimethyl sulfide, in a solvent such as, but not limited to, THF Scheme 5: General synthesis of certain 1H-pyrazolo[3,4-b]pyridine derivatives.

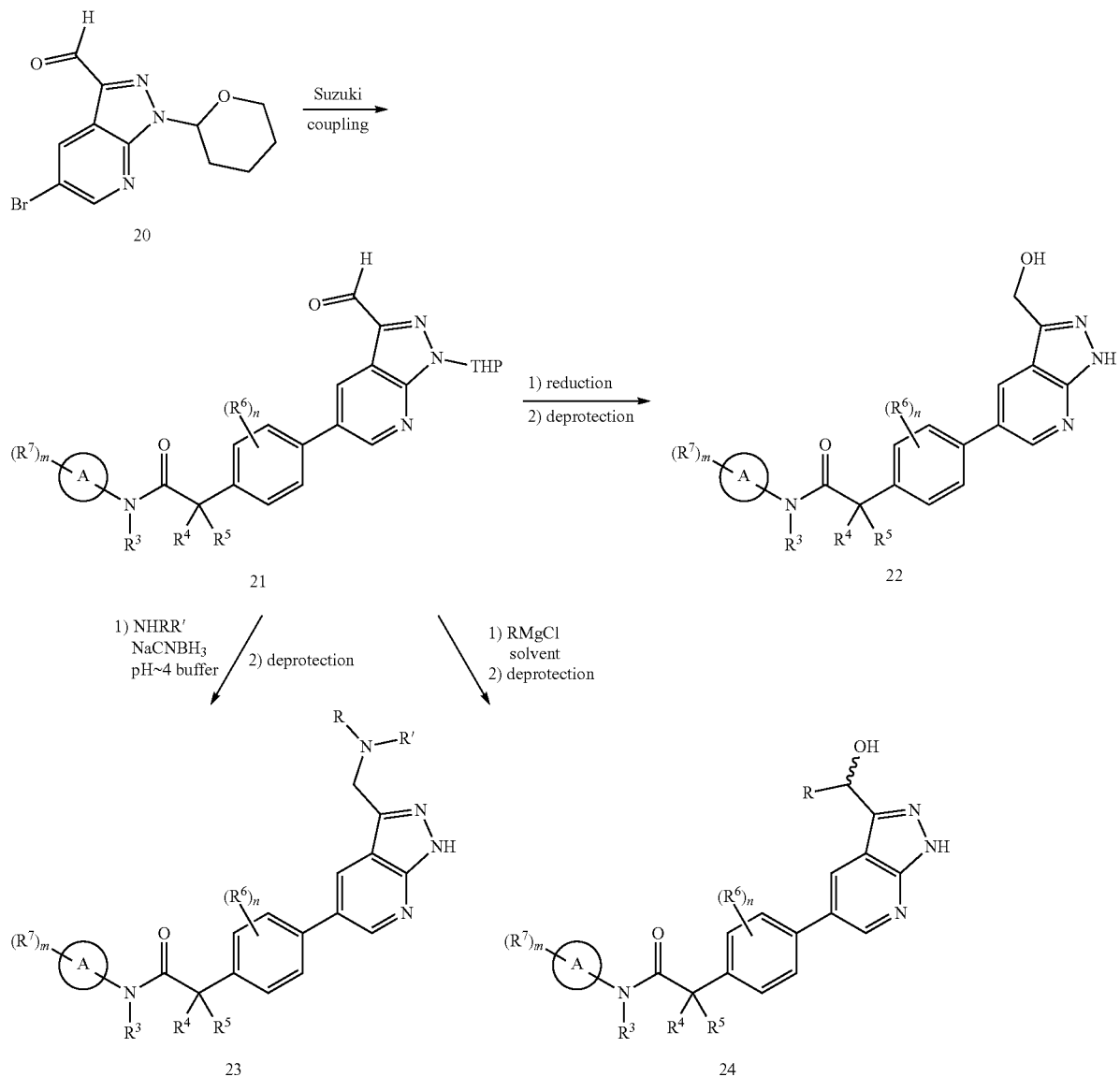

In an illustrative method, certain 1H-pyrrolo[2,3-b]pyridine compounds of formula (I) may be routinely prepared according to the synthetic route outlined in Scheme 6. The commercially available 5-bromo-1H-pyrrolo[2,3-b]pyrior DME at elevated temperature if necessary. Coupling of alcohol 28 with boronate esters 4 using a Pd-catalyzed Suzuki coupling protocol as described in Scheme 1 provides biaryl acetamides 29. Oxidation of the alcohols 29 using oxidizers such as, but not limited to, Dess-Martin periodinane or 2-iodoxybenzoic acid (IBX) provides aldehydes 30. The aldehydes 30 can undergo a variety of further reactions, for example reductive amination with various amines as described in Scheme 5 to afford biaryl acetamide analogs 31, or alternatively Grignard reaction to form secondary alcohols.

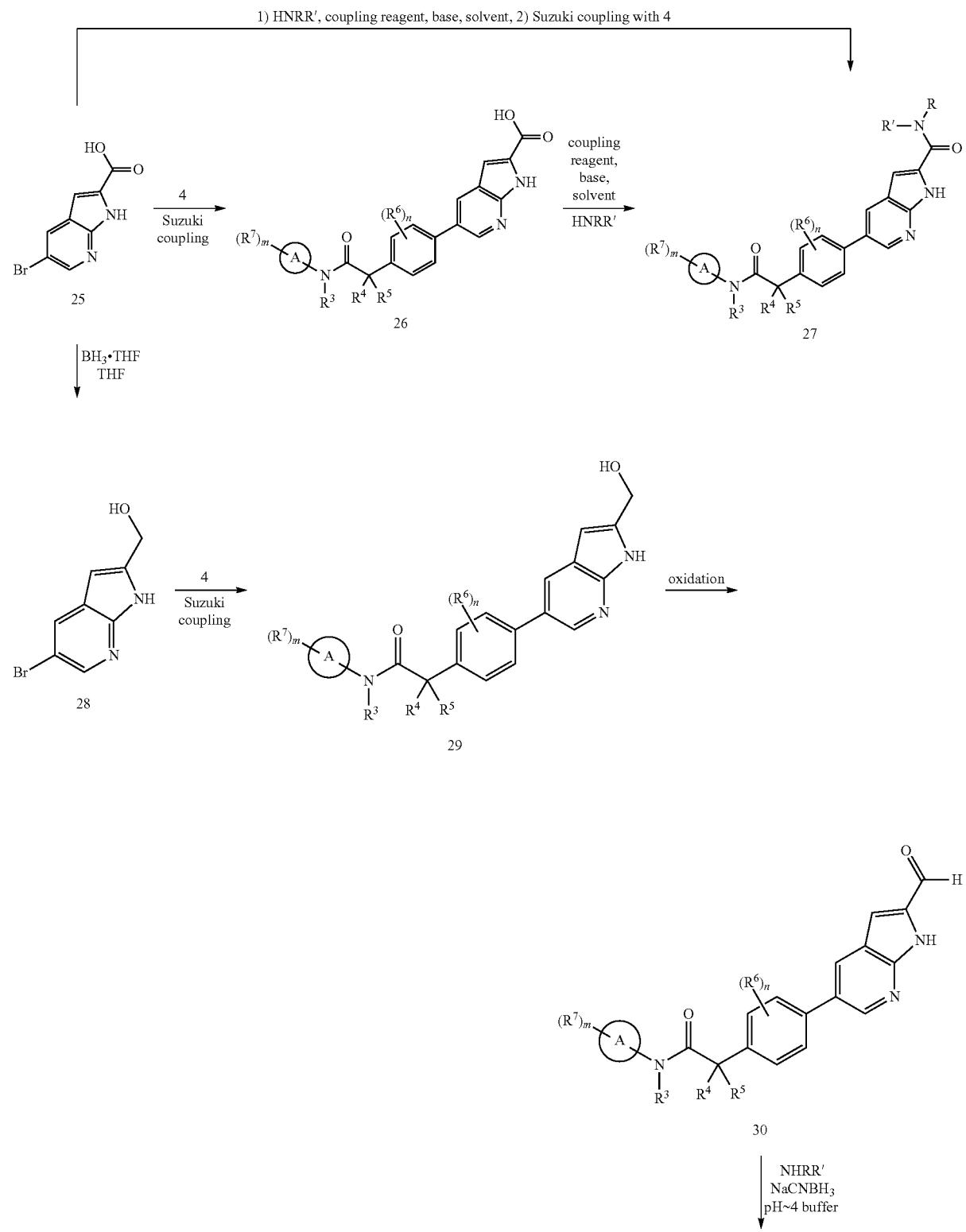

Scheme 6: General synthesis of certain 1H-pyrrolo[2,3-b]pyridine derivatives.

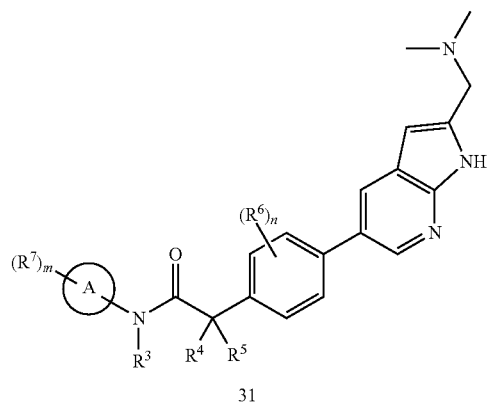

31

In an illustrative method, intermediates 14b (which are examples of general structure 5 used in Schemes 1 and 2) can be prepared using methods illustrated in Scheme 7. Starting with an aryl/heteroaryl amine 32, nitration under standard conditions affords 1-amino-2-nitroaryl/heteroaryl intermediates 33. Reaction of 33 with diketene with heating followed by treatment with a base such as, but not limited to, TEA affords the 1,3-dicarbonyl derivatives 34. Treatment of 34 with alkali and heat followed by reducing conditions such as, but not limited to, treatment with NaBH$_4$, affords a fused 2-piperazinol 35. Conversion of the hydroxyl group of 35 to a halide using a reagent such as, but not limited to, POCl$_3$ or POBr$_3$ with heating as required affords halide 14b. In Scheme 7, it is understood that a Q group during the synthesis may be one that is temporary and subsequently convertible to a final Q group of formula (I). For example, a temporary Q group during the synthesis may be protected hydroxyl which, at an appropriate step in the synthesis of the compound of formula (I), can be deprotected and subsequently alkylated to give the desired Q group of formula (I). As another example, a temporary Q group during the synthesis may be a halogen which at an appropriate step in the synthetic process can be selectively converted to the desired Q group of formula (I) by a suitable transition metal-catalyzed coupling reaction, for example, under Suzuki or Buchwald-Hartwig conditions.

Scheme 7: General synthesis of certain fused pyrazinyl halides.

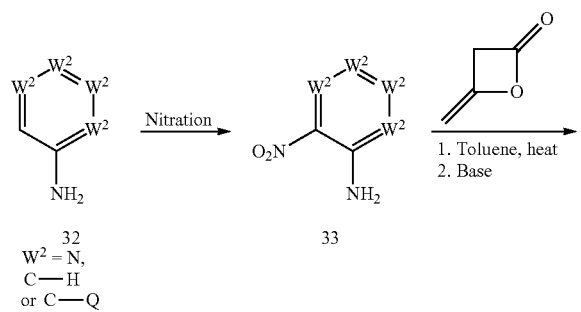

In an illustrative method, intermediates 14b (which are examples of general structure 5 used in Schemes 1 and 2) can be prepared using methods illustrated in Scheme 8. Starting with a 1-amino-2-nitroaryl/heteroaryl intermediate 33 from Scheme 7, amide coupling with cyanoacetic acid is effected by any of a number of well-known amide coupling protocols such as, but not limited to, via the corresponding acid chloride or through a coupling agent such as HATU or EDCI in the presence of a base such as, but not limited to, TEA, DIEA, or pyridine in a solvent such as, but not limited to, DMF, THF, or DCM. Treatment under basic conditions in the presence of pyridine effects cyclization to N-oxide 37. Treatment of 37 with a reducing agent known to reduce N—O bonds such as, but not limited to, sodium dithionite affords fused piperazinol 35, which is converted to 14b as described in Scheme 7. In Scheme 8, it is understood that a Q group during the synthesis may be one that is temporary and subsequently convertible to a final Q group of formula (I). For example, a temporary Q group during the synthesis may be protected hydroxyl which, at an appropriate step in the synthesis of the compound of formula (I), can be deprotected and subsequently alkylated to give the desired Q group of formula (I). As another example, a temporary Q group during the synthesis may be a halogen which at an appropriate step in the synthetic process can be selectively converted to the desired Q group of formula (I) by a suitable transition metal-catalyzed coupling reaction, for example, under Suzuki or Buchwald-Hartwig conditions.

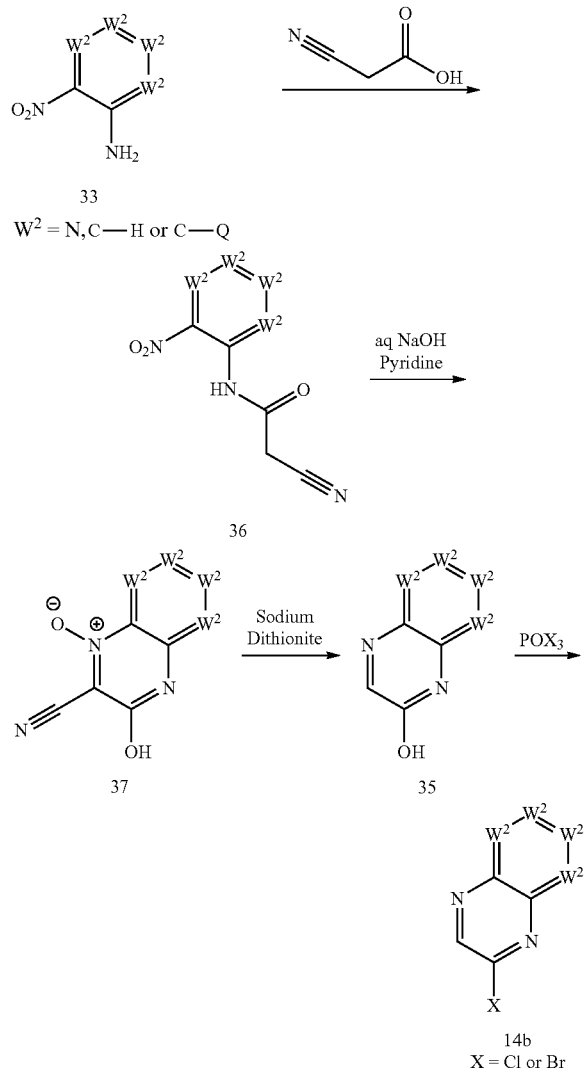

Intermediates 14b (which are examples of general structure 5 used in Schemes 1 and 2) can also be prepared using methods illustrated in Scheme 9. Starting with a nitro-aryl or nitro-heteroaryl derivative 38, reduction of the nitro group under standard conditions, such as hydrogenation in the presence of a transition metal-derived catalyst such as, but not limited to, palladium on activated carbon, or palladium hydroxide on activated carbon, or by treatment with another nitro group reducing agent such as, but not limited to, tin (II) chloride in alcoholic solvent or DMF, or iron in acetic acid affords aryl/heteroarylamine 39. Treatment of 39 with trifluoroacetic anhydride and ammonium nitrate in a suitable solvent such as, but not limited to, dichloromethane affords trifluoroacetamido-containing nitro-aryl/nitro-heteroaryl 40. Reduction of the nitro group of 40 under conditions such as, but not limited to, those described immediately above affords aryl/heteroarylamine 41. Reaction of 41 with a 2,2-di-alkoxy acetic acid derivative 42 in the presence of an amide coupling agent such as, but not limited to, DCC, EDCI, HATU, or PyBOP, optionally in the presence of an additive such as, but not limited to, HOBt or HOAt, and optionally in the presence of an organic base such as, but not limited to, DIEA or TEA in a suitable solvent such as DMF or THF affords aryl/heteroaryl amide-derivative 43. Reaction of 43 with potassium carbonate in a solvent such as MeOH or EtOH, optionally with heating affords aryl/heteroaryl amine 44. Alternatively, treatment of 43 with aqueous LiOH in a suitable solvent such as MeOH or THF optionally with heating affords 44. Treatment of 44 with an acidic reagent such as, but not limited to, aqueous HCl, formic acid, acetic acid, p-tolylsulfonic acid, or TFA, and in a suitable solvent such as dichloromethane, chloroform, acetonitrile, or THF, and with heating as required affords hydroxypyrazine derivative 35. Alternatively, 35 may be obtained by treatment of 44 with trimethylsilyl iodide in a solvent such as dichloromethane or chloroform. Conversion of the hydroxyl group of 35 to a halide using a reagent such as, but not limited to, $POCl_3$ or $POBr_3$ with heating as required affords halide 14b. In Scheme 9, it is understood that a Q group during the synthesis may be one that is temporary and subsequently convertible to a final Q group of formula (I). For example, a temporary Q group during the synthesis may be protected hydroxyl which, at an appropriate step in the synthesis of the compound of formula (I), can be deprotected and subsequently alkylated to give the desired Q group of formula (I). As another example, a temporary Q group during the synthesis may be a halogen which at an appropriate step in the synthetic process can be selectively converted to the desired Q group of formula (I) by a suitable transition metal-catalyzed coupling reaction, for example, under Suzuki or Buchwald-Hartwig conditions.

Scheme 9: Alternative general synthesis of certain fused pyrazinyl halides

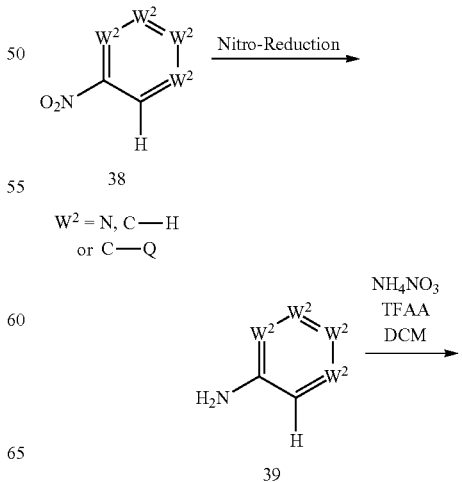

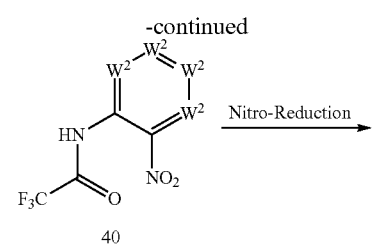

40

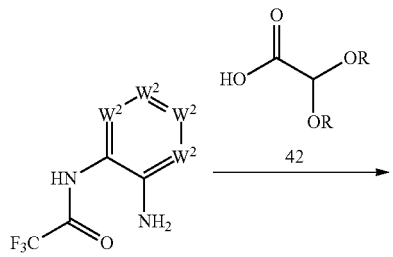

41

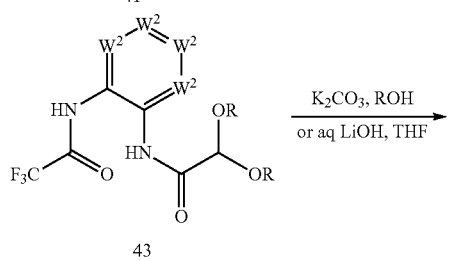

43

R = Me, Et, other lower alkyl

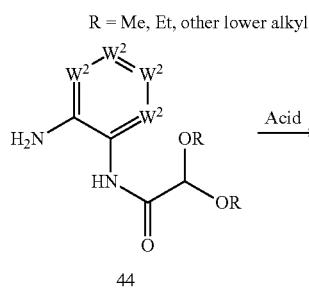

44          35 aqueous LiOH in a suitable solvent such as MeOH or THF with or without heating as required, affords 46. Subsequent oxidation of 46 under conditions typical for a Swern-type or Dess-Martin periodinane-mediated oxidation affords hydroxypyrazine derivative 35. Conversion of the hydroxyl group of 35 to a halide using a reagent such as, but not limited to, $POCl_3$ or $POBr_3$ with heating as required affords halide 14b. In Scheme 10, it is understood that a Q group during the synthesis may be one that is temporary and subsequently convertible to a final Q group of formula (I). For example, a temporary Q group during the synthesis may be protected hydroxyl which, at an appropriate step in the synthesis of the compound of formula (I), can be deprotected and subsequently alkylated to give the desired Q group of formula (I). As another example, a temporary Q group during the synthesis may be a halogen which at an appropriate step in the synthetic process can be selectively converted to the desired Q group of formula (I) by a suitable transition metal-catalyzed coupling reaction, for example, under Suzuki or Buchwald-Hartwig conditions.

Scheme 10: Alternative general synthesis of certain fused pyrazinyl halides

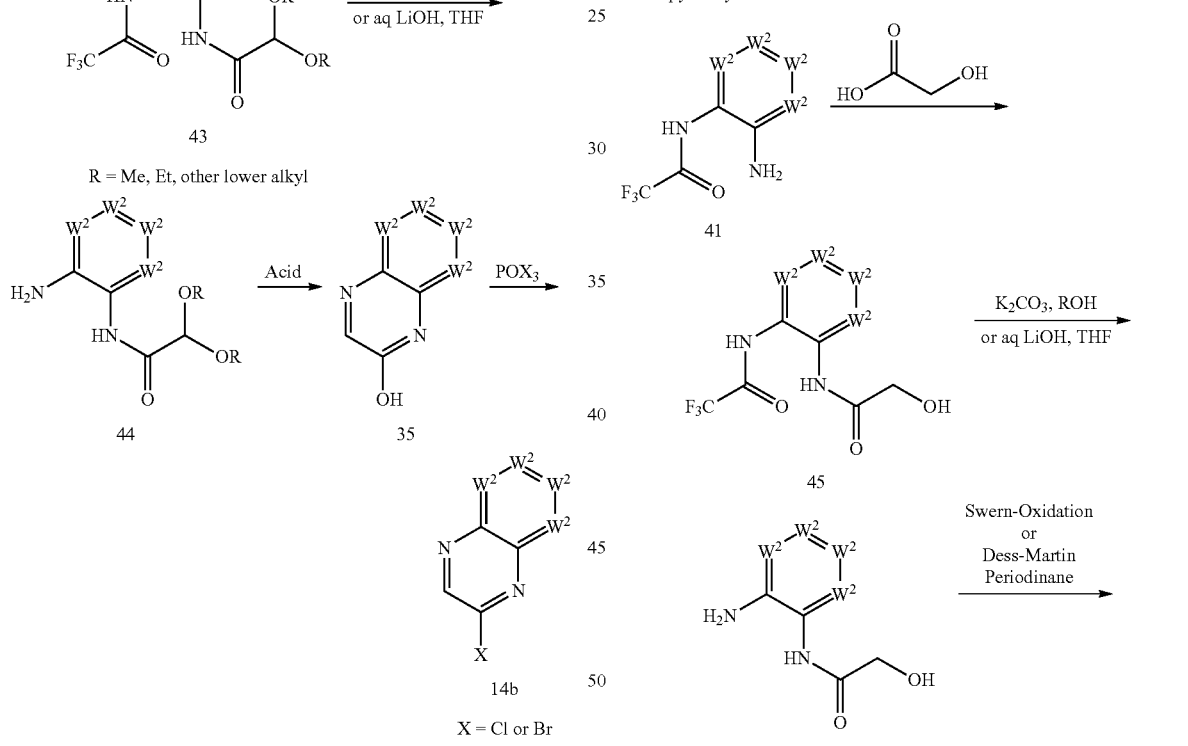

Intermediates 14b (which are examples of general structure 5 used in Schemes 1 and 2) can also be prepared using methods illustrated in Scheme 10. Starting with 41 (Scheme 9), reaction with 2-hydroxyacetic acid in the presence of an amide coupling agent such as, but not limited to, DCC, EDCI, HATU, or PyBOP, optionally in the presence of an additive such as, but not limited to, HOBt or HOAt, and optionally in the presence of an organic base such as, but not limited to, DIEA or TEA in a suitable solvent such as DMF or THF affords aryl/heteroaryl amide-derivative 45. Reaction of 45 with potassium carbonate in a solvent such as MeOH or EtOH, with or without heating as required, affords aryl/heteroaryl amine 46. Alternatively, treatment of 45 with

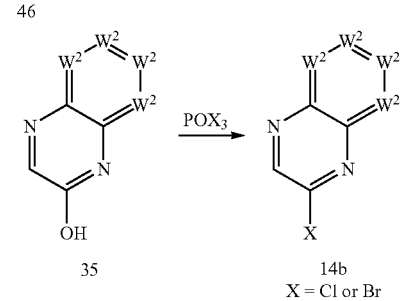

35          14b
            X = Cl or Br

In an illustrative method, certain quinoxaline compounds of formula (I) may be routinely prepared according to the synthetic route outlined in Scheme 11. The commercially available compound 47 can undergo complete demethylation with a reagent such as, but not limited to, boron tribromide or trimethylsilyl iodide, in a solvent such as, but not limited to, DCM, optionally with heating to give dihydroxyquinoxaline 48. Alkylation of the phenolic hydroxyl group of 48 with alkyl halides or alkyl sulfonates provides quinoxalines 49. The alkylations can be conducted in a solvent such as, but not limited to, DMF or $CH_3CN$, and can be promoted with a base, such as, but not limited to, $K_2CO_3$ or $Cs_2CO_3$, optionally with heating. Subsequent coupling between bromoquinoxalines 49 and boronic esters 4 using a Pd-catalyzed Suzuki coupling protocol as described for Scheme 1 affords quinoxaline derivatives 50a, which may represent compounds of the invention. When $R^a$ of quinoxalines 50a contain one or more protected functional groups such as, but not limited to, acetate or silyl ether for alcohols, or t-butylcarbamate for amines, subsequent deprotection releases the intended functional groups using the standard deprotection procedures to give quinoxaline derivatives 50b. On the other hand, alkylation of the phenol 48 with bis-halides or bis-sulfonates provides tricyclic quinoxaline derivatives 51, which can be subsequently coupled with boronic esters 4 using the Suzuki coupling protocol as described for Scheme 1 to provide quinoxaline derivatives 52.

Scheme 11: General synthesis of certain quinoxaline derivatives.

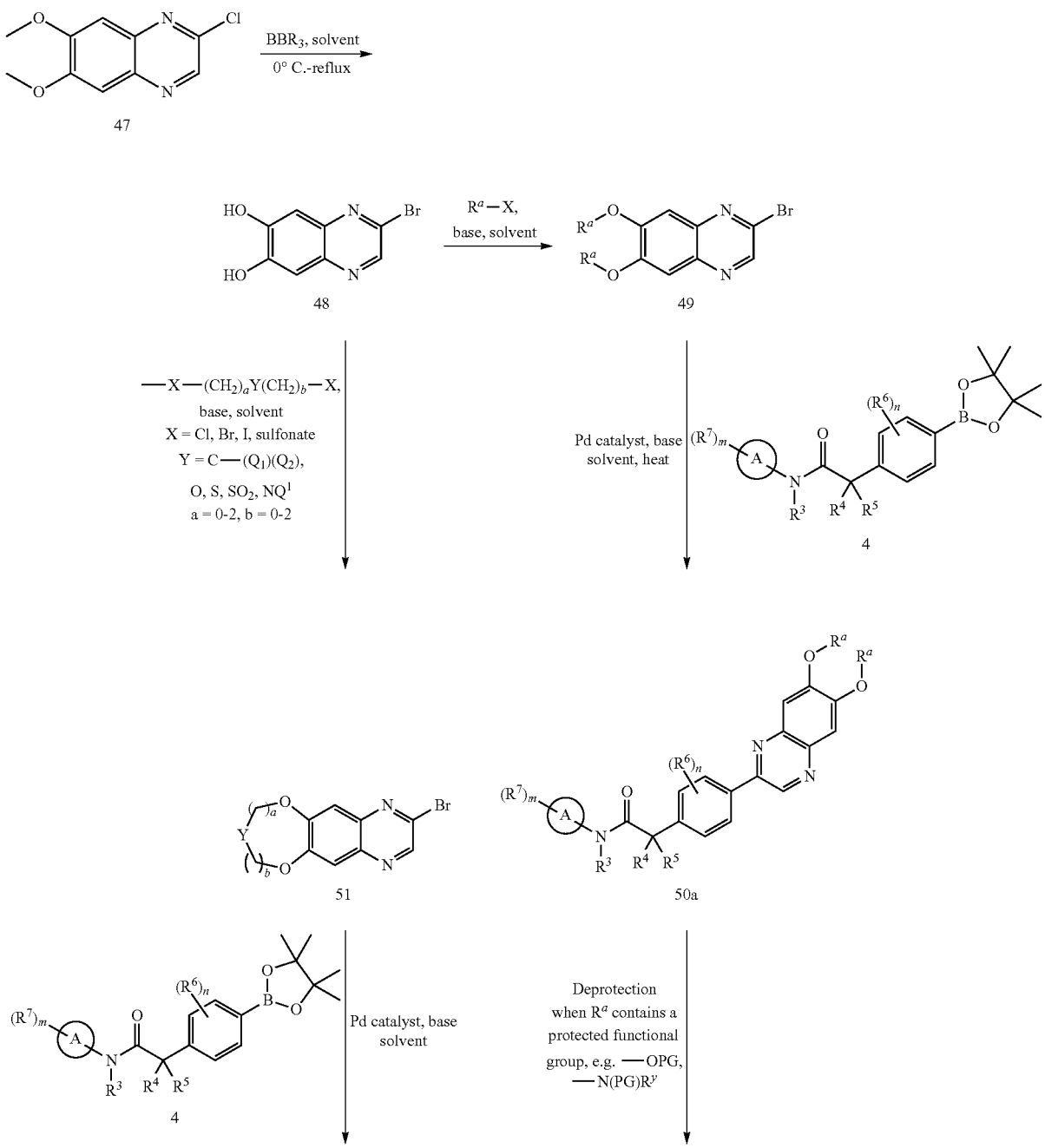

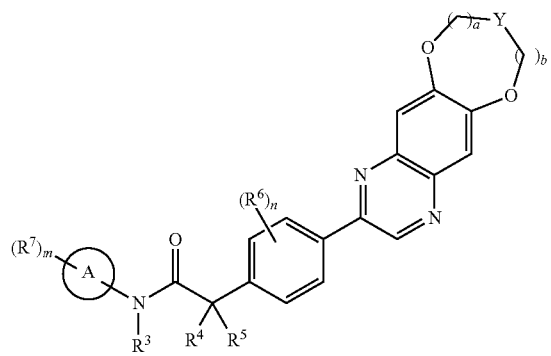
52

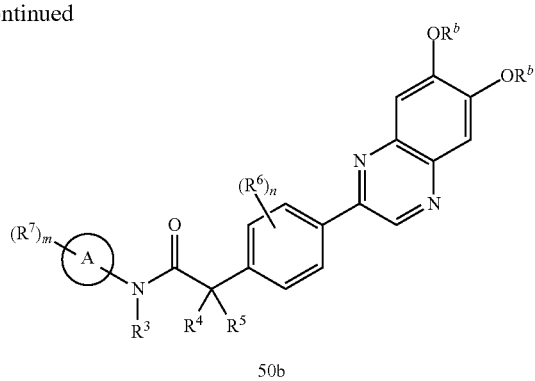
50b
$R^b$ contains deprotection funtionality
e.g. —OH, —NHR$^y$

In an illustrative method, certain quinoxaline compounds of formula (I) may be routinely prepared according to the synthetic route outlined in Scheme 12. The readily available phenolic nitroanilines 53 (ref: WO2004/14899 A1, when $R^c$ is a methyl group) can be chemoselectively O-alkylated with an alkyl halide or alkyl sulfonate under conditions similar to those described for alkylation of 48 (Scheme 11) to afford nitroanilines 54. The alkylation can be further promoted with a reagent such as, but not limited to, potassium iodide or sodium iodide. Reduction of the nitro group of 54 can be effected with a metal such as, but not limited to, zinc or iron in the presence of an acid such as, but not limited to, acetic acid or $NH_4Cl$ in a solvent such as, but not limited to, DCM or EtOH. The diamino benzene intermediates generated can be condensed in situ with a glyoxylate ester to generate a mixture of quinoxalinones (56a and 56b) together with 55a and 55b, which are products of further reduction of 56a and 56b, respectively. Exposure of the mixture to oxidizing conditions such as, but not limited to, $MnO_2$ or $H_2O_2$ in a solvent such as, but not limited to, DCM or DMF returns a mixture of 56a and 56b, which is treated with a triflating reagent such as, but not limited to, trifluoromethanesulfonic anhydride or N-phenyl-bis(trifluoromethanesulfonimide) in the presence of a base such as, but not limited to, $Et_3N$ or pyridine in a solvent such as, but not limited to, DCM or THF to provide a mixture of quinoxalinone triflates (57a and 57b), which can be separated by column chromatography. Subsequent coupling between 57a or 57b and boronic esters 4 using a Pd-catalyzed Suzuki coupling protocol as described for Scheme 1 affords, respectively, quinoxaline derivative 58a or 58b.

Scheme 12: General synthesis of certain quinoxaline derivatives.

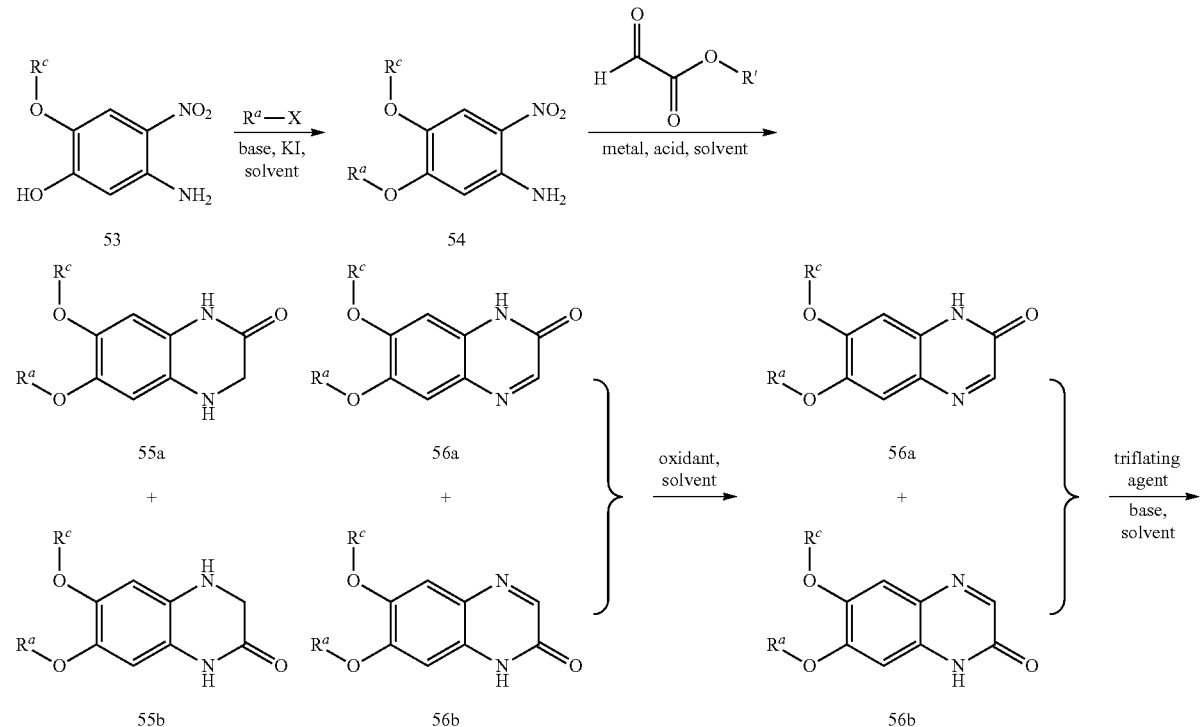

-continued

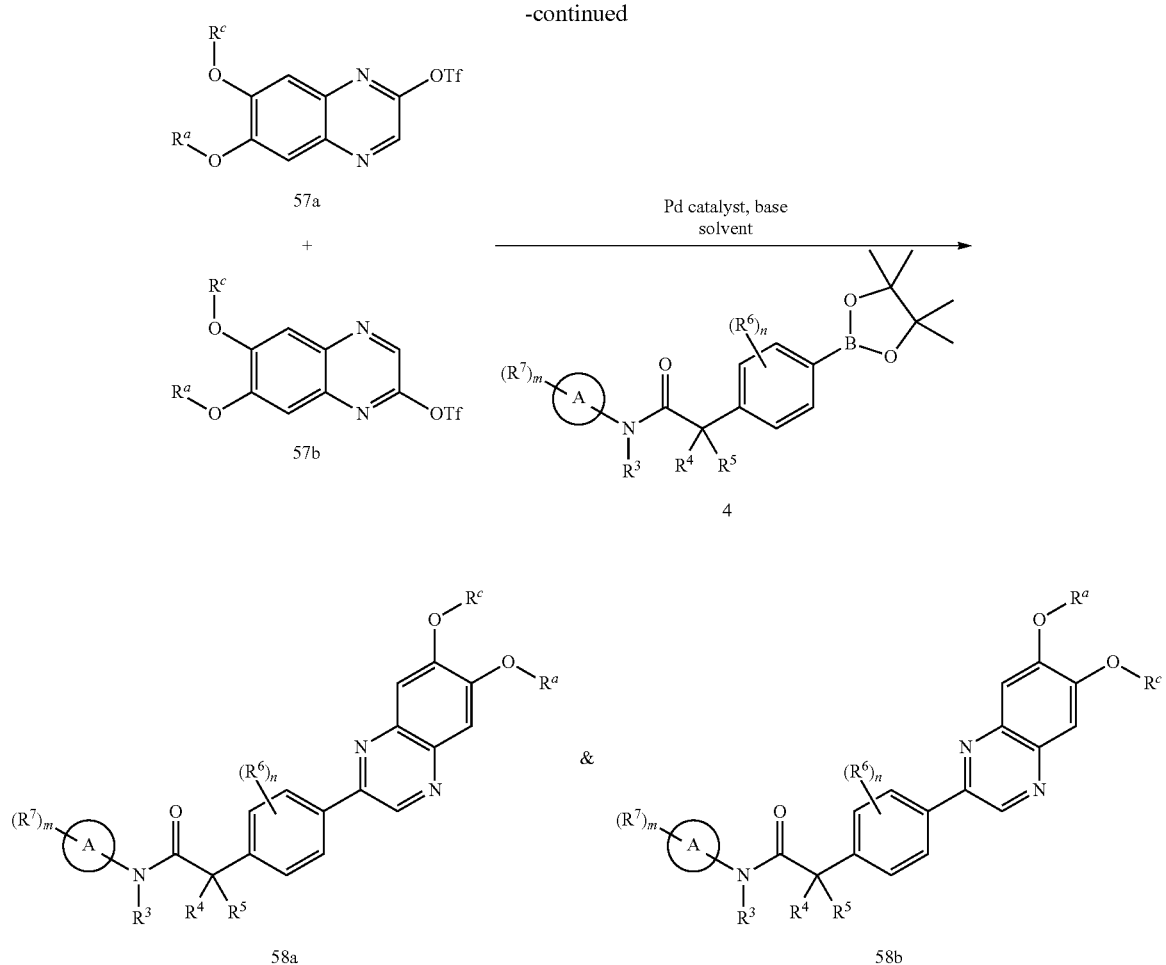

In an illustrative method, certain quinoxaline compounds of formula (I) may be routinely prepared according to the synthetic route outlined in Scheme 13. Nitroanilines 54 from Scheme 12 can be condensed with a glyoxylate ester to form imino compounds 59. The condensation is realized by heating the mixture in a solvent such as, but not limited to, toluene or xylene employing a Dean-Stark trap to collect generated water, and may be further promoted with a dehydrating agent such as, but not limited to, $Na_2SO_4$ or $MgSO_4$. The nitro group of 59 can be reduced to an amino group under conditions similar to those described for reduction of 54 in Scheme 12, or can also be realized with a catalyst such as, but not limited to, palladium on carbon, under a hydrogen atmosphere, in a solvent such as, but not limited to, MeOH or EtOAc. Nitro reduction is followed by intramolecular cyclization to give quinoxalinones 56a and the corresponding over-reduced products 55a. Regiochemical scrambling may be observed during the reduction step, leading to the additional presence of 56b and corresponding over-reduced compounds 55b. Exposure of such a mixture containing over-reduced compounds 55a and/or 55b to oxidizing conditions as described for Scheme 12 simplifies the mixture to one containing 56a and 56b, which is further processed to compounds of the invention 58a and 58b as described in Scheme 12. Chromatographic separation of regioisomeric intermediates or final products is conducted at an appropriate stage of the synthesis.

Scheme 13: General synthesis of certain quinoxaline derivatives.

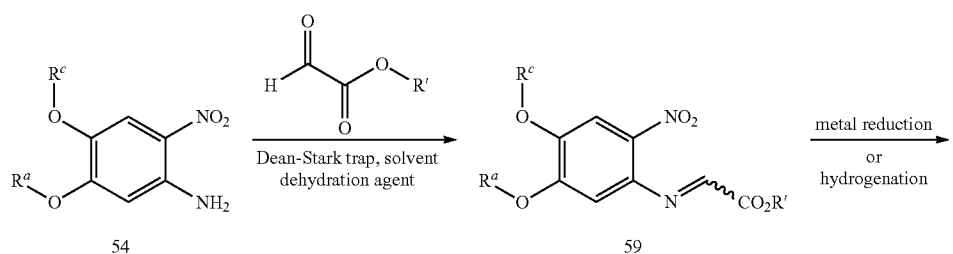

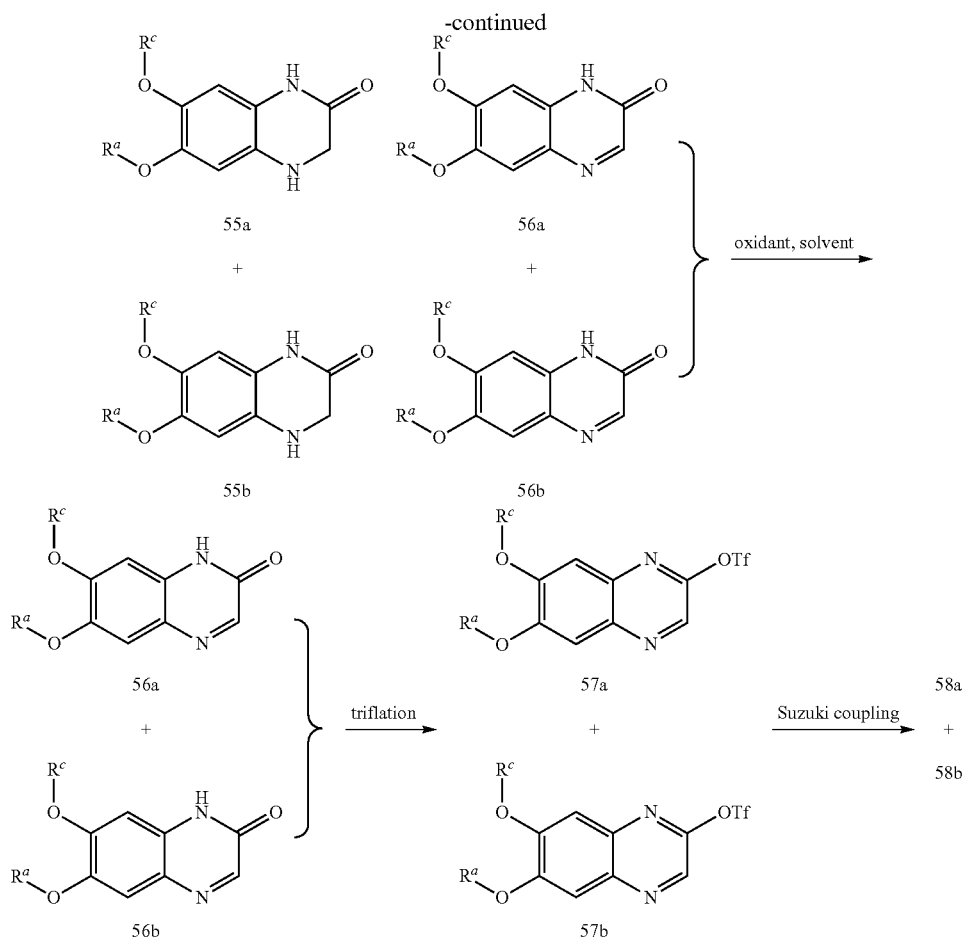

In an illustrative method, certain quinoxaline compounds of formula (I) may be regioselectively prepared according to the synthetic route outlined in Scheme 14. The amino group of anilines 54 can be protected as the bis-tert-butyloxycarbonyl derivatives 60 using a reagent such as, but not limited to, di-tert-butyl dicarbonate ($Boc_2O$) or 2-(tert-butoxycarbonyloxyimino)-2-phenylacetonitrile (Boc-ON). The reaction can be catalyzed with a reagent such as, but not limited to, dimethylaminopyridine (DMAP) in a solvent such as, but not limited to, THF or DCM with optional heating. One of the tert-butyloxycarbonyl groups of 60 can be removed by treatment with a base such as, but not limited to, $K_2CO_3$ or $Na_2CO_3$ in an alcoholic solvent such as, but not limited to, MeOH or EtOH with optional heating to provide compounds 61. Alkylation of compounds 61 with a 2-haloacetic ester generates aminoesters 62. The alkylation can be conducted in a solvent such as, but not limited to, DMF or $CH_3CN$, can be promoted with a base, such as, but not limited to, $K_2CO_3$ or $Cs_2CO_3$, and can be catalyzed with potassium iodide or sodium iodide, optionally with heating. Reduction of the nitro group of 62 under a hydrogen atmosphere with a catalyst such as, but not limited to, palladium on carbon, in a solvent such as, but not limited to, MeOH or EtOAc yields anilines 63. Acid-induced cyclization of anilines 63 accompanied by the removal of the tert-butyloxycarbonyl group is effected using an acid such as, but not limited to, 4N HCl in dioxane or trifluoroacetic acid in a solvent such as MeOH or DCM, to provide dihydroquinoxalinones, which are oxidized to the corresponding quinoxalinones 56a upon exposure to air. Quinoxalinones 56a are converted to quinoxaline products 58a according to the procedures previously described for Scheme 12. Alternatively, quinoxalinones 56a can be converted to chloroquinoxalines 64 by heating with an agent such as, but not limited to, phosphoryl oxychloride or phosphorus pentachloride catalyzed by a reagent such as, but not limited to, DMF or DMA. Subsequent Suzuki coupling between 64 and boronic esters 4 as described for Scheme 1 affords quinoxaline products 58a.

Scheme 14: Regioselective synthesis of certain quinoxaline derivatives.

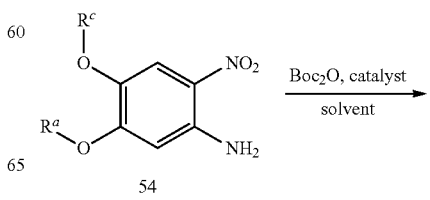

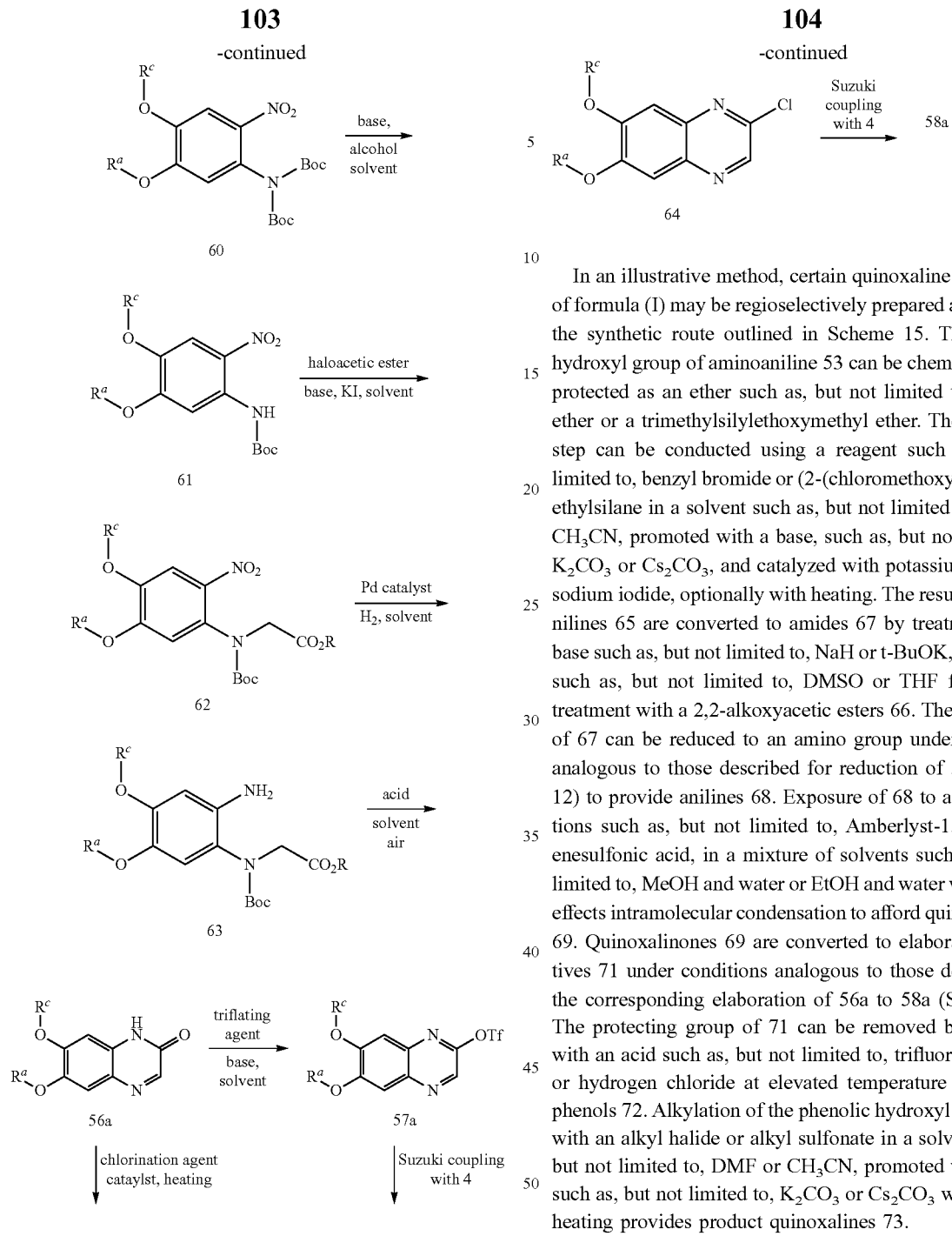

In an illustrative method, certain quinoxaline compounds of formula (I) may be regioselectively prepared according to the synthetic route outlined in Scheme 15. The phenolic hydroxyl group of aminoaniline 53 can be chemoselectively protected as an ether such as, but not limited to, a benzyl ether or a trimethylsilylethoxymethyl ether. The protection step can be conducted using a reagent such as, but not limited to, benzyl bromide or (2-(chloromethoxy)ethyl)trimethylsilane in a solvent such as, but not limited to, DMF or $CH_3CN$, promoted with a base, such as, but not limited to, $K_2CO_3$ or $Cs_2CO_3$, and catalyzed with potassium iodide or sodium iodide, optionally with heating. The resulting nitroanilines 65 are converted to amides 67 by treatment with a base such as, but not limited to, NaH or t-BuOK, in a solvent such as, but not limited to, DMSO or THF followed by treatment with a 2,2-alkoxyacetic esters 66. The nitro group of 67 can be reduced to an amino group under conditions analogous to those described for reduction of 54 (Scheme 12) to provide anilines 68. Exposure of 68 to acidic conditions such as, but not limited to, Amberlyst-15 or p-toluenesulfonic acid, in a mixture of solvents such as, but not limited to, MeOH and water or EtOH and water with heating effects intramolecular condensation to afford quinoxalinones 69. Quinoxalinones 69 are converted to elaborated derivatives 71 under conditions analogous to those described for the corresponding elaboration of 56a to 58a (Scheme 12). The protecting group of 71 can be removed by treatment with an acid such as, but not limited to, trifluoroacetic acid or hydrogen chloride at elevated temperature to generate phenols 72. Alkylation of the phenolic hydroxyl group of 72 with an alkyl halide or alkyl sulfonate in a solvent such as, but not limited to, DMF or $CH_3CN$, promoted with a base, such as, but not limited to, $K_2CO_3$ or $Cs_2CO_3$ with optional heating provides product quinoxalines 73.

Scheme 15: Regioselective synthesis of certian quinoxaline derivatives.

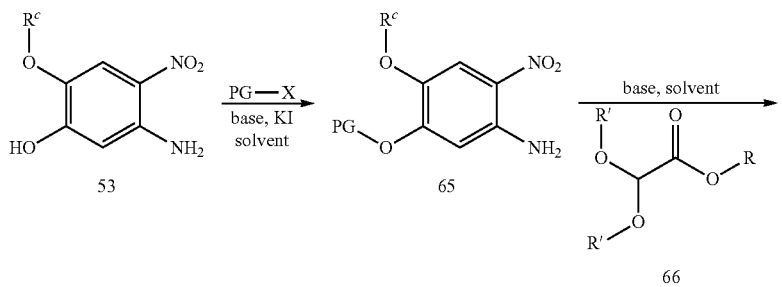

-continued
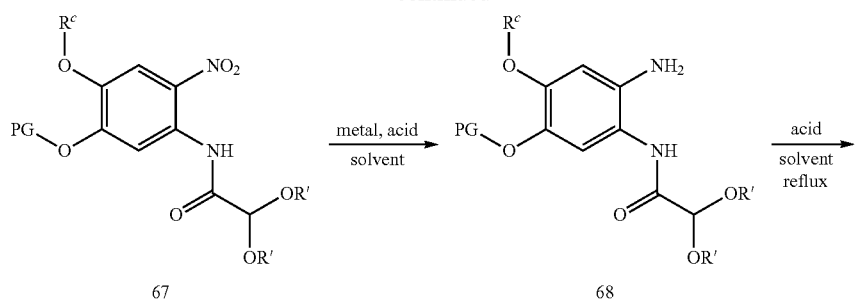
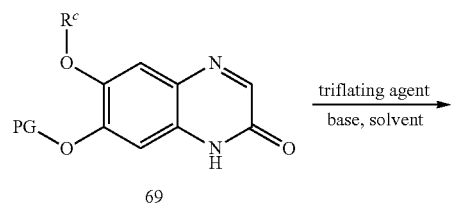
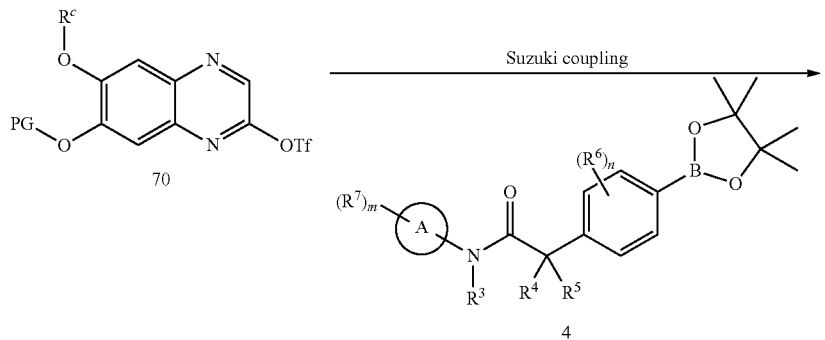
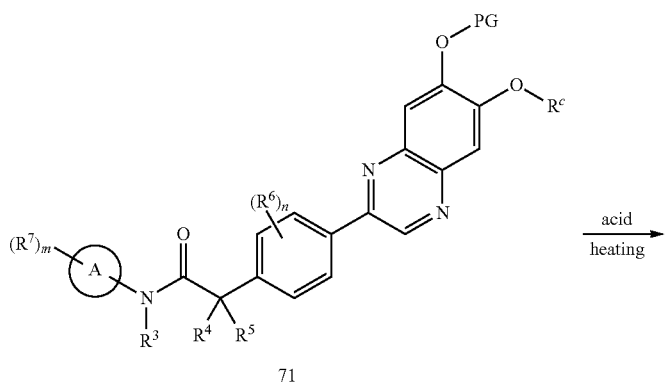
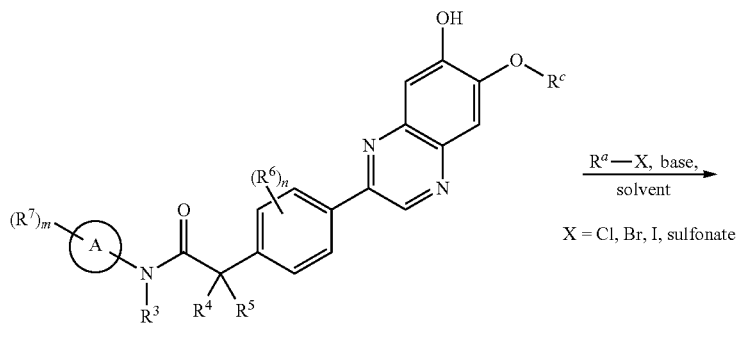

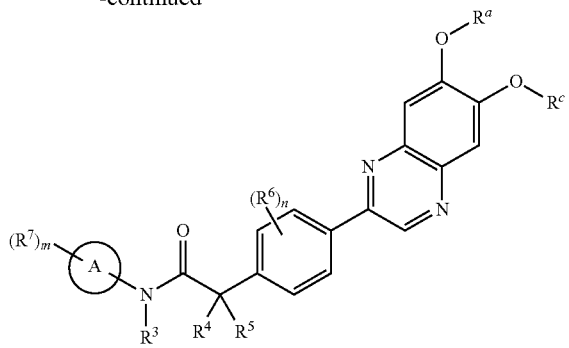

73

In an illustrative method, certain quinoxaline compounds of formula (I) may be prepared according to the synthetic route outlined in Scheme 16. Chemoselective alkylation of the phenolic hydroxyl group of nitroaniline 53 with an alkyl halide 74 under conditions analogous to those described for O-alkylation of 53 in Scheme 12 provides intermediates 75, which can then be converted to quinoxaline triflates 76 using methods analogous to those described in Scheme 14 for preparation of 57a from 54. Suzuki coupling with boronic esters 4 as described in Scheme 1 provides quinoxaline derivatives 77. The hydroxyl group of 77 can be activated as a sulfonate (78) using a reagent such as, but not limited to, methanesulfonyl chloride or p-toluenesulfonyl chloride, promoted by a base such as, but not limited to, triethylamine or pyridine. Displacement of the sulfonate group of 78 with various amines affords amine-containing quinoxaline derivatives 79. The displacements can be conducted in a solvent such as, but not limited to, DMF or CH$_3$CN, can be promoted with a base such as, but not limited to, K$_2$CO$_3$ or Cs$_2$CO$_3$, and can be catalyzed by an iodide such as, but not limited to, potassium iodide or sodium iodide, optionally with heating.

Scheme 16: General synthesis of certain quinoxaline derivatives.

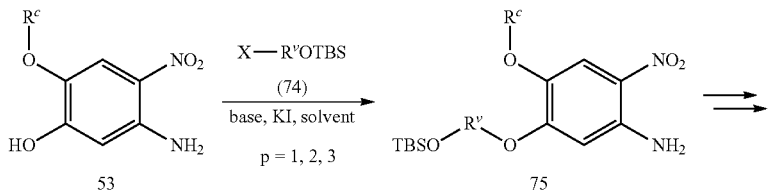

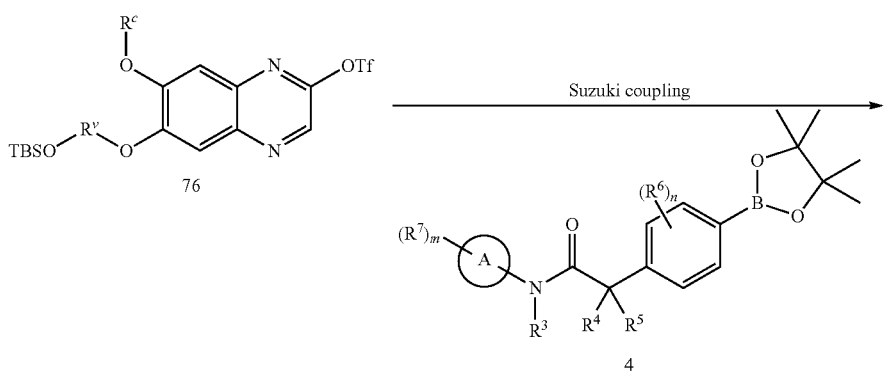

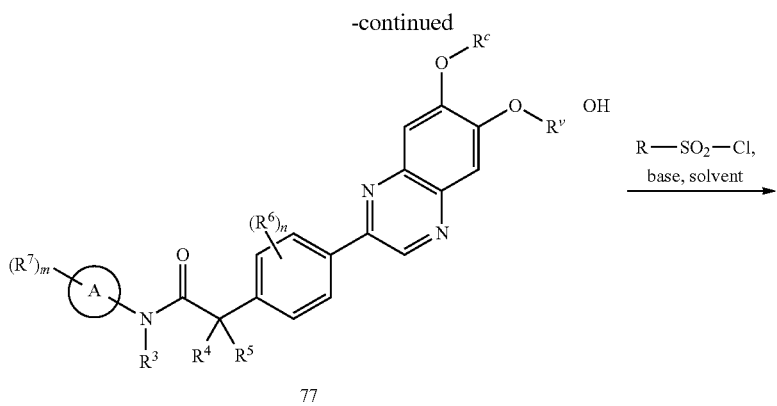

77

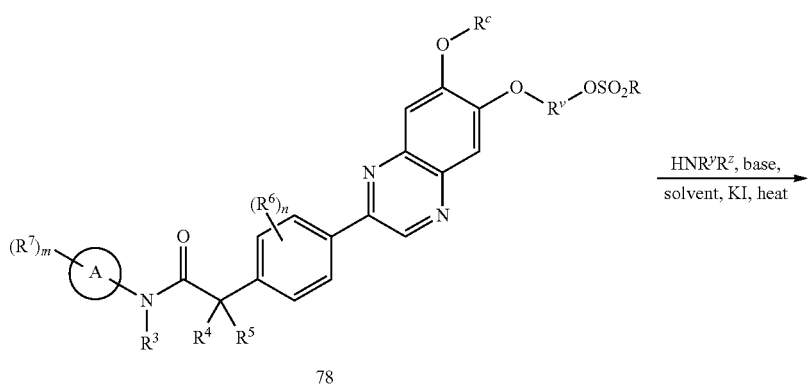

78

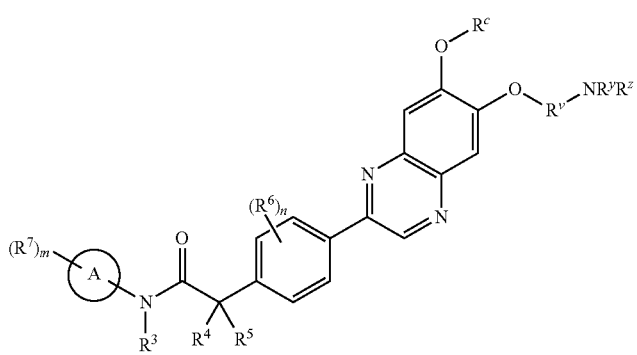

79

In an illustrative method, certain quinoxaline compounds of formula (I) may be prepared according to the synthetic route outlined in Scheme 17. By analogy to the procedures used to convert nitroaniline 54 to product 58a (Scheme 14), nitroanilines 65 (PG=benzyl or trimethylsilylethoxymethyl) from Scheme 15 is converted to protected quinoxaline intermediates 80. The protecting group of 80 can be removed with an acid as described for deprotection of 71 to 72 in Scheme 15 to afford phenols 81. Alkylation of the phenolic hydroxyl group of 80 with bifunctional halides under conditions analogous to those used for conversion of 72 to 73 (Scheme 15) affords quinoxaline derivatives as chlorides 82, which can be treated with various amines to provide amine-containing quinoxaline derivatives 79.

Scheme 17: General synthesis of certain quinoxaline derivatives.

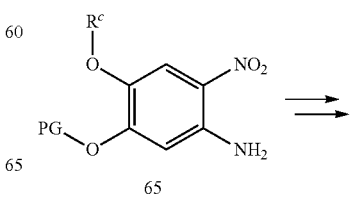

65

-continued

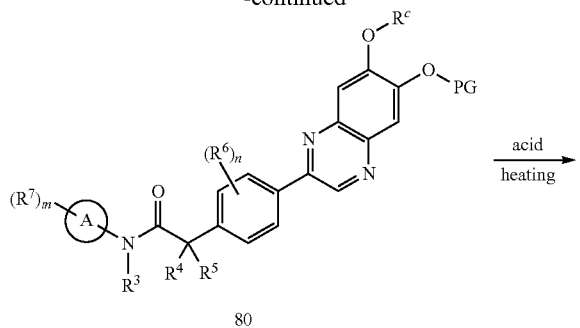

80

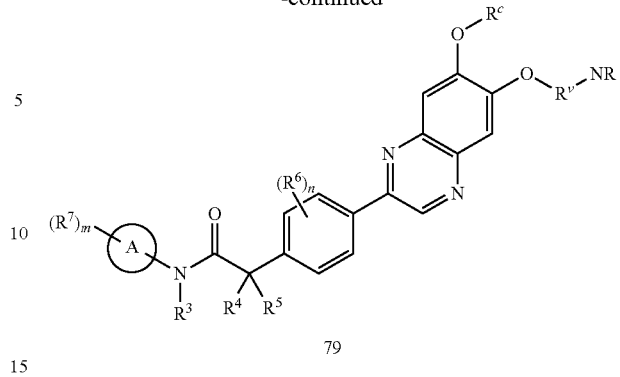

79

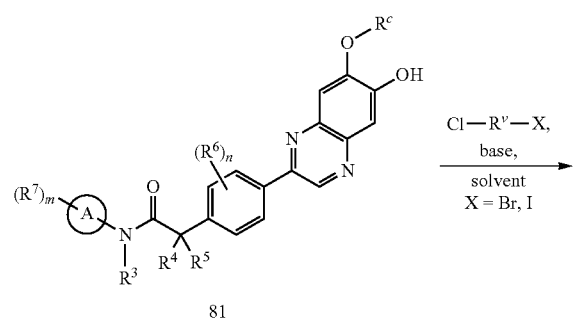

81

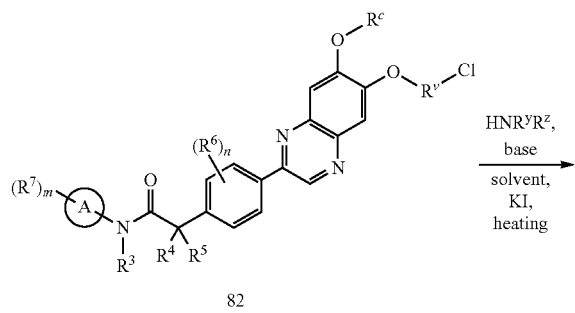

82

In an illustrative method, certain quinoxaline compounds of formula (I) may be prepared according to the synthetic route outlined in Scheme 18. The readily available acetamides 83 can be alkylated with a 2-haloacetic ester to give acetylamino esters 84 under conditions analogous to those described in Scheme 14 for the synthesis of 62. Cleavage of the acetamide of 84 by heating with a concentrated acid such as, but not limited to, hydrogen chloride or sulfuric acid in an alcoholic solvent such as, but not limited to, methanol or ethanol generates compounds 85. Reduction of the nitro group of 85 followed by intramolecular cyclization and oxidation in air analogous to the process described in Scheme 14 generates quinoxalinones 87. Chlorination of 87 to yield 88 as described in Scheme 14 followed by a chemoselective Suzuki coupling with boronic esters 4 as described in Scheme 1 provides bromoquinoxalines 89. A subsequent Suzuki coupling with allylic or vinylic boronates 90 affords quinoxalines 91. The olefin groups of 91 can be dihydroxylated to give compounds 92 with a reagent such as, but not limited to, $OsO_4$, optionally augmented by an additional oxidant such as, but not limited to, morpholine N-oxide (NMO) or $H_2O_2$, in a mixed solvent such as, but not limited to, t-butanol/THF/$H_2O$. Compounds 89 can also undergo Buchwald-Hartwig coupling with various amines to generate amine-containing quinoxalines 93. The coupling is effected using a catalyst such as, but not limited to, $Pd(OAc)_2$ or $Pd_2(dba)_3$, and can be promoted with a ligand such as, but not limited to, 4,5-bis(diphenylphosphino)-9,9-dimethylxanthene (xantphos) or 2-di-tert-butylphosphino-2'-(N,N-dimethylamino)biphenyl (tBuDavePhos). The coupling can be conducted in a solvent such as, but not limited to, toluene or 1,4-dioxane, and can be promoted with a base, such as, but not limited to, $Cs_2CO_3$ or t-BuONa, and by heating at an elevated temperature either with an oil bath or in a microwave reactor.

Scheme 18: General synthesis of certain quinoxaline derivatives.

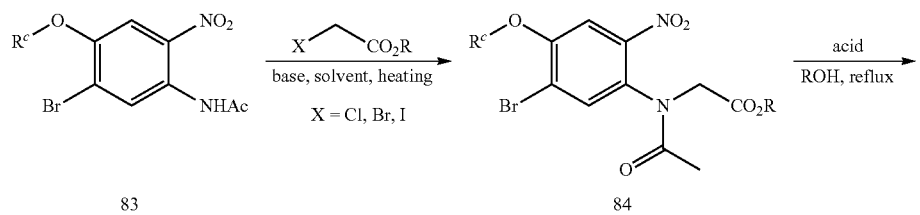

-continued
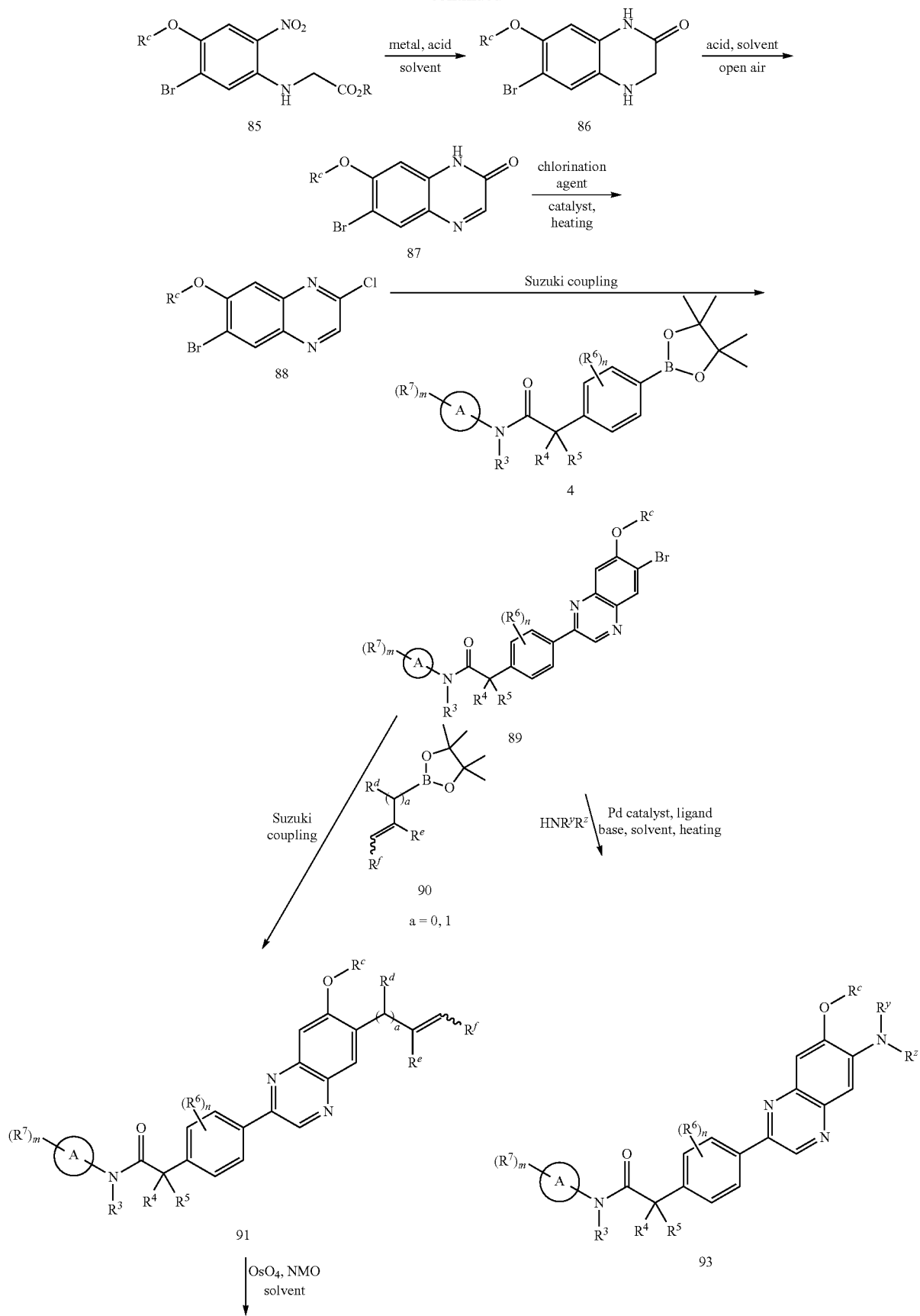

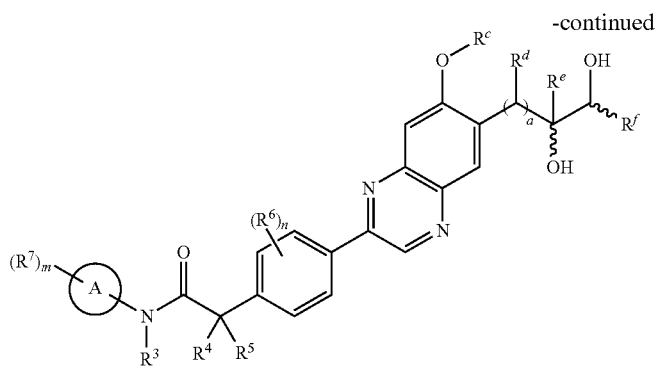

92

In an illustrative method, certain quinoline compounds of formula (I) may be prepared according to the synthetic route outlined in Scheme 19. Condensation of substituted hydroxyanilines 94 with bromomalonaldehyde at elevated temperature generates bromo-hydroxyquinolines 95. The condensation is promoted with an acid such as, but not limited to, HBr in a solvent such as, but not limited to, EtOH or i-PrOH. Alkylation of the hydroxyl group of 95 as described under conditions analogous to those described for alkylation of 48 (Scheme 11) affords bromoquinolines 96, which can be coupled with boronic esters 4 as described in Scheme 1 to afford quinoline products 97.

Scheme 19: General synthesis of certain quinoline derivatives.

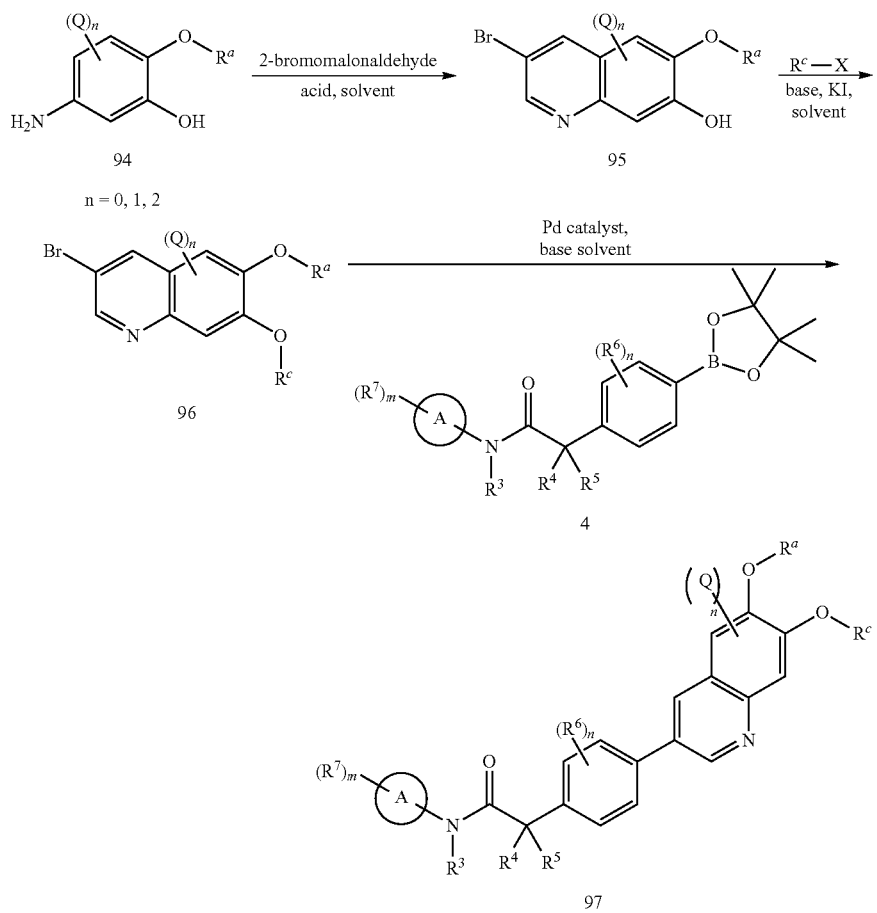

In an illustrative method, certain quinoline compounds of formula (I) may be prepared regioselectively according to the synthetic route outlined in Scheme 20. Readily available nitrophenols 98 can be alkylated under conditions analogous to those described in Scheme 11 for alkylation of 48, followed by reduction of the nitro group by one of the methods described in Schemes 12 and 13 to provide anilines 99. Condensation of anilines 99 with bromomalonaldehyde as described for Scheme 19 affords quinolines 100, which can then be coupled with boronic esters 4 as described in Scheme 1 to afford quinoline derivatives 101, which are compounds of the invention as well as intermediates toward additional compounds of the invention. Activation of the hydroxyl group of 101 with a sulfonating agent as described in Scheme 16 generates sulfonates 102. Subsequent displacement of the sulfonate with various amines as described in Scheme 16 affords amine-containing quinoline derivatives 103.

Scheme 20: General synthesis of certain quinoline derivatives.

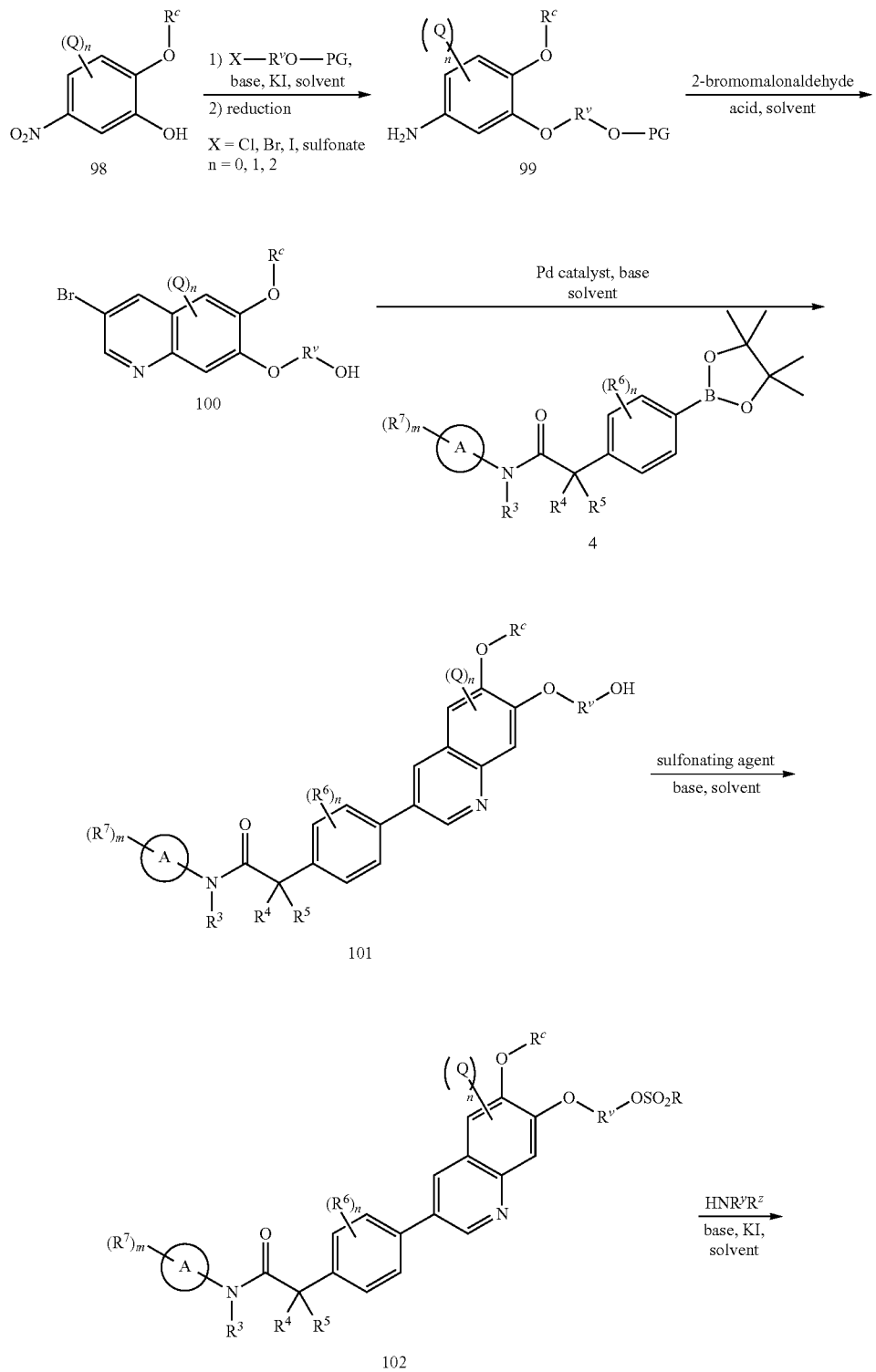

-continued

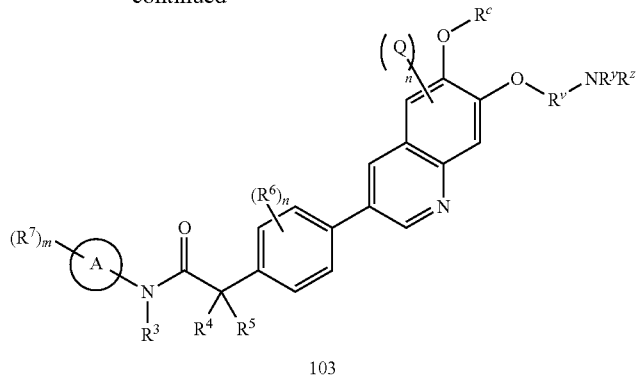

103

In an illustrative method, certain quinoline compounds of formula (I) may be prepared regioselectively according to the synthetic route outlined in Scheme 21. Nitrophenols 104 can be O-alkylated with various diol carbonates 111, for example, optionally substituted 1,3-dioxolan-2-ones, to provide nitrobenzenes 105. Acylation of the hydroxyl group of 105 using acetyl chloride and triethylamine in a suitable solvent followed by reduction of the nitro groups as described in Schemes 12 and 13 yields anilines 106. Condensation of anilines 106 with bromomalonaldehyde as described in Scheme 18 affords quinolines 107, which can then be coupled with boronic esters 4 as described in Scheme 1 to afford quinoline derivatives 108, which are compounds of the invention as well as intermediates toward additional compounds of the invention. In analogy to the previous description for conversion of 102 to 103 (Scheme 20), activation of alcohols 108 with a sulfonylating agent and subsequent treatment of the resulting sulfonates 109 with various amines affords amine-containing quinoline derivatives 110.

Scheme 21: General synthesis of certain quinoline derivatives.

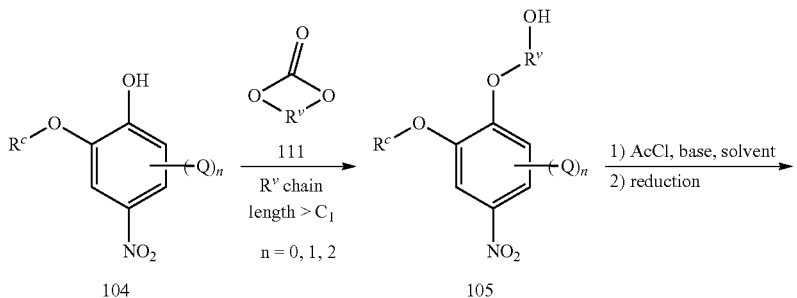

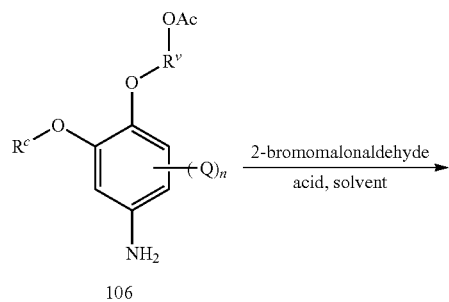

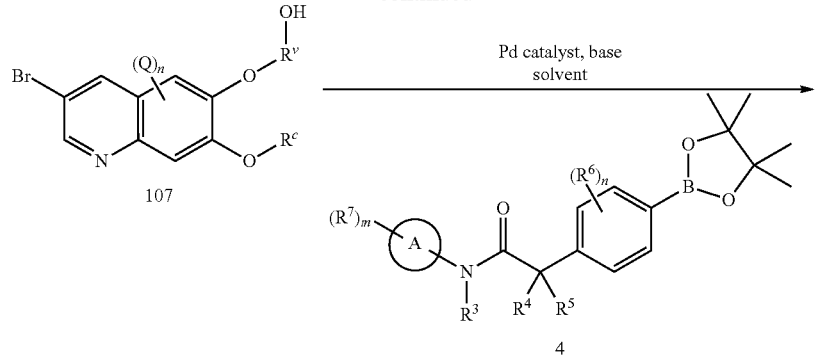
107
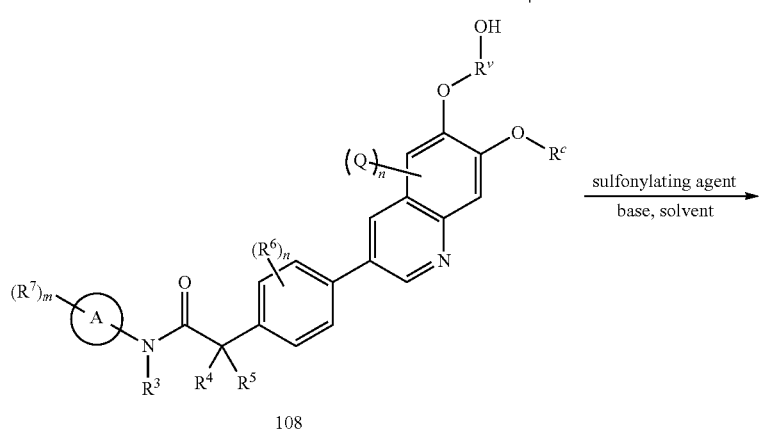
108
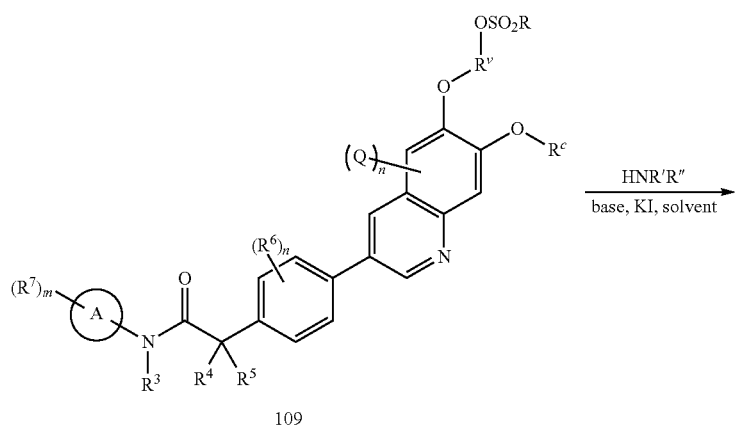
109
110
The subject matter has been described in an illustrative manner, and it is to be understood that the terminology used is intended to be in the nature of description rather than of limitation. Thus, it will be appreciated by those of skill in the

EXAMPLES

Example 1

Preparation of 2-(4-(6,7-dimethoxyquinoxalin-2-yl)phenyl)-N-(5-(1-(trifluoromethyl)cyclopropyl)isoxazol-3-yl)acetamide

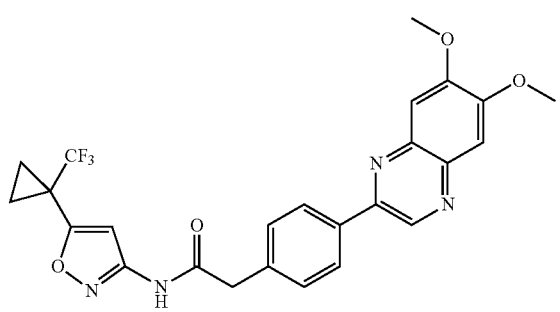 [SMILES: COc1cc2ncc(-c3ccc(CC(=O)Nc4cc(C5(C(F)(F)F)CC5)on4)cc3)nc2cc1OC]

A stirred mixture of 2-chloro-6,7-dimethoxyquinoxaline (67 mg, 0.30 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide (130 mg, 0.30 mmol) (Ref: S. Abraham et al, WO 2011022473 A1), potassium carbonate (90 mg, 0.65 mmol), 1,4-dioxane (1.5 mL), and water (0.25 mL) was flushed with a stream of argon for 10 min. Tetrakis(triphenylphosphine)palladium (0) (35 mg, 0.030 mmol) was added and the reaction vessel was sealed. The mixture was heated at 90° C. for 45 min, then cooled to rt. The mixture was partitioned between EtOAc and water and the organic layer was separated, dried over $MgSO_4$, filtered, and concentrated under reduced pressure. The residue was purified by reverse-phase preparative HPLC using a mixture of water (containing 5% $CH_3CN$ and 0.05% HCOOH) and $CH_3CN$ (containing 0.05% HCOOH) as the mobile phase and Varian Pursuit XRs diphenyl column as the stationary phase to afford 2-(4-(6,7-dimethoxyquinoxalin-2-yl)phenyl)-N-(5-(1-(trifluoromethyl)cyclopropyl)isoxazol-3-yl)acetamide (45 mg, 30%) as a solid. $^1$H NMR (500 MHz, DMSO-$d_6$) δ 11.42 (br s, 1H), 9.33 (s, 1H), 8.24 (d, J=8.5 Hz, 2H), 7.51 (d, J=8.5 Hz, 2H), 7.45 (s, 1H), 7.44 (s, 1H), 6.94 (s, 1H), 4.00 (s, 3H), 3.99 (s, 3H), 3.79 (s, 2H), 1.47-1.52 (m, 4H); LC-MS (ESI) m/z 500 (M+H)$^+$.

Example 2

Preparation of 2-(4-(7-methoxyquinolin-3-yl)phenyl)-N-(5-(1-(trifluoromethyl)cyclopropyl)isoxazol-3-yl)acetamide

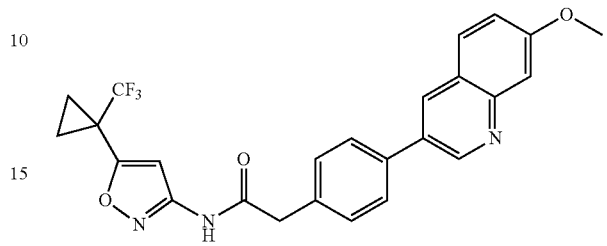

2-(4-(7-Methoxyquinolin-3-yl)phenyl)-N-(5-(1-(trifluoromethyl)cyclopropyl)isoxazol-3-yl)acetamide (7 mg, 14%) was obtained as a solid using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (prepared as described in S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting 3-bromo-7-methoxyquinoline (Ref: M. Frotscher et al, *J. Med. Chem.* 2008, 51, 2158-69) for the 2-chloro-6,7-dimethoxyquinoxaline used in Example 4. $^1$H NMR (500 MHz, DMSO-$d_6$) δ 11.41 (br s, 1H), 9.16 (d, J=2.0 Hz, 1H), 8.55 (d, J=2.0 Hz, 1H), 7.95 (d, J=9.0 Hz, 1H), 7.82 (d, J=8.0 Hz, 2H), 7.47 (d, J=8.0 Hz, 2H), 7.42 (d, J=2 Hz, 1H), 7.30 (dd, J=9.0, 2.5 Hz, 1H), 6.94 (s, 1H), 3.94 (s, 3H), 3.77 (s, 2H), 1.46-1.54 (m, 4H); LC-MS (ESI) m/z 468 (M+H)$^+$.

Example 3

Preparation of 2-(4-(5H-pyrrolo[2,3-b]pyrazin-2-yl)phenyl)-N-(5-(1-(trifluoromethyl)cyclopropyl)isoxazol-3-yl)acetamide

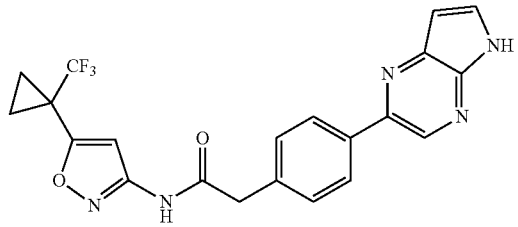 [SMILES: O=C(Cc1ccc(-c2cnc3[nH]ccc3n2)cc1)Nc1cc(C2(C(F)(F)F)CC2)on1]

2-(4-(5H-Pyrrolo[2,3-b]pyrazin-2-yl)phenyl)-N-(5-(1-(trifluoromethyl)cyclopropyl)isoxazol-3-yl)acetamide (26 mg, 13%) was obtained as a solid using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (Ref: S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting 2-bromo-5H-pyrrolo[2,3-b]pyrazine for the 2-chloro-6,7- dimethoxyquinoxaline used in Example 4. ¹H NMR (500 MHz, DMSO-d₆) δ 12.08 (br s, 1H), 11.41 (br s, 1H), 8.82 (s, 1H), 8.08 (d, J=8.0 Hz, 2H), 7.90 (m, 1H), 7.44 (d, J=8.5 Hz, 2H), 6.94 (s, 1H), 6.67 (m, 1H), 3.76 (s, 2H), 1.46-1.53 (m, 4H); LC-MS (ESI) m/z 428 (M+H)⁺.

Example 4

Preparation of 2-(4-(6,7-dimethoxyquinoxalin-2-yl)-2-fluorophenyl)-N-(5-(1-(trifluoromethyl)cyclopropyl)isoxazol-3-yl)acetamide

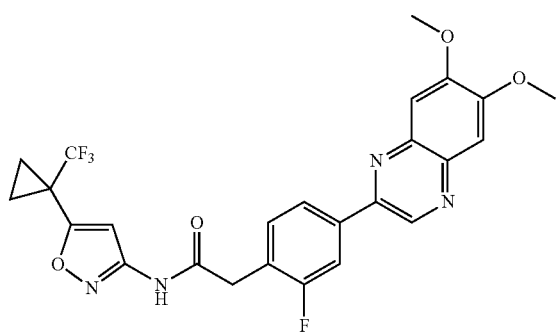 [SMILES: COc1cc2ncc(-c3ccc(CC(=O)Nc4cc(C5(C(F)(F)F)CC5)on4)c(F)c3)nc2cc1OC]

Step 1: To a mixture of 2-(4-bromo-2-fluorophenyl)acetic acid (5.0 g, 21.5 mmol), 4,4,4',4',5,5,5',5'-octamethyl-2,2'-bi(1,3,2-dioxaborolane) (6.54 g, 25.6 mmol), and potassium acetate (8.4 g, 85.6 mmol) in a pressure tube was added DMF (50 mL). The reaction mixture was flushed thoroughly with argon while [1,1'-bis(diphenylphosphino)ferrocene]dichloropalladium(II) dichloromethane complex (880 mg, 1.08 mmol) was added. The reaction mixture was then capped and heated at 90° C. overnight. After cooling to rt, the reaction mixture was diluted with water (50 mL) and the pH of the mixture was adjusted to ~5 with 3N HCl. The resulting mixture was extracted with EtOAc (2×75 mL) and the combined organic layers were washed with brine, dried over MgSO₄, and concentrated under reduced pressure. The residue was purified by silica gel flash column chromatography eluting with 0-35% EtOAc in hexanes to give 2-(2-fluoro-4-(4,4,5,5-tetramethyl-1,3,2-dioxaborolan-2-yl)phenyl)acetic acid (5.7 g, 95%) as an off-white solid. ¹H NMR (300 MHz, DMSO-d₆) δ 12.49 (br s, 1H), 7.41-7.48 (m, 1H), 7.38 (d, J=7.2 Hz, 1H), 7.32 (d, J=10.4 Hz, 1H), 3.66 (s, 2H), 1.30 (s, 12H). LC-MS (ESI) m/z 279 (M−H)⁻.

Step 2: To a stirred mixture of 2-(2-fluoro-4-(4,4,5,5-tetramethyl-1,3,2-dioxaborolan-2-yl)phenyl)acetic acid (2.0 g, 7.14 mmol) and 5-(1-(trifluoromethyl)cyclopropyl)isoxazol-3-amine (2.74 g, 14.3 mmol) in anhydrous DMF (50 mL) were added O-(7-azabenzotriazol-1-yl)-N,N,N',N'-tetramethyluronium hexafluorophosphate (3.54 g, 9.3 mmol) and DIEA (3.72 mL, 21.4 mmol). The resulting mixture was stirred at rt for 1 h, heated at 55° C. for 1 h, and then stirred at rt overnight. The mixture was partitioned between EtOAc (100 mL) and water (100 mL), and the aqueous layer was separated and extracted with EtOAc (1×100 mL). The combined organic layers were washed with brine (50 mL), dried over Na₂SO₄, filtered, and concentrated under reduced pressure. The residue was purified by silica gel chromatography eluting with 0-20% EtOAc in hexanes to give 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide (1.2 g, 37%) as a white solid. LC-MS (ESI) m/z 455 (M+H)⁺. Further elution with 20-40% EtOAc in hexanes afforded unreacted 5-(1-(trifluoromethyl)cyclopropyl)isoxazol-3-amine (2.0 g).

Step 3: To a stirred mixture of 2-chloro-6,7-dimethoxyquinoxaline (71 mg, 0.32 mmol), 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide (130 mg, 0.29 mmol) in CH₃CN were added 2M aq Na₂CO₃ (0.43 mL, 0.86 mmol) and Pd(dppf)Cl₂ dichloromethane complex (23 mg, 0.032 mmol). The reaction mixture was flushed with argon for 10 min and then the reaction vessel was capped and heated at 90° C. for 3 h. After cooling to rt, the reaction mixture was partitioned between EtOAc and brine. The organic layer was dried over Na₂SO₄, filtered, and concentrated under reduced pressure. The residue was purified by silica gel chromatography eluting with 0-2% MeOH in DCM and the isolated product was triturated with Et₂O to give 2-(4-(6,7-dimethoxyquinoxalin-2-yl)-2-fluorophenyl)-N-(5-(1-(trifluoromethyl)cyclopropyl)isoxazol-3-yl)acetamide (110 mg, 75%) as a light pink solid. ¹H NMR (500 MHz, DMSO-d₆) δ 11.47 (br s, 1H), 9.38 (s, 1H), 7.95-8.24 (m, 2H), 7.57 (t, J=7.7 Hz, 1H), 7.46 (d, J=10.4 Hz, 2H), 6.94 (s, 1H), 4.00 (br s, 3H), 3.99 (br s, 3H), 3.88 (br s, 2H), 1.52 (d, J=3.8 Hz, 2H), 1.48 (br s, 2H). LC-MS (ESI) m/z 517 (M+H)⁺.

Example 5

Preparation of 2-(4-(6,7-dimethoxyquinolin-3-yl)phenyl)-N-(5-(1-(trifluoromethyl)cyclopropyl)isoxazol-3-yl)acetamide

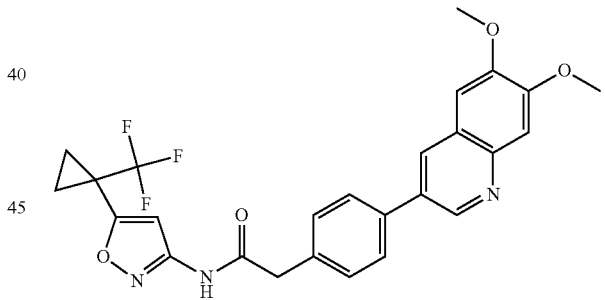

2-(4-(6,7-Dimethoxyquinolin-3-yl)phenyl)-N-(5-(1-(trifluoromethyl)cyclopropyl)isoxazol-3-yl)acetamide (65 mg, 47%) was obtained as a light yellow solid using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (Ref: Abraham, S. et al. WO2011/22473 A1, 2011) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting 3-bromo-6,7-dimethoxyquinoline for the 2-chloro-6,7-dimethoxyquinoxaline used in Example 4. ¹H NMR (500 MHz, DMSO-d₆) δ 11.41 (s, 1H), 9.00 (d, J=2.2 Hz, 1H), 8.43 (d, J=1.6 Hz, 1H), 7.78 (d, J=8.2 Hz, 2H), 7.46 (d, J=8.2 Hz, 2H), 7.40 (d, J=2.7 Hz, 2H), 6.94 (s, 1H), 3.95 (s, 3H), 3.93 (s, 3H), 3.76 (s, 2H), 1.52 (d, J=3.8 Hz, 2H), 1.47 (br s, 2H). LC-MS (ESI) m/z 498 (M+H)⁺.

Example 6

Preparation of N-(5-(tert-butyl)isoxazol-3-yl)-2-(4-(6,7-dimethoxyquinoxalin-2-yl)phenyl)acetamide

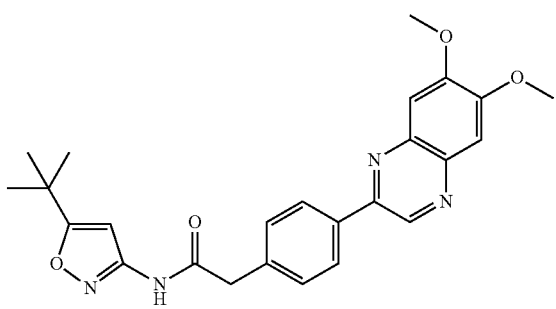 [SMILES: COc1cc2ncc(-c3ccc(CC(=O)Nc4cc(C(C)(C)C)on4)cc3)nc2cc1OC]

N-(5-(tert-Butyl)isoxazol-3-yl)-2-(4-(6,7-dimethoxyquinoxalin-2-yl)phenyl)acetamide (80 mg, 57%) was obtained as a tan solid using a procedure analogous to that described in Step 3 of Example 4, substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)acetic acid used in Example 4. $^1$H NMR (500 MHz, DMSO-$d_6$) δ 11.26 (s, 1H), 9.33 (s, 1H), 8.24 (d, J=8.2 Hz, 2H), 7.50 (d, J=8.2 Hz, 2H), 7.45 (d, J=8.2 Hz, 2H), 6.59 (s, 1H), 4.00 (s, 3H), 3.99 (s, 3H), 3.77 (s, 2H), 1.27 (s, 9H). LC-MS (ESI) m/z 447 (M+H)$^+$.

Example 7

Preparation of 2-(4-(3-aminoquinoxalin-2-yl)phenyl)-N-(5-(1-(trifluoromethyl)cyclopropyl)isoxazol-3-yl)acetamide

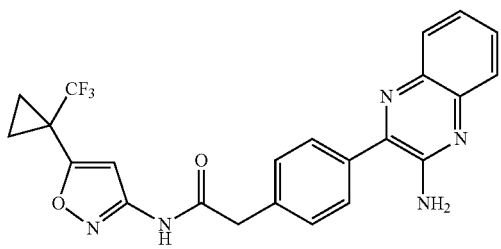 [SMILES: Nc1nc2ccccc2nc1-c1ccc(CC(=O)Nc2cc(C3(C(F)(F)F)CC3)on2)cc1]

Step 1: 2-(4-(3-Chloroquinoxalin-2-yl)phenyl)acetic acid (184 mg, 62%) was obtained as a brown solid using a procedure analogous to that described in Step 1 of Example 8, substituting 2,3-dichloroquinoxaline for the 2-chloro-6,7-dimethoxyquinoxaline used in Example 8. LC-MS (ESI) m/z 299 (M+H)+.

Step 2: A stirred mixture of 2-(4-(3-chloroquinoxalin-2-yl)phenyl)acetic acid (184 mg, 0.60 mmol) and NH4OH (2.0 mL, excess) was heated at 100° C. overnight in a pressure vessel. LC-MS analysis showed nearly complete reaction. After cooling to rt, the reaction mixture was concentrated under reduced pressure and the residue was taken up in water and acidified with 3N aq HCl to pH~5. The resulting solid precipitate was collected and dried to give crude 2-(4-(3-aminoquinoxalin-2-yl)phenyl)acetic acid (67 mg). LC-MS (ESI) m/z 280 (M+H)+.

Step 3: 2-(4-(3-Aminoquinoxalin-2-yl)phenyl)-N-(5-(1-(trifluoromethyl)cyclopropyl)isoxazol-3-yl)acetamide (10 mg, 9.2%) was obtained as a yellow powder using a procedure analogous to that described in Step 2 of Example 4, substituting 2-(4-(3-aminoquinoxalin-2-yl)phenyl)acetic acid for the 2-(2-fluoro-4-(4,4,5,5-tetramethyl-1,3,2-dioxaborolan-2-yl)phenyl)acetic acid used in Example 4. $^1$H NMR (500 MHz, DMSO-d6) 11.43 (s, 1H), 7.79 (d, J=8.2 Hz, 1H), 7.75 (d, J=8.2 Hz, 2H), 7.57 (d, J=3.8 Hz, 2H), 7.49 (d, J=8.2 Hz, 2H), 7.30-7.41 (m, 1H), 6.95 (s, 1H), 6.56 (br s, 2H), 3.79 (s, 2H), 1.50-1.57 (m, 2H), 1.48 (br s, 2H). LC-MS (ESI) m/z 454 (M+H)$^+$.

Example 8

Preparation of 2-(4-(6,7-dimethoxyquinoxalin-2-yl)phenyl)-N-(5-(1,1,1-trifluoro-2-methylpropan-2-yl)isoxazol-3-yl)acetamide

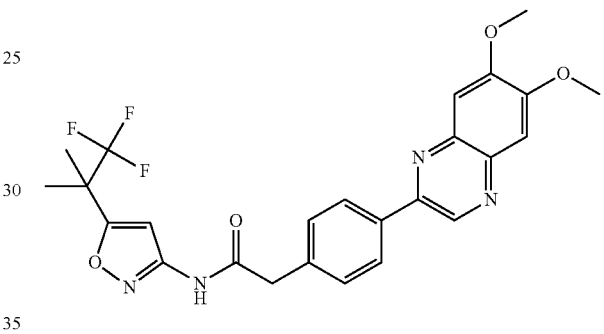

Step 1: To a stirred mixture of 2-(4-(4,4,5,5-tetramethyl-1,3,2-dioxaborolan-2-yl)phenyl)acetic acid (500 mg, 1.91 mmol) and 2-chloro-6,7-dimethoxyquinoxaline (429 mg, 1.91 mmol) in CH3CN (15 mL) were added 2M aq Na2CO3 (3.3 mL, 6.68 mmol) and Pd(dppf)Cl2 dichloromethane complex (78 mg, 0.095 mmol). The reaction mixture was flushed with argon for 10 min before the reaction vessel was capped and heated at 100° C. for 3 h. After cooling to rt, the reaction mixture was treated with 3N aq HCl to pH~5. The brown solid precipitate was collected by filtration and dried to give crude 2-(4-(6,7-dimethoxyquinoxalin-2-yl)phenyl)acetic acid (650 mg). LC-MS (ESI) m/z 325 (M+H)+.

Step 2: 2-(4-(6,7-Dimethoxyquinoxalin-2-yl)phenyl)-N-(5-(1,1,1-trifluoro-2-methylpropan-2-yl)isoxazol-3-yl)acetamide (100 mg, 52%) was obtained as a yellow solid using a procedure analogous to that described in Step 2 of Example 4, substituting 2-(4-(6,7-dimethoxyquinoxalin-2-yl)phenyl)acetic acid for the 2-(2-fluoro-4-(4,4,5,5-tetramethyl-1,3,2-dioxaborolan-2-yl)phenyl)acetic acid used in Example 4 and substituting 5-(1,1,1-trifluoro-2-methylpropan-2-yl)isoxazol-3-amine for the 5-(1-(trifluoromethyl)cyclopropyl)isoxazol-3-amine used in Example 4. $^1$H NMR (500 MHz, DMSO-d6) 11.43 (s, 1H), 9.33 (s, 1H), 8.24 (d, J=8.2 Hz, 2H), 7.51 (d, J=8.2 Hz, 2H), 7.44 (d, J=7.7 Hz, 2H), 6.96 (s, 1H), 4.00 (s, 3H), 3.99 (s, 3H), 3.80 (s, 2H), 1.54 (s, 6H). LC-MS (ESI) m/z 501 (M+H)$^+$.

Example 9

Preparation of 2-(4-(5-methyl-5H-pyrrolo[2,3-b]pyrazin-3-yl)phenyl)-N-(5-(1-(trifluoromethyl)cyclopropyl)isoxazol-3-yl)acetamide

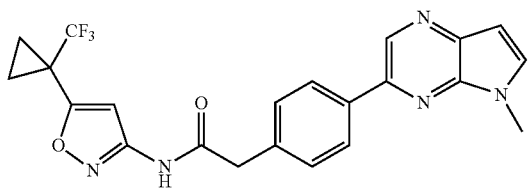 [SMILES: Cn1ccc2ncc(-c3ccc(CC(=O)Nc4cc(C5(C(F)(F)F)CC5)on4)cc3)nc21]

Step 1: To a solution of 2-(4-(4,4,5,5-tetramethyl-1,3,2-dioxaborolan-2-yl)phenyl)acetic acid (886 mg, 3.38 mmol), 5-(1-(trifluoromethyl)cyclopropyl)isoxazol-3-amine (500 mg, 2.6 mmol), HATU (1.98 g, 5.2 mmol) and 1-hydroxy-7-azabenzotriazole (1.41 g, 10.4 mmol) in dry DCM (10 mL) was added DIEA (1.0 g, 7.8 mmol). The reaction mixture was stirred at rt overnight, and then filtered. The filtrated was concentrated under reduced pressure and the residue was purified by silica gel chromatography eluting with 10% EtOAc in petroleum ether to give crude 2-(4-(4,4,5,5-tetramethyl-1,3,2-dioxaborolan-2-yl)phenyl)-N-(5-(1-(trifluoromethyl)cyclopropyl)isoxazol-3-yl)acetamide as a yellow solid (590 mg, 52%). $^1$H NMR (300 MHz, CDCl$_3$) δ 7.79-7.83 (m, 2H), 7.31-7.33 (m, 2H), 5.90 (s, 1H), 3.76 (s, 2H), 1.36 (m, 4H), 1.34 (s, 12H). LC-MS (ESI) m/z 437 (M+H)$^+$.

Step 2: To a solution of 2-(4-(4,4,5,5-tetramethyl-1,3,2-dioxaborolan-2-yl)phenyl)-N-(5-(1-(trifluoromethyl)cyclopropyl)isoxazol-3-yl)acetamide (310 mg, 0.71 mmol), 3-chloro-5-methyl-5H-pyrrolo[2,3-b]pyrazine (119 mg, 0.71 mmol) and 2M aq Na$_2$CO$_3$ (1.5 mL) in 7:1 CH$_3$CN:H$_2$O (6 mL) was added Pd(dppf)Cl$_2$ dichloromethane complex (58 mg, 0.071 mmol) under N$_2$. The reaction mixture was heated at 100° C. for 30 min under microwave conditions. After cooling to rt, the mixture was filtered and the filtrate was concentrated under reduced pressure. The residue was purified by preparative reverse-phase HPLC to give 2-(4-(5-methyl-5H-pyrrolo[2,3-b]pyrazin-3-yl)phenyl)-N-(5-(1-(trifluoromethyl)cyclopropyl)isoxazol-3-yl)acetamide as a yellow solid (40 mg, 13%). $^1$H NMR (300 MHz, CD$_3$OD) δ 8.87 (s, 1H), 8.13 (d, J=8.1 Hz, 2H), 7.74 (d, J=3.6 Hz, 1H), 7.48 (d, J=7.8 Hz, 2H), 6.92 (s, 1H), 6.63 (d, J=3.6 Hz, 1H), 3.95 (s, 3H), 3.79 (s, 2H), 1.43-1.51 (m, 4H). LC-MS (ESI) m/z 442 (M+H)$^+$.

Example 10

Preparation of 2-(4-(thieno[3,2-b]pyridin-6-yl)phenyl)-N-(5-(1-(trifluoromethyl)cyclopropyl)isoxazol-3-yl)acetamide

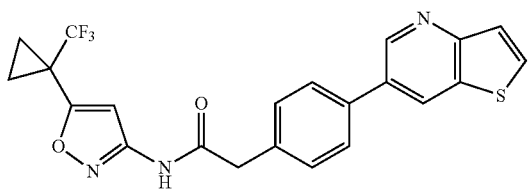 [SMILES: O=C(Cc1ccc(-c2cnc3ccsc3c2)cc1)Nc1cc(C2(C(F)(F)F)CC2)on1]

Step 1: To a solution of thiophen-3-amine oxalate (1.0 g, 5.3 mmol) and 2-bromomalonaldehyde (894 mg, 5.9 mmol) in EtOH (13.2 mL) was added concentrated HCl (3.3 mL) under N2. The reaction mixture was heated at 105° C. for 8 h, then cooled to rt and concentrated under reduced pressure. The residue was purified by silica gel chromatography eluting with 2% MeOH in DCM to give a mixture of 6-bromothieno[3,2-b]pyridine and 3-bromothieno[3,4-b]pyridine as yellow solid (580 mg, 51%). LC-MS (ESI) m/z 215 (M+H)+.

Step 2: To a solution of the mixture of 6-bromothieno[3,2-b]pyridine and 3-bromothieno[3,4-b]pyridine (200 mg, 0.93 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (200 mg, 0.46 mmol) and 2M aq Na2CO3 (2 mL) in 7:1 CH3CN:H2O (8 mL) was added Pd(dppf)Cl2 dichloromethane complex (38 mg, 0.046 mmol) under N2. The reaction mixture was heated at 100° C. for 30 min under microwave conditions. After cooling to rt, the mixture was filtered and the filtrate was concentrated under reduced pressure. The residue was purified by preparative reverse-phase HPLC to give 2-(4-(thieno[3,2-b]pyridin-6-yl)phenyl)-N-(5-(1-(trifluoromethyl)cyclopropyl)isoxazol-3-yl)acetamide as a yellow solid (67 mg, 26%). $^1$H NMR (300 MHz, DMSO-d6 11.41 (s, 1H), 8.95 (s, 1H), 8.75 (s, 1H), 8.14 (d, J=5.4 Hz, 1H), 7.76 (d, J=7.8 Hz, 2H), 7.58 (d, J=5.4 Hz, 1H), 7.44 (d, J=8.4 Hz, 2H), 6.92 (s, 1H), 3.74 (s, 2H), 1.47 (d, J=11.1 Hz, 4H). LC-MS (ESI) m/z 444 (M+H)$^+$.

Example 11

Preparation of 2-(4-(1,5-naphthyridin-3-yl)phenyl)-N-(5-(1-(trifluoromethyl)cyclopropyl)isoxazol-3-yl)acetamide

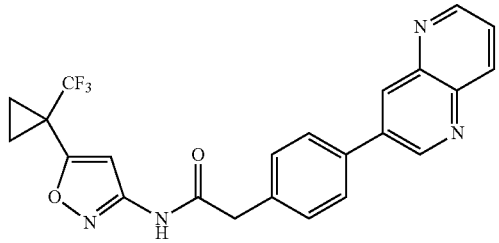 [SMILES: O=C(Cc1ccc(-c2cnc3cccnc3c2)cc1)Nc1cc(C2(C(F)(F)F)CC2)on1]

2-(4-(1,5-Naphthyridin-3-yl)phenyl)-N-(5-(1-(trifluoromethyl)cyclopropyl)isoxazol-3-yl)acetamide (49 mg, 16%) was obtained as a solid using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (Ref: S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting 3-bromo-1,5-naphthyridine for the 2-chloro-6,7-dimethoxyquinoxaline used in Example 4. $^1$H NMR (300 MHz, DMSO-d$_6$) δ 11.44 (br s, 1H), 9.37 (d, J=1.2 Hz, 1H), 9.05 (d, J=2.4 Hz, 1H), 8.86 (s, 1H), 8.47 (d, J=6.0 Hz, 1H), 7.93 (m, 2H), 7.81 (m, 1H), 7.64 (m, 2H), 6.95 (s, 1H), 3.79 (s, 2H), 1.48-1.54 (m, 4H); LC-MS (ESI) m/z 439 (M+H)$^+$.

Example 12

Preparation of 2-(4-(1,6-naphthyridin-3-yl)phenyl)-N-(5-(1-(trifluoromethyl)cyclopropyl)isoxazol-3-yl)acetamide

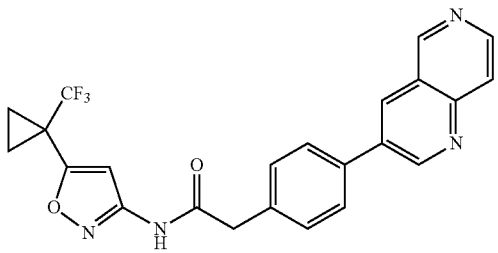 [SMILES: O=C(Cc1ccc(-c2cnc3ccncc3c2)cc1)Nc1cc(C2(C(F)(F)F)CC2)on1]

2-(4-(1,6-Naphthyridin-3-yl)phenyl)-N-(5-(1-(trifluoromethyl)cyclopropyl)isoxazol-3-yl)acetamide (33 mg, 24%) was obtained as a solid using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (Ref: S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting 3-bromo-1,6-naphthyridine for the 2-chloro-6,7-dimethoxyquinoxaline used in Example 4. $^1$H NMR (300 MHz, MeOH-d$_4$) δ 9.58-9.59 (m, 2H), 8.91 (s, 1H), 8.75 (d, J=6.3 Hz, 1H), 8.21 (d, J=6.0 Hz, 1H), 7.87 (d, J=8.4 Hz, 2H), 7.57 (d, J=8.4 Hz, 2H), 6.92 (s, 1H), 3.83 (s, 2H), 1.43-1.52 (m, 4H); LC-MS (ESI) m/z 439 (M+H)$^+$.

Example 13

Preparation of 2-(4-(5,7-dimethoxyquinolin-3-yl)phenyl)-N-(5-(1-(trifluoromethyl)cyclopropyl)isoxazol-3-yl)acetamide

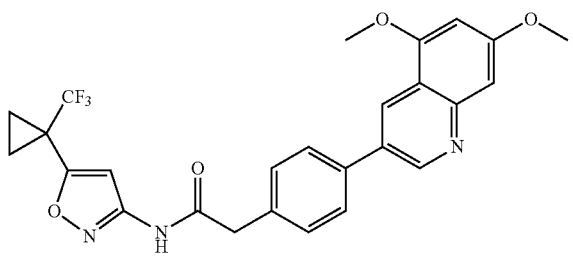 [SMILES: COc1cc(OC)c2cc(-c3ccc(CC(=O)Nc4cc(C5(C(F)(F)F)CC5)on4)cc3)cnc2c1]

2-(4-(5,7-Dimethoxyquinolin-3-yl)phenyl)-N-(5-(1-(trifluoromethyl)cyclopropyl)isoxazol-3-yl)acetamide (19 mg, 8%) was obtained as a solid using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (Ref: S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting the mixture of 3-chloro-5,7-dimethoxyquinoline and 3-bromo-5,7-dimethoxyquinoline from Step 1 of Example 36 for the 2-chloro-6,7-dimethoxyquinoxaline used in Example 4. $^1$H NMR (300 MHz, MeOH-d$_4$) δ 9.00 (m, 1H), 8.99 (m, 1H), 7.72 (d, J=8.1 Hz, 2H), 7.49 (d, J=8.4 Hz, 2H), 6.98 (d, J=2.1 Hz, 1H), 6.92 (s, 1H), 6.68 (d, J=1.8 Hz, 1H), 4.03 (s, 3H), 3.96 (s, 3H), 3.79 (s, 2H), 1.43-1.51 (m, 4H); LC-MS (ESI) m/z 498 (M+H)$^+$.

Example 14

Preparation of 2-(4-(1H-imidazo[4,5-b]pyrazin-5-yl)phenyl)-N-(5-(1-(trifluoromethyl)cyclopropyl)isoxazol-3-yl)acetamide

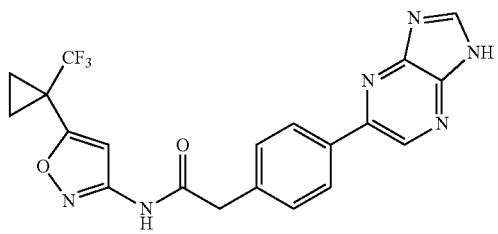 [SMILES: O=C(Cc1ccc(-c2cnc3[nH]cnc3n2)cc1)Nc1cc(C2(C(F)(F)F)CC2)on1]

Step 1: To a suspension of 60% NaH in mineral oil (60 mg, 1.5 mmol) in DMF (4 mL) at 0° C. was added 5-bromo-1H-imidazo[4,5-b]pyrazine (200 mg, 1.0 mmol). The mixture was warmed to rt and stirred for 25 min before cooling to 0° C. 2-(trimethylsilyl)ethoxymethyl chloride (0.212 mL, 1.2 mmol) was added dropwise and the mixture was stirred at 0° C. for 30 min. The mixture was then partitioned between EtOAc and brine. The organic layer was separated, dried over MgSO$_4$, filtered, and concentrated under reduced pressure. The residue was purified by silica gel chromatography eluting with 0-20% EtOAc in hexanes to afford either 5-bromo-1-((2-(trimethylsilyl)ethoxy)methyl)-1H-imidazo[4,5-b]pyrazine or 6-bromo-1-((2-(trimethylsilyl)ethoxy)methyl)-1H-imidazo[4,5-b]pyrazine as a single compound (115 mg, 35%), the absolute structure of which was not determined. $^1$H NMR (500 MHz, DMSO-d$_6$) δ 9.02 (s, 1H), 8.65 (s, 1H), 5.67 (s, 2H), 3.59 (t, J=8.0 Hz, 2H), 0.84 (t, J=8.0 Hz, 2H), −0.09 (s, 9H); LC-MS (ESI) m/z 329, 331 (M+H)$^+$.

Step 2: To a stirred solution of 2-(4-(4,4,5,5-tetramethyl-1,3,2-dioxaborolan-2-yl)phenyl)-N-(5-(1-(trifluoromethyl)cyclopropyl) isoxazol-3-yl)acetamide (102 mg, 0.23 mmol) (Ref: S. Abraham et al, WO 2011022473 A1) in CH$_3$CN (1.2 mL) were added the product from Step 1 of this example (115 mg, 0.349 mmol) and 2M aq Na$_2$CO$_3$ (0.25 mL, 0.50 mmol), and the mixture was flushed with a stream of argon for 20 min at rt. [1,1'-Bis(diphenylphosphino)ferrocene]dichloropalladium(II) dichloromethane complex (18 mg, 0.023 mmol) was then added and the mixture was stirred at 100° C. for 1 h in a sealed vessel. The mixture was partitioned between DCM and H$_2$O and the organic layer was separated, dried over MgSO$_4$, filtered, and concentrated under reduced pressure. The residue was purified by silica gel chromatography eluting with 20% to 60% EtOAc in hexanes to afford either N-(5-(1-(trifluoromethyl)cyclopropyl)isoxazol-3-yl)-2-(4-(1-((2-(trimethylsilyl)ethoxy)methyl)-1-H-imidazo[4,5-b]pyrazin-5-yl)phenyl)acetamide or N-(5-(1-(trifluoromethyl)cyclopropyl)isoxazol-3-yl)-2-(4-(1-((2-(trimethylsilyl)ethoxy)methyl)-1H-imidazo[4,5-b]pyrazin-6-yl)phenyl)acetamide as a single compound (54 mg, 40%), the absolute structure of which was not determined. $^1$H NMR (500 MHz, DMSO-d$_6$) δ 11.41 (s, 1H), 9.06

(s, 1H), 8.97 (s, 1H), 8.13 (d, J=8.2 Hz, 2H), 7.48 (d, J=8.2 Hz, 2H), 6.94 (s, 1H), 5.69 (s, 2H), 3.78 (s, 2H), 3.63 (t, J=8.0 Hz, 2H), 1.50-1.54 (m, 2H), 1.44-1.49 (m, 2H), 0.86 (t, J=8.0 Hz, 2H), −0.08 (s, 9H) LC-MS (ESI) m/z 559 (M+H)+.

Step 3: To a stirred solution of the product from Step 2 of this example (54 mg, 0.097 mmol) in DCM (2 mL) was added trifluoroacetic acid (1 mL), and the mixture was stirred at rt for 3 h. The mixture was concentrated under reduced pressure and the residue was purified directly via reverse-phase preparative HPLC using a mixture of water (containing 5% CH$_3$CN and 0.05% HCOOH), and CH$_3$CN (containing 0.05% HCOOH) as the mobile phase and a Phenomenex Luna C-18 column as the stationary phase to afford 2-(4-(1H-imidazo[4,5-b]pyrazin-5-yl)phenyl)-N-(5-(1-(trifluoromethyl)cyclopropyl)isoxazol-3-yl)acetamide (0.92 mg, 2.2%) as a solid. $^1$H NMR (500 MHz, DMSO-d$_6$) δ 11.41 (s, 1H), 9.01 (s, 1H), 8.75 (s, 1H), 8.10 (d, J=8.2 Hz, 2H), 7.47 (d, J=8.2 Hz, 2H), 6.94 (s, 1H), 3.77 (s, 2H), 1.50-1.54 (m, 2H), 1.45-1.48 (m, 2H); LC-MS (ESI) m/z 429 (M+H)+.

Example 15

Preparation of 2-(4-(1H-pyrazolo[3,4-b]pyridin-5-yl)phenyl)-N-(5-(1-(trifluoromethyl)cyclopropyl)isoxazol-3-yl)acetamide

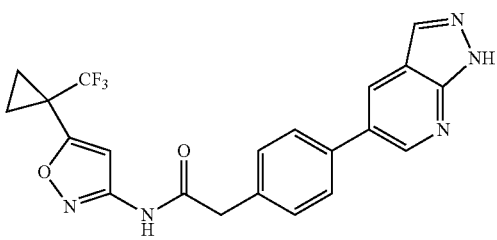 [SMILES: O=C(Cc1ccc(-c2cnc3[nH]ncc3c2)cc1)Nc1cc(C2(C(F)(F)F)CC2)on1]

Step 1: To a stirred solution of 5-bromo-1H-pyrazolo[3,4-b]pyridine (400 mg, 2.02 mmol) in DMF (3 mL) at rt was added 60% sodium hydride in mineral oil (121 mg, 3.03 mmol) and the mixture stirred for 30 mins. A solution of (2-(chloromethoxy)ethyl)trimethylsilane (438 mg, 2.63 mmol) in DMF (1 mL) was added dropwise and the reaction mixture was stirred at rt for a further 2 h. The mixture was partitioned between EtOAc and water and the organic layer was separated, washed with brine, dried over anhydrous MgSO$_4$, filtered, and concentrated under reduced pressure. The residue was purified by silica gel chromatography eluting with 0-30% EtOAc in hexanes to afford either 5-bromo-1-((2-(trimethylsilyl)ethoxy)methyl)-1H-pyrazolo[3,4-b]pyridine or 5-bromo-2-((2-(trimethylsilyl)ethoxy)methyl)-2H-pyrazolo[3,4-b]pyridine (440 mg, 66%) as a colorless oil. $^1$H NMR (500 MHz, DMSO-d$_6$) δ 8.68 (d, J=2.0 Hz, 1H), 8.58 (d, J=2.5 Hz, 1H), 8.24 (s, 1H), 5.76 (s, 2H), 3.58 (t, J=8.0 Hz, 2H), 0.81 (t, J=8.0 Hz, 2H), 0.12 (s, 9H); LC-MS (ESI) m/z 328 and 330 (M+H)+.

Step 2: A single product which was either N-(5-(1-(trifluoromethyl)cyclopropyl)isoxazol-3-yl)-2-(4-(1-((2-(trimethylsilyl)ethoxy)methyl)-1H-pyrazolo[3,4-b]pyridin-5-yl)phenyl)acetamide or N-(5-(1-(trifluoromethyl)cyclopropyl)isoxazol-3-yl)-2-(4-(2-((2-(trimethylsilyl)ethoxy)methyl)-2H-pyrazolo[3,4-b]pyridin-5-yl)phenyl)acetamide (85 mg, 44%) was obtained as a colorless oil using a procedure analogous to that described in Step 3 of Example 4, substituting 2-(4-(4,4,5,5-tetramethyl-1,3,2-dioxaborolan-2-yl)phenyl)-N-(5-(1-(trifluoromethyl)cyclopropyl)isoxazol-3-yl)acetamide (Ref: S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4 and substituting the product obtained from Step 1 of this example for the 2-chloro-6,7-dimethoxyquinoxaline used in Example 4. The crude product was purified by silica gel chromatography eluting with 0-30% EtOAc in hexanes. LC-MS (ESI) m/z 558 (M+H)+.

Step 3: To a stirred mixture of the product obtained in Step 2 of this example (85 mg, 0.153 mmol) and dichloromethane (2 mL) at rt was added trifluoroacetic acid (4 mL) and the mixture was stirred for 3 h. The mixture was concentrated under reduced pressure and the residue purified directly by reverse-phase preparative HPLC using a mixture of water (containing 5% CH$_3$CN and 0.05% HCOOH) and CH$_3$CN (containing 0.05% HCOOH) as the mobile phase and Varian Pursuit XRs diphenyl column as the stationary phase to afford 2-(4-(1H-pyrazolo[3,4-b]pyridin-5-yl)phenyl)-N-(5-(1-(trifluoromethyl)cyclopropyl)isoxazol-3-yl)acetamide (6 mg, 9%) as a solid. $^1$H NMR (500 MHz, DMSO-d$_6$) δ 13.71 (br s, 1H), 11.40 (s, 1H), 8.82 (d, J=2.5 Hz, 1H), 8.45 (d, J=2.0 Hz, 1H), 8.19 (s, 1H), 7.71 (d, J=8.5 Hz, 2H), 7.44 (d, J=8.5 Hz, 2H), 6.94 (s, 1H), 3.75 (s, 2H), 1.46-1.54 (m, 4H); LC-MS (ESI) m/z 428 (M+H)+.

Example 16

Preparation of 2-(4-(6,7-dimethoxyquinoxalin-2-yl)phenyl)-N-(5-(1-hydroxy-2-methylpropan-2-yl)isoxazol-3-yl)acetamide

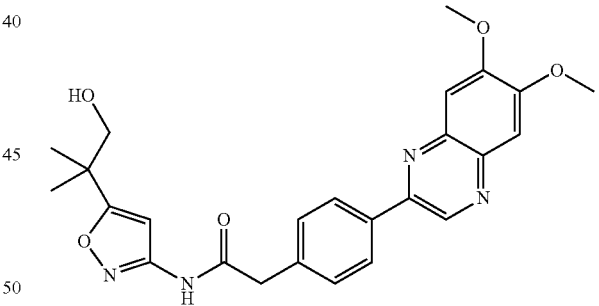

2-(4-(6,7-Dimethoxyquinoxalin-2-yl)phenyl)-N-(5-(1-hydroxy-2-methylpropan-2-yl)isoxazol-3-yl)acetamide (15 mg, 8.4%) was obtained as a yellow solid using a procedure analogous to that described in Step 2 of Example 4, substituting 2-(4-(6,7-dimethoxyquinoxalin-2-yl)phenyl)acetic acid from Step 1 of Example 8 for the 2-(2-fluoro-4-(4,4,5,5-tetramethyl-1,3,2-dioxaborolan-2-yl)phenyl)acetic acid used in Example 4 and substituting 2-(3-aminoisoxazol-5-yl)-2-methylpropan-1-ol (Ref: Apuy, Julius, L. et al. WO2010/54058 A1, 2010) for the 5-(1-(trifluoromethyl)cyclopropyl)isoxazol-3-amine used in Example 4. $^1$H NMR (500 MHz, DMSO-d$_6$) δ 9.33 (s, 1H), 8.23 (d, J=8.2 Hz, 2H), 7.44 (t, J=10.7 Hz, 4H), 5.59 (s, 1H), 5.50 (s, 2H), 4.11 (s, 2H), 4.00 (br s, 3H), 3.99 (br s, 3H), 3.78 (s, 2H), 1.21 (s, 6H). LC-MS (ESI) m/z 463 (M+H)+.

Example 17

Preparation of 2-(4-(6,7,8,9-tetrahydro-5H-pyrazino[2,3-b]indol-2-yl)phenyl)-N-(5-(1-(trifluoromethyl)cyclopropyl)isoxazol-3-yl)acetamide

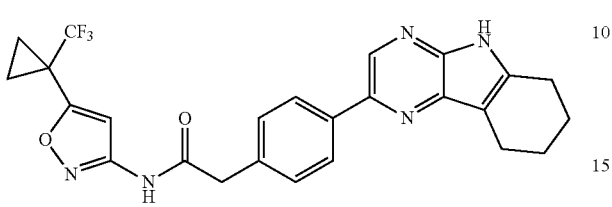

Step 1: A mixture of 2-hydrazinylpyrazine (3.0 g, 27.3 mmol), cyclohexanone (2.67 g, 27.3 mmol) and EtOH was stirred at reflux for 1 h. After cooling to rt, the mixture was concentrated under reduced pressure to afford 2-(2-cyclohexylidenehydrazinyl)pyrazine (3.6 g, 69%). $^1$H NMR (300 MHz, DMSO-d$_6$) δ 9.79 (s, 1H), 8.41 (s, 1H), 8.04-8.05 (m, 1H), 7.84-7.85 (m, 1H), 2.45-2.51 (m, 2H), 2.26-2.29 (m, 2H), 1.57-1.63 (m, 6H).

Step 2: A solution of 2-(2-cyclohexylidenehydrazinyl)pyrazine (1.87 g, 9.83 mmol) in 4% aq H2SO4 (20 mL) was heated to 160° C. for 30 min under microwave conditions. After cooling to rt, the reaction mixture was adjusted to pH ~9 and concentrated under reduced pressure. The residue was purified by silica gel chromatography eluting with 100:1 to 50:1 DCM/MeOH to afford 6,7,8,9-tetrahydro-5H-pyrazino[2,3-b]indole as a yellow solid (300 mg, 18%). $^1$H NMR (300 MHz, CDCl$_3$) 7.81 (s, 1H), 7.63 (s, 1H), 7.59 (s, 1H), 2.94 (t, J=6.6 Hz, 2H), 2.87 (t, J=6.0 Hz, 2H), 1.82-1.94 (m, 4H).

Step 3: To a solution of 6,7,8,9-tetrahydro-5H-pyrazino[2,3-b]indole (300 mg, 1.73 mmol) in DMF (5 mL) was added NBS (307 mg, 1.73 mmol). The mixture was stirred at rt for 20 min and then filtered through a pad of silica gel to afford 2-bromo-6,7,8,9-tetrahydro-5H-pyrazino[2,3-b]indole as a yellow solid (400 mg, 92%). $^1$H NMR (300 MHz, DMSO-d6) 7.63 (s, 1H), 7.59 (s, 1H), 3.04 (t, J=6.3 Hz, 2H), 2.90 (t, J=6.3 Hz, 2H), 1.83-1.96 (m, 4H).

Step 4: To a solution of 2-bromo-6,7,8,9-tetrahydro-5H-pyrazino[2,3-b]indole (116 mg, 0.46 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (200 mg, 0.46 mmol), and 2M aq Na2CO3 (1 mL) in 7:1 CH3CN:H2O (4 mL) was added Pd(dppf)Cl2 dichloromethane complex (28 mg, 0.034 mmol) under N2. The reaction mixture was heated to 100° C. for 30 min under microwave conditions. After cooling to rt, the reaction mixture was filtered and the filtrate was concentrated under reduced pressure. The residue was purified by preparative reverse-phase HPLC to afford 2-(4-(6,7,8,9-tetrahydro-5H-pyrazino[2,3-b]indol-2-yl)phenyl)-N-(5-(1-(trifluoromethyl)cyclopropyl)isoxazol-3-yl)acetamide as a white solid (8 mg, 4%). $^1$H NMR (300 MHz, CD3OD 8.10 (d, J=8.1 Hz, 2H), 7.95 (s, 1H), 7.69 (s, 1H), 7.45 (d, J=8.1 Hz, 2H), 6.91 (s, 1H), 3.77 (s, 2H), 3.03 (t, J=6.3 Hz, 2H), 2.96 (t, J=6.3 Hz, 2H), 1.87-1.99 (m, 4H), 1.43-1.54 (m, 4H). LC-MS (ESI) m/z 482 (M+H)$^+$.

Example 18

Preparation of 2-(4-(1H-pyrrolo[2,3-b]pyridin-5-yl)phenyl)-N-(5-(1-(trifluoromethyl)cyclopropyl)isoxazol-3-yl)acetamide

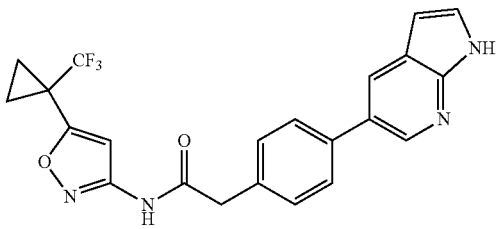 [SMILES: O=C(Cc1ccc(-c2cnc3[nH]ccc3c2)cc1)Nc1cc(C2(C(F)(F)F)CC2)on1]

To a solution of 5-bromo-1H-pyrrolo[2,3-b]pyridine (59 mg, 0.30 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (130 mg, 0.3 mmol) and 2M aq Na$_2$CO$_3$ (1 mL) in 7:1 CH$_3$CN:H$_2$O (4 mL) was added Pd(dppf)Cl$_2$ dichloromethane complex (28 mg, 0.034 mmol) under N$_2$. The reaction mixture was heated to 100° C. for 30 min under microwave conditions. After cooling to rt, the reaction mixture was filtered and the filtrate was concentrated under reduced pressure. The residue was purified by preparative reverse-phase HPLC to give 2-(4-(1H-pyrrolo[2,3-b]pyridin-5-yl)phenyl)-N-(5-(1-(trifluoromethyl)cyclopropyl)isoxazol-3-yl)acetamide as a white solid (41 mg, 32%). $^1$H NMR (300 MHz, DMSO-d$_6$) δ 11.69 (s, 1H), 11.38 (s, 1H), 8.47 (d, J=2.1 Hz, 1H), 8.16 (d, J=2.1 Hz, 1H), 7.64 (d, J=8.4 Hz, 2H), 7.49 (t, J=3.0 Hz, 1H), 7.39 (d, J=8.4 Hz, 2H), 6.92 (s, 1H), 6.47-6.49 (m, 1H), 3.71 (s, 2H), 1.46-1.49 (m, 4H). LC-MS (ESI) m/z 427 (M+H)$^+$.

Example 19

Preparation of 2-(4-(thieno[2,3-b]pyridin-5-yl)phenyl)-N-(5-(1-(trifluoromethyl)cyclopropyl)isoxazol-3-yl)acetamide

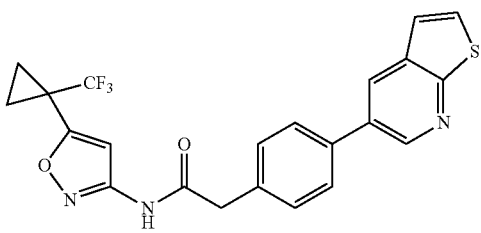 [SMILES: O=C(Cc1ccc(-c2cnc3sccc3c2)cc1)Nc1cc(C2(C(F)(F)F)CC2)on1]

Step 1: To a solution of tert-butyl thiophen-2-ylcarbamate (3.0 g, 15 mmol) and 2-bromomalonaldehyde (2.57 g, 17 mmol) in EtOH (30 mL) was added concentrated HCl (7.5 mL) under N2. The reaction mixture was heated to 105° C. for 24 h. After cooling to rt, the reaction mixture was filtered and the filtrate was concentrated under reduced pressure. The residue was purified by silica gel chromatography eluting with 2% MeOH in DCM to give 5-bromothieno[2,3-b]pyridine as a yellow solid (90 mg, 3%). $^1$H NMR (300 MHz, CDCl$_3$ 8.60 (d, J=2.1 Hz, 1H), 8.11 (d, J=2.4 Hz, 1H), 7.55-7.60 (m, 1H), 7.19-7.22 (m, 1H). LC-MS (ESI) m/z 215 (M+H)+.

Step 2: To a solution of 5-bromothieno[2,3-b]pyridine (81 mg, 0.38 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (150 mg, 0.34 mmol) and 2M aq Na2CO3 (1 mL) in 7:1 CH3CN:H2O (4 mL) was added Pd(dppf)Cl2 dichloromethane complex (28 mg, 0.034 mmol) under N2. The reaction mixture was heated to 100° C. for 30 min under microwave conditions. After cooling to rt, the mixture was filtered and the filtrate was concentrated under reduced pressure. The residue was purified by preparative reverse-phase HPLC to give 2-(4-(thieno[2,3-b]pyridin-5-yl)phenyl)-N-(5-(1-(trifluoromethyl)cyclopropyl)isoxazol-3-yl)acetamide as a yellow solid (44 mg, 26%). $^1$H NMR (300 MHz, DMSO-d6) δ 11.40 (s, 1H), 8.85 (s, 1H), 8.51 (s, 1H), 7.92 (d, J=5.7 Hz, 1H), 7.74 (d, J=7.8 Hz, 2H), 7.43-7.49 (m, 3H), 6.92 (s, 1H), 3.74 (s, 2H), 1.46-1.49 (m, 4H). LC-MS (ESI) m/z 444 (M+H)$^+$.

Example 20

Preparation of 2-(4-(2-methyl-3H-imidazo[4,5-b]pyridin-6-yl)phenyl)-N-(5-(1-(trifluoromethyl)cyclopropyl)isoxazol-3-yl)acetamide

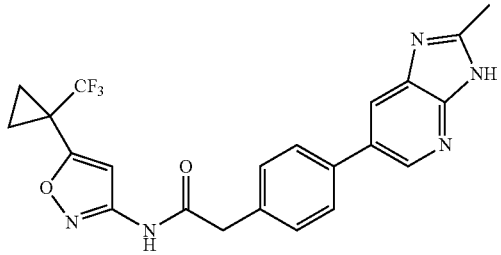 [SMILES: Cc1nc2cc(-c3ccc(CC(=O)Nc4cc(C5(C(F)(F)F)CC5)on4)cc3)cnc2[nH]1]

Step 1: To a stirred solution of 6-bromo-2-methyl-3H-imidazo[4,5-b]pyridine (269 mg, 1.275 mmol) in DMF (3 mL) was added 60% NaH in mineral oil (61 mg, 1.53 mmol) in one portion, and the mixture was stirred at rt for 20 min. Then 2-(trimethylsilyl)ethoxymethyl chloride (276 mg, 1.658 mmol) in DMF (1 mL) was added dropwise, and the mixture was stirred at rt for 15 h. The mixture was then partitioned between EtOAc and water and the aqueous layer was separated and further extracted with EtOAc. The combined organic layers were washed with brine, dried over MgSO4, filtered, and concentrated under reduced pressure. The residue was purified by silica gel chromatography eluting with 0-30% EtOAc in hexanes to afford either 6-bromo-2-methyl-3-((2-(trimethylsilyl)ethoxy)methyl)-3H-imidazo[4,5-b]pyridine or 6-bromo-2-methyl-1-((2-(trimethylsilyl)ethoxy)methyl)-1H-imidazo[4,5-b]pyridine as a single compound (141 mg, 32%), the absolute structure of which was not determined. $^1$H NMR (500 MHz, DMSO-d6) 8.40 (d, J=1.6 Hz, 1H), 8.26 (d, J=2.2 Hz, 1H), 5.62 (s, 2H), 3.54 (t, J=8.0 Hz, 2H), 2.62 (s, 3H), 0.83 (t, J=8.0 Hz, 2H), −0.11 (s, 9H) LC-MS (ESI) m/z 342, 344 (M+H)+.

Step 2: A single compound (133 mg, 85%) (either 2-(4-(2-methyl-3-((2-(trimethylsilyl)ethoxy)methyl)-3H-imidazo[4,5-b]pyridine-6-yl)phenyl)-N-(5-(1-(trifluoromethyl)cyclopropyl)isoxazol-3-yl)acetamide or 2-(4-(2-methyl-1-((2-(trimethylsilyl)ethoxy)methyl)-1H-imidazo[4,5-b]pyridine-6-yl)phenyl)-N-(5-(1-(trifluoromethyl)cyclopropyl)isoxazol-3-yl)acetamide was obtained as a solid using a procedure analogous to that described in Step 2 of Example 14, substituting the product obtained in Step 1 of this example for the 5-bromo-1-((2-(trimethylsilyl)ethoxy)methyl)-1H-imidazo[4,5-b]pyrazine used in Example 14. LC-MS (ESI) m/z 572 (M+H)+.

Step 3: 2-(4-(2-Methyl-3H-imidazo[4,5-b]pyridin-6-yl)phenyl)-N-(5-(1-(trifluoromethyl)cyclopropyl)iso xazol-3-yl)acetamide (33 mg, 33%) was obtained as a solid using a procedure analogous to that described in Step 3 of Example 14, substituting the product obtained in Step 2 of this example for the starting material used in Example 14. $^1$H NMR (500 MHz, DMSO-d6) δ 12.84 (br s, 1H) 11.40 (br s, 1H), 8.56 (m, 1H), 8.05 (m, 1H), 7.68 (d, J=7.7 Hz, 2H), 7.42 (d, J=8.2 Hz, 2H), 6.93 (s, 1H), 3.74 (s, 2H), 2.54 (s, 3H), 1.50-1.54 (m, 2H), 1.45-1.49 (m, 2H); LC-MS (ESI) m/z 442 (M+H)+.

Example 21

Preparation of 2-(4-(1-methyl-1H-pyrazolo[4,3-b]pyridin-6-yl)phenyl)-N-(5-(1-(trifluoromethyl)cyclopropyl)isoxazol-3-yl)acetamide

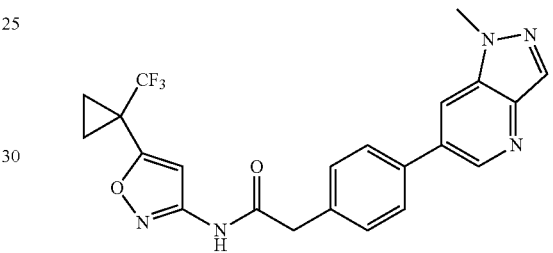

Step 1: To a solution of 6-bromo-1H-pyrazolo[4,3-b]pyridine (400 mg, 2.02 mmol) in DMF (10 mL) at 0° C. was added 60% NaH in mineral oil (80.8 mg, 2.02 mmol) and the mixture was stirred at rt for 30 min. A solution of MeI (287 mg, 2.02 mmol) in DMF (5 mL) was added and the mixture was stirred at rt for 30 min. Then the mixture was poured into water and extracted with EtOAc. The combined organic layers were washed with brine, dried over Na2SO4, filtered and concentrated under reduced pressure. The residue was purified by preparative reverse-phase HPLC to give 6-bromo-1-methyl-1H-pyrazolo[4,3-b]pyridine as a white solid (150 mg, 35%). $^1$H NMR (300 MHz, DMSO-d6) 8.58-8.60 (m, 2H), 8.30-8.31 (m, 1H), 4.06 (s, 3H).

Step 2: To a solution of 6-bromo-1-methyl-1H-pyrazolo[4,3-b]pyridine (54 mg, 0.255 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (111 mg, 0.255 mmol) and 2M aq Na2CO3 (1 mL) in 7:1 CH$_3$CN:H$_2$O (4 mL) was added Pd(dppf)Cl$_2$ dichloromethane complex (28 mg, 0.034 mmol) under N$_2$. The reaction mixture was heated to 100° C. for 30 min under microwave conditions. After cooling to rt, the reaction mixture was filtered and the filtrate was concentrated under reduced pressure. The residue was purified by preparative reverse-phase HPLC to give 2-(4-(1-methyl-1H-pyrazolo[4,3-b]pyridin-6-yl)phenyl)-N-(5-(1-(trifluoromethyl)cyclopropyl)isoxazol-3-yl)acetamide as a white solid (48 mg, 43%). $^1$H NMR (300 MHz, DMSO-d$_6$) δ 11.42 (s, 1H), 8.85 (d, J=2.1 Hz, 1H), 8.41 (t, J=1.2 Hz, 1H), 8.29 (s, 1H), 7.81 (d, J=8.4 Hz, 2H), 7.48 (d, J=8.1 Hz, 2H), 6.94 (s, 1H), 4.13 (s, 3H), 3.77 (s, 2H), 1.48-1.52 (m, 4H). LC-MS (ESI) m/z 442 (M+H)$^+$.

Example 22

Preparation of 2-(4-(6-methoxyquinoxalin-2-yl)phenyl)-N-(5-(1-(trifluoromethyl)cyclopropyl)isoxazol-3-yl)acetamide

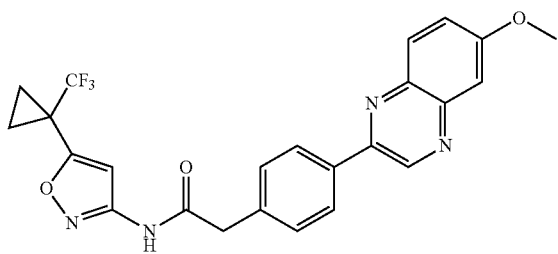 [SMILES: COc1ccc2nc(-c3ccc(CC(=O)Nc4cc(C5(C(F)(F)F)CC5)on4)cc3)cnc2c1]

Step 1: To a solution of 4-methoxybenzene-1,2-diamine (3.58 g, 25.9 mmol) in dry EtOH (30 mL) was added 50% ethyl 2-oxoacetate in toluene (6.2 mL) and the mixture was heated under reflux for 2 h. After cooling to rt, the mixture was concentrated under reduced pressure. The residue was washed with EtOH to give a mixture of 6-methoxyquinoxalin-2-ol and 7-methoxyquinoxalin-2-ol as a brown solid (2.6 g, 57%). $^1$H NMR (300 MHz, DMSO-d6 12.30 (s, 1H), 8.13 (s, 1H), 7.23-7.25 (m, 1H), 7.15-7.20 (m, 2H), 3.78 (s, 3H). LC-MS (ESI) m/z 177 (M+H)+.

Step 2: The mixture of 6-methoxyquinoxalin-2-ol and 7-methoxyquinoxalin-2-ol (1.6 g, 9.1 mmol) in POCl$_3$ (30 mL) was heated under reflux for 1 h. After cooling to rt, the reaction mixture was concentrated under reduced pressure. The residue was quenched with ice, basified with saturated aq Na2CO3, and extracted with EtOAc. The organic layer was dried over Na2SO4, filtered and concentrated under reduced pressure. The residue was purified by silica gel chromatography eluting with 3% EtOAc in petroleum ether to give the following products:

Pure 2-chloro-6-methoxyquinoxaline as a white solid (150 mg), $^1$H NMR (300 MHz, CDCl$_3$ 8.71 (s, 1H), 7.90 (d, J=9.3 Hz, 1H), 7.44 (dd, J=9.3, 2.7 Hz, 1H), 7.37 (d, J=2.7 Hz, 1H), 3.95 (s, 3H). LC-MS (ESI) m/z 195 (M+H)+.

Pure 2-chloro-7-methoxyquinoxaline as a white solid (100 mg). $^1$H NMR (300 MHz, CDCl$_3$ 8.62 (s, 1H), 7.97 (d, J=9.3 Hz, 1H), 7.41 (dd, J=9.3, 2.7 Hz, 1H), 7.29 (d, J=2.7 Hz, 1H), 3.96 (s, 3H). LC-MS (ESI) m/z 195 (M+H)+.

A mixture of 2-chloro-6-methoxy quinoxaline and 2-chloro-7-methoxyquinoxaline as a white solid (1.27 g, 85%).

Step 3: To a solution of 2-chloro-6-methoxyquinoxaline (81 mg, 0.42 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (150 mg, 0.34 mmol) and 2M aq Na$_2$CO$_3$ (1 mL) in 7:1 CH$_3$CN/H$_2$O (4 mL) was added Pd(dppf)Cl$_2$ dichloromethane complex (28 mg, 0.034 mmol) under N$_2$. The reaction mixture was heated to 100° C. for 30 min under microwave conditions. After cooling to rt, the reaction mixture was filtered and the filtrate was concentrated under reduced pressure. The residue was purified by preparative reverse-phase HPLC to give 2-(4-(6-methoxyquinoxalin-2-yl)phenyl)-N-(5-(1-(trifluoromethyl)cyclopropyl)isoxazol-3-yl)acetamide as a pink solid (74 mg, 47%). $^1$H NMR (300 MHz, DMSO-d$_6$) δ 11.41 (s, 1H), 9.47 (s, 1H), 8.23 (d, J=8.1 Hz, 2H), 8.01 (d, J=9.0 Hz, 1H), 7.46-7.51 (m, 4H), 6.92 (s, 1H), 3.95 (s, 3H), 3.78 (s, 2H), 1.46-1.49 (m, 4H). LC-MS (ESI) m/z 469 (M+H)+.

Example 23

Preparation of 2-(4-(7-methoxyquinoxalin-2-yl)phenyl)-N-(5-(1-(trifluoromethyl)cyclopropyl)isoxazol-3-yl)acetamide

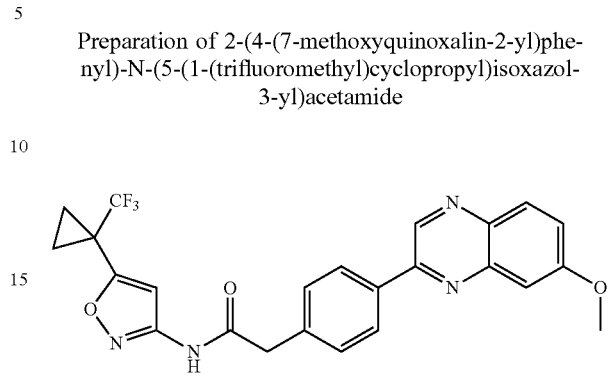

To a solution of 2-chloro-7-methoxyquinoxaline from Step 2 of Example 22 (81 mg, 0.42 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (150 mg, 0.34 mmol) and 2M aq Na$_2$CO$_3$ (1 mL) in 7:1 CH$_3$CN/H$_2$O (4 mL) was added Pd(dppf)Cl$_2$ dichloromethane complex (28 mg, 0.034 mmol) under N$_2$. The reaction mixture was heated to 100° C. for 30 min under microwave conditions. After cooling to rt, the mixture was filtered and the filtrate was concentrated under reduced pressure. The residue was purified by preparative reverse-phase HPLC to give 2-(4-(7-methoxyquinoxalin-2-yl)phenyl)-N-(5-(1-(trifluoromethyl)cyclopropyl)isoxazol-3-yl)acetamide as a white solid (112 mg, 71%). $^1$H NMR (300 MHz, DMSO-d$_6$): δ 11.45 (s, 1H), 9.40 (s, 1H), 8.29 (d, J=8.1 Hz, 2H), 8.01 (d, J=9.3 Hz, 1H), 7.45-7.55 (m, 4H), 6.95 (s, 1H), 3.98 (s, 3H), 3.82 (s, 2H), 1.48-1.52 (m, 4H). LC-MS (ESI) m/z 469 (M+H)+.

Example 24

Preparation of 2-(4-(6-(2-methoxyethoxy)quinoxalin-2-yl)phenyl)-N-(5-(1-(trifluoromethyl)cyclopropyl)isoxazol-3-yl)acetamide

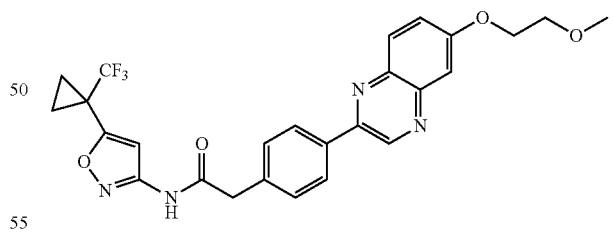

Step 1: To a solution of 4-amino-3-nitrophenol (10 g, 65 mmol) and 1-bromo-2-methoxyethane (10.8 g, 78 mmol) in dry DMF (150 mL) was added K2CO3 (2.69 g, 195 mmol), and the reaction mixture was heated to 100° C. for 4 h. After cooling to rt, the mixture was filtered, and the filtrate was poured into cooled water and extracted with EtOAc. The organic layer was washed with brine, dried over Na2SO4, filtered and concentrated under reduced pressure. The residue was purified by silica gel chromatography eluting with 30% EtOAc in petroleum ether to give 4-(2-methoxyethoxy)-2-nitroaniline as a yellow solid (12 g, 87%). $^1$H NMR (300 MHz, DMSO-d6 7.53-7.54 (m, 1H), 7.08-7.12 (m, 1H), 6.74 (d, J=9.3 Hz, 1H), 5.95 (br s, 2H), 4.06-4.09 (m, 2H), 3.71-3.74 (m, 2H), 3.43 (s, 3H). LC-MS (ESI) m/z 213 (M+H)+.

Step 2: To a solution of 4-(2-methoxyethoxy)-2-nitroaniline (8.0 g, 38 mmol) in 10:1 MeOH/THF (100 mL) was added 10% Pd/C (1.6 g), and the mixture was stirred at 40° C. under H2 for 2 d. After cooling to rt, the mixture was filtered and the filtrate was concentrated under reduced pressure to give crude 4-(2-methoxyethoxy)benzene-1,2-diamine (5.0 g, 73%) which was used to the next step without further purification. $^1$H NMR (300 MHz, CDCl$_3$ 6.59 (d, J=8.4 Hz, 1H), 6.32 (d, J=2.7 Hz, 1H), 6.25 (dd, J=8.4, 2.7 Hz, 1H), 3.99-4.02 (m, 2H), 3.67-3.70 (m, 2H), 3.42 (s, 3H). LC-MS (ESI) m/z 183 (M+H)+.

Step 3: To a solution of 4-(2-methoxyethoxy)benzene-1,2-diamine (3.0 g, 16.5 mmol) in dry EtOH (50 mL) was added 50% ethyl 2-oxoacetate in toluene (4 mL) at rt and the mixture was heated under reflux for 2 h. After cooling to rt, the mixture was concentrated under reduced pressure, and the residue was washed with EtOH and dried to give 6-(2-methoxyethoxy)quinoxalin-2-ol as a yellow solid (1.7 g, 47%). $^1$H NMR (300 MHz, DMSO-d$_6$) δ 12.32 (s, 1H), 8.14 (s, 1H), 7.28 (d, J=1.2 Hz, 1H), 7.21 (s, 2H), 4.12-4.15 (m, 2H), 3.64-3.67 (m, 2H), 3.29 (s, 3H). LC-MS (ESI) m/z 221 (M+H)$^+$.

Step 4: A solution of 6-(2-methoxyethoxy)quinoxalin-2-ol (1.7 g, 7.7 mmol) in POCl3 (50 mL) was heated under reflux for 1 h. After cooling to rt, the mixture was concentrated under reduced pressure. The residue was treated with ice, basified with saturated aq Na2CO3, and extracted with EtOAc. The organic layer was dried over Na2SO4, filtered and concentrated under reduced pressure. The residue was purified by silica gel chromatography eluting with 10% EtOAc in petroleum ether to give 2-chloro-6-(2-methoxyethoxy)quinoxaline as a yellow solid (1.5 g, 83%). $^1$H NMR (300 MHz, CDCl$_3$ 8.71 (s, 1H), 7.90 (d, J=9.6 Hz, 1H), 7.50 (dd, J=9.3, 2.7 Hz, 1H), 7.38 (d, J=2.7 Hz, 1H), 4.27-4.30 (m, 2H), 3.83-3.86 (m, 2H), 3.48 (s, 3H). LC-MS (ESI) m/z 239 (M+H)+.

Step 5: To a solution of 2-chloro-6-(2-methoxyethoxy)quinoxaline (81 mg, 0.34 mmol), 2-(4-(4,4,5,5-tetramethyl-1,3,2-dioxaborolan-2-yl)phenyl)-N-(5-(1-(trifluoromethyl)cyclopropyl)isoxazol-3-yl)acetamide from Step 1 of Example 9 (150 mg, 0.34 mmol) and 2M aq Na2CO3 (1 mL) in 7:1 CH3CN/H2O (4 mL) was added Pd(dppf)Cl2 dichloromethane complex (28 mg, 0.034 mmol) under N2. The reaction mixture was heated to 100° C. for 30 min under microwave conditions. After cooling to rt, the mixture was filtered and the filtrate was concentrated under reduced pressure. The residue was purified by preparative reverse-phase HPLC to give 2-(4-(6-(2-methoxyethoxy)quinoxalin-2-yl)phenyl)-N-(5-(1-(trifluoromethyl)cyclopropyl)isoxazol-3-yl)acetamide as a white solid (50 mg, 29%). $^1$H NMR (300 MHz, DMSO-d$_6$) δ 11.44 (s, 1H), 9.48 (s, 1H), 8.26 (d, J=8.1 Hz, 2H), 8.03 (d, J=9.0 Hz, 1H), 7.49-7.55 (m, 4H), 6.95 (s, 1H), 4.31-4.34 (m, 2H), 3.75-3.81 (m, 4H), 3.34 (s, 3H), 1.48-1.52 (m, 4H). LC-MS (ESI) m/z 513 (M+H)$^+$.

Example 25

Preparation of 2-(4-(1H-pyrrolo[2,3-b]pyridin-5-yl)phenyl)-N-(5-(tert-butyl)isoxazol-3-yl)acetamide

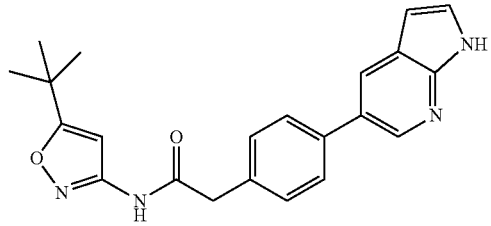 [SMILES: CC(C)(C)c1cc(NC(=O)Cc2ccc(-c3cnc4[nH]ccc4c3)cc2)no1]

To a stirred solution of N-(5-(tert-butyl)isoxazol-3-yl)-2-(4-(4,4,5,5-tetramethyl-1,3,2-dioxaborolan-2-yl)phenyl)acetamide (130 mg, 0.34 mmol) in CH3CN (3.4 mL) were added 5-bromo-7-azaindole (66 mg, 0.34 mmol), 2M aq Na2CO3 (1 mL), and H2O (0.6 mL). The mixture was flushed with a stream of argon for 20 min at rt. [1,1'-Bis(diphenylphosphino)ferrocene]dichloropalladium(II) dichloromethane complex (18 mg, 0.023 mmol) was added and the mixture was stirred at 100° C. for 1 h in a sealed vessel. The mixture was concentrated under reduced pressure and the residue was purified by reverse-phase preparative HPLC using a mixture of water (containing 5% CH3CN and 0.05% HCOOH) and CH3CN (containing 0.05% HCOOH) as the mobile phase and a Varian Pursuit XRs diphenyl column as the stationary phase to afford 2-(4-(1H-pyrrolo[2,3-b]pyridin-5-yl)phenyl)-N-(5-(tert-butyl)isoxazol-3-yl)acetamide (33 mg, 26%) as a solid. $^1$H NMR (500 MHz, DMSO-d$_6$) δ11.70 (br s, 1H), 11.22 (s, 1H), 8.49 (d, J=1.6 Hz, 1H), 8.18 (d, J=1.6 Hz, 1H), 7.66 (d, J=8.2 Hz, 2H), 7.51 (m, 1H), 7.41 (d, J=8.2 Hz, 2H), 6.58 (s, 1H), 6.50 (m, 1H), 3.71 (s, 2H), 1.27 (s, 9H).

Example 26

Preparation of 2-(4-(1H-pyrrolo[2,3-b]pyridin-5-yl)phenyl)-N-(5-(1,1,1-trifluoro-2-methylpropan-2-yl)isoxazol-3-yl)acetamide

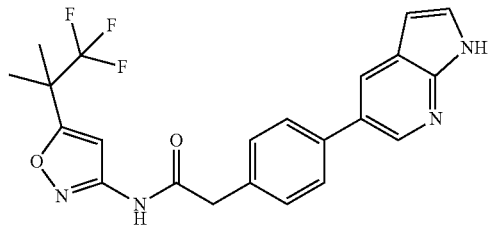 [SMILES: CC(C)(c1cc(NC(=O)Cc2ccc(-c3cnc4[nH]ccc4c3)cc2)no1)C(F)(F)F]

2-(4-(1H-Pyrrolo[2,3-b]pyridin-5-yl)phenyl)-N-(5-(1,1,1-trifluoro-2-methylpropa n-2-yl)isoxazol-3-yl)acetamide (24 mg, 16%) was obtained as a solid using a procedure analogous to that described in Example 25, substituting 2-(4-(4,4,5,5-tetramethyl-1,3,2-dioxaborolan-2-yl)phenyl)-N-(5-(1,1,1-trifluoro-2-methylpropan-2-yl)isoxazol-3-yl) acetamide (Ref: Abraham, S. et al.; WO2011/22473 A1, 2011) for the N-(5-(tert-butyl)isoxazol-3-yl)-2-(4-(4,4,5,5-tetramethyl-1,3,2-dioxaborolan-2-yl)phenyl)acetamide used in Example 25. $^1$H NMR (500 MHz, DMSO-d6) 11.70 (br s, 1H), 11.40 (s, 1H), 8.49 (d, J=2.2 Hz, 1H), 8.18 (d, J=1.6 Hz, 1H), 7.66 (d, J=8.2 Hz, 2H), 7.51 (m, 1H), 7.42 (d, J=8.2 Hz, 2H), 6.96 (s, 1H), 6.50 (m, 1H), 3.74 (s, 2H), 1.54 (s, 6H); LC-MS (ESI) m/z 429 (M+H)+.

Example 27

Preparation of N-(5-(tert-butyl)isoxazol-3-yl)-2-(2-fluoro-4-(1H-pyrrolo[2,3-b]pyridin-5-yl)phenyl)acetamide

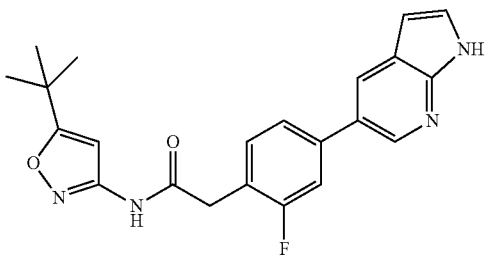 [SMILES: CC(C)(C)c1cc(NC(=O)Cc2ccc(-c3cnc4[nH]ccc4c3)cc2F)no1]

Step 1: A mixture of 2-(4-bromo-2-fluorophenyl)acetic acid (5 g, 21.4 mmol), 4,4,4',4',5,5,5',5'-octamethyl-2,2'-bi(1,3,2-dioxaborolane) (6.54 g, 25.75 mmol), and potassium acetate (8.42 g, 85.9 mmol) in DMF (50 mL) was flushed with a stream of argon at rt for 20 min. [1,1'-Bis(diphenylphosphino)ferrocene]dichloropalladium(II) dichloromethane complex (876 mg, 1.07 mmol) was then added and the mixture was stirred at 90° C. for 15 h in a sealed vessel. The mixture was partitioned between EtOAc and H$_2$O. The aqueous layer was separated and adjusted to pH 4 with 2N aq HCl, then extracted with EtOAc (2×200 mL). The combined organic layers were washed with brine, dried over MgSO$_4$, filtered, and concentrated under reduced pressure. The residue was purified by silica gel chromatography eluting with 0-30% EtOAc in hexanes to afford 2-(2-fluoro-4-(4,4,5,5-tetramethyl-1,3,2-dioxaborolan-2-yl)phenyl)acetic acid (4.60 g, 77%) as a solid. $^1$H NMR (500 MHz, DMSO-d$_6$) δ 12.49 (br s, 1H), 7.44 (d, J=7.7 Hz, 1H), 7.36 (m, 1H), 7.31 (d, J=9.9 Hz, 1H), 3.65 (s, 2H), 1.29 (s, 12H); LC-MS (ESI) m/z 281 (M+H)+.

Step 2: A mixture of 2-(2-fluoro-4-(4,4,5,5-tetramethyl-1,3,2-dioxaborolan-2-yl)phenyl)acetic acid (500 mg, 1.79 mmol), 5-bromo-7-azaindole (352 mg, 1.79 mmol), 2M aq Na$_2$CO$_3$ (5.37 mL, 10.74 mmol), CH-3CN (17.2 mL), and H$_2$O (2.8 mL) was flushed with a stream argon at rt for 20 min. [1,1'-Bis(diphenylphosphino)ferrocene]dichloropalladium(II) dichloromethane complex (147 mg, 0.18 mmol) was then added and the mixture was stirred at 120° C. for 24 h in a sealed vessel. The mixture was acidified to pH~5 with 2N aq HCl. The precipitate was collected by filtration and dried under reduced pressure to afford 2-(2-fluoro-4-(1H-pyrrolo[2,3-b]pyridin-5-yl)phenyl)acetic acid (411 mg, 85%) as a solid. $^1$H NMR (500 MHz, DMSO-d$_6$) δ 11.75 (s, 1H), 8.55 (s, 1H), 8.25 (s, 1H), 7.48-7.59 (m, 3H), 7.42 (m, 1H), 6.51 (s, 1H), 3.70 (s, 2H); LC-MS (ESI) m/z 271 (M+H)+.

Step 3: To a stirred solution of 2-(2-fluoro-4-(1H-pyrrolo[2,3-b]pyridine-5-yl)phenyl)acetic acid (100 mg, 0.37 mmol) in DMF (2 mL) was added O-(7-azabenzotriazol-1-yl)-N,N,N',N'-tetramethyluronium hexafluorophosphate (211 mg, 0.56 mmol) and the mixture was stirred at rt for 0.5 h. Then 3-amino-5-tert-butylisoxazole (52 mg, 0.37 mmol) and triethylamine (0.129 mL, 0.93 mmol) in DMF (1 mL) were added, and the mixture was stirred at rt for 15 h. The reaction mixture was partitioned between EtOAc and water. The aqueous layer was separated and further extracted with EtOAc (2×20 mL). The combined organic layers were dried over MgSO4, filtered, and concentrated under reduced pressure. The residue was purified by reverse-phase preparative HPLC using a mixture of water (containing 5% CH3CN and 0.05% HCOOH), CH3CN (containing 0.05% HCOOH) as the mobile phase and a Varian Pursuit XRs diphenyl column as the stationary phase to afford N-(5-(tert-butyl)isoxazol-3-yl)-2-(2-fluoro-4-(1H-pyrrolo[2,3-b]pyridin-5-yl)phenyl)acetamide (19 mg, 13%) as a solid. $^1$H NMR (500 MHz, DMSO-d$_6$) δ 11.76 (br s, 1H), 11.25 (s, 1H), 8.55 (d, J=1.6 Hz, 1H), 8.26 (d, J=1.6 Hz, 1H), 7.50-7.59 (m, 3H), 7.45 (m, 1H), 6.58 (s, 1H), 6.51 (m, 1H), 3.80 (s, 2H), 1.28 (s, 9H).

Example 28

Preparation of 2-(2-fluoro-4-(1H-pyrrolo[2,3-b]pyridin-5-yl)phenyl)-N-(5-(1-(trifluoromethyl)cyclopropyl)isoxazol-3-yl)acetamide

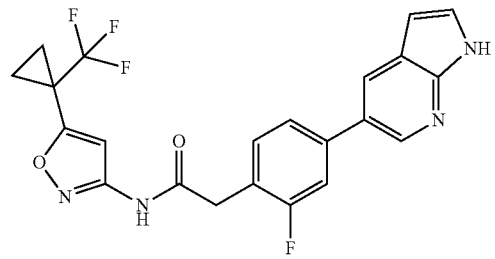 [SMILES: O=C(Cc1ccc(-c2cnc3[nH]ccc3c2)cc1F)Nc1cc(C2(C(F)(F)F)CC2)on1]

2-(2-Fluoro-4-(1H-pyrrolo[2,3-b]pyridine-5-yl)phenyl)-N-(5-(1-(trifluoromethyl)cyclopropyl)isoxazol-3-yl)acetamide (10 mg, 4%) was obtained as a solid using a procedure analogous to that described in Step 3 of Example 27, substituting 5-(1-(trifluoromethyl)cyclopropyl)isoxazol-3-amine (Ref: M. W. Rowbottom et al, J. Med. Chem. 2012, 55(3), 1082-1105) for the 3-amino-5-tert-butylisoxazole used in Example 27. $^1$H NMR (500 MHz, DMSO-d$_6$) δ 11.78 (s, 1H), 11.42 (s, 1H), 8.55 (d, J=1.6 Hz, 1H), 8.27 (d, J=1.6 Hz, 1H), 7.58 (s, 1H), 7.51-7.56 (m, 2H), 7.46 (m, 1H), 6.93 (s, 1H), 6.52 (dd, J=3.3, 1.6 Hz, 1H), 3.82 (s, 2H), 1.51-1.55 (m, 2H), 1.45-1.50 (m, 2H).

Example 29

Preparation of 2-(2-fluoro-4-(1H-pyrrolo[2,3-b]pyridin-5-yl)phenyl)-N-(5-(1,1,1-trifluoro-2-methylpropan-2-yl)isoxazol-3-yl)acetamide

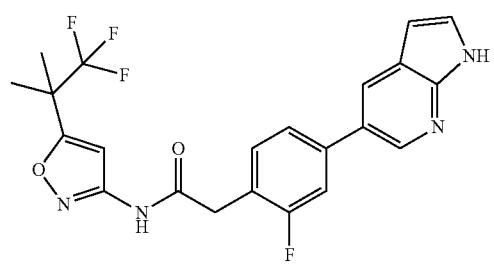 [SMILES: CC(C)(c1cc(NC(=O)Cc2ccc(-c3cnc4[nH]ccc4c3)cc2F)no1)C(F)(F)F]

2-(2-Fluoro-4-(1H-pyrrolo[2,3-b]pyridine-5-yl)phenyl)-N-(5-(1,1,1-trifluoro-2-m ethylpropan-2-yl)isoxazol-3-yl) acetamide (36 mg, 14%) was obtained as a solid using a procedure analogous to that described in Step 3 of Example 27, substituting 5-(1,1,1-trifluoro-2-methylpropan-2-yl) isoxazol-3-amine Ref: M. W. Rowbottom et al, *J. Med. Chem.* 2012, 55(3), 1082-1105) for the 3-amino-5-tert-butylisoxazole used in Example 27. $^1$H NMR (500 MHz, DMSO-d$_6$) δ 11.75 (br s, 1H), 11.43 (br s, 1H), 8.55 (d, J=2.2 Hz, 1H), 8.25 (d, J=1.6 Hz, 1H), 7.51-7.59 (m, 3H), 7.46 (m, 1H), 6.95 (s, 1H), 6.51 (m, 1H), 3.83 (s, 2H), 1.54 (s, 6H); LC-MS (ESI) m/z 447 (M+H)$^+$.

Example 30

Preparation of 2-(2-fluoro-4-(5H-pyrrolo[2,3-b]pyrazin-2-yl)phenyl)-N-(5-(1-(trifluoromethyl)cyclopropyl)isoxazol-3-yl)acetamide

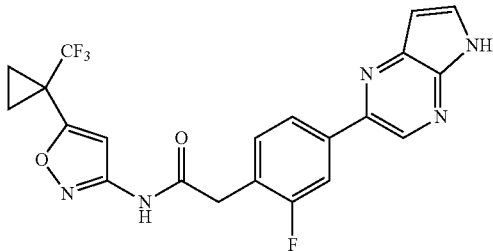 [SMILES: O=C(Cc1ccc(-c2cnc3[nH]ccc3n2)cc1F)Nc1cc(C2(C(F)(F)F)CC2)on1]

2-(2-Fluoro-4-(5H-pyrrolo[2,3-b]pyrazin-2-yl)phenyl)-N-(5-(1-(trifluoromethyl)cyclopropyl)isoxazol-3-yl)acetamide (30 mg, 31%) was obtained as a solid using a procedure analogous to that described in Step 3 of Example 4, substituting 2-bromo-5H-pyrrolo[2,3-b]pyrazine for the 2-chloro-6,7-dimethoxyquinoxaline used in Example 4. $^1$H NMR (500 MHz, DMSO-d$_6$) δ 12.14 (br s, 1H), 11.44 (br s, 1H), 8.89 (s, 1H), 7.92-7.97 (m, 3H), 7.49 (dd, J=8.0, 8.0 Hz, 1H), 6.94 (s, 1H), 6.69 (d, J=3.5 Hz, 1H), 3.85 (s, 2H), 1.46-1.54 (m, 4H); LC-MS (ESI) m/z 446 (M+H)$^+$.

Example 31

Preparation of 2-(4-(1H-pyrazolo[3,4-b]pyridin-5-yl)phenyl)-N-(5-(tert-butyl)isoxazol-3-yl)acetamide

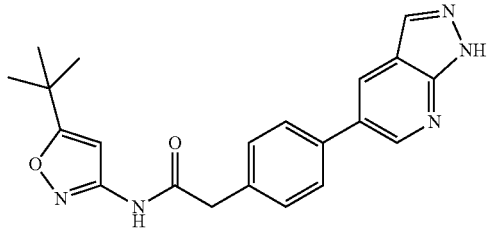 [SMILES: CC(C)(C)c1cc(NC(=O)Cc2ccc(-c3cnc4[nH]ncc4c3)cc2)no1]

Step 1: 2-(4-(1H-Pyrazolo[3,4-b]pyridin-5-yl)phenyl) acetic acid (150 mg, 28%) was obtained as a brown solid using a procedure analogous to that described in Step 1 of Example 8, substituting 5-bromo-1H-pyrazolo[3,4-b]pyridine for the 2-chloro-6,7-dimethoxyquinoxaline used in Example 8. LC-MS (ESI) m/z 254 (M+H)$^+$.

Step 2: 2-(4-(1H-Pyrazolo[3,4-b]pyridin-5-yl)phenyl)-N-(5-(tert-butyl)isoxazol-3-yl)acetamide (4 mg, 7.3%) was obtained as a tan solid using a procedure analogous to that described in Step 2 of Example 4, substituting 2-(4-(1H-pyrazolo[3,4-b]pyridin-5-yl)phenyl)acetic acid for the 2-(2-fluoro-4-(4,4,5,5-tetramethyl-1,3,2-dioxaborolan-2-yl)phenyl)acetic acid used in Example 4 and substituting 5-(tert-butyl)isoxazol-3-amine for the 5-(1-(trifluoromethyl) cyclopropyl)isoxazol-3-amine used in Example 4. $^1$H NMR (500 MHz, DMSO-d$_6$) δ 11.23 (s, 1H), 8.82 (d, J=1.6 Hz, 1H), 8.46 (d, J=2.2 Hz, 1H), 8.20 (s, 1H), 7.71 (d, J=8.2 Hz, 2H), 7.44 (d, J=8.2 Hz, 2H), 6.58 (s, 1H), 3.73 (s, 2H), 1.27 (s, 9H). LC-MS (ESI) m/z 376 (M+H)$^+$.

Example 32

Preparation of N-(5-(tert-butyl)isoxazol-3-yl)-2-(2-fluoro-4-(1H-pyrazolo[3,4-b]pyridin-5-yl)phenyl) acetamide

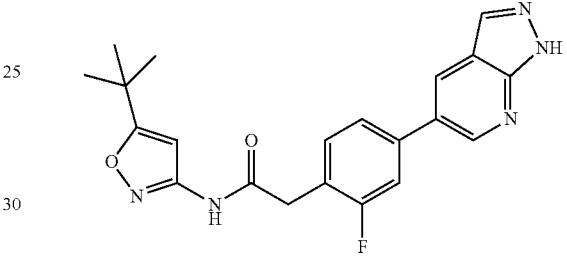

Step 1: 2-(2-Fluoro-4-(1-((2-(trimethylsilyl)ethoxy) methyl)-1H-pyrazolo[3,4-b]pyridin-5-yl)phenyl)acetic acid was obtained as a dark brown oil using a procedure analogous to that described in Step 1 of Example 8, substituting 2-(2-fluoro-4-(4,4,5,5-tetramethyl-1,3,2-dioxaborolan-2-yl) phenyl)acetic acid for the 2-(4-(4,4,5,5-tetramethyl-1,3,2-dioxaborolan-2-yl)phenyl)acetic acid used in Example 8 and substituting 5-bromo-1-((2-(trimethylsilyl)ethoxy)methyl)-1H-pyrazolo[3,4-b]pyridine (Ref: Ahrendt, K. A. et al; WO2009/111279 A1, 2009) for the 2-chloro-6,7-dimethoxyquinoxaline used in Example 8. LC-MS (ESI) m/z 402 (M+H)+.

Step 2: N-(5-(tert-butyl)isoxazol-3-yl)-2-(2-fluoro-4-(1-((2-(trimethylsilyl)ethoxy)methyl)-1H-pyrazolo[3,4-b]pyridin-5-yl)phenyl)acetamide (100 mg, 51%) was obtained as a light yellow solid using a procedure analogous to that described in Step 2 of Example 4, substituting 2-(2-fluoro-4-(1-((2-(trimethylsilyl)ethoxy)methyl)-1H-pyrazolo[3,4-b] pyridin-5-yl)phenyl)acetic acid for the 2-(2-fluoro-4-(4,4,5,5-tetramethyl-1,3,2-dioxaborolan-2-yl)phenyl)acetic acid used in Example 4 and substituting 5-(tert-butyl)isoxazol-3-amine for the 5-(1-(trifluoromethyl)cyclopropyl)isoxazol-3-amine used in Example 4. LC-MS (ESI) m/z 524 (M+H)$^+$.

Step 3: N-(5-(tert-butyl)isoxazol-3-yl)-2-(2-fluoro-4-(14 (2-(trimethylsilyl)ethoxy)methyl)-1H-pyrazolo[3,4-b]pyridin-5-yl)phenyl)acetamide (100 mg, 0.19 mmol) was treated with 1:1 TFA/DCM (5 mL) and the mixture was stirred at rt overnight. The mixture was concentrated under reduced pressure and the residue was purified by reverse-phase preparative HPLC using a mixture of water (containing 5% CH$_3$CN and 0.05% HCOOH), and CH$_3$CN (containing 0.05% HCOOH) as the mobile phase and a Varian Pursuit XRs diphenyl column as the stationary phase to afford N-(5-(tert-butyl)isoxazol-3-yl)-2-(2-fluoro-4-(1H-pyrazolo

[3,4-b]pyridin-5-yl)phenyl)acetamide (22 mg, 29%) as a white powder. $^1$H NMR (500 MHz, DMSO-$d_6$) δ 13.75 (br s, 1H), 11.26 (s, 1H), 8.87 (d, J=1.6 Hz, 1H), 8.53 (d, J=1.6 Hz, 1H), 8.21 (s, 1H), 7.63 (d, J=11.5 Hz, 1H), 7.54-7.60 (m, 1H), 7.44-7.52 (m, 1H), 6.57 (s, 1H), 3.81 (s, 2H), 1.28 (s, 9H). LC-MS (ESI) m/z 394 (M+H)$^+$.

Example 33

Preparation of 2-(2-fluoro-4-(1H-pyrazolo[3,4-b]pyridin-5-yl)phenyl)-N-(5-(1-(trifluoromethyl)cyclopropyl)isoxazol-3-yl)acetamide

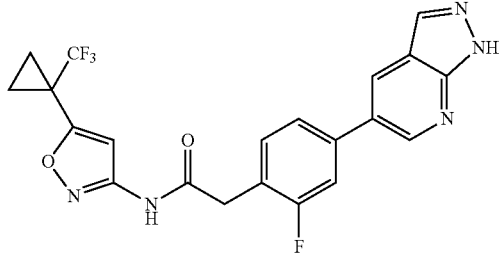 [SMILES: O=C(Cc1ccc(-c2cnc3[nH]ncc3c2)cc1F)Nc1cc(C2(C(F)(F)F)CC2)on1]

2-(2-Fluoro-4-(1H-pyrazolo[3,4-b]pyridin-5-yl)phenyl)-N-(5-(1-(trifluoromethyl)cyclopropyl)isoxazol-3-yl)acetamide (22 mg) was obtained as a white powder using a procedure analogous to that described in Steps 2-3 of Example 32, substituting 5-(1-(trifluoromethyl)cyclopropyl)isoxazol-3-amine for the 5-(tert-butyl)isoxazol-3-amine used in Step 2 of Example 32. $^1$H NMR (500 MHz, DMSO-$d_6$) δ 13.73 (br s, 1H), 11.42 (s, 1H), 8.86 (d, J=2.2 Hz, 1H), 8.52 (d, J=1.6 Hz, 1H), 8.19 (s, 1H), 7.62 (d, J=11.0 Hz, 1H), 7.57 (dd, J=1.4, 8.0 Hz, 1H), 7.43-7.51 (m, 1H), 6.91 (s, 1H), 3.82 (s, 2H), 1.50 (d, J=3.8 Hz, 2H), 1.46 (br s, 2H). LC-MS (ESI) m/z 446 (M+H)+.

Example 34

Preparation of 2-(2-fluoro-4-(1H-pyrazolo[3,4-b]pyridin-5-yl)phenyl)-N-(5-(1,1,1-trifluoro-2-methylpropan-2-yl)isoxazol-3-yl)acetamide

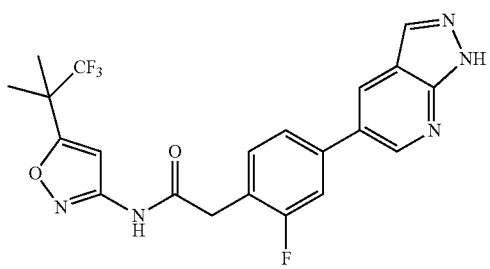 [SMILES: CC(C)(c1cc(NC(=O)Cc2ccc(-c3cnc4[nH]ncc4c3)cc2F)no1)C(F)(F)F]

2-(2-Fluoro-4-(1H-pyrazolo[3,4-b]pyridin-5-yl)phenyl)-N-(5-(1,1,1-trifluoro-2-methylpropan-2-yl)isoxazol-3-yl)acetamide (23 mg) was obtained as a white powder using a procedure analogous to that described in Steps 2-3 of Example 32, substituting 5-(1,1,1-trifluoro-2-methylpropan-2-yl)isoxazol-3-amine for the 5-(tert-butyl)isoxazol-3-amine used in Step 2 of Example 32. $^1$H NMR (500 MHz, DMSO-$d_6$) δ 13.73 (br s, 1H), 11.42 (s, 1H), 8.86 (d, J=2.2 Hz, 1H), 8.52 (d, J=1.6 Hz, 1H), 8.19 (s, 1H), 7.62 (d, J=11.5 Hz, 1H), 7.54-7.59 (m, 1H), 7.48 (t, J=7.7 Hz, 1H), 6.93 (s, 1H), 3.82 (s, 2H), 1.53 (s, 6H). LC-MS (ESI) m/z 448 (M+H)$^+$.

Example 35

Preparation of 2-(4-(3-methoxy-1H-pyrazolo[3,4-b]pyridin-5-yl)phenyl)-N-(5-(1,1,1-trifluoro-2-methylpropan-2-yl)isoxazol-3-yl)acetamide

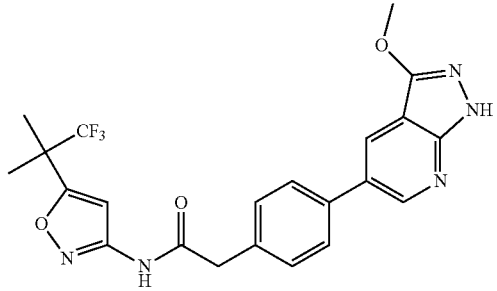 [SMILES: COc1n[nH]c2ncc(-c3ccc(CC(=O)Nc4cc(C(C)(C)C(F)(F)F)on4)cc3)cc12]

Step 1: A stirred mixture of methyl 5-bromo-2-chloronicotinate (5 g, 19.96 mmol), anhydrous hydrazine (7.68 g, 240 mmol) and ethanol (200 mL) was heated at 85° C. for 15 h. The mixture was cooled to rt and the resulting solid was collected by filtration, washed with 50% ethanol in diethyl ether, and dried to afford 5-bromo-1H-pyrazolo[3,4-b]pyridin-3-ol (4.27 g, 100%) as a yellow solid. $^1$H NMR (500 MHz, DMSO-$d_6$) δ 8.36 (d, J=2.0 Hz, 1H), 8.21 (d, J=2.5 Hz, 1H); LC-MS (ESI) m/z 214 and 216 (M+H)$^+$.

Step 2: To a stirred solution of 5-bromo-1H-pyrazolo[3,4-b]pyridin-3-ol (1.63 g, 7.62 mmol) and 4-methoxybenzyl chloride (3.57 g, 22.85 mmol) in DMSO (50 mL) at rt was added powdered sodium hydroxide (457 mg, 11.43 mmol), and the mixture was stirred at rt for 24 h. The mixture was partitioned between water (500 mL) and EtOAc (100 mL) and the organic layer was separated. The aq layer was re-extracted with additional EtOAc (2×150 mL) and the combined organic layers were washed with saturated aq NaHCO$_3$ and brine. The organic layer was dried over MgSO$_4$, filtered, and concentrated under reduced pressure to give a red solid. The solid was purified by trituration with diethyl ether to afford 5-bromo-1-(4-methoxybenzyl)-1H-pyrazolo[3,4-b]pyridin-3-ol (611 mg) as a brown solid, which was not purified further. $^1$H NMR (500 MHz, DMSO-$d_6$) δ 11.23 (br s, 1H), 8.55 (d, J=2.0 Hz, 1H), 8.32 (d, J=2.0 Hz, 1H), 7.16 (d, J=9.0 Hz, 2H), 6.85 (d, J=9.0 Hz, 2H), 5.33 (s, 2H), 3.69 (s, 3H); LC-MS (ESI) m/z 334 and 336 (M+H)$^+$.

Step 3: To a stirred suspension of 5-bromo-1-(4-methoxybenzyl)-1H-pyrazolo[3,4-b]pyridin-3-ol (611 mg, 1.83 mmol) in DMF (3 mL) at rt was added 60% sodium hydride in mineral oil (91 mg, 2.29 mmol) and the mixture was stirred at rt for 10 min. Additional DMF (3 mL) was added and the mixture was stirred for a further 45 min. Methyl iodide (390 mg, 2.74 mmol) was added and the mixture was stirred at rt for 3.5 h. The mixture was partitioned between water and EtOAc and the organic layer was separated. The aq layer was re-extracted with additional EtOAc and the combined organic layers were washed with saturated aq NaHCO$_3$ and brine. The organic layer was dried over MgSO$_4$, filtered, and concentrated under reduced pressure. The residue was purified by silica gel flash chromatography eluting with 0-80% EtOAc in hexane to afford 5-bromo-3-methoxy-1-(4-methoxybenzyl)-1H-pyrazolo[3,4-b]pyridine (193 mg, 30%) as a colorless oil. $^1$H NMR (500 MHz, DMSO-$d_6$) δ 8.61 (d, J=2.5 Hz, 1H), 8.40 (d, J=2.0 Hz, 1H), 7.17 (d, J=9.0 Hz, 2H), 6.85 (m, 2H), 5.41 (s, 2H), 3.99 (s, 3H), 3.70 (s, 3H); LC-MS (ESI) m/z 348 and 350 (M+H)$^+$.

Step 4: To a stirred solution of 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (Ref: S. Abraham et al, WO 2011022473 A1) (162 mg, 0.37 mmol) in CH$_3$CN (3 mL) were added 5-bromo-3-methoxy-1-(4-methoxybenzyl)-1H-pyrazolo[3,4-b]pyridine (193 mg, 0.56 mmol) and 2M aq Na$_2$CO$_3$ (1 mL, 2 mmol) and the mixture was flushed with a stream of argon for 20 min at rt. [1,1'-Bis(diphenylphosphino)ferrocene]dichloropalladium (II) dichloromethane complex (30 mg, 0.037 mmol) was then added and the mixture was stirred at 100° C. for 1.5 h in a sealed vessel. The mixture was partitioned between EtOAc and H$_2$O, and the organic layer was separated and dried over MgSO$_4$, filtered, and concentrated under reduced pressure. The residue was purified by silica gel chromatography eluting with 0-50% EtOAc in hexanes to afford 2-(4-(3-methoxy-1-(4-methoxybenzyl)-1H-pyrazolo[3,4-b]pyridin-5-yl)phenyl)-N-(5-(1,1,1-trifluoro-2-methylpropan-2-yl)isoxazol-3-yl)acetamide (140 mg, 66%) as a white solid. $^1$H NMR (500 MHz, DMSO-$d_6$) δ 11.39 (s, 1H), 8.83 (d, J=2.0 Hz, 1H), 8.31 (d, J=2.0 Hz, 1H), 7.70 (d, J=8.0 Hz, 2H), 7.42 (d, J=8.5 Hz, 2H), 7.20 (d, J=8.5 Hz, 2H), 6.94 (s, 1H), 6.86 (m, 2H), 5.45 (s, 2H), 4.01 (s, 3H), 3.73 (s, 2H), 3.69 (s, 3H), 1.52 (s, 6H); LC-MS (ESI) m/z 580 (M+H)$^+$.

Step 5: 2-(4-(3-Methoxy-1H-pyrazolo[3,4-b]pyridin-5-yl)phenyl)-N-(5-(1,1,1-trifluoro-2-methylpropan-2-yl)isoxazol-3-yl)acetamide (47 mg, 42%) was obtained as a solid using a procedure analogous to that described in Step 3 of Example 40, substituting 2-(4-(3-methoxy-1-(4-methoxybenzyl)-1H-pyrazolo[3,4-b]pyridin-5-yl)phenyl)-N-(5-(1,1,1-trifluoro-2-methylpropan-2-yl)isoxazol-3-yl)acetamide for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. $^1$H NMR (500 MHz, DMSO-$d_6$) δ 12.62 (br s, 1H), 11.40 (br s, 1H), 8.78 (d, J=2.0 Hz, 1H), 8.28 (d, J=2.0 Hz, 1H), 7.70 (d, J=8.5 Hz, 2H), 7.42 (d, J=8.0 Hz, 2H), 6.94 (s, 1H), 4.03 (s, 3H), 3.73 (s, 2H), 1.53 (s, 6H); LC-MS (ESI) m/z 460 (M+H)$^+$.

Example 36

Preparation of 2-(4-(5,7-dimethoxyquinolin-3-yl)-2-fluorophenyl)-N-(5-(1-(trifluoromethyl)cyclopropyl)isoxazol-3-yl)acetamide

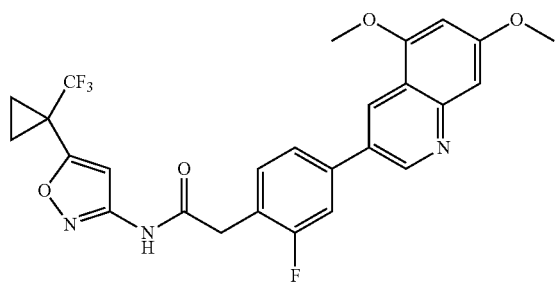 [SMILES: COc1cc(OC)c2cc(-c3ccc(CC(=O)Nc4cc(C5(C(F)(F)F)CC5)on4)c(F)c3)cnc2c1]

Step 1: A stirred mixture of 3,5-dimethoxyaniline (3 g, 19.61 mmol), 2-bromomalonaldehyde (3.38 g, 22.4 mmol), concentrated HCl (10 mL), and ethanol (40 mL) was heated at 100° C. for 15 h. After cooling to rt, the mixture was basified to pH 9 with saturated aq NaHCO$_3$. The mixture was extracted with EtOAc (×3) and the combined organic layers were washed with brine, dried over MgSO$_4$, filtered, and concentrated under reduced pressure. The residue was purified by silica gel flash chromatography eluting with 0-50% EtOAc in hexane to afford a 1:1 mixture of 3-chloro-5,7-dimethoxyquinoline and 3-bromo-5,7-dimethoxyquinoline (509 mg) as a solid, which was not purified further. LC-MS (ESI) m/z 224 (M+H)$^+$ (for the chloride) and m/z 268 and 270 (M+H)$^+$ (for the bromide)

Step 2: 2-(4-(5,7-Dimethoxyquinolin-3-yl)-2-fluorophenyl)-N-(5-(1-(trifluoromethyl)cyclopropyl)isoxazol-3-yl)acetamide (13 mg, 8%) was obtained as a solid using a procedure analogous to that described in Step 3 of Example 4, substituting the product obtained from Step 1 of this example for the 2-chloro-6,7-dimethoxyquinoxaline used in Example 4. $^1$H NMR (500 MHz, DMSO-$d_6$) δ 11.44 (br s, 1H), 9.16 (d, J=2 Hz, 1H), 8.59 (d, J=2.0 Hz, 1H), 7.63-7.72 (m, 2H), 7.50 (m, 1H), 7.03 (d, J=1.5 Hz, 1H), 6.93 (s, 1H), 6.74 (d, J=2.0 Hz, 1H), 4.00 (s, 3H), 3.93 (s, 3H), 3.85 (s, 2H), 1.46-1.54 (m, 4H).

Example 37

Preparation of N-(5-(tert-butyl)isoxazol-3-yl)-2-(4-(3-cyano-1H-pyrazolo[3,4-b]pyridin-5-yl)phenyl)acetamide

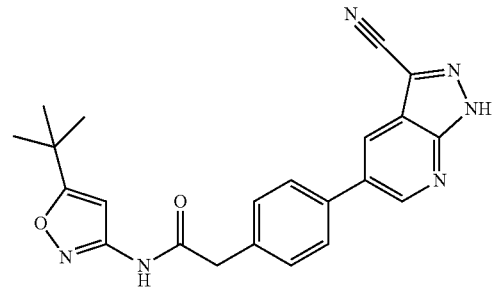 [SMILES: CC(C)(C)c1cc(NC(=O)Cc2ccc(-c3cnc4[nH]nc(C#N)c4c3)cc2)no1]

Step 1: A stirred mixture of 5-bromo-3-iodo-1-((2-(trimethylsilyl)ethoxy)methyl)-1H-pyrazolo[3,4-b]pyridine (ref: Ahrendt, K. A. et al; WO2009/111279 A1, 2009) (350 mg, 0.77 mmol), Zn(CN)$_2$ (45 mg, 0.38 mmol), dppf (43 mg, 0.078 mmol), and Pd$_2$(dba)$_3$ (35 mg, 0.039 mmol) in DMF (5 mL) was flushed with argon for 5 min. The reaction vesses was capped and the mixture was heated at 80° C. overnight. The reaction mixture was cooled to rt and partitioned between EtOAc (50 mL) and water (50 mL). The organic layer was washed with brine, dried over Na$_2$SO$_4$, filtered, and concentrated under reduced pressure. The residue was purified by silica gel chromatography eluting with 0-30% EtOAc in hexanes to give 5-bromo-1-((2-(trimethylsilyl)ethoxy)methyl)-1H-pyrazolo[3,4-b]pyridine-3-carbonitrile as a yellow solid (130 mg, 48%). LC-MS (ESI) m/z 353 (M+H)$^+$.

Step 2: N-(5-(tert-Butyl)isoxazol-3-yl)-2-(4-(3-cyano-1-((2-(trimethylsilyl)ethoxy)methyl)-1H-pyrazolo[3,4-b]pyridin-5-yl)phenyl)acetamide (160 mg, 82%) was obtained using a procedure analogous to that described in Step 3 of Example 4, substituting 5-bromo-1-((2-(trimethylsilyl)ethoxy)methyl)-1H-pyrazolo[3,4-b]pyridine-3-carbonitrile for the 2-chloro-6,7-dimethoxyquinoxaline used in Example 4 and substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. LC-MS (ESI) m/z 531 (M+H)⁺.

Step 3: N-(5-(tert-Butyl)isoxazol-3-yl)-2-(4-(3-cyano-1H-pyrazolo[3,4-b]pyridin-5-yl)phenyl)acetamide (32 mg, 26%) was obtained as a white powder using a procedure analogous to that described in Step 3 of Example 32, substituting N-(5-(tert-butyl)isoxazol-3-yl)-2-(4-(3-cyano-1-((2-(trimethylsilyl)ethoxy)methyl)-1H-pyrazolo[3,4-b]pyridin-5-yl)phenyl)acetamide for the N-(5-(tert-butyl)isoxazol-3-yl)-2-(2-fluoro-4-(1-((2-(trimethylsilyl)ethoxy)methyl)-1H-pyrazolo[3,4-b]pyridin-5-yl)phenyl)acetamide used in Example 32. ¹H NMR (500 MHz, DMSO-d₆) δ 15.07 (br s, 1H), 11.24 (s, 1H), 9.04 (d, J=1.6 Hz, 1H), 8.65 (d, J=1.6 Hz, 1H), 7.82 (d, J=8.2 Hz, 2H), 7.47 (d, J=7.7 Hz, 2H), 6.58 (s, 1H), 3.74 (s, 2H), 1.27 (s, 9H). LC-MS (ESI) m/z 401 (M+H)⁺.

Example 38

Preparation of N-(5-(tert-butyl)isoxazol-3-yl)-2-(4-(3-chloro-1H-pyrazolo[3,4-b]pyridin-5-yl)phenyl)acetamide

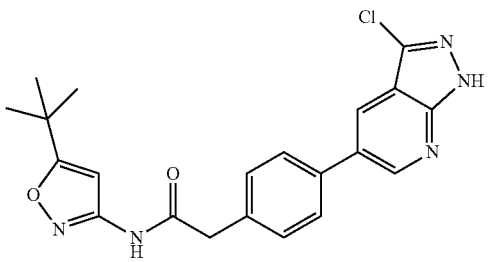 [SMILES: CC(C)(C)c1cc(NC(=O)Cc2ccc(-c3cnc4[nH]nc(Cl)c4c3)cc2)no1]

Step 1: A stirred mixture of 5-bromo-1H-pyrazolo[3,4-b]pyridine (300 mg, 1.51 mmol) and N-chlorosuccinimide (223 mg, 1.67 mmol) in CH₃CN (5 mL) was heated at reflux overnight. The mixture was cooled to rt and quenched with 1:3 water/saturated aq NaHCO₃ (40 mL). The yellow solid was collected by filtration, washed with water, and air-dried to give crude 5-bromo-3-chloro-1H-pyrazolo[3,4-b]pyridine (390 mg). LC-MS (ESI) m/z 232, 234 (M+H)⁺.

Step 2: N-(5-(tert-Butyl)isoxazol-3-yl)-2-(4-(3-chloro-1H-pyrazolo[3,4-b]pyridin-5-yl)phenyl)acetamide (13 mg, 8%) was obtained as a tan powder using a procedure analogous to that described in Step 3 of Example 4, substituting 5-bromo-3-chloro-1H-pyrazolo[3,4-b]pyridine for the 2-chloro-6,7-dimethoxyquinoxaline used in Example 4 and substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. ¹H NMR (500 MHz, DMSO-d₆) δ 13.99 (br s, 1H), 11.23 (s, 1H), 8.94 (d, J=1.6 Hz, 1H), 8.37 (d, J=1.6 Hz, 1H), 7.77 (d, J=8.2 Hz, 2H), 7.45 (d, J=7.7 Hz, 2H), 6.58 (s, 1H), 3.73 (s, 2H), 1.27 (s, 9H). LC-MS (ESI) m/z 410, 412 (M+H)⁺.

Example 39

Preparation of 2-(4-(3-ethoxy-1H-pyrazolo[3,4-b]pyridin-5-yl)phenyl)-N-(5-(1,1,1-trifluoro-2-methylpropan-2-yl)isoxazol-3-yl)acetamide

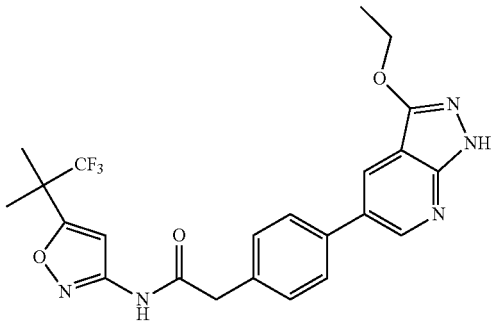 [SMILES: CCOc1n[nH]c2ncc(-c3ccc(CC(=O)Nc4cc(C(C)(C)C(F)(F)F)on4)cc3)cc12]

Step 1: To a stirred suspension of 5-bromo-1-(4-methoxybenzyl)-1H-pyrazolo[3,4-b]pyridin-3-ol from Step 2 of Example 35 (200 mg, 0.60 mmol), triphenylphosphine (235 mg, 0.90 mmol), and ethanol (83 mg, 1.80 mmol) in THF (4 mL) at rt was added a solution of diisopropyl azodicarboxylate (182 mg, 0.90 mmol) in THF (4 mL) dropwise over 30 min, and the mixture was stirred at rt for 1.5 h. The mixture was partitioned between water and EtOAc and the aqueous layer was separated and further extracted with EtOAc. The combined organic layers were washed with saturated aq NaHCO₃ and brine, dried over MgSO₄, filtered, and concentrated under reduced pressure. The residue was purified by silica gel flash chromatography eluting with 0-40% EtOAc in hexanes to afford 5-bromo-3-ethoxy-1-(4-methoxybenzyl)-1H-pyrazolo[3,4-b]pyridine (106 mg, 49%) as a solid. ¹H NMR (500 MHz, DMSO-d₆) δ 8.60 (d, J=2.0 Hz, 1H), 8.38 (d, J=2.0 Hz, 1H), 7.16 (d, J=9.0 Hz, 2H), 6.85 (m, 2H), 5.40 (s, 2H), 4.36 (q, J=7.0 Hz, 2H), 3.70 (s, 3H), 1.38 (t, J=7.0 Hz, 3H); LC-MS (ESI) m/z 362 and 364 (M+H)⁺.

Step 2: 2-(4-(3-Ethoxy-1-(4-methoxybenzyl)-1H-pyrazolo[3,4-b]pyridin-5-yl)phenyl)-N-(5-(1,1,1-trifluoro-2-methylpropan-2-yl)isoxazol-3-yl)acetamide (68 mg, 42%) was obtained as a solid using a procedure analogous to that described in Step 4 of Example 35, substituting 5-bromo-3-ethoxy-1-(4-methoxybenzyl)-1H-pyrazolo[3,4-b]pyridine for the 5-bromo-3-methoxy-1-(4-methoxybenzyl)-1H-pyrazolo[3,4-b]pyridine used in Example 35. LC-MS (ESI) m/z 594 (M+H)⁺.

Step 3: 2-(4-(3-Ethoxy-1H-pyrazolo[3,4-b]pyridin-5-yl)phenyl)-N-(5-(1,1,1-trifluoro-2-methylpropan-2-yl)isoxazol-3-yl)acetamide (28 mg, 52%) was obtained as a solid using a procedure analogous to that described in Step 3 of Example 40, substituting 2-(4-(3-ethoxy-1-(4-methoxybenzyl)-1H-pyrazolo[3,4-b]pyridin-5-yl)phenyl)-N-(5-(1,1,1-trifluoro-2-methylpropan-2-yl)isoxazol-3-yl)acetamide for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. ¹H NMR (500 MHz, DMSO-d₆) δ 12.59 (br s, 1H), 11.38 (br s, 1H), 8.78 (d, J=2.0 Hz, 1H), 8.27 (d, J=2.0 Hz, 1H), 7.72 (d, J=8.5 Hz, 2H), 7.42 (d, J=8.0 Hz, 2H), 6.95 (s, 1H), 4.42 (q, J=7.0 Hz, 2H), 3.74 (s, 2H), 1.53 (s, 6H), 1.42 (t, J=7.0 Hz, 3H); LC-MS (ESI) m/z 474 (M+H)⁺.

Example 40

Preparation of N-(5-(tert-butyl)isoxazol-3-yl)-2-(4-(3-methyl-1H-pyrazolo[3,4-b]pyridin-5-yl)phenyl)acetamide

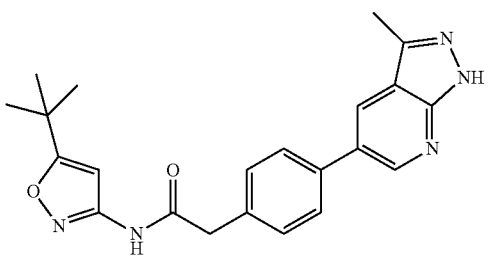 [SMILES: Cc1n[nH]c2ncc(-c3ccc(CC(=O)Nc4cc(C(C)(C)C)on4)cc3)cc12]

Step 1: To a stirred mixture of 5-bromo-3-methyl-1H-pyrazolo[3,4-b]pyridine (200 mg, 0.94 mmol) and DMF (5 mL) under argon at 0° C. was added 60% NaH in mineral oil (45 mg, 1.13 mmol) and the mixture was stirred at rt for 20 min. Then 1-(chloromethyl)-4-methoxybenzene (154 µL, 1.13 mmol) was added, and the mixture was stirred at rt for 2 h before it was partitioned between EtOAc (50 mL) and water (50 mL). The organic layer was washed with brine, dried over $Na_2SO_4$, filtered, and concentrated under reduced pressure. The residue was purified by silica gel chromatography eluting with 0-30% EtOAc in hexanes to give 5-bromo-1-(4-methoxybenzyl)-3-methyl-1H-pyrazolo[3,4-b]pyridine as a white solid (200 mg, 64%). LC-MS (ESI) m/z 344 $(M+H)^+$.

Step 2: Crude N-(5-(tert-butyl)isoxazol-3-yl)-2-(4-(1-(4-methoxybenzyl)-3-methyl-1H-pyrazolo[3,4-b]pyridin-5-yl)phenyl)acetamide (160 mg) was obtained using a procedure analogous to that described in Step 3 of Example 4, substituting 5-bromo-1-(4-methoxybenzyl)-3-methyl-1H-pyrazolo[3,4-b]pyridine for the 2-chloro-6,7-dimethoxyquinoxaline used in Example 4 and substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. LC-MS (ESI) m/z 510 $(M+H)^+$.

Step 3: A stirred mixture of crude N-(5-(tert-butyl)isoxazol-3-yl)-2-(4-(1-(4-methoxybenzyl)-3-methyl-1H-pyrazolo[3,4-b]pyridin-5-yl)phenyl)acetamide (160 mg) in trifluoroacetic acid (2 mL) was heated to 80° C. for 2 h. After cooling to rt, the mixture was concentrated under reduced pressure, aided by addition of acetonitrile. The residue was purified by reverse-phase preparative HPLC using a mixture of water (containing 5% $CH_3CN$ and 0.05% HCOOH) and $CH_3CN$ (containing 0.05% HCOOH) as the mobile phase and a Varian Pursuit XRs diphenyl column as the stationary phase to afford N-(5-(tert-butyl)isoxazol-3-yl)-2-(4-(3-methyl-1H-pyrazolo[3,4-b]pyridin-5-yl)phenyl)acetamide as a tan powder (80 mg, 79% over two steps). $^1$H NMR (500 MHz, DMSO-$d_6$) δ 13.25 (s, 1H), 11.22 (s, 1H), 8.79 (d, J=1.6 Hz, 1H), 8.44 (d, J=1.6 Hz, 1H), 7.73 (d, J=8.2 Hz, 2H), 7.44 (d, J=8.2 Hz, 2H), 6.58 (s, 1H), 3.72 (s, 2H), 2.54 (s, 3H), 1.27 (s, 9H). LC-MS (ESI) m/z 390 $(M+H)^+$.

Example 41

Preparation of 2-(4-(3H-[1,2,3]triazolo[4,5-b]pyridin-6-yl)phenyl)-N-(5-(1,1,1-trifluoro-2-methylpropan-2-yl)isoxazol-3-yl)acetamide

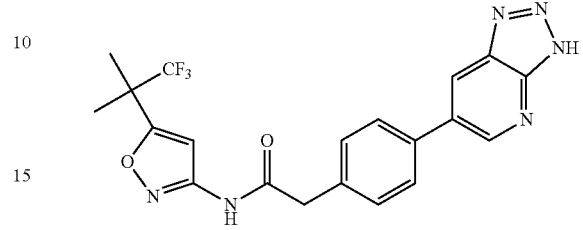

Step 1: To a stirred solution of 6-bromo-1H-1,2,3-triazolo[4,5-b]pyridine (250 mg, 1.26 mmol) in DMF (5 mL) at rt was added 60% sodium hydride in mineral oil (55 mg, 1.38 mmol) and the mixture was stirred at rt for 30 mins. (2-(Chloromethoxy)ethyl)trimethylsilane (419 mg, 2.51 mmol) was added and the mixture was stirred for 15 h. The reaction mixture was partitioned between water and EtOAc and the aqueous layer was separated and further extracted with EtOAc. The combined organic layers were dried over $MgSO_4$, filtered, and concentrated under reduced pressure. The residue was purified by silica gel flash chromatography eluting with 0-20% EtOAc in hexanes to afford a 1:1 mixture of 6-bromo-1-((2-(trimethylsilyl)ethoxy)methyl)-1H-[1,2,3]triazolo[4,5-b]pyridine and 6-bromo-3-((2-(trimethylsilyl)ethoxy)methyl)-3H-[1,2,3]triazolo[4,5-b]pyridine (240 mg) as an oil, which was not purified further. LC-MS (ESI) m/z 329 and 331 $(M+H)^+$.

Step 2: A 1:1 mixture of N-(5-(1,1,1-trifluoro-2-methylpropan-2-yl)isoxazol-3-yl)-2-(4-(1-((2-(trimethylsilyl)ethoxy)methyl)-1H-[1,2,3]triazolo[4,5-b]pyridin-6-yl)phenyl)acetamide and N-(5-(1,1,1-trifluoro-2-methylpropan-2-yl)isoxazol-3-yl)-2-(4-(3-((2-(trimethylsilyl)ethoxy)methyl)-3H-[1,2,3]triazolo[4,5-b]pyridin-6-yl)phenyl)acetamide (71 mg, 40%) was obtained as a solid using a procedure analogous to that described in Step 3 of Example 4, substituting the product obtained from Step 1 of this example for the 2-chloro-6,7-dimethoxyquinoxaline used in Example 4 and substituting 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (Ref: S. Abraham et al, WO 2011022473 A1) for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. LC-MS (ESI) m/z 561 $(M+H)^+$.

Step 3: To a 1:1 mixture of N-(5-(1,1,1-trifluoro-2-methylpropan-2-yl)isoxazol-3-yl)-2-(4-(1-((2-(trimethylsilyl)ethoxy)methyl)-1H-[1,2,3]triazolo[4,5-b]pyridin-6-yl)phenyl)acetamide and N-(5-(1,1,1-trifluoro-2-methylpropan-2-yl)isoxazol-3-yl)-2-(4-(3-((2-(trimethylsilyl)ethoxy)methyl)-3H-[1,2,3]triazolo[4,5-b]pyridin-6-yl)phenyl)acetamide (71 mg, 0.127 mmol) was added trifluoroacetic acid (5 mL), and the mixture was stirred at rt for 1 h. The mixture was concentrated under reduced pressure and the residue was purified by reverse-phase preparative HPLC using a mixture of water (containing 5% $CH_3CN$ and 0.05% HCOOH) and $CH_3CN$ (containing 0.05% HCOOH) as the mobile phase and Varian Pursuit XRs diphenyl column as the stationary phase to afford 2-(4-(3H-[1,2,3]triazolo[4,5-b]pyridin-6-yl)phenyl)-N-(5-(1,1,1-trifluoro-2-methylpropan-2-yl)isoxazol-3-yl)acetamide (12 mg, 22%) as a solid. $^1$H NMR (500 MHz, DMSO-d$_6$) δ 11.41 (br s, 1H), 9.00 (d, J=2.0 Hz, 1H), 8.60 (br s, 1H), 7.80 (d, J=8.5 Hz, 2H), 7.48 (d, J=8.5 Hz, 2H), 6.95 (s, 1H), 3.77 (s, 2H), 1.53 (s, 6H); LC-MS (ESI) m/z 431 (M+H)$^+$.

Example 42

Preparation of 2-(4-(6,7-dimethoxyquinoxalin-2-yl)-3-fluorophenyl)-N-(5-(1-(trifluoromethyl)cyclopropyl)isoxazol-3-yl)acetamide

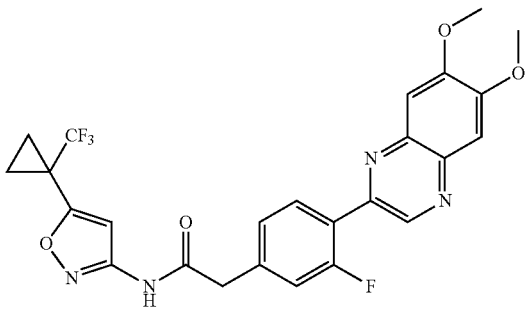 [SMILES: COc1cc2ncc(-c3ccc(CC(=O)Nc4cc(C5(C(F)(F)F)CC5)on4)cc3F)nc2cc1OC]

Step 1: 2-(3-Fluoro-4-(4,4,5,5-tetramethyl-1,3,2-dioxaborolan-2-yl)phenyl)acetic acid (200 mg, 33%) was obtained as a solid using a procedure analogous to that described in Step 1 of Example 27, substituting 2-(4-bromo-3-fluorophenyl)acetic acid for the 2-(4-bromo-2-fluorophenyl)acetic acid used in Example 27. $^1$H NMR (500 MHz, DMSO-d$_6$) δ 12.44 (br s, 1H), 7.58 (m, 1H), 7.11 (m, 1H), 7.06 (m, 1H), 3.63 (s, 2H), 1.29 (s, 12H); LC-MS (ESI) m/z 281 (M+H)$^+$.

Step 2: 2-(4-(6,7-Dimethoxyquinoxalin-2-yl)-3-fluorophenyl)acetic acid (140 mg 57%) was obtained as a solid using a procedure analogous to that described in Step 2 of Example 27, substituting 2-(3-fluoro-4-(4,4,5,5-tetramethyl-1,3,2-dioxaborolan-2-yl)phenyl)acetic acid for the 2-(2-fluoro-4-(4,4,5,5-tetramethyl-1,3,2-dioxaborolan-2-yl)phenyl)acetic acid used in Example 27 and substituting 2-chloro-6,7-dimethoxyquinoxaline for the 5-bromo-7-azaindole used in Example 27. $^1$H NMR (500 MHz, DMSO-d$_6$) δ 12.51 (br s, 1H), 9.08 (s, 1H), 7.54 (m, 1H), 7.47 (d, J=6.0 Hz, 2H), 7.28-7.38 (m, 2H), 4.00 (s, 6H), 3.73 (s, 2H); LC-MS (ESI) m/z 343 (M+H)$^+$.

Step 3: 2-(4-(6,7-Dimethoxyquinoxalin-2-yl)-3-fluorophenyl)-N-(5-(1-(trifluoromethyl)cyclopropyl)isoxazol-3-yl)acetamide (6 mg, 3%) was obtained as a solid using a procedure analogous to that described in Step 3 of Example 27, substituting 2-(4-(6,7-dimethoxyquinoxalin-2-yl)-3-fluorophenyl)acetic acid for the 2-(2-fluoro-4-(1H-pyrrolo[2,3-b]pyridine-5-yl)phenyl)acetic acid used in Example 27 and substituting 5-(1-(trifluoromethyl)cyclopropyl)isoxazol-3-amine (Ref: M. W. Rowbottom et al, *J. Med. Chem.* 2012, 55(3), 1082-1105) for the 3-amino-5-tert-butylisoxazole used in Example 27. $^1$H NMR (500 MHz, DMSO-d$_6$) δ 11.45 (br s, 1H), 9.07 (d, J=2.7 Hz, 1H), 8.01 (t, J=8.2 Hz, 1H), 7.47 (d, J=4.4 Hz, 2H), 7.33-7.40 (m, 2H), 6.95 (s, 1H), 4.00 (s, 6H), 3.84 (s, 2H), 1.51-1.55 (m, 2H), 1.45-1.50 (m, 2H); LC-MS (ESI) m/z 517 (M+H)$^+$.

Example 43

Preparation of N-(5-(tert-butyl)isoxazol-3-yl)-2-(4-(6,7-dimethoxyquinoxalin-2-yl)-2-fluorophenyl)acetamide

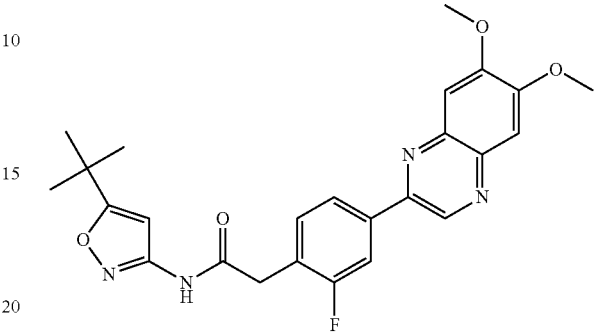

N-(5-(tert-Butyl)isoxazol-3-yl)-2-(4-(6,7-dimethoxyquinoxalin-2-yl)-2-fluorophenyl)acetamide (9 mg, 7%) was obtained as a solid using a procedure analogous to that described in Step 3 of Example 27, substituting 2-(4-(6,7-dimethoxyquinoxalin-2-yl)-2-fluorophenyl)acetic acid from Step 1 of Example 46 for the 2-(2-fluoro-4-(1H-pyrrolo[2,3-b]pyridine-5-yl)phenyl)acetic acid used in Example 27. $^1$H NMR (500 MHz, DMSO-d$_6$) δ 11.29 (br s, 1H), 9.38 (s, 1H), 8.08-8.12 (m, 2H), 7.56 (dd, J=7.5, 7.5 Hz, 1H), 7.45-7.47 (m, 2H), 6.58 (s, 1H), 4.00 (s, 3H), 3.99 (s, 3H), 3.86 (s, 2H), 1.28 (s, 9H); LC-MS (ESI) m/z 465 (M+H)$^+$.

Example 44

Preparation of 2-(4-(1H-pyrazolo[3,4-b]pyridin-5-yl)phenyl)-N-(5-(1,1,1-trifluoro-2-methylpropan-2-yl)isoxazol-3-yl)acetamide

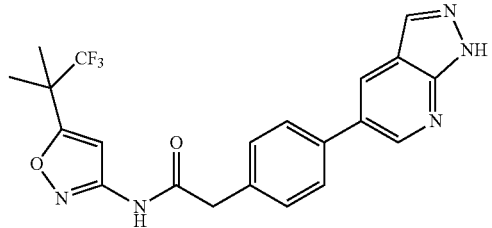 [SMILES: CC(C)(c1cc(NC(=O)Cc2ccc(-c3cnc4[nH]ncc4c3)cc2)no1)C(F)(F)F]

Step 1: Crude N-(5-(1,1,1-trifluoro-2-methylpropan-2-yl)isoxazol-3-yl)-2-(4-(1-((2-(trimethylsilyl)ethoxy)methyl)-1H-pyrazolo[3,4-b]pyridin-5-yl)phenyl)acetamide (300 mg) was obtained using a procedure analogous to that described in Step 3 of Example 4, substituting 5-bromo-1-((2-(trimethylsilyl)ethoxy)methyl)-1H-pyrazolo[3,4-b]pyridine for the 2-chloro-6,7-dimethoxyquinoxaline used in Example 4 and substituting 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. LC-MS (ESI) m/z 560 (M+H)$^+$.

Step 2: To crude N-(5-(1,1,1-trifluoro-2-methylpropan-2-yl)isoxazol-3-yl)-2-(4-(1-((2-(trimethylsilyl)ethoxy)

methyl)-1H-pyrazolo[3,4-b]pyridin-5-yl)phenyl)acetamide (300 mg) was added TFA (3 mL) and the mixture was stirred at rt overnight. The mixture was concentrated under reduced pressure and the residue was taken up in 5 mL of MeOH and ethylenediamine (250 µL) was added. After stirring at rt for 2 h, the mixture was purified by reverse-phase preparative HPLC using a mixture of water (containing 5% CH$_3$CN and 0.05% HCOOH) and CH$_3$CN (containing 0.05% HCOOH) as the mobile phase and a Varian Pursuit XRs diphenyl column as the stationary phase to afford 2-(4-(1H-pyrazolo[3,4-b]pyridin-5-yl)phenyl)-N-(5-(1,1,1-trifluoro-2-methylpropan-2-yl)isoxazol-3-yl)acetamide (101 mg, 62% over two steps) as a tan powder. $^1$H NMR (500 MHz, DMSO-d$_6$) δ 13.71 (br s, 1H), 11.40 (s, 1H), 8.82 (d, J=2.2 Hz, 1H), 8.45 (d, J=1.6 Hz, 1H), 8.19 (s, 1H), 7.71 (d, J=7.7 Hz, 2H), 7.45 (d, J=8.2 Hz, 2H), 6.95 (s, 1H), 3.75 (s, 2H), 1.54 (s, 6H). LC-MS (ESI) m/z 430 (M+H)$^+$.

Example 45

Preparation of 5-(4-(2-((5-(tert-butyl)isoxazol-3-yl)amino)-2-oxoethyl)phenyl)-N,N-dimethyl-1H-pyrazolo[3,4-b]pyridine-3-carboxamide

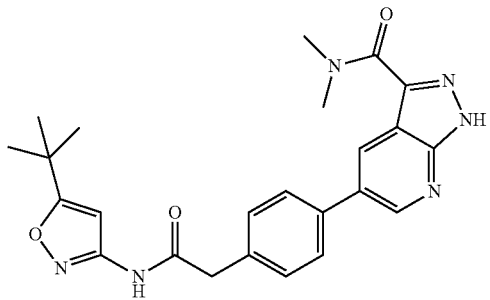 [SMILES: CN(C)C(=O)c1n[nH]c2ncc(-c3ccc(CC(=O)Nc4cc(C(C)(C)C)on4)cc3)cc12]

Step 1: 5-Bromo-N,N-dimethyl-1H-pyrazolo[3,4-b]pyridine-3-carboxamide (300 mg, 90%) was obtained using a procedure analogous to that described in Step 2 of Example 4, substituting 5-bromo-1H-pyrazolo[3,4-b]pyridine-3-carboxylic acid for the 2-(2-fluoro-4-(4,4,5,5-tetramethyl-1,3,2-dioxaborolan-2-yl)phenyl)acetic acid used in Example 4 and dimethylamine hydrochloride for the 5-(1-(trifluoromethyl)cyclopropyl)isoxazol-3-amine used in Example 4. LC-MS (ESI) m/z 269, 271 (M+H)$^+$.

Step 2: 5-(4-(2-((5-(tert-Butyl)isoxazol-3-yl)amino)-2-oxo ethyl)phenyl)-N,N-dimethyl-1H-pyrazolo[3,4-b]pyridine-3-carboxamide (9 mg, 8%) was obtained as a tan powder using a procedure analogous to that described in Step 3 of Example 4, substituting 5-bromo-N,N-dimethyl-1H-pyrazolo[3,4-b]pyridine-3-carboxamide for the 2-chloro-6,7-dimethoxyquinoxaline used in Example 4 and substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. $^1$H NMR (500 MHz, DMSO-d$_6$) δ 14.16 (br s, 1H), 11.24 (s, 1H), 8.90 (d, J=1.6 Hz, 1H), 8.56 (d, J=1.6 Hz, 1H), 7.72 (d, J=7.7 Hz, 2H), 7.46 (d, J=7.7 Hz, 2H), 6.58 (s, 1H), 3.73 (s, 2H), 3.41 (s, 3H), 3.09 (s, 3H), 1.27 (s, 9H). LC-MS (ESI) m/z 447 (M+H)$^+$.

Example 46

Preparation of 2-(4-(6,7-dimethoxyquinoxalin-2-yl)-2-fluorophenyl)-N-(5-(1,1,1-trifluoro-2-methylpropan-2-yl)isoxazol-3-yl)acetamide

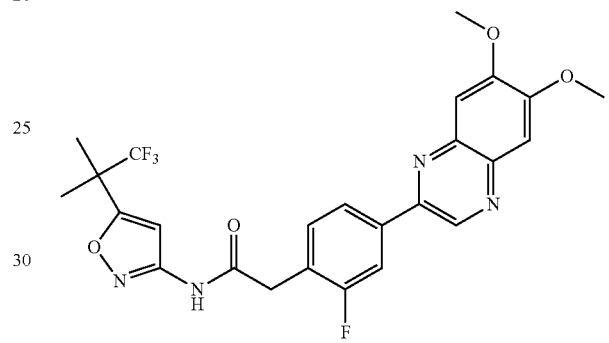

Step 1: A stirred mixture of 2-(2-fluoro-4-(4,4,5,5-tetramethyl-1,3,2-dioxaborolan-2-yl)phenyl)acetic acid from Step 1 of Example 4 (200 mg, 0.714 mmol), 2-chloro-6,7-dimethoxyquinoxaline (241 mg, 1.07 mmol), 2M aq sodium carbonate (1.5 mL) and acetonitrile (5 mL) was flushed with a stream of argon for 10 min. [1,1'-Bis(diphenylphosphino)ferrocene]dichloropalladium (II) dichloromethane complex (58 mg, 0.071 mmol) was added and the mixture was heated at 100° C. for 15 h in a sealed vessel. After the mixture had cooled to rt, 2M aq HCl was added to pH 5, and the precipitate was collected via filtration to afford 2-(4-(6,7-dimethoxyquinoxalin-2-yl)-2-fluorophenyl)acetic acid (300 mg) as a purple solid which was not purified further. LC-MS (ESI) m/z 343 (M+H)$^+$.

Step 2: 2-(4-(6,7-Dimethoxyquinoxalin-2-yl)-2-fluorophenyl)-N-(5-(1,1,1-trifluoro-2-methylpropan-2-yl)isoxazol-3-yl)acetamide (9 mg, 6%) was obtained as a solid using a procedure analogous to that described in Step 3 of Example 27, substituting 5-(1,1,1-trifluoro-2-methylpropan-2-yl)isoxazol-3-amine (Ref: M. W. Rowbottom et al, *J. Med. Chem.* 2012, 55(3), 1082-1105) for the 3-amino-5-tert-butylisoxazole used in Example 27. $^1$H NMR (500 MHz, DMSO-d$_6$) δ 11.47 (br s, 1H), 9.38 (br s, 1H), 8.08-8.12 (m, 2H), 7.57 (dd, J=7.5, 7.5 Hz, 1H), 7.45-7.47 (m, 2H), 6.96 (s, 1H), 4.00 (s, 3H), 3.99 (s, 3H), 3.89 (s, 2H), 1.54 (s, 6H); LC-MS (ESI) m/z 519 (M+H)$^+$.

Example 47

Preparation of 2-(4-(3-(2-methoxyethoxy)-1H-pyrazolo[3,4-b]pyridin-5-yl)phenyl)-N-(5-(1,1,1-trifluoro-2-methylpropan-2-yl)isoxazol-3-yl)acetamide

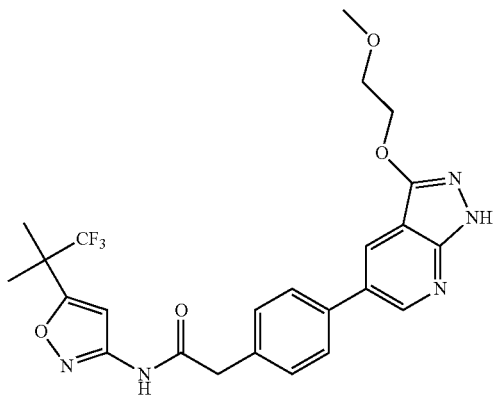 [SMILES: COCCOc1n[nH]c2ncc(-c3ccc(CC(=O)Nc4cc(C(C)(C)C(F)(F)F)on4)cc3)cc12]

Step 1: 5-Bromo-1-(4-methoxybenzyl)-3-(2-methoxyethoxy)-1H-pyrazolo[3,4-b]pyridine (98 mg, 28%) was obtained as a solid using a procedure analogous to that described in Step 1 of Example 39, substituting 2-methoxyethanol for the ethanol used in Example 39. $^1$H NMR (500 MHz, DMSO-$d_6$) δ 8.61 (d, J=2.0 Hz, 1H), 8.41 (d, J=2.0 Hz, 1H), 7.17 (d, J=9.0 Hz, 2H), 6.85 (m, 2H), 5.41 (s, 2H), 4.43 (m, 2H), 3.69-3.71 (m, 5H), 3.30 (s, 3H); LC-MS (ESI) m/z 392 and 394 (M+H)$^+$.

Step 2:

2-(4-(1-(4-Methoxybenzyl)-3-(2-methoxyethoxy)-1H-pyrazolo[3,4-b]pyridin-5-yl)phenyl)-N-(5-(1,1,1-trifluoro-2-methylpropan-2-yl)isoxazol-3-yl)acetamide (65 mg, 42%) was obtained as a solid using a procedure analogous to that described in Step 4 of Example 35, substituting 5-bromo-1-(4-methoxybenzyl)-3-(2-methoxyethoxy)-1H-pyrazolo[3,4-b]pyridine for the 5-bromo-3-methoxy-1-(4-methoxybenzyl)-1H-pyrazolo[3,4-b]pyridine used in Example 35. LC-MS (ESI) m/z 624 (M+H)$^+$.

Step 3: 2-(4-(3-(2-Methoxyethoxy)-1H-pyrazolo[3,4-b]pyridin-5-yl)phenyl)-N-(5-(1,1,1-trifluoro-2-methylpropan-2-yl)isoxazol-3-yl)acetamide (1.5 mg, 3%) was obtained as a solid using a procedure analogous to that described in Step 3 of Example 40, substituting 2-(4-(1-(4-methoxybenzyl)-3-(2-methoxyethoxy)-1H-pyrazolo[3,4-b]pyridin-5-yl)phenyl)-N-(5-(1,1,1-trifluoro-2-methylpropan-2-yl)isoxazol-3-yl)acetamide for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. $^1$H NMR (500 MHz, DMSO-$d_6$) δ 12.63 (br s, 1H), 11.40 (br s, 1H), 8.79 (d, J=2.0 Hz, 1H), 8.29 (d, J=2.0 Hz, 1H), 7.73 (d, J=8.5 Hz, 2H), 7.42 (d, J=8.0 Hz, 2H), 6.95 (s, 1H), 4.48 (m, 2H), 3.74-3.76 (m, 4H), 3.33 (s, 3H), 1.53 (s, 6H); LC-MS (ESI) m/z 504 (M+H)$^+$.

Example 48

Preparation of 2-(4-(3-(piperidin-4-yloxy)-1H-pyrazolo[3,4-b]pyridin-5-yl)phenyl)-N-(5-(1,1,1-trifluoro-2-methylpropan-2-yl)isoxazol-3-yl)acetamide formate salt

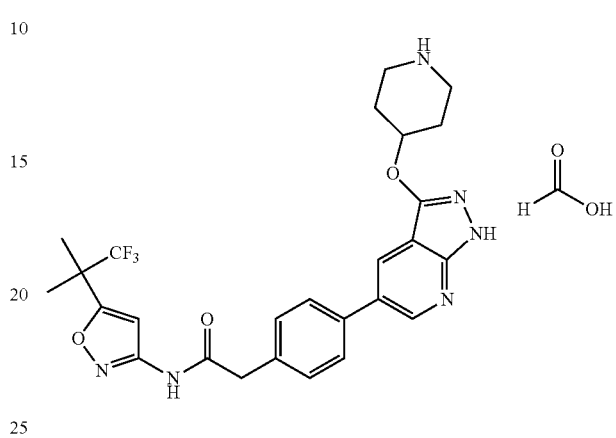

Step 1: tert-Butyl 4-((5-bromo-1-(4-methoxybenzyl)-1H-pyrazolo[3,4-b]pyridin-3-yl)oxy)piperidine-1-carboxylate (242 mg, 52%) was obtained as a solid using a procedure analogous to that described in Step 1 of Example 39, substituting tert-butyl 4-hydroxypiperidine-1-carboxylate for the ethanol used in Example 39. $^1$H NMR (500 MHz, DMSO-$d_6$) δ 8.61 (d, J=2.0 Hz, 1H), 8.41 (d, J=2.0 Hz, 1H), 7.16 (d, J=9.0 Hz, 2H), 6.85 (m, 2H), 5.41 (s, 2H), 4.98 (m, 1H), 3.70 (s, 3H), 3.62-3.67 (m, 2H), 3.20-3.30 (m, 2H), 1.96-2.00 (m, 2H), 1.62-1.68 (m, 2H), 1.41 (s, 9H); LC-MS (ESI) m/z 517 and 519 (M+H)$^+$.

Step 2: tert-Butyl 4-((1-(4-methoxybenzyl)-5-(4-(2-oxo-2-((5-(1,1,1-trifluoro-2-methylpropan-2-yl)isoxazol-3-yl)amino)ethyl)phenyl)-1H-pyrazolo[3,4-b]pyridin-3-yl)oxy)piperidine-1-carboxylate (110 mg, 50%) was obtained as a solid using a procedure analogous to that described in Step 4 of Example 35, substituting tert-butyl 4-((5-bromo-1-(4-methoxybenzyl)-1H-pyrazolo[3,4-b]pyridin-3-yl)oxy)piperidine-1-carboxylate for the 5-bromo-3-methoxy-1-(4-methoxybenzyl)-1H-pyrazolo[3,4-b]pyridine used in Example 35. LC-MS (ESI) m/z 749 (M+H)$^+$.

Step 3: 2-(4-(3-(Piperidin-4-yloxy)-1H-pyrazolo[3,4-b]pyridin-5-yl)phenyl)-N-(5-(1,1,1-trifluoro-2-methylpropan-2-yl)isoxazol-3-yl)acetamide formate salt (18 mg, 21%) was obtained as a solid using a procedure analogous to that described in Step 3 of Example 40, substituting tert-butyl 4-((1-(4-methoxybenzyl)-5-(4-(2-oxo-2-((5-(1,1,1-trifluoro-2-methylpropan-2-yl)isoxazol-3-yl)amino)ethyl)phenyl)-1H-pyrazolo[3,4-b]pyridin-3-yl)oxy)piperidine-1-carboxylate for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. $^1$H NMR (500 MHz, DMSO-$d_6$) δ 12.67 (br s, 1H), 11.42 (br s, 1H), 8.80 (d, J=2.0 Hz, 1H), 8.33 (s, 1H), 8.29 (d, J=2.0 Hz, 1H), 7.73 (d, J=8.5 Hz, 2H), 7.43 (d, J=8.0 Hz, 2H), 6.95 (s, 1H), 4.98 (m, 1H), 3.74 (s, 2H), 3.13-3.16 (m, 2H), 2.82-2.86 (m, 2H), 2.13-2.15 (m, 2H), 1.77-1.79 (m, 2H), 1.53 (s, 6H).

Example 49

Preparation of 5-(4-(2-((5-(tert-butyl)isoxazol-3-yl)amino)-2-oxoethyl)phenyl)-N,N-dimethyl-1H-pyrrolo[2,3-b]pyridine-2-carboxamide

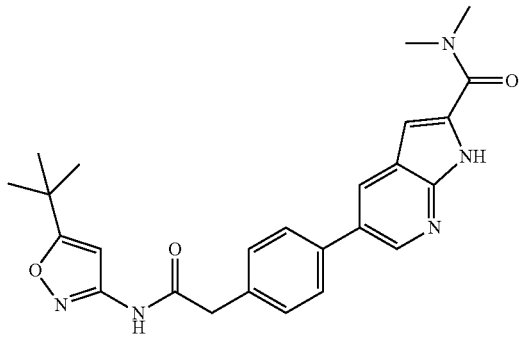 [SMILES: CN(C)C(=O)c1cc2cc(-c3ccc(CC(=O)Nc4cc(C(C)(C)C)on4)cc3)cnc2[nH]1]

Step 1: 5-Bromo-N,N-dimethyl-1H-pyrrolo[2,3-b]pyridine-2-carboxamide (90 mg, 81%) was obtained using a procedure analogous to that described in Step 2 of Example 4, substituting 5-bromo-1H-pyrrolo[2,3-b]pyridine-2-carboxylic acid for the 2-(2-fluoro-4-(4,4,5,5-tetramethyl-1,3,2-dioxaborolan-2-yl)phenyl)acetic acid used in Example 4 and substituting dimethylamine hydrochloride for the 5-(1-(trifluoromethyl)cyclopropyl)isoxazol-3-amine used in Example 4. LC-MS (ESI) m/z 268, 270 (M+H)+.

Step 2: 5-(4-(2-((5-(tert-Butyl)isoxazol-3-yl)amino)-2-oxoethyl)phenyl)-N,N-dimethyl-1H-pyrrolo[2,3-b]pyridine-2-carboxamide (50 mg, 43%) was obtained as a tan solid using a procedure analogous to that described in Step 3 of Example 4, substituting 5-bromo-N,N-dimethyl-1H-pyrrolo[2,3-b]pyridine-2-carboxamide for the 2-chloro-6,7-dimethoxyquinoxaline used in Example 4 and substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. $^1$H NMR (500 MHz, DMSO-$d_6$) δ 12.14 (br s, 1H), 11.22 (s, 1H), 8.61 (s, 1H), 8.26 (d, J=1.1 Hz, 1H), 7.67 (d, J=8.2 Hz, 2H), 7.42 (d, J=8.2 Hz, 2H), 6.86 (d, J=1.1 Hz, 1H), 6.58 (s, 1H), 3.72 (s, 2H), 3.26 (br s, 3H), 3.06 (br s, 3H), 1.27 (s, 9H). LC-MS (ESI) m/z 446 (M+H)+.

Example 50

Preparation of N-(5-(tert-butyl)isoxazol-3-yl)-2-(4-(2-(hydroxymethyl)-1H-pyrrolo[2,3-b]pyridin-5-yl)phenyl)acetamide

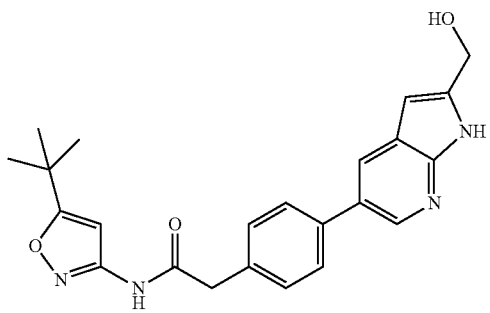 [SMILES: CC(C)(C)c1cc(NC(=O)Cc2ccc(-c3cnc4[nH]c(CO)cc4c3)cc2)no1]

Step 1: To a stirred suspension of 5-bromo-1H-pyrrolo[2,3-b]pyridine-2-carboxylic acid (505 mg, 2.1 mmol) in 20 mL of THF at 0° C. was added dropwise 1 M borane in THF (8.4 mL, 8.4 mmol). The resulting mixture was stirred at rt for 1 h and then heated at 55° C. for 2 h. The reaction was then cooled to 0° C. and quenched with 3 N HCl. After 30 min at rt, the mixture was extracted with EtOAc (2×30 mL). The combined organic layers were washed with brine, dried over Na$_2$SO$_4$, and concentrated under reduced pressure to give crude 5-bromo-1H-pyrrolo[2,3-b]pyridin-2-yl)methanol (500 mg) as a light yellow solid. LC-MS (ESI) m/z 227, 229 (M+H)+.

Step 2: N-(5-(tert-Butyl)isoxazol-3-yl)-2-(4-(2-(hydroxymethyl)-1H-pyrrolo[2,3-b]pyridin-5-yl)phenyl)acetamide (125 mg, 25% over two steps) was obtained as a tan solid using a procedure analogous to that described in Step 3 of Example 4, substituting 5-bromo-1H-pyrrolo[2,3-b]pyridin-2-yl)methanol for the 2-chloro-6,7-dimethoxyquinoxaline used in Example 4 and substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. $^1$H NMR (500 MHz, DMSO-$d_6$) δ 11.58 (br s, 1H), 11.21 (br s, 1H), 8.42 (br s, 1H), 8.10 (br s, 1H), 7.65 (d, J=7.7 Hz, 2H), 7.40 (d, J=7.7 Hz, 2H), 6.58 (s, 1H), 6.35 (br s, 1H), 5.29 (br s, 1H), 4.62 (br s, 2H), 3.70 (br s, 2H), 1.27 (s, 9H).

Example 51

Preparation of N-(5-(tert-butyl)isoxazol-3-yl)-2-(2-fluoro-4-(3-methyl-1H-pyrazolo[3,4-b]pyridin-5-yl)phenyl)acetamide

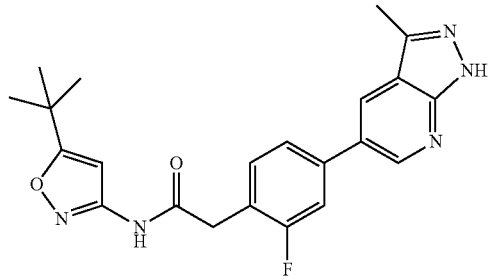 [SMILES: Cc1n[nH]c2ncc(-c3ccc(CC(=O)Nc4cc(C(C)(C)C)on4)c(F)c3)cc12]

Step 1: N-(5-(tert-Butyl)isoxazol-3-yl)-2-(2-fluoro-4-(4,4,5,5-tetramethyl-1,3,2-dioxaborolan-2-yl)phenyl)acetamide (730 mg, 51%) was obtained using a procedure analogous to that described in Step 2 of Example 4, substituting 5-(tert-butyl)isoxazol-3-amine for the 5-(1-(trifluoromethyl)cyclopropyl)isoxazol-3-amine used in Example 4.

Step 2: N-(5-(tert-Butyl)isoxazol-3-yl)-2-(2-fluoro-4-(3-methyl-1H-pyrazolo[3,4-b]pyridin-5-yl)phenyl)acetamide (95 mg, 70%) was obtained using a procedure analogous to that described in Steps 2-3 of Example 40, substituting N-(5-(tert-butyl)isoxazol-3-yl)-2-(2-fluoro-4-(4,4,5,5-tetramethyl-1,3,2-dioxaborolan-2-yl)phenyl)acetamide for the N-(5-(tert-butyl)isoxazol-3-yl)-2-(4-(4,4,5,5-tetramethyl-1,3,2-dioxaborolan-2-yl)phenyl)acetamide used in Example 40. $^1$H NMR (500 MHz, DMSO-$d_6$) δ 13.29 (br s, 1H), 11.25 (s, 1H), 8.84 (d, J=1.6 Hz, 1H), 8.53 (d, J=1.1 Hz, 1H), 7.65 (d, J=11.5 Hz, 1H), 7.60 (d, J=8.2 Hz, 1H), 7.48 (t, J=8.0 Hz, 1H), 6.57 (s, 1H), 3.81 (s, 2H), 2.55 (s, 3H), 1.28 (s, 9H). LC-MS (ESI) m/z 408 (M+H)⁺.

Example 52

Preparation of N-(5-(tert-butyl)isoxazol-3-yl)-2-(4-(2-((dimethylamino)methyl)-1H-pyrrolo[2,3-b]pyridin-5-yl)phenyl)acetamide

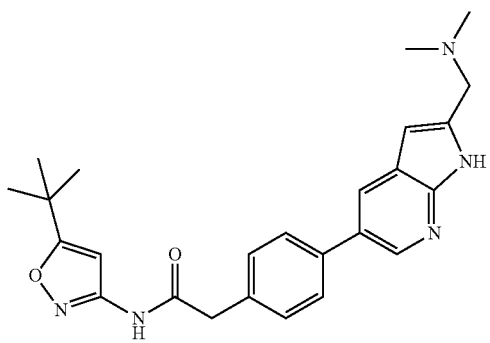 [SMILES: CN(C)Cc1cc2cc(-c3ccc(CC(=O)Nc4cc(C(C)(C)C)on4)cc3)cnc2[nH]1]

Step 1: To a stirred solution of N-(5-(tert-butyl)isoxazol-3-yl)-2-(4-(2-(hydroxymethyl)-1H-pyrrolo[2,3-b]pyridin-5-yl)phenyl)acetamide from Example 50 (125 mg, 0.31 mmol) in 1:1 CH₃CN/DMF (5 mL) at rt was added Dess-Martin periodinane (144 mg, 0.34 mmol). The resulting mixture was stirred at rt for 1 h and then partitioned between aq Na₂S₂O₃ and EtOAc. The organic layer was washed with brine, dried over Na₂SO₄, filtered, and concentrated under reduced pressure. The resulting crude N-(5-(tert-butyl)isoxazol-3-yl)-2-(4-(2-formyl-1H-pyrrolo[2,3-b]pyridin-5-yl)phenyl)acetamide (ca. 125 mg) was used directly for the next step. LC-MS (ESI) m/z 403 (M+H)⁺.

Step 2: A NaOAc/MeOH buffer was prepared from a mixture of NaOAc.3H₂O (21 g) and AcOH (48 mL) diluted to 1.0 L with methanol. To a stirred solution of crude N-(5-(tert-butyl)isoxazol-3-yl)-2-(4-(2-formyl-1H-pyrrolo[2,3-b]pyridin-5-yl)phenyl)acetamide (125 mg) in the above NaOAc/MeOH buffer were added N,N-dimethylamine hydrochloride (63 mg, 0.77 mmol) and NaCNBH₃ (100 mg, excess). The resulting mixture was stirred at rt for 3 h, and then heated at 60° C. for 3 h. LC-MS indicated that the reaction was nearly complete. The crude mixture was purified directly by reverse-phase preparative HPLC using a mixture of water (containing 5% CH₃CN and 0.05% HCOOH), and CH₃CN (containing 0.05% HCOOH) as the mobile phase and a Varian Pursuit XRs diphenyl column as the stationary phase to afford N-(5-(tert-butyl)isoxazol-3-yl)-2-(4-(2-((dimethylamino)methyl)-1H-pyrrolo[2,3-b]pyridin-5-yl)phenyl)acetamide as a pale yellow powder (75 mg, 56% yield over two steps). ¹H NMR (500 MHz, DMSO-d₆) δ 11.81 (br s, 1H), 11.22 (s, 1H), 8.53 (d, J=1.1 Hz, 1H), 8.20 (s, 1H), 7.66 (d, J=8.2 Hz, 2H), 7.42 (d, J=8.2 Hz, 2H), 6.60 (br s, 1H), 6.57 (s, 1H), 4.13 (br s, 2H), 3.71 (s, 2H), 2.58 (br s, 6H), 1.27 (s, 9H).

Example 53

Preparation of 2-(2-fluoro-4-(3-methoxy-1H-pyrazolo[3,4-b]pyridin-5-yl)phenyl)-N-(5-(1-(trifluoromethyl)cyclopropyl)isoxazol-3-yl)acetamide

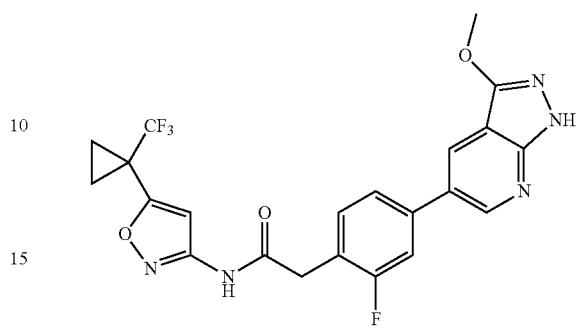

Step 1: 2-(2-Fluoro-4-(3-methoxy-1-(4-methoxybenzyl)-1H-pyrazolo[3,4-b]pyridin-5-yl)phenyl)-N-(5-(1-(trifluoromethyl)cyclopropyl)isoxazol-3-yl)acetamide (20 mg, 11%) was obtained as a solid using a procedure analogous to that described in Step 4 of Example 35, substituting 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide (Ref: S. Abraham et al, WO 2011022473 A1) for the 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide used in Example 35. LC-MS (ESI) m/z 596 (M+H)¹.

Step 2: 2-(2-Fluoro-4-(3-methoxy-1H-pyrazolo[3,4-b]pyridin-5-yl)phenyl)-N-(5-(1-(trifluoromethyl)cyclopropyl)isoxazol-3-yl)acetamide (2 mg, 13%) was obtained as a solid using a procedure analogous to that described in Step 3 of Example 40, substituting 2-(2-fluoro-4-(3-methoxy-1-(4-methoxybenzyl)-1H-pyrazolo[3,4-b]pyridin-5-yl)phenyl)-N-(5-(1-(trifluoromethyl)cyclopropyl)isoxazol-3-yl)acetamide for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. ¹H NMR (500 MHz, DMSO-d₆) δ 12.68 (br s, 1H), 11.42 (br s, 1H), 8.83 (d, J=2.0 Hz, 1H), 8.38 (d, J=2.0 Hz, 1H), 7.64 (m, 1H), 7.58 (m, 1H), 7.46 (m, 1H), 6.93 (s, 1H), 4.03 (s, 3H), 3.82 (s, 2H), 1.46-1.54 (m, 4H); LC-MS (ESI) m/z 476 (M+H)⁺.

Example 54

Preparation of N-(5-(tert-butyl)isoxazol-3-yl)-2-(4-(3-((methylamino)methyl)-1H-pyrrolo[2,3-b]pyridin-5-yl)phenyl)acetamide

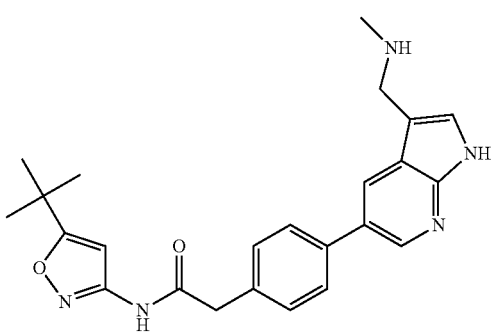 [SMILES: CNCc1c[nH]c2ncc(-c3ccc(CC(=O)Nc4cc(C(C)(C)C)on4)cc3)cc12]

Step 1: N-(5-(tert-Butyl)isoxazol-3-yl)-2-(4-(3-formyl-1H-pyrrolo[2,3-b]pyridin-5-yl)phenyl)acetamide (200 mg, 19%) was obtained as a yellow solid using a procedure analogous to that described in Step 4 of Example 35, substituting N-(5-(tert-butyl)isoxazol-3-yl)-2-(4-(4,4,5,5-tetramethyl-1,3,2-dioxaborolan-2-yl)phenyl)acetamide (Ref: S. Abraham et al, WO 2011022473 A1) for the 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide used in Example 35 and substituting the 5-bromo-1H-pyrrolo[2,3-b]pyridine-3-carbaldehyde for 5-bromo-3-methoxy-1-(4-methoxybenzyl)-1H-pyrazolo[3,4-b]pyridine used in Example 35. $^1$H NMR (500 MHz, DMSO-$d_6$) δ 12.79 (br s, 1H), 11.23 (br s, 1H), 9.96 (s, 1H), 8.66 (d, J=2.0 Hz, 1H), 8.58 (d, J=2.0 Hz, 1H), 8.51 (s, 1H), 7.69 (d, J=8.0 Hz, 2H), 7.45 (d, J=8.0 Hz, 2H), 6.58 (s, 1H), 3.73 (s, 2H), 1.27 (s, 9H); LC-MS (ESI) m/z 403 (M+H)$^+$.

Step 2: To a stirred mixture of N-(5-(tert-butyl)isoxazol-3-yl)-2-(4-(3-formyl-1H-pyrrolo[2,3-b]pyridin-5-yl)phenyl)acetamide (100 mg, 0.25 mmol) and 33% methylamine in EtOH (1 mL, 10.6 mmol) in MeOH (2 mL) at rt was added sodium cyanoborohydride (107 mg, 1.74 mmol) and the mixture was stirred at rt for 15 h. Sodium borohydride (100 mg, 2.63 mmol) was added and the mixture stirred at rt for an additional 30 min. The mixture was concentrated under reduced pressure and the residue was purified directly via reverse-phase preparative HPLC using a mixture of water (containing 5% CH$_3$CN and 0.05% HCOOH) and CH$_3$CN (containing 0.05% HCOOH) as the mobile phase and Varian Pursuit XRs diphenyl column as the stationary phase to afford N-(5-(tert-butyl)isoxazol-3-yl)-2-(4-(3-((methylamino)methyl)-1H-pyrrolo[2,3-b]pyridin-5-yl)phenyl)acetamide (17 mg, 16%) as a solid. $^1$H NMR (500 MHz, DMSO-$d_6$) δ 11.73 (br s, 1H), 11.23 (br s, 1H), 8.53 (d, J=2.0 Hz, 1H), 8.38-8.39 (m, 2H), 7.69 (d, J=8.0 Hz, 2H), 7.53 (s, 1H), 7.42 (d, J=8.0 Hz, 2H), 6.58 (s, 1H), 4.08 (s, 2H), 3.72 (s, 2H), 2.43 (s, 3H), 1.27 (s, 9H).

Example 55

Preparation of N-(5-(tert-butyl)isoxazol-3-yl)-2-(2-fluoro-4-(3-(hydroxymethyl)-1H-pyrazolo[3,4-b]pyridin-5-yl)phenyl)acetamide

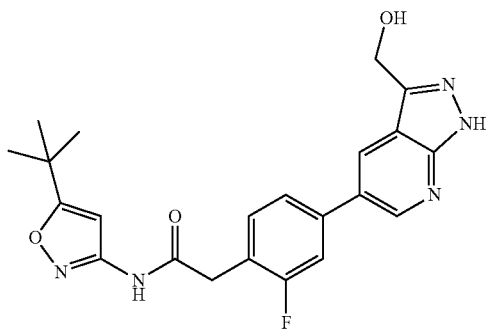 [SMILES: CC(C)(C)c1cc(NC(=O)Cc2ccc(-c3cnc4[nH]nc(CO)c4c3)cc2F)no1]

Step 1: N-(5-(tert-Butyl)isoxazol-3-yl)-2-(2-fluoro-4-(3-formyl-1-(tetrahydro-2H-pyran-2-yl)-1H-pyrazolo[3,4-b]pyridin-5-yl)phenyl)acetamide (430 mg, 73%) was obtained as a white solid using a procedure analogous to that described in Step 3 of Example 4, substituting 5-bromo-1-(tetrahydro-2H-pyran-2-yl)-1H-pyrazolo[3,4-b]pyridine-3-carbaldehyde (Ref: Hood, J. et al. WO2011/84486 A1, 2011) for the 2-chloro-6,7-dimethoxyquinoxaline used in Example 4 and substituting N-(5-(tert-butyl)isoxazol-3-yl)-2-(2-fluoro-4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. LC-MS (ESI) m/z 506 (M+H)$^+$.

Step 2: To a stirred solution of N-(5-(tert-butyl)isoxazol-3-yl)-2-(2-fluoro-4-(3-formyl-1-(tetrahydro-2H-pyran-2-yl)-1H-pyrazolo[3,4-b]pyridin-5-yl)phenyl)acetamide (60 mg, 0.12 mmol) in MeOH (3 mL) was added NaBH$_4$ (15 mg, 0.36 mmol) and the resulting mixture was stirred at rt overnight. LC-MS indicated that the reaction was mostly complete. 4N HCl in dioxane (3 mL) was then added and the mixture was stirred for 2 h. The crude mixture was purified directly via reverse-phase preparative HPLC using a mixture of water (containing 5% CH$_3$CN and 0.05% HCOOH), and CH$_3$CN (containing 0.05% HCOOH) as the mobile phase and a Varian Pursuit XRs diphenyl column as the stationary phase to afford N-(5-(tert-butyl)isoxazol-3-yl)-2-(2-fluoro-4-(3-(hydroxymethyl)-1H-pyrazolo[3,4-b]pyridin-5-yl)phenyl)acetamide as an off-white powder (10 mg, 20% yield over two steps). $^1$H NMR (500 MHz, DMSO-$d_6$) δ 13.47 (br s, 1H), 11.25 (s, 1H), 8.86 (d, J=2.2 Hz, 1H), 8.59 (d, J=2.2 Hz, 1H), 7.62 (d, J=11.5 Hz, 1H), 7.55-7.60 (m, 1H), 7.45-7.52 (m, 1H), 6.57 (s, 1H), 5.38 (br s, 1H), 4.82 (d, J=4.9 Hz, 2H), 3.82 (s, 2H), 1.28 (s, 9H). LC-MS (ESI) m/z 424 (M+H)$^+$.

Example 56

Preparation of 2-(2-fluoro-4-(1H-pyrazolo[3,4-b]pyridin-5-yl)phenyl)-N-(5-(1-(trifluoromethyl)cyclobutyl)isoxazol-3-yl)acetamide

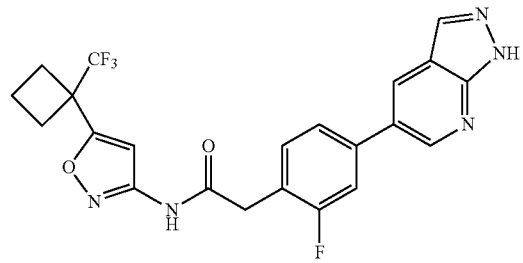 [SMILES: O=C(Cc1ccc(-c2cnc3[nH]ncc3c2)cc1F)Nc1cc(C2(C(F)(F)F)CCC2)on1]

Step 1: To a stirred suspension of 2-(4-bromo-2-fluorophenyl)acetic acid (1.0 g, 4.3 mmol) in DCM (15 mL) were added SOCl$_2$ (0.34 mL, 4.7 mmol) and DMF (2 drops), and the mixture was heated at reflux for 1 h. More SOCl$_2$ (0.34 mL, 4.7 mmol) was added and heating at reflux was continued for 1 h. After cooling to rt, the reaction mixture was concentrated under reduced pressure to give crude 2-(4-bromo-2-fluorophenyl)acetyl chloride as a brown oil.

Step 2: To a stirred solution of 5-(1-(trifluoromethyl)cyclobutyl)isoxazol-3-amine (Ref: Abraham, S. et al. WO2011/22473 A1, 2011) (170 mg, 0.83 mmol) in THF (3 mL) was added 2-(4-bromo-2-fluorophenyl)acetyl chloride (228 mg, 0.91 mmol) in THF (1 mL). After 30 min at rt, DMAP (101 mg, 0.83 mmol) was added, and resulting mixture was heated at 55° C. for 30 min. Pyridine (268 uL, 3.32 mmol) and additional 2-(4-bromo-2-fluorophenyl)acetyl chloride (228 mg, 0.91 mmol) were added, and heating at 55° C. was continued until most of the aminoisoxazole was consumed according to LC-MS analysis.

After cooling to rt, the reaction mixture was partitioned between EtOAc (50 mL) and 3N HCl (50 mL). The organic layer was washed with saturated aq NaHCO$_3$ and brine, dried over Na$_2$SO$_4$, filtered, and concentrated under reduced pressure. The residue was purified by silica gel column chromatography eluting with 0-25% EtOAc in hexanes to give 2-(4-bromo-2-fluorophenyl)-N-(5-(1-(trifluoromethyl)cyclobutyl)isoxazol-3-yl)acetamide (330 mg, 95%) as a light brown oil. LC-MS (ESI) m/z 421, 423 (M+H)$^+$.

Step 3: 1-(4-Methoxybenzyl)-5-(4,4,5,5-tetramethyl-1,3,2-dioxaborolan-2-yl)-1H-pyrazolo[3,4-b]pyridine (300 mg, 52%) was obtained as a tan solid using a procedure analogous to that described in Step 1 of Example 4, substituting 5-bromo-1-(4-methoxybenzyl)-1H-pyrazolo[3,4-b]pyridine (Ref: WO2009/16460 A2, 2009) for the 2-(4-bromo-2-fluorophenyl)acetic acid used in Example 4. LC-MS (ESI) m/z 366 (M+H)$^1$.

Step 4: 2-(2-Fluoro-4-(1H-pyrazolo[3,4-b]pyridin-5-yl)phenyl)-N-(5-(1-(trifluoromethyl)cyclobutyl)isoxazol-3-yl)acetamide (22 mg, 13%) was obtained as a tan powder using a procedure analogous to that described in Steps 2-3 of Example 40, substituting 2-(4-bromo-2-fluorophenyl)-N-(5-(1-(trifluoromethyl)cyclobutyl)isoxazol-3-yl)acetamide from Step 2 of this example for the 5-bromo-1-(4-methoxybenzyl)-3-methyl-1H-pyrazolo[3,4-b]pyridine used in Example 40 and substituting 1-(4-methoxybenzyl)-5-(4,4,5,5-tetramethyl-1,3,2-dioxaborolan-2-yl)-1H-pyrazolo[3,4-b]pyridine for the N-(5-(tert-butyl)isoxazol-3-yl)-2-(4-(4,4,5,5-tetramethyl-1,3,2-dioxaborolan-2-yl)phenyl)acetamide used in Example 40. $^1$H NMR (500 MHz, DMSO-d$_6$) δ 13.75 (br s, 1H), 12.13 (s, 1H), 8.87 (d, J=1.6 Hz, 1H), 8.53 (d, J=2.2 Hz, 1H), 8.21 (s, 1H), 7.64 (d, J=11.5 Hz, 1H), 7.59 (dd, J=1.4, 8.0 Hz, 1H), 7.46-7.54 (m, 1H), 6.24 (s, 1H), 3.88 (s, 2H), 2.53-2.64 (m, 4H), 1.94-2.07 (m, 2H). LC-MS (ESI) m/z 460 (M+H)$^1$.

Example 57

Preparation of N-(5-(tert-butyl)isoxazol-3-yl)-2-(2-fluoro-4-(3-((methylamino)methyl)-1H-pyrazolo[3,4-b]pyridin-5-yl)phenyl)acetamide

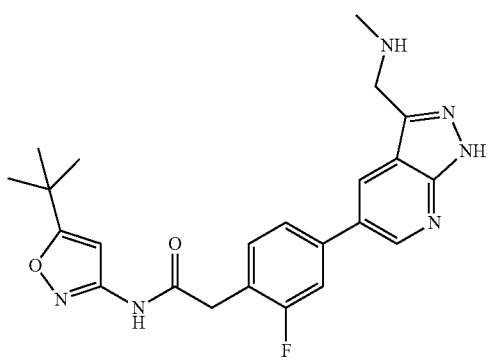 [SMILES: CNCc1n[nH]c2ncc(-c3ccc(CC(=O)Nc4cc(C(C)(C)C)on4)c(F)c3)cc12]

Step 1: Crude N-(5-(tert-butyl)isoxazol-3-yl)-2-(2-fluoro-4-(3-((methylamino)methyl)-1-(tetrahydro-2H-pyran-2-yl)-1H-pyrazolo[3,4-b]pyridin-5-yl)phenyl)acetamide was obtained using a procedure analogous to that described in Step 2 of Example 52, substituting N-(5-(tert-butyl)isoxazol-3-yl)-2-(2-fluoro-4-(3-formyl-1-(tetrahydro-2H-pyran-2-yl)-1H-pyrazolo[3,4-b]pyridin-5-yl)phenyl)acetamide from Step 1 of Example 55 for the N-(5-(tert-butyl)isoxazol-3-yl)-2-(4-(2-formyl-1H-pyrrolo[2,3-b]pyridin-5-yl)phenyl)acetamide used in Example 52 and substituting methylamine in THF for the N,N-dimethylamine hydrochloride used in Example 52. LC-MS (ESI) m/z 521 (M+H)$^+$.

Step 2: A mixture of crude N-(5-(tert-butyl)isoxazol-3-yl)-2-(2-fluoro-4-(3-((methylamino)methyl)-1-(tetrahydro-2H-pyran-2-yl)-1H-pyrazolo[3,4-b]pyridin-5-yl)phenyl)acetamide and 4N HCl in dioxane (3 mL) was stirred at rt overnight. The crude mixture was purified directly via reverse-phase preparative HPLC using a mixture of water (containing 5% CH$_3$CN and 0.05% HCOOH), and CH$_3$CN (containing 0.05% HCOOH) as the mobile phase and a Varian Pursuit XRs diphenyl column as the stationary phase to afford N-(5-(tert-butyl)isoxazol-3-yl)-2-(2-fluoro-4-(3-((methylamino)methyl)-1H-pyrazolo[3,4-b]pyridin-5-yl)phenyl)acetamide (10 mg, 9.6%) as a white powder. $^1$HNMR (500 MHz, DMSO-d$_6$) δ 11.26 (br s, 1H), 8.86 (d, J=1.6 Hz, 1H), 8.65 (d, J=2.2 Hz, 1H), 8.27 (s, 1H), 7.64 (d, J=11.0 Hz, 1H), 7.57-7.62 (m, 1H), 7.45-7.53 (m, 1H), 6.57 (s, 1H), 4.09 (s, 2H), 2.35 (s, 3H), 1.28 (s, 9H).

Example 58

Preparation of N-(5-(tert-butyl)isoxazol-3-yl)-2-(4-(3-((dimethylamino)methyl)-1H-pyrazolo[3,4-b]pyridin-5-yl)-2-fluorophenyl)acetamide

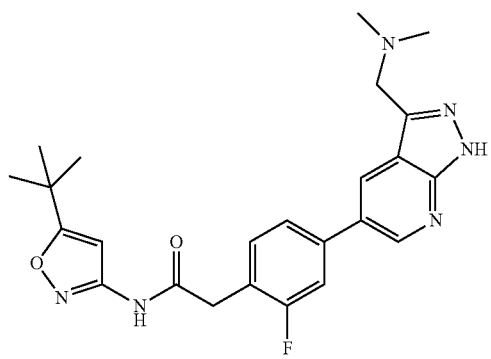 [SMILES: CN(C)Cc1n[nH]c2ncc(-c3ccc(CC(=O)Nc4cc(C(C)(C)C)on4)c(F)c3)cc12]

N-(5-(tert-Butyl)isoxazol-3-yl)-2-(4-(3-((dimethylamino)methyl)-1H-pyrazolo[3,4-b]pyridin-5-yl)-2-fluorophenyl)acetamide (18 mg, 17%) was obtained as a white powder using a procedure analogous to that described in Steps 1-2 of Example 57, substituting N,N-dimethylamine hydrochloride for the methylamine in THF used in Example 57. $^1$H NMR (500 MHz, DMSO-d$_6$) δ 13.52 (br s, 1H), 11.25 (s, 1H), 8.85 (d, J=2.2 Hz, 1H), 8.53 (d, J=2.2 Hz, 1H), 7.60-7.65 (m, 1H), 7.54-7.60 (m, 1H), 7.45-7.52 (m, 1H), 6.57 (s, 1H), 3.78-3.81 (m, 2H), 3.28-3.31 (m, 2H), 2.23 (s, 6H), 1.28 (s, 9H).

Example 59

Preparation of N-(5-(tert-butyl)isoxazol-3-yl)-2-(4-(3-((dimethylamino)methyl)-1H-pyrrolo[2,3-b]pyridin-5-yl)phenyl)acetamide formate salt

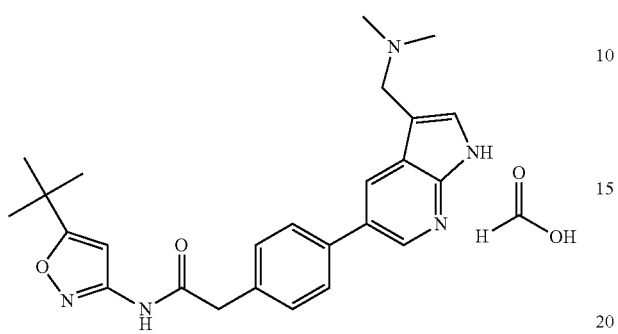

N-(5-(tert-Butyl)isoxazol-3-yl)-2-(4-(3-((dimethylamino)methyl)-1H-pyrrolo[2,3-b]pyridin-5-yl)phenyl)acetamide formate salt (9 mg, 8%) was obtained as a solid using a procedure analogous to that described in Step 2 of Example 54, substituting 40% dimethylamine in H$_2$O for the 33% methylamine in EtOH used in Example 54. $^1$H NMR (500 MHz, DMSO-d$_6$) δ 11.56 (br s, 1H), 11.22 (br s, 1H), 8.48 (d, J=2.0 Hz, 1H), 8.31 (br s, 2H), 8.20 (d, J=2.0 Hz, 1H), 7.65 (d, J=8.0 Hz, 2H), 7.39-7.45 (m, 3H), 6.58 (s, 1H), 3.71 (s, 2H), 3.62 (s, 2H), 2.19 (s, 6H), 1.27 (s, 9H).

Example 60

Preparation of N-(5-(tert-butyl)isoxazol-3-yl)-2-(4-(3-(hydroxymethyl)-1H-pyrrolo[2,3-b]pyridin-5-yl)phenyl)acetamide

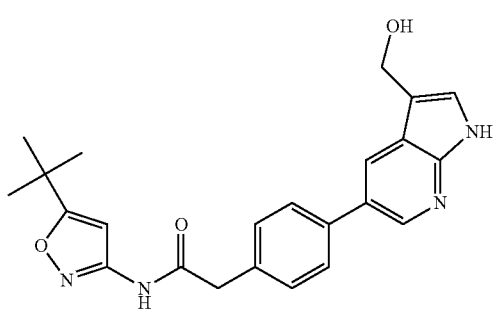 [SMILES: CC(C)(C)c1cc(NC(=O)Cc2ccc(-c3cnc4[nH]cc(CO)c4c3)cc2)no1]

To a stirred mixture of N-(5-(tert-butyl)isoxazol-3-yl)-2-(4-(3-formyl-1H-pyrrolo[2,3-b]pyridin-5-yl)phenyl)acetamide from Step 1 of Example 54 (100 mg, 0.248 mmol) and methanol (2 mL) at rt was added sodium borohydride (47 mg, 1.24 mmol) and the mixture was stirred at rt for 1 h. The mixture was diluted with 1:1 MeOH:DMSO and purified directly by reverse-phase preparative HPLC using a mixture of water (containing 5% CH$_3$CN and 0.05% HCOOH) and CH$_3$CN (containing 0.05% HCOOH) as the mobile phase and Varian Pursuit XRs diphenyl column as the stationary phase to afford N-(5-(tert-butyl)isoxazol-3-yl)-2-(4-(3-(hydroxymethyl)-1H-pyrrolo[2,3-b]pyridin-5-yl)phenyl)acetamide (7 mg, 7%) as a solid. $^1$H NMR (500 MHz, DMSO-d$_6$) δ 11.48 (br s, 1H), 11.21 (br s, 1H), 8.49 (d, J=2.0 Hz, 1H), 8.24 (d, J=2.0 Hz, 1H), 7.67 (d, J=8.0 Hz, 2H), 7.42 (d, J=8.0 Hz, 2H), 7.39 (d, J=2.0 Hz, 1H), 6.57 (s, 1H), 4.67 (s, 2H), 3.71 (s, 2H), 1.27 (s, 9H).

Example 61

Preparation of 2-(4-(3-(dimethylamino)-1H-pyrazolo[3,4-b]pyridin-5-yl)-2-fluorophenyl)-N-(5-(1-(trifluoromethyl)cyclopropyl)isoxazol-3-yl)acetamide

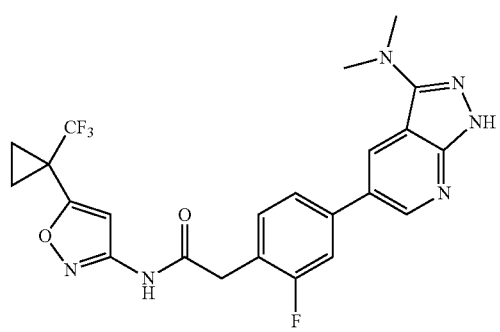 [SMILES: CN(C)c1n[nH]c2ncc(-c3ccc(CC(=O)Nc4cc(C5(C(F)(F)F)CC5)on4)c(F)c3)cc12]

Step 1: To a stirred solution of 5-bromo-1H-pyrazolo[3,4-b]pyridin-3-amine (700 mg, 3.29 mmol) in DMF (7 mL) at 0° C. was added 60% sodium hydride in mineral oil (154 mg, 3.85 mmol) and the mixture was stirred at 0° C. for 10 min. 4-(Methoxy)benzyl chloride (511 μL, 3.78 mmol) was added and the mixture was allowed to warm to rt and stir for an additional 1 h. To the reaction mixture was added water and the precipitate was collected via filtration. The solid was added to diethyl ether and the resulting mixture was filtered. The filtrate was concentrated under reduced pressure to afford 5-bromo-1-(4-methoxybenzyl)-1H-pyrazolo[3,4-b]pyridin-3-amine (840 mg) as a yellow solid which was not purified further. LC-MS (ESI) m/z 333 and 335 (M+H)$^+$.

Step 2: To a stirred solution of 5-bromo-1-(4-methoxybenzyl)-1H-pyrazolo[3,4-b]pyridin-3-amine (400 mg, 1.2 mmol) in a mixture of MeOH (4 mL) and THF (4 mL) at rt was added sodium cyanoborohydride (302 mg, 4.8 mmol). The pH of the mixture was adjusted to ~5 by addition of acetic acid, and the mixture was stirred at rt for 15 min. The pH of the reaction mixture was adjusted to ~10 by addition of 2M aq Na$_2$C$_3$, and the resulting mixture was extracted three times with dichloromethane. The combined organic layers were dried over MgSO$_4$, filtered, and concentrated under reduced pressure. The residue was purified by silica gel flash chromatography eluting with 0-70% EtOAc in hexanes to afford 5-bromo-1-(4-methoxybenzyl)-N,N-dimethyl-1H-pyrazolo[3,4-b]pyridin-3-amine (200 mg, 46%) as a yellow solid. $^1$H NMR (500 MHz, DMSO-d$_6$) δ 8.53 (d, J=2.0 Hz, 1H), 8.50 (d, J=2.0 Hz, 1H), 7.14-7.16 (m, 2H), 6.83-6.85 (m, 2H), 5.36 (s, 2H), 3.69 (s, 3H), 3.02 (3, 6H); LC-MS (ESI) m/z 361 and 363 (M+H)$^+$.

Step 3: 2-(4-(3-(Dimethylamino)-1-(4-methoxybenzyl)-1H-pyrazolo[3,4-b]pyridin-5-O-2-fluorophenyl)-N-(5-(1-(trifluoromethyl)cyclopropyl)isoxazol-3-yl)acetamide (200 mg, 45%) was obtained as a solid using a procedure analogous to that described in Step 3 of Example 4, substituting 5-bromo-1-(4-methoxybenzyl)-N,N-dimethyl-1H-pyrazolo[3,4-b]pyridin-3-amine for the 2-chloro-6,7-dimethoxyquinoxaline used in Example 4. $^1$H NMR (500 MHz, DMSO-d$_6$) δ 11.41 (br s, 1H), 8.78 (d, J=2.0 Hz, 1H), 8.50 (d, J=2.0

Hz, 1H), 7.65 (dd, J=11.5, 1.5 Hz, 1H), 7.58 (dd, J=8.0, 1.5 Hz, 1H), 7.45-7.48 (m, 1H), 7.19 (d, J=9.0 Hz, 2H), 6.92 (s, 1H), 6.83-6.86 (m, 2H), 5.41 (s, 2H), 3.82 (s, 2H), 3.70 (s, 3H), 3.08 (s, 6H), 1.47-1.52 (m, 4H); LC-MS (ESI) m/z 609 (M+H)$^+$.

Step 4: 2-(4-(3-(Dimethylamino)-1H-pyrazolo[3,4-b]pyridin-5-yl)-2-fluorophenyl)-N-(5-(1-(trifluoromethyl)cyclopropyl)isoxazol-3-yl)acetamide (17 mg, 11%) was obtained as a solid using a procedure analogous to that described in Step 3 of Example 40, substituting 2-(4-(3-(dimethylamino)-1-(4-methoxybenzyl)-1H-pyrazolo[3,4-b]pyridin-5-yl)-2-fluorophenyl)-N-(5-(1-(trifluoromethyl)cyclopropyl)isoxazol-3-yl)acetamide for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. $^1$H NMR (500 MHz, DMSO-d$_6$) δ 12.49 (br s, 1H), 11.41 (br s, 1H), 8.73 (d, J=2.0 Hz, 1H), 8.48 (d, J=2.0 Hz, 1H), 7.65 (dd, J=11.5, 1.5 Hz, 1H), 7.58 (dd, J=8.0, 1.5 Hz, 1H), 7.44-7.47 (m, 1H), 6.92 (s, 1H), 3.82 (s, 2H), 3.07 (s, 6H), 1.48-1.54 (m, 4H); LC-MS (ESI) m/z 489 (M+H)$^+$.

Example 62

Preparation of N-(5-(tert-butyl)isoxazol-3-yl)-2-(2-fluoro-4-(3-(1-hydroxyethyl)-1H-pyrazolo[3,4-b]pyridin-5-yl)phenyl)acetamide

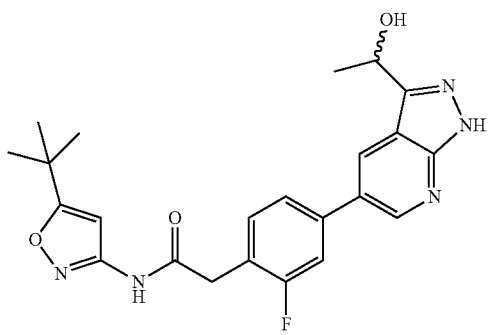 [SMILES: CC(O)c1n[nH]c2ncc(-c3ccc(CC(=O)Nc4cc(C(C)(C)C)on4)c(F)c3)cc12]

Step 1: To a stirred solution of crude N-(5-(tert-butyl)isoxazol-3-yl)-2-(2-fluoro-4-(3-formyl-1-(tetrahydro-2H-pyran-2-yl)-1H-pyrazolo[3,4-b]pyridin-5-yl)phenyl)acetamide from Step 1 of Example 55 (160 mg, 0.32 mmol) in THF at −78° C. under argon was added dropwise 3M MeMgCl in ether (210 µL, 0.64 mmol). The resulting mixture was stirred at −78° C. for 1 h while another one equivalent of MeMgCl/ether solution (105 µL, 0.32 mmol) was added in the process. The reaction mixture was quenched with saturated aq NH$_4$Cl at −78° C. After warming to rt, the mixture was partitioned between EtOAc (50 mL) and water (35 mL). The organic layer was washed with brine, dried over Na$_2$SO$_4$, filtered, and concentrated under reduced pressure. The residue containing N-(5-(tert-butyl)isoxazol-3-yl)-2-(2-fluoro-4-(3-(1-hydroxyethyl)-1-(tetrahydro-2H-pyran-2-yl)-1H-pyrazolo[3,4-b]pyridin-5-yl)phenyl)acetamide was used directly for the next step. LC-MS (ESI) m/z 522 (M+H)$^+$.

Step 2: N-(5-(tert-Butyl)isoxazol-3-yl)-2-(2-fluoro-4-(3-(1-hydroxyethyl)-1H-pyrazolo[3,4-b]pyridin-5-yl)phenyl)acetamide (20 mg, 14% over two steps) was obtained as a white powder using a procedure analogous to that described in Step 2 of Example 57, substituting N-(5-(tert-butyl)isoxazol-3-yl)-2-(2-fluoro-4-(3-(1-hydroxyethyl)-1-(tetrahydro-2H-pyran-2-yl)-1H-pyrazolo[3,4-b]pyridin-5-yl)phenyl)acetamide for the N-(5-(tert-butyl)isoxazol-3-yl)-2-(2-fluoro-4-(3-((methylamino)methyl)-1-(tetrahydro-2H-pyran-2-yl)-1H-pyrazolo[3,4-b]pyridin-5-yl)phenyl) acetamide used in Example 57. $^1$H NMR (500 MHz, DMSO-d$_6$) δ 13.39 (br s, 1H), 11.25 (s, 1H), 8.84 (d, J=2.2 Hz, 1H), 8.59 (d, J=1.6 Hz, 1H), 7.61 (d, J=11.5 Hz, 1H), 7.57 (dd, J=1.4, 8.0 Hz, 1H), 7.44-7.52 (m, 1H), 6.57 (s, 1H), 5.46 (d, J=4.4 Hz, 1H), 5.05-5.18 (m, 1H), 3.82 (s, 2H), 3.38 (br s, 1H), 1.58 (d, J=6.6 Hz, 3H), 1.28 (s, 9H). LC-MS (ESI) m/z 438 (M+H)$^+$.

Example 63

Preparation of 2-(2-fluoro-4-(3-methoxy-1H-pyrazolo[3,4-b]pyridin-5-yl)phenyl)-N-(5-(1,1,1-trifluoro-2-methylpropan-2-yl)isoxazol-3-yl)acetamide

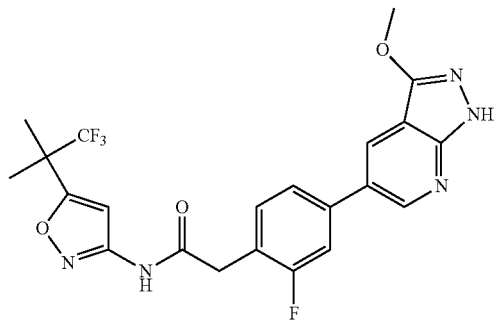 [SMILES: COc1n[nH]c2ncc(-c3ccc(CC(=O)Nc4cc(C(C)(C)C(F)(F)F)on4)c(F)c3)cc12]

Step 1: 2-(2-Fluoro-4-(3-methoxy-1-(4-methoxybenzyl)-1H-pyrazolo[3,4-b]pyridin-5-yl)phenyl)-N-(5-(1,1,1-trifluoro-2-methylpropan-2-yl)isoxazol-3-yl)acetamide (140 mg, 45%) was obtained as a solid using a procedure analogous to that described in Step 4 of Example 35, substituting 2-(2-fluoro-4-(4,4,5,5-tetramethyl-1,3,2-dioxaborolan-2-yl)phenyl)-N-(5-(1,1,1-trifluoro-2-methylpropan-2-yl)isoxazol-3-yl)acetamide (Ref: S. Abraham et al, WO 2011022473 A1) for the 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide used in Example 35. $^1$H NMR (500 MHz, DMSO-d$_6$) δ 11.42 (br s, 1H), 8.89 (d, J=2.0 Hz, 1H), 8.41 (d, J=2.0 Hz, 1H), 7.65 (dd, J=11.0, 1.5 Hz, 1H), 7.59 (dd, J=7.5, 1.5 Hz, 1H), 7.47 (m, 1H), 7.20-7.22 (m, 2H), 6.95 (s, 1H), 6.85-6.88 (m, 2H), 5.46 (s, 2H), 4.03 (s, 3H), 3.83 (br s, 2H), 3.70 (s, 3H), 1.54 (s, 6H); LC-MS (ESI) m/z 598 (M+H)$^+$.

Step 2: 2-(2-Fluoro-4-(3-methoxy-1H-pyrazolo[3,4-b]pyridin-5-yl)phenyl)-N-(5-(1,1,1-trifluoro-2-methylpropan-2-yl)isoxazol-3-yl)acetamide (28 mg, 24%) was obtained as a solid using a procedure analogous to that described in Step 3 of Example 40, substituting 2-(2-fluoro-4-(3-methoxy-1-(4-methoxybenzyl)-1H-pyrazolo[3,4-b]pyridin-5-yl)phenyl)-N-(5-(1,1,1-trifluoro-2-methylpropan-2-yl)isoxazol-3-yl)acetamide for the N-(5-(tert-butyl)isoxazol-3-yl)-2-(4-(1-(4-methoxybenzyl)-3-methyl-1H-pyrazolo[3,4-b]pyridin-5-yl)phenyl)acetamide used in Example 40. $^1$H NMR (500 MHz, DMSO-d$_6$) δ 12.67 (br s, 1H), 11.42 (br s, 1H), 8.83 (d, J=2.0 Hz, 1H), 8.38 (d, J=2.0 Hz, 1H), 7.64 (dd, J=11.5, 1.5 Hz, 1H), 7.58 (dd, J=8.0, 1.5 Hz, 1H), 7.47 (m, 1H), 6.95 (s, 1H), 4.04 (s, 3H), 3.83 (s, 2H), 1.54 (s, 6H); LC-MS (ESI) m/z 478 (M+H)$^+$.

Example 64

Preparation of 5-(4-(2-((5-(tert-butyl)isoxazol-3-yl)amino)-2-oxoethyl)phenyl)-N-(2-hydroxyethyl)-1H-pyrrolo[2,3-b]pyridine-2-carboxamide

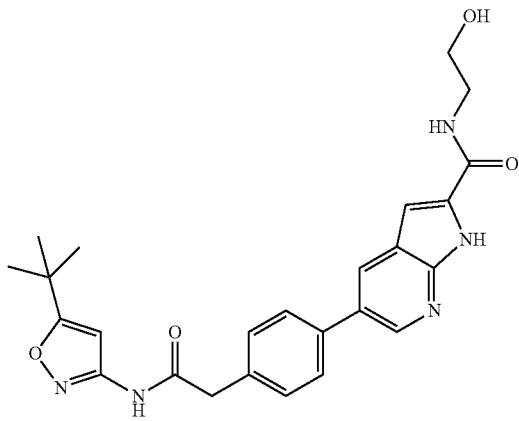 [SMILES: CC(C)(C)c1cc(NC(=O)Cc2ccc(-c3cnc4[nH]c(C(=O)NCCO)cc4c3)cc2)no1]

Step 1: Crude 5-(4-(2-((5-(tert-butyl)isoxazol-3-yl)amino)-2-oxoethyl)phenyl)-1H-pyrrolo[2,3-b]pyridine-2-carboxylic acid (580 mg) was obtained as a tan solid using a procedure analogous to that Step 1 of Example 8, substituting 5-bromo-1H-pyrrolo[2,3-b]pyridine-2-carboxylic acid for the 2-chloro-6,7-dimethoxyquinoxaline used in Example 8 and substituting N-(5-(tert-butyl)isoxazol-3-yl)-2-(4-(4,4,5,5-tetramethyl-1,3,2-dioxaborolan-2-yl)phenyl)acetamide for the 2-(4-(4,4,5,5-tetramethyl-1,3,2-dioxaborolan-2-yl)phenyl)acetic acid used in Example 8. LC-MS (ESI) m/z 419 (M+H)$^+$.

Step 2: 5-(4-(2-((5-(tert-Butyl)isoxazol-3-yl)amino)-2-oxoethyl)phenyl)-N-(2-hydroxyethyl)-1H-pyrrolo[2,3-b]pyridine-2-carboxamide (26 mg, 24% over two steps) was obtained as a tan solid using a procedure analogous to that described in Step 2 of Example 4, substituting 5-(4-(2-((5-(tert-butyl)isoxazol-3-yl)amino)-2-oxoethyl)phenyl)-1H-pyrrolo[2,3-b]pyridine-2-carboxylic acid for the 2-(2-fluoro-4-(4,4,5,5-tetramethyl-1,3,2-dioxaborolan-2-yl)phenyl)acetic acid used in Example 4 and substituting 2-aminoethanol for the 5-(1-(trifluoromethyl)cyclopropyl)isoxazol-3-amine used in Example 4. $^1$H NMR (500 MHz, DMSO-d$_6$) δ 12.17 (br s, 1H), 11.21 (s, 1H), 8.62 (s, 1H), 8.55 (t, J=5.2 Hz, 1H), 8.33 (s, 1H), 7.72 (d, J=7.7 Hz, 1H), 7.69 (d, J=8.2 Hz, 2H), 7.43 (d, J=7.7 Hz, 2H), 7.26 (d, J=7.7 Hz, 1H), 7.18 (s, 1H), 6.58 (s, 1H), 3.66 (br s, 2H), 3.54 (d, J=5.5 Hz, 2H), 3.35-3.40 (m, 2H), 1.27 (s, 9H). LC-MS (ESI) m/z 462 (M+H)$^+$.

Example 65

Preparation of 5-(4-(2-((5-(tert-butyl)isoxazol-3-yl)amino)-2-oxoethyl)phenyl)-N-methyl-1H-pyrrolo[2,3-b]pyridine-2-carboxamide

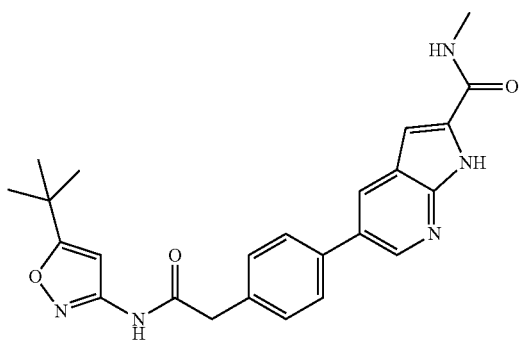 [SMILES: CNC(=O)c1cc2cc(-c3ccc(CC(=O)Nc4cc(C(C)(C)C)on4)cc3)cnc2[nH]1]

Step 1: 5-Bromo-N-methyl-1H-pyrrolo[2,3-b]pyridine-2-carboxamide (200 mg) was obtained as a tan solid using a procedure analogous to that described in Step 2 of Example 4, substituting 5-bromo-1H-pyrrolo[2,3-b]pyridine-2-carboxylic acid for the 2-(2-fluoro-4-(4,4,5,5-tetramethyl-1,3,2-dioxaborolan-2-yl)phenyl)acetic acid used in Example 4 and substituting methylamine in THF for the 5-(1-(trifluoromethyl)cyclopropyl)isoxazol-3-amine used in Example 4. LC-MS (ESI) m/z 254, 256 (M+H)$^+$.

Step 2: 5-(4-(2-((5-(tert-Butyl)isoxazol-3-yl)amino)-2-oxoethyl)phenyl)-N-methyl-1H-pyrrolo[2,3-b]pyridine-2-carboxamide (35 mg) was obtained as a tan solid using a procedure analogous to that described in Step 3 of Example 4, substituting N-(5-(tert-butyl)isoxazol-3-yl)-2-(4-(4,4,5,5-tetramethyl-1,3,2-dioxaborolan-2-yl)phenyl)acetamide for the 2-(2-fluoro-4-(4,4,5,5-tetramethyl-1,3,2-dioxaborolan-2-yl)phenyl)acetic acid used in Example 4 and substituting 5-bromo-N-methyl-1H-pyrrolo[2,3-b]pyridine-2-carboxamide for the 2-chloro-6,7-dimethoxyquinoxaline used in Example 4. $^1$H NMR (500 MHz, DMSO-d$_6$) δ 12.14 (br s, 1H), 11.22 (br s, 1H), 8.61 (br s, 1H), 8.53 (br s, 1H), 8.30 (br s, 1H), 7.68 (d, J=7.1 Hz, 2H), 7.42 (d, J=7.1 Hz, 2H), 7.11 (br s, 1H), 6.58 (br s, 1H), 3.72 (br s, 2H), 2.83 (d, J=3.8 Hz, 3H), 1.27 (s, 9H). LC-MS (ESI) m/z 432 (M+H)$^+$.

Example 66

Preparation of 5-(4-(2-((5-(tert-butyl)isoxazol-3-yl)amino)-2-oxoethyl)phenyl)-N-(2-(dimethylamino)ethyl)-1H-pyrrolo[2,3-b]pyridine-2-carboxamide

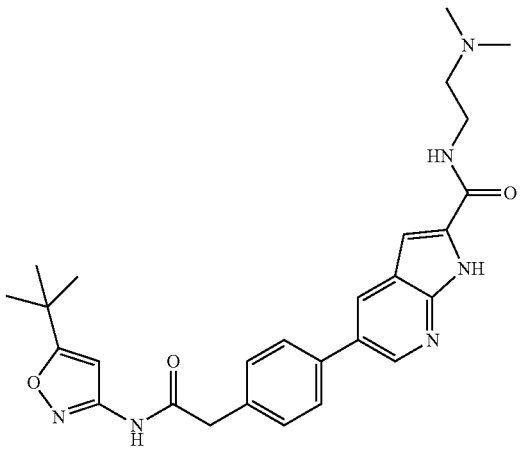 [SMILES: CN(C)CCNC(=O)c1cc2cc(-c3ccc(CC(=O)Nc4cc(C(C)(C)C)on4)cc3)cnc2[nH]1]

5-(4-(2-((5-(tert-Butyl)isoxazol-3-yl)amino)-2-oxo ethyl)phenyl)-N-(2-(dimethylamino)ethyl)-1H-pyrrolo[2,3-b]pyridine-2-carboxamide (35 mg) was obtained as a tan solid using a procedure analogous to that described in Step 2 of Example 4, substituting 5-(4-(2-((5-(tert-butyl)isoxazol-3-yl)amino)-2-oxo ethyl)phenyl)-1H-pyrrolo[2,3-b]pyridine-2-carboxylic acid from Step 1 of Example 64 for the 2-(2-fluoro-4-(4,4,5,5-tetramethyl-1,3,2-dioxaborolan-2-yl)phenyl)acetic acid used in Example 4, and substituting N$^1$,N$^1$-dimethylethane-1,2-diamine for the 5-(1-(trifluoromethyl)cyclopropyl)isoxazol-3-amine used in Example 4. $^1$H NMR (500 MHz, DMSO-d$_6$) δ 12.21 (br s, 1H), 11.22 (s, 1H), 8.68 (br s, 1H), 8.64 (d, J=2.2 Hz, 1H), 8.34 (d, J=1.6 Hz, 1H), 7.69 (d, J=7.7 Hz, 2H), 7.43 (d, J=7.7 Hz, 2H), 7.16 (s, 1H), 6.57 (s, 1H), 3.72 (s, 2H), 3.58 (d, J=4.4 Hz, 2H), 2.70 (br s, 6H), 1.28 (s, 9H). LC-MS (ESI) m/z 489 (M+H)$^+$.

Example 67

Preparation of 5-(4-(2-((5-(tert-butyl)isoxazol-3-yl)amino)-2-oxoethyl)phenyl)-N-(3-(dimethylamino)propyl)-N-methyl-1H-pyrrolo[2,3-b]pyridine-2-carboxamide

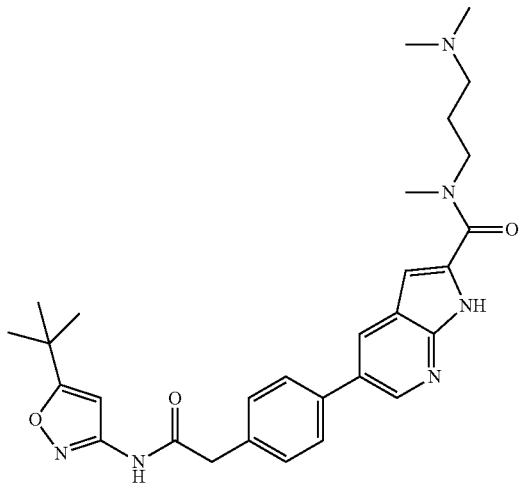 [SMILES: CN(C)CCCN(C)C(=O)c1cc2cc(-c3ccc(CC(=O)Nc4cc(C(C)(C)C)on4)cc3)cnc2[nH]1]

5-(4-(2-((5-(tert-Butyl)isoxazol-3-yl)amino)-2-oxoethyl)phenyl)-N-(3-(dimethylamino)propyl)-N-methyl-1H-pyrrolo[2,3-b]pyridine-2-carboxamide (45 mg) was obtained as a tan solid using a procedure analogous to that described in Step 2 of Example 4, substituting 5-(4-(2-((5-(tert-butyl)isoxazol-3-yl)amino)-2-oxoethyl)phenyl)-1H-pyrrolo[2,3-b]pyridine-2-carboxylic acid from Step 1 of Example 64 for the 2-(2-fluoro-4-(4,4,5,5-tetramethyl-1,3,2-dioxaborolan-2-yl)phenyl)acetic acid used in Example 4, and substituting $N^1,N^1,N^3$-trimethylpropane-1,3-diamine for the 5-(1-(trifluoromethyl)cyclopropyl)isoxazol-3-amine used in Example 4. $^1$H NMR (500 MHz, DMSO-$d_6$) δ 11.22 (s, 1H), 8.62 (d, J=1.6 Hz, 1H), 8.26 (s, 1H), 7.68 (d, J=8.2 Hz, 2H), 7.43 (d, J=8.2 Hz, 2H), 6.88 (br s, 1H), 6.58 (s, 1H), 3.56 (br s, 2H), 3.31 (br s, 8H), 3.03 (br s, 1H), 2.73 (br s, 1H), 2.28-2.45 (m, 2H), 1.81-1.94 (m, 2H), 1.27 (s, 9H). LC-MS (ESI) m/z 517 (M+H)$^+$.

Example 68

Preparation of 5-(4-(2-((5-(tert-butyl)isoxazol-3-yl)amino)-2-oxoethyl)phenyl)-N-(2-(methylsulfonyl)ethyl)-1H-pyrrolo[2,3-b]pyridine-2-carboxamide

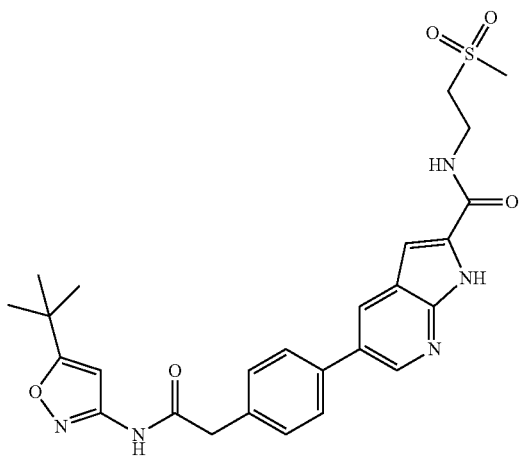 [SMILES: CC(C)(C)c1cc(NC(=O)Cc2ccc(-c3cnc4[nH]c(C(=O)NCCS(C)(=O)=O)cc4c3)cc2)no1]

5-(4-(2-((5-(tert-Butyl)isoxazol-3-yl)amino)-2-oxoethyl)phenyl)-N-(2-(methylsulfonyl)ethyl)-1H-pyrrolo[2,3-b]pyridine-2-carboxamide (46 mg) was obtained as a tan solid using a procedure analogous to that described in Step 2 of Example 4, substituting 5-(4-(2-((5-(tert-butyl)isoxazol-3-yl)amino)-2-oxoethyl)phenyl)-1H-pyrrolo[2,3-b]pyridine-2-carboxylic acid from Step 1 of Example 64 for the 2-(2-fluoro-4-(4,4,5,5-tetramethyl-1,3,2-dioxaborolan-2-yl)phenyl)acetic acid used in Example 4, and substituting 2-(methylsulfonyl)ethanamine hydrochloride for the 5-(1-(trifluoromethyl)cyclopropyl)isoxazol-3-amine used in Example 4. $^1$H NMR (500 MHz, DMSO-$d_6$) δ 12.22 (br s, 1H), 11.21 (s, 1H), 8.82 (t, J=5.2 Hz, 1H), 8.63 (d, J=1.6 Hz, 1H), 8.33 (d, J=1.6 Hz, 1H), 7.69 (d, J=7.7 Hz, 2H), 7.43 (d, J=8.2 Hz, 2H), 7.16 (d, J=1.6 Hz, 1H), 6.58 (s, 1H), 3.67-3.75 (m, 4H), 3.42 (t, J=6.9 Hz, 3H), 3.06 (s, 3H), 1.28 (s, 9H).

Example 69

Preparation of 5-(4-(2-((5-(tert-butyl)isoxazol-3-yl)amino)-2-oxoethyl)phenyl)-N-(1-methylpiperidin-4-yl)-1H-pyrrolo[2,3-b]pyridine-2-carboxamide

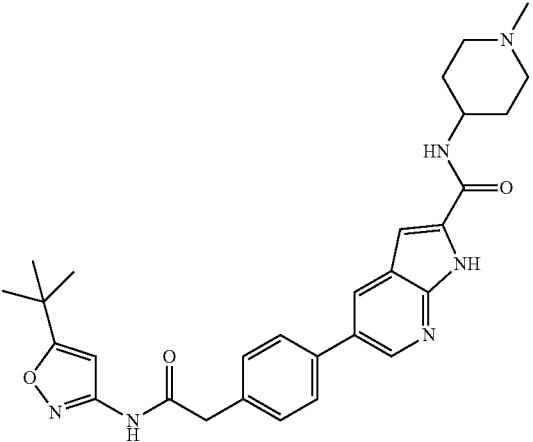 [SMILES: CN1CCC(NC(=O)c2cc3cc(-c4ccc(CC(=O)Nc5cc(C(C)(C)C)on5)cc4)cnc3[nH]2)CC1]

5-(4-(2-((5-(tert-Butyl)isoxazol-3-yl)amino)-2-oxoethyl)phenyl)-N-(1-methylpiperidin-4-yl)-1H-pyrrolo[2,3-b]pyridine-2-carboxamide (31 mg) was obtained as a white powder using a procedure analogous to that described in Step 2 of Example 4, substituting 5-(4-(2-((5-(tert-butyl)isoxazol-3-yl)amino)-2-oxoethyl)phenyl)-1H-pyrrolo[2,3-b]pyridine-2-carboxylic acid from Step 1 of Example 64 for the 2-(2-fluoro-4-(4,4,5,5-tetramethyl-1,3,2-dioxaborolan-2-yl)phenyl)acetic acid used in Example 4, and substituting 1-methylpiperidin-4-amine for the 5-(1-(trifluoromethyl)cyclopropyl)isoxazol-3-amine used in Example 4. $^1$H NMR (500 MHz, DMSO-$d_6$) δ 12.16 (s, 1H), 11.21 (s, 1H), 9.15 (br s, 1H), 8.63 (d, J=2.2 Hz, 1H), 8.52 (d, J=7.1 Hz, 1H), 8.32 (d, J=1.6 Hz, 1H), 7.69 (d, J=7.7 Hz, 2H), 7.43 (d, J=8.2 Hz, 2H), 7.21 (d, J=1.6 Hz, 1H), 6.57 (s, 1H), 3.98-4.10 (m, 1H), 3.72 (s, 2H), 3.49 (d, J=12.1 Hz, 2H), 3.07-3.19 (m, 2H), 2.72-2.86 (m, 4H), 2.47-2.49 (m, 3H), 2.09 (d, J=13.7 Hz, 2H), 1.68-1.83 (m, 2H), 1.28 (s, 9H).

Example 70

Preparation of 2-(2-fluoro-4-(2-(hydroxymethyl)-1H-pyrrolo[2,3-b]pyridin-5-yl)phenyl)-N-(5-(1-(trifluoromethyl)cyclopropyl)isoxazol-3-yl)acetamide

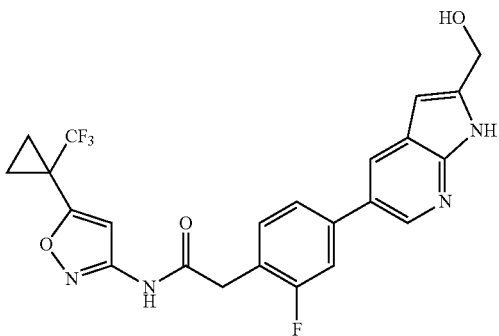 [SMILES: O=C(Cc1ccc(-c2cnc3[nH]c(CO)cc3c2)cc1F)Nc1cc(C2(C(F)(F)F)CC2)on1]

2-(2-Fluoro-4-(2-(hydroxymethyl)-1H-pyrrolo[2,3-b]pyridin-5-yl)phenyl)-N-(5-(1-(trifluoromethyl)cyclopropyl)isoxazol-3-yl)acetamide (46 mg) was obtained as a tan solid using a procedure analogous to that described in Step 3 of Example 4, substituting (5-bromo-1H-pyrrolo[2,3-b]pyridin-2-yl)methanol from Step 1 of Example 50 for the 2-chloro-6,7-dimethoxyquinoxaline used in Example 4. $^1$H NMR (500 MHz, DMSO-$d_6$) δ 11.63 (s, 1H), 11.41 (s, 1H), 8.48 (d, J=1.6 Hz, 1H), 8.17 (d, J=2.2 Hz, 1H), 7.49-7.59 (m, 2H), 7.39-7.48 (m, 1H), 6.93 (s, 1H), 6.37 (s, 1H), 5.29 (t, J=5.5 Hz, 1H), 4.62 (d, J=5.5 Hz, 2H), 3.82 (s, 2H), 1.52 (d, J=3.8 Hz, 2H), 1.48 (br s, 2H). LC-MS (ESI) m/z 475 (M+H)$^+$.

Example 71

Preparation of 2-(4-(1H-pyrrolo[2,3-b]pyridin-5-yl)phenyl)-N-(3-(tert-butyl)isoxazol-5-yl)acetamide

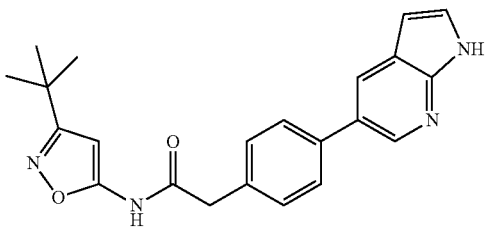 [SMILES: CC(C)(C)c1cc(NC(=O)Cc2ccc(-c3cnc4[nH]ccc4c3)cc2)on1]

2-(4-(1H-Pyrrolo[2,3-b]pyridin-5-yl)phenyl)-N-(3-(tert-butyl)isoxazol-5-yl)acetamide (4 mg, 3%) was obtained as a solid using a procedure analogous to that described in Example 25, substituting N-(3-(tert-butyl)isoxazol-5-yl)-2-(4-(4,4,5,5-tetramethyl-1,3,2-dioxaborolan-2-yl)phenyl)acetamide (Ref: S. Abraham et al, WO 2011022473 A1) for the N-(5-(tert-butyl)isoxazol-3-yl)-2-(4-(4,4,5,5-tetramethyl-1,3,2-dioxaborolan-2-yl)phenyl)acetamide used in Example 25. $^1$H NMR (500 MHz, DMSO-$d_6$) δ 11.82 (br s, 1H), 11.71 (br s, 1H), 8.49 (d, J=2.2 Hz, 1H), 8.18 (d, J=1.6 Hz, 1H), 7.67 (d, J=8.2 Hz, 2H), 7.51 (m, 1H), 7.41 (d, J=7.7 Hz, 2H), 6.50 (m, 1H), 6.21 (s, 1H), 3.74 (s, 2H), 1.24 (s, 9H).

Example 72

Preparation of 2-(4-(6,7-dimethoxyquinoxalin-2-yl)phenyl)-N-(3-(1-(trifluoromethyl)cyclopropyl)isoxazol-5-yl)acetamide

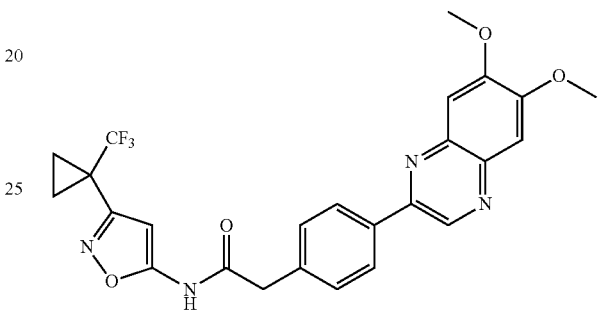

Step 1: To a stirred mixture of 3-oxo-3-(1-(trifluoromethyl)cyclopropyl)propanenitrile (Ref: M. W. Rowbottom et al, J. Med. Chem. 2012, 55, 1082), (2.7 g, 15.24 mmol), sodium hydroxide (670 mg, 16.75 mmol) and 1:1 ethanol:water (30 mL) at rt was added hydroxylamine sulfate (2.75 g, 16.75 mmol), and the mixture was heated at 80° C. for 15 h. The mixture was cooled to rt and partitioned between EtOAc and water. The organic layer was separated, washed with brine, dried over MgSO$_4$, filtered, and concentrated under reduced pressure. The residue was purified by silica gel flash chromatography eluting with 0-20% EtOAc in hexanes to afford 3-(1-(trifluoromethyl)cyclopropyl)isoxazol-5-amine (706 mg, 24%) as a red oil. $^1$H NMR (300 MHz, CDCl$_3$) δ 5.31 (s, 1H), 4.45 (br s, 2H), 1.30-1.40 (m, 4H); LC-MS (ESI) m/z 193 (M+H)$^+$.

Step 2: 2-(4-(6,7-Dimethoxyquinoxalin-2-yl)phenyl)-N-(3-(1-(trifluoromethyl)cyclopropyl)isoxazol-5-yl)acetamide (86 mg, 72%) was obtained as a solid using a procedure analogous to that described in Step 3 of Example 27, substituting 2-(4-(6,7-dimethoxyquinoxalin-2-yl)phenyl)acetic acid from Step 1 of Example 8 for the 2-(2-fluoro-4-(1H-pyrrolo[2,3-b]pyridine-5-yl)phenyl)acetic acid used in Example 27 and substituting 3-(1-(trifluoromethyl)cyclopropyl)isoxazol-5-amine for the 3-amino-5-tert-butylisoxazole used in Example 27. $^1$H NMR (500 MHz, DMSO-$d_6$) δ 12.09 (br s, 1H), 9.33 (s, 1H), 8.24 (d, J=8.0 Hz, 2H), 7.51 (s, 1H), 7.49 (s, 1H), 7.44 (d, J=8.0 Hz, 2H), 6.31 (s, 1H), 4.00 (s, 3H), 3.99 (s, 3H), 3.83 (s, 2H), 1.30-1.46 (m, 4H); LC-MS (ESI) m/z 499 (M+H)$^+$.

Example 73

Preparation of N-(3-(tert-butyl)isoxazol-5-yl)-2-(4-(6,7-dimethoxyquinoxalin-2-yl)phenyl)acetamide

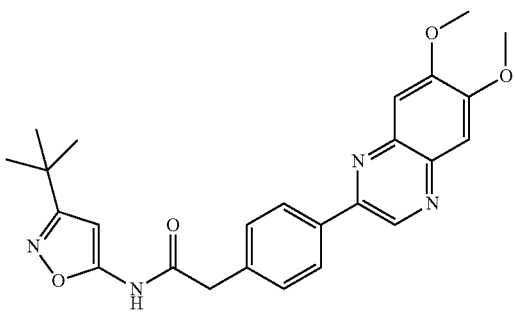 [SMILES: COc1cc2ncc(-c3ccc(CC(=O)Nc4cc(C(C)(C)C)no4)cc3)nc2cc1OC]

N-(3-(tert-Butyl)isoxazol-5-yl)-2-(4-(6,7-dimethoxyquinoxalin-2-yl)phenyl)acetamide (175 mg, 51%) was obtained as a yellow solid using a procedure analogous to that described in Step 2 of Example 4, substituting 2-(4-(6,7-dimethoxyquinoxalin-2-yl)phenyl)acetic acid from Step 1 of Example 8 for the 2-(2-fluoro-4-(4,4,5,5-tetramethyl-1,3,2-dioxaborolan-2-yl)phenyl)acetic acid used in Example 4 and substituting 3-(tert-butyl)isoxazol-5-amine for the 5-(1-(trifluoromethyl)cyclopropyl)isoxazol-3-amine used in Example 4. $^1$H NMR (500 MHz, DMSO-$d_6$) δ 11.83 (s, 1H), 9.33 (s, 1H), 8.24 (d, J=8.2 Hz, 2H), 7.95 (s, 2H), 7.50 (d, J=8.2 Hz, 2H), 7.45 (d, J=8.2 Hz, 2H), 6.22 (s, 1H), 4.00 (s, 3H), 3.99 (s, 3H), 3.80 (s, 2H), 1.24 (s, 9H). LC-MS (ESI) m/z 447 (M+H)$^+$.

Example 74

Preparation of ((2-(3-fluoro-4-(2-oxo-2-((5-(1-(trifluoromethyl)cyclopropyl)isoxazol-3-yl)amino)ethyl)phenyl)quinoxaline-6,7-diyl)bis(oxy))bis(ethane-2,1-diyl) diacetate

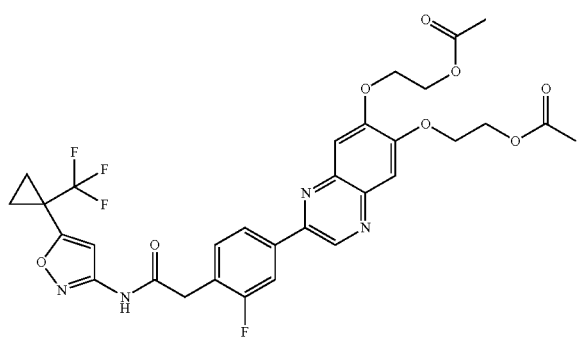 [SMILES: CC(=O)OCCOc1cc2ncc(-c3ccc(CC(=O)Nc4cc(C5(C(F)(F)F)CC5)on4)c(F)c3)nc2cc1OCCOC(C)=O]

Step 1: To a stirred solution of 2-chloro-6,7-dimethoxyquinoxaline (1.58 g, 7.0 mmol) at rt in 20 mL of DCM was slowly added BBr$_3$ (1.0 M in DCM, 28.1 mL, 28.1 mmol). The resulting mixture was heated under reflux for 2 h before more BBr$_3$ (1.0 M in DCM, 14.0 mL, 14.0 mmol) was added. The mixture was refluxed for 2 h, stirred at rt overnight, then refluxed for 4 h, and stirred at rt for 3 d. Ice chips were carefully added to the reaction mixture to quench the unreacted BBr$_3$. The organic volatiles were removed under reduced pressure to give a suspension. The solid residues were collected by filtration, washed with cold water, and dried in a vacuum oven to give crude 2-bromoquinoxaline-6,7-diol (1.5 g) as a greenish yellow solid. LC-MS (ESI) m/z 241, 243 (M+H)$^+$.

Step 2: To a stirred solution of 2-bromoquinoxaline-6,7-diol (100 mg, 0.41 mmol) and K$_2$CO$_3$ (285 mg, 2.1 mmol) in 5 mL of DMF at rt were added 2-bromoethyl acetate (114 μL, 1.0 mmol), and KI (50 mg, 0.30 mmol). The mixture was heated at 100° C. for 1 h. LC-MS showed that most of the starting material had been consumed. The reaction mixture was cooled, quenched with water, and extracted with EtOAc (2×25 mL). The combined organic layers were washed with brine, dried over Na$_2$SO$_4$, and concentrated under reduced pressure. The residue was triturated with diethyl ether and the solid was collected by filtration and air-dried to give ((2-bromoquinoxaline-6,7-diyl)bis(oxy))bis(ethane-2,1-diyl) diacetate (80 mg, 47%) as a tan solid. LC-MS (ESI) m/z 413, 415 (M+H)$^+$.

Step 3: ((2-(3-Fluoro-4-(2-oxo-2-((5-(1-(trifluoromethyl)cyclopropyl)isoxazol-3-yl)amino)ethyl)phenyl)quinoxaline-6,7-diyl)bis(oxy))bis(ethane-2,1-diyl) diacetate (120 mg, 94%) was obtained as a tan solid using a procedure analogous to that described in Step 3 of Example 4, substituting ((2-bromoquinoxaline-6,7-diyl)bis(oxy))bis(ethane-2,1-diyl) diacetate from Step 2 of this example for the 2-chloro-6,7-dimethoxyquinoxaline used in Example 4. $^1$H NMR (500 MHz, DMSO-$d_6$) δ 11.45 (s, 1H), 9.39 (s, 1H), 8.02-8.17 (m, 2H), 7.57 (t, J=8.0 Hz, 1H), 7.54 (s, 1H), 7.52 (s, 1H), 6.94 (s, 1H), 4.45 (d, J=3.8 Hz, 8H), 3.89 (s, 2H), 2.06 (s, 6H), 1.40-1.58 (m, 4H). LC-MS (ESI) m/z 661 (M+H)$^+$.

Example 75

Preparation of 2-(4-(6,7-bis(2-hydroxyethoxy)quinoxalin-2-yl)-2-fluorophenyl)-N-(5-(1-(trifluoromethyl)cyclopropyl)isoxazol-3-yl)acetamide

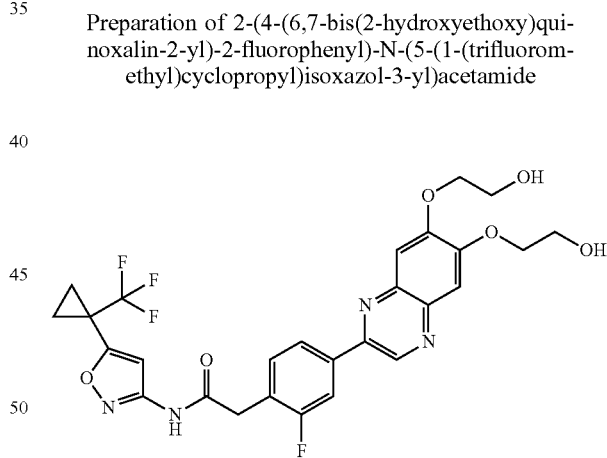

To a stirred solution of ((2-(3-fluoro-4-(2-oxo-2-((5-(1-(trifluoromethyl)cyclopropyl)isoxazol-3-yl)amino)ethyl)phenyl)quinoxaline-6,7-diyl)bis(oxy))bis(ethane-2,1-diyl) diacetate (98 mg, 0.15 mmol) from Example 74 in 5 mL of MeOH and THF (2:1, v/v) at rt was added 3N NaOH (0.15 mL, 0.45 mmol). The resulting mixture was stirred for 1 h before the mixture was concentrated under reduced pressure. The residue was quenched with water and the solid was collected by filtration, washed with cold water, and dried in a vacuum oven to give 2-(4-(6,7-bis(2-hydroxyethoxy)quinoxalin-2-yl)-2-fluorophenyl)-N-(5-(1-(trifluoromethyl)cyclopropyl)isoxazol-3-yl)acetamide (70 mg, 82%) as a light yellow solid. $^1$H NMR (500 MHz, DMSO-$d_6$) δ 9.36 (s, 1H), 8.03-8.14 (m, 2H), 7.56 (t, J=8.0 Hz, 1H), 7.49 (s, 1H), 7.47

(s, 1H), 6.93 (s, 1H), 4.95 (br s, 2H), 4.18-4.32 (m, 4H), 3.85 (d, J=5.5 Hz, 6H), 1.41-1.56 (m, 4H). LC-MS (ESI) m/z 577 (M+H)[1].

Example 76

Preparation of 2-(4-(2,3-dihydro-[1,4]dioxino[2,3-g]quinoxalin-7-yl)-2-fluorophenyl)-N-(5-(1-(trifluoromethyl)cyclopropyl)isoxazol-3-yl)acetamide

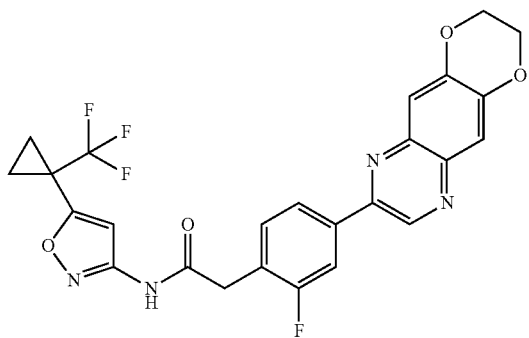 [SMILES: O=C(Cc1ccc(-c2cnc3cc4c(cc3n2)OCCO4)cc1F)Nc1cc(C2(C(F)(F)F)CC2)on1]

Step 1: 7-Bromo-2,3-dihydro-[1,4]dioxino[2,3-g]quinoxaline (120 mg) was obtained as a tan solid using a procedure analogous to that described in Step 2 of Example 74, substituting 1,2-dibromoethane for the 2-bromoethyl acetate used in Example 74. LC-MS (ESI) m/z 267, 269 (M+H)$^+$.

Step 2: 2-(4-(2,3-Dihydro-[1,4]dioxino[2,3-g]quinoxalin-7-yl)-2-fluorophenyl)-N-(5-(1-(trifluoromethyl)cyclopropyl)isoxazol-3-yl)acetamide (35 mg, 30%) was obtained as a white powder using a procedure analogous to that described in Step 3 of Example 4, substituting 7-bromo-2,3-dihydro-[1,4]dioxino[2,3-g]quinoxaline for 2-chloro-6,7-dimethoxyquinoxaline used in Example 4. $^1$H NMR (500 MHz, DMSO-$d_6$) δ 11.45 (s, 1H), 9.38 (s, 1H), 8.02-8.15 (m, 2H), 7.57 (t, J=8.0 Hz, 1H), 7.51 (s, 1H), 7.49 (s, 1H), 6.93 (s, 1H), 4.45 (s, 4H), 3.88 (s, 2H), 1.40-1.56 (m, 4H). LC-MS (ESI) m/z 515 (M+H)$^+$.

Example 77a

Preparation of 2-(2-fluoro-4-(6-methoxy-7-(2-methoxyethoxy)quinoxalin-2-yl)phenyl)-N-(5-(1-(trifluoromethyl)cyclopropyl)isoxazol-3-yl)acetamide

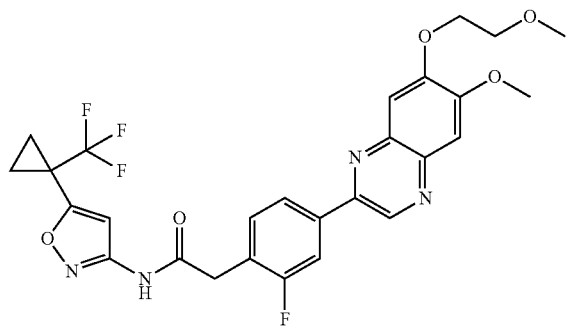 [SMILES: COCCOc1cc2nc(-c3ccc(CC(=O)Nc4cc(C5(C(F)(F)F)CC5)on4)c(F)c3)cnc2cc1OC]

Step 1: 4-Methoxy-5-(2-methoxyethoxy)-2-nitroaniline (6.6 g) was prepared as a crude reddish oil using a procedure analogous to that described in Step 1 of Example 78, substituting 1-bromo-2-methoxyethane for benzyl bromide used in Example 78. LC-MS (ESI) m/z 243 (M+H)$^+$.

Step 2: To a stirred solution of crude 4-methoxy-5-(2-methoxyethoxy)-2-nitroaniline (6.6 g) in 50 mL of toluene at rt was added ethyl glyoxylate (50% in toluene, 5.9 mL, 30.0 mmol). The resulting mixture was heated under reflux for 2 h using a Dean-Stark trap to remove the water generated. Excess $Na_2SO_4$ and $MgSO_4$ were then added, and the mixture was heated at 130° C. for a further 2 h. The reaction mixture was then cooled and filtered through a Celite plug washing with 100 mL of DCM. The filtrate was concentrated under reduced pressure and the residue was purified by silica gel column chromatography, eluting with 0-25% EtOAc in DCM, to give partially purified ethyl 2-((4-methoxy-5-(2-methoxyethoxy)-2-nitrophenyl)imino)acetate (5.4 g) as an orange-red gum. LC-MS (ESI) m/z 327 (M+H)$^+$.

Step 3: Ethyl 2-((4-methoxy-5-(2-methoxyethoxy)-2-nitrophenyl)imino)acetate (5.4 g) from Step 2 of this example in 50 mL of EtOH was treated with 10% Pd/C (850 mg) and shaken in a Parr apparatus under 50 psi of hydrogen at rt for 3 d. The reaction mixture was then transferred to a round bottom flask and 10% Pd/C (500 mg) was added. The resulting mixture was then stirred under a hydrogen balloon at 65° C. for an additional 7 h. The mixture was allowed to cool to rt, and then was filtered through a Celite plug washing with 150 mL of EtOAc. The filtrate was concentrated under reduced pressure to give a crude mixture of 7-methoxy-6-(2-methoxyethoxy)-3,4-dihydroquinoxalin-2(1H)-one, 6-methoxy-7-(2-methoxyethoxy)-3,4-dihydroquinoxalin-2(1H)-one, 7-methoxy-6-(2-methoxyethoxy)quinoxalin-2(1H)-one and 6-methoxy-7-(2-methoxyethoxy)quinoxalin-2(1H)-one. The total weight of the mixture was approximately 4.3 g. LC-MS (ESI) m/z 253 and 251 (M+H)$^+$.

Step 4: To a stirred solution of the crude mixture of dihydroquinoxalines and quinoxalines (~4.3 g) from Step 3 of this example in 100 mL of DCM at rt was added activated $MnO_2$ (2.2 g). The resulting mixture was stirred at rt overnight before another 1.0 g of $MnO_2$ was added. After 1 h, the mixture was filtered through a Celite plug washing with 150 mL of DCM. The filtrate was concentrated under reduced pressure to give a crude mixture (2.3 g) of 7-methoxy-6-(2-methoxyethoxy)quinoxalin-2(1H)-one and 6-methoxy-7-(2-methoxyethoxy)quinoxalin-2(1H)-one, which was carried on to the next step. The filter cake was triturated with 100 mL of MeOH/DCM (1:1, v/v) aided by sonication. The resulting mixture was filtered through a Celite plug and washed with 100 mL of DCM, and the filtrate was concentrated under reduced pressure to give a sample (0.72 g) of pure 7-methoxy-6-(2-methoxyethoxy)quinoxalin-2(1H)-one. LC-MS (ESI) m/z 251 (M+H)$^+$.

Step 5: A mixture (1.2 g) of 7-methoxy-6-(2-methoxyethoxy)quinoxalin-2-yl trifluoromethanesulfonate and 6-methoxy-7-(2-methoxyethoxy)quinoxalin-2-yl trifluoromethanesulfonate was obtained as a light brown oil using a procedure analogous to that described in Step 4 of Example 78, substituting the mixture of 7-methoxy-6-(2-methoxyethoxy)quinoxalin-2(1H)-one and 6-methoxy-7-(2-methoxyethoxy)quinoxalin-2(1H)-one from Step 4 of this example for the mixture of 6-(benzyloxy)-7-methoxyquinoxalin-2(1H)-one and 7-(benzyloxy)-6-methoxyquinoxalin-2(1H)-one used in Example 78. LC-MS (ESI) m/z 383 (M+H)⁺.

Step 6: A mixture of 2-(2-fluoro-4-(7-methoxy-6-(2-methoxyethoxy)quinoxalin-2-yl)phenyl)-N-(5-(1-(trifluoromethyl)cyclopropyl)isoxazol-3-yl)acetamide and 2-(2-fluoro-4-(6-methoxy-7-(2-methoxyethoxy)quinoxalin-2-yl)phenyl)-N-(5-(1-(trifluoromethyl)cyclopropyl)isoxazol-3-yl)acetamide was obtained as a crude tan solid using a procedure analogous to that described in Step 3 of Example 4, substituting the mixture of 7-methoxy-6-(2-methoxyethoxy)quinoxalin-2-yl trifluoromethanesulfonate and 6-methoxy-7-(2-methoxyethoxy)quinoxalin-2-yltrifluoromethanesulfonate from Step 5 of this example for 2-chloro-6,7-dimethoxyquinoxaline used in Example 4. The mixture of products was then purified by silica gel column chromatography, eluting with 0-36% EtOAc in DCM, to yield first 2-(2-fluoro-4-(6-methoxy-7-(2-methoxyethoxy)quinoxalin-2-yl)phenyl)-N-(5-(1-(trifluoromethyl)cyclopropyl)isoxazol-3-yl)acetamide (300 mg) as a white solid. ¹H NMR (500 MHz, DMSO-d₆) δ 11.45 (br s, 1H), 9.37 (s, 1H), 8.03-8.15 (m, 2H), 7.57 (t, J=8.0 Hz, 1H), 7.49 (s, 1H), 7.45 (s, 1H), 6.93 (s, 1H), 4.30-4.39 (m, 2H), 4.00 (s, 3H), 3.88 (s, 2H), 3.73-3.81 (m, 2H), 3.35 (s, 3H), 1.42-1.58 (m, 4H). LC-MS (ESI) m/z 561 (M+H)⁺.

Example 77b

Preparation of 2-(2-fluoro-4-(7-methoxy-6-(2-methoxyethoxy)quinoxalin-2-yl)phenyl)-N-(5-(1-(trifluoromethyl)cyclopropyl)isoxazol-3-yl)acetamide

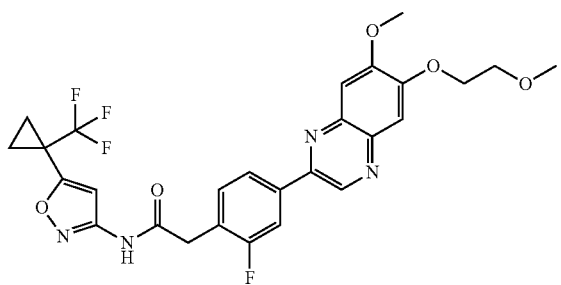 [SMILES: COCCOc1cc2ncc(-c3ccc(CC(=O)Nc4cc(C5(C(F)(F)F)CC5)on4)c(F)c3)nc2cc1OC]

Further elution of the chromatography column in Step 6 of Example 77a afforded 2-(2-fluoro-4-(7-methoxy-6-(2-methoxyethoxy)quinoxalin-2-yl)phenyl)-N-(5-(1-(trifluoromethyl)cyclopropyl)isoxazol-3-yl)acetamide (200 mg) as a light yellow solid. ¹H NMR (500 MHz, DMSO-d₆) δ 11.44 (s, 1H), 9.37 (s, 1H), 8.04-8.15 (m, 2H), 7.57 (t, J=8.0 Hz, 1H), 7.48 (s, 1H), 7.47 (s, 1H), 6.93 (s, 1H), 4.28-4.38 (m, 2H), 4.01 (s, 3H), 3.88 (s, 2H), 3.71-3.82 (m, 2H), 3.35 (s, 3H), 1.43-1.59 (m, 4H). LC-MS (ESI) m/z 561 (M+H)⁺.

Example 78

Preparation of 2-(2-fluoro-4-(6-hydroxy-7-methoxyquinoxalin-2-yl)phenyl)-N-(5-(1-(trifluoromethyl)cyclopropyl)isoxazol-3-yl)acetamide

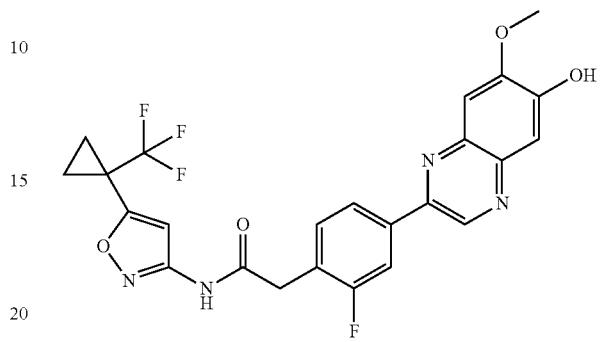

Step 1: To a stirred solution of 5-amino-2-methoxy-4-nitrophenol (ref: WO2004/14899 A1, 2004) (5.0 g, 27.2 mmol) at rt in 50 mL of DMF were added Cs₂CO₃ (14.2 g, 43.6 mmol) and KI (4.5 g, 27.2 mmol), followed by slow addition of benzyl bromide (3.4 mL, 28.5 mmol). The resulting mixture was heated at 80° C. for 1 h, after which LC-MS showed that most of the starting material had been consumed. The reaction mixture was allowed to cool to rt and then quenched with ice water. The solid was collected by filtration washing with cold water, and dried in a vacuum oven to give 5-(benzyloxy)-4-methoxy-2-nitroaniline (6.3 g, 85%) as an orange-red solid. LC-MS (ESI) m/z 275 (M+H)⁺.

Step 2: To a stirred solution of 5-(benzyloxy)-4-methoxy-2-nitroaniline (5.0 g, 18.2 mmol) in 50 mL of DCM at rt were added AcOH (10.5 mL, 182 mmol) and ethyl glyoxylate (50% in toluene, 4.0 mL, 20.0 mmol). Freshly activated zinc (6.0 g, 91 mmol) was added in portions, and the resulting mixture was stirred at rt for 3 h before it was partitioned between 1 N HCl (75 mL) and DCM (200 mL). The aqueous layer was separated and extracted with DCM (100 mL) once. The combined organic layers were washed with brine, dried over Mg₂SO₄, and concentrated under reduced pressure to afford a crude mixture of 6-(benzyloxy)-7-methoxy-3,4-dihydroquinoxalin-2(1H)-one, 7-(benzyloxy)-6-methoxy-3,4-dihydroquinoxalin-2(1H)-one, 6-(benzyloxy)-7-methoxyquinoxalin-2(1H)-one and 7-(benzyloxy)-6-methoxyquinoxalin-2(1H)-one. LC-MS (ESI) m/z 283, 285 (M+H)⁺.

Step 3: To a stirred solution of the crude mixture of dihydroquinoxalines and quinoxalines (~5 g) from Step 2 of this example in 50 mL of DCM was added activated MnO₂ (6.9 g). The resulting mixture was stirred at rt for 1 h before it was filtered through a Celite plug washing with DCM (3×100 mL). The filtrate was concentrated under reduced pressure to give a crude mixture of 6-(benzyloxy)-7-methoxyquinoxalin-2(1H)-one and 7-(benzyloxy)-6-methoxyquinoxalin-2(1H)-one (~5 g). LC-MS (ESI) m/z 283 (M+H)⁺.

Step 4: To a stirred solution of the crude mixture (~5 g) of 6-(benzyloxy)-7-methoxyquinoxalin-2(1H)-one and 7-(benzyloxy)-6-methoxyquinoxalin-2(1H)-one from Step 3 of this example in 100 mL of DCM at 0° C. was added Et₃N (5.5 mL, 39.5 mmol), followed by dropwise addition of Tf₂O (4.8 mL, 28.6 mmol). The resulting mixture was stirred at rt for 1 h before it was partitioned between saturated aq NH₄Cl (100 mL) and DCM (200 mL). The aqueous layer was extracted with DCM (100 mL) once. The combined organic layers were washed with brine, dried over Mg₂SO₄, and evaporated under reduced pressure. The residue was purified by silica gel column chromatography, eluting with 0-15% EtOAc in hexanes, to give 6-(benzyloxy)-7-methoxyquinoxalin-2-yl trifluoromethanesulfonate (670 mg) as the less polar (faster eluting) product and 7-(benzyloxy)-6-methoxyquinoxalin-2-yl trifluoromethanesulfonate (1.07 g) as the more polar product. LC-MS (ESI) m/z 415 (M+H)[1].

Step 5: Crude 2-(4-(6-(Benzyloxy)-7-methoxyquinoxalin-2-yl)-2-fluorophenyl)-N-(5-(1-(trifluoromethyl)cyclopropyl)isoxazol-3-yl)acetamide (1.05 g) was obtained as a tan solid using a procedure analogous to that described in Step 3 of Example 4, substituting 6-(benzyloxy)-7-methoxyquinoxalin-2-yl trifluoromethanesulfonate from Step 4 of this example for the 2-chloro-6,7-dimethoxyquinoxaline used in Example 4. LC-MS (ESI) m/z 593 (M+H)[1].

Step 6: A stirred mixture of crude 2-(4-(6-(benzyloxy)-7-methoxyquinoxalin-2-yl)-2-fluorophenyl)-N-(5-(1-(trifluoromethyl)cyclopropyl)isoxazol-3-yl)acetamide (160 mg) in 3 mL of TFA was heated at 80° C. for 1 h. The resulting mixture was allowed to cool and then concentrated under reduced pressure, and the residue was purified via reverse-phase preparative HPLC using a mixture of water (containing 5% CH₃CN and 0.05% HCOOH), and CH₃CN (containing 0.05% HCOOH) as the mobile phase and a Varian Pursuit XRs diphenyl column as the stationary phase to afford 2-(2-fluoro-4-(6-hydroxy-7-methoxyquinoxalin-2-yl)phenyl)-N-(5-(1-(trifluoromethyl)cyclopropyl)isoxazol-3-yl)acetamide (10 mg) as a yellow powder. ¹H NMR (500 MHz, DMSO-d₆) δ 11.44 (br s, 1H), 9.30 (s, 1H), 8.00-8.13 (m, 2H), 7.55 (t, J=8.0 Hz, 1H), 7.44 (s, 1H), 7.30 (s, 1H), 6.93 (s, 1H), 4.01 (s, 3H), 3.88 (s, 2H), 1.39-1.59 (m, 4H)LC-MS (ESI) m/z 503 (M+H)⁺.

Example 79

Preparation of 2-(2-fluoro-4-(7-methoxy-6-(2-morpholinoethoxy)quinoxalin-2-yl)phenyl)-N-(5-(1-(trifluoromethyl)cyclopropyl)isoxazol-3-yl)acetamide

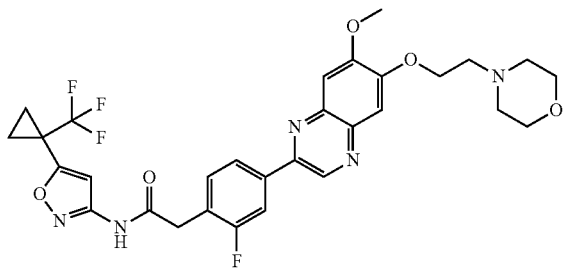 [SMILES: COc1cc2nc(-c3ccc(CC(=O)Nc4cc(C5(C(F)(F)F)CC5)on4)c(F)c3)cnc2cc1OCCN1CCOCC1]

Step 1: 4-Methoxy-5-(2-morpholinoethoxy)-2-nitroaniline (6.0 g) was obtained as an orange solid using a procedure analogous to that described in Step 1 of Example 78, substituting 4-(2-chloroethyl)morpholine hydrochloride for benzyl bromide used in Example 78. LC-MS (ESI) m/z 298 (M+H)⁺.

Step 2: To a stirred suspension of 4-methoxy-5-(2-morpholinoethoxy)-2-nitroaniline (7.1 g, 23.9 mmol) in 25 mL of THF was added Boc₂O (15.6 g, 71.7 mmol). The resulting mixture was heated in a pressure vessel for 3 d, cooled to rt, and concentrated under reduced pressure. The residue was taken up in 50 mL of MeOH, and K₂CO₃ (9.9 g, 71.7 mmol) was added. The resulting mixture was heated at 50° C. for 3 h. LC-MS showed that the most of the product is tert-butyl (4-methoxy-5-(2-morpholinoethoxy)-2-nitrophenyl)carbamate. The reaction mixture was then cooled to rt, concentrated under reduced pressure, and dried in a vacuum oven to give an orange solid, which was used directly for the next step. LC-MS (ESI) m/z 398 (M+H)⁺.

Step 3: Methyl 2-((tert-butoxycarbonyl)(4-methoxy-5-(2-morpholinoethoxy)-2-nitrophenyl)amino)acetate (8.3 g) was obtained as a light brown oil using a procedure analogous to that described in Step 1 of Example 78, substituting methyl 2-bromoacetate for benzyl bromide, and tert-butyl (4-methoxy-5-(2-morpholinoethoxy)-2-nitrophenyl)carbamate from Step 2 of this example for the 5-amino-2-methoxy-4-nitrophenol used in Example 78. LC-MS (ESI) m/z 470 (M+H)⁺.

Step 4: A mixture of methyl 2-((tert-butoxycarbonyl)(4-methoxy-5-(2-morpholinoethoxy)-2-nitrophenyl)amino)acetate (1.65 g, 3.5 mmol) from Step 3 of this example and 165 mg of 10% Pd/C in 30 mL of MeOH was stirred under a hydrogen-filled balloon for 30 min. The resulting mixture was filtered through a Celite plug washing with 30 mL of MeOH. The filtrate containing methyl 2-((2-amino-4-methoxy-5-(2-morpholinoethoxy)phenyl)(tert-butoxycarbonyl)amino)acetate was used directly for the next step. LC-MS (ESI) m/z 440 (M+H)⁺.

Step 5: To a stirred solution of methyl 2-((2-amino-4-methoxy-5-(2-morpholinoethoxy)phenyl)(tert-butoxycarbonyl)amino)acetate (7.1 g) from Step 4 of this example in 50 mL of MeOH was added 4N HCl in dioxane (25 mL). The resulting mixture was stirred at rt for 3 d under open air. The resulting mixture was concentrated under reduced pressure to afford a brown solid residue that was mostly 7-methoxy-6-(2-morpholinoethoxy)quinoxalin-2(1H)-one (3.0 g). LC-MS (ESI) m/z 306 (M+H)⁺.

Step 6: To a stirred mixture of crude 7-methoxy-6-(2-morpholinoethoxy)quinoxalin-2(1H)-one (3.0 g, 9.8 mmol) from Step 5 of this example and POCl₃ (15 mL) at rt was added DMF (3 drops). The resulting mixture was heated at 110° C. for 1 h. LC-MS showed that the starting material was completely consumed. The mixture was concentrated under reduced pressure and the residue was quenched carefully with ice chips and saturated aq NaHCO₃. The mixture was extracted with EtOAc (2×100 mL), and the combined organic layers were washed with brine, dried over Na₂SO₄, and concentrated under reduced pressure. The residue was triturated with diethyl ether aided by sonication. The yellow solid was collected by filtration to give 4-(2-((2-chloro-7-methoxyquinoxalin-6-yl)oxy)ethyl)morpholine (1.6 g). LC-MS (ESI) m/z 324, 326 (M+H)⁺.

Step 7: 2-(2-Fluoro-4-(7-methoxy-6-(2-morpholinoethoxy)quinoxalin-2-yl)phenyl)-N-(5-(1-(trifluoromethyl)cyclopropyl)isoxazol-3-yl)acetamide (57 mg) was obtained as a tan solid using a procedure analogous to that described in Step 3 of Example 4, substituting 4-(2-((2-chloro-7-methoxyquinoxalin-6-yl)oxy)ethyl)morpholine from Step 6 of this example for the 2-chloro-6,7-dimethoxyquinoxaline used in Example 4. ¹H NMR (500 MHz, DMSO-d₆) δ 11.44 (br s, 1H), 9.37 (s, 1H), 8.02-8.16 (m, 2H), 7.57 (t, J=7.7 Hz, 1H), 7.49 (s, 1H), 7.47 (s, 1H), 6.93 (s, 1H), 4.33 (t, J=5.5 Hz, 2H), 4.00 (s, 3H), 3.88 (s, 2H), 3.60 (t, J=4.4 Hz, 4H), 2.81 (t, J=5.8 Hz, 2H), 2.53 (br s, 4H), 1.40-1.58 (m, 4H).

Example 80

Preparation of 2-(2-fluoro-4-(7-(2-hydroxyethoxy)-6-methoxyquinoxalin-2-yl)phenyl)-N-(5-(1-(trifluoromethyl)cyclopropyl)isoxazol-3-yl)acetamide

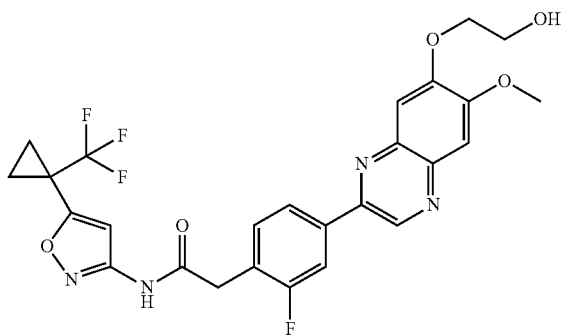 [SMILES: COc1cc2ncc(-c3ccc(CC(=O)Nc4cc(C5(C(F)(F)F)CC5)on4)c(F)c3)nc2cc1OCCO]

Step 1: To a stirred solution of NaH (60% dispersion in mineral oil, 0.21 g, 5.3 mmol) in 10 mL of DMSO under argon was added 5-(benzyloxy)-4-methoxy-2-nitroaniline from step 1 of Example 78 (1.33 g, 4.8 mmol) in 5 mL of DMSO. The resulting red solution was stirred at rt for 30 min before methyl 2,2-dimethoxyacetate (0.65 mL, 5.3 mmol) was added in one portion. The resulting mixture was stirred at rt for 2 h before it was quenched with water and extracted with EtOAc (2×50 mL). The combined organic layers were washed with brine, dried over $Na_2SO_4$, and evaporated under reduced pressure. The residue was purified by a silica gel column chromatography eluting with 0-25% EtOAc in hexanes to give impure N-(5-(benzyloxy)-4-methoxy-2-nitrophenyl)-2,2-dimethoxyacetamide (1.05 g) as a yellow solid. LC-MS (ESI) m/z 377 (M+H)$^+$.

Step 2: Crude N-(2-Amino-5-(benzyloxy)-4-methoxyphenyl)-2,2-dimethoxyacetamide (1.0 g) was obtained as a dark greenish oil using a procedure analogous to that described in Step 2 of Example 78, substituting N-(5-(benzyloxy)-4-methoxy-2-nitrophenyl)-2,2-dimethoxyacetamide from Step 1 of this example for 5-(benzyloxy)-4-methoxy-2-nitroaniline used in Example 78, and without the addition of ethyl glyoxylate. LC-MS (ESI) m/z 347 (M+H)$^+$.

Step 3: To a stirred solution of the crude N-(2-amino-5-(benzyloxy)-4-methoxyphenyl)-2,2-dimethoxyacetamide (1.0 g) from Step 2 of this example in 25 mL of EtOH/$H_2O$ (4:1, v/v) was added Amberlyst-15 (1.0 g). The resulting mixture was heated under reflux for 30 min before it was cooled and filtered through a Celite plug washing with hot EtOH (2×50 mL). The filtrate was concentrated under reduced pressure to give crude 7-(benzyloxy)-6-methoxyquinoxalin-2(1H)-one (~1 g), which was used directly without further purification. LC-MS (ESI) m/z 283 (M+H)$^+$.

Step 4: 7-(Benzyloxy)-6-methoxyquinoxalin-2(1H)-one (205 mg) was obtained as a light brown oil using a procedure analogous to that described in Step 4 of Example 78, substituting 7-(benzyloxy)-6-methoxyquinoxalin-2(1H)-one from Step 3 of this example for the mixture of 6-(benzyloxy)-7-methoxyquinoxalin-2(1H)-one and 7-(benzyloxy)-6-methoxyquinoxalin-2(1H)-one used in Example 78. LC-MS (ESI) m/z 415 (M+H)$^+$.

Step 5: 2-(4-(7-(Benzyloxy)-6-methoxyquinoxalin-2-yl)-2-fluorophenyl)-N-(5-(1-(trifluoromethyl)cyclopropyl)isoxazol-3-yl)acetamide (250 mg) was obtained as a crude tan solid using a procedure analogous to that described in Step 3 of Example 4, substituting 7-(benzyloxy)-6-methoxyquinoxalin-2-yl trifluoromethanesulfonate from Step 4 of this example for the 2-chloro-6,7-dimethoxyquinoxaline used in Example 4. LC-MS (ESI) m/z 593 (M+H)$^+$.

Step 6: 2-(2-Fluoro-4-(7-hydroxy-6-methoxyquinoxalin-2-yl)phenyl)-N-(5-(1-(trifluoromethyl)cyclopropyl)isoxazol-3-yl)acetamide (25 mg) was obtained as a tan powder using a procedure analogous to that described in Step 6 of Example 78, substituting 2-(4-(7-(benzyloxy)-6-methoxyquinoxalin-2-yl)-2-fluorophenyl)-N-(5-(1-(trifluoromethyl)cyclopropyl)isoxazol-3-yl)acetamide from Step 5 of this example for the 2-(4-(6-(benzyloxy)-7-methoxyquinoxalin-2-yl)-2-fluorophenyl)-N-(5-(1-(trifluoromethyl)cyclopropyl)isoxazol-3-yl)acetamide used in Example 78. LC-MS (ESI) m/z 503 (M+H)$^+$.

Step 7: 2-((3-(3-Fluoro-4-(2-oxo-2-((5-(1-(trifluoromethyl)cyclopropyl)isoxazol-3-yl)amino)ethyl)phenyl)-7-methoxyquinoxalin-6-yl)oxy)ethyl acetate (38 mg) was obtained as a yellow solid using a procedure analogous to that described in Step 2 of Example 74, substituting 2-(2-fluoro-4-(7-hydroxy-6-methoxyquinoxalin-2-yl)phenyl)-N-(5-(1-(trifluoromethyl)cyclopropyl)isoxazol-3-yl)acetamide from Step 6 of this example for the 2-bromoquinoxaline-6,7-diol used in Example 74. LC-MS (ESI) m/z 589 (M+H)$^+$.

Step 8: 2-(2-Fluoro-4-(7-(2-hydroxyethoxy)-6-methoxyquinoxalin-2-yl)phenyl)-N-(5-(1-(trifluoromethyl)cyclopropyl)isoxazol-3-yl)acetamide was obtained as a yellow solid using a procedure analogous to that described in Example 75, substituting 2-((3-(3-Fluoro-4-(2-oxo-2-((5-(1-(trifluoromethyl)cyclopropyl)isoxazol-3-yl)amino)ethyl)phenyl)-7-methoxyquinoxalin-6-yl)oxy)ethyl acetate from Step 7 of this example for ((2-(3-fluoro-4-(2-oxo-2-((5-(1-(trifluoromethyl)cyclopropyl)isoxazol-3-yl)amino)ethyl)phenyl)quinoxaline-6,7-diyl)bis(oxy))bis(ethane-2,1-diyl) diacetate used in Example 75. $^1$H NMR (500 MHz, DMSO-$d_6$) δ 11.45 (s, 1H), 9.37 (s, 1H), 8.03-8.16 (m, 2H), 7.57 (t, J=7.7 Hz, 1H), 7.47 (s, 1H), 7.45 (s, 1H), 6.94 (s, 1H), 4.96 (t, J=5.2 Hz, 1H), 4.24 (t, J=4.9 Hz, 2H), 4.00 (s, 3H), 3.88 (s, 2H), 3.78-3.86 (m, 2H), 1.43-1.58 (m, 4H) LC-MS (ESI) m/z 547 (M+H)$^+$.

Example 81

Preparation of 2-(2-fluoro-4-(7-methoxy-6-(2-(4-methylpiperazin-1-yl)ethoxy)quinoxalin-2-yl)phenyl)-N-(5-(1-(trifluoromethyl)cyclopropyl)isoxazol-3-yl)acetamide

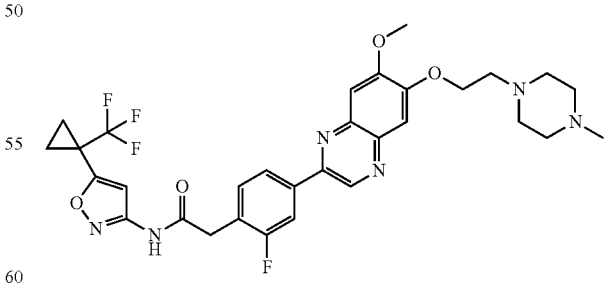

Step 1: 6-(2-Hydroxyethoxy)-7-methoxyquinoxalin-2(1H)-one (500 mg) was obtained as a light yellow solid using a procedure analogous to that described in Steps 1-5 of Example 79, substituting (2-bromoethoxy)(tert-butyl)dimethylsilane for 4-(2-chloroethyl)morpholine hydrochloride used in Example 79. LC-MS (ESI) m/z 237 (M+H)$^+$.

Step 2: 6-(2-Hydroxyethoxy)-7-methoxyquinoxalin-2-yl trifluoromethanesulfonate (193 mg) was obtained as a light yellow solid using a procedure analogous to that described in Step 4 of Example 78, substituting 6-(2-hydroxyethoxy)-7-methoxyquinoxalin-2(1H)-one from Step 1 of this example for the mixture of 6-(benzyloxy)-7-methoxyquinoxalin-2(1H)-one and 7-(benzyloxy)-6-methoxyquinoxalin-2(1H)-one used in Example 78. LC-MS (ESI) m/z 369 (M+H)+.

Step 3: 2-(2-Fluoro-4-(6-(2-hydroxyethoxy)-7-methoxyquinoxalin-2-yl)phenyl)-N-(5-(1-(trifluoromethyl)cyclopropyl)isoxazol-3-yl)acetamide (287 mg) was obtained as a light yellow solid using a procedure analogous to that described in Step 3 of Example 4, substituting 6-(2-hydroxyethoxy)-7-methoxyquinoxalin-2-yl trifluoromethanesulfonate from Step 2 of this example for the 2-chloro-6,7-dimethoxyquinoxaline used in Example 4. LC-MS (ESI) m/z 547 (M+H)+.

Step 4: To a stirred solution of crude 2-(2-fluoro-4-(6-(2-hydroxyethoxy)-7-methoxyquinoxalin-2-yl)phenyl)-N-(5-(1-(trifluoromethyl)cyclopropyl)isoxazol-3-yl)acetamide (235 mg, 0.43 mmol) from Step 3 of this example in 5 mL of DCM at rt were added TEA (180 µL, 1.3 mmol) and methanesulfonyl chloride (67 µL, 0.86 mmol). The resulting mixture was stirred at rt for 1 h before the mixture was concentrated under reduced pressure. The residue was quenched with water and the resulting mixture was sonicated. The yellow solid was collected by filtration and dried in a vacuum oven to give 2-((2-(3-fluoro-4-(2-oxo-2-((5-(1-(trifluoromethyl)cyclopropyl)isoxazol-3-yl)amino)ethyl)phenyl)-7-methoxyquinoxalin-6-yl)oxy)ethyl methanesulfonate (260 mg). LC-MS (ESI) m/z 625 (M+H)+.

Step 5: 2-(2-Fluoro-4-(7-methoxy-6-(2-(4-methylpiperazin-1-yl)ethoxy)quinoxalin-2-yl)phenyl)-N-(5-(1-(trifluoromethyl)cyclopropyl)isoxazol-3-yl)acetamide (35 mg) was obtained as a tan powder using a procedure analogous to that described in Step 4 of Example 82, substituting 2-((2-(3-fluoro-4-(2-oxo-2-((5-(1-(trifluoromethyl)cyclopropyl)isoxazol-3-yl)amino)ethyl)phenyl)-7-methoxyquinoxalin-6-yl)oxy)ethyl methanesulfonate from Step 4 of this example for the 2-(4-(6-(2-chloroethoxy)-7-methoxyquinoxalin-2-yl)-2-fluorophenyl)-N-(5-(1-(trifluoromethyl)cyclopropyl)isoxazol-3-yl)acetamide used in Example 82. 1H NMR (500 MHz, DMSO-d6) δ 11.44 (br s, 1H), 9.37 (s, 1H), 8.02-8.14 (m, 2H), 7.57 (t, J=8.0 Hz, 1H), 7.48 (s, 1H), 7.47 (s, 1H), 6.93 (s, 1H), 4.31 (t, J=5.8 Hz, 2H), 4.00 (s, 3H), 3.88 (s, 2H), 2.80 (t, J=5.8 Hz, 2H), 2.54 (br s, 4H), 2.35 (br s, 4H), 2.16 (s, 3H), 1.42-1.57 (m, 4H).

Example 82

Preparation of 2-(4-(6-(2-(3,3-difluoropyrrolidin-1-yl)ethoxy)-7-methoxyquinoxalin-2-yl)-2-fluorophenyl)-N-(5-(1-(trifluoromethyl)cyclopropyl)isoxazol-3-yl)acetamide

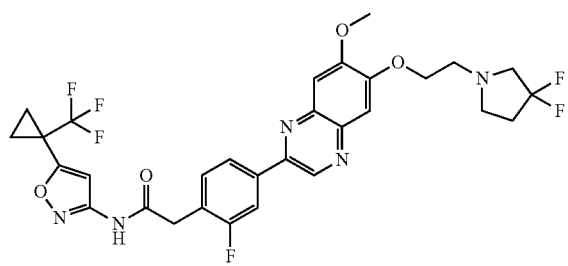 [SMILES: COc1cc2nc(-c3ccc(CC(=O)Nc4cc(C5(C(F)(F)F)CC5)on4)c(F)c3)cnc2cc1OCCN1CCC(F)(F)C1]

Step 1: 2-(2-Fluoro-4-(7-methoxy-6-((2-(trimethylsilyl)ethoxy)methoxy)quinoxalin-2-yl)phenyl)-N-(5-(1-(trifluoromethyl)cyclopropyl)isoxazol-3-yl)acetamide (530 mg) was obtained as a light yellow solid using a procedure analogous to that described in Steps 1-6 of Example 77a, substituting (2-(chloromethoxy)ethyl)trimethylsilane for the 1-bromo-2-methoxyethane used in Example 77a. LC-MS (ESI) m/z 633 (M+H)+.

Step 2: To a stirred solution of 2-(2-fluoro-4-(7-methoxy-6-((2-(trimethylsilyl)ethoxy)methoxy)quinoxalin-2-yl)phenyl)-N-(5-(1-(trifluoromethyl)cyclopropyl)isoxazol-3-yl)acetamide (530 mg, 0.84 mmol) from Step 1 of this example at rt in 12 mL of DCM/MeOH (2:1, v/v) was slowly added 4N HCl in 1,4-dioxane (3 mL, 12 mmol). The resulting mixture was stirred at rt overnight. LC-MS showed most of the starting material has been consumed. The reaction mixture was concentrated under reduced pressure, and the residue was dried in a vacuum oven to give crude 2-(2-fluoro-4-(6-hydroxy-7-methoxyquinoxalin-2-yl)phenyl)-N-(5-(1-(trifluoromethyl)cyclopropyl)isoxazol-3-yl)acetamide hydrochloride (650 mg) as a yellow solid. LC-MS (ESI) m/z 503 (M+H)+.

Step 3: To a stirred solution of crude 2-(2-fluoro-4-(6-hydroxy-7-methoxyquinoxalin-2-yl)phenyl)-N-(5-(1-(trifluoromethyl)cyclopropyl)isoxazol-3-yl)acetamide hydrochloride (650 mg, 1.2 mmol) in 5 mL of DMF at rt was added K2CO3 (577 mg, 7.2 mmol), followed by 1-bromo-2-chloroethane (694 µL, 14.5 mmol). The resulting mixture was stirred at rt for 24 h before it was quenched with water (50 mL). The yellow precipitate was collected via filtration, washed with cold water, and dried in a vacuum oven to give crude 2-(4-(6-(2-chloroethoxy)-7-methoxyquinoxalin-2-yl)-2-fluorophenyl)-N-(5-(1-(trifluoromethyl)cyclopropyl)isoxazol-3-yl)acetamide (450 mg). LC-MS (ESI) m/z 565, 567 (M+H)+.

Step 4: To a stirred solution of crude 2-(4-(6-(2-chloroethoxy)-7-methoxyquinoxalin-2-yl)-2-fluorophenyl)-N-(5-(1-(trifluoromethyl)cyclopropyl)isoxazol-3-yl)acetamide (105 mg) from Step 3 of this example in 2 mL of DMF were added DIEA (200 µL), 3,3-difluoropyrrolidine hydrochloride (200 µL), and KI (50 mg). The resulting mixture was heated at 80° C. for 1 d, and at 100° C. for an additional day before it was diluted with MeOH and purified by reverse-phase preparative HPLC using a mixture of water (containing 5% CH3CN and 0.05% HCOOH), and CH3CN (containing 0.05% HCOOH) as the mobile phase and a Varian Pursuit XRs diphenyl column as the stationary phase to afford 2-(4-(6-(2-(3,3-difluoropyrrolidin-1-yl)ethoxy)-7-methoxyquinoxalin-2-O-2-fluorophenyl)-N-(5-(1-(trifluoromethyl)cyclopropyl)isoxazol-3-yl)acetamide (47 mg) as a tan powder. 1H NMR (500 MHz, DMSO-d6) δ 11.45 (br s, 1H), 9.36 (s, 1H), 8.03-8.15 (m, 2H), 7.56 (t, J=8.0 Hz, 1H), 7.47 (s, 1H), 7.47 (s, 1H), 6.93 (s, 1H), 4.31 (t, J=5.5 Hz, 2H), 4.01 (s, 3H), 3.88 (s, 2H), 3.05 (t, J=13.4 Hz, 2H), 2.95 (t, J=5.5 Hz, 2H), 2.86 (t, J=6.9 Hz, 2H), 2.15-2.32 (m, 2H), 1.41-1.58 (m, 4H).

Example 83

Preparation of 2-(4-(6-bromo-7-methoxyquinoxalin-2-yl)-2-fluorophenyl)-N-(5-(1-(trifluoromethyl)cyclopropyl)isoxazol-3-yl)acetamide

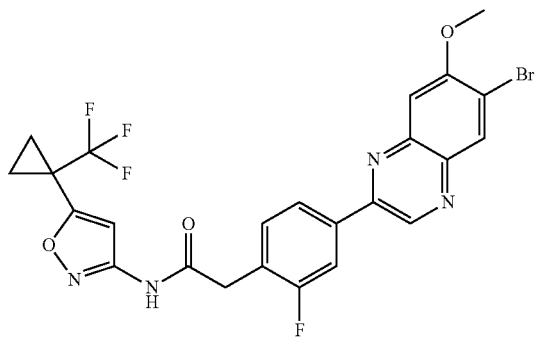 [SMILES: COc1cc2nc(-c3ccc(CC(=O)Nc4cc(C5(C(F)(F)F)CC5)on4)c(F)c3)cnc2cc1Br]

Step 1: Methyl 2-(N-(5-bromo-4-methoxy-2-nitrophenyl)acetamido)acetate (5.5 g) was obtained as a light greenish yellow solid using a procedure analogous to that described in Step 2 of Example 74, substituting methyl 2-bromoacetate for the 2-bromoethyl acetate used in Example 74. LC-MS (ESI) m/z 361, 363 (M+H)$^+$.

Step 2: A stirred mixture of methyl 2-(N-(5-bromo-4-methoxy-2-nitrophenyl)acetamido)acetate (5.5 g) from Step 1 of this example in 150 mL of MeOH with 20 mL of conc. sulfuric acid was heated under reflux for 5 d. The resulting mixture was cooled to rt and concentrated under reduced pressure. The residue was quenched with ice water, and the red solid was collected by filtration and dried in a vacuum oven to give methyl 2-((5-bromo-4-methoxy-2-nitrophenyl)amino)acetate (4.7 g). LC-MS (ESI) m/z 319, 321 (M+H)$^+$.

Step 3: To a stirred solution of methyl 2-((5-bromo-4-methoxy-2-nitrophenyl)amino)acetate (4.7 g, 14.7 mmol) from Step 2 of this example in 50 mL of DCM at rt was added AcOH (8.4 mL, 147 mmol). Freshly activated zinc (4.8 g, 73.4 mmol) was added in portions. The resulting mixture was stirred at rt overnight before it was partitioned between saturated aq NH$_4$Cl (75 mL) and DCM (200 mL). The aqueous layer was extracted with DCM (100 mL) once. The combined organic layers were washed with brine, dried over Mg$_2$SO$_4$, and concentrated under reduced pressure. The residue was taken up in 50 mL of MeOH, 4 N HCl in 1,4-dioxane (10 mL) was added, and the suspension was stirred at rt for 1 d. The mixture was concentrated under reduced pressure to give crude 6-bromo-7-methoxyquinoxalin-2(1H)-one (3.7 g). LC-MS (ESI) m/z 255, 257 (M+H)$^+$.

Step 4: 2-(4-(6-Bromo-7-methoxyquinoxalin-2-yl)-2-fluorophenyl)-N-(5-(1-(trifluoromethyl)cyclopropyl)isoxazol-3-yl)acetamide (360 mg) was obtained as a tan solid using a procedure analogous to that described in Steps 6-7 of Example 79, substituting 6-bromo-7-methoxyquinoxalin-2(1H)-one from Step 3 of this example for the 7-methoxy-6-(2-morpholinoethoxy)quinoxalin-2(1H)-one used in Example 79. $^1$H NMR (500 MHz, DMSO-d$_6$) δ 11.46 (br s, 1H), 9.48 (s, 1H), 8.41 (s, 1H), 8.10-8.20 (m, 2H), 7.64 (s, 1H), 7.61 (t, J=7.7 Hz, 1H), 6.93 (s, 1H), 4.09 (s, 3H), 3.90 (s, 2H), 1.44-1.56 (m, 4H). LC-MS (ESI) m/z 565, 567 (M+H)$^+$.

Example 84

Preparation of 2-(4-(6-(2,3-dihydroxypropyl)-7-methoxyquinoxalin-2-yl)-2-fluorophenyl)-N-(5-(1-(trifluoromethyl)cyclopropyl)isoxazol-3-yl)acetamide

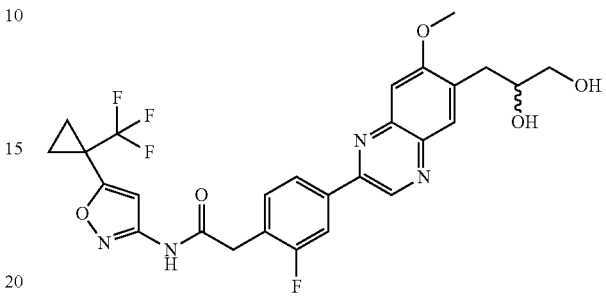

Step 1: To 2-(4-(6-bromo-7-methoxyquinoxalin-2-yl)-2-fluorophenyl)-N-(5-(1-(trifluoromethyl)cyclopropyl)isoxazol-3-yl)acetamide (100 mg, 0.18 mmol) from Example 83 were added CsF (81 mg, 0.53 mmol) and 2-allyl-4,4,5,5-tetramethyl-1,3,2-dioxaborolane (36 mg, 0.21 mmol). The resulting mixture was flushed with Ar while 3 mL of THF and Pd(PPh$_3$)$_4$ (20 mg, 0.018 mmol) were added with stirring. The resulting mixture was capped and heated at 80° C. for 2 h before cooling to rt. The mixture was partitioned between EtOAc (30 mL) and brine (20 mL). The organic layer was dried over Na$_2$SO$_4$, and concentrated under reduced pressure to give crude 2-(4-(6-allyl-7-methoxyquinoxalin-2-yl)-2-fluorophenyl)-N-(5-(1-(trifluoromethyl)cyclopropyl)isoxazol-3-yl)acetamide (95 mg), which was used directly for the next step. LC-MS (ESI) m/z 527 (M+H)$^+$.

Step 2: To a stirred solution of crude 2-(4-(6-allyl-7-methoxyquinoxalin-2-yl)-2-fluorophenyl)-N-(5-(1-(trifluoromethyl)cyclopropyl)isoxazol-3-yl)acetamide (95 mg, 0.18 mmol) from Step 1 of this example in 6 mL of THF/t-BuOH/H$_2$O (1:1:1, v/v/v) at rt was added OsO$_4$ (40 μL, 2.5 wt. % in t-BuOH) and N-methylmorpholine N-oxide (25 mg, 0.21 mmol). The resulting mixture was then stirred at rt for 5 h before it was diluted with MeOH and purified by reverse-phase preparative HPLC using a mixture of water (containing 5% CH$_3$CN and 0.05% HCOOH), and CH$_3$CN (containing 0.05% HCOOH) as the mobile phase and a Varian Pursuit XRs diphenyl column as the stationary phase to afford 2-(4-(6-(2,3-dihydroxypropyl)-7-methoxyquinoxalin-2-yl)-2-fluorophenyl)-N-(5-(1-(trifluoromethyl)cyclopropyl)isoxazol-3-yl)acetamide (23 mg, 23% over two steps) as a light tan powder. $^1$H NMR (500 MHz, DMSO-d$_6$) δ 11.43 (s, 1H), 9.36 (s, 1H), 8.03-8.15 (m, 2H), 7.57 (t, J=7.7 Hz, 1H), 7.48 (s, 1H), 7.45 (s, 1H), 6.93 (s, 1H), 5.03 (d, J=4.9 Hz, 1H), 4.71 (t, J=5.5 Hz, 1H), 4.24 (dd, J=3.8, 10.4 Hz, 1H), 4.11 (dd, J=6.3, 10.2 Hz, 1H), 4.01 (s, 3H), 3.90-3.96 (m, 1H), 3.88 (s, 2H), 3.51 (t, J=5.5 Hz, 2H), 1.43-1.57 (m, 4H). LC-MS (ESI) m/z 561 (M+H)$^+$.

Example 85

Preparation of 2-(2-fluoro-4-(7-methoxy-6-((2-morpholinoethyl)amino)quinoxalin-2-yl)phenyl)-N-(5-(1-(trifluoromethyl)cyclopropyl)isoxazol-3-yl)acetamide

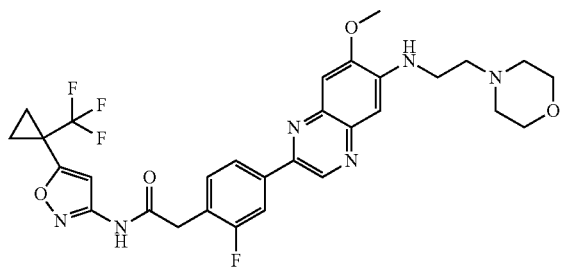 [SMILES: COc1cc2nc(-c3ccc(CC(=O)Nc4cc(C5(C(F)(F)F)CC5)on4)c(F)c3)cnc2cc1NCCN1CCOCC1]

Step 1: A stirred solution of 2-(4-(6-bromo-7-methoxyquinoxalin-2-yl)-2-fluorophenyl)-N-(5-(1-(trifluoromethyl)cyclopropyl)isoxazol-3-yl)acetamide (100 mg, 0.18 mmol) from Example 83 and 2-morpholinoethanamine (35 mg, 0.27 mmol) in 2 mL of 1,4-dioxane was flushed with argon while $Cs_2CO_3$ (115 mg, 0.35 mmol) was added, followed by addition of $Pd_2(dba)_3$ (8 mg, 0.009 mmol) and 4,5-bis(diphenylphosphino)-9,9-dimethylxanthene (10 mg, 0.17 mmol). The resulting mixture was capped and heated at 100° C. for 4 h and then stirred at rt overnight. The mixture was diluted with MeOH and DMSO, and purified by reverse-phase preparative HPLC using a mixture of water (containing 5% $CH_3CN$ and 0.05% HCOOH), and $CH_3CN$ (containing 0.05% HCOOH) as the mobile phase and a Varian Pursuit XRs diphenyl column as the stationary phase to afford 2-(2-fluoro-4-(7-methoxy-6-((2-morpholino ethyl) amino)quinoxalin-2-yl)phenyl)-N-(5-(1-(trifluoromethyl) cyclopropyl)isoxazol-3-yl)acetamide as a yellow powder. (5.0 mg, 5% yield). $^1$H NMR (500 MHz, DMSO-$d_6$) δ 9.21 (s, 1H), 8.34 (s, 1H), 7.99-8.09 (m, 2H), 7.52 (t, J=7.7 Hz, 1H), 7.32 (s, 1H), 7.14 (s, 1H), 6.87 (s, 1H), 6.01 (t, J=5.2 Hz, 1H), 4.05 (s, 3H), 3.88 (br s, 2H), 3.61 (t, J=4.4 Hz, 4H), 3.52-3.57 (m, 1H), 3.35-3.39 (m, 2H), 2.64 (t, J=6.6 Hz, 2H), 2.46 (br s, 4H), 1.37-1.44 (m, 2H), 1.28 (br s, 2H). LC-MS (ESI) m/z 615 (M+H)$^+$.

Example 86

Preparation of 2-(4-(7-ethoxy-6-methoxyquinolin-3-yl)-2-fluorophenyl)-N-(5-(1-(trifluoromethyl)cyclopropyl)isoxazol-3-yl)acetamide

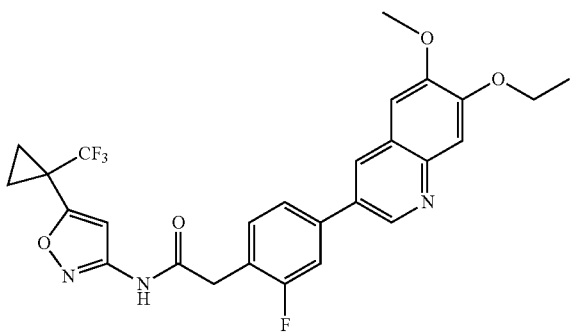 [SMILES: CCOc1cc2ncc(-c3ccc(CC(=O)Nc4cc(C5(C(F)(F)F)CC5)on4)c(F)c3)cc2cc1OC]

Step 1: A mixture of 5-amino-2-methoxyphenol (3.0 g, 21.56 mmol), 2-bromomalonaldehyde (4.23 g, 28.03 mmol), hydrobromic acid (5 mL of a 48% solution in water) and ethanol (40 mL) was stirred in a sealed pressure vessel at 90° C. for 15 h. After cooling to rt, the mixture was basified to pH ~8 with aq 1M NaOH. The mixture was filtered and the filtrate was concentrated under reduced pressure. The residue was partitioned between water and EtOAc, and the separated aqueous layer was re-extracted with EtOAc. The combined organic layers were washed with brine, dried over $MgSO_4$, filtered, and concentrated under reduced pressure. The residue was purified by silica gel flash chromatography eluting with 100% hexane to 100% EtOAc to afford 3-bromo-6-methoxyquinolin-7-ol (225 mg, 4%) as a solid. $^1$H NMR (500 MHz, DMSO-$d_6$) δ 10.21 (s, 1H), 8.62 (d, J=2.0 Hz, 1H), 8.40 (d, J=2.0 Hz, 1H), 7.30 (s, 1H), 7.25 (s, 1H), 3.91 (s, 3H); LC-MS (ESI) m/z 254 and 256 (M+H)$^1$.

Step 2: To a stirred mixture of 3-bromo-6-methoxyquinolin-7-ol (225 mg, 0.89 mmol) and anhydrous DMF (1 mL) at rt was added cesium carbonate (578 mg, 1.77 mmol). The mixture was stirred at rt for 15 min. A solution of iodoethane (208 mg, 1.34 mmol) in DMF (0.5 mL) was added, and the mixture was stirred at rt for 1.5 h. Saturated aq $NH_4Cl$ (3 mL) and water (15 mL) were added, and the mixture was stirred at rt for 5 min. The separated aqueous phase was extracted with EtOAc (×3) and the combined organic layers were washed with brine, dried over $MgSO_4$, filtered, and concentrated under reduced pressure to afford 3-bromo-7-ethoxy-6-methoxyquinoline (250 mg) as a yellow solid, which was not purified further. $^1$H NMR (500 MHz, DMSO-$d_6$) 8.68 (d, J=2.0 Hz, 1H), 8.45 (d, J=2.0 Hz, 1H), 7.35 (s, 1H), 7.33 (s, 1H), 4.20 (q, J=7.0 Hz, 2H), 3.91 (s, 3H), 1.41 (t, J=7.0 Hz, 3H); LC-MS (ESI) m/z 282 and 284 (M+H)$^1$.

Step 3: 2-(4-(7-Ethoxy-6-methoxyquinolin-3-yl)-2-fluorophenyl)-N-(5-(1-(trifluoromethyl)cyclopropyl)isoxazol-3-yl)acetamide (26 mg, 15%) was obtained as a solid using a procedure analogous to that described in Step 3 of Example 4, substituting 3-bromo-7-ethoxy-6-methoxyquinoline for the 2-chloro-6,7-dimethoxyquinoxaline used in Example 4. $^1$H NMR (500 MHz, DMSO-$d_6$) δ 11.43 (br s, 1H), 9.03 (s, 1H), 8.49 (s, 1H), 7.64-7.70 (m, 2H), 7.51 (m, 1H), 7.38-7.39 (m, 2H), 6.93 (s, 1H), 4.21 (q, J=6.5 Hz, 2H), 3.93 (s, 3H), 3.85 (s, 2H), 1.42-1.53 (m, 7H); LC-MS (ESI) m/z 530 (M+H)$^1$.

Example 87

Preparation of 2-(2-Fluoro-4-{6-[2-(3-fluoro-4-hydroxy-piperidin-1-yl)-ethoxy]-7-methoxy-quinolin-3-yl}-phenyl)-N-[5-(2,2,2-trifluoro-1,1-dimethyl-ethyl)-isoxazol-3-yl]-acetamide

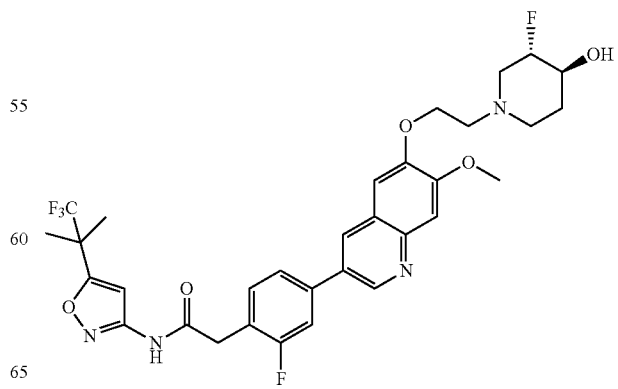

Step 1: A mixture of 2-methoxy-4-nitro-phenol (1.0 g, 6.0 mmol), (1,3)dioxolan-2-one (0.57 g, 6.5 mmol) and tetrabutylammonium iodide (0.21 g, 0.57 mmol) was stirred at 160° C. for 2 h. After cooling to rt, EtOAc was added and the solution was washed with brine. The organic layer was dried over $Na_2SO_4$ and concentrated under reduced pressure to afford 2-(2-methoxy-4-nitro-phenoxy)-ethanol as a yellow solid (1.3 g, 100% yield). $^1$H NMR (300 MHz, $CDCl_3$) δ 7.88 (dd, 1H), 7.74 (d, 1H), 6.93 (d, 2H), 4.23 (t, 2H), 4.11 (t, 2H), 3.93 (s, 3H), 2.27 (t, 1H).

Step 2: To a solution of 2-(2-methoxy-4-nitro-phenoxy)-ethanol (1.3 g, 6.0 mmol) and pyridine (0.57 g, 7.2 mmol) in THF was added acetyl chloride (0.56 g, 7.2 mmol) at 0° C. The mixture was stirred at 0° C. for 2 h, and then warmed to rt. The resulting solution was poured into water and extracted with EtOAc. The organic layer was washed with brine, dried over $Na_2SO_4$, and concentrated under reduced pressure to afford 2-(2-methoxy-4-nitrophenoxy)ethyl acetate as a yellow solid. (1.5 g, 100% yield). $^1$H NMR (300 MHz, $CDCl_3$) δ 7.88 (dd, 1H), 7.74 (d, 1H), 6.91 (d, 2H), 4.46 (t, 2H), 4.30 (t, 2H), 3.92 (s, 3H), 2.10 (s, 1H).

Step 3: To a solution of 2-(2-methoxy-4-nitrophenoxy)ethyl acetate (1.5 g) in EtOAc (20 mL) and THF (20 mL) was added 50% wet Pd/C (0.3 g), and the mixture was stirred at rt under 50 psi of $H_2$ for 16 h. The mixture was filtered through a Celite plug, and the filtrate was concentrated under reduced pressure to afford 2-(4-amino-2-methoxyphenoxy)ethyl acetate as a red oil (1.3 g, 100% yield).

Step 4: To a mixture of 2-(4-amino-2-methoxyphenoxy)ethyl acetate (450 mg, 2.0 mmol) from Step 3 of this example in EtOH (12 mL) was added 2-bromo-malonaldehyde (363 mg, 2.4 mmol), aq 40% HBr (1.2 g), the mixture was stirred at 110° C. in a microwave reactor for 1 h. The mixture was cooled to rt, then adjusted to pH~7 with saturated aq $NaHCO_3$. The mixture was extracted with EtOAc, and the organic layer was washed with brine and dried over $Na_2SO_4$ and filtered. The filtrate was concentrated under reduced pressure and purified by silica gel column chromatography, eluted with EtOAc, to afford 2-(3-bromo-7-methoxy-quinolin-6-yloxy)-ethanol (85 mg, 14% yield).

Step 5: To a mixture of 2-(3-bromo-7-methoxy-quinolin-6-yloxy)-ethanol (1.0 g, 3.37 mmol) and TEA (1.0 g, 10.1 mmol) and DCM (10 mL) was added dropwise methanesulfonyl chloride (0.58 g, 5.05 mmol) in DCM (2 mL) with stirring at 0° C. The mixture was stirred at 0° C. for 2 h. EtOAc (50 mL) was added and the solution was washed with brine (3×). The organic layer was dried over $Na_2SO_4$ and concentrated under reduced pressure to afford 2-((3-bromo-7-methoxyquinolin-6-yl)oxy)ethyl methanesulfonate as a solid (0.9 g, 71% yield), which was used directly in the next step.

Step 6: To a solution of 2-((3-bromo-7-methoxyquinolin-6-yl)oxy)ethyl methanesulfonate (260 mg, 0.69 mmol) in $CH_3CN$ (5 mL) were added 2-[2-fluoro-4-(4,4,5,5-tetramethyl-[1,3,2]dioxaborolan-2-yl)-phenyl]-N-[5-(2,2,2-trifluoro-1,1-dimethyl-ethyl)-isoxazol-3-yl]-acetamide (314 mg, 0.69 mmol), $Pd(dppf)Cl_2$ (51 mg, 0.069 mmol), $Na_2CO_3$ (220 mg, 2.1 mmol) and water (2 mL) under argon. The mixture was heated at reflux under argon for 2 h. EtOAc and $Na_2SO_4$ were added to the cooled mixture, and then the mixture was filtered. The filtrate was concentrated under reduced pressure and the residue was purified by silica gel column chromatography eluting with petroleum ether/EtOAc (v/v=8/1 to 0/1) to afford 2-((3-(3-fluoro-4-(2-oxo-2-((5-(1,1,1-trifluoro-2-methylpropan-2-yl)isoxazol-3-yl)amino)ethyl)phenyl)-7-methoxyquinolin-6-yl)oxy)ethyl methanesulfonate as a solid (200 mg, 46% yield).

Step 7: A mixture of tert-butyl (3S,4S)-3-fluoro-4-hydroxypiperidinecarboxylate (110 mg, 0.5 mmol) in 2 mL $HCl/Et_2O$ was stirred for 16 h, filtered and concentrated to give (3S,4S)-3-fluoropiperidin-4-ol hydrochloride salt as a white solid. The solid was added to a mixture of 2-((3-(3-fluoro-4-(2-oxo-2-((5-(1,1,1-trifluoro-2-methylpropan-2-yl)isoxazol-3-yl)amino)ethyl)phenyl)-7-methoxyquinolin-6-yl)oxy)ethyl methanesulfonate (210 mg, 0.34 mmol), $K_2CO_3$ (138 mg, 1.0 mmol), KI (15 mg) and DMF (3 mL). The mixture was stirred at 60° C. for 16 h, cooled to rt, and concentrated under reduced pressure. The residue was purified by preparative HPLC (214 nm, flow rate 15 mL/min, mobile phase: 0.1% $NH_4OH/H_2O$:ACN (gradient 75:25 to 5:95) followed by preparative TLC to afford 2-(2-fluoro-4-(6-(2-(((3S,4S)-3-fluoro-4-hydroxypiperidin-1-yl)ethoxy)-7-methoxyquinolin-3-yl)phenyl)-N-(5-(1,1,1-trifluoro-2-methylpropan-2-yl)isoxazol-3-yl)acetamide as a yellow solid (30 mg, 14% yield). $^1$H NMR (300 MHz, DMSO-d6) δ 11.48 (s, 1H), 9.04 (d, 1H), 8.47 (d, 1H), 7.64 (m, 2H), 7.52 (t, 2H), 7.45 (s, 1H), 7.41 (s, 1H), 6.96 (s, 1H), 5.18 (d, 1H), 4.31 (m, 1H), 4.21 (t, 2H), 3.95 (s, 3H), 3.86 (s, 2H), 3.40 (m, 1H), 3.17 (m, 1H), 2.84 (m, 3H), 2.20 (m, 2H), 1.70 (m, 1H), 1.54 (s, 6H), 1.35 (m, 1H). LCMS (ESI) m/z 649

Example 88

Preparation of 2-(2-fluoro-4-(7-(2-hydroxyethoxy)-6-methoxyquinolin-3-yl)phenyl)-N-(5-(1-(trifluoromethyl)cyclopropyl)isoxazol-3-yl)acetamide

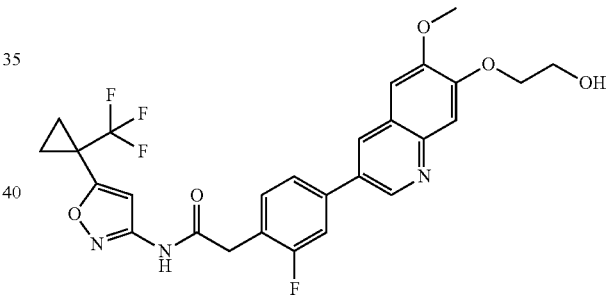

Step 1: 2-(2-Methoxy-5-nitrophenoxy)ethyl acetate was obtained as a yellow solid using a procedure analogous to that described in Step 2 of Example 74, substituting 2-methoxy-5-nitrophenol for the 2-bromoquinoxaline-6,7-diol used in Example 74. LC-MS (ESI) m/z 256 (M+H)$^1$.

Step 2: 2-(5-Amino-2-methoxyphenoxy)ethyl acetate was obtained as a brown oil using a procedure analogous to that described in Step 3 of Example 87, substituting 2-(2-methoxy-5-nitrophenoxy)ethyl acetate from Step 1 of this example for the 2-(2-methoxy-4-nitrophenoxy)ethyl acetate used in Example 87. LC-MS (ESI) m/z 226 (M+H)$^+$.

Step 3: To a stirred solution of 2-(5-amino-2-methoxyphenoxy)ethyl acetate (1.0 g, 4.4 mmol) in 7 mL of EtOH were added 2-bromomalonaldehyde (0.87 g, 5.8 mmol) and 48% HBr (0.85 mL). The resulting dark brown mixture was heated at 140° C. for 30 min in a microwave reactor. The same process was repeated two more times and the combined reaction mixtures were treated with 3N NaOH to pH~10. The resulting mixture was extracted with DCM/MeOH (5:1) twice. The combined organic layers were washed with brine, dried over $MgSO_4$, and concentrated under reduced pressure. The residue was purified by silica gel column chromatography eluting with 0-95% EtOAc in hexanes to give 2-((3-bromo-6-methoxyquinolin-7-yl)oxy)ethanol (450 mg, 11% yield) as a yellow solid. LC-MS (ESI) m/z 298, 300 (M+H)+.

Step 4: 2-(2-Fluoro-4-(7-(2-hydroxyethoxy)-6-methoxyquinolin-3-yl)phenyl)-N-(5-(1-(trifluoromethyl)cyclopropyl)isoxazol-3-yl)acetamide (260 mg) was obtained as a white solid using a procedure analogous to that described in Step 3 of Example 4, substituting 2-((3-bromo-6-methoxyquinolin-7-yl)oxy)ethanol for the 2-chloro-6,7-dimethoxyquinoxaline used in Example 4. $^1$H NMR (500 MHz, DMSO-d$_6$) δ 11.44 (br s, 1H), 9.03 (d, J=2.2 Hz, 1H), 8.49 (d, J=2.2 Hz, 1H), 7.69 (d, J=11.0 Hz, 1H), 7.65 (d, J=7.7 Hz, 1H), 7.52 (t, J=8.0 Hz, 1H), 7.41 (br s, 1H), 7.40 (br s, 1H), 6.94 (s, 1H), 4.93 (t, J=5.2 Hz, 1H), 4.18 (t, J=4.9 Hz, 2H), 3.94 (s, 3H), 3.85 (s, 2H), 3.77-3.84 (m, 2H), 1.44-1.57 (m, 4H). LC-MS (ESI) m/z 546 (M+H)+.

Example 89

Preparation of 2-(4-(6-(azetidin-3-yloxy)-7-methoxyquinoxalin-2-yl)-2-fluorophenyl)-N-(5-(1-(trifluoromethyl)cyclopropyl)isoxazol-3-yl)acetamide

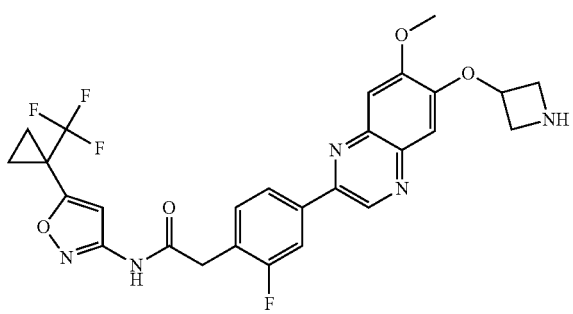 [SMILES: COc1cc2nc(-c3ccc(CC(=O)Nc4cc(C5(C(F)(F)F)CC5)on4)c(F)c3)cnc2cc1OC1CNC1]

Step 1: A procedure analogous to that described in steps 1-6 of Example 77a was followed, substituting tert-butyl 3-((methylsulfonyl)oxy)azetidine-1-carboxylate for the 1-bromo-2-methoxyethane used in Step 1 of Example 77'. The crude tert-butyl 3-((2-(3-fluoro-4-(2-oxo-2-((5-(1-(trifluoromethyl)cyclopropyl)isoxazol-3-yl)amino)ethyl)phenyl)-7-methoxyquinoxalin-6-yl)oxy)azetidine-1-carboxylate (430 mg) from the last step of the sequence was isolated as a light tan oil and carried directly to the next step . . . LC-MS (ESI) m/z 658 (M+H)+.

Step 2: To a stirred solution of tert-butyl 3-((2-(3-fluoro-4-(2-oxo-2-((5-(1-(trifluoromethyl)cyclopropyl)isoxazol-3-yl)amino)ethyl)phenyl)-7-methoxyquinoxalin-6-yl)oxy)azetidine-1-carboxylate (430 mg) in 5 mL of DCM at rt was added TFA (5 mL). The resulting mixture was stirred at rt for 30 min before the mixture was concentrated under reduced pressure. A portion of the residue was purified by reverse-phase preparative HPLC using a mixture of water (containing 5% CH$_3$CN and 0.05% HCOOH), and CH$_3$CN (containing 0.05% HCOOH) as the mobile phase and a Varian Pursuit XRs diphenyl column as the stationary phase to afford 2-(4-(6-(azetidin-3-yloxy)-7-methoxyquinoxalin-2-yl)-2-fluorophenyl)-N-(5-(1-(trifluoromethyl)cyclopropyl)isoxazol-3-yl)acetamide (20 mg) as a white powder. $^1$H NMR (500 MHz, DMSO-d$_6$) δ 11.45 (br s, 1H), 9.38 (s, 1H), 8.06-8.16 (m, 2H), 7.57 (t, J=8.0 Hz, 1H), 7.52 (s, 1H), 7.18 (s, 1H), 6.93 (s, 1H), 5.27 (br s, 1H), 4.13 (br s, 2H), 3.98-4.06 (m, 3H), 3.78 (br s, 2H), 1.41-1.58 (m, 4H).

Example 90

Preparation of 2-(2-fluoro-4-(7-methoxy-6-((1-methylazetidin-3-yl)oxy)quinoxalin-2-yl)phenyl)-N-(5-(1-(trifluoromethyl)cyclopropyl)isoxazol-3-yl)acetamide

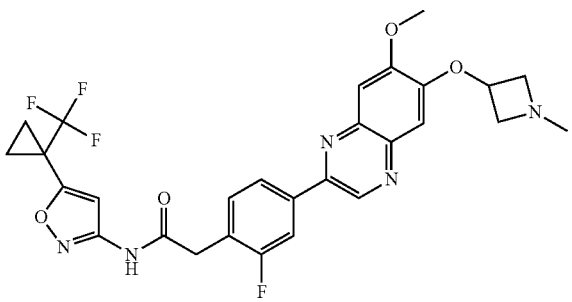 [SMILES: COc1cc2nc(-c3ccc(CC(=O)Nc4cc(C5(C(F)(F)F)CC5)on4)c(F)c3)cnc2cc1OC1CN(C)C1]

Step 1: To a stirred solution of crude 2-(4-(6-(azetidin-3-yloxy)-7-methoxyquinoxalin-2-yl)-2-fluorophenyl)-N-(5-(1-(trifluoromethyl)cyclopropyl)isoxazol-3-yl)acetamide (150 mg) from Example 89 in 3 mL of pH 4 MeOH buffer at 0° C. was added HCHO (37% in water, 100 μL), followed by NaCNBH$_3$ (100 mg). The resulting mixture was stirred at rt for 30 min before it was purified by reverse-phase preparative HPLC using a mixture of water (containing 5% CH$_3$CN and 0.05% HCOOH), and CH$_3$CN (containing 0.05% HCOOH) as the mobile phase and a Varian Pursuit XRs diphenyl column as the stationary phase to afford 2-(2-fluoro-4-(7-methoxy-6-((1-methylazetidin-3-yl)oxy)quinoxalin-2-yl)phenyl)-N-(5-(1-(trifluoromethyl)cyclopropyl)isoxazol-3-yl)acetamide. $^1$H NMR (500 MHz, DMSO-d$_6$) δ 11.45 (s, 1H), 9.37 (s, 1H), 8.04-8.17 (m, 3H), 7.57 (t, J=7.7 Hz, 1H), 7.50 (s, 1H), 7.16-7.22 (m, 1H), 6.93 (s, 1H), 5.01-5.10 (m, 1H), 4.02 (s, 3H), 3.91-3.98 (m, 2H), 3.88 (s, 2H), 3.25 (d, J=4.9 Hz, 2H), 2.39 (s, 3H), 1.43-1.56 (m, 4H).

Example 91

Preparation of 2-(2-fluoro-4-(7-(2-hydroxyethoxy)-6-methoxyquinolin-3-yl)phenyl)-N-(5-(1,1,1-trifluoro-2-methylpropan-2-yl)isoxazol-3-yl)acetamide

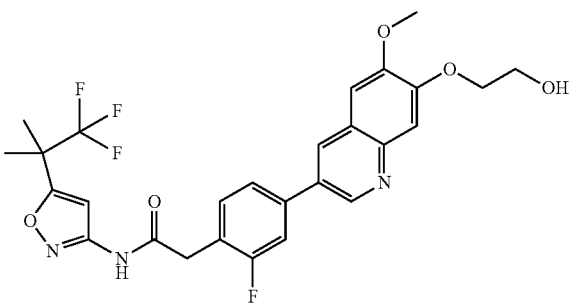 [SMILES: COc1cc2cc(-c3ccc(CC(=O)Nc4cc(C(C)(C)C(F)(F)F)on4)c(F)c3)cnc2cc1OCCO]

Step 1: 2-(2-Fluoro-4-(7-(2-hydroxyethoxy)-6-methoxyquinolin-3-yl)phenyl)-N-(5-(1,1,1-trifluoro-2-methylpropan-2-yl)isoxazol-3-yl)acetamide (120 mg) was obtained as a yellow solid using a procedure analogous to that described in Step 3 of Example 4, substituting 2-((3-bromo-6-methoxyquinolin-7-yl)oxy)ethanol from Example 88 and 2-(2-fluoro-4-(4,4,5,5-tetramethyl-1,3,2-dioxaborolan-2-yl)phenyl)-N-(5-(1,1,1-trifluoro-2-methylpropan-2-yl)isoxazol-3-yl)acetamide for, respectively, the 2-chloro-6,7-dimethoxyquinoxaline and the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. $^1$H NMR (500 MHz, DMSO-d$_6$) δ 11.44 (s, 1H), 9.03 (d, J=2.2 Hz, 1H), 8.49 (d, J=1.6 Hz, 1H), 7.69 (d, J=11.0 Hz, 1H), 7.65 (d, J=7.7 Hz, 1H), 7.52 (t, J=8.0 Hz, 1H), 7.41 (br s, 1H), 7.40 (br s, 1H), 6.95 (s, 1H), 4.93 (t, J=5.2 Hz, 1H), 4.18 (t, J=4.9 Hz, 2H), 3.94 (s, 3H), 3.86 (s, 2H), 3.82 (q, J=4.9 Hz, 2H), 1.54 (s, 6H). LC-MS (ESI) m/z 548 (M+H)$^+$.

Example 92

Preparation of N-(5-(tert-butyl)isoxazol-3-yl)-2-(2-fluoro-4-(7-methoxy-6-(2-morpholinoethoxy)quinoxalin-2-yl)phenyl)acetamide

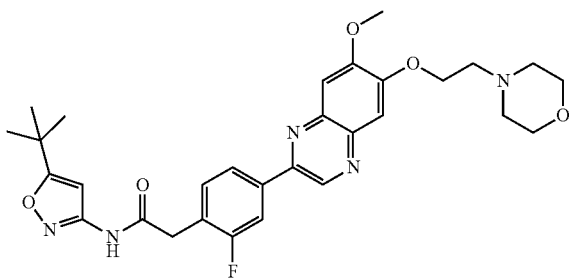 [SMILES: COc1cc2nc(-c3ccc(CC(=O)Nc4cc(C(C)(C)C)on4)c(F)c3)cnc2cc1OCCN1CCOCC1]

Step 1: N-(5-(tert-Butyl)isoxazol-3-yl)-2-(2-fluoro-4-(7-methoxy-6-(2-morpholinoethoxy)quinoxalin-2-yl)phenyl)acetamide (86 mg) was obtained as a tan powder using a procedure analogous to that described in Step 3 of Example 4, substituting 4-(2-((2-chloro-7-methoxyquinoxalin-6-yl)oxy)ethyl)morpholine from Step 6 of Example 79 and N-(5-(tert-butyl)isoxazol-3-yl)-2-(2-fluoro-4-(4,4,5,5-tetramethyl-1,3,2-dioxaborolan-2-yl)phenyl)acetamide, respectively, for the 2-chloro-6,7-dimethoxyquinoxaline and the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. $^1$HNMR (500 MHz, DMSO-d$_6$) δ 11.27 (br s, 1H), 9.36 (s, 1H), 8.05-8.15 (m, 2H), 7.56 (t, J=8.0 Hz, 1H), 7.48 (s, 1H), 7.46 (s, 1H), 6.58 (s, 1H), 4.32 (t, J=5.8 Hz, 2H), 4.00 (s, 3H), 3.86 (s, 2H), 3.60 (t, J=4.4 Hz, 4H), 2.80 (t, J=5.8 Hz, 2H), 2.53 (br s, 4H), 1.28 (s, 9H).

Example 93

Preparation of 2-(4-(7-methoxy-6-(2-morpholinoethoxy)quinoxalin-2-yl)phenyl)-N-(5-(1,1,1-trifluoro-2-methylpropan-2-yl)isoxazol-3-yl)acetamide

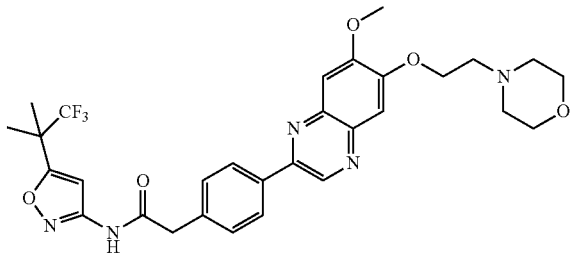 [SMILES: COc1cc2nc(-c3ccc(CC(=O)Nc4cc(C(C)(C)C(F)(F)F)on4)cc3)cnc2cc1OCCN1CCOCC1]

Step 1: 2-(4-(7-Methoxy-6-(2-morpholinoethoxy)quinoxalin-2-yl)phenyl)-N-(5-(1,1,1-trifluoro-2-methylpropan-2-yl)isoxazol-3-yl)acetamide (22 mg) was obtained as a yellow powder using a procedure analogous to that described in Step 3 of Example 4, substituting 4-(2-((2-chloro-7-methoxyquinoxalin-6-yl)oxy)ethyl)morpholine from Step 6 of Example 79 and 2-(4-(4,4,5,5-tetramethyl-1,3,2-dioxaborolan-2-yl)phenyl)-N-(5-(1,1,1-trifluoro-2-methylpropan-2-yl)isoxazol-3-yl)acetamide, respectively, for the 2-chloro-6,7-dimethoxyquinoxaline and the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. $^1$H NMR (500 MHz, DMSO-d$_6$) δ 11.41 (br s, 1H), 9.32 (s, 1H), 8.24 (d, J=8.2 Hz, 2H), 7.51 (d, J=8.2 Hz, 2H), 7.47 (s, 1H), 7.45 (s, 1H), 6.96 (s, 1H), 4.32 (t, J=5.5 Hz, 2H), 4.00 (s, 3H), 3.80 (s, 2H), 3.60 (t, J=4.4 Hz, 4H), 2.80 (t, J=5.5 Hz, 2H), 2.54 (d, J=4.4 Hz, 4H), 1.54 (s, 6H).

Example 94

Preparation of 2-(2-fluoro-4-(7-methoxy-6-(2-morpholinoethoxy)quinoxalin-2-yl)phenyl)-N-(1-methyl-3-(1,1,1-trifluoro-2-methylpropan-2-yl)-1H-pyrazol-5-yl)acetamide

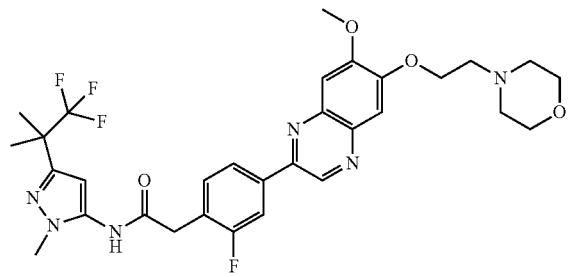 [SMILES: COc1cc2nc(-c3ccc(CC(=O)Nc4cc(C(C)(C)C(F)(F)F)nn4C)c(F)c3)cnc2cc1OCCN1CCOCC1]

Step 1: To a stirred mixture of 1-methyl-3-(1,1,1-trifluoro-2-methylpropan-2-yl)-1H-pyrazol-5-amine (125 mg, 0.603 mmol), 2-(2-fluoro-4-(4,4,5,5-tetramethyl-1,3,2-dioxaborolan-2-yl)phenyl)acetic acid (169 mg, 0.603 mmol), pyridine (146 μL, 1.81 mmol), and ethyl acetate (1 mL) at 0° C. was slowly added propylphosphonic anhydride (50% in EtOAc, 718 iut, 1.21 mmol). The resulting mixture was stirred at rt for 30 min, then heated at 60° C. for 2 h. The mixture was then partitioned between EtOAc and saturated aq NH₄Cl. The organic layer was separated, dried over MgSO₄ and concentrated under reduced pressure. The residue was purified by silica gel flash chromatography eluting with 0 to 100% EtOAc in hexanes to afford 2-(2-fluoro-4-(4,4,5,5-tetramethyl-1,3,2-dioxaborolan-2-yl)phenyl)-N-(1-methyl-3-(1,1,1-trifluoro-2-methylpropan-2-yl)-1H-pyrazol-5-yl)acetamide as a white solid (154 mg, 54%). LC-MS (ESI) m/z 470 (M+H)⁺.

Step 2: 2-(2-Fluoro-4-(7-methoxy-6-(2-morpholinoethoxy)quinoxalin-2-yl)phenyl)-N-(1-methyl-3-(1,1,1-trifluoro-2-methylpropan-2-yl)-1H-pyrazol-5-yl)acetamide (60 mg, 45%) was obtained as a cream solid using a procedure analogous to that described in Step 3 of Example 4, substituting 4-(2-((2-chloro-7-methoxyquinoxalin-6-yl)oxy)ethyl)morpholine from Step 6 of Example 79 and 2-(2-fluoro-4-(4,4,5,5-tetramethyl-1,3,2-dioxaborolan-2-yl)phenyl)-N-(1-methyl-3-(1,1,1-trifluoro-2-methylpropan-2-yl)-1H-pyrazol-5-yl)acetamide from Step 1 of this Example, respectively, for the 2-chloro-6,7-dimethoxyquinoxaline and the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. ¹H NMR (500 MHz, DMSO-d₆) δ 10.28 (s, 1H), 9.37 (s, 1H), 8.05-8.15 (m, 2H), 7.59 (t, J=7.7 Hz, 1H), 7.49 (s, 1H), 7.47 (s, 1H), 6.29 (s, 1H), 4.33 (t, J=5.8 Hz, 2H), 4.00 (s, 3H), 3.88 (s, 2H), 3.60 (t, J=4.4 Hz, 4H), 3.30 (s, 3H), 2.81 (t, J=5.8 Hz, 2H), 2.53 (br s, 4H), 1.44 (s, 6H).

Example 95

Preparation of 2-(2-fluoro-4-(7-methoxy-6-(2-morpholinoethoxy)quinoxalin-2-yl)phenyl)-N-(3-(1-methylcyclopropyl)isoxazol-5-yl)acetamide

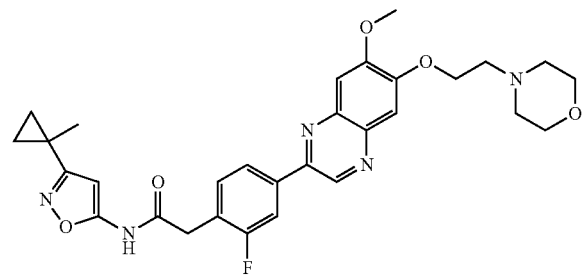 [SMILES: COc1cc2nc(-c3ccc(CC(=O)Nc4cc(C5(C)CC5)no4)c(F)c3)cnc2cc1OCCN1CCOCC1]

Step 1: 2-(2-Fluoro-4-(4,4,5,5-tetramethyl-1,3,2-dioxaborolan-2-yl)phenyl)-N-(3-(1-methylcyclopropyl)isoxazol-5-yl)acetamide was obtained as a white solid (650 mg, 90%) using a procedure analogous to that described in Step 1 of Example 94, substituting 3-(1-methylcyclopropyl)isoxazol-5-amine for the 1-methyl-3-(1,1,1-trifluoro-2-methylpropan-2-yl)-1H-pyrazol-5-amine used in Example 94. LC-MS (ESI) m/z 401 (M+H)⁺.

Step 2: 2-(2-Fluoro-4-(7-methoxy-6-(2-morpholinoethoxy)quinoxalin-2-yl)phenyl)-N-(3-(1-methylcyclopropyl)isoxazol-5-yl)acetamide (83 mg, 45%) was obtained as a cream solid using a procedure analogous to that described in Step 3 of Example 4, substituting 4-(2-((2-chloro-7-methoxyquinoxalin-6-yl)oxy)ethyl)morpholine from Step 6 of Example 79 and 2-(2-fluoro-4-(4,4,5,5-tetramethyl-1,3,2-dioxaborolan-2-yl)phenyl)-N-(3-(1-methylcyclopropyl)isoxazol-5-yl)acetamide from Step 1 of this Example, respectively, for the 2-chloro-6,7-dimethoxyquinoxaline and the 2-(2-fluoro-4-(4,4,5,5-tetramethyl-1,3,2-dioxaborolan-2-yl)phenyl)-N-(5-(1-(trifluoromethyl)cyclopropyl)isoxazol-3-yl)acetamide used in Example 4. ¹H NMR (499 MHz, DMSO-d₆) δ 11.84 (br s, 1H), 9.36 (s, 1H), 8.03-8.18 (m, 2H), 7.56 (t, J=8.0 Hz, 1H), 7.47-7.52 (m, 1H), 7.47 (s, 1H), 5.96 (s, 1H), 4.32 (t, J=5.8 Hz, 2H), 4.00 (s, 3H), 3.88 (s, 2H), 3.60 (t, J=4.4 Hz, 4H), 2.81 (t, J=5.5 Hz, 2H), 2.53 (br s, 4H), 1.36 (s, 3H), 0.88-0.96 (m, 2H), 0.77-0.84 (m, 2H).

Example 96

Preparation of 2-(4-(6-(2-(3,3-dimethylmorpholino)ethoxy)-7-methoxyquinoxalin-2-yl)-2-fluorophenyl)-N-(5-(1-(trifluoromethyl)cyclopropyl)isoxazol-3-yl)acetamide

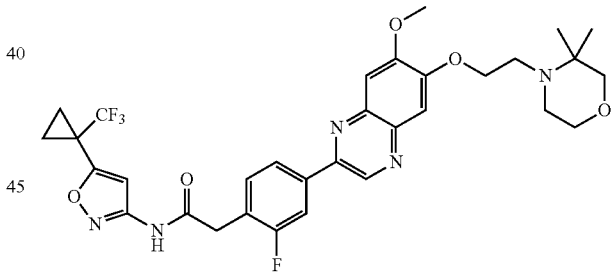

Step 1: 2-(4-(6-(2-(3,3-Dimethylmorpholino)ethoxy)-7-methoxyquinoxalin-2-yl)-2-fluorophenyl)-N-(5-(1-(trifluoromethyl)cyclopropyl)isoxazol-3-yl)acetamide (30 mg, 45%) was obtained as a tan solid using a procedure analogous to that described in Step 5 of Example 81, substituting 3,3-dimethyl morpholine for the N-methylpiperazine used in Example 81. ¹H NMR (500 MHz, DMSO-d₆) δ 11.41 (br s, 1H), 9.36 (s, 1H), 8.04-8.14 (m, 2H), 7.57 (t, J=8.0 Hz, 1H), 7.46 (s, 1H), 7.46 (br s, 1H), 6.93 (s, 1H), 4.22 (t, J=6.0 Hz, 2H), 4.00 (s, 3H), 3.88 (s, 2H), 3.61 (t, J=4.7 Hz, 2H), 3.22 (s, 2H), 2.79 (br s, 2H), 2.66-2.72 (m, 2H), 1.45-1.55 (m, 4H), 0.99 (s, 6H). LC-MS (ESI) m/z 644 (M+H)⁺.

The compounds in Table 1 were prepared using similar processes as shown in the previous examples.

TABLE 1

| Chemical Structure | Example Number | Example Name | Observed m/z |
|---|---|---|---|
| 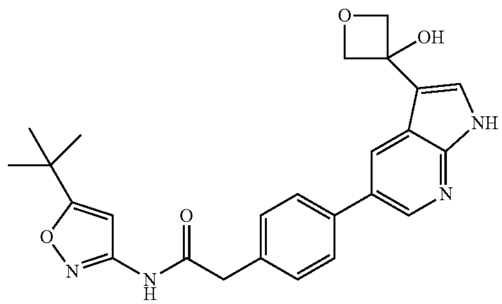 [SMILES: CC(C)(C)c1cc(NC(=O)Cc2ccc(-c3cnc4[nH]cc(C5(O)COC5)c4c3)cc2)no1] | 97 | N-(5-tert-butylisoxazol-3-yl)-2-[4-[3-(3-hydroxyoxetan-3-yl)-1H-pyrrolo[2,3-b]pyridin-5-yl]phenyl]acetamide | 447 (M + H)+ |
| 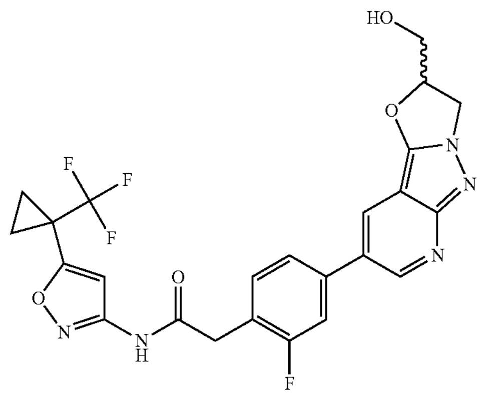 [SMILES: O=C(Cc1ccc(-c2cnc3nn4c(c3c2)OC(CO)C4)cc1F)Nc1cc(C2(C(F)(F)F)CC2)on1] | 98 | 2-[2-fluoro-4-[2-(hydroxymethyl)-2,3-dihydro-oxazolo[3,4]pyrazolo[1,3-b]pyridin-8-yl]phenyl]-N-[5-[1-(trifluoromethyl)cyclopropyl]isoxazol-3-yl]acetamide | 518 (M + H)+ |
| 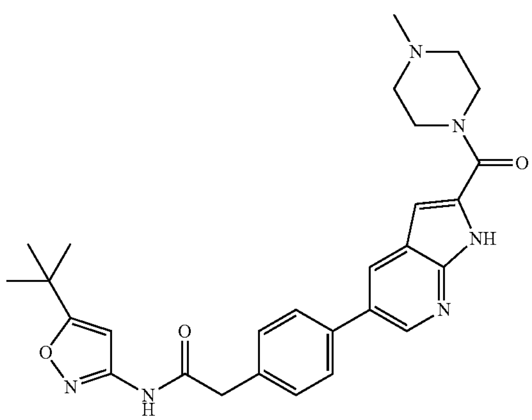 [SMILES: CN1CCN(C(=O)c2cc3cc(-c4ccc(CC(=O)Nc5cc(C(C)(C)C)on5)cc4)cnc3[nH]2)CC1] | 99 | N-(5-tert-butylisoxazol-3-yl)-2-[4-[2-(4-methylpiperazine-1-carbonyl)-1H-pyrrolo[2,3-b]pyridin-5-yl]phenyl]acetamide | 501 (M + H)+ |
| 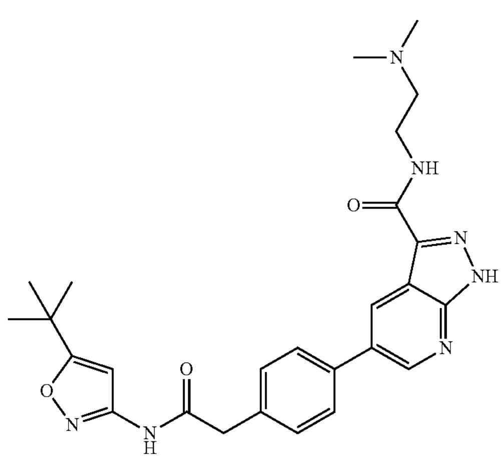 [SMILES: CN(C)CCNC(=O)c1n[nH]c2ncc(-c3ccc(CC(=O)Nc4cc(C(C)(C)C)on4)cc3)cc12] | 100 | 5-[4-[2-[(5-tert-butylisoxazol-3-yl)amino]-2-oxo-ethyl]phenyl]-N-[2-(dimethylamino)ethyl]-1H-pyrazolo[3,4-b]pyridine-3-carboxamide | 490 (M + H)+ |

TABLE 1-continued

| Chemical Structure | Example Number | Example Name | Observed m/z |
|---|---|---|---|
| 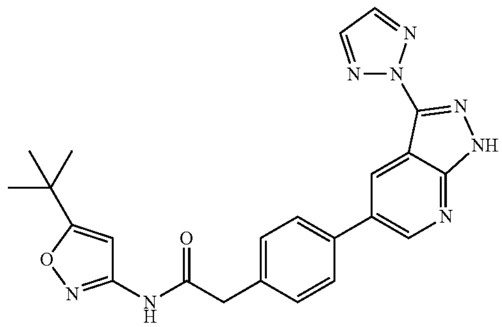 [SMILES: CC(C)(C)c1cc(NC(=O)Cc2ccc(-c3cnc4[nH]nc(-n5nccn5)c4c3)cc2)no1] | 101 | N-(5-tert-butylisoxazol-3-yl)-2-[4-[3-(triazol-2-yl)-1H-pyrazolo[3,4-b]pyridin-5-yl]phenyl]acetamide | 443 (M + H)+ |
| 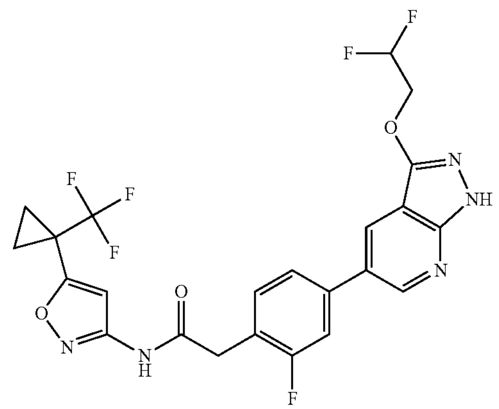 [SMILES: O=C(Cc1ccc(-c2cnc3[nH]nc(OCC(F)F)c3c2)cc1F)Nc1cc(C2(C(F)(F)F)CC2)on1] | 102 | 2-[4-[3-(2,2-difluoroethoxy)-1H-pyrazolo[3,4-b]pyridin-5-yl]-2-fluoro-phenyl]-N-[5-[1-(trifluoromethyl)cyclopropyl]isoxazol-3-yl]acetamide | 526 (M + H)+ |
| 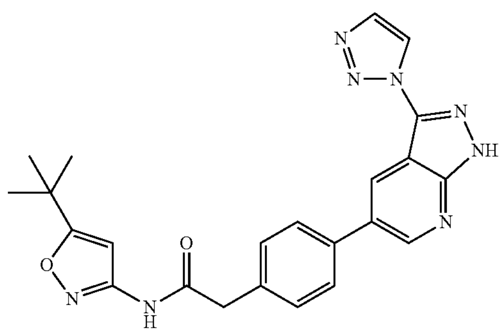 [SMILES: CC(C)(C)c1cc(NC(=O)Cc2ccc(-c3cnc4[nH]nc(-n5ccnn5)c4c3)cc2)no1] | 103 | N-(5-tert-butylisoxazol-3-yl)-2-[4-[3-(triazol-1-yl)-1H-pyrazolo[3,4-b]pyridin-5-yl]phenyl]acetamide | 443 (M + H)+ |
| 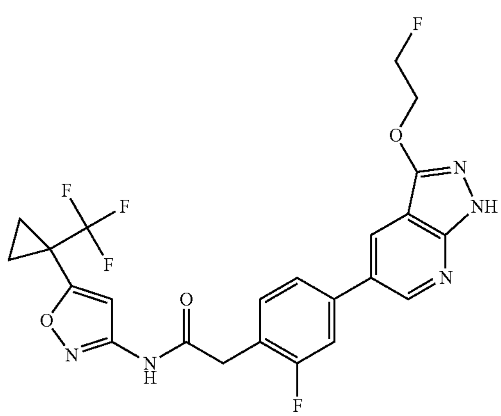 [SMILES: O=C(Cc1ccc(-c2cnc3[nH]nc(OCCF)c3c2)cc1F)Nc1cc(C2(C(F)(F)F)CC2)on1] | 104 | 2-[2-fluoro-4-[3-(2-fluoroethoxy)-1H-pyrazolo[3,4-b]pyridin-5-yl]phenyl]-N-[5-[1-(trifluoromethyl)cyclopropyl]isoxazol-3-yl]acetamide | 506 (M − H)− |

TABLE 1-continued

| Chemical Structure | Example Number | Example Name | Observed m/z |
|---|---|---|---|
| 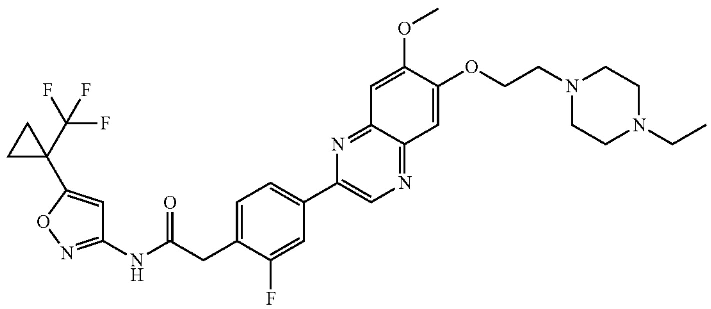 [SMILES: CCN1CCN(CCOc2cc3ncc(-c4ccc(CC(=O)Nc5cc(C6(C(F)(F)F)CC6)on5)c(F)c4)nc3cc2OC)CC1] | 105 | 2-[4-[6-[2-(4-ethylpiperazin-1-yl)ethoxy]-7-methoxy-quinoxalin-2-yl]-2-fluoro-phenyl]-N-[5-[1-(trifluoromethyl)cyclopropyl]isoxazol-3-yl]acetamide | 643 (M + H)+ |
| 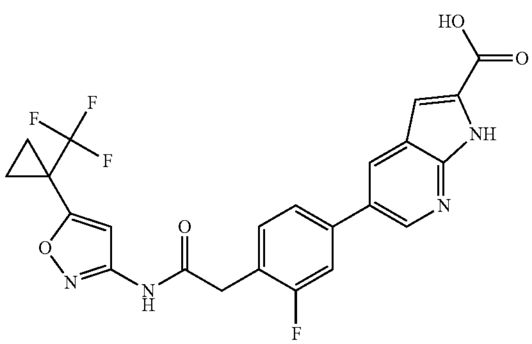 [SMILES: O=C(Cc1ccc(-c2cnc3[nH]c(C(=O)O)cc3c2)cc1F)Nc1cc(C2(C(F)(F)F)CC2)on1] | 106 | 5-[3-fluoro-4-[2-oxo-2-[[5-[1-(trifluoromethyl)cyclopropyl]isoxazol-3-yl]amino]ethyl]phenyl]-1H-pyrrolo[2,3-b]pyridine-2-carboxylic acid | 489 (M + H)+ |
| 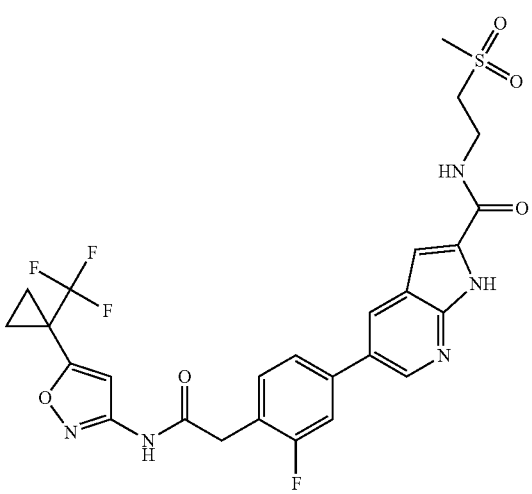 [SMILES: CS(=O)(=O)CCNC(=O)c1cc2cc(-c3ccc(CC(=O)Nc4cc(C5(C(F)(F)F)CC5)on4)c(F)c3)cnc2[nH]1] | 107 | 5-[3-fluoro-4-[2-oxo-2-[[5-[1-(trifluoromethyl)cyclopropyl]isoxazol-3-yl]amino]ethyl]phenyl]-N-(2-methylsulfonylethyl)-1H-pyrrolo[2,3-b]pyridine-2-carboxamide | 594 (M + H)+ |

TABLE 1-continued

| Chemical Structure | Example Number | Example Name | Observed m/z |
|---|---|---|---|
| 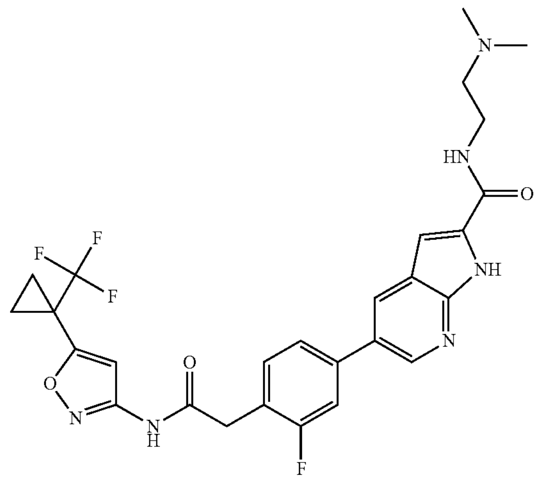 [SMILES: CN(C)CCNC(=O)c1cc2cc(-c3ccc(CC(=O)Nc4cc(C5(C(F)(F)F)CC5)on4)c(F)c3)cnc2[nH]1] | 108 | N-[2-(dimethylamino)ethyl]-5-[3-fluoro-4-[2-oxo-2-[[5-[1-(trifluoromethyl)cyclopropyl]isoxazol-3-yl]amino]ethyl]phenyl]-1H-pyrrolo[2,3-b]pyridine-2-carboxamide | 559 (M + H)+ |
| 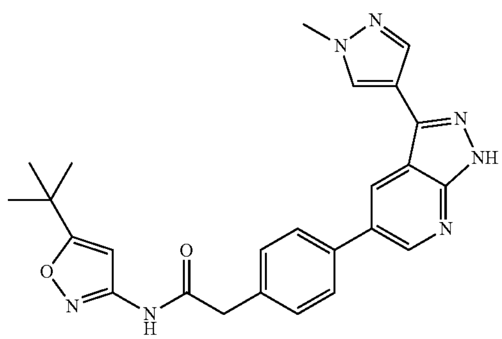 [SMILES: Cn1cc(-c2n[nH]c3ncc(-c4ccc(CC(=O)Nc5cc(C(C)(C)C)on5)cc4)cc23)cn1] | 109 | N-(5-tert-butylisoxazol-3-yl)-2-[4-[3-(1-methylpyrazol-4-yl)-1H-pyrazolo[3,4-b]pyridin-5-yl]phenyl]acetamide | 456 (M + H)+ |
| 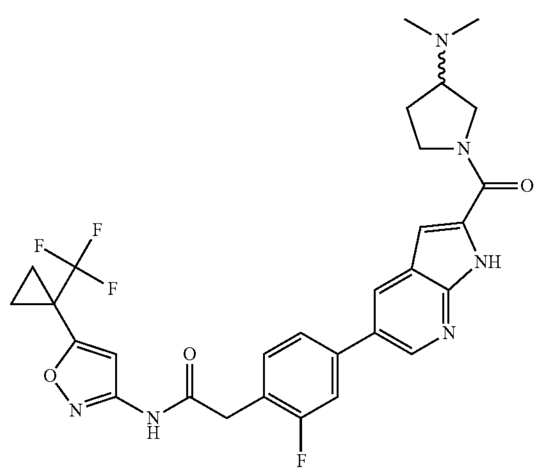 [SMILES: CN(C)C1CCN(C(=O)c2cc3cc(-c4ccc(CC(=O)Nc5cc(C6(C(F)(F)F)CC6)on5)c(F)c4)cnc3[nH]2)C1] | 110 | 2-[4-[2-[3-(dimethylamino)pyrrolidine-1-carbonyl]-1H-pyrrolo[2,3-b]pyridin-5-yl]-2-fluoro-phenyl]-N-[5-[1-(trifluoromethyl)cyclopropyl]isoxazol-3-yl]acetamide | 585 (M + H)+ |

TABLE 1-continued

| Chemical Structure | Example Number | Example Name | Observed m/z |
|---|---|---|---|
| 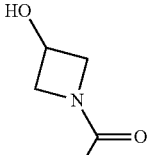 | 111 | 2-[2-fluoro-4-[2-(3-hydroxyazetidine-1-carbonyl)-1H-pyrrolo[2,3-b]pyridin-5-yl]phenyl]-N-[5-[1-(trifluoromethyl)cyclopropyl]isoxazol-3-yl]acetamide | |
| 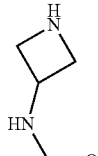 | 112 | N-(azetidin-3-yl)-5-[3-fluoro-4-[2-oxo-2-[[5-[1-(trifluoromethyl)cyclopropyl]isoxazol-3-yl]amino]ethyl]phenyl]-1H-pyrrolo[2,3-b]pyridine-2-carboxamide | 543 (M + H)+ |
| 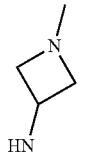 | 113 | 5-[3-fluoro-4-[2-oxo-2-[[5-[1-(trifluoromethyl)cyclopropyl]isoxazol-3-yl]amino]ethyl]phenyl]-N-(1-methylazetidin-3-yl)-1H-pyrrolo[2,3-b]pyridine-2-carboxamide | 557 (M + H)+ |

TABLE 1-continued

| Chemical Structure | Example Number | Example Name | Observed m/z |
|---|---|---|---|
| 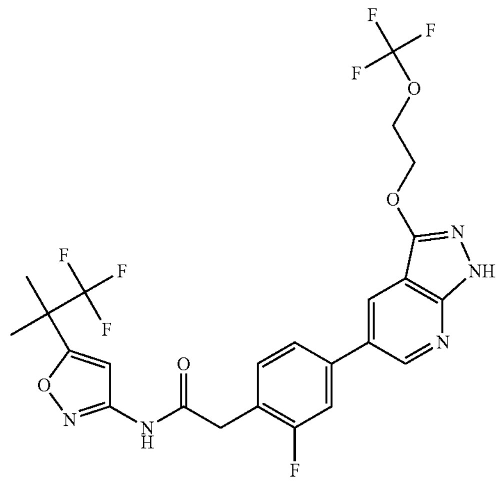 [SMILES: CC(C)(c1cc(NC(=O)Cc2ccc(-c3cnc4[nH]nc(OCCOC(F)(F)F)c4c3)cc2F)no1)C(F)(F)F] | 114 | 2-[2-fluoro-4-[3-[2-(trifluoromethoxy)ethoxy]-1H-pyrazolo[3,4-b]pyridin-5-yl]phenyl]-N-[5-(2,2,2-trifluoro-1,1-dimethyl-ethyl)isoxazol-3-yl]acetamide | 574 (M − H)$^-$ |
| 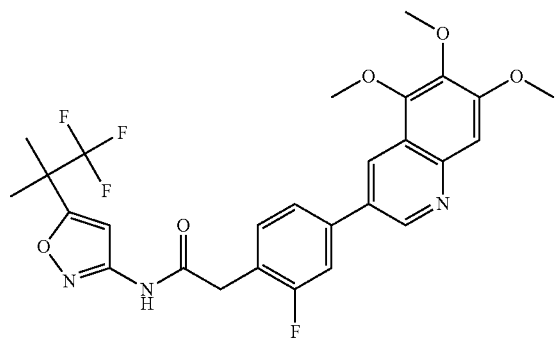 [SMILES: COc1cc2ncc(-c3ccc(CC(=O)Nc4cc(C(C)(C)C(F)(F)F)on4)c(F)c3)cc2c(OC)c1OC] | 115 | 2-[2-fluoro-4-(5,6,7-trimethoxy-3-quinolyl)phenyl]-N-[5-(2,2,2-trifluoro-1,1-dimethyl-ethyl)isoxazol-3-yl]acetamide | 548 (M + H)$^+$ |
| 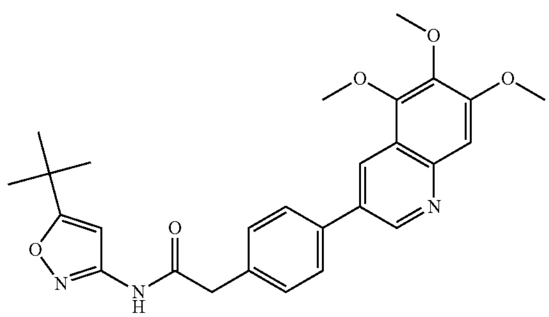 [SMILES: COc1cc2ncc(-c3ccc(CC(=O)Nc4cc(C(C)(C)C)on4)cc3)cc2c(OC)c1OC] | 116 | N-(5-tert-butylisoxazol-3-yl)-2-[4-(5,6,7-trimethoxy-3-quinolyl)phenyl]acetamide | 476 (M + H)$^+$ |
| 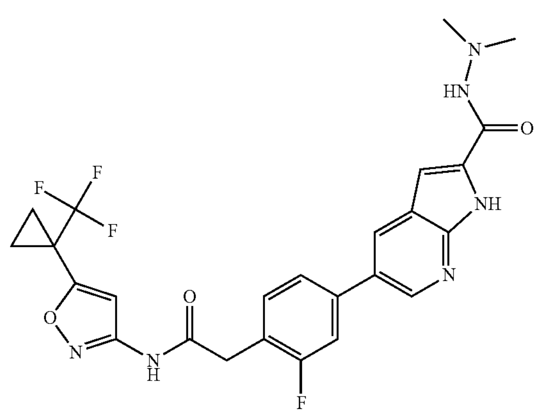 [SMILES: CN(C)NC(=O)c1cc2cc(-c3ccc(CC(=O)Nc4cc(C5(C(F)(F)F)CC5)on4)c(F)c3)cnc2[nH]1] | 117 | 2-[4-[2-(dimethylaminocarbamoyl)-1H-pyrrolo[2,3-b]pyridin-5-yl]-2-fluoro-phenyl]-N-[5-[1-(trifluoro-methyl)cyclopropyl]isoxazol-3-yl]acetamide | 531 (M + H)$^+$ |

TABLE 1-continued

| Chemical Structure | Example Number | Example Name | Observed m/z |
|---|---|---|---|
| 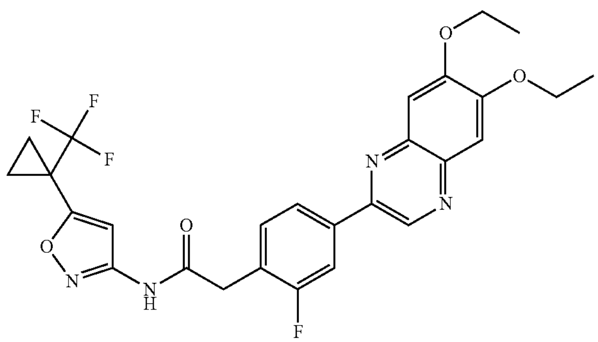 [SMILES: CCOc1cc2ncc(-c3ccc(CC(=O)Nc4cc(C5(C(F)(F)F)CC5)on4)c(F)c3)nc2cc1OCC] | 118 | 2-[4-(6,7-diethoxyquinoxalin-2-yl)-2-fluoro-phenyl]-N-[5-[1-(trifluoromethyl)cyclopropyl]isoxazol-3-yl]acetamide | 545 (M + H)+ |
| 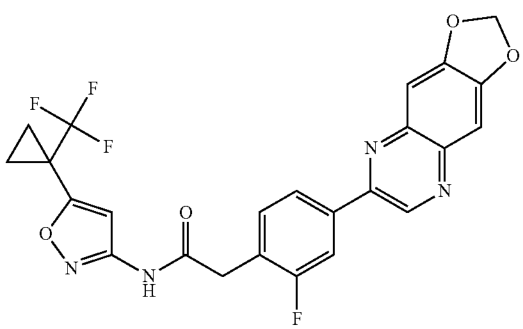 [SMILES: O=C(Cc1ccc(-c2cnc3cc4c(cc3n2)OCO4)cc1F)Nc1cc(C2(C(F)(F)F)CC2)on1] | 119 | 2-[4-([1,3]dioxolo[4,5-g]quinoxalin-6-yl)-2-fluoro-phenyl]-N-[5-[1-(trifluoromethyl)cyclopropyl]isoxazol-3-yl]acetamide | 501 (M + H)+ |
| 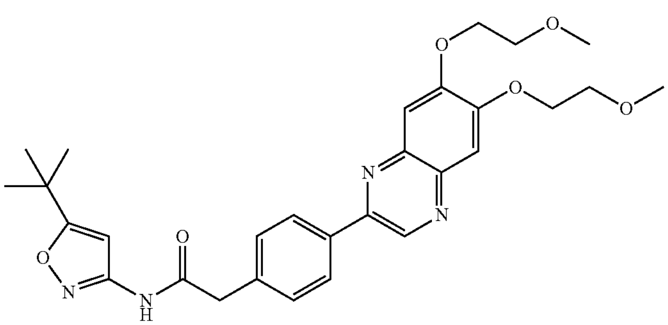 [SMILES: COCCOc1cc2ncc(-c3ccc(CC(=O)Nc4cc(C(C)(C)C)on4)cc3)nc2cc1OCCOC] | 120 | 2-[4-[6,7-bis(2-methoxyethoxy)quinoxalin-2-yl]phenyl]-N-(5-tert-butylisoxazol-3-yl)acetamide | 535 (M + H)+ |
| 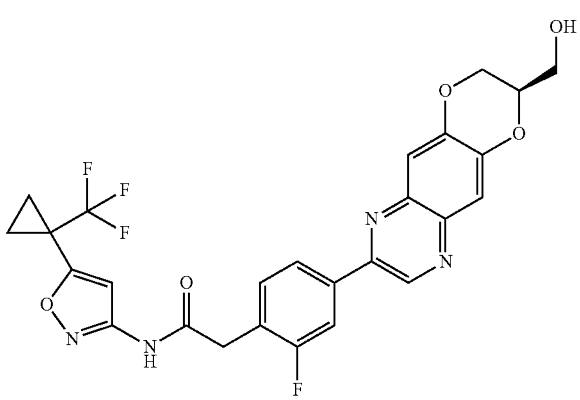 [SMILES: O=C(Cc1ccc(-c2cnc3cc4c(cc3n2)OC[C@@H](CO)O4)cc1F)Nc1cc(C2(C(F)(F)F)CC2)on1] | 121 | 2-[2-fluoro-4-[(2R)-2-(hydroxymethyl)-2,3-dihydro-[1,4]dioxino[2,3-g]quinoxalin-7-yl]phenyl]-N-[5-[1-(trifluoromethyl)cyclopropyl]isoxazol-3-yl]acetamide | 545 (M + H)+ |

TABLE 1-continued

| Chemical Structure | Example Number | Example Name | Observed m/z |
|---|---|---|---|
| 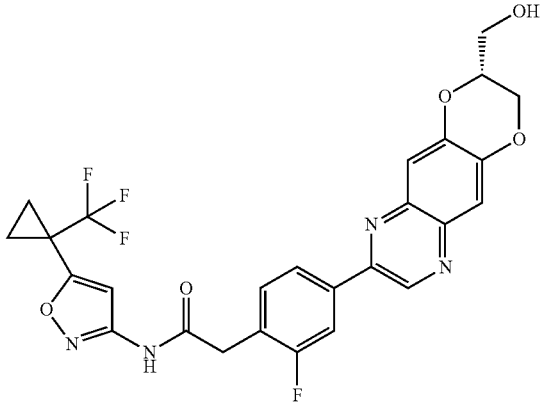 [SMILES: O=C(Cc1ccc(-c2cnc3cc4c(cc3n2)O[C@H](CO)CO4)cc1F)Nc1cc(C2(C(F)(F)F)CC2)on1] | 122 | 2-[2-fluoro-4-[(3R)-3-(hydroxymethyl)-2,3-dihydro-[1,4]dioxino[2,3-g]quinoxalin-7-yl]phenyl]-N-[5-[1-(trifluoromethyl)cyclopropyl]isoxazol-3-yl]acetamide | 545 (M + H)+ |
| 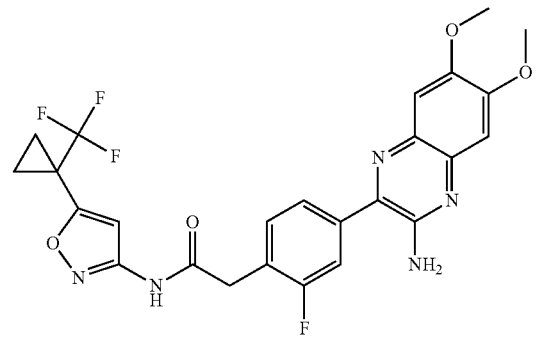 | 123 | 2-[4-(3-amino-6,7-dimethoxy-quinoxalin-2-yl)-2-fluoro-phenyl]-N-[5-[1-(trifluoromethyl)cyclopropyl]isoxazol-3-yl]acetamide | 532 (M + H)+ |
| 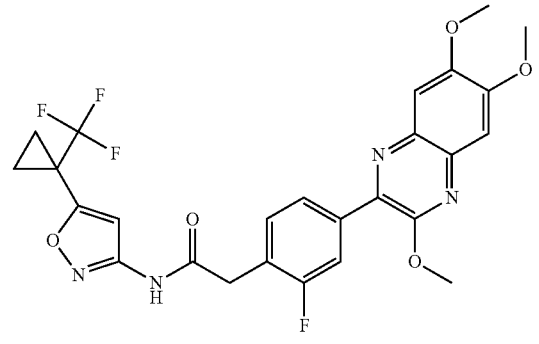 [SMILES: COc1cc2nc(OC)c(-c3ccc(CC(=O)Nc4cc(C5(C(F)(F)F)CC5)on4)c(F)c3)nc2cc1OC] | 124 | 2-[2-fluoro-4-(3,6,7-trimethoxyquinoxalin-2-yl)phenyl]-N-[5-[1-(trifluoromethyl)cyclopropyl]isoxazol-3-yl]acetamide | 547 (M + H)+ |
| 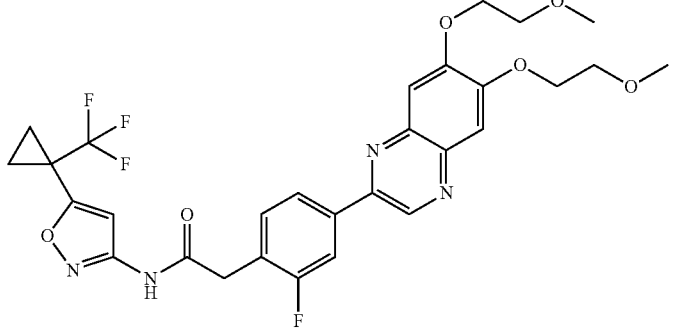 | 125 | 2-[4-[6,7-bis(2-methoxyethoxy)quinoxalin-2-yl]-2-fluoro-phenyl]-N-[5-[1-(trifluoromethyl)cyclopropyl]isoxazol-3-yl]acetamide | 605 (M + H)+ |

TABLE 1-continued

| Chemical Structure | Example Number | Example Name | Observed m/z |
|---|---|---|---|
| 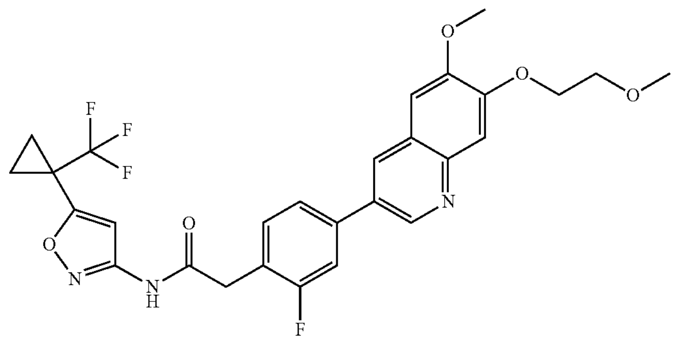 [SMILES: COCCOc1cc2ncc(-c3ccc(CC(=O)Nc4cc(C5(C(F)(F)F)CC5)on4)c(F)c3)cc2cc1OC] | 126 | 2-[2-fluoro-4-[6-methoxy-7-(2-methoxyethoxy)-3-quinolyl]phenyl]-N-[5-[1-(trifluoromethyl)cyclopropyl]isoxazol-3-yl]acetamide | 560 (M + H)+ |
| 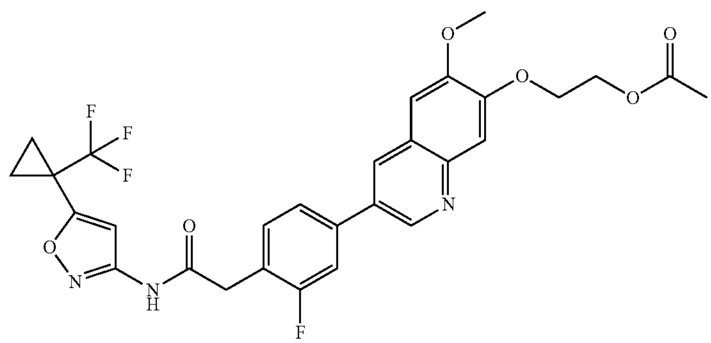 [SMILES: COc1cc2cc(-c3ccc(CC(=O)Nc4cc(C5(C(F)(F)F)CC5)on4)c(F)c3)cnc2cc1OCCOC(C)=O] | 127 | 2-[[3-[3-fluoro-4-[2-oxo-2-[[5-[1-(trifluoromethyl)cyclopropyl]isoxazol-3-yl]amino]ethyl]phenyl]-6-methoxy-7-quinolyl]oxy]ethyl acetate | 588 (M + H)+ |
| 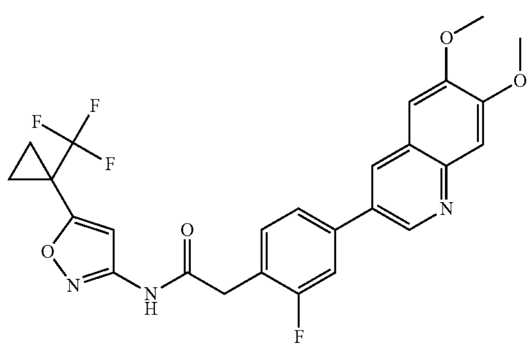 | 128 | 2-[4-(6,7-dimethoxy-3-quinolyl)-2-fluoro-phenyl]-N-[5-[1-(trifluoromethyl)cyclopropyl]isoxazol-3-yl]acetamide | 514 (M − H)− |
| 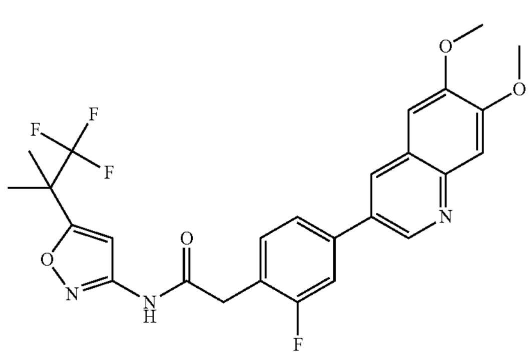 [SMILES: COc1cc2cc(-c3ccc(CC(=O)Nc4cc(C(C)(C)C(F)(F)F)on4)c(F)c3)cnc2cc1OC] | 129 | 2-[4-(6,7-dimethoxy-3-quinolyl)-2-fluoro-phenyl]-N-[5-(2,2,2-trifluoro-1,1-dimethyl-ethyl)isoxazol-3-yl]acetamide | 516 (M − H)− |

TABLE 1-continued

| Chemical Structure | Example Number | Example Name | Observed m/z |
|---|---|---|---|
| 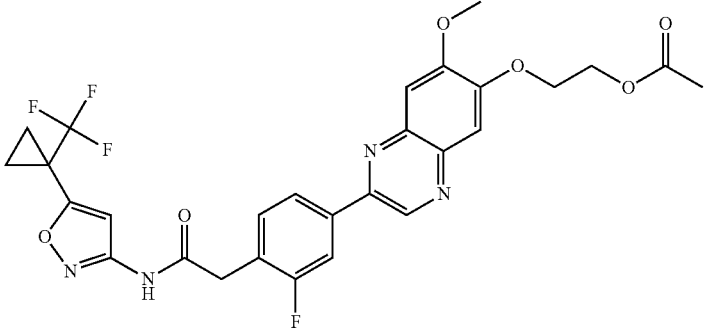 [SMILES: COc1cc2nc(-c3ccc(CC(=O)Nc4cc(C5(C(F)(F)F)CC5)on4)c(F)c3)cnc2cc1OCCOC(C)=O] | 130 | 2-[2-[3-fluoro-4-[2-oxo-2-[[5-[1-(trifluoromethyl)cyclo-propyl]isoxazol-3-yl]amino]ethyl]phenyl]-7-methoxy-quinoxalin-6-yl]oxyethyl acetate | 589 (M + H)+ |
| 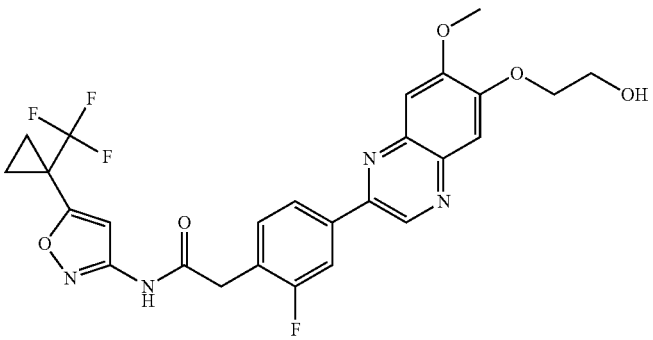 [SMILES: COc1cc2nc(-c3ccc(CC(=O)Nc4cc(C5(C(F)(F)F)CC5)on4)c(F)c3)cnc2cc1OCCO] | 131 | 2-[2-fluoro-4-[6-(2-hydroxyethoxy)-7-methoxy-quinoxalin-2-yl]phenyl]-N-[5-[1-(trifluoromethyl)cyclo-propyl]isoxazol-3-yl]acetamide | 547 (M + H)+ |
| 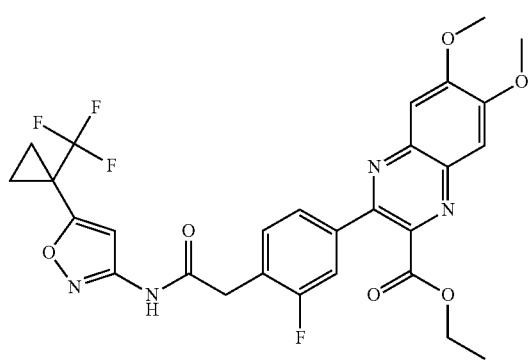 [SMILES: CCOC(=O)c1nc2cc(OC)c(OC)cc2nc1-c1ccc(CC(=O)Nc2cc(C3(C(F)(F)F)CC3)on2)c(F)c1] | 132 | ethyl 3-[3-fluoro-4-[2-oxo-2-[[5-[1-(trifluoro-methyl)cyclopropyl]isoxazol-3-yl]amino]ethyl]phenyl]-6,7-dimethoxy-quinoxaline-2-carboxylate | 589 (M + H)+ |
| 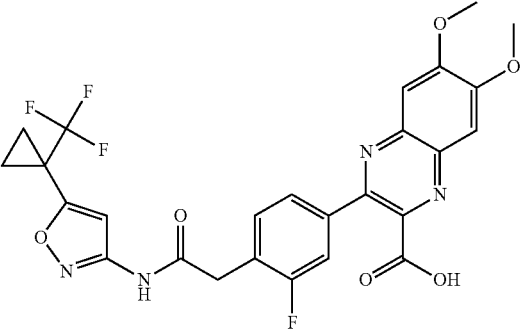 [SMILES: COc1cc2nc(C(=O)O)c(-c3ccc(CC(=O)Nc4cc(C5(C(F)(F)F)CC5)on4)c(F)c3)nc2cc1OC] | 133 | 3-[3-fluoro-4-[2-oxo-2-[[5-[1-(trifluoro-methyl)cyclopropyl]isoxazol-3-yl]amino]ethyl]phenyl]-6,7-dimethoxy-quinoxaline-2-carboxylic acid | 561 (M + H)+ |

TABLE 1-continued

| Chemical Structure | Example Number | Example Name | Observed m/z |
|---|---|---|---|
| 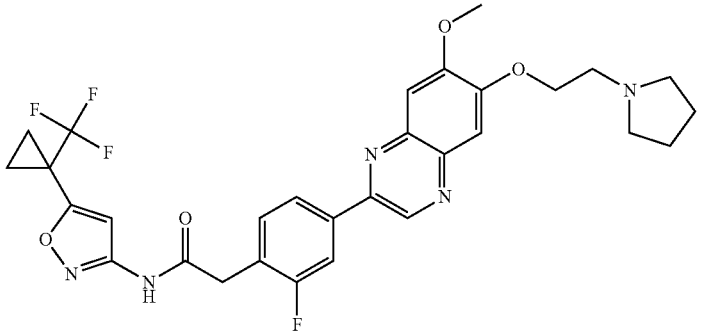 | 134 | 2-[2-fluoro-4-[7-methoxy-6-(2-pyrrolidin-1-ylethoxy)quinoxalin-2-yl]phenyl]-N-[5-[1-(trifluoromethyl)cyclopropyl]isoxazol-3-yl]acetamide | 600 (M + H)+ |
| 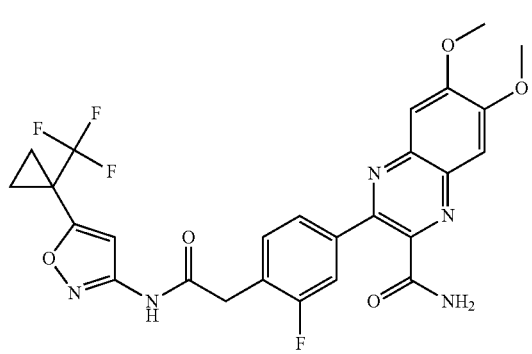 [SMILES: COc1cc2nc(C(N)=O)c(-c3ccc(CC(=O)Nc4cc(C5(C(F)(F)F)CC5)on4)c(F)c3)nc2cc1OC] | 135 | 3-[3-fluoro-4-[2-oxo-2-[[5-[1-(trifluoromethyl)cyclopropyl]isoxazol-3-yl]amino]ethyl]phenyl]-6,7-dimethoxy-quinoxaline-2-carboxamide | 560 (M + H)+ |
| 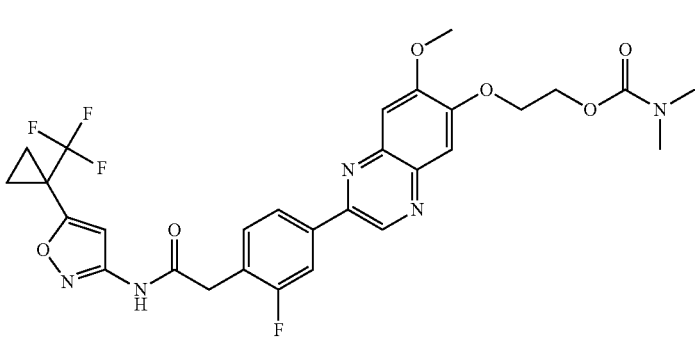 [SMILES: COc1cc2nc(-c3ccc(CC(=O)Nc4cc(C5(C(F)(F)F)CC5)on4)c(F)c3)cnc2cc1OCCOC(=O)N(C)C] | 136 | 2-[2-[3-fluoro-4-[2-oxo-2-[[5-[1-(trifluoromethyl)cyclopropyl]isoxazol-3-yl]amino]ethyl]phenyl]-7-methoxy-quinoxalin-6-yl]oxyethyl N,N-dimethylcarbamate | 618 (M + H)+ |
| 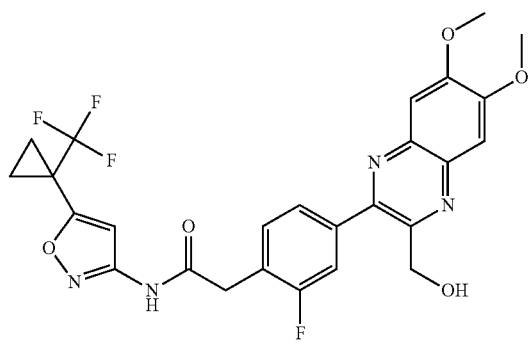 [SMILES: COc1cc2nc(CO)c(-c3ccc(CC(=O)Nc4cc(C5(C(F)(F)F)CC5)on4)c(F)c3)nc2cc1OC] | 137 | 2-[2-fluoro-4-[3-(hydroxymethyl)-6,7-dimethoxy-quinoxalin-2-yl]phenyl]-N-[5-[1-(trifluoromethyl)cyclopropyl]isoxazol-3-yl]acetamide | 547 (M + H)+ |

TABLE 1-continued

| Chemical Structure | Example Number | Example Name | Observed m/z |
|---|---|---|---|
| 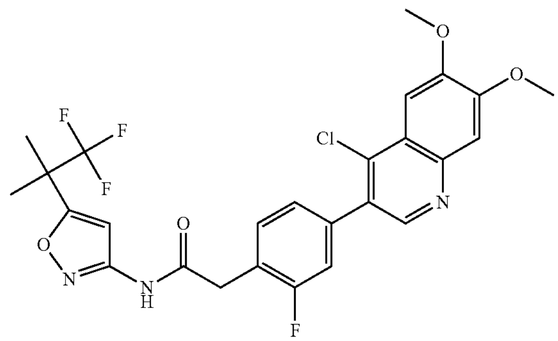 [SMILES: COc1cc2ncc(-c3ccc(CC(=O)Nc4cc(C(C)(C)C(F)(F)F)on4)c(F)c3)c(Cl)c2cc1OC] | 138 | 2-[4-(4-chloro-6,7-dimethoxy-3-quinolyl)-2-fluoro-phenyl]-N-[5-(2,2,2-trifluoro-1,1-dimethyl-ethyl)isoxazol-3-yl]acetamide | 552 (M + H)+ |
| 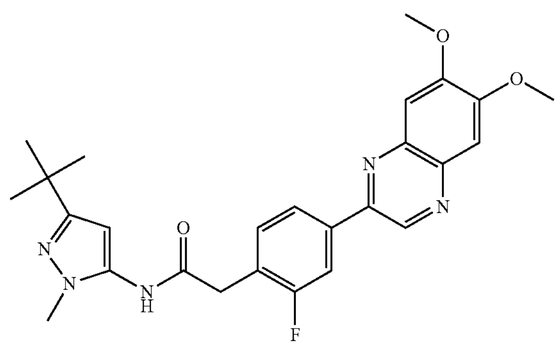 [SMILES: COc1cc2ncc(-c3ccc(CC(=O)Nc4cc(C(C)(C)C)nn4C)c(F)c3)nc2cc1OC] | 139 | N-(5-tert-butyl-2-methyl-pyrazol-3-yl)-2-[4-(6,7-dimethoxyquinoxalin-2-yl)-2-fluoro-phenyl]acetamide | 478 (M + H)+ |
| 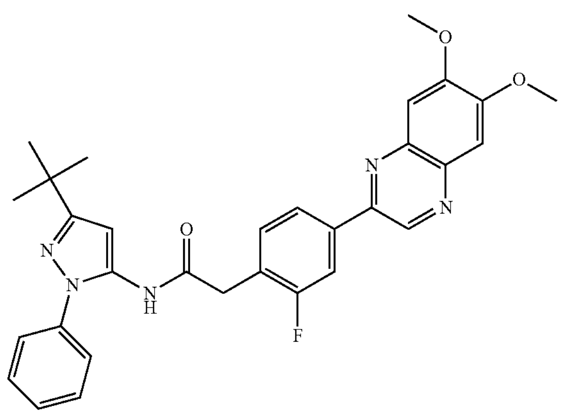 [SMILES: COc1cc2ncc(-c3ccc(CC(=O)Nc4cc(C(C)(C)C)nn4-c4ccccc4)c(F)c3)nc2cc1OC] | 140 | N-(5-tert-butyl-2-phenyl-pyrazol-3-yl)-2-[4-(6,7-dimethoxyquinoxalin-2-yl)-2-fluoro-phenyl]acetamide | 540 (M + H)+ |
| 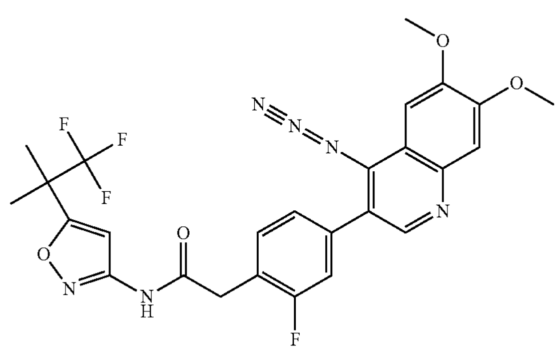 [SMILES: COc1cc2ncc(-c3ccc(CC(=O)Nc4cc(C(C)(C)C(F)(F)F)on4)c(F)c3)c(N=[N+]=[N-])c2cc1OC] | 141 | 2-[4-(4-azido-6,7-dimethoxy-3-quinolyl)-2-fluoro-phenyl]-N-[5-(2,2,2-trifluoro-1,1-dimethyl-ethyl)isoxazol-3-yl]acetamide | 559 (M + H)+ |

TABLE 1-continued

| Chemical Structure | Example Number | Example Name | Observed m/z |
|---|---|---|---|
| 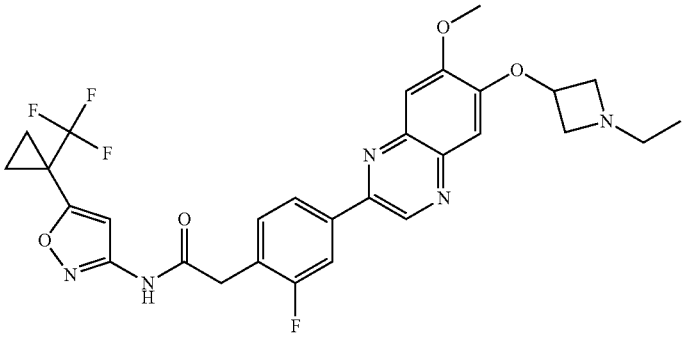 [SMILES: CCN1CC(Oc2cc3ncc(-c4ccc(CC(=O)Nc5cc(C6(C(F)(F)F)CC6)on5)c(F)c4)nc3cc2OC)C1] | 142 | 2-[4-[6-(1-ethylazetidin-3-yl)oxy-7-methoxy-quinoxalin-2-yl]-2-fluoro-phenyl]-N-[5-[1-(trifluoro-methyl)cyclopropyl]isoxazol-3-yl]acetamide | 586 (M + H)+ |
| 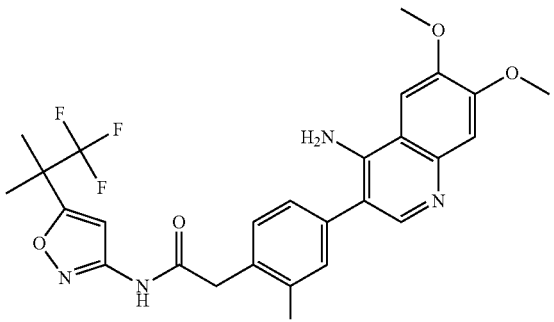 | 143 | 2-[4-(4-amino-6,7-dimethoxy-3-quinolyl)-2-fluoro-phenyl]-N-[5-(2,2,2-trifluoro-1,1-dimethyl-ethyl)isoxazol-3-yl]acetamide | 533 (M + H)+ |
| 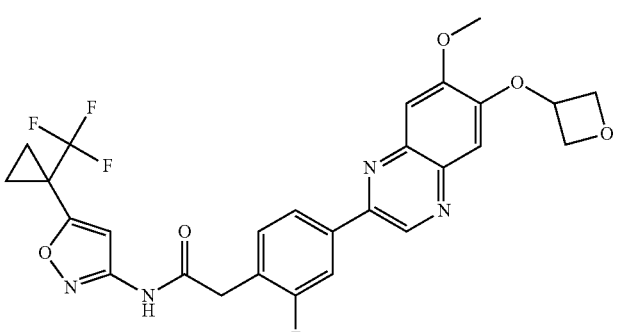 | 144 | 2-[2-fluoro-4-[7-methoxy-6-(oxetan-3-yloxy)quinoxalin-2-yl]phenyl]-N-[5-[1-(trifluoro-methyl)cyclopropyl]isoxazol-3-yl]acetamide | 559 (M + H)+ |
| 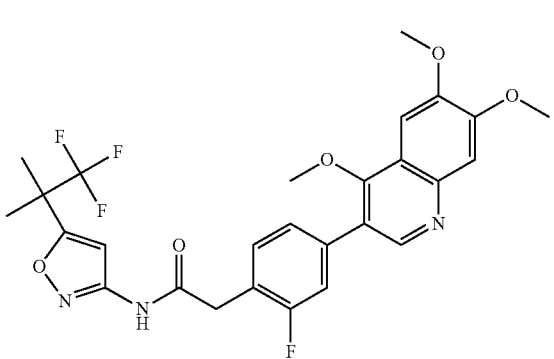 [SMILES: COc1cc2ncc(-c3ccc(CC(=O)Nc4cc(C(C)(C)C(F)(F)F)on4)c(F)c3)c(OC)c2cc1OC] | 145 | 2-[2-fluoro-4-(4,6,7-trimethoxy-3-quinolyl)phenyl]-N-[5-(2,2,2-trifluoro-1,1-dimethyl-ethyl)isoxazol-3-yl]acetamide | 548 (M + H)+ |

TABLE 1-continued

| Chemical Structure | Example Number | Example Name | Observed m/z |
|---|---|---|---|
| 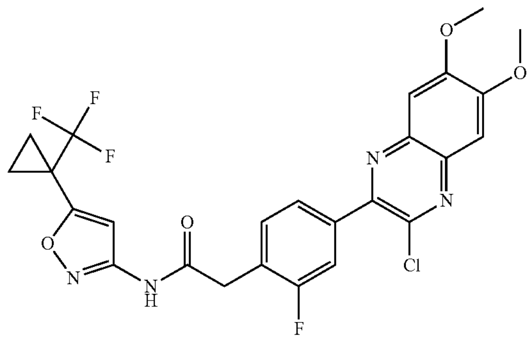 [SMILES: COc1cc2nc(Cl)c(-c3ccc(CC(=O)Nc4cc(C5(C(F)(F)F)CC5)on4)c(F)c3)nc2cc1OC] | 146 | 2-[4-(3-chloro-6,7-dimethoxy-quinoxalin-2-yl)-2-fluoro-phenyl]-N-[5-[1-(trifluoromethyl)cyclopropyl]isoxazol-3-yl]acetamide | 551 (M + H)+ |
| 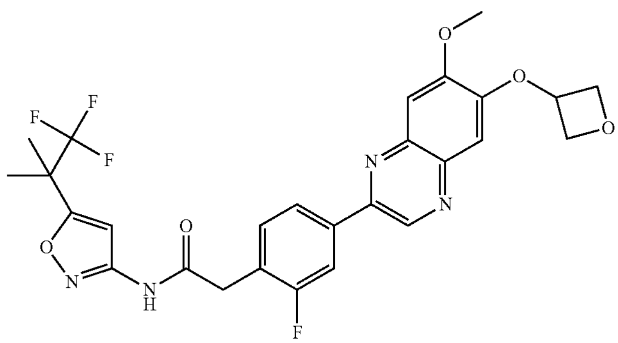 [SMILES: COc1cc2nc(-c3ccc(CC(=O)Nc4cc(C(C)(C)C(F)(F)F)on4)c(F)c3)cnc2cc1OC1COC1] | 147 | 2-[2-fluoro-4-[7-methoxy-6-(oxetan-3-yloxy)quinoxalin-2-yl]phenyl]-N-[5-(2,2,2-trifluoro-1,1-dimethyl-ethyl)isoxazol-3-yl]acetamide | 561 (M + H)+ |
| 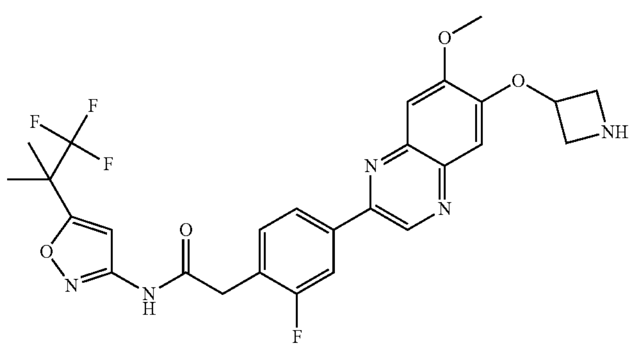 [SMILES: COc1cc2nc(-c3ccc(CC(=O)Nc4cc(C(C)(C)C(F)(F)F)on4)c(F)c3)cnc2cc1OC1CNC1] | 148 | 2-[4-[6-(azetidin-3-yloxy)-7-methoxy-quinoxalin-2-yl]-2-fluoro-phenyl]-N-[5-(2,2,2-trifluoro-1,1-dimethyl-ethyl)isoxazol-3-yl]acetamide | 560 (M + H)+ |
| 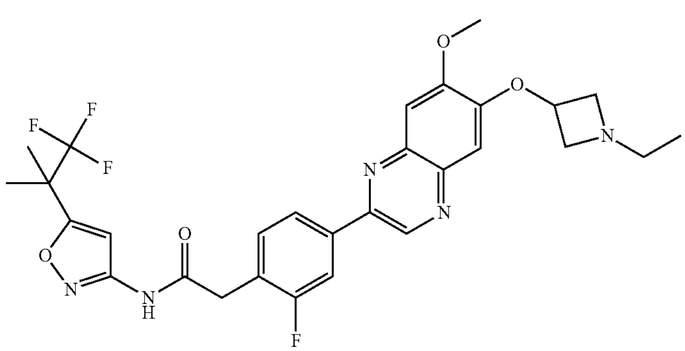 [SMILES: CCN1CC(Oc2cc3ncc(-c4ccc(CC(=O)Nc5cc(C(C)(C)C(F)(F)F)on5)c(F)c4)nc3cc2OC)C1] | 149 | 2-[4-[6-(1-ethylazetidin-3-yl)oxy-7-methoxy-quinoxalin-2-yl]-2-fluoro-phenyl]-N-[5-(2,2,2-trifluoro-1,1-dimethyl-ethyl)isoxazol-3-yl]acetamide | 588 (M + H)+ |

TABLE 1-continued

| Chemical Structure | Example Number | Example Name | Observed m/z |
|---|---|---|---|
| 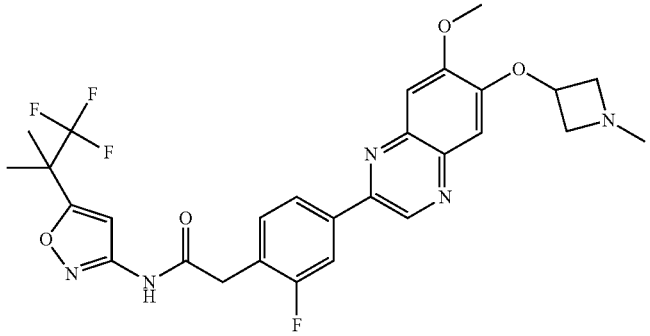 [SMILES: COc1cc2nc(-c3ccc(CC(=O)Nc4cc(C(C)(C)C(F)(F)F)on4)c(F)c3)cnc2cc1OC1CN(C)C1] | 150 | 2-[2-fluoro-4-[7-methoxy-6-(1-methylazetidin-3-yl)oxy-quinoxalin-2-yl]phenyl]-N-[5-(2,2,2-trifluoro-1,1-dimethyl-ethyl)isoxazol-3-yl]acetamide | 574 (M + H)+ |
| 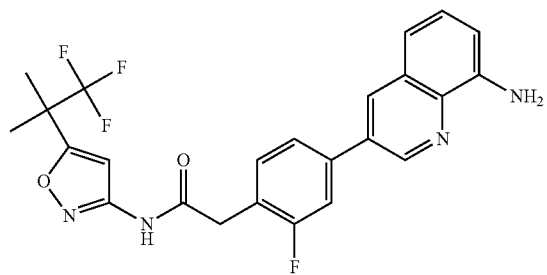 [SMILES: CC(C)(c1cc(NC(=O)Cc2ccc(-c3cnc4c(N)cccc4c3)cc2F)no1)C(F)(F)F] | 151 | 2-[4-(8-amino-3-quinolyl)-2-fluoro-phenyl]-N-[5-(2,2,2-trifluoro-1,1-dimethyl-ethyl)isoxazol-3-yl]acetamide | 473 (M + H)+ |
| 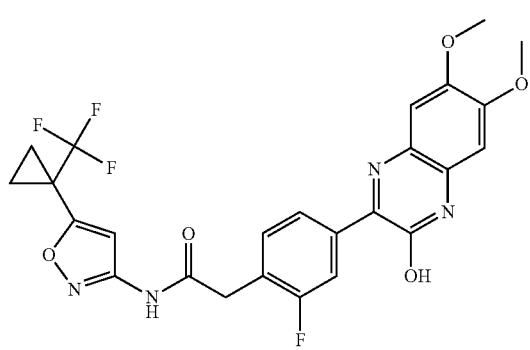 [SMILES: COc1cc2nc(O)c(-c3ccc(CC(=O)Nc4cc(C5(C(F)(F)F)CC5)on4)c(F)c3)nc2cc1OC] | 152 | 2-[4-(6,7-dimethoxy-3-hydroxy-quinoxalin-2-yl)-2-fluoro-phenyl]-N-[5-[1-(trifluoromethyl)cyclopropyl]isoxazol-3-yl]acetamide | 533 (M + H)+ |
| 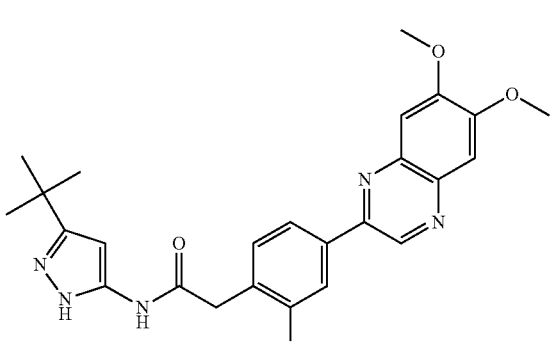 | 153 | N-(3-tert-butyl-1H-pyrazol-5-yl)-2-[4-(6,7-dimethoxyquinoxalin-2-yl)-2-fluoro-phenyl]acetamide | 464 (M + H)+ |

TABLE 1-continued

| Chemical Structure | Example Number | Example Name | Observed m/z |
|---|---|---|---|
| 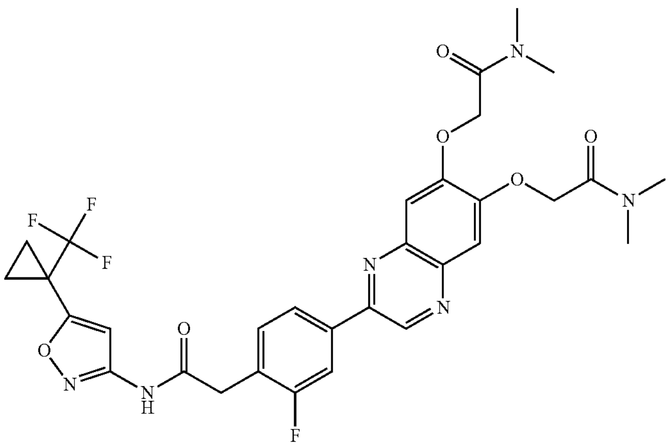 [SMILES: CN(C)C(=O)COc1cc2ncc(-c3ccc(CC(=O)Nc4cc(C5(C(F)(F)F)CC5)on4)c(F)c3)nc2cc1OCC(=O)N(C)C] | 154 | 2-[4-[6,7-bis[2-(dimethylamino)-2-oxo-ethoxy]quinoxalin-2-yl]-2-fluoro-phenyl]-N-[5-[1-(trifluoromethyl)cyclo-propyl]isoxazol-3-yl]acetamide | 659 (M + H)+ |
| | 155 | 2-[2-fluoro-4-(6-methoxypyrido[2,3-b]pyrazin-3-yl)phenyl]-N-[5-[1-(trifluoromethyl)cyclo-propyl]isoxazol-3-yl]acetamide OR | 488 (M + H)+ |
| | | 2-[2-fluoro-4-(6-methoxypyrido[2,3-b]pyrazin-2-yl)phenyl]-N-[5-[1-(trifluoromethyl)cyclo-propyl]isoxazol-3-yl]acetamide | |

TABLE 1-continued

| Chemical Structure | Example Number | Example Name | Observed m/z |
|---|---|---|---|
| 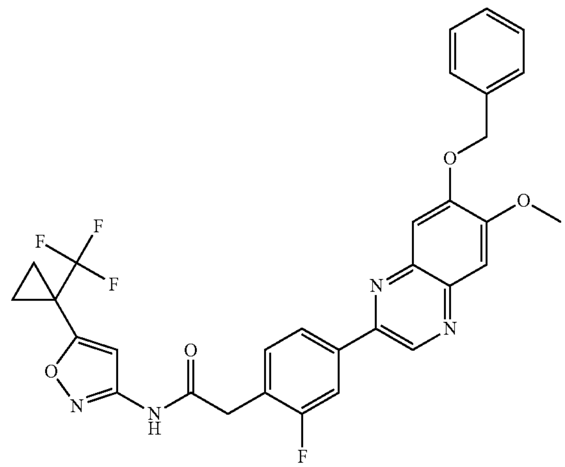 [SMILES: COc1cc2ncc(-c3ccc(CC(=O)Nc4cc(C5(C(F)(F)F)CC5)on4)c(F)c3)nc2cc1OCc1ccccc1] | 156 | 2-[4-(7-benzyloxy-6-methoxy-quinoxalin-2-yl)-2-fluoro-phenyl]-N-[5-[1-(trifluoromethyl)cyclopropyl]isoxazol-3-yl]acetamide | 593 (M + H)+ |
| 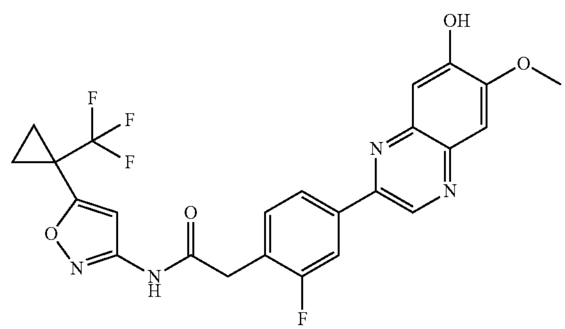 [SMILES: COc1cc2ncc(-c3ccc(CC(=O)Nc4cc(C5(C(F)(F)F)CC5)on4)c(F)c3)nc2cc1O] | 157 | 2-[2-fluoro-4-(7-hydroxy-6-methoxy-quinoxalin-2-yl)phenyl]-N-[5-[1-(trifluoromethyl)cyclopropyl]isoxazol-3-yl]acetamide | 503 (M + H)+ |
| 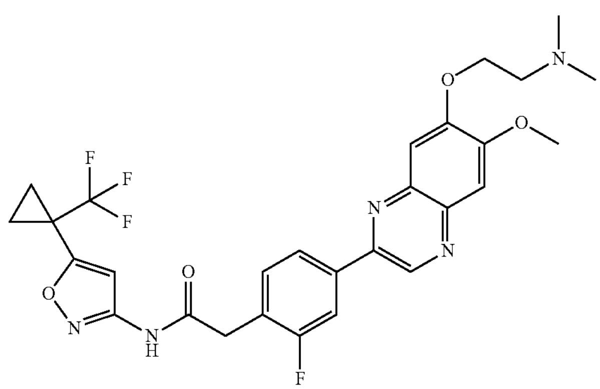 [SMILES: COc1cc2ncc(-c3ccc(CC(=O)Nc4cc(C5(C(F)(F)F)CC5)on4)c(F)c3)nc2cc1OCCN(C)C] | 158 | 2-[4-[7-[2-(dimethylamino)ethoxy]-6-methoxy-quinoxalin-2-yl]-2-fluoro-phenyl]-N-[5-[1-(trifluoromethyl)cyclopropyl]isoxazol-3-yl]acetamide | 574 (M + H)+ |
| 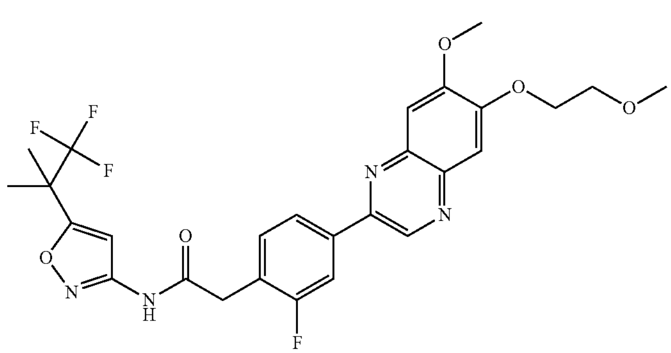 [SMILES: COCCOc1cc2ncc(-c3ccc(CC(=O)Nc4cc(C(C)(C)C(F)(F)F)on4)c(F)c3)nc2cc1OC] | 159 | 2-[2-fluoro-4-[7-methoxy-6-(2-methoxyethoxy)quinoxalin-2-yl]phenyl]-N-[5-(2,2,2-trifluoro-1,1-dimethylethyl)isoxazol-3-yl]acetamide | 563 (M + H)+ |

TABLE 1-continued

| Chemical Structure | Example Number | Example Name | Observed m/z |
|---|---|---|---|
| 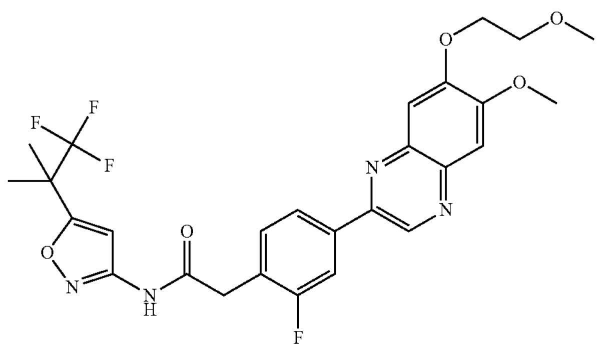 [SMILES: COCCOc1cc2nc(-c3ccc(CC(=O)Nc4cc(C(C)(C)C(F)(F)F)on4)c(F)c3)cnc2cc1OC] | 160 | 2-[2-fluoro-4-[6-methoxy-7-(2-methoxy-ethoxy)quinoxalin-2-yl]phenyl]-N-[5-(2,2,2-trifluoro-1,1-dimethyl-ethyl)isoxazol-3-yl]acetamide | 563 (M + H)+ |
| 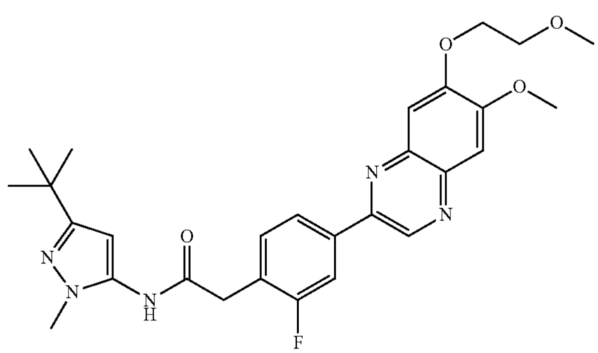 [SMILES: COCCOc1cc2nc(-c3ccc(CC(=O)Nc4cc(C(C)(C)C)nn4C)c(F)c3)cnc2cc1OC] | 161 | N-(5-tert-butyl-2-methyl-pyrazol-3-yl)-2-[2-fluoro-4-[6-methoxy-7-(2-methoxyethoxy)quinoxalin-2-yl]phenyl]acetamide | 522 (M + H)+ |
| 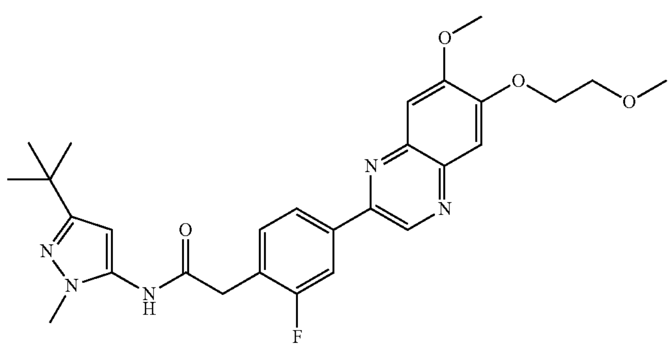 [SMILES: COCCOc1cc2ncc(-c3ccc(CC(=O)Nc4cc(C(C)(C)C)nn4C)c(F)c3)nc2cc1OC] | 162 | N-(5-tert-butyl-2-methyl-pyrazol-3-yl)-2-[2-fluoro-4-[7-methoxy-6-(2-methoxyethoxy)quinoxalin-2-yl]phenyl]acetamide | 522 (M + H)+ |
| 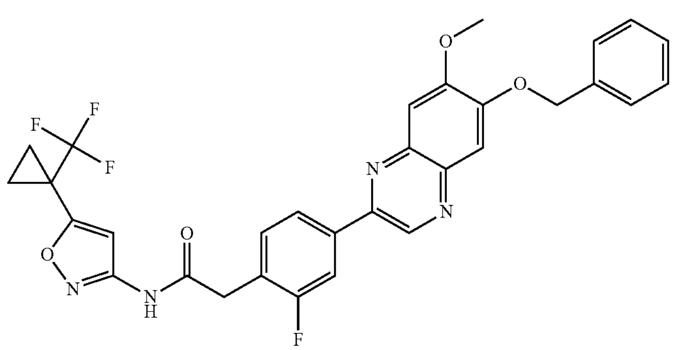 [SMILES: COc1cc2nc(-c3ccc(CC(=O)Nc4cc(C5(C(F)(F)F)CC5)on4)c(F)c3)cnc2cc1OCc1ccccc1] | 163 | 2-[4-(6-benzyloxy-7-methoxy-quinoxalin-2-yl)-2-fluoro-phenyl]-N-[5-[1-(trifluoromethyl)cyclo-propyl]isoxazol-3-yl]acetamide | 593 (M + H)+ |

TABLE 1-continued

| Chemical Structure | Example Number | Example Name | Observed m/z |
|---|---|---|---|
| 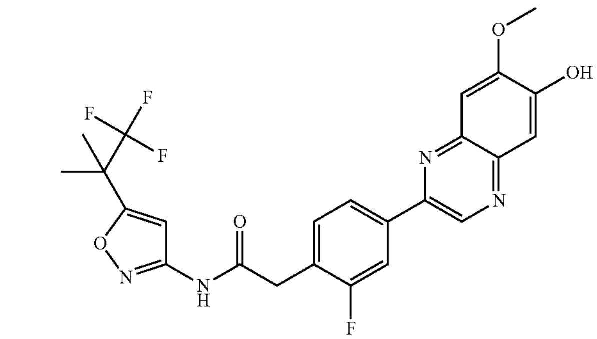 [SMILES: COc1cc2nc(-c3ccc(CC(=O)Nc4cc(C(C)(C)C(F)(F)F)on4)c(F)c3)cnc2cc1O] | 164 | 2-[2-fluoro-4-(6-hydroxy-7-methoxy-quinoxalin-2-yl)phenyl]-N-[5-(2,2,2-trifluoro-1,1-dimethyl-ethyl)isoxazol-3-yl]acetamide | 505 (M + H)+ |
| 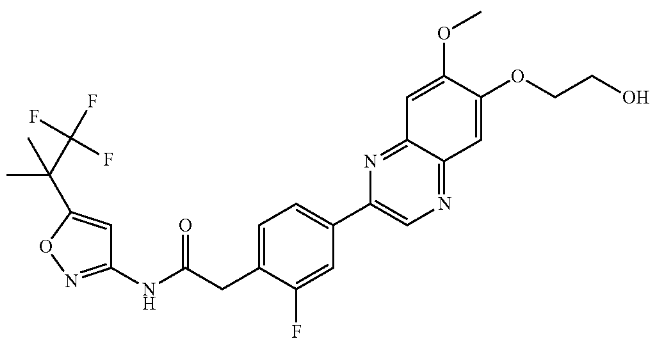 [SMILES: COc1cc2nc(-c3ccc(CC(=O)Nc4cc(C(C)(C)C(F)(F)F)on4)c(F)c3)cnc2cc1OCCO] | 165 | 2-[2-fluoro-4-[6-(2-hydroxyethoxy)-7-methoxy-quinoxalin-2-yl]phenyl]-N-[5-(2,2,2-trifluoro-1,1-dimethyl-ethyl)isoxazol-3-yl]acetamide | 549 (M + H)+ |
| 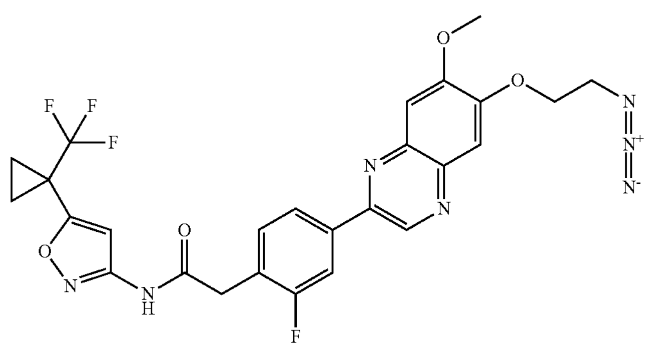 [SMILES: COc1cc2nc(-c3ccc(CC(=O)Nc4cc(C5(C(F)(F)F)CC5)on4)c(F)c3)cnc2cc1OCCN=[N+]=[N-]] | 166 | 2-[4-[6-(2-azidoethoxy)-7-methoxy-quinoxalin-2-yl]-2-fluoro-phenyl]-N-[5-[1-(trifluoromethyl)cyclo-propyl]isoxazol-3-yl]acetamide | 572 (M + H)+ |
| 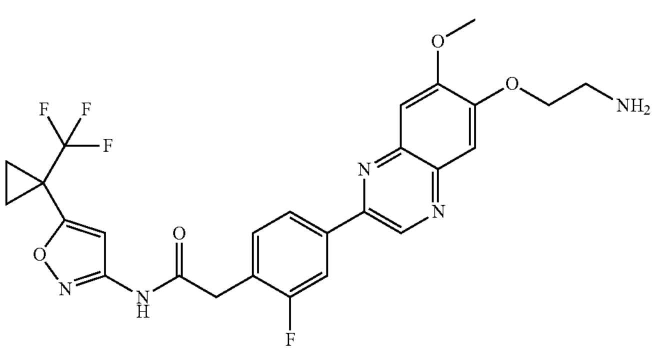 [SMILES: COc1cc2nc(-c3ccc(CC(=O)Nc4cc(C5(C(F)(F)F)CC5)on4)c(F)c3)cnc2cc1OCCN] | 167 | 2-[4-[6-(2-aminoethoxy)-7-methoxy-quinoxalin-2-yl]-2-fluoro-phenyl]-N-[5-[1-(trifluoromethyl)cyclo-propyl]isoxazol-3-yl]acetamide | 546 (M + H)+ |

TABLE 1-continued

| Chemical Structure | Example Number | Example Name | Observed m/z |
|---|---|---|---|
| 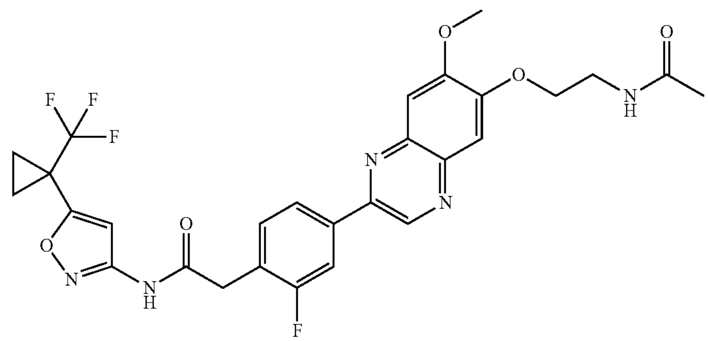 [SMILES: COc1cc2nc(-c3ccc(CC(=O)Nc4cc(C5(C(F)(F)F)CC5)on4)c(F)c3)cnc2cc1OCCNC(C)=O] | 168 | 2-[4-[6-(2-acetamidoethoxy)-7-methoxy-quinoxalin-2-yl]-2-fluoro-phenyl]-N-[5-[1-(trifluoromethyl)cyclopropyl]isoxazol-3-yl]acetamide | 588 (M + H)+ |
| 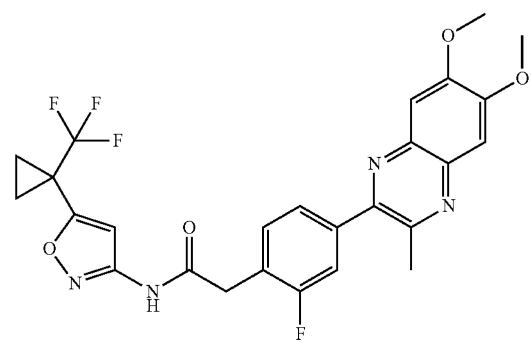 [SMILES: COc1cc2nc(C)c(-c3ccc(CC(=O)Nc4cc(C5(C(F)(F)F)CC5)on4)c(F)c3)nc2cc1OC] | 169 | 2-[4-(6,7-dimethoxy-3-methyl-quinoxalin-2-yl)-2-fluoro-phenyl]-N-[5-[1-(trifluoromethyl)cyclopropyl]isoxazol-3-yl]acetamide | 531 (M + H)+ |
| 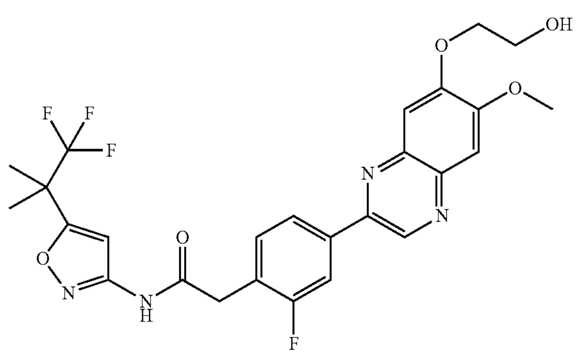 [SMILES: COc1cc2ncc(-c3ccc(CC(=O)Nc4cc(C(C)(C)C(F)(F)F)on4)c(F)c3)nc2cc1OCCO] | 170 | 2-[2-fluoro-4-[7-(2-hydroxyethoxy)-6-methoxy-quinoxalin-2-yl]phenyl]-N-[5-(2,2,2-trifluoro-1,1-dimethyl-ethyl)isoxazol-3-yl]acetamide | 549 (M + H)+ |
| 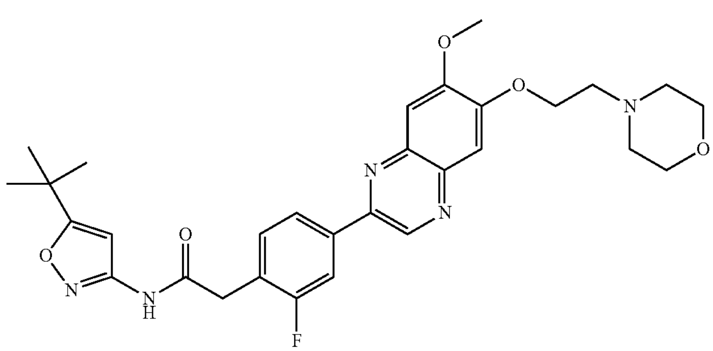 | 171 | 2-[2-fluoro-4-[7-methoxy-6-(2-morpholino-ethoxy)quinoxalin-2-yl]phenyl]-N-[5-(2,2,2-trifluoro-1,1-dimethyl-ethyl)isoxazol-3-yl]acetamide | 618 (M + H)+ |

TABLE 1-continued

| Chemical Structure | Example Number | Example Name | Observed m/z |
|---|---|---|---|
| 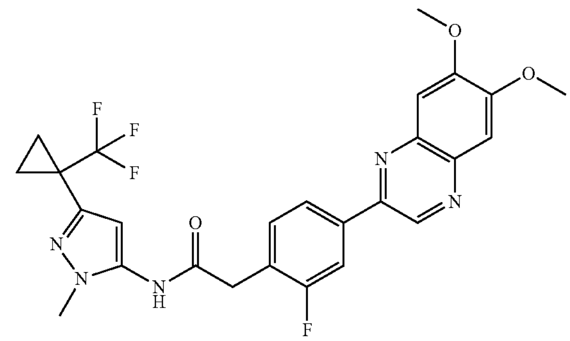 [SMILES: COc1cc2ncc(-c3ccc(CC(=O)Nc4cc(C5(C(F)(F)F)CC5)nn4C)c(F)c3)nc2cc1OC] | 172 | 2-[4-(6,7-dimethoxyquinoxalin-2-yl)-2-fluoro-phenyl]-N-[2-methyl-5-[1-(trifluoromethyl)cyclopropyl]pyrazol-3-yl]acetamide | 530 (M + H)+ |
| 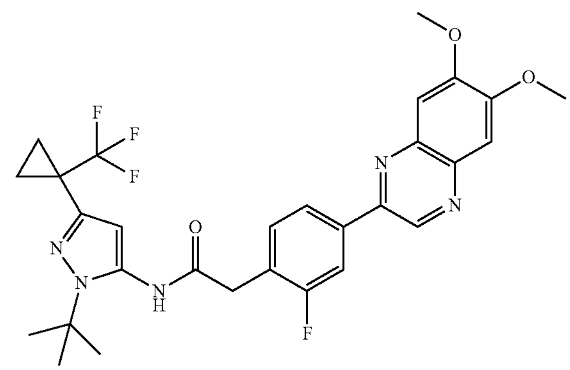 [SMILES: COc1cc2ncc(-c3ccc(CC(=O)Nc4cc(C5(C(F)(F)F)CC5)nn4C(C)(C)C)c(F)c3)nc2cc1OC] | 173 | N-[2-tert-butyl-5-[1-(trifluoromethyl)cyclopropyl]pyrazol-3-yl]-2-[4-(6,7-dimethoxy-quinoxalin-2-yl)-2-fluoro-phenyl]acetamide | 572 (M + H)+ |
| 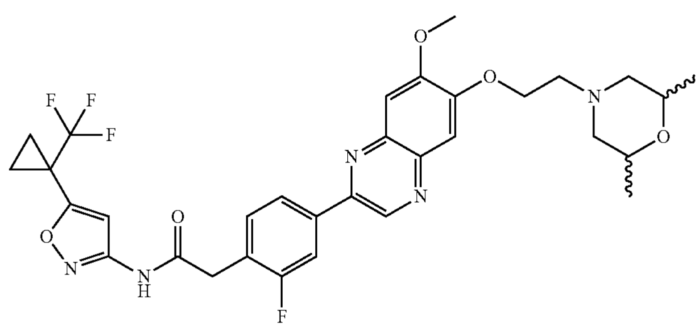 | 174 | 2-[4-[6-[2-(2,6-dimethylmorpholin-4-yl)ethoxy]-7-methoxy-quinoxalin-2-yl]-2-fluoro-phenyl]-N-[5-[1-(trifluoromethyl)cyclopropyl]isoxazol-3-yl]acetamide | 644 (M + H)+ |
| 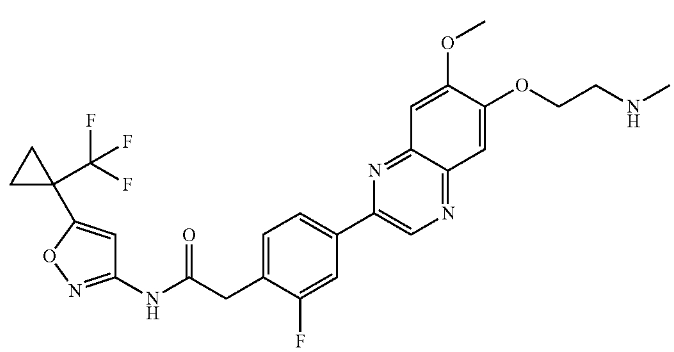 [SMILES: CNCCOc1cc2ncc(-c3ccc(CC(=O)Nc4cc(C5(C(F)(F)F)CC5)on4)c(F)c3)nc2cc1OC] | 175 | 2-[2-fluoro-4-[7-methoxy-6-[2-(methylamino)ethoxy]quinoxalin-2-yl]phenyl]-N-[5-[1-(trifluoromethyl)cyclopropyl]isoxazol-3-yl]acetamide | 560 (M + H)+ |

TABLE 1-continued

| Chemical Structure | Example Number | Example Name | Observed m/z |
|---|---|---|---|
| 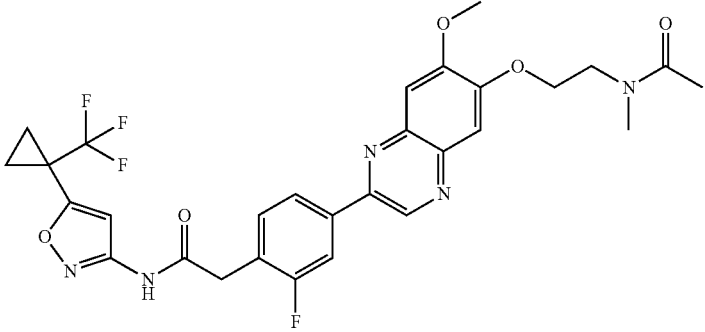 [SMILES: COc1cc2nc(-c3ccc(CC(=O)Nc4cc(C5(C(F)(F)F)CC5)on4)c(F)c3)cnc2cc1OCCN(C)C(C)=O] | 176 | 2-[4-[6-[2-[acetyl(methyl)amino]ethoxy]-7-methoxy-quinoxalin-2-yl]-2-fluoro-phenyl]-N-[5-[1-(trifluoromethyl)cyclo-propyl]isoxazol-3-yl]acetamide | 600 (M − H)⁻ |
| 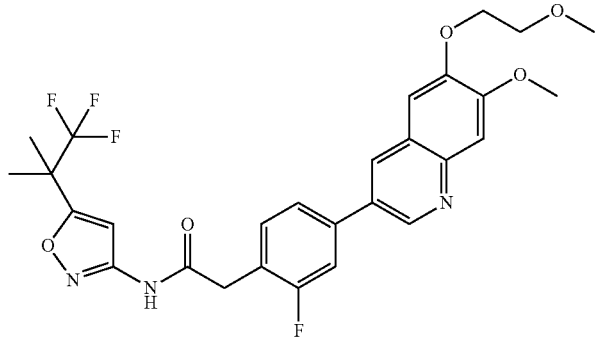 [SMILES: COCCOc1cc2cc(-c3ccc(CC(=O)Nc4cc(C(C)(C)C(F)(F)F)on4)c(F)c3)cnc2cc1OC] | 177 | 2-[2-fluoro-4-[7-methoxy-6-(2-methoxyethoxy)-3-quinolyl]phenyl]-N-[5-(2,2,2-trifluoro-1,1-dimethyl-ethyl)isoxazol-3-yl]acetamide | 562 (M + H)⁺ |
| 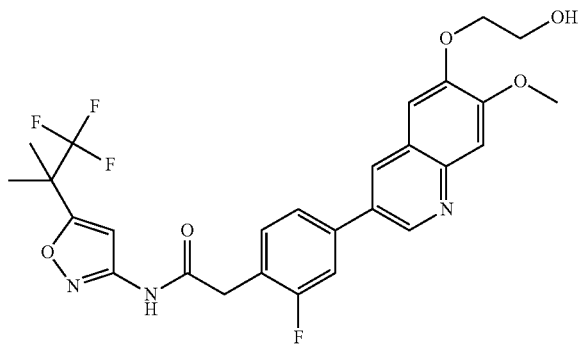 [SMILES: COc1cc2ncc(-c3ccc(CC(=O)Nc4cc(C(C)(C)C(F)(F)F)on4)c(F)c3)cc2cc1OCCO] | 178 | 2-[2-fluoro-4-[6-(2-hydroxyethoxy)-7-methoxy-3-quinolyl]phenyl]-N-[5-(2,2,2-trifluoro-1,1-dimethyl-ethyl)isoxazol-3-yl]acetamide | 548 (M + H)⁺ |
| 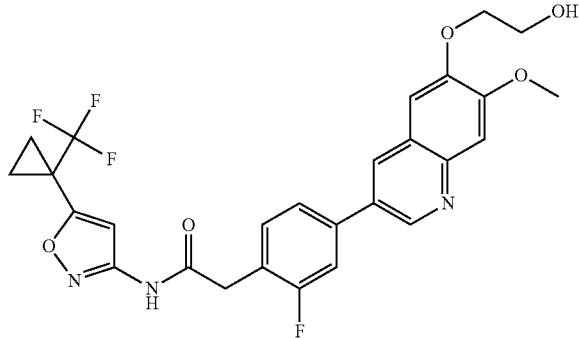 [SMILES: COc1cc2ncc(-c3ccc(CC(=O)Nc4cc(C5(C(F)(F)F)CC5)on4)c(F)c3)cc2cc1OCCO] | 179 | 2-[2-fluoro-4-[6-(2-hydroxyethoxy)-7-methoxy-3-quinolyl]phenyl]-N-[5-[1-(trifluoromethyl)cyclo-propyl]isoxazol-3-yl]acetamide | 546 (M + H)⁺ |

TABLE 1-continued

| Chemical Structure | Example Number | Example Name | Observed m/z |
|---|---|---|---|
| 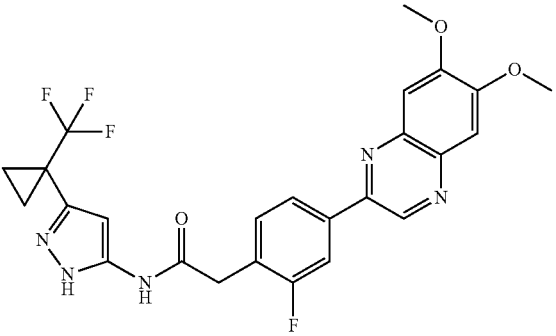 [SMILES: COc1cc2ncc(-c3ccc(CC(=O)Nc4cc(C5(C(F)(F)F)CC5)n[nH]4)c(F)c3)nc2cc1OC] | 180 | 2-[4-(6,7-dimethoxyquinoxalin-2-yl)-2-fluoro-phenyl]-N-[3-[1-(trifluoromethyl)cyclopropyl]-1H-pyrazol-5-yl]acetamide | 516 (M + H)+ |
| 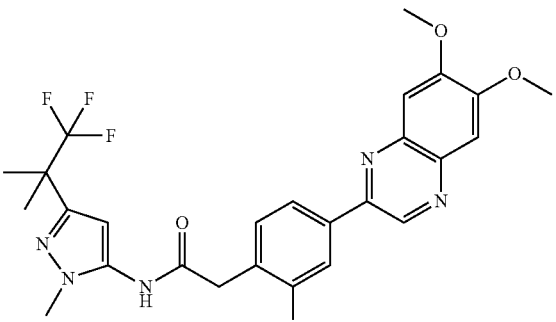 | 181 | 2-[4-(6,7-dimethoxyquinoxalin-2-yl)-2-fluoro-phenyl]-N-[2-methyl-5-(2,2,2-trifluoro-1,1-dimethyl-ethyl)pyrazol-3-yl]acetamide | 532 (M + H)+ |
| 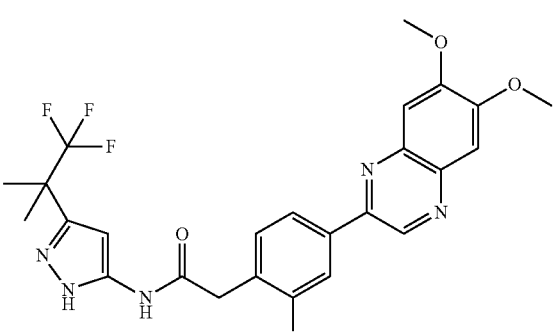 | 182 | 2-[4-(6,7-dimethoxyquinoxalin-2-yl)-2-fluoro-phenyl]-N-[3-(2,2,2-trifluoro-1,1-dimethyl-ethyl)-1H-pyrazol-5-yl]acetamide | 518 (M + H)+ |
| 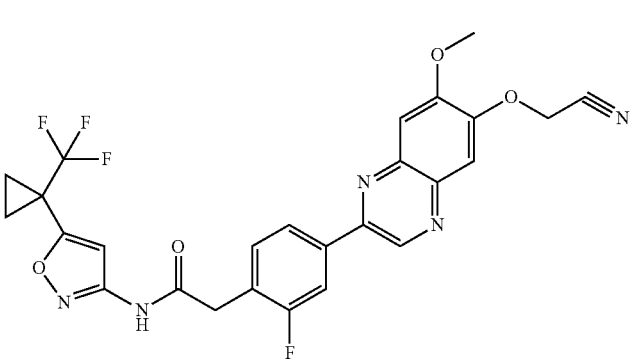 [SMILES: COc1cc2nc(-c3ccc(CC(=O)Nc4cc(C5(C(F)(F)F)CC5)on4)c(F)c3)cnc2cc1OCC#N] | 183 | 2-[4-[6-(cyanomethoxy)-7-methoxy-quinoxalin-2-yl]-2-fluoro-phenyl]-N-[5-[1-(trifluoromethyl)cyclopropyl]isoxazol-3-yl]acetamide | |

TABLE 1-continued

| Chemical Structure | Example Number | Example Name | Observed m/z |
|---|---|---|---|
| 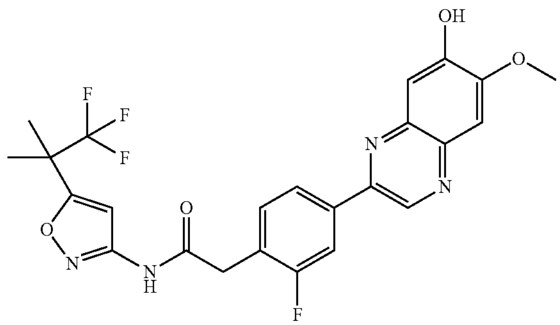 [SMILES: COc1cc2ncc(-c3ccc(CC(=O)Nc4cc(C(C)(C)C(F)(F)F)on4)c(F)c3)nc2cc1O] | 184 | 2-[2-fluoro-4-(7-hydroxy-6-methoxy-quinoxalin-2-yl)phenyl]-N-[5-(2,2,2-trifluoro-1,1-dimethyl-ethyl)isoxazol-3-yl]acetamide | 505 (M + H)+ |
| 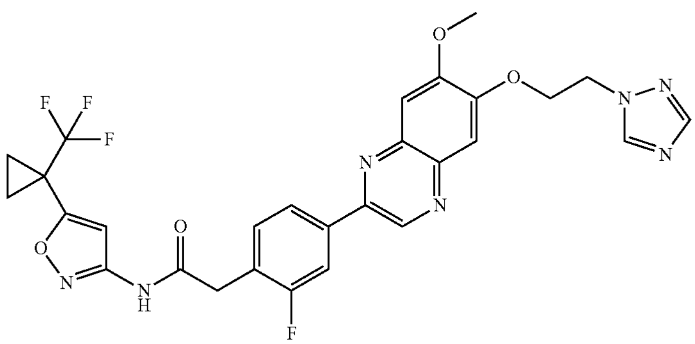 [SMILES: COc1cc2nc(-c3ccc(CC(=O)Nc4cc(C5(C(F)(F)F)CC5)on4)c(F)c3)cnc2cc1OCCn1cncn1] | 185 | 2-[2-fluoro-4-[7-methoxy-6-[2-(1,2,4-triazol-1-yl)ethoxy]quinoxalin-2-yl]phenyl]-N-[5-[1-(trifluoromethyl)cyclopropyl]isoxazol-3-yl]acetamide | 598 (M + H)+ |
| 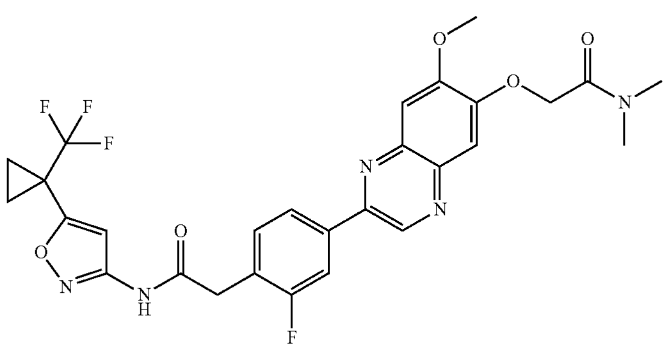 [SMILES: COc1cc2nc(-c3ccc(CC(=O)Nc4cc(C5(C(F)(F)F)CC5)on4)c(F)c3)cnc2cc1OCC(=O)N(C)C] | 186 | 2-[4-[6-[2-(dimethylamino)-2-oxo-ethoxy]-7-methoxy-quinoxalin-2-yl]-2-fluoro-phenyl]-N-[5-[1-(trifluoromethyl)cyclopropyl]isoxazol-3-yl]acetamide | 588 (M + H)+ |
| 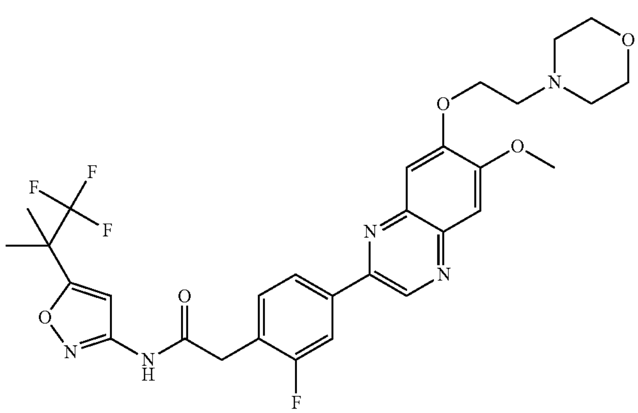 [SMILES: COc1cc2ncc(-c3ccc(CC(=O)Nc4cc(C(C)(C)C(F)(F)F)on4)c(F)c3)nc2cc1OCCN1CCOCC1] | 187 | 2-[2-fluoro-4-[6-methoxy-7-(2-morpholino-ethoxy)quinoxalin-2-yl]phenyl]-N-[5-(2,2,2-trifluoro-1,1-dimethyl-ethyl)isoxazol-3-yl]acetamide | 618 (M + H)+ |

TABLE 1-continued

| Chemical Structure | Example Number | Example Name | Observed m/z |
|---|---|---|---|
| 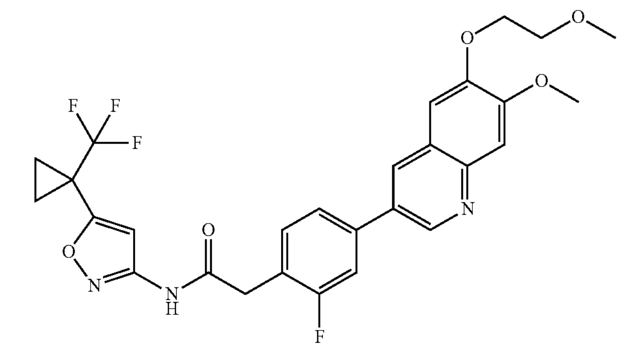 [SMILES: COCCOc1cc2cc(-c3ccc(CC(=O)Nc4cc(C5(C(F)(F)F)CC5)on4)c(F)c3)cnc2cc1OC] | 188 | 2-[2-fluoro-4-[7-methoxy-6-(2-methoxyethoxy)-3-quinolyl]phenyl]-N-[5-[1-(trifluoromethyl)cyclopropyl]isoxazol-3-yl]acetamide | 560 (M + H)+ |
| 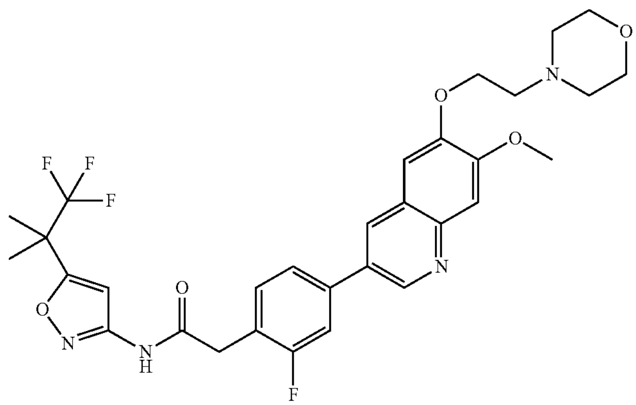 [SMILES: COc1cc2ncc(-c3ccc(CC(=O)Nc4cc(C(C)(C)C(F)(F)F)on4)c(F)c3)cc2cc1OCCN1CCOCC1] | 189 | 2-[2-fluoro-4-[7-methoxy-6-(2-morpholinoethoxy)-3-quinolyl]phenyl]-N-[5-(2,2,2-trifluoro-1,1-dimethyl-ethyl)isoxazol-3-yl]acetamide | 617 (M + H)+ |
| 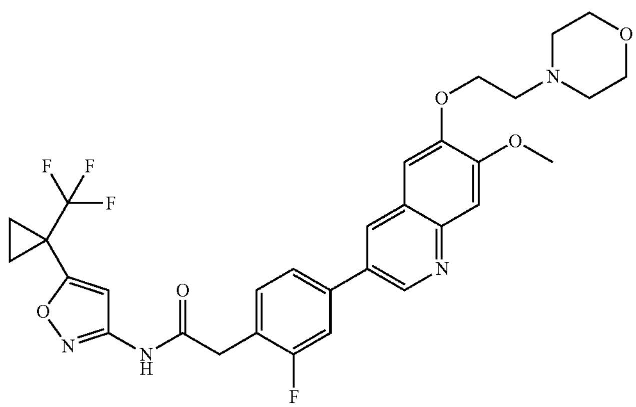 [SMILES: COc1cc2ncc(-c3ccc(CC(=O)Nc4cc(C5(C(F)(F)F)CC5)on4)c(F)c3)cc2cc1OCCN1CCOCC1] | 190 | 2-[2-fluoro-4-[7-methoxy-6-(2-morpholinoethoxy)-3-quinolyl]phenyl]-N-[5-[1-(trifluoromethyl)cyclopropyl]isoxazol-3-yl]acetamide | 615 (M + H)+ |
| 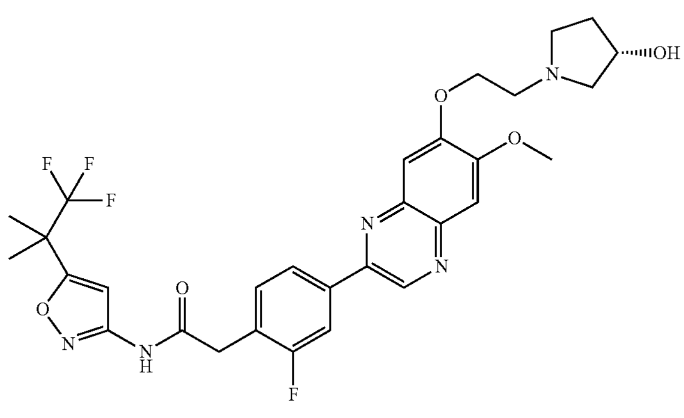 [SMILES: COc1cc2ncc(-c3ccc(CC(=O)Nc4cc(C(C)(C)C(F)(F)F)on4)c(F)c3)nc2cc1OCCN1CC[C@H](O)C1] | 191 | 2-[2-fluoro-4-[7-[2-[(3S)-3-hydroxypyrrolidin-1-yl]ethoxy]-6-methoxy-quinoxalin-2-yl]phenyl]-N-[5-(2,2,2-trifluoro-1,1-dimethyl-ethyl)isoxazol-3-yl]acetamide | 618 (M + H)+ |

TABLE 1-continued

| Chemical Structure | Example Number | Example Name | Observed m/z |
|---|---|---|---|
| 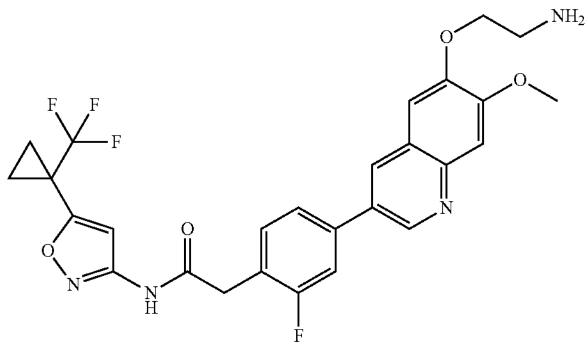 [SMILES: COc1cc2ncc(-c3ccc(CC(=O)Nc4cc(C5(C(F)(F)F)CC5)on4)c(F)c3)cc2cc1OCCN] | 192 | 2-[4-[6-(2-aminoethoxy)-7-methoxy-3-quinolyl]-2-fluoro-phenyl]-N-[5-[1-(trifluoromethyl)cyclopropyl]isoxazol-3-yl]acetamide | 545 (M + H)+ |
| 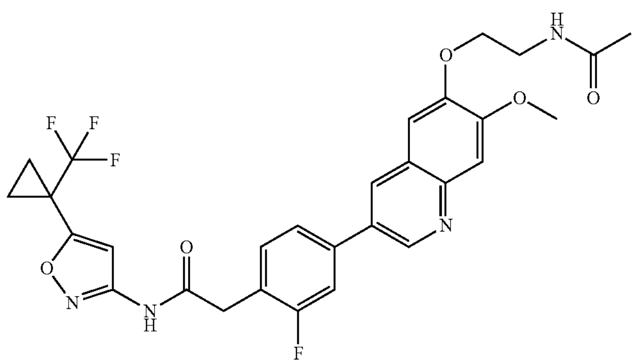 [SMILES: COc1cc2ncc(-c3ccc(CC(=O)Nc4cc(C5(C(F)(F)F)CC5)on4)c(F)c3)cc2cc1OCCNC(C)=O] | 193 | 2-[4-[6-(2-acetamidoethoxy)-7-methoxy-3-quinolyl]-2-fluoro-phenyl]-N-[5-[1-(trifluoromethyl)cyclopropyl]isoxazol-3-yl]acetamide | 587 (M + H)+ |
| 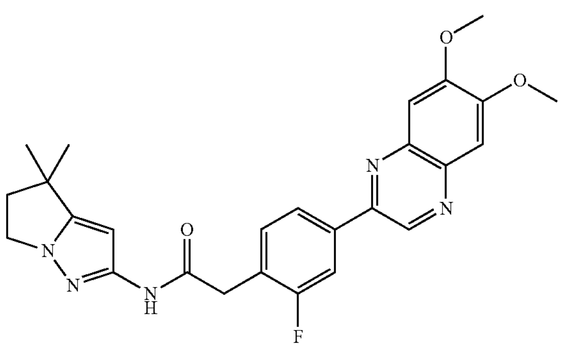 [SMILES: COc1cc2ncc(-c3ccc(CC(=O)Nc4cc5n(n4)CCC5(C)C)c(F)c3)nc2cc1OC] | 194 | 2-[4-(6,7-dimethoxyquinoxalin-2-yl)-2-fluoro-phenyl]-N-(4,4-dimethyl-5,6-dihydropyrrolo[1,2-b]pyrazol-2-yl)acetamide | 476 (M + H)+ |
| 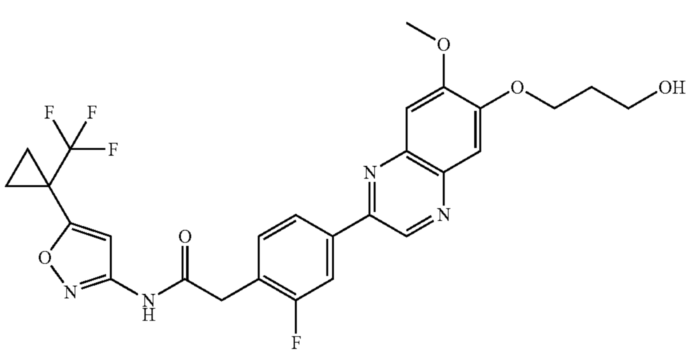 [SMILES: COc1cc2nc(-c3ccc(CC(=O)Nc4cc(C5(C(F)(F)F)CC5)on4)c(F)c3)cnc2cc1OCCCO] | 195 | 2-[2-fluoro-4-[6-(3-hydroxypropoxy)-7-methoxy-quinoxalin-2-yl]phenyl]-N-[5-[1-(trifluoromethyl)cyclopropyl]isoxazol-3-yl]acetamide | 561 (M + H)+ |

TABLE 1-continued

| Chemical Structure | Example Number | Example Name | Observed m/z |
|---|---|---|---|
| 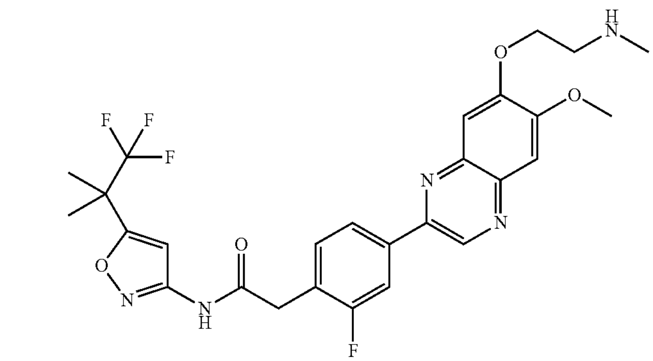 [SMILES: CNCCOc1cc2nc(-c3ccc(CC(=O)Nc4cc(C(C)(C)C(F)(F)F)on4)c(F)c3)cnc2cc1OC] | 196 | 2-[2-fluoro-4-[6-methoxy-7-[2-(methyl-amino)ethoxy]quinoxalin-2-yl]phenyl]-N-[5-(2,2,2-trifluoro-1,1-dimethyl-ethyl)isoxazol-3-yl]acetamide | 562 (M + H)+ |
| 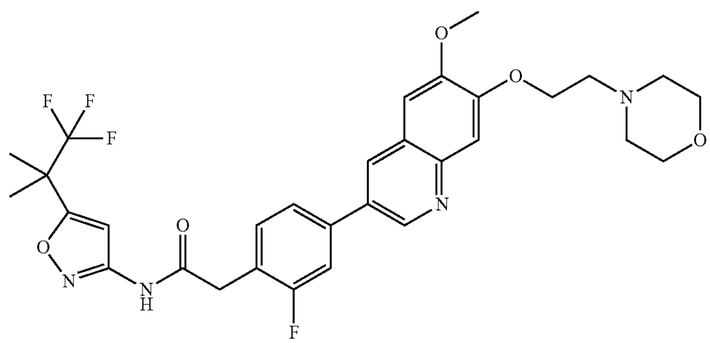 [SMILES: COc1cc2cc(-c3ccc(CC(=O)Nc4cc(C(C)(C)C(F)(F)F)on4)c(F)c3)cnc2cc1OCCN1CCOCC1] | 197 | 2-[2-fluoro-4-[6-methoxy-7-(2-morpholinoethoxy)-3-quinolyl]phenyl]-N-[5-(2,2,2-trifluoro-1,1-dimethyl-ethyl)isoxazol-3-yl]acetamide | 617 (M + H)+ |
| 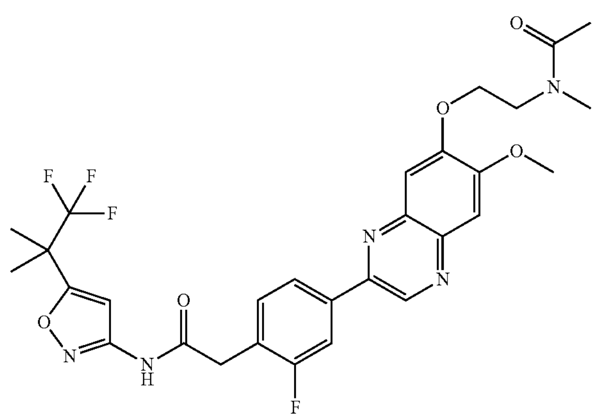 [SMILES: COc1cc2ncc(-c3ccc(CC(=O)Nc4cc(C(C)(C)C(F)(F)F)on4)c(F)c3)nc2cc1OCCN(C)C(C)=O] | 198 | 2-[4-[7-[2-[acetyl(methyl)amino]ethoxy]-6-methoxy-quinoxalin-2-yl]-2-fluoro-phenyl]-N-[5-(2,2,2-trifluoro-1,1-dimethyl-ethyl)isoxazol-3-yl]acetamide | 604 (M + H)+ |
| 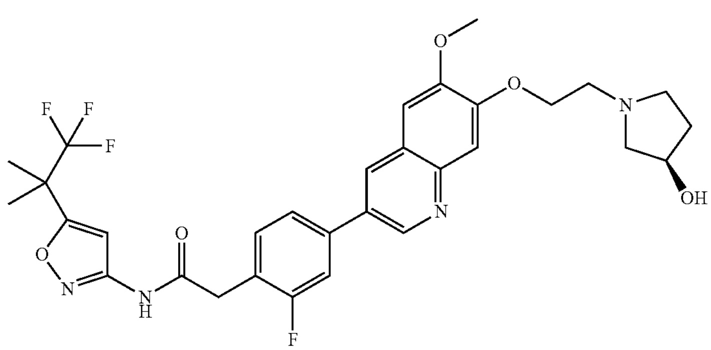 [SMILES: COc1cc2cc(-c3ccc(CC(=O)Nc4cc(C(C)(C)C(F)(F)F)on4)c(F)c3)cnc2cc1OCCN1CC[C@@H](O)C1] | 199 | 2-[2-fluoro-4-[7-[2-[(3R)-3-hydroxypyrrolidin-1-yl]ethoxy]-6-methoxy-3-quinolyl]phenyl]-N-[5-(2,2,2-trifluoro-1,1-dimethyl-ethyl)isoxazol-3-yl]acetamide | 617 (M + H)+ |

TABLE 1-continued

| Chemical Structure | Example Number | Example Name | Observed m/z |
|---|---|---|---|
| 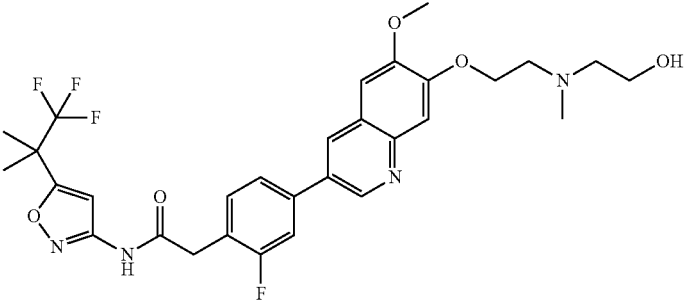 [SMILES: COc1cc2cc(-c3ccc(CC(=O)Nc4cc(C(C)(C)C(F)(F)F)on4)c(F)c3)cnc2cc1OCCN(C)CCO] | 200 | 2-[2-fluoro-4-[7-[2-[2-hydroxy-ethyl(methyl)amino]ethoxy]-6-methoxy-3-quinolyl]phenyl]-N-[5-(2,2,2-trifluoro-1,1-dimethyl-ethyl)isoxazol-3-yl]acetamide | 605 (M + H)+ |
| 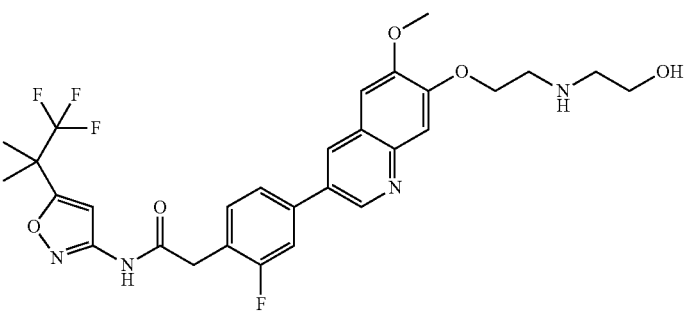 [SMILES: COc1cc2cc(-c3ccc(CC(=O)Nc4cc(C(C)(C)C(F)(F)F)on4)c(F)c3)cnc2cc1OCCNCCO] | 201 | 2-[2-fluoro-4-[7-[2-(2-hydroxyethylamino)ethoxy]-6-methoxy-3-quinolyl]phenyl]-N-[5-(2,2,2-trifluoro-1,1-dimethyl-ethyl)isoxazol-3-yl]acetamide | 591 (M + H)+ |
| 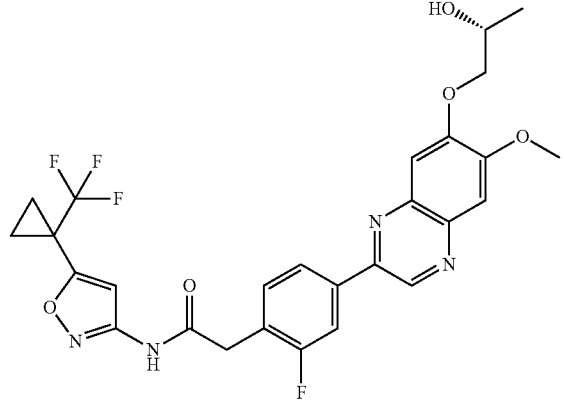 [SMILES: COc1cc2ncc(-c3ccc(CC(=O)Nc4cc(C5(C(F)(F)F)CC5)on4)c(F)c3)nc2cc1OC[C@@H](C)O] | 202 | 2-[2-fluoro-4-[7-[(2R)-2-hydroxypropoxy]-6-methoxy-quinoxalin-2-yl]phenyl]-N-[5-[1-(trifluoromethyl)cyclo-propyl]isoxazol-3-yl]acetamide | 561 (M + H)+ |
| 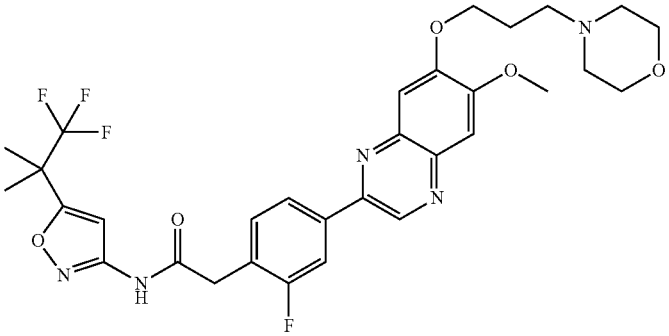 [SMILES: COc1cc2ncc(-c3ccc(CC(=O)Nc4cc(C(C)(C)C(F)(F)F)on4)c(F)c3)nc2cc1OCCCN1CCOCC1] | 203 | 2-[2-fluoro-4-[6-methoxy-7-(3-morpholino-propoxy)quinoxalin-2-yl]phenyl]-N-[5-(2,2,2-trifluoro-1,1-dimethyl-ethyl)isoxazol-3-yl]acetamide | 632 (M + H)+ |

TABLE 1-continued

| Chemical Structure | Example Number | Example Name | Observed m/z |
|---|---|---|---|
| 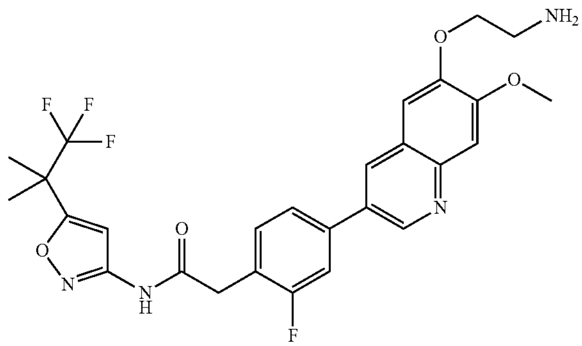 [SMILES: COc1cc2ncc(-c3ccc(CC(=O)Nc4cc(C(C)(C)C(F)(F)F)on4)c(F)c3)cc2cc1OCCN] | 204 | 2-[4-[6-(2-aminoethoxy)-7-methoxy-3-quinolyl]-2-fluoro-phenyl]-N-[5-(2,2,2-trifluoro-1,1-dimethyl-ethyl)isoxazol-3-yl]acetamide | 547 (M + H)+ |
| 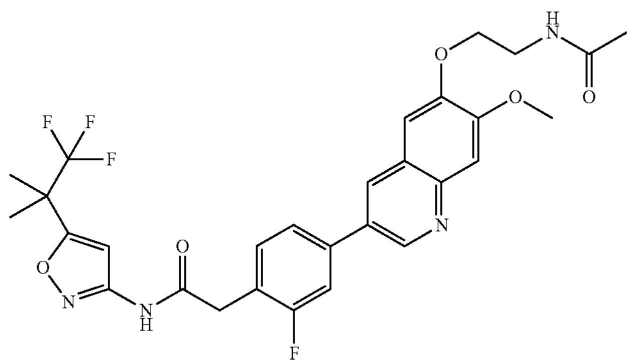 [SMILES: COc1cc2ncc(-c3ccc(CC(=O)Nc4cc(C(C)(C)C(F)(F)F)on4)c(F)c3)cc2cc1OCCNC(C)=O] | 205 | 2-[4-[6-(2-acetamidoethoxy)-7-methoxy-3-quinolyl]-2-fluoro-phenyl]-N-[5-(2,2,2-trifluoro-1,1-dimethyl-ethyl)isoxazol-3-yl]acetamide | 589 (M + H)+ |
| 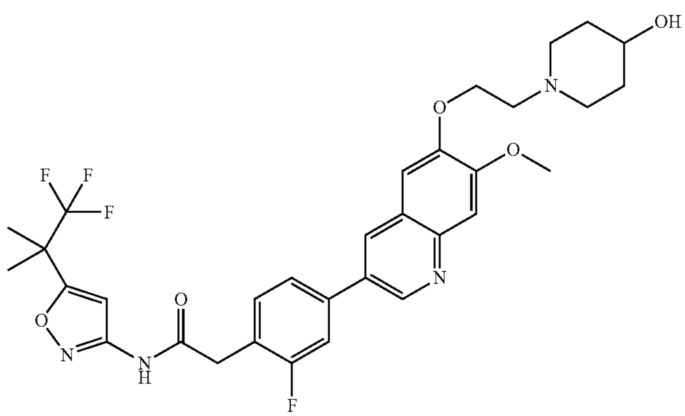 [SMILES: COc1cc2ncc(-c3ccc(CC(=O)Nc4cc(C(C)(C)C(F)(F)F)on4)c(F)c3)cc2cc1OCCN1CCC(O)CC1] | 206 | 2-[2-fluoro-4-[6-[2-(4-hydroxy-1-piperidyl)ethoxy]-7-methoxy-3-quinolyl]phenyl]-N-[5-(2,2,2-trifluoro-1,1-dimethyl-ethyl)isoxazol-3-yl]acetamide | 631 (M + H)+ |
| 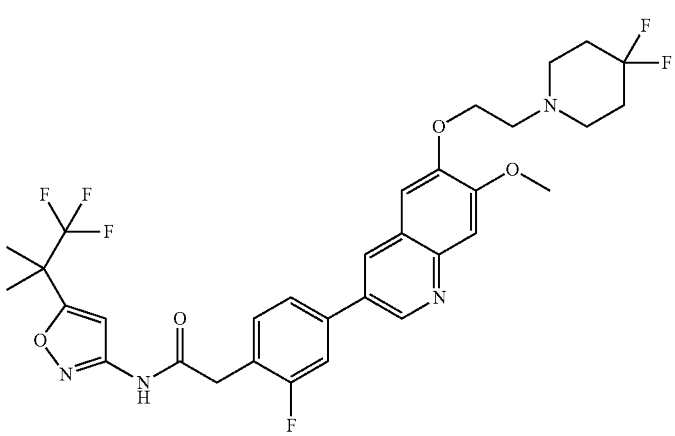 [SMILES: COc1cc2ncc(-c3ccc(CC(=O)Nc4cc(C(C)(C)C(F)(F)F)on4)c(F)c3)cc2cc1OCCN1CCC(F)(F)CC1] | 207 | 2-[4-[6-[2-(4,4-difluoro-1-piperidyl)ethoxy]-7-methoxy-3-quinolyl]-2-fluoro-phenyl]-N-[5-(2,2,2-trifluoro-1,1-dimethyl-ethyl)isoxazol-3-yl]acetamide | 651 (M + H)+ |

TABLE 1-continued

| Chemical Structure | Example Number | Example Name | Observed m/z |
|---|---|---|---|
| 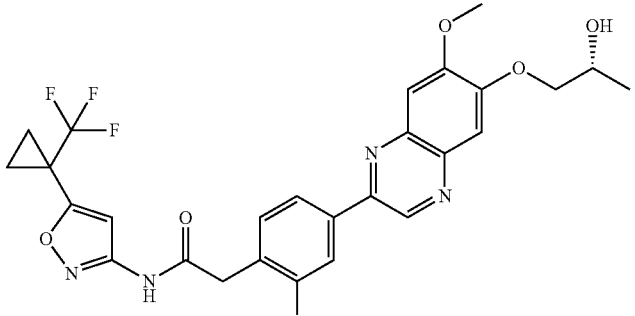 | 208 | 2-[2-fluoro-4-[6-[(2R)-2-hydroxypropoxy]-7-methoxy-quinoxalin-2-yl]phenyl]-N-[5-[1-(trifluoromethyl)cyclopropyl]isoxazol-3-yl]acetamide | 561 (M + H)+ |
| 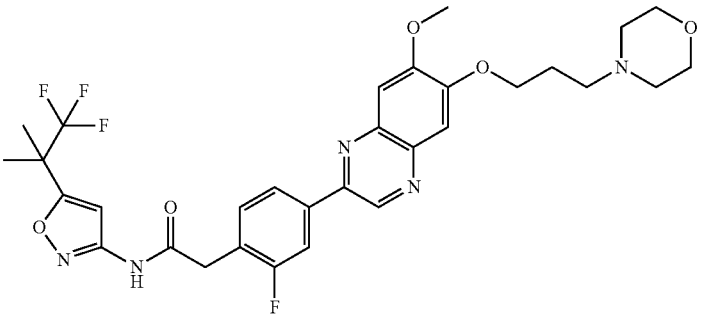 [SMILES: COc1cc2nc(-c3ccc(CC(=O)Nc4cc(C(C)(C)C(F)(F)F)on4)c(F)c3)cnc2cc1OCCCN1CCOCC1] | 209 | 2-[2-fluoro-4-[7-methoxy-6-(3-morpholino-propoxy)quinoxalin-2-yl]phenyl]-N-[5-(2,2,2-trifluoro-1,1-dimethyl-ethyl)isoxazol-3-yl]acetamide | 632 (M + H)+ |
| 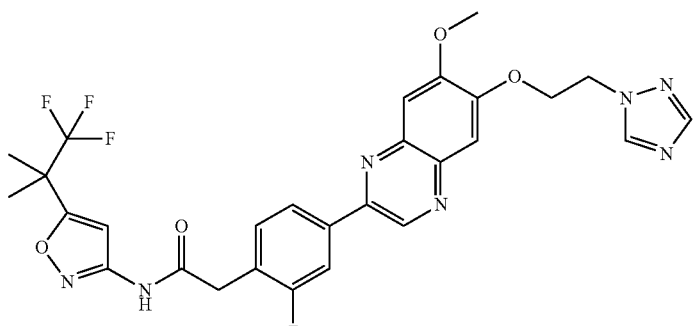 | 210 | 2-[2-fluoro-4-[7-methoxy-6-[2-(1,2,4-triazol-1-yl)ethoxy]quinoxalin-2-yl]phenyl]-N-[5-(2,2,2-trifluoro-1,1-dimethyl-ethyl)isoxazol-3-yl]acetamide | 600 (M + H)+ |
| 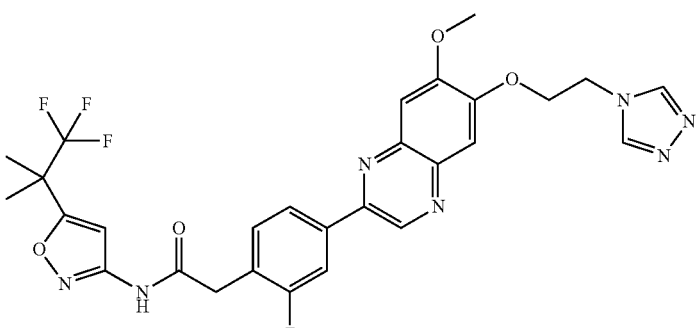 | 211 | 2-[2-fluoro-4-[7-methoxy-6-[2-(1,2,4-triazol-4-yl)ethoxy]quinoxalin-2-yl]phenyl]-N-[5-(2,2,2-trifluoro-1,1-dimethyl-ethyl)isoxazol-3-yl]acetamide | 600 (M + H)+ |

TABLE 1-continued

| Chemical Structure | Example Number | Example Name | Observed m/z |
|---|---|---|---|
| 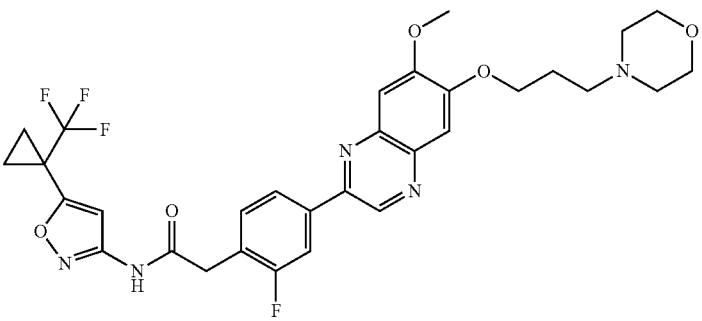 [SMILES: COc1cc2nc(-c3ccc(CC(=O)Nc4cc(C5(C(F)(F)F)CC5)on4)c(F)c3)cnc2cc1OCCCN1CCOCC1] | 212 | 2-[2-fluoro-4-[7-methoxy-6-(3-morpholino-propoxy)quinoxalin-2-yl]phenyl]-N-[5-[1-(trifluoro-methyl)cyclopropyl]isoxazol-3-yl]acetamide | 630 (M + H)+ |
| 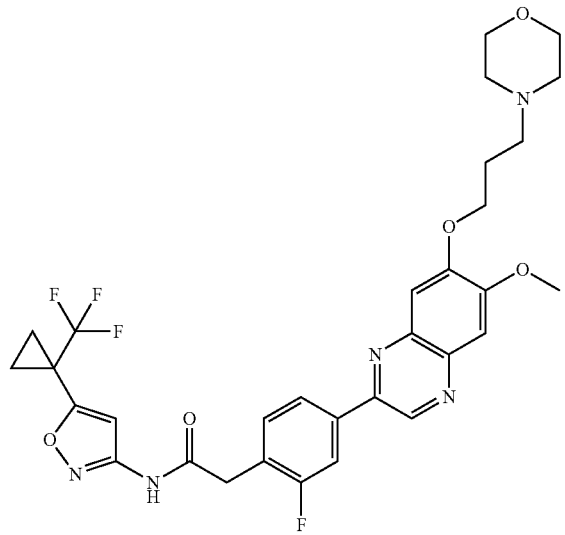 [SMILES: COc1cc2ncc(-c3ccc(CC(=O)Nc4cc(C5(C(F)(F)F)CC5)on4)c(F)c3)nc2cc1OCCCN1CCOCC1] | 213 | 2-[2-fluoro-4-[6-methoxy-7-(3-morpholino-propoxy)quinoxalin-2-yl]phenyl]-N-[5-[1-(trifluoro-methyl)cyclopropyl]isoxazol-3-yl]acetamide | 630 (M + H)+ |
| 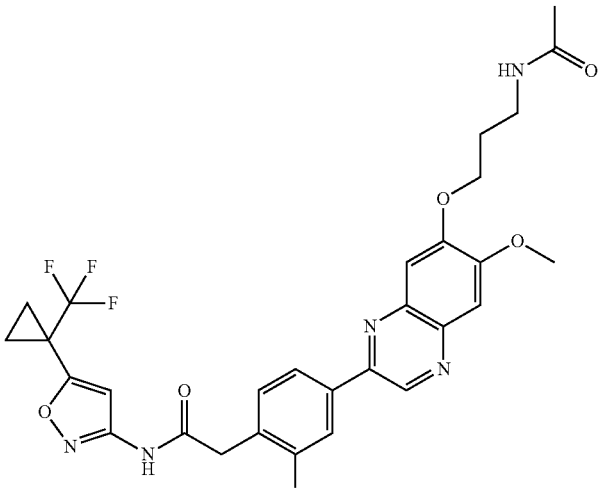 | 214 | 2-[4-[7-(3-acetamidopropoxy)-6-methoxy-quinoxalin-2-yl]-2-fluoro-phenyl]-N-[5-[1-(trifluoromethyl)cyclo-propyl]isoxazol-3-yl]acetamide | 602 (M + H)+ |

TABLE 1-continued

| Chemical Structure | Example Number | Example Name | Observed m/z |
|---|---|---|---|
| 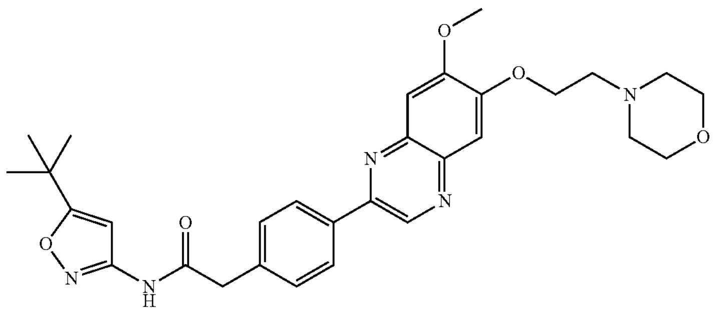 [SMILES: COc1cc2nc(-c3ccc(CC(=O)Nc4cc(C(C)(C)C)on4)cc3)cnc2cc1OCCN1CCOCC1] | 215 | N-(5-tert-butylisoxazol-3-yl)-2-[4-[7-methoxy-6-(2-morpholino-ethoxy)quinoxalin-2-yl]phenyl]acetamide | 546 (M + H)+ |
| 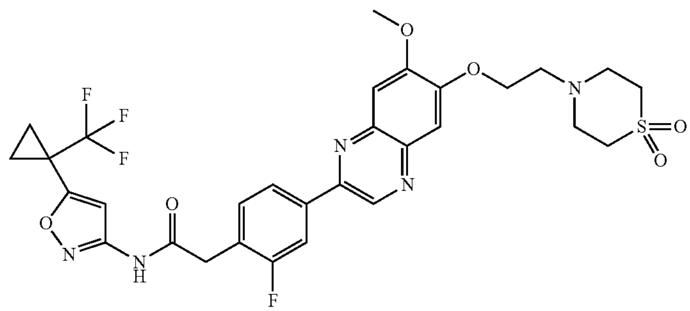 [SMILES: COc1cc2nc(-c3ccc(CC(=O)Nc4cc(C5(C(F)(F)F)CC5)on4)c(F)c3)cnc2cc1OCCN1CCS(=O)(=O)CC1] | 216 | 2-[4-[6-[2-(1,1-dioxo-1,4-thiazinan-4-yl)ethoxy]-7-methoxy-quinoxalin-2-yl]-2-fluoro-phenyl]-N-[5-[1-(trifluoromethyl)cyclo-propyl]isoxazol-3-yl]acetamide | 664 (M + H)+ |
| 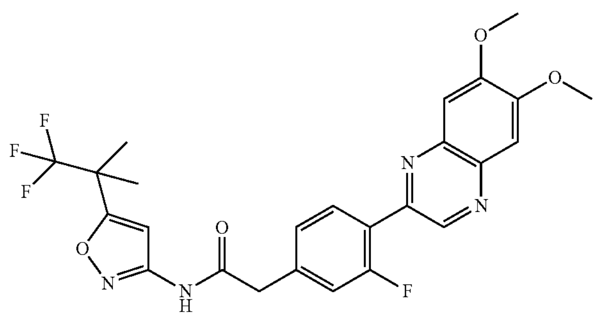 [SMILES: COc1cc2ncc(-c3ccc(CC(=O)Nc4cc(C(C)(C)C(F)(F)F)on4)cc3F)nc2cc1OC] | 217 | 2-[4-(6,7-dimethoxyquinoxalin-2-yl)-3-fluoro-phenyl]-N-[5-(2,2,2-trifluoro-1,1-dimethyl-ethyl)isoxazol-3-yl]acetamide | 519 (M + H)+ |
| 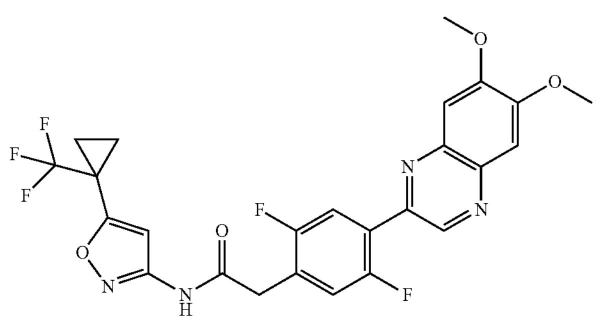 [SMILES: COc1cc2ncc(-c3cc(F)c(CC(=O)Nc4cc(C5(C(F)(F)F)CC5)on4)cc3F)nc2cc1OC] | 218 | 2-[4-(6,7-dimethoxyquinoxalin-2-yl)-2,5-difluoro-phenyl]-N-[5-[1-(trifluoro-methyl)cyclopropyl]isoxazol-3-yl]acetamide | 535 (M + H)+ |
| 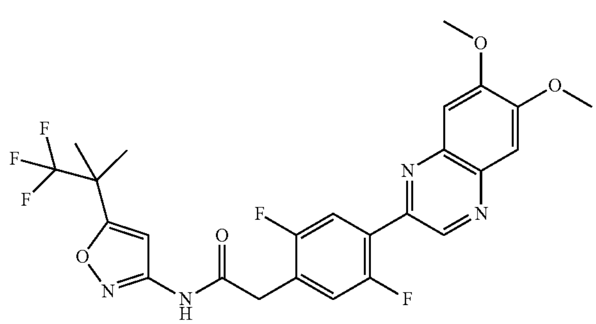 [SMILES: COc1cc2ncc(-c3cc(F)c(CC(=O)Nc4cc(C(C)(C)C(F)(F)F)on4)cc3F)nc2cc1OC] | 219 | 2-[4-(6,7-dimethoxyquinoxalin-2-yl)-2,5-difluoro-phenyl]-N-[5-(2,2,2-trifluoro-1,1-dimethyl-ethyl)isoxazol-3-yl]acetamide | 537 (M + H)+ |

TABLE 1-continued

| Chemical Structure | Example Number | Example Name | Observed m/z |
|---|---|---|---|
| 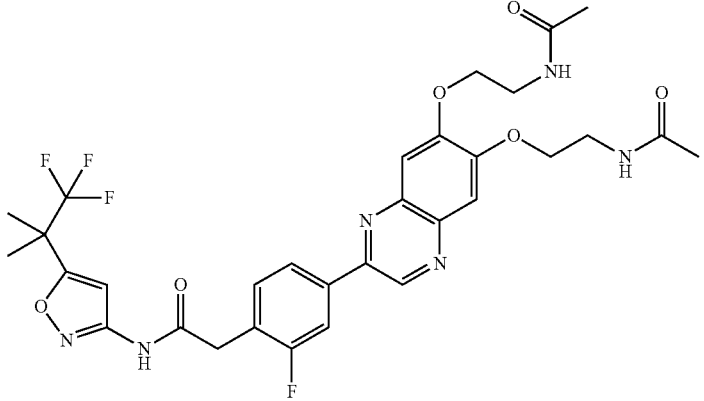 [SMILES: CC(=O)NCCOc1cc2ncc(-c3ccc(CC(=O)Nc4cc(C(C)(C)C(F)(F)F)on4)c(F)c3)nc2cc1OCCNC(C)=O] | 220 | 2-[4-[6,7-bis(2-acetamidoethoxy)quinoxalin-2-yl]-2-fluoro-phenyl]-N-[5-(2,2,2-trifluoro-1,1-dimethyl-ethyl)isoxazol-3-yl]acetamide | 661 (M + H)⁺ |
| 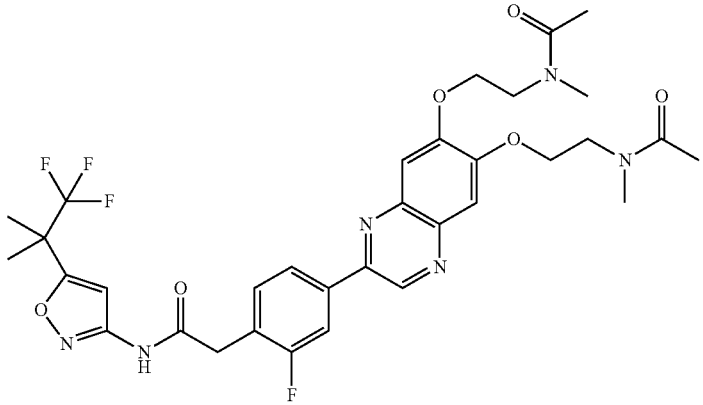 [SMILES: CC(=O)N(C)CCOc1cc2ncc(-c3ccc(CC(=O)Nc4cc(C(C)(C)C(F)(F)F)on4)c(F)c3)nc2cc1OCCN(C)C(C)=O] | 221 | 2-[4-[6,7-bis[2-[acetyl(methyl)amino]ethoxy]quinoxalin-2-yl]-2-fluoro-phenyl]-N-[5-(2,2,2-trifluoro-1,1-dimethyl-ethyl)isoxazol-3-yl]acetamide | 689 (M + H)⁺ |
| 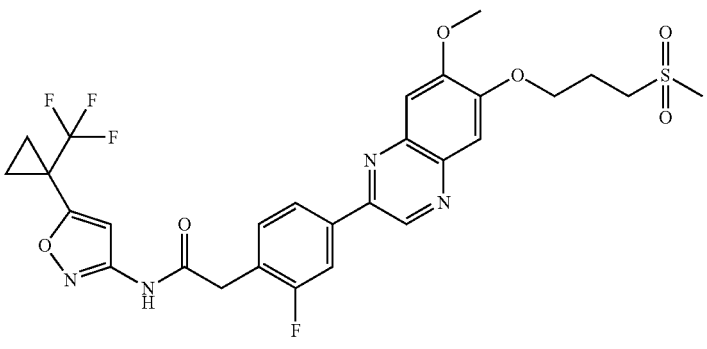 [SMILES: COc1cc2nc(-c3ccc(CC(=O)Nc4cc(C5(C(F)(F)F)CC5)on4)c(F)c3)cnc2cc1OCCCS(C)(=O)=O] | 222 | 2-[2-fluoro-4-[7-methoxy-6-(3-methylsulfonylpropoxy)quinoxalin-2-yl]phenyl]-N-[5-[1-(trifluoromethyl)cyclopropyl]isoxazol-3-yl]acetamide | 623 (M + H)⁺ |
| 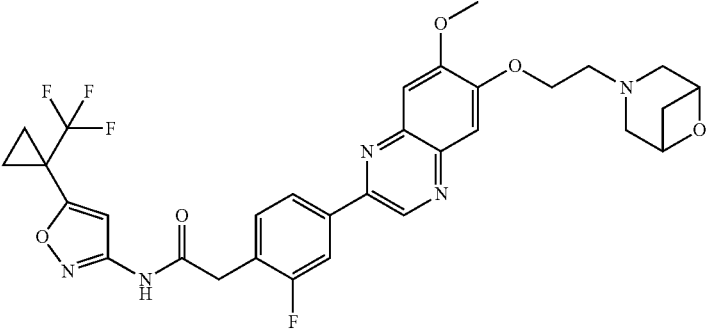 [SMILES: COc1cc2nc(-c3ccc(CC(=O)Nc4cc(C5(C(F)(F)F)CC5)on4)c(F)c3)cnc2cc1OCCN1CC2CC(C1)O2] | 223 | 2-[2-fluoro-4-[7-methoxy-6-[2-(6-oxa-3-azabicyclo[3.1.1]heptan-3-yl)ethoxy]quinoxalin-2-yl]phenyl]-N-[5-[1-(trifluoromethyl)cyclopropyl]isoxazol-3-yl]acetamide | 628 (M + H)⁺ |

TABLE 1-continued

| Chemical Structure | Example Number | Example Name | Observed m/z |
|---|---|---|---|
| 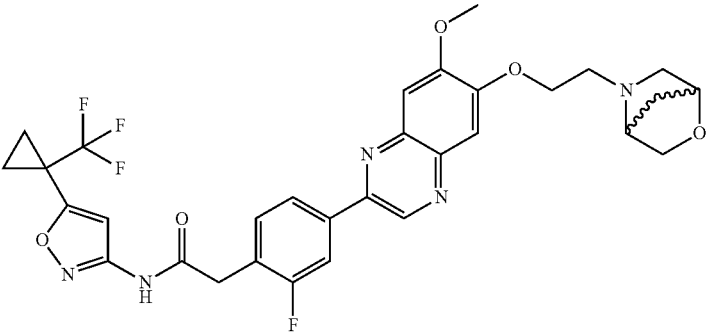 | 224 | 2-[2-fluoro-4-[7-methoxy-6-[2-(2-oxa-5-azabicyclo[2.2.1]heptan-5-yl)ethoxy]quinoxalin-2-yl]phenyl]-N-[5-[1-(trifluoromethyl)cyclopropyl]isoxazol-3-yl]acetamide | 628 (M + H)+ |
| 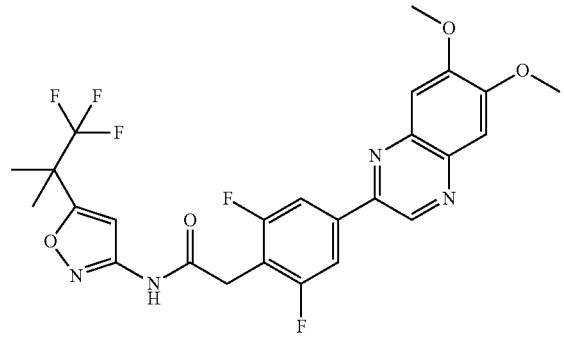 [SMILES: COc1cc2ncc(-c3cc(F)c(CC(=O)Nc4cc(C(C)(C)C(F)(F)F)on4)c(F)c3)nc2cc1OC] | 225 | 2-[4-(6,7-dimethoxyquinoxalin-2-yl)-2,6-difluoro-phenyl]-N-[5-(2,2,2-trifluoro-1,1-dimethyl-ethyl)isoxazol-3-yl]acetamide | 537 (M + H)+ |
| 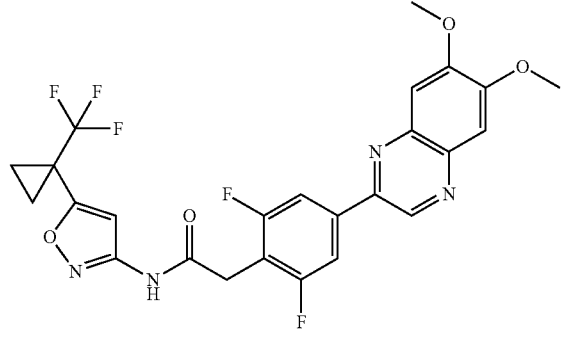 | 226 | 2-[4-(6,7-dimethoxyquinoxalin-2-yl)-2,6-difluoro-phenyl]-N-[5-[1-(trifluoromethyl)cyclopropyl]isoxazol-3-yl]acetamide | 535 (M + H)+ |
| 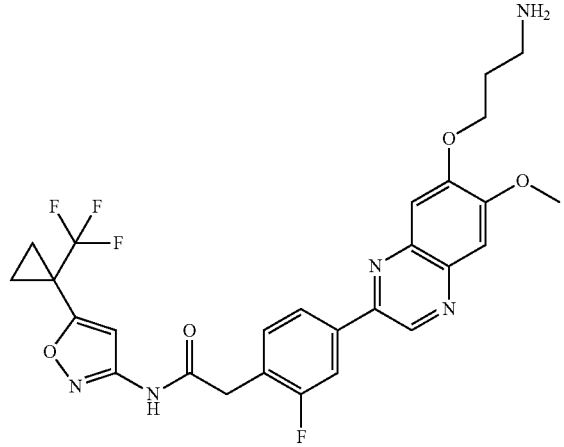 [SMILES: COc1cc2ncc(-c3ccc(CC(=O)Nc4cc(C5(C(F)(F)F)CC5)on4)c(F)c3)nc2cc1OCCCN] | 227 | 2-[4-[7-(3-aminopropoxy)-6-methoxy-quinoxalin-2-yl]-2-fluoro-phenyl]-N-[5-[1-(trifluoromethyl)cyclopropyl]isoxazol-3-yl]acetamide | 560 (M + H)+ |

TABLE 1-continued

| Chemical Structure | Example Number | Example Name | Observed m/z |
|---|---|---|---|
| 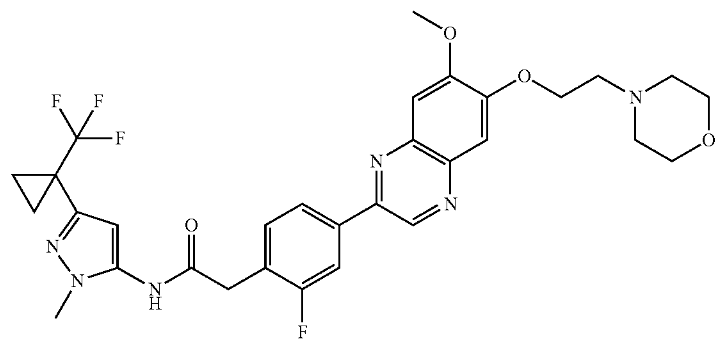 [SMILES: COc1cc2nc(-c3ccc(CC(=O)Nc4cc(C5(C(F)(F)F)CC5)nn4C)c(F)c3)cnc2cc1OCCN1CCOCC1] | 228 | 2-[2-fluoro-4-[7-methoxy-6-(2-morpholino-ethoxy)quinoxalin-2-yl]phenyl]-N-[2-methyl-5-[1-(trifluoromethyl)cyclo-propyl]pyrazol-3-yl]acetamide | 629 (M + H)+ |
| 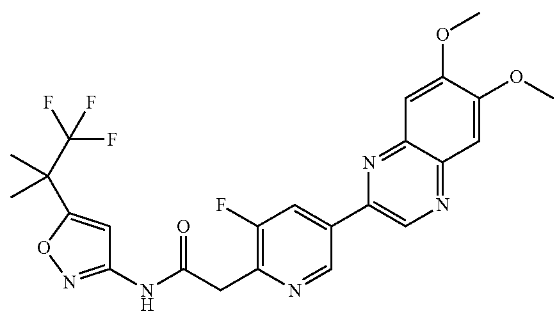 [SMILES: COc1cc2ncc(-c3cnc(CC(=O)Nc4cc(C(C)(C)C(F)(F)F)on4)c(F)c3)nc2cc1OC] | 229 | 2-[5-(6,7-dimethoxyquinoxalin-2-yl)-3-fluoro-2-pyridyl]-N-[5-(2,2,2-trifluoro-1,1-dimethyl-ethyl)isoxazol-3-yl]acetamide | 520 (M + H)+ |
| 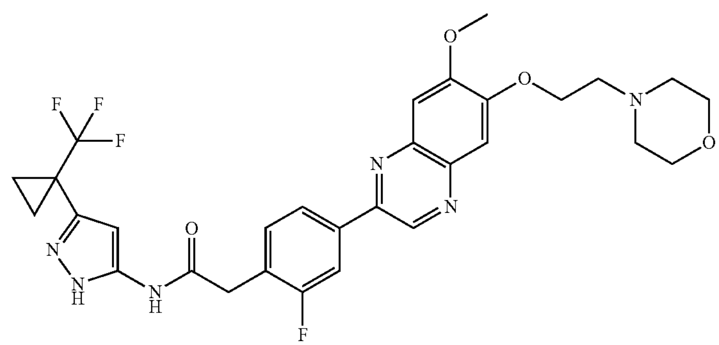 [SMILES: COc1cc2nc(-c3ccc(CC(=O)Nc4cc(C5(C(F)(F)F)CC5)n[nH]4)c(F)c3)cnc2cc1OCCN1CCOCC1] | 230 | 2-[2-fluoro-4-[7-methoxy-6-(2-morpholino-ethoxy)quinoxalin-2-yl]phenyl]-N-[3-[1-(trifluoro-methyl)cyclopropyl]-1H-pyrazol-5-yl]acetamide | 615 (M + H)+ |
| 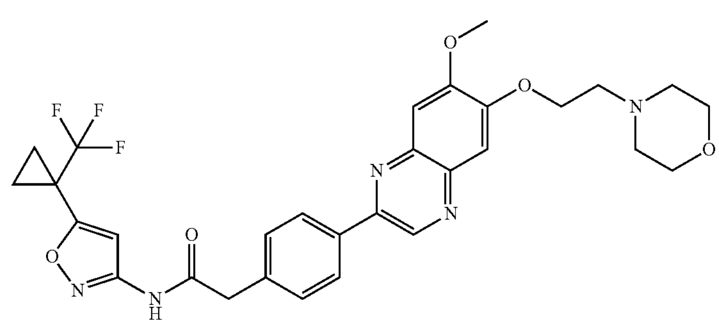 [SMILES: COc1cc2nc(-c3ccc(CC(=O)Nc4cc(C5(C(F)(F)F)CC5)on4)cc3)cnc2cc1OCCN1CCOCC1] | 231 | 2-[4-[7-methoxy-6-(2-morpholinoethoxy)quinoxalin-2-yl]phenyl]-N-[5-[1-(trifluoromethyl)cyclo-propyl]isoxazol-3-yl]acetamide | 598 (M + H)+ |

TABLE 1-continued

| Chemical Structure | Example Number | Example Name | Observed m/z |
|---|---|---|---|
| 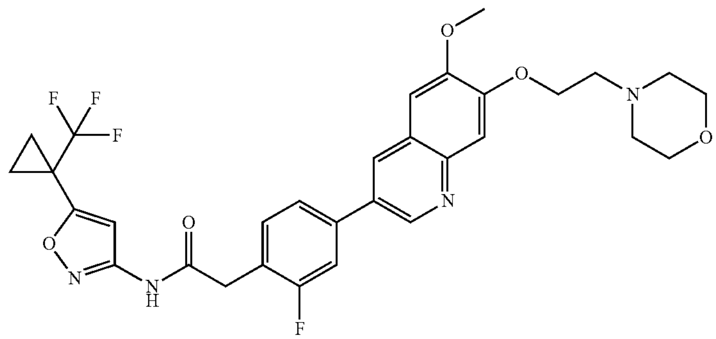 [SMILES: COc1cc2cc(-c3ccc(CC(=O)Nc4cc(C5(C(F)(F)F)CC5)on4)c(F)c3)cnc2cc1OCCN1CCOCC1] | 232 | 2-[2-fluoro-4-[6-methoxy-7-(2-morpholinoethoxy)-3-quinolyl]phenyl]-N-[5-[1-(trifluoromethyl)cyclopropyl]isoxazol-3-yl]acetamide | 615 (M + H)+ |
| 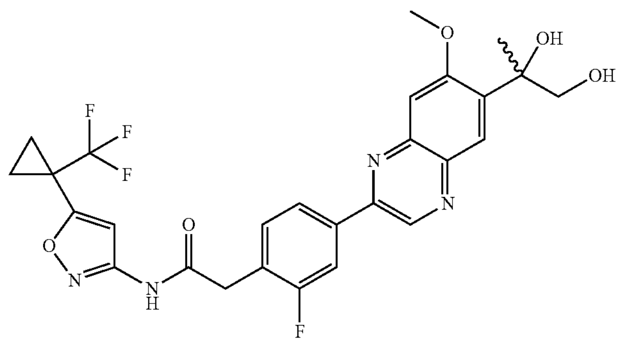 [SMILES: COc1cc2nc(-c3ccc(CC(=O)Nc4cc(C5(C(F)(F)F)CC5)on4)c(F)c3)cnc2cc1C(C)(O)CO] | 233 | 2-[4-[6-(1,2-dihydroxy-1-methyl-ethyl)-7-methoxy-quinoxalin-2-yl]-2-fluoro-phenyl]-N-[5-[1-(trifluoromethyl)cyclopropyl]isoxazol-3-yl]acetamide | 561 (M + H)+ |
| 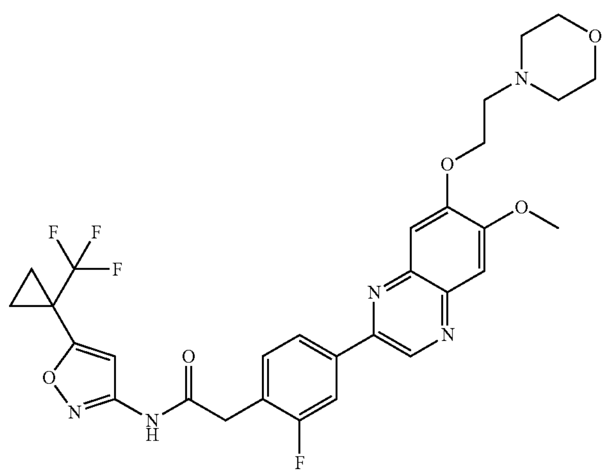 [SMILES: COc1cc2ncc(-c3ccc(CC(=O)Nc4cc(C5(C(F)(F)F)CC5)on4)c(F)c3)nc2cc1OCCN1CCOCC1] | 234 | 2-[2-fluoro-4-[6-methoxy-7-(2-morpholino-ethoxy)quinoxalin-2-yl]phenyl]-N-[5-[1-(trifluoromethyl)cyclopropyl]isoxazol-3-yl]acetamide | 616 (M + H)+ |
| 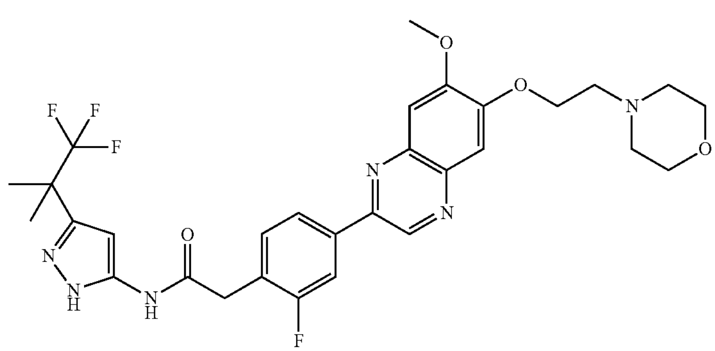 [SMILES: COc1cc2nc(-c3ccc(CC(=O)Nc4cc(C(C)(C)C(F)(F)F)n[nH]4)c(F)c3)cnc2cc1OCCN1CCOCC1] | 235 | 2-[2-fluoro-4-[7-methoxy-6-(2-morpholino-ethoxy)quinoxalin-2-yl]phenyl]-N-[3-(2,2,2-trifluoro-1,1-dimethyl-ethyl)-1H-pyrazol-5-yl]acetamide | 617 (M + H)+ |

TABLE 1-continued

| Chemical Structure | Example Number | Example Name | Observed m/z |
|---|---|---|---|
| 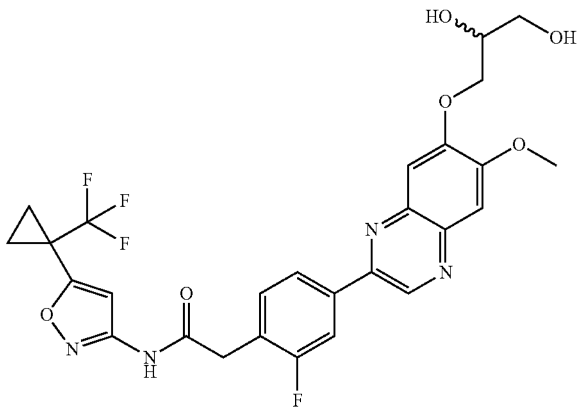 [SMILES: COc1cc2ncc(-c3ccc(CC(=O)Nc4cc(C5(C(F)(F)F)CC5)on4)c(F)c3)nc2cc1OCC(O)CO] | 236 | 2-[4-[7-(2,3-dihydroxypropoxy)-6-methoxy-quinoxalin-2-yl]-2-fluoro-phenyl]-N-[5-[1-(trifluoromethyl)cyclopropyl]isoxazol-3-yl]acetamide | 577 (M + H)+ |
| 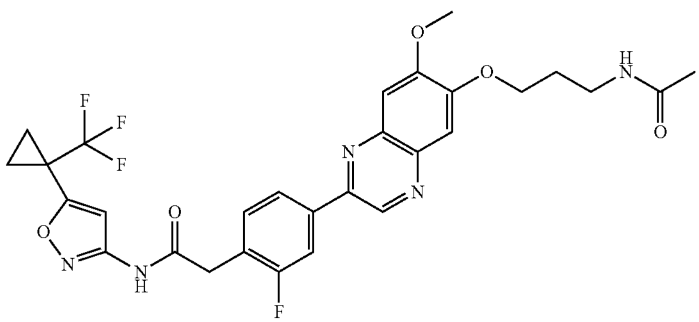 [SMILES: COc1cc2nc(-c3ccc(CC(=O)Nc4cc(C5(C(F)(F)F)CC5)on4)c(F)c3)cnc2cc1OCCCNC(C)=O] | 237 | 2-[4-[6-(3-acetamidopropoxy)-7-methoxy-quinoxalin-2-yl]-2-fluoro-phenyl]-N-[5-[1-(trifluoromethyl)cyclopropyl]isoxazol-3-yl]acetamide | 602 (M + H)+ |
| 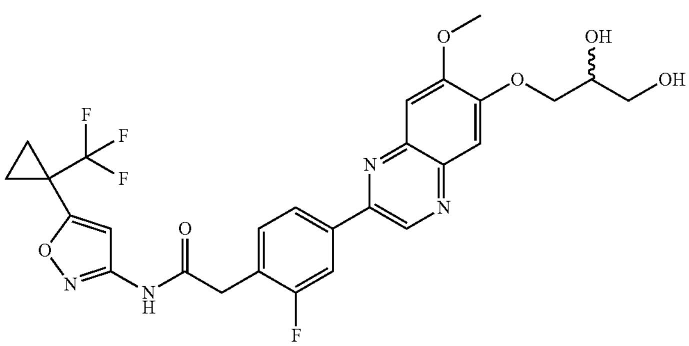 [SMILES: COc1cc2nc(-c3ccc(CC(=O)Nc4cc(C5(C(F)(F)F)CC5)on4)c(F)c3)cnc2cc1OCC(O)CO] | 238 | 2-[4-[6-(2,3-dihydroxypropoxy)-7-methoxy-quinoxalin-2-yl]-2-fluoro-phenyl]-N-[5-[1-(trifluoromethyl)cyclopropyl]isoxazol-3-yl]acetamide | 577 (M + H)+ |
| 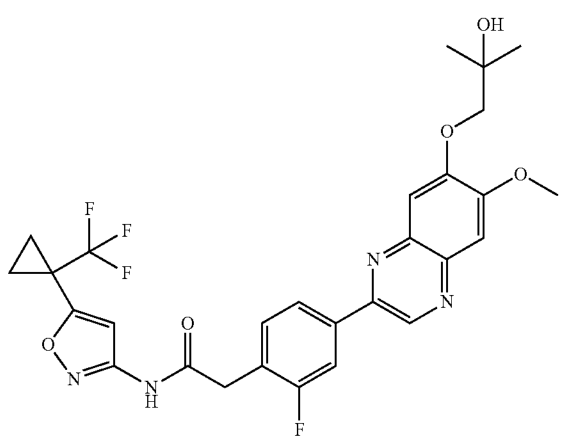 [SMILES: COc1cc2ncc(-c3ccc(CC(=O)Nc4cc(C5(C(F)(F)F)CC5)on4)c(F)c3)nc2cc1OCC(C)(C)O] | 239 | 2-[2-fluoro-4-[7-(2-hydroxy-2-methyl-propoxy)-6-methoxy-quinoxalin-2-yl]phenyl]-N-[5-[1-(trifluoromethyl)cyclopropyl]isoxazol-3-yl]acetamide | 575 (M + H)+ |

TABLE 1-continued

| Chemical Structure | Example Number | Example Name | Observed m/z |
|---|---|---|---|
| 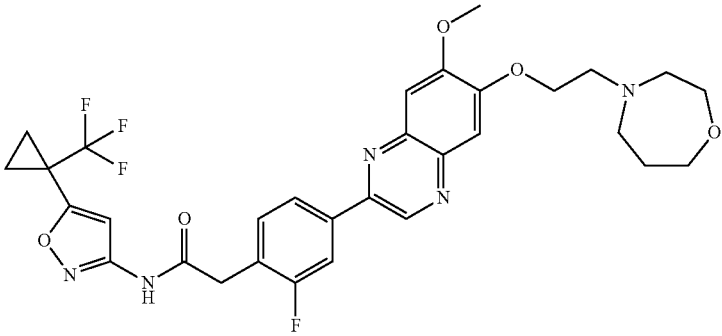 [SMILES: COc1cc2nc(-c3ccc(CC(=O)Nc4cc(C5(C(F)(F)F)CC5)on4)c(F)c3)cnc2cc1OCCN1CCCOCC1] | 240 | 2-[2-fluoro-4-[7-methoxy-6-[2-(1,4-oxazepan-4-yl)ethoxy]quinoxalin-2-yl]phenyl]-N-[5-[1-(trifluoromethyl)cyclopropyl]isoxazol-3-yl]acetamide | 628 (M − H)⁻ |
| 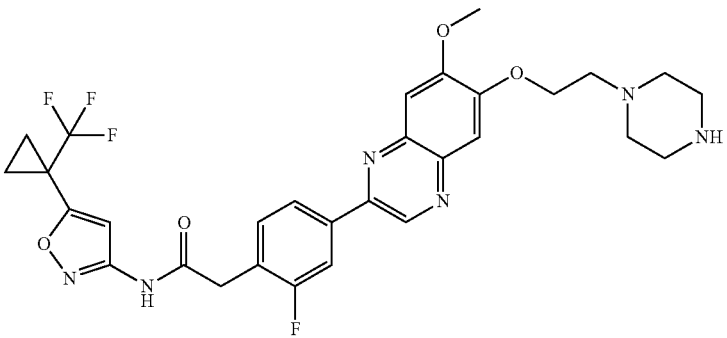 [SMILES: COc1cc2nc(-c3ccc(CC(=O)Nc4cc(C5(C(F)(F)F)CC5)on4)c(F)c3)cnc2cc1OCCN1CCNCC1] | 241 | 2-[2-fluoro-4-[7-methoxy-6-(2-piperazin-1-ylethoxy)quinoxalin-2-yl]phenyl]-N-[5-[1-(trifluoromethyl)cyclopropyl]isoxazol-3-yl]acetamide | 615 (M + H)⁺ |
| 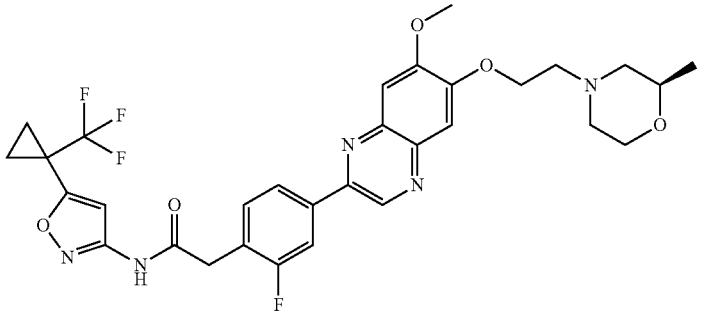 [SMILES: COc1cc2nc(-c3ccc(CC(=O)Nc4cc(C5(C(F)(F)F)CC5)on4)c(F)c3)cnc2cc1OCCN1CCO[C@H](C)C1] | 242 | 2-[2-fluoro-4-[7-methoxy-6-[2-[(2R)-2-methylmorpholin-4-yl]ethoxy]quinoxalin-2-yl]phenyl]-N-[5-[1-(trifluoromethyl)cyclopropyl]isoxazol-3-yl]acetamide | 630 (M + H)⁺ |
| 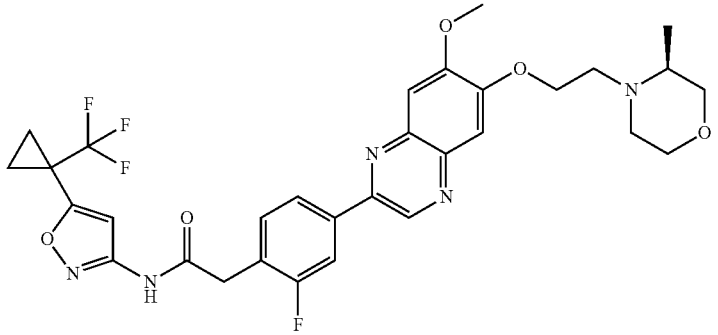 [SMILES: COc1cc2nc(-c3ccc(CC(=O)Nc4cc(C5(C(F)(F)F)CC5)on4)c(F)c3)cnc2cc1OCCN1CCOC[C@@H]1C] | 243 | 2-[2-fluoro-4-[7-methoxy-6-[2-[(3S)-3-methylmorpholin-4-yl]ethoxy]quinoxalin-2-yl]phenyl]-N-[5-[1-(trifluoromethyl)cyclopropyl]isoxazol-3-yl]acetamide | 630 (M + H)⁺ |

TABLE 1-continued

| Chemical Structure | Example Number | Example Name | Observed m/z |
|---|---|---|---|
| 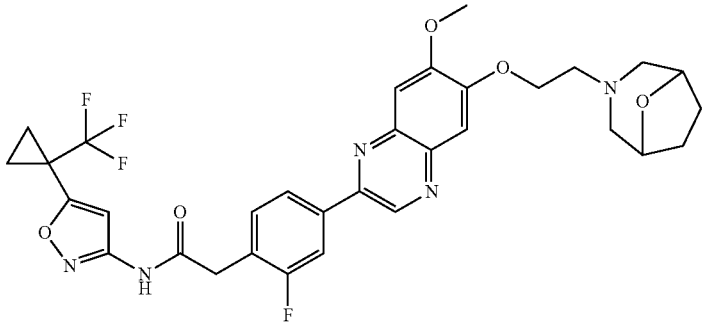 [SMILES: COc1cc2nc(-c3ccc(CC(=O)Nc4cc(C5(C(F)(F)F)CC5)on4)c(F)c3)cnc2cc1OCCN1CC2CCC(C1)O2] | 244 | 2-[2-fluoro-4-[7-methoxy-6-[2-(8-oxa-3-azabicyclo[3.2.1]octan-3-yl)ethoxy]quinoxalin-2-yl]phenyl]-N-[5-[1-(trifluoromethyl)cyclo-propyl]isoxazol-3-yl]acetamide | 642 (M + H)+ |
| 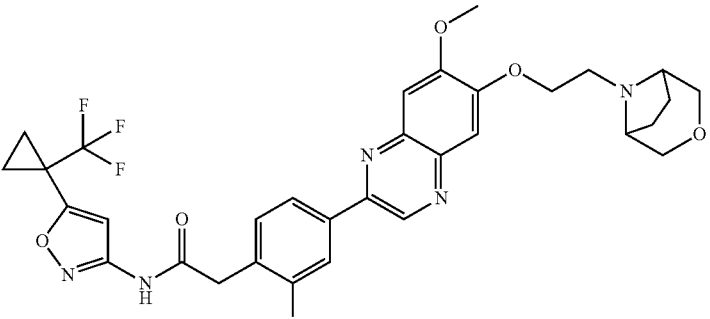 | 245 | 2-[2-fluoro-4-[7-methoxy-6-[2-(3-oxa-8-azabicyclo[3.2.1]octan-8-yl)ethoxy]quinoxalin-2-yl]phenyl]-N-[5-[1-(trifluoromethyl)cyclo-propyl]isoxazol-3-yl]acetamide | 642 (M + H)+ |
| 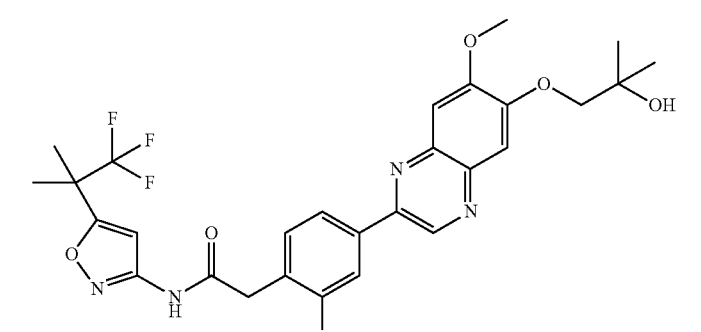 | 246 | 2-[2-fluoro-4-[6-(2-hydroxy-2-methyl-propoxy)-7-methoxy-quinoxalin-2-yl]phenyl]-N-[5-(2,2,2-trifluoro-1,1-dimethyl-ethyl)isoxazol-3-yl]acetamide | 577 (M + H)+ |
| 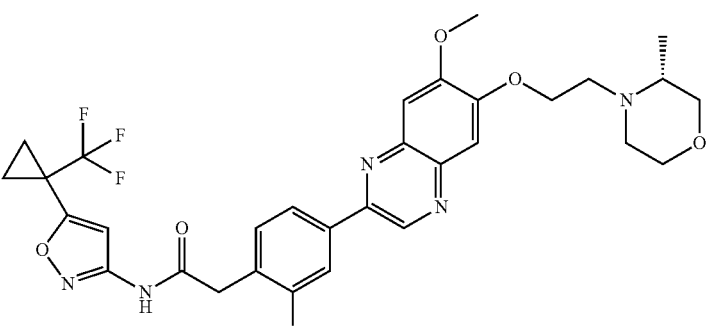 | 247 | 2-[2-fluoro-4-[7-methoxy-6-[2-[(3R)-3-methylmorpholin-4-yl]ethoxy]quinoxalin-2-yl]phenyl]-N-[5-[1-(trifluoromethyl)cyclo-propyl]isoxazol-3-yl]acetamide | 630 (M + H)+ |

| Chemical Structure | Example Number | Example Name | Observed m/z |
|---|---|---|---|
| 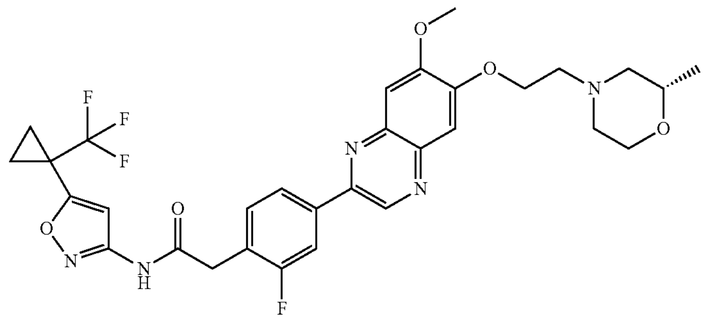 [SMILES: COc1cc2nc(-c3ccc(CC(=O)Nc4cc(C5(C(F)(F)F)CC5)on4)c(F)c3)cnc2cc1OCCN1CCO[C@@H](C)C1] | 248 | 2-[2-fluoro-4-[7-methoxy-6-[2-[(2S)-2-methylmorpholin-4-yl]ethoxy]quinoxalin-2-yl]phenyl]-N-[5-[1-(trifluoromethyl)cyclopropyl]isoxazol-3-yl]acetamide | 630 (M + H)+ |
| 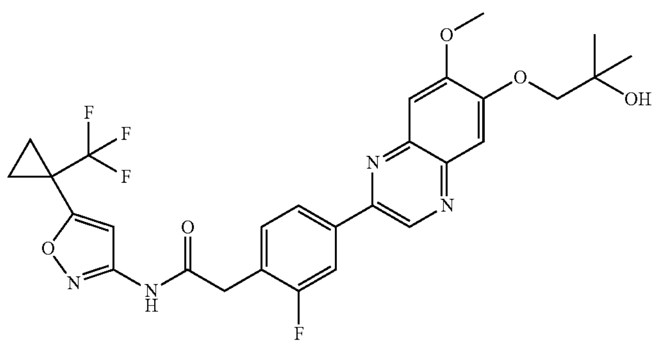 [SMILES: COc1cc2nc(-c3ccc(CC(=O)Nc4cc(C5(C(F)(F)F)CC5)on4)c(F)c3)cnc2cc1OCC(C)(C)O] | 249 | 2-[2-fluoro-4-[6-(2-hydroxy-2-methyl-propoxy)-7-methoxy-quinoxalin-2-yl]phenyl]-N-[5-[1-(trifluoromethyl)cyclopropyl]isoxazol-3-yl]acetamide | 575 (M + H)+ |

Example 250

Competition Binding Assay to Determine Binding Constants (Kd) for the Compounds Against Selected Kinases and Selectivity Scores Against a Panel of Kinases Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005,310). For the binding assays, streptavidin-coated magnetic beads were treated with biotinylated affinity ligands for 30 min at room temperature to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17×PBS, 0.05% Tween 20, 6 mM DTT). Test compounds were prepared as 100× stocks in DMSO and diluted into the aqueous environment. Kds were determined using an eleven point threefold serial dilutions. DMSO or control compounds were was added to control assays lacking a test compound. Primary screen assays for determination of selectivity scores were performed in polypropylene 384-well plates in a final volume of 20-40 µL, while $K_d$ determinations were performed in polystyrene 96-well plates in a final volume of 135 µL. The assay plates were incubated at room temperature with shaking for 1 hour to allow the binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 0.5 µM non-biotinylated affinity ligand) and incubated at room temperature with shaking for 30 min. The kinase concentration in the eluates was measured by quantitative PCR.

A selectivity score (S35) is a quantitative measure of selectivity of a compound against a panel of kinases. An S35 was calculated for a compound by dividing the number of kinases found to have a percent of control (DMSO) less than 35 by the total number of distinct kinases tested (excluding mutant variants). Percent of control (POC) is calculated by subtracting the signal of the control compound (POC=0) from the signal of the test compound and dividing the outcome by the signal of DMSO (POC=100) minus the signal of the control compound. For the compounds disclosed herein, S35 scores were obtained by testing the compounds at 100 nM concentration in a kinase panel containing 395 distinct kinases. The Kd values for representative compounds of Formula I are provided in Table 2 below.

Example 251

FLT3-Expressing Ba/F3 Cell-Based Assays

Gene constructs containing the human FLT3 sequences FLT3-ITD, FLT3-ITD-F691L, FLT3-ITD-D835V and FLT3-D835V were synthesized by reverse translation of the human protein sequences, with codons optimized for mammalian expression. Sequence of the internal tandem duplication (ITD) was based on the MV4-11 ITD sequence. Synthetic DNA constructs were cloned into the pMSCV puro retroviral vector (Clontech) and transfected into the EcoPack2-293 packaging cell line (Clontech) to generate retroviruses that contain the different FLT3 constructs. Viruses were transduced into the IL-3-dependent, murine macrophage cell line, Ba/F3, and selected for puromycin resistance and IL-3 independence. All cell lines were cloned by limiting dilution and clones were used for all subsequent cell assays. Overexpression of the FLT3 mutants in the Ba/F3 cells results in constitutive phosphorylation of the exogenous FLT3 protein, which is required for IL-3 independence.

pFLT3 MSD Assays:

The effects of the compounds of Formula I provided herein, on the tyrosine kinase activity of the FLT3 mutants were determined by pFLT3 MSD (Meso Scale Discovery) electrochemiluminescence assay. Briefly, cell lines were serum starved overnight in media containing 0.5% FBS. Cells were plated at 200,000 cells/well in 96-well round bottom plates in low serum, and 3-fold serial dilutions of test compounds were added for 2 hours at 37° C. Cells were washed with PBS, lysed with 30 uL/well of cell lysis buffer (Cell Signaling Technology), and 25 uL/well were applied to FLT3 MSD capture plates that were pre-coated with anti-FLT3 monoclonal antibody (R&D Systems Catalog #MAB8121). After an overnight incubation at 4° C. shaking at 450 rpm, plates were washed with MSD wash buffer, and captured FLT3 was detected with biotinylated-anti-phosphotyrosine antibody 4G10 (Millipore) and SulfoTAG-streptavidin (MSD) for 1 hour at room temperature, and read on an MSD SECTOR Imager 6000. Percent remaining phospho-FLT3 in compound-treated cells was normalized to DMSO-treated cells, and $IC_{50}$s were determined using Igor Pro software. All compounds are assayed in duplicate cell and MSD plates.

CTB Viability Assays:

Cell lines were serum starved overnight in media containing 0.5% FBS, plated at 15,000 cells/well in 96-well white-walled tissue culture plates, and 3-fold serial dilutions of test compounds of Formula I were added for 72 hours at 37° C. CellTiter Blue (CTB, Promega) was added and incubated for an additional 3 hours at 37° C. Fluorescence was read at 560 nm excitation, 590 nm emission. Wells with CTB+media only were used for background subtraction, and the fluorescence of compound-treated cells was normalized to the fluorescence of DMSO-treated cells. $IC_{50}$s were determined using Igor Pro software. All compounds are assayed in duplicate cell plates. $IC_{50}$s for the compounds having the Formula I are provided in Table 2.

TABLE 2

| Ex # | FLT3Kd (nM) | KIT Kd (nM) | BaF3-FLT3-ITD pFlt3 IC50 (nM) | BaF3-FLT3-ITD-F691L pFlt3 IC50 (nM) | BaF3-FLT3-ITD-D835V pFlt3 IC50 (nM) | BaF3-FLT3 ITD CTB IC50 (nM) | BaF3-FLT3-ITD-F691L CTB IC50 (nM) | BaF3-FLT3-ITD-D835V CTB IC50 (nM) |
|---|---|---|---|---|---|---|---|---|
| 1 | A | A | A | A | A | A | A | A |
| 2 | A | A | A | A | C | ND | A | C |
| 3 | A | A | A | A | A | ND | ND | ND |
| 4 | A | A | A | A | A | A | A | A |
| 5 | A | A | A | A | A | A | A | A |
| 6 | A | A | A | A | A | A | A | A |
| 7 | A | A | ND | ND | ND | ND | D | D |
| 8 | A | A | A | A | A | A | A | A |
| 9 | A | A | ND | ND | ND | ND | C | B |
| 10 | A | A | ND | A | A | ND | A | A |
| 11 | A | A | ND | A | B | ND | B | C |
| 12 | A | A | ND | A | B | ND | C | C |
| 13 | A | B | ND | A | B | ND | A | A |
| 14 | A | A | ND | B | C | ND | C | D |
| 15 | ND | A | A | A | A | A | A | A |
| 16 | ND | ND | ND | D | D | ND | D | D |
| 17 | ND | ND | ND | C | A | ND | D | A |
| 18 | ND | A | A | A | A | A | A | A |
| 19 | ND | ND | ND | C | D | ND | C | D |
| 20 | ND | ND | ND | A | B | ND | A | A |
| 21 | ND | ND | ND | A | A | ND | A | B |
| 22 | ND | ND | ND | A | A | ND | A | A |
| 23 | ND | ND | ND | A | B | ND | A | A |
| 24 | ND | ND | ND | A | A | ND | A | A |
| 25 | ND | ND | A | A | A | ND | ND | ND |
| 26 | ND | ND | A | A | A | ND | ND | ND |
| 27 | ND | ND | A | A | A | ND | ND | ND |
| 28 | ND | ND | A | A | A | ND | ND | ND |
| 29 | ND | ND | A | A | A | ND | ND | ND |
| 30 | ND | ND | A | A | A | ND | ND | ND |
| 31 | ND | ND | A | A | A | ND | ND | ND |
| 32 | ND | ND | A | A | A | ND | ND | ND |
| 33 | ND | ND | A | A | A | A | A | A |
| 34 | ND | ND | A | A | A | ND | ND | ND |
| 35 | ND | ND | A | A | A | A | A | A |
| 36 | ND | ND | A | A | A | ND | ND | ND |
| 37 | ND | ND | A | B | C | ND | ND | ND |
| 38 | ND | ND | A | A | A | ND | ND | ND |
| 39 | ND | ND | A | A | A | A | A | A |
| 40 | ND | ND | A | A | A | ND | ND | ND |
| 41 | ND | ND | A | D | D | ND | ND | ND |
| 42 | ND | ND | A | A | A | ND | ND | ND |

TABLE 2-continued

| Ex # | FLT3Kd (nM) | KIT Kd (nM) | BaF3-FLT3-ITD pFlt3 IC50 (nM) | BaF3-FLT3-ITD-F691L pFlt3 IC50 (nM) | BaF3-FLT3-ITD-D835V pFlt3 IC50 (nM) | BaF3-FLT3-ITD CTB IC50 (nM) | BaF3-FLT3-ITD-F691L CTB IC50 (nM) | BaF3-FLT3-ITD-D835V CTB IC50 (nM) |
|---|---|---|---|---|---|---|---|---|
| 43 | ND | ND | A | A | A | A | A | A |
| 44 | ND | ND | A | A | A | ND | ND | ND |
| 45 | ND | ND | A | A | B | ND | ND | ND |
| 46 | A | B | A | A | A | A | A | A |
| 47 | ND | ND | A | A | A | A | A | A |
| 48 | ND | ND | A | B | B | ND | ND | ND |
| 49 | ND | ND | A | A | A | ND | ND | ND |
| 50 | ND | ND | A | A | A | ND | ND | ND |
| 51 | ND | ND | A | A | A | ND | ND | ND |
| 52 | ND | ND | A | C | D | ND | ND | ND |
| 53 | ND | ND | A | A | A | ND | ND | ND |
| 54 | ND | ND | B | D | D | ND | ND | ND |
| 55 | ND | ND | A | A | A | ND | ND | ND |
| 56 | ND | ND | A | A | A | ND | ND | ND |
| 57 | ND | ND | A | C | D | ND | ND | ND |
| 58 | ND | ND | A | B | C | ND | ND | ND |
| 59 | ND | ND | A | D | D | ND | ND | ND |
| 60 | ND | ND | A | A | A | ND | ND | ND |
| 61 | ND | ND | A | A | A | ND | ND | ND |
| 62 | A | A | A | A | A | A | A | A |
| 63 | A | A | A | A | A | A | A | A |
| 64 | A | A | A | A | A | A | A | A |
| 65 | A | A | A | A | A | A | A | A |
| 66 | A | A | A | A | A | A | A | A |
| 67 | A | A | A | A | A | A | A | A |
| 68 | A | A | A | A | A | A | A | A |
| 69 | A | A | A | A | A | A | A | A |
| 70 | A | A | A | A | A | A | A | A |
| 71 | ND | ND | A | A | A | ND | ND | ND |
| 72 | ND | ND | A | A | A | ND | ND | ND |
| 73 | ND | ND | A | A | B | ND | ND | ND |
| 74 | A | B | A | A | A | ND | ND | ND |
| 75 | A | A | A | A | A | ND | ND | ND |
| 76 | A | B | A | B | C | ND | ND | ND |
| 77 | A | A | A | A | A | A | A | A |
| 77 | A | A | A | A | A | A | A | A |
| 78 | A | A | A | A | A | ND | ND | ND |
| 79 | A | A | A | A | A | A | A | A |
| 79 | A | A | A | A | A | A | A | A |
| 80 | A | A | A | A | A | A | A | A |
| 81 | A | A | ND | ND | ND | A | A | A |
| 82 | A | A | ND | ND | ND | A | A | A |
| 83 | A | A | ND | ND | ND | A | A | A |
| 84 | A | A | ND | ND | ND | A | C | D |
| 85 | A | A | ND | ND | ND | A | A | B |
| 86 | A | A | A | A | A | ND | ND | ND |
| 87 | A | A | ND | ND | ND | A | A | A |
| 88 | A | A | A | A | A | A | A | A |
| 89 | A | B | A | C | C | A | A | B |
| 90 | A | A | A | B | B | A | A | A |
| 91 | A | A | A | A | A | A | A | A |
| 92 | A | A | ND | ND | ND | A | A | A |
| 93 | A | A | ND | ND | ND | A | A | A |
| 94 | A | A | ND | ND | ND | A | A | A |
| 95 | A | A | ND | ND | ND | A | A | A |
| 96 | A | A | ND | ND | ND | A | A | A |
| 97 | A | A | A | A | A | A | A | A |
| 98 | A | A | A | D | D | A | D | D |
| 99 | A | A | A | A | A | A | A | B |
| 100 | A | B | A | C | C | A | A | D |
| 101 | A | A | A | A | A | A | A | A |
| 102 | A | A | A | A | A | A | A | A |
| 103 | A | A | A | A | A | A | A | A |
| 104 | A | A | A | A | A | A | A | A |
| 105 | A | A | ND | ND | ND | A | A | A |
| 106 | A | A | B | D | D | ND | ND | ND |
| 107 | A | A | A | A | A | ND | ND | ND |
| 108 | A | A | A | A | A | ND | ND | ND |
| 109 | A | A | A | A | A | ND | ND | ND |
| 110 | A | A | A | A | A | ND | ND | ND |
| 111 | A | A | A | A | A | A | ND | ND |
| 112 | A | A | A | C | C | A | ND | ND |

TABLE 2-continued

| Ex # | FLT3Kd (nM) | KIT Kd (nM) | BaF3-FLT3-ITD pFlt3 IC50 (nM) | BaF3-FLT3-ITD-F691L pFlt3 IC50 (nM) | BaF3-FLT3-ITD-D835V pFlt3 IC50 (nM) | BaF3-FLT3-ITD CTB IC50 (nM) | BaF3-FLT3-ITD-F691L CTB IC50 (nM) | BaF3-FLT3-ITD-D835V CTB IC50 (nM) |
|---|---|---|---|---|---|---|---|---|
| 113 | A | A | A | A | A | A | ND | ND |
| 114 | A | B | A | A | A | ND | ND | ND |
| 115 | A | B | A | A | B | ND | ND | ND |
| 116 | A | A | A | B | C | ND | ND | ND |
| 117 | A | A | A | A | A | ND | ND | ND |
| 118 | A | A | A | A | A | ND | ND | ND |
| 119 | A | A | A | A | B | ND | ND | ND |
| 120 | A | A | A | A | A | ND | ND | ND |
| 121 | A | A | A | A | A | ND | ND | ND |
| 122 | A | A | A | A | A | ND | ND | ND |
| 123 | A | A | A | A | A | ND | ND | ND |
| 124 | A | B | B | D | D | ND | ND | ND |
| 125 | A | A | A | A | A | A | A | A |
| 126 | A | A | A | A | A | A | A | A |
| 127 | A | A | A | A | A | A | A | A |
| 128 | A | A | A | A | A | A | A | A |
| 129 | A | A | A | A | A | A | A | A |
| 130 | A | A | A | A | A | A | A | A |
| 131 | A | A | A | A | A | A | A | A |
| 132 | D | D | D | D | D | ND | ND | ND |
| 133 | C | D | D | D | D | ND | ND | ND |
| 134 | A | A | A | A | A | A | A | A |
| 135 | D | D | D | D | D | ND | ND | ND |
| 136 | A | B | A | A | A | ND | ND | ND |
| 137 | A | A | A | C | D | ND | ND | ND |
| 138 | A | A | A | C | D | ND | ND | ND |
| 139 | A | A | A | A | A | ND | ND | ND |
| 140 | A | B | A | A | A | ND | ND | ND |
| 141 | A | B | A | C | C | ND | ND | ND |
| 142 | A | A | A | B | B | A | A | A |
| 143 | A | B | B | D | D | ND | ND | ND |
| 144 | A | A | A | A | A | ND | ND | ND |
| 145 | B | D | D | D | D | ND | ND | ND |
| 146 | A | A | A | C | C | ND | ND | ND |
| 147 | A | A | A | A | A | ND | ND | ND |
| 148 | A | B | A | B | C | A | A | A |
| 149 | A | A | A | C | B | A | A | A |
| 150 | A | A | A | B | A | A | A | A |
| 151 | A | A | A | C | D | ND | ND | ND |
| 152 | A | A | A | D | D | ND | ND | ND |
| 153 | A | A | A | A | A | ND | ND | ND |
| 154 | A | A | A | D | D | ND | ND | ND |
| 155 | A | B | A | A | A | ND | ND | ND |
| 156 | D | D | A | C | C | ND | ND | ND |
| 157 | A | A | A | A | A | A | A | A |
| 158 | A | A | A | A | A | A | A | A |
| 159 | A | A | A | A | A | ND | ND | ND |
| 160 | A | A | A | A | A | ND | ND | ND |
| 161 | A | A | A | A | A | ND | ND | ND |
| 162 | A | A | A | A | A | ND | ND | ND |
| 163 | D | D | A | C | C | ND | ND | ND |
| 164 | A | B | A | A | A | ND | ND | ND |
| 165 | A | A | A | A | A | A | A | A |
| 166 | A | A | A | A | A | ND | ND | ND |
| 167 | A | A | A | A | A | A | A | A |
| 168 | A | A | A | A | A | ND | ND | ND |
| 169 | A | A | A | C | D | ND | ND | ND |
| 170 | A | A | A | A | A | A | A | A |
| 171 | A | A | A | A | A | A | A | A |
| 172 | A | A | ND | ND | ND | A | A | A |
| 173 | B | D | ND | ND | ND | A | C | D |
| 174 | A | A | ND | ND | ND | A | A | A |
| 175 | A | A | ND | ND | ND | A | A | A |
| 176 | A | A | ND | ND | ND | A | A | A |
| 177 | A | A | ND | ND | ND | A | A | A |
| 178 | A | A | ND | ND | ND | A | A | A |
| 179 | A | A | ND | ND | ND | A | A | A |
| 180 | A | A | ND | ND | ND | A | A | A |
| 181 | A | A | ND | ND | ND | A | A | A |
| 182 | A | A | ND | ND | ND | A | A | A |
| 183 | A | A | ND | ND | ND | A | A | A |
| 184 | A | A | ND | ND | ND | A | A | A |

TABLE 2-continued

| Ex # | FLT3Kd (nM) | KIT Kd (nM) | BaF3-FLT3-ITD pFlt3 IC50 (nM) | BaF3-FLT3-ITD-F691L pFlt3 IC50 (nM) | BaF3-FLT3-ITD-D835V pFlt3 IC50 (nM) | BaF3-FLT3-ITD CTB IC50 (nM) | BaF3-FLT3-ITD-F691L CTB IC50 (nM) | BaF3-FLT3-ITD-D835V CTB IC50 (nM) |
|---|---|---|---|---|---|---|---|---|
| 185 | A | A | ND | ND | ND | A | A | A |
| 186 | A | A | ND | ND | ND | A | A | A |
| 187 | A | A | ND | ND | ND | A | A | A |
| 188 | A | A | ND | ND | ND | A | A | A |
| 189 | A | A | ND | ND | ND | A | A | A |
| 190 | A | A | ND | ND | ND | A | A | A |
| 191 | A | A | ND | ND | ND | A | A | A |
| 192 | A | A | ND | ND | ND | A | A | B |
| 193 | A | A | ND | ND | ND | A | A | A |
| 194 | A | A | ND | ND | ND | A | A | A |
| 195 | A | A | ND | ND | ND | A | A | A |
| 196 | A | A | ND | ND | ND | A | A | A |
| 197 | A | A | ND | ND | ND | A | A | A |
| 198 | A | A | ND | ND | ND | A | A | A |
| 199 | A | A | ND | ND | ND | A | A | A |
| 200 | A | A | ND | ND | ND | A | A | A |
| 201 | A | A | ND | ND | ND | A | A | A |
| 202 | A | A | ND | ND | ND | A | A | A |
| 203 | A | A | ND | ND | ND | A | A | A |
| 204 | A | A | ND | ND | ND | A | A | B |
| 205 | A | A | ND | ND | ND | A | A | A |
| 206 | A | A | ND | ND | ND | A | A | B |
| 207 | A | C | ND | ND | ND | A | A | C |
| 208 | A | A | ND | ND | ND | A | A | A |
| 209 | A | A | ND | ND | ND | A | A | A |
| 210 | A | A | ND | ND | ND | A | A | A |
| 211 | A | A | ND | ND | ND | A | A | A |
| 212 | A | A | ND | ND | ND | A | A | A |
| 213 | A | A | ND | ND | ND | A | A | A |
| 214 | A | A | ND | ND | ND | A | A | A |
| 215 | A | A | ND | ND | ND | A | A | A |
| 216 | A | A | ND | ND | ND | A | A | A |
| 217 | A | A | ND | ND | ND | A | A | A |
| 218 | A | A | ND | ND | ND | A | A | A |
| 219 | A | A | ND | ND | ND | A | A | A |
| 220 | A | A | ND | ND | ND | A | A | A |
| 221 | A | A | ND | ND | ND | A | A | A |
| 222 | A | A | ND | ND | ND | A | A | A |
| 223 | A | A | ND | ND | ND | A | A | A |
| 224 | A | A | ND | ND | ND | A | A | A |
| 225 | A | A | ND | ND | ND | A | A | B |
| 226 | A | A | ND | ND | ND | A | A | C |
| 227 | A | A | ND | ND | ND | A | B | B |
| 228 | A | A | ND | ND | ND | A | A | A |
| 229 | A | A | ND | ND | ND | A | A | A |
| 230 | A | A | ND | ND | ND | A | A | A |
| 231 | A | A | ND | ND | ND | A | A | A |
| 232 | A | A | ND | ND | ND | A | A | A |
| 233 | A | A | ND | ND | ND | A | C | D |
| 234 | A | A | ND | ND | ND | A | A | A |
| 235 | A | A | ND | ND | ND | A | A | A |
| 236 | A | A | ND | ND | ND | A | A | A |
| 237 | A | A | ND | ND | ND | A | A | A |
| 238 | A | A | ND | ND | ND | A | A | A |
| 239 | A | A | ND | ND | ND | A | A | A |
| 240 | A | A | ND | ND | ND | A | A | A |
| 241 | A | A | ND | ND | ND | A | A | A |
| 242 | A | A | ND | ND | ND | A | A | A |
| 243 | A | A | ND | ND | ND | A | A | A |
| 244 | A | A | ND | ND | ND | A | A | A |
| 245 | A | A | ND | ND | ND | A | A | A |
| 246 | A | A | ND | ND | ND | A | A | A |
| 247 | A | A | ND | ND | ND | A | A | A |
| 248 | A | A | ND | ND | ND | A | A | A |
| 249 | A | A | ND | ND | ND | A | A | B |

In Table 2,
FLT3 Kd (nM): A ≤ 5, 5 < B ≤ 20, 20 < C ≤ 50, D > 50; and ND = no data;
KIT Kd (nM): A ≤ 5, 5 < B ≤ 20, 20 < C ≤ 50, D > 50; and ND = no data;
For all Ba/F3 CTB Assays IC$_{50}$ (nM): A ≤ 10, 10 < B ≤ 20, 20 < C ≤ 50, D > 50;
For all Ba/F3 pFLT3 Assays (MSD) IC$_{50}$ (nM): A ≤ 10, 10 < B ≤ 20, 20 < C ≤ 50, D > 50;
ND = no data

Example 252

Anti-Tumor Effects of Compound A on FLT3-ITD and FLT3-ITD/D835 BaF3 Cell Lines in nu/nu Mice Representative compounds of Formula I were tested for their antitumor effects on FLT3-ITD and FLT3-ITD/D835 BaF3 cells in the female nu/nu mouse (Harlan Laboratories). BaF3 cells harboring the FLT3-ITD and FLT3-ITD/D835 transgene (Ambit Biosciences) were maintained in RPMI media and supplemented with 100 U/mL penicillin, 50 mg/mL streptomycin, and 10% fetal bovine serum (FBS) in a 37° C. humidified incubator with 5% carbon dioxide ($CO_2$). Cells were harvested during logarithmic phase of growth, washed free of media and FBS and re-suspended in sterile PBS. On Day 1 of study, mice were inoculated intravenously in the lateral tail vein with $5'10^5$ cells/200 uL per test mouse to establish BaF3 FLT3-ITD or FLT3-ITD/D835 leukemia and randomized into treatment, reference and control groups. Five days post-cell inoculation, Compound A of Formula I, vehicle control (1% hydroxypropylmethylcellulose (HPMC)) and reference compound AC220 were administered by oral gavage (p.o.) once daily for 14 days to the treatment, control and reference groups, respectively. Compound A was administered at 1 mpk (mg/kg), 3 mpk or 10 mpk in 1% HPMC. Reference compound AC220 was administered at 30 mpk in 5% hydroxypropylbetacyclodextrin. In both cell lines, Compound A prolonged the survival of the mice in a dose-dependent manner compared with untreated mice. Survival time to endpoint (TTE) and increased lifespan (% ILS) obtained for Compound A in the two leukemia cell lines are shown in Table 3:

TABLE 3

| | BaF3 FLT3-ITD | | BaF3 FLT3-ITD/D835 | |
|---|---|---|---|---|
| | TTE | % ILS | TTE | % ILS |
| Vehicle | 17.5 | — | 16 | — |
| Compound A (10 mpk) | 37 | 111 | 23 | 44 |
| AC220 (30 mpk) | 34 | 94 | 20 | 25 |

The embodiments described above are intended to be merely exemplary and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

Since modifications will be apparent to those of skill in the art, it is intended that the claimed subject matter be limited only by the scope of the appended claims.

What is claimed is:
1. A compound having the Formula IIa:

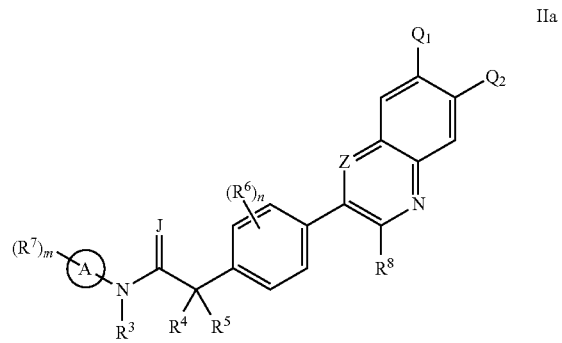

or a pharmaceutically acceptable salt, solvate, clathrate, hydrate, a single stereoisomer, a mixture of stereoisomers or a racemic mixture of stereoisomers thereof, wherein:

Ring A is isoxazolyl or pyrazolyl;
J is O;
Z is N or $CR^9$;
$Q^1$ and $Q^2$ are selected from —$R^uOR^x$ and —$R^uOR^vOR^x$; each $R^u$ is independently alkylene, alkenylene, alkynylene or a direct bond; each $R^v$ is independently alkylene, alkenylene or alkynylene; and each $R^x$ is independently hydrogen, alkyl, haloalkyl, alkenyl, alkynyl or heterocyclyl;
$R^3$ is hydrogen, alkyl or haloalkyl;
$R^4$ and $R^5$ are both hydrogen or halo;
$R^6$ is halo,
each $R^7$ is independently selected from —$CH(CH_3)_2$, —$C(CH_3)_2CH_2OH$, —$CF_3$, —$C(CH_3)_3$, —$CF_2(CH_3)$, —$C(CH_3)(CH_2F)_2$, —$C(CH_3)_2CF_3$, —$C(CH_3)_2CH_2F$, —$CF(CH_3)_2$, cyclopropyl, cyclobutyl, cyclopentyl, cyclohexyl,

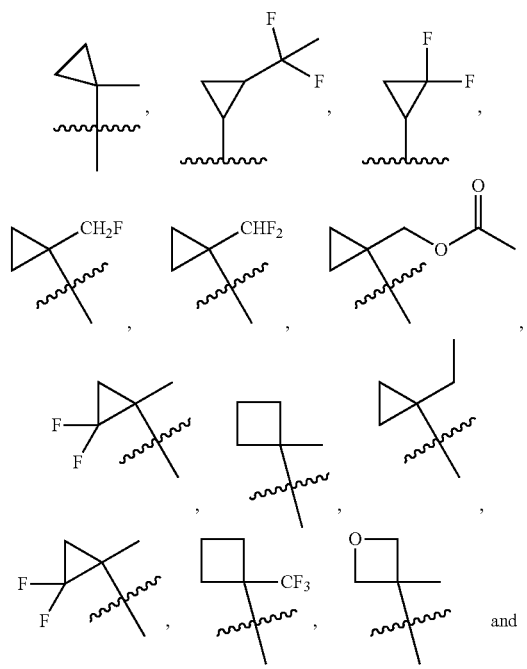

and

-continued

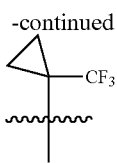

R⁸ is hydrogen,
R⁹ is hydrogen,
m is 0 or 1, and
n is 0 or 1,
wherein the compound is selected such that when ring A is pyrazolyl, m is 1 and Z is CH, R⁷ is not cyclopropyl.

2. The compound of claim 1, wherein the compound is selected from:
2-(4-(6,7-dimethoxyquinoxalin-2-yl)-2-fluorophenyl)-N-(5-(1-(trifluoromethyl)cyclopropyl)isoxazol-3-yl)acetamide;
2-(4-(6,7-dimethoxyquinolin-3-yl)phenyl)-N-(5-(1-(trifluoromethyl)cyclopropyl)isoxazol-3-yl)acetamide;
N-(5-(tert-butyl)isoxazol-3-yl)-2-(4-(6,7-dimethoxyquinoxalin-2-yl)phenyl)acetamide;
2-(4-(6,7-dimethoxyquinoxalin-2-yl)phenyl)-N-(5-(1,1,1-trifluoro-2-methylpropan-2-yl)isoxazol-3-yl)acetamide;
2-(4-(6,7-dimethoxyquinoxalin-2-yl)phenyl)-N-(5-(1-hydroxy-2-methylpropan-2-yl)isoxazol-3-yl)acetamide;
2-(4-(6,7-dimethoxyquinoxalin-2-yl)-3-fluorophenyl)-N-(5-(1-(trifluoromethyl)cyclopropyl)isoxazol-3-yl)acetamide;
N-(5-(tert-butyl)isoxazol-3-yl)-2-(4-(6,7-dimethoxyquinoxalin-2-yl)-2-fluorophenyl)acetamide;
2-(4-(6,7-dimethoxyquinoxalin-2-yl)-2-fluorophenyl)-N-(5-(1,1,1-trifluoro-2-methylpropan-2-yl)isoxazol-3-yl)acetamide;
2-(4-(6,7-dimethoxyquinoxalin-2-yl)phenyl)-N-(3-(1-(trifluoromethyl)cyclopropyl)isoxazol-5-yl)acetamide;
N-(3-(tert-butyl)isoxazol-5-yl)-2-(4-(6,7-dimethoxyquinoxalin-2-yl)phenyl)acetamide;
2-(4-(6,7-bis(2-hydroxyethoxy)quinoxalin-2-yl)-2-fluorophenyl)-N-(5-(1-(trifluoromethyl)cyclopropyl)isoxazol-3-yl)acetamide;
2-(2-fluoro-4-(6-methoxy-7-(2-methoxyethoxy)quinoxalin-2-yl)phenyl)-N-(5-(1-(trifluoromethyl)cyclopropyl)isoxazol-3-yl)acetamide;
2-(2-fluoro-4-(7-methoxy-6-(2-methoxyethoxy)quinoxalin-2-yl)phenyl)-N-(5-(1-(trifluoromethyl)cyclopropyl)isoxazol-3-yl)acetamide;
2-(2-fluoro-4-(6-hydroxy-7-methoxyquinoxalin-2-yl)phenyl)-N-(5-(1-(trifluoromethyl)cyclopropyl)isoxazol-3-yl)acetamide;
2-(2-fluoro-4-(7-methoxy-6-(2-morpholinoethoxy)quinoxalin-2-yl)phenyl)-N-(5-(1-(trifluoromethyl)cyclopropyl)isoxazol-3-yl)acetamide;
2-(2-fluoro-4-(7-(2-hydroxyethoxy)-6-methoxyquinoxalin-2-yl)phenyl)-N-(5-(1-(trifluoromethyl)cyclopropyl)isoxazol-3-yl)acetamide;
2-(2-fluoro-4-(7-methoxy-6-(2-(4-methylpiperazin-1-yl)ethoxy)quinoxalin-2-yl)phenyl)-N-(5-(1-(trifluoromethyl)cyclopropyl)isoxazol-3-yl)acetamide;
2-(4-(6-(2,3-dihydroxypropyl)-7-methoxyquinoxalin-2-yl)-2-fluorophenyl)-N-(5-(1-(trifluoromethyl)cyclopropyl)isoxazol-3-yl)acetamide;
2-(4-(7-ethoxy-6-methoxyquinolin-3-yl)-2-fluorophenyl)-N-(5-(1-(trifluoromethyl)cyclopropyl)isoxazol-3-yl)acetamide;
2-(2-fluoro-4-(7-(2-hydroxyethoxy)-6-methoxyquinolin-3-yl)phenyl)-N-(5-(1-(trifluoromethyl)cyclopropyl)isoxazol-3-yl)acetamide;
2-(4-(6-(azetidin-3-yloxy)-7-methoxyquinoxalin-2-yl)-2-fluorophenyl)-N-(5-(1-(trifluoromethyl)cyclopropyl)isoxazol-3-yl)acetamide;
2-(2-fluoro-4-(7-(2-hydroxyethoxy)-6-methoxyquinolin-3-yl)phenyl)-N-(5-(1,1,1-trifluoro-2-methylpropan-2-yl)isoxazol-3-yl)acetamide;
N-(5-(tert-butyl)isoxazol-3-yl)-2-(2-fluoro-4-(7-methoxy-6-(2-morpholinoethoxy)quinoxalin-2-yl)phenyl)acetamide;
2-(4-(7-methoxy-6-(2-morpholinoethoxy)quinoxalin-2-yl)phenyl)-N-(5-(1,1,1-trifluoro-2-methylpropan-2-yl)isoxazol-3-yl)acetamide;
2-(2-fluoro-4-(7-methoxy-6-(2-morpholinoethoxy)quinoxalin-2-yl)phenyl)-N-(1-methyl-3-(1,1,1-trifluoro-2-methylpropan-2-yl)-1H-pyrazol-5-yl)acetamide;
2-(2-fluoro-4-(7-methoxy-6-(2-morpholinoethoxy)quinoxalin-2-yl)phenyl)-N-(3-(1-methylcyclopropyl)isoxazol-5-yl)acetamide;
2-[4-(6,7-diethoxyquinoxalin-2-yl)-2-fluoro-phenyl]-N-[5-[1-(trifluoromethyl)cyclopropyl]isoxazol-3-yl]acetamide;
2-[4-[6,7-bis(2-methoxyethoxy)quinoxalin-2-yl]phenyl]-N-(5-tert-butylisoxazol-3-yl)acetamide;
2-[4-[6,7-bis(2-methoxyethoxy)quinoxalin-2-yl]-2-fluoro-phenyl]-N-[5-[1-(trifluoromethyl)cyclopropyl]isoxazol-3-yl]acetamide;
2-[2-fluoro-4-[6-methoxy-7-(2-methoxyethoxy)-3-quinolyl]phenyl]-N-[5-[1-(trifluoromethyl)cyclopropyl]isoxazol-3-yl]acetamide;
2-[4-(6,7-dimethoxy-3-quinolyl)-2-fluoro-phenyl]-N-[5-[1-(trifluoromethyl)cyclopropyl]isoxazol-3-yl]acetamide;
2-[4-(6,7-dimethoxy-3-quinolyl)-2-fluoro-phenyl]-N-[5-(2,2,2-trifluoro-1,1-dimethyl-ethyl)isoxazol-3-yl]acetamide;
2-[2-fluoro-4-[6-(2-hydroxyethoxy)-7-methoxy-quinoxalin-2-yl]phenyl]-N-[5-[1-(trifluoromethyl)cyclopropyl]isoxazol-3-yl]acetamide;
2-[2-fluoro-4-[7-methoxy-6-(2-pyrrolidin-1-ylethoxy)quinoxalin-2-yl]phenyl]-N-[5-[1-(trifluoromethyl)cyclopropyl]isoxazol-3-yl]acetamide;
2-[2-fluoro-4-[7-methoxy-6-(oxetan-3-yloxy)quinoxalin-2-yl]phenyl]-N-[5-[1-(trifluoromethyl)cyclopropyl]isoxazol-3-yl]acetamide;
2-[2-fluoro-4-[7-methoxy-6-(oxetan-3-yloxy)quinoxalin-2-yl]phenyl]-N-[5-(2,2,2-trifluoro-1,1-dimethyl-ethyl)isoxazol-3-yl]acetamide;
2-[4-[6-(azetidin-3-yloxy)-7-methoxy-quinoxalin-2-yl]-2-fluoro-phenyl]-N-[5-(2,2,2-trifluoro-1,1-dimethyl-ethyl)isoxazol-3-yl]acetamide;
N-(3-tert-butyl-1H-pyrazol-5-yl)-2-[4-(6,7-dimethoxy-quinoxalin-2-yl)-2-fluoro-phenyl]acetamide;
2-[4-(7-benzyloxy-6-methoxy-quinoxalin-2-yl)-2-fluoro-phenyl]-N-[5-[1-(trifluoromethyl)cyclopropyl]isoxazol-3-yl]acetamide;
2-[2-fluoro-4-(7-hydroxy-6-methoxy-quinoxalin-2-yl)phenyl]-N-[5-[1-(trifluoromethyl)cyclopropyl]isoxazol-3-yl]acetamide;
2-[2-fluoro-4-[7-methoxy-6-(2-methoxyethoxy)quinoxalin-2-yl]phenyl]-N-[5-(2,2,2-trifluoro-1,1-dimethyl-ethyl)isoxazol-3-yl]acetamide;
2-[2-fluoro-4-[6-methoxy-7-(2-methoxyethoxy)quinoxalin-2-yl]phenyl]-N-[5-(2,2,2-trifluoro-1,1-dimethyl-ethyl)isoxazol-3-yl]acetamide;

2-[2-fluoro-4-(6-hydroxy-7-methoxy-quinoxalin-2-yl)phenyl]-N-[5-(2,2,2-trifluoro-1,1-dimethyl-ethyl)isoxazol-3-yl]acetamide;

2-[2-fluoro-4-[6-(2-hydroxyethoxy)-7-methoxy-quinoxalin-2-yl]phenyl]-N-[5-(2,2,2-trifluoro-1,1-dimethyl-ethyl)isoxazol-3-yl]acetamide;

2-[4-[6-(2-azidoethoxy)-7-methoxy-quinoxalin-2-yl]-2-fluoro-phenyl]-N-[5-[1-(trifluoromethyl)cyclopropyl]isoxazol-3-yl]acetamide;

2-[4-[6-(2-aminoethoxy)-7-methoxy-quinoxalin-2-yl]-2-fluoro-phenyl]-N-[5-[1-(trifluoromethyl)cyclopropyl]isoxazol-3-yl]acetamide;

2-[2-fluoro-4-[7-(2-hydroxyethoxy)-6-methoxy-quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(2-morpholinoethoxy)quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(2-methoxyethoxy)-3-quinolyl]phenyl]-N-[5-(2,2,2-trifluoro-1,1-dimethyl-ethyl)isoxazol-3-yl]acetamide;

2-[2-fluoro-4-[6-(2-hydroxyethoxy)-7-methoxy-3-quinolyl]phenyl]-N-[5-(2,2,2-trifluoro-1,1-dimethyl-ethyl)isoxazol-3-yl]acetamide;

2-[2-fluoro-4-[6-(2-hydroxyethoxy)-7-methoxy-3-quinolyl]phenyl]-N-[5-[1-(trifluoromethyl)cyclopropyl]isoxazol-3-yl]acetamide;

2-[4-(6,7-dimethoxyquinoxalin-2-yl)-2-fluoro-phenyl]-N-[3-[1-(trifluoromethyl)cyclopropyl]-1H-pyrazol-5-yl]acetamide;

2-[4-(6,7-dimethoxyquinoxalin-2-yl)-2-fluoro-phenyl]-N-[3-(2,2,2-trifluoro-1,1-dimethyl-ethyl)-1H-pyrazol-5-yl]acetamide;

2-[2-fluoro-4-(7-hydroxy-6-methoxy-quinoxalin-2-yl)phenyl]-N-[5-(2,2,2-trifluoro-1,1-dimethyl-ethyl)isoxazol-3-yl]acetamide;

2-[2-fluoro-4-[6-methoxy-7-(2-morpholinoethoxy)quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(2-methoxyethoxy)-3-quinolyl]phenyl]-N-[5-[1-(trifluoromethyl)cyclopropyl]isoxazol-3-yl]acetamide;

2-[2-fluoro-4-[7-methoxy-6-(2-morpholinoethoxy)-3-quinolyl]phenyl]-N-[5-(2,2,2-trifluoro-1,1-dimethyl-ethyl)isoxazol-3-yl]acetamide;

2-[2-fluoro-4-[7-methoxy-6-(2-morpholinoethoxy)-3-quinolyl]phenyl]-N-[5-[1-(trifluoromethyl)cyclopropyl]isoxazol-3-yl]acetamide;

2-[2-fluoro-4-[7-[2-[(3S)-3-hydroxypyrrolidin-1-yl]ethoxy]-6-methoxy-quinoxalin-2-yl]phenyl]-N-[5-(2,2,2-trifluoro-1,1-dimethyl-ethyl)isoxazol-3-yl]acetamide;

2-[2-fluoro-4-[6-(3-hydroxypropoxy)-7-methoxy-quinoxalin-2-yl]phenyl]-N-[5-[1-(trifluoromethyl)cyclopropyl]isoxazol-3-yl]acetamide;

2-[2-fluoro-4-[6-methoxy-7-(2-morpholinoethoxy)-3-quinolyl]phenyl]-N-[5-(2,2,2-trifluoro-1,1-dimethyl-ethyl)isoxazol-3-yl]acetamide;

2-[2-fluoro-4-[7-[(2R)-2-hydroxypropoxy]-6-methoxy-quinoxalin-2-yl]phenyl]-N-[5-[1-(trifluoromethyl)cyclopropyl]isoxazol-3-yl]acetamide;

2-[2-fluoro-4-[6-methoxy-7-(3-morpholinopropoxy)quinoxalin-2-yl]phenyl]-N-[5-(2,2,2-trifluoro-1,1-dimethyl-ethyl)isoxazol-3-yl]acetamide;

2-[2-fluoro-4-[6-[(2R)-2-hydroxypropoxy]-7-methoxy-quinoxalin-2-yl]phenyl]-N-[5-[1-(trifluoromethyl)cyclopropyl]isoxazol-3-yl]acetamide;

2-[2-fluoro-4-[7-methoxy-6-(3-morpholinopropoxy)quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-[2-(1,2,4-triazol-1-yl)ethoxy]quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-[2-(1,2,4-triazol-4-yl)ethoxy]quinoxalin-2-yl]phenyl]-N-[5-(2,2,2-trifluoro-1,1-dimethyl-ethyl)isoxazol-3-yl]acetamide;

2-[2-fluoro-4-[7-methoxy-6-(3-morpholinopropoxy)quinoxalin-2-yl]phenyl]-N-[5-[1-(trifluoromethyl)cyclopropyl]isoxazol-3-yl]acetamide;

2-[2-fluoro-4-[6-methoxy-7-(3-morpholinopropoxy)quinoxalin-2-yl]phenyl]-N-[5-[1-(trifluoromethyl)cyclopropyl]isoxazol-3-yl]acetamide;

N-(5-tert-butylisoxazol-3-yl)-2-[4-[7-methoxy-6-(2-morpholinoethoxy)quinoxalin-2-yl]phenyl]acetamide;

2-[4-(6,7-dimethoxyquinoxalin-2-yl)-3-fluoro-phenyl]-N-[5-(2,2,2-trifluoro-1,1-dimethyl-ethyl)isoxazol-3-yl]acetamide;

2-[2-fluoro-4-[7-methoxy-6-[2-(6-oxa-3-azabicyclo[3.1.1]heptan-3-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-(2-oxa-5-azabicyclo[2.2.1]heptan-5-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-(2-morpholinoethoxy)quinoxalin-2-yl]phenyl]-N-[3-[1-(trifluoromethyl)cyclopropyl]-1H-pyrazol-5-yl]acetamide;

2-[4-[7-methoxy-6-(2-morpholinoethoxy)quinoxalin-2-yl]phenyl]-N-[5-[1-(trifluoromethyl)cyclopropyl]isoxazol-3-yl]acetamide;

2-[2-fluoro-4-[6-methoxy-7-(2-morpholinoethoxy)-3-quinolyl]phenyl]-N-[5-[1-(trifluoromethyl)cyclopropyl]isoxazol-3-yl]acetamide;

2-[2-fluoro-4-[6-methoxy-7-(2-morpholinoethoxy)quinoxalin-2-yl]phenyl]-N-[5-[1-(trifluoromethyl)cyclopropyl]isoxazol-3-yl]acetamide;

2-[2-fluoro-4-[7-methoxy-6-(2-morpholinoethoxy)quinoxalin-2-yl]phenyl]-N-[3-(2,2,2-trifluoro-1,1-dimethyl-ethyl)-1H-pyrazol-5-yl]acetamide;

2-[2-fluoro-4-[7-(2-hydroxy-2-methyl-propoxy)-6-methoxy-quinoxalin-2-yl]phenyl]-N-[5-[1-(trifluoromethyl)cyclopropyl]isoxazol-3-yl]acetamide;

2-[2-fluoro-4-[7-methoxy-6-[2-(1,4-oxazepan-4-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-(2-piperazin-1-ylethoxy)quinoxalin-2-yl]phenyl]-N-[5-[1-(trifluoromethyl)cyclopropyl]isoxazol-3-yl]acetamide;

2-[2-fluoro-4-[7-methoxy-6-[2-(9-oxa-3-azabicyclo[3.3.1]nonan-3-yl)ethoxy]quinoxalin-2-yl]phenyl]-N-[5-[1-(trifluoromethyl)cyclopropyl]isoxazol-3-yl]acetamide;

2-[2-fluoro-4-[7-methoxy-6-[2-(3-oxa-8-azabicyclo[3.2.1]octan-8-yl)ethoxy]quinoxalin-2-yl]phenyl]-N-[5-[1-(trifluoromethyl)cyclopropyl]isoxazol-3-yl]acetamide;

2-[2-fluoro-4-[6-(2-hydroxy-2-methyl-propoxy)-7-methoxy-quinoxalin-2-yl]phenyl]-N-[5-(2,2,2-trifluoro-1,1-dimethyl-ethyl)isoxazol-3-yl]acetamide; and 2-[2-fluoro-4-[6-(2-hydroxy-2-methyl-propoxy)-7-methoxy-quinoxalin-2-yl]phenyl]-N-[5-[1-(trifluoromethyl)cyclopropyl]isoxazol-3-yl]acetamide.

3. A pharmaceutical composition comprising a compound of claim 1 and a pharmaceutically acceptable carrier.

4. The compound of claim 1, wherein the compound is 2-(4-(6,7-dimethoxyquinoxalin-2-yl)phenyl)-N-(5-(1,1,1-trifluoro-2-methylpropan-2-yl)isoxazol-3-yl)acetamide.

* * * * *